US009789116B2

(12) United States Patent
Markowitz et al.

(10) Patent No.: US 9,789,116 B2
(45) Date of Patent: *Oct. 17, 2017

(54) COMPOSITIONS AND METHODS OF MODULATING SHORT-CHAIN DEHYDROGENASE ACTIVITY

(71) Applicants: CASE WESTERN RESERVE UNIVERSITY, Cleveland, OH (US); BOARD OF REGENTS OF THE UNIVERSITY OF TEXAS SYSTEM, Austin, TX (US)

(72) Inventors: Sanford Markowitz, Pepper Pike, OH (US); James K. V. Willson, Dallas, TX (US); Bruce Posner, Richardson, TX (US); Joseph Ready, Carrolton, TX (US); Monika Antczak, Ft. Worth, TX (US); Yongyou Zhang, Cleveland, OH (US); Amar Desai, Cleveland, OH (US); Stanton Gerson, Hunting Valley, OH (US); William Greenlee, Cleveland, OH (US)

(73) Assignees: Case Western Reserve University, Cleveland, OH (US); Board of Regents of the University of Texas System, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/029,943

(22) PCT Filed: Oct. 15, 2014

(86) PCT No.: PCT/US2014/060761
§ 371 (c)(1),
(2) Date: Apr. 15, 2016

(87) PCT Pub. No.: WO2015/065716
PCT Pub. Date: May 7, 2015

(65) Prior Publication Data
US 2017/0173028 A1 Jun. 22, 2017

Related U.S. Application Data

(60) Provisional application No. 61/891,260, filed on Oct. 15, 2013, provisional application No. 61/954,202, filed on Mar. 17, 2014, provisional application No. 62/019,597, filed on Jul. 1, 2014, provisional application No. 62/043,694, filed on Aug. 29, 2014.

(51) Int. Cl.
| | | |
|---|---|---|
| A61K 31/535 | (2006.01) | |
| A61K 31/5377 | (2006.01) | |
| A61K 31/4365 | (2006.01) | |
| A61K 31/519 | (2006.01) | |
| A61K 31/437 | (2006.01) | |
| A61K 31/444 | (2006.01) | |
| A61K 31/496 | (2006.01) | |

(52) U.S. Cl.
CPC ........ *A61K 31/5377* (2013.01); *A61K 31/437* (2013.01); *A61K 31/4365* (2013.01); *A61K 31/444* (2013.01); *A61K 31/496* (2013.01); *A61K 31/519* (2013.01)

(58) Field of Classification Search
CPC .................................................. A61K 31/5377
USPC ...................................................... 514/233.8
See application file for complete search history.

(56) References Cited

U.S. PATENT DOCUMENTS

| | | | |
|---|---|---|---|
| 4,966,974 A | 10/1990 | Klausener et al. | |
| 7,091,216 B2 | 8/2006 | Toupence et al. | |
| 7,320,967 B2 | 1/2008 | Michelet et al. | |
| 7,396,525 B2 | 7/2008 | Rozot et al. | |
| 8,202,882 B2 | 6/2012 | Hoelzemann et al. | |
| 2004/0087593 A1 | 5/2004 | Clark et al. | |
| 2006/0034786 A1 | 2/2006 | Michelet et al. | |
| 2007/0071699 A1 | 3/2007 | Boulle et al. | |
| 2007/0078175 A1 | 4/2007 | Boulle et al. | |
| 2007/0219234 A1 | 9/2007 | Oizumi et al. | |
| 2008/0206320 A1 | 8/2008 | Michelet et al. | |
| 2008/0249117 A1 | 10/2008 | Michelet et al. | |
| 2010/0022521 A1 | 1/2010 | Nogradi et al. | |
| 2011/0014250 A1 | 1/2011 | Michelet et al. | |
| 2011/0142816 A1 | 6/2011 | Landry et al. | |
| 2011/0269954 A1 | 11/2011 | Cho et al. | |

FOREIGN PATENT DOCUMENTS

| | | |
|---|---|---|
| FR | 2838641 A1 | 4/2002 |
| KR | 2010137090 A | 12/2010 |
| KR | 20101374090 A | 12/2010 |
| KR | 2013103945 A | 9/2013 |
| WO | 2007/038519 A1 | 4/2007 |
| WO | 2011/042860 A2 | 4/2011 |
| WO | 2013082243 A1 | 6/2013 |
| WO | 2013/158649 A2 | 10/2013 |

OTHER PUBLICATIONS

Antczak et al Publication Date (Web): Apr. 11, 2017.*
Supplementary European Search Report for Application No. 14859042.5-1462 / 3057973 dated Mar. 6, 2017.
A. Archelas et al: "Absolute Configuration of [alpha]-Methylstyrene Oxide: The Correct Absolute Configuration/Optical Rotation Correlation", The Journal of Organic Chemistry, vol . 64, No. 16, Aug. 1, 1999 (Aug. 1, 1999), pp. 6112-6114.
Frank H. Niesen et al: "High-Affinity Inhibitors of Human NAD+-Dependent 15-Hydroxyprostaglandin Dehydrogenase: Mechanisms of Inhibition and Structure-Activity Relationships", PLOS ONE, vol. 5, No. 11, Nov. 2, 2010 (Nov. 2, 2010), p. e13719.

(Continued)

*Primary Examiner* — Nizal Chandrakumar
(74) *Attorney, Agent, or Firm* — Tarolli, Sundheim, Covell & Tummino LLP

(57) ABSTRACT

Compounds and methods of modulating 15-PGDH activity, modulating tissue prostaglandin levels, treating disease, diseases disorders, or conditions in which it is desired to modulate 15-PGDH activity and/or prostaglandin levels include 15-PGDH inhibitors described herein.

15 Claims, 126 Drawing Sheets

(56) References Cited

OTHER PUBLICATIONS

Japanese Office action for Application No. 2015-507115, dated Jan. 31, 2017.
Baker, Michael E., Licorice and enzymes other than 1 I β-hydroxysteroid dehydrogenase: An evolutionary perspective,Department of Medicine, University of California, Steroids, Feb. 1994. vol. 59, p. 136-141.
Tatsuwaki, Hiroshi, et al., Reduction of 15-hydroxyprostaglandin dehydrogenase expression is an independent Dehydrogenase expression is an independent predictor of poor survival associated with enhanced cell proliferation in gastric adenocarcinoma, Cancer Science, Feb. 2010, vol. 100, No. 2, p. 550-558.
Wu, Ying, et al., "Synthesis and Biological Evaluation of Novel Thiazolidinedione Analogues as 15-Hydroxyprostaglandin Dehydrogenase Inhibitors", J Med Chem, Apr. 5, 2011, 54, 5260-5264.
International Search Report for Application No. PCT/US2013/036790, dated Jul. 29, 2011.
Obeid, J., et al., "Tyr-179 and Lys-183 are essential for enzymatic activity of 11 beta-hydroxysteroid dehydroxysteroid dehydrogenase", Biochem Biophys Res Commun. Oct. 15, 1992;188(1):222-7.
Ensor, CM, et al., "Site-directed mutagenesis of the conversed tyrosine 151 of human placental Nad(+)-dependent 15-hydroxyprostaglandin dehydrogenase yields a catalytically inactive enzyme", Biochem Biophys Res Commun. Apr. 30, 1991;176(2):840-5.
Tanaka, N., et al., "Crystal Structures of the binary and ternary complexes of 7 alpha-hydroxysteroid dehydrogenase from *Escherichia coli*.", Biochemistry Jun. 18, 1996;35(24):7715-30.
Duveau, Dy, et al., "Structure-activity relationship studies and biological characterization of human NAO(+)-dependent 15 hydroxyprostaglandin dehydrogenase", Bioorg Med Chem Lett. Jan. 15, 2014;24(2):630-5.
Piao, Yu Lan, et al., Wound healing effects of new 15-hydroxyprostaglandin dehydrogenase inhibitors, Prostaglandins, Leukotrienes and Essential Fatty Acids 91 (2014)325-332.
Bray, James E., et al. "The human short-chain dehydrogenase/ reductase (SOR) superfamily: A bioinformatics Summary", Chemico-Biological Interactions 178(2009) 99-109.
Markowitz, Sanford, et al., "Molecular Basis of Colorectal Cancer", N Engl J Med 2009;361 :2449-60.
Yan, Min, et al., "15-Hydroxyprostaglandin dehydrogenase, a COX-2 oncogene antagonist, is a TGF-β-induced suppressor of human gastrointestinal cancers", PNAS, Dec. 14, 2004, vol. 101, No. 50, 17468-17473.
Ensor, Charles Mark, et al., "Bacterial expression and site-directed mutagenesis of two critical residues ( tyrosine-151 and lysine-155) of human placental NAO +-dependent 15-hydroxyprostaglandin dehydrogenase", Biochimica et Biophysica Acta 1208 (1994) 151-156.
Yan, Min, et al, "15-Hydroxyprostaglandin dehydrogenase inactivation as a mechanism of resistance to celecoxib chemoprevention of colon tumors", PNAS, Jun. 9, 2009, vol. 106, No. 23, 9409-9413.
Tai, Hsin-Hsiung, et al., "Prostaglandin catabolizing enzymes", Prostaglandins & other Lipid Mediators 68-69 (2002) 483-493.
Choi, Dubok, et al., "Control of the intracellular levels of prostaglandin E2 through inhibition of the 15-hydroxyprostaglandin dehydrogenase for wound healing", Choi, D.; et al. Bioorg. Med. Chem. (2013), http://dx.doi.org/10.1016/j.bmc.2013.05.049.
Myung, Seung-Jae, et al., "15-Hydroxyprostaglandin dehydrogenase is an in vivo suppressor of colon tumorigenesis" PNAS, Aug. 8, 2006, vol. 103, No. 32, 12098-12102.
Otani, Taisuke, et al., "Levels of NAD+-dependent 15-hydroxyprostaglandin dehydrogenase are reduced in inflammatory bowel disease: evidence for involvement of TNF-a", Am J Physiol Gastrointest Liver Physiol 290: G361-G368, 2006.

Cho, Hoon, et al., "Role of glutamine 148 of human 15-hydroxyprostaglandin dehydrogenase in catalytic oxidation of prostaglandin E2", Bioorganic & Medicinal Chemistry 14 (2006) 6486-6491.
Clifford, P.C., et al., "Treatment of Vasospastic disease with prostaglandin E1", British Medical Journal vol. 281, Oct. 18, 1980, pp. 1031-1034.
Jadhav, Ajit, et al., "Potent and Selective Inhibitors of NAD+- dependent 15-hydroxyprostaglandin dehydrogenase (HPGD)", Probe Report 2011.
Markowitz, Sanford, et al., "Aspirin and Colon Cancer—Targeting Prevention", N Engl J med 256;21, May 27, 2007.
North, Trista E., "PGE2-regulated wnt signaling and N-acetylcysteine are synergistically hepatoprotective in zebrafish acetaminophen injury", PNAS, Oct. 5, 2010, vol. 107, No. 40, pp. 17315-17320.
Cho, et al., "Inhibition of NAD+-dependent 15-hydroxyprostaglandin dehydrogenase (15-PGDH) by cyclooxygenase inhibitors and chemopreventive agents", Prostaglandins, Leukotrienes and Essential FattyAcids (2002) 67(6), 461-465.
Hamza, Adel, et al., "Understanding human 15-hydroxyprostaglandin dehydrogenase binding with NAO+ and PGE2 by homology modeling, docking and molecular dynamics simulation", Bioorganic & Medicinal Chemistry 13 (2005) 4544-4551.
Berg, Daniel J., et al. "Rapid Development of Colitis in NSAID-Treated IL-10-Deficient Mice", Gastroenterology 2002; 123: 1527-1542.
Kabashima, Kenji, et al., "The prostaglandin receptor EP4 suppresses colitis, mucosal damage and CD4 cell activation in the gut", J_Clin. Invest. 109:883-893 (2002).
Berk, L.B., et al., "16, 16-Dimethyl Prostaglandin E2 and/or Syngeneic Bone Marrow Transplantation Increase Mouse Survival After Supra-Lethal Total Body Irradiation", Int. J Radiation Oncology Biol. Phys .. vol. 18. pp. 1387-1392.
Goessling, Wolfram, et al., "Prostaglandin E2 Enhances Human Cord Blood Stem Cell Xenotransplants and Shows Long-Term Safety in Preclinical Nonhuman Primate Transplant Models", Cell Stem Cell 8, 445-458, Apr. 8, 2011.
Porter, Rebecca L., et al., "Prostaglandin E2 Increases Hematopoietic Stem Cell Survival and Accelerates Hematopoietic Recovery After Radiation Injury", Stem Cells 2013;31:372-383.
Krland, JI, et al., "prostaglandin E in the positive and negative feedback control of myeloid Role for monocyte-macrophage-derived colony-stimulating factor and stem cell proliferation" Blood 1978 52: 388-407.
Hoffman, Corey M., et al., "Minireview: Complexity of Hematopoietic Stem Cell Regulation in the Bone Marrow Microenvironmenl", Mol Endocrinol, 2014.
Hoggatt, Jonathan, et al., "Prostaglandin E2 enhances long-term repopulation but does not permanently alter inherent stem cell competitiveness," Blood 2013 122:2997-3000.
Frisch, Benjamin J., et al., "In vivo prostaglandin E2 treatment alters the bone marrow stem cells microenvironment and preferentially expands short-term hematopoietic", Blood 2009 114: 4054-4063.
Gentile, P., et al., "In vivo modulation of murine myelopoiesis following intravenous administration of prostaglandin E2", Blood 1983 62: 1100-1107.
Speth, Jennifer, et al., "Pharmacologic increase in HIF1a enhances hematopoietic stem and progenitor homing and engraftmenl", Blood 2014 123: 203-207.
Hoggatt, Jonathan, et al., "Prostaglandin E2 enhances hematopoietic stem cell homing, survival, and proliferation", Blood 2009 113: 5444-5455.
Hoggatt, Jonathan, et al., "Recovery from hematopoietic injury by modulating prostaglandin E2 signaling post-irradiation", Blood Cells, Molecules and Diseases 50 (2013) 147-153.
Pelus, Louis, M., et al., Pleiotropic effects of prostaglandin E2 in hematopoiesis; prostaglandin E2 and other eicosanoids regulate hematopoietic stem and progenitor cell function, Prostaglandins & other Lipid Mediators 96 (2011) 3-9.

(56) References Cited

OTHER PUBLICATIONS

Pelus, L.M., et al., "Pulse exposure of haematopoietic grafts to prostaglandin E2 in vitro facilitates engraftment and recovery", Cell Prolif., 2011, 44 (Suppl. 1), 22-29.
Hoggatt, Jonathan, et al., "Differential stem- and progenitor-cell trafficking by prostaglandin E2", Nature, 2011.
Sasaki, S., et al., "Prostaglandin E2 Inhibits Lesion Formation in Dextran Sodium Sulphate-Induced Colitis in Rats and Reduces the Levels of Mucosal Inflammatory Cytokines", Scand. J_Immunol. 51, 23-28, 2000.
Tessner, Teresa, G., et al., "Prostaglandins Prevent Decreased Epithelial Cell Proliferation Associated With Dextran Sodium Sulfate Injury in Mice", Gastroenterology 1998;115:874-882.
Cutler, Corey, et al., "Prostaglandin-modulated umbilical cord blood hematopoietic stem cell transplantation" Blood, 2013.
Geossling, Wolfram, et al., "Genetic Interaction of PGE2 and Wnt Signaling Regulates Developmental Specification of Stem Cells and Regeneration", Cell 136, 1136-1147, Mar. 20, 2009.
Hagedorn, Elliott J., et al., "Getting more for your marrow: Boosting hematopoietic stem cell numbers with PGE2", BoostinghematopoieticstemcellnumberswithPGE2, Exp Cell Res (2014), http://dx.doi.org/10.1016/j.yexcr.2014.07.030.
North, Trista E., et al., "Prostaglandin E2 regulates vertebrate haematopoietic stem cell homeostasis", vol. 447, Jun. 21, 2007.
Karna, Sandeep,et al., "Novel Potent 15-Hydroxyprostaglandin Dehydrogenase Inhibitors", J_of Advanced Engineering and Technology, vol. 3, No. 3 (2010) pp. 301-304.
Castellone, Maria Domenica, et al., "Prostaglandin E2 Promotes Colon Cancer Cell Growth Through a Gs-Axin-II-Catenin Signaling Axis", Science, vol. 310, Dec. 2, 2005.

Zhang, Youngyou, et al. "Inhibition of the Prostaglandin Degrading Enzyme 15-PGDH Potentiates Tissue Regeneration" Science. Jun. 12, 2015; 348(6240): aaa2340. doi:10.1126/science.aaa2340. Online"http://web.archive.org/web/20071219115313/http://www.akosgmbh.de/AKosSamples/index.html"2011, accessed Oct. 10, 2015.
Frisch, Benjamin, et al., "In vivo prostaglandin E2 treatment alters the bone marrow microenvironment and preferentially expands short-term hematopoietic stem cells", Blood, Nov. 5, 2009 z vol. 114, No. 19, pp. 4054-4063.
Hoggati, Jonathan, et al., "Prostaglandin E2 enhances long-term repopulation but does not permanently alter inherent stem cell competitiveness", Blood, Oct. 24, 2013 x vol. 122, No. 17, pp. 2997-3000.
Jung, Peter, et al., "Isolation and in vitro expansion of human colonic stem cells", Nature Medicine 17, 1225-1227 (2011).
Brown, Jr, et al., "COX-2: a molecular target for colorectal cancer prevention", J_Clin Oneal. Apr. 20, 2005;23 (12):2840-55.
Kalugin "Functionalized sulfurcontaining compounds. 13.* Synthesis of substituted 3amino2(organylsulfinyl) and (organylsulfonyl)thieno[2,3b]pyridines." Russian Chemical Bulletin, International Edition, vol. 55, No. 3, pp. 529-534, Mar. 2006.
Pubchem Database compound CID 3337991, 2-butylsulfonyl-4-phenyl-6-thiophen-2-ylthieno[2,3-b]pyridin-3-amine, entered into the database on Sep. 7, 2005, Online "http://pubchem.ncbi.nlm.nih.gov/compound/3337991#section=Top" accessed Oct. 10, 2015.
PubChem Substance summary for CID 52943190 Deposit date Jun. 16, 2011 (Jun. 16, 2011) p. 1.
PubChem Substance summary for CID 3337839 Deposit date Sep. 7, 2005 (Sep. 7, 2005) p. 1.

* cited by examiner

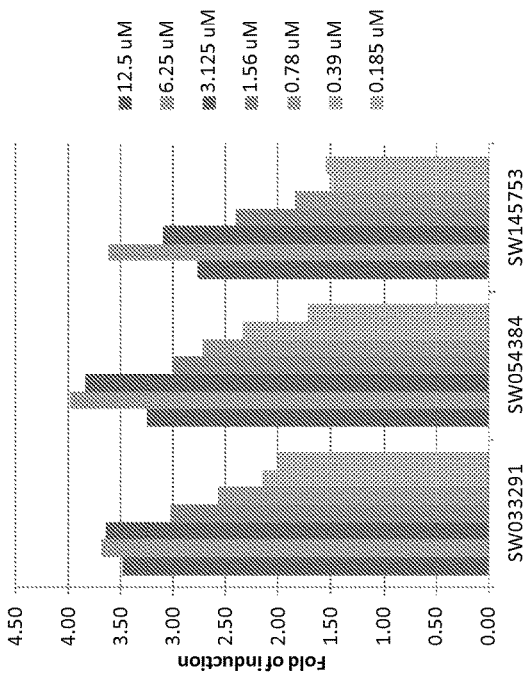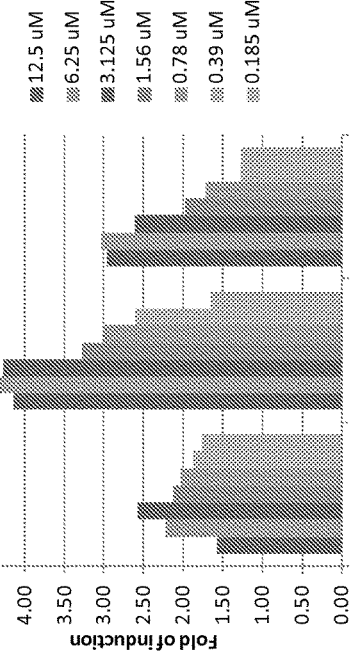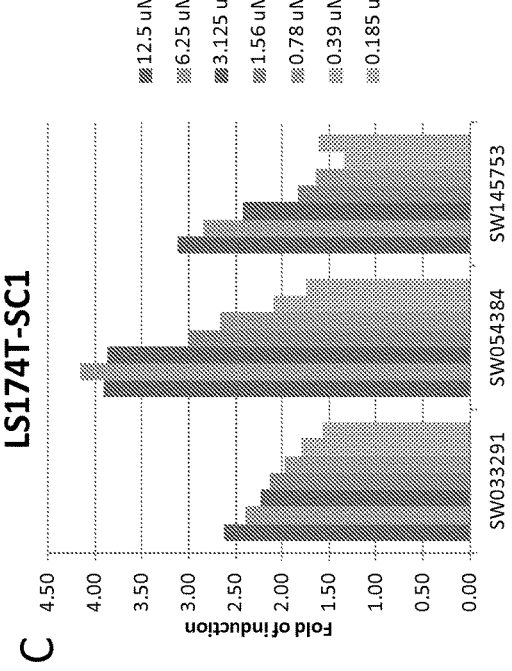
Figs. 1A-C

All three compounds increase 15-PGDH protein level ( 7.5uM)

Figs. 3A-C

SW124531:
1) Stabilized WT/MU 15-PGDH
2) didn't change the HSD17B4 protein level Mutant PGDH: (Y151L and K155E): lacks enzyme activity

SW124531 up-regulates 15-PGDH protein expression in V503
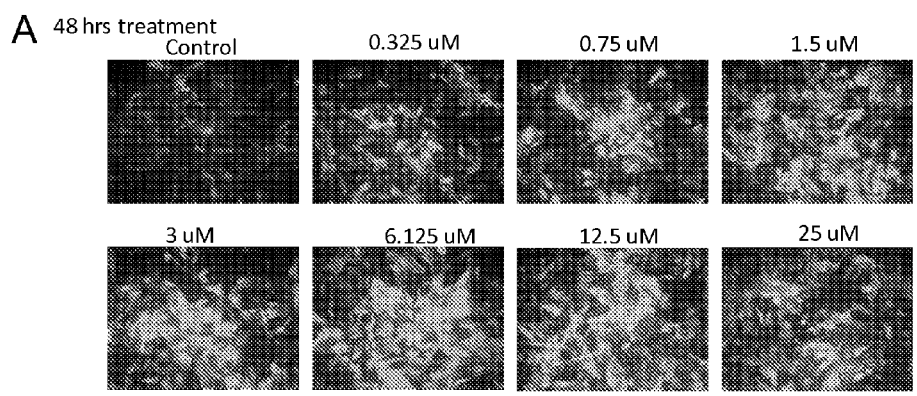
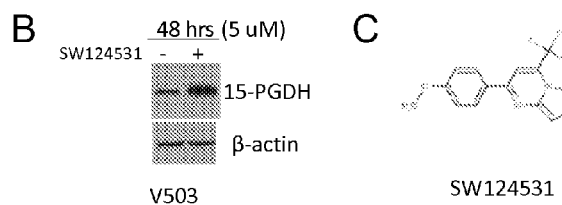
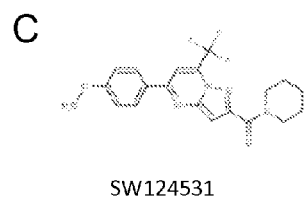
also stabilize the 15-PGDH protein in V9M, LS174T, SW480, FET SW837, V235
Figs. 5A-C

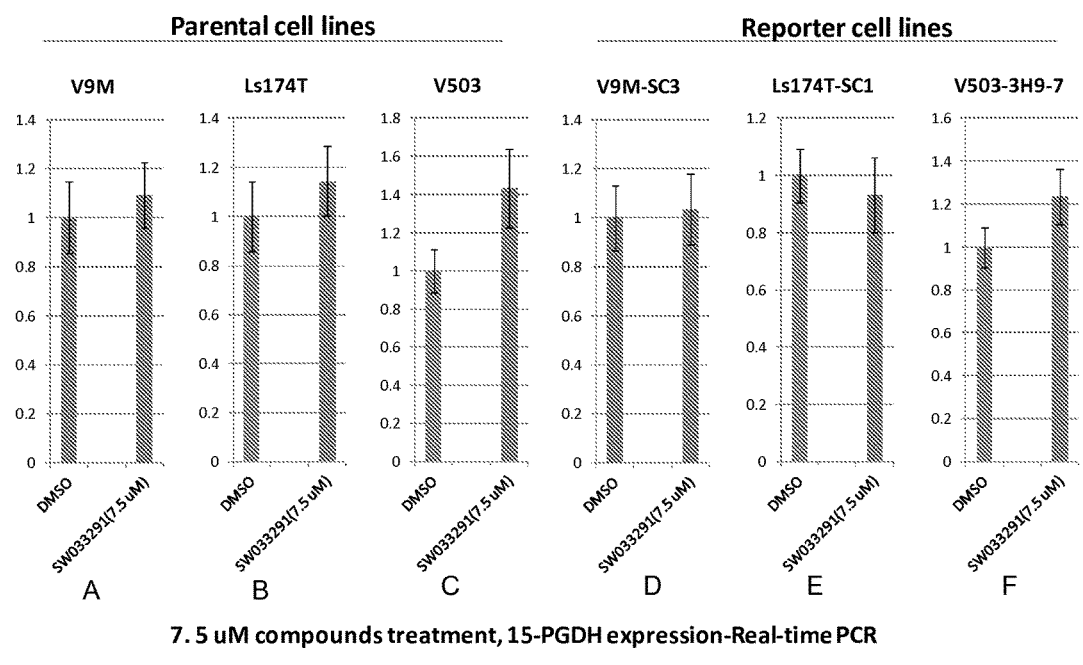
Figs. 6A-F

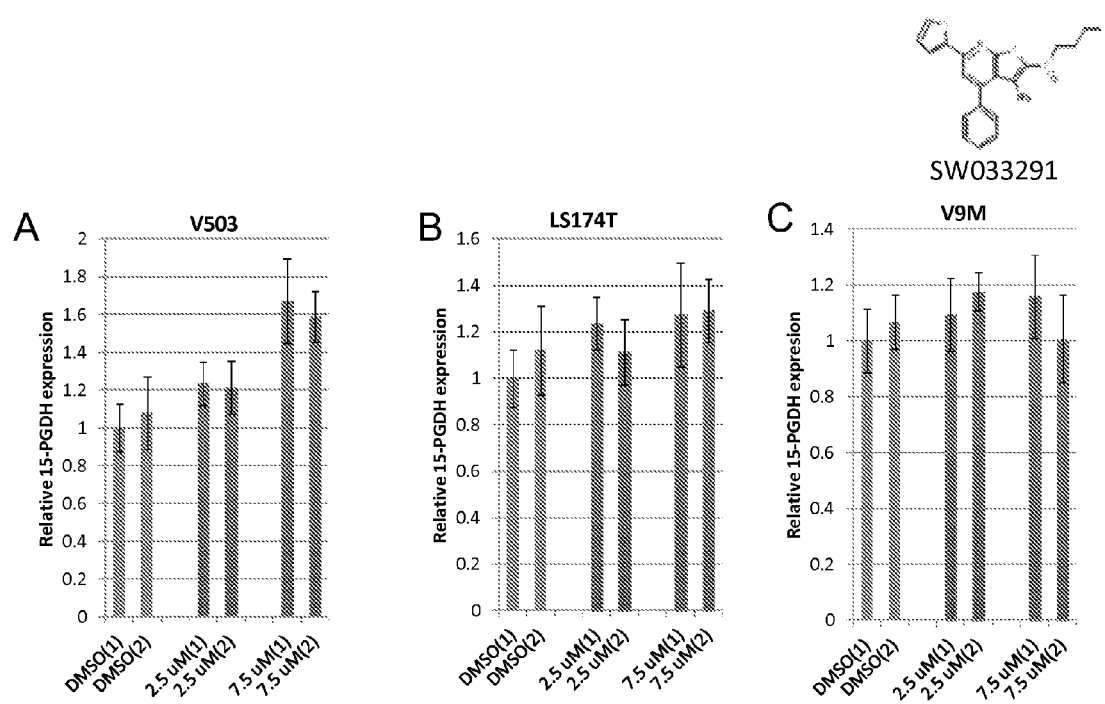
Figs. 7A-C

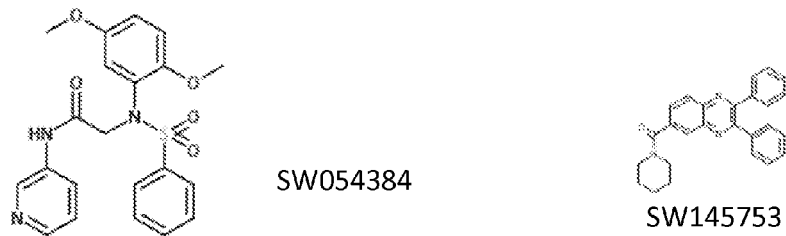
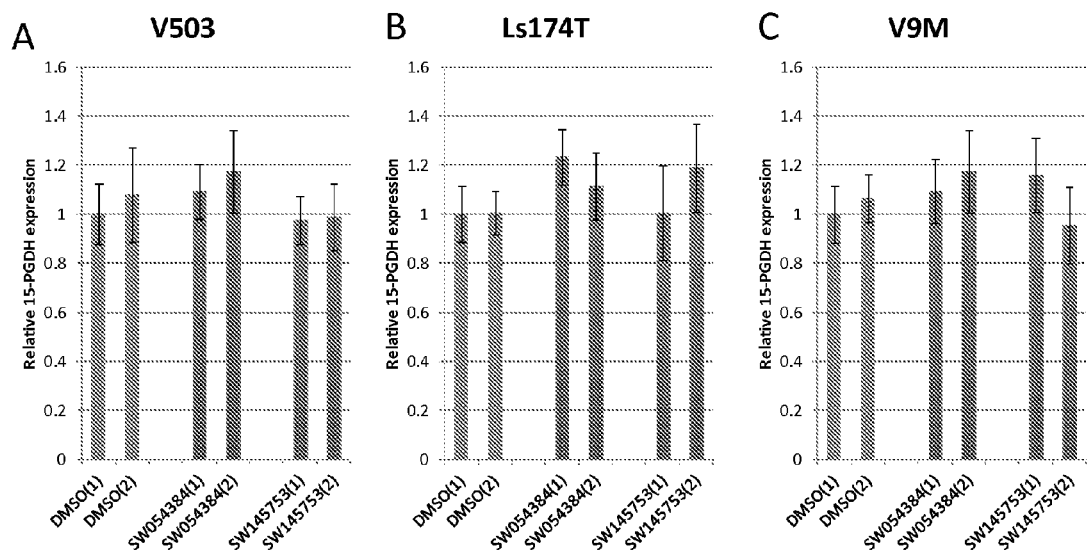
Figs. 8A-C

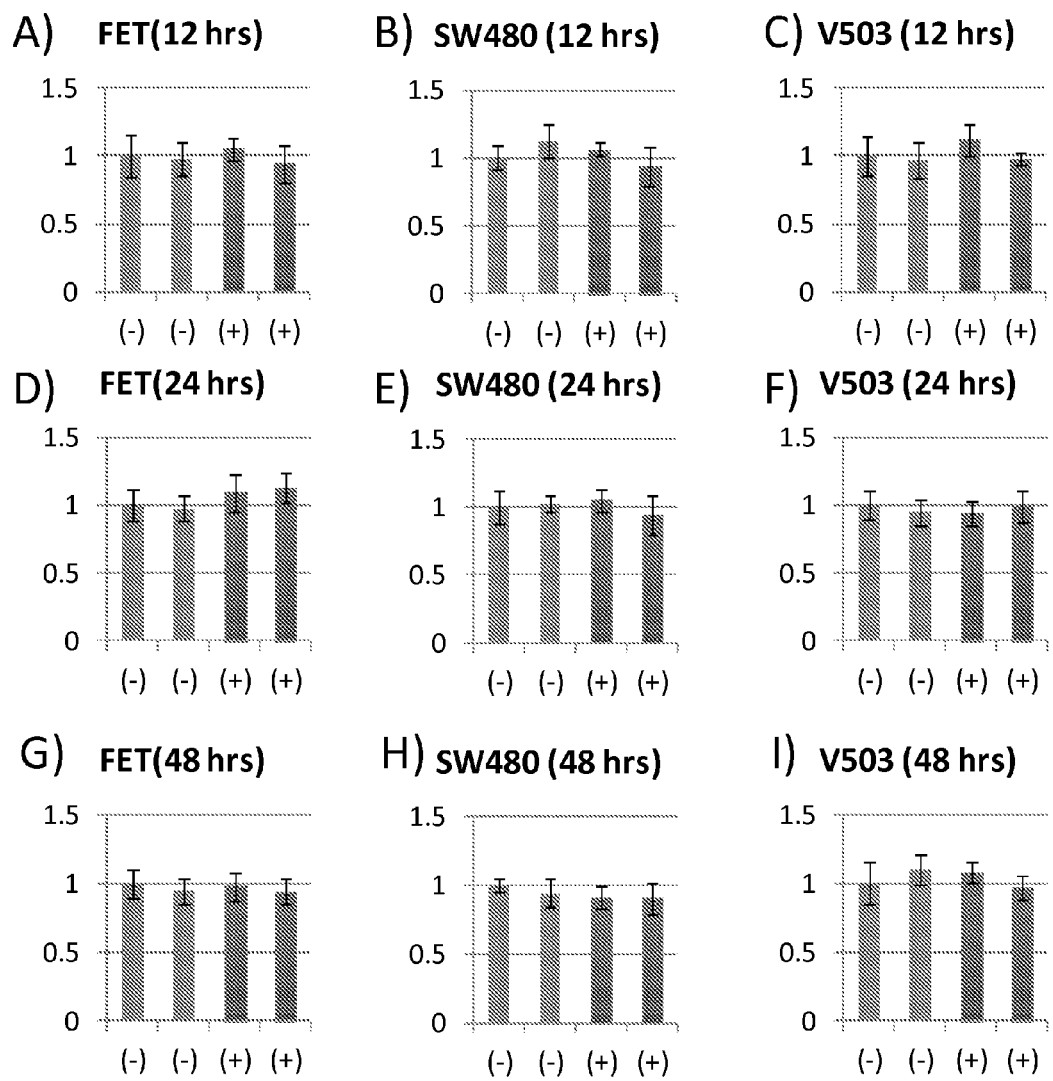
Figs. 9A-I

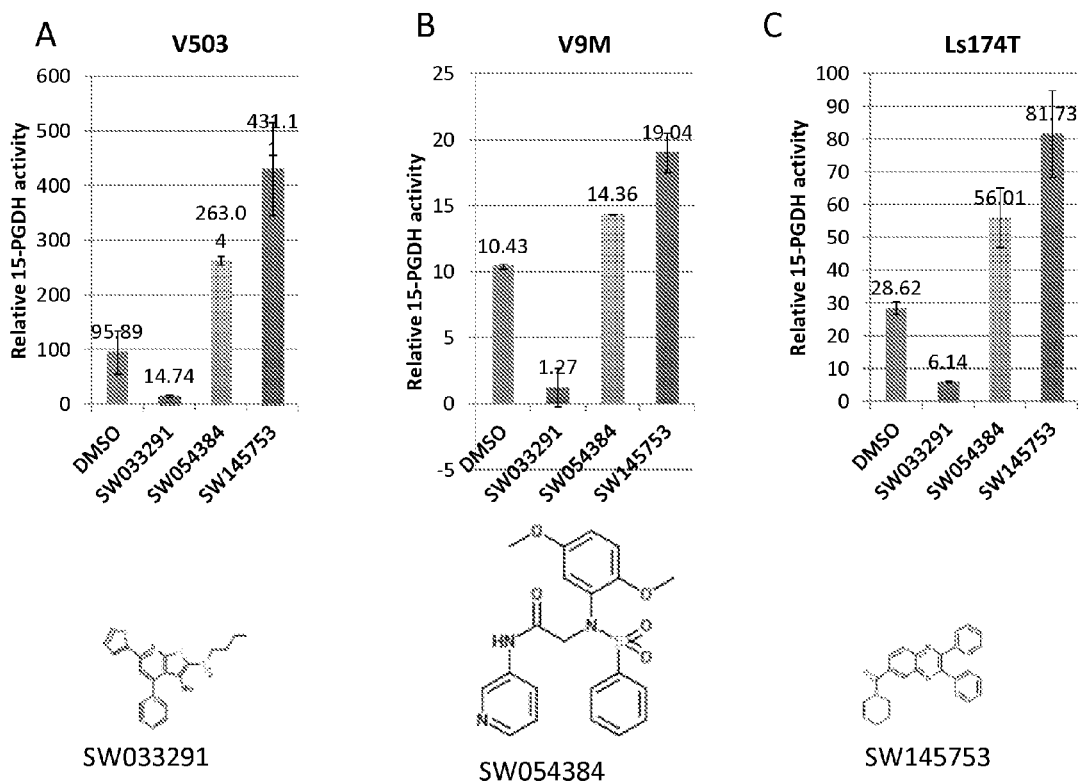
Figs. 10A-C

In Vitro activity assay of recombinant 15-PGDH when treated with compounds (04/28/2011)
| [drug] nM | 50000 | 5000 | 2500 | 1250 | 500 | 250 | 125 | 50 | 25 | 12.5 | 6.25 | 5 | 1.25 | 0 | IC50 |
|---|---|---|---|---|---|---|---|---|---|---|---|---|---|---|---|
| sw0543 84 | 438 | 1767 | | 2504 | 2904 | | | 2809 | | | | 2857 | | 2869 | >5000 |
| sw1457 53 | 141 | 151 | | 125 | 145 | 217 | 291 | 441 | 798 | 1186 | 1652 | 2198 | | 2198 | <12.5 |
| Cay1 | 213 | 163 | 223 | 278 | 538 | 815 | 1272 | 1781 | 2286 | 2782 | 2870 | | | 2959 | 25 to 62.5 |
| SW033291 | 117 | 139 | 113 | 95 | 96 | 81 | 135 | 113 | 204 | 303 | 260 | 598 | | 2729 | <1nm |
A) SW145753 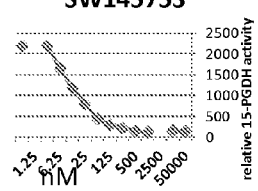
B) SW054384 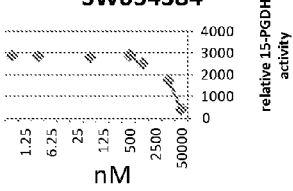
C) Cayman 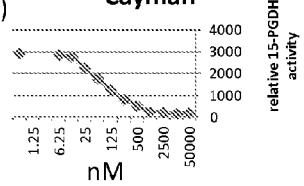
D) SW033291 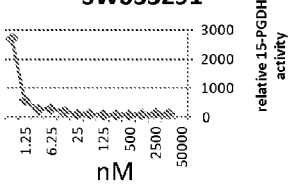
Figs. 11A-D

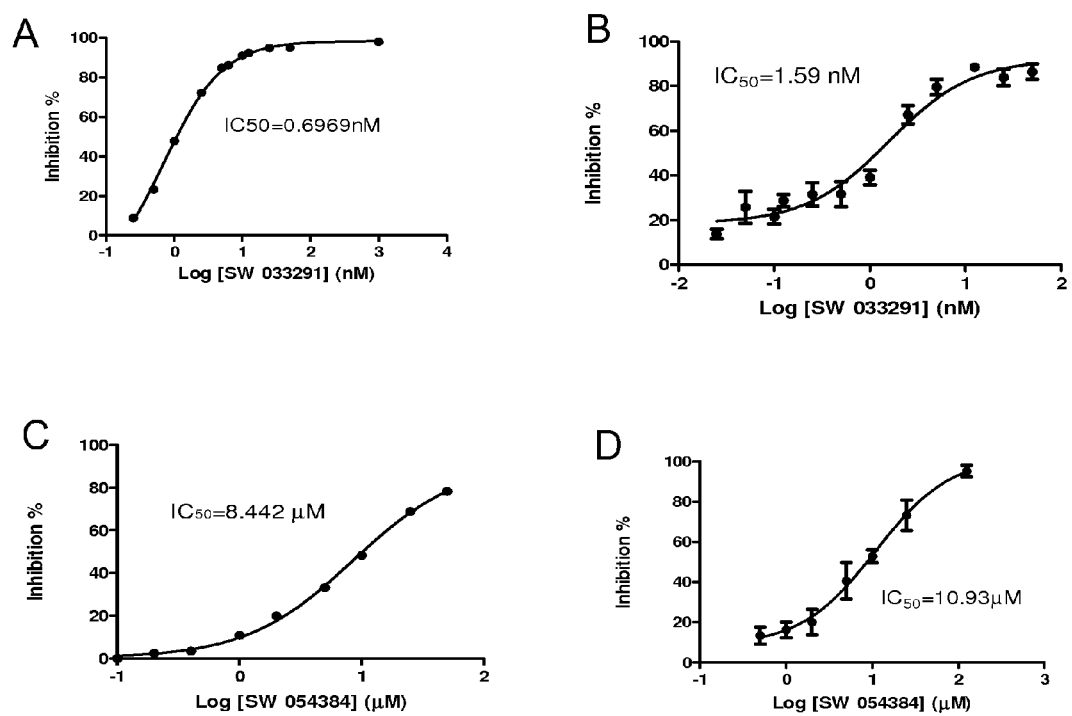
Figs. 12A-D

Increased PGDH activity in pellets of SW124531 treated cells

Table A

| Treatment / Activity / Cell | DMSO(1) | DMSO(2) | SW124531(1) | SW124531(2) | TGFb(1) | TGFb(2) |
|---|---|---|---|---|---|---|
| SW480 | 87.5 | 139.0476 | 204.3796 | 191.0256 | | |
| V235 | 634.0336 | 691.2371 | 1049.474 | 1068.852 | 1054.327 | 854.2017 |
| V9M | 16.28788 | 9.803922 | 19.55128 | 21.69118 | | |
| V503 | 101.2987 | 105.5556 | 296.5278 | 284.8684 | | |
| V400 | 7.420925 | 5.080831 | 6.730769 | 5.865103 | | |
| V400-S2-36 | 652.2059 | 653.5354 | 1428.235 | 2004.487 | | |
| SW837 | 905.102 | 885.1351 | 1122.34 | 1180.899 | | |

SW124531 is an in vitro inhibitor of PGDH

IC50=54.68 nM

DSF for compounds at 10 uM for WT-PGDH
-------- test the binding of the compound with 15-PGDH

A

B

| Tm \ CP  CF | DMSO | SW054384 | SW145753 | SW033291 | SW124531 | 15-PGDH inhibitor( Cayman) | Lapatinib |
|---|---|---|---|---|---|---|---|
| Water | 50 | 50.5 | 50 | 50 | 50 | 50.5 | 50.5 |
| NAD(+), 10 uM | 50 | 50 | 56.5 | 51.5, 64.5 | 53 | 51.5 | 50.5 |
| NADH, 10 uM | 50.5 | 50.5 | 57 | 51.5, 65.5 | 53.5 | 51.5 | 50.5 |
|  |  |  |  |  |  |  |  |
| NAD(+), 100 uM | 52 | 52.5 | 58, 64 | 53, 70.5 | 59.5 | 57.5 | 52.5 |
| NADH, 100 uM | 51 | 51 | 58 | 52, 68 | 54.5 | 55 | 50.5 |

Figs. 14A-B

DSF for compounds at 10 uM for Mu-PGDH

A                                    B

No obvious Tm shift, could be due to absent binding or weak binding

Mutant PGDH: (Y151L and K155E)

IL1β, 18 hrs-> 2. 5 uM compound 5 hrs,
IL1b+SW054384(2), pretreated with 2.5 uM SW054384 24 hrs.

Scratch wound healing of HaCaT confluent monolayer treated with PGDH Inhibitor SW033291 or With TGF-beta

Scratch width of HaCaT monolayer at 0 and 48 hours when treated with TGF-beta or with PGDH-Inhibitor SW033291 (denoted PGDH-I)
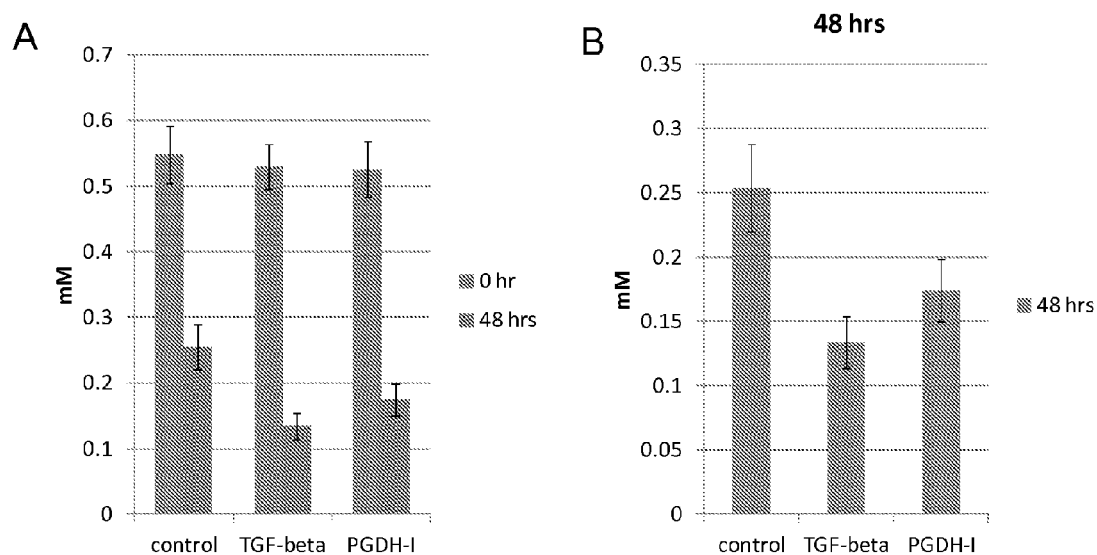
Figs. 20A-B

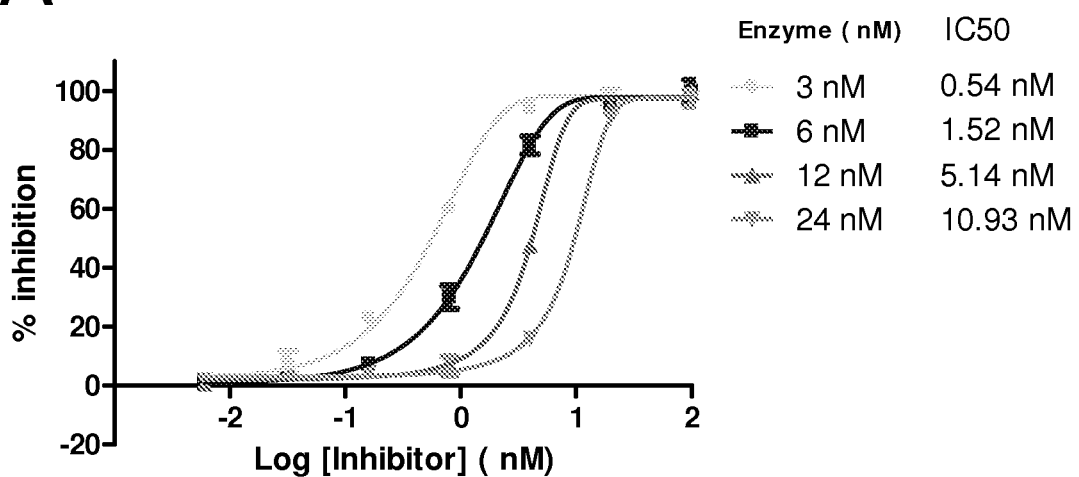
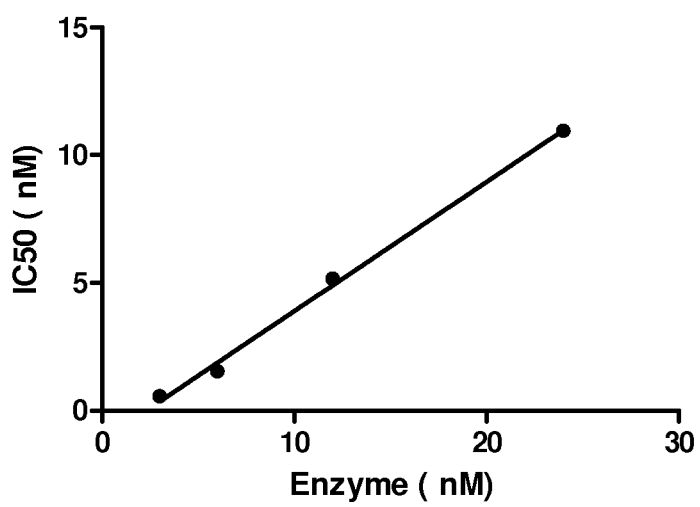
Figs. 21A-B

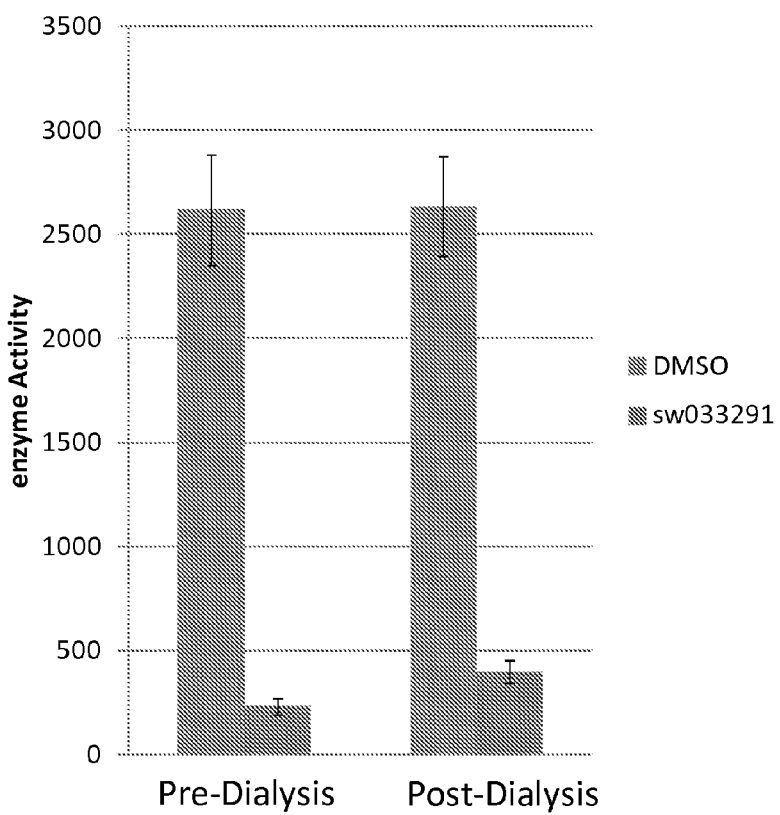
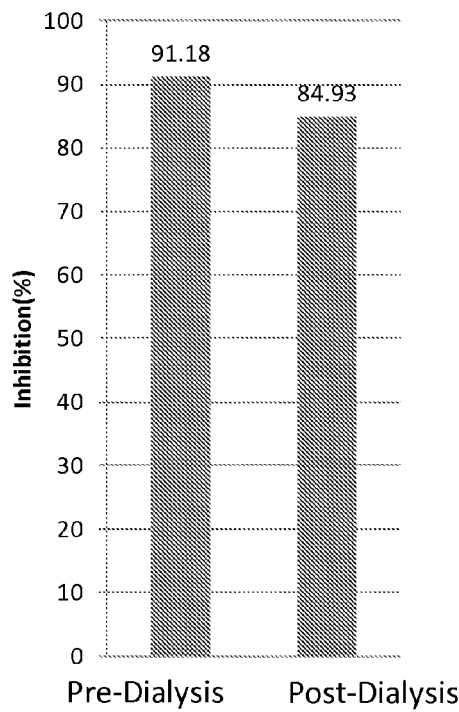
Figs. 22A-B

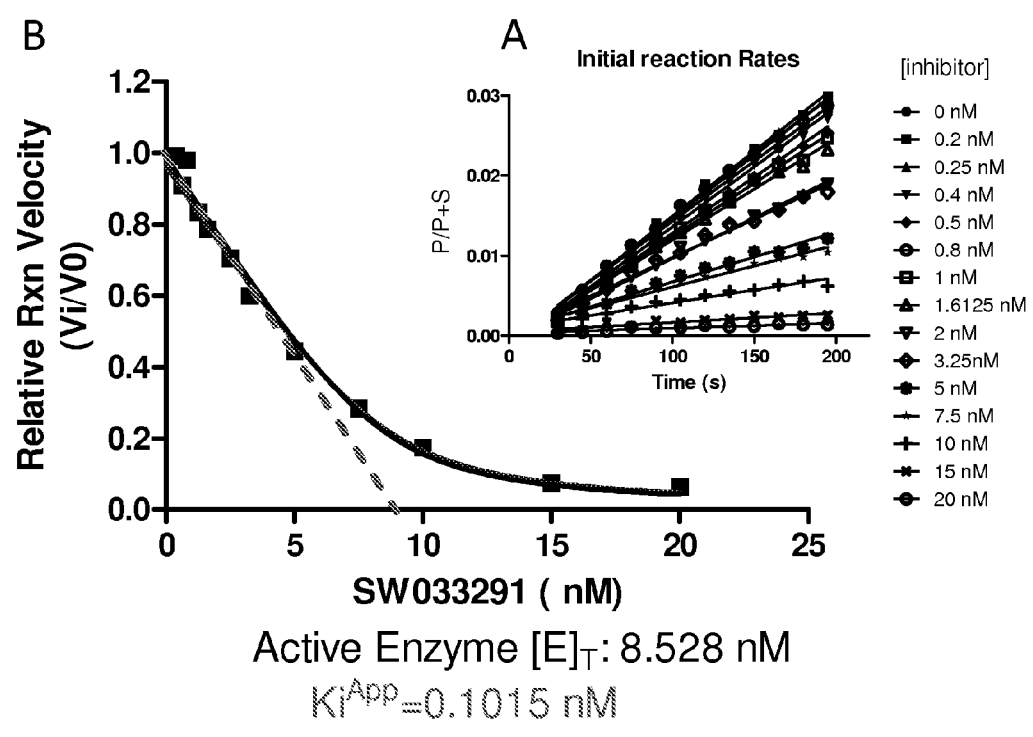
Figs. 23A-B

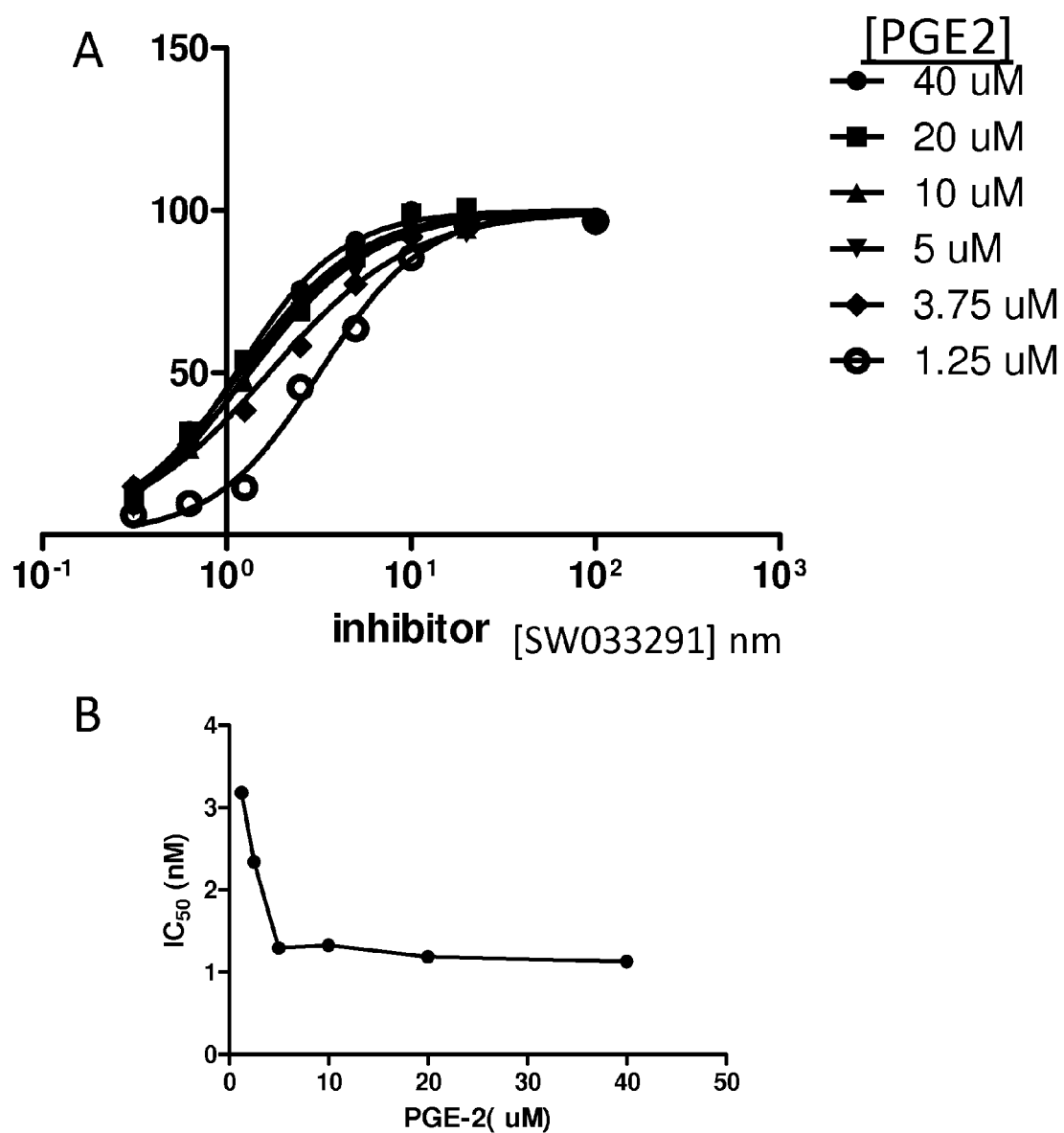
Figs. 24A-B

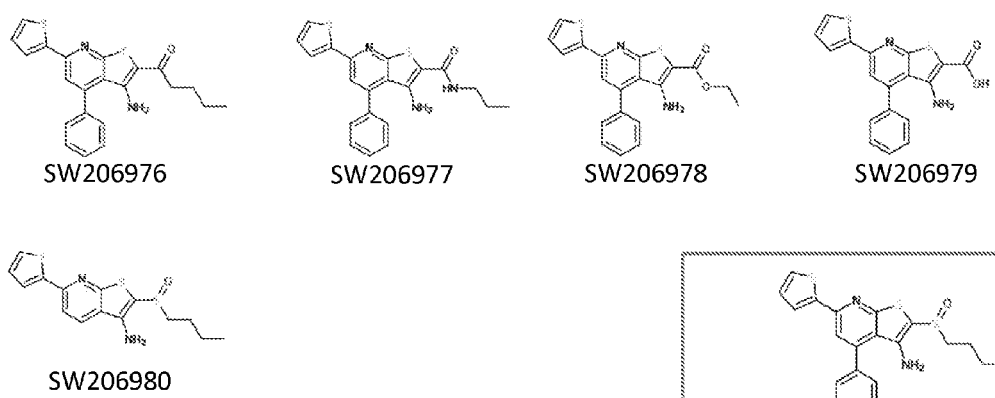
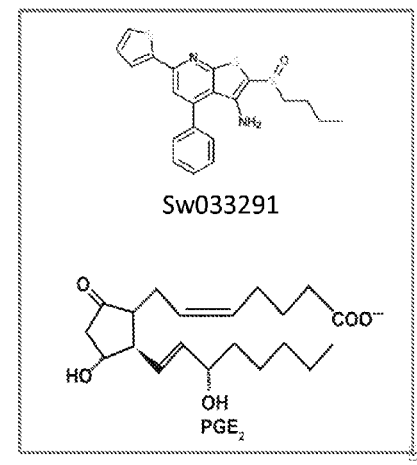
Fig. 26

Figs. 27A-C

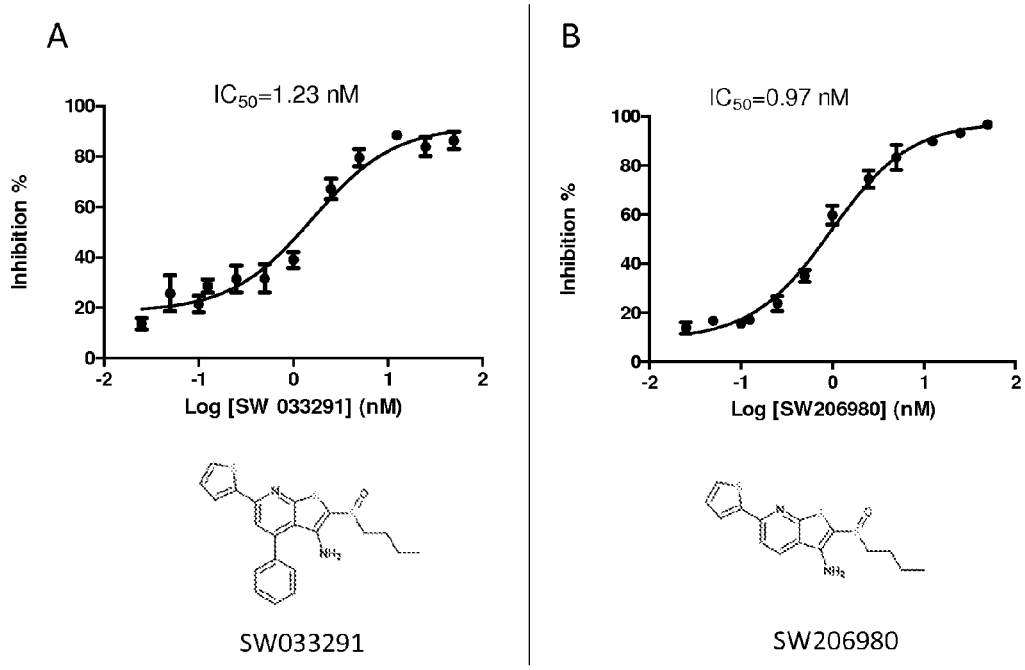
Figs. 29A-B
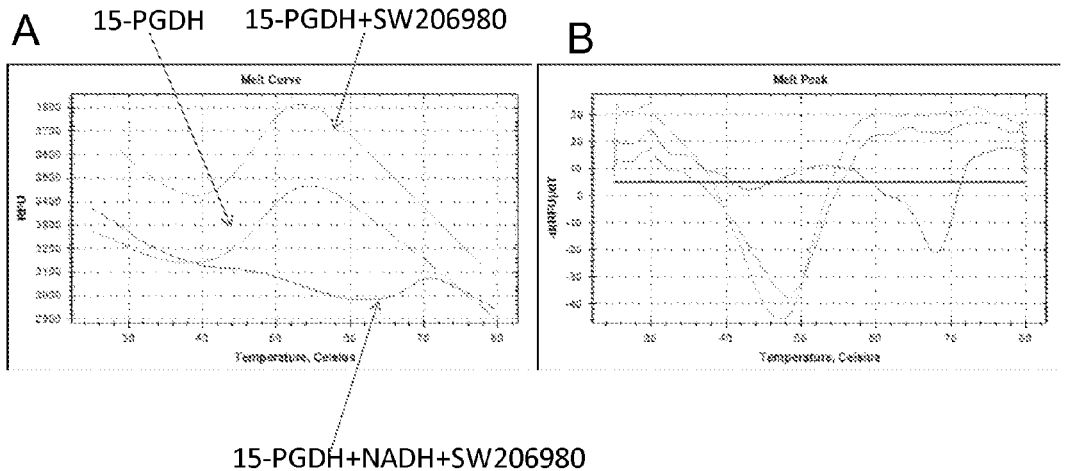
The same Melting profile as SW033291, Major peak at 68c
10 uM protein+ 125 uM NADH+10 uM Compound
Figs. 30A-B

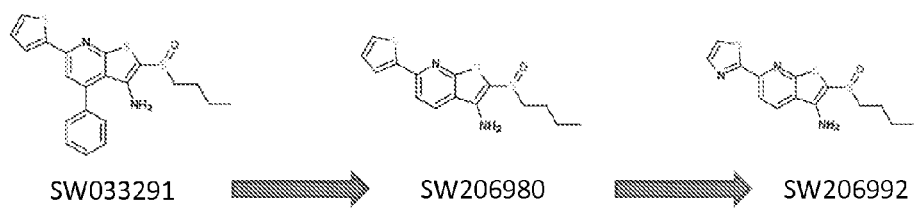
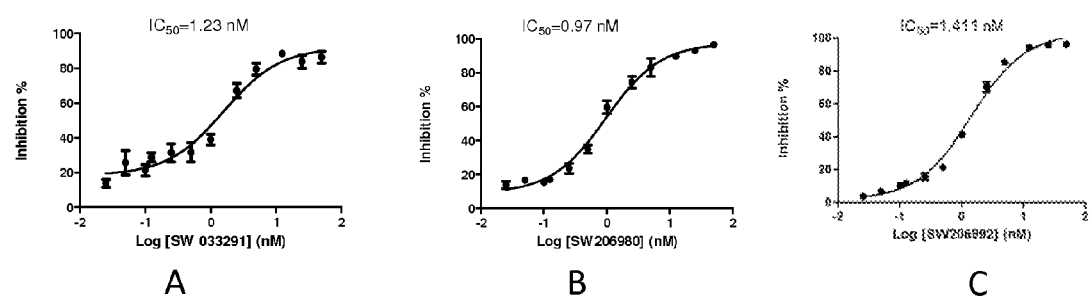
Figs. 31A-C

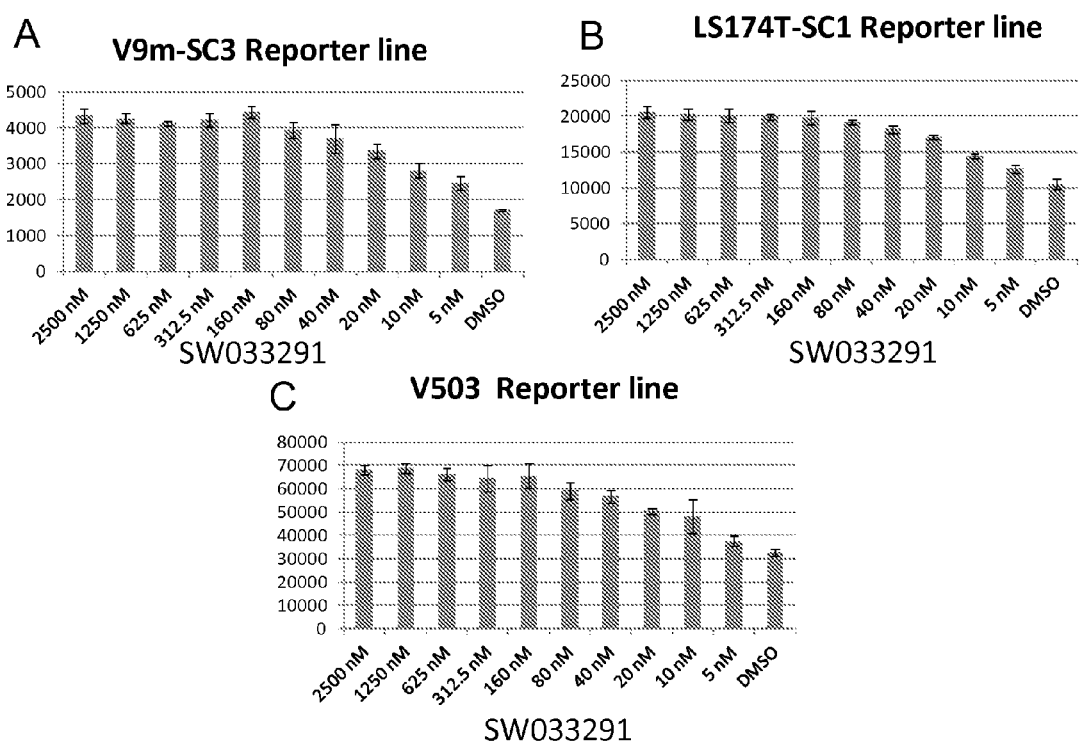
Figs. 32A-C

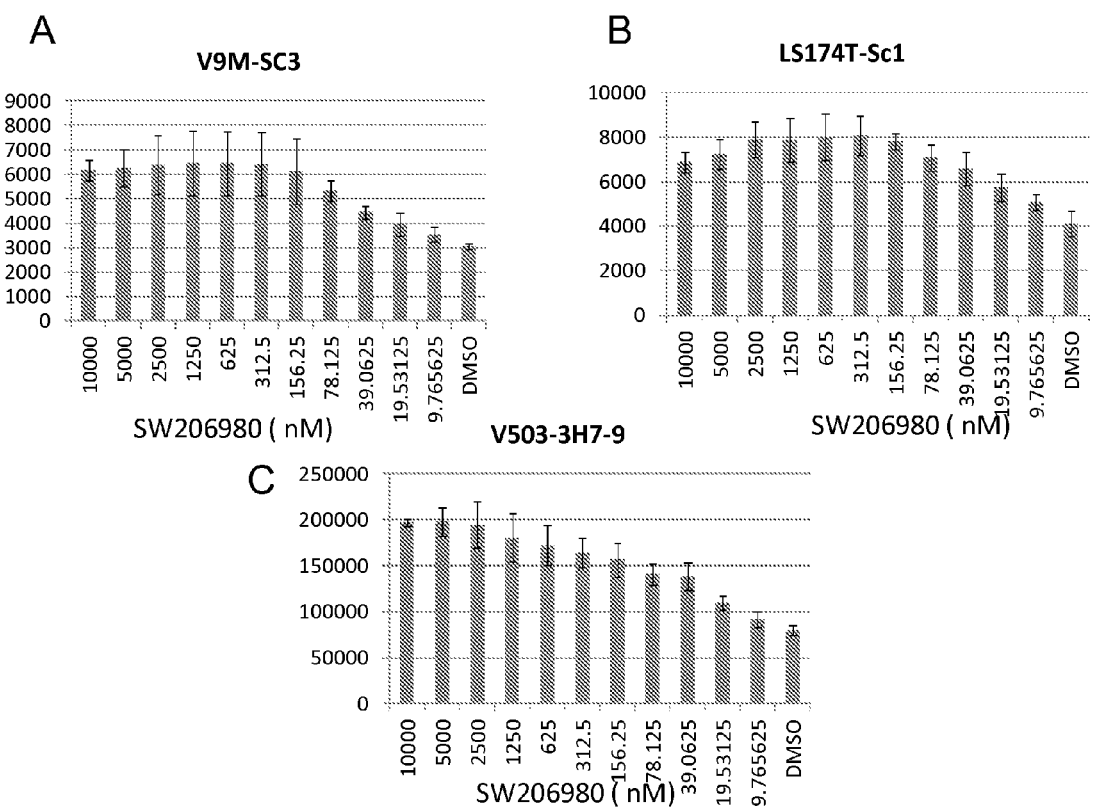
Figs. 33A-C

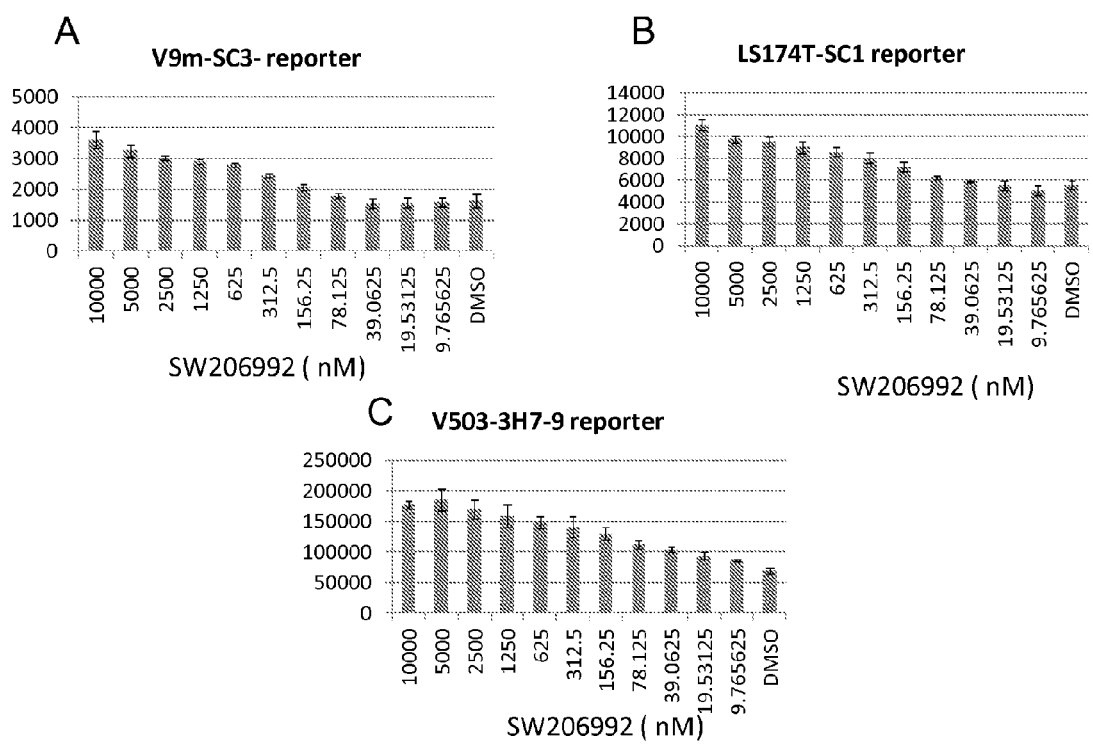
Figs. 34A-C

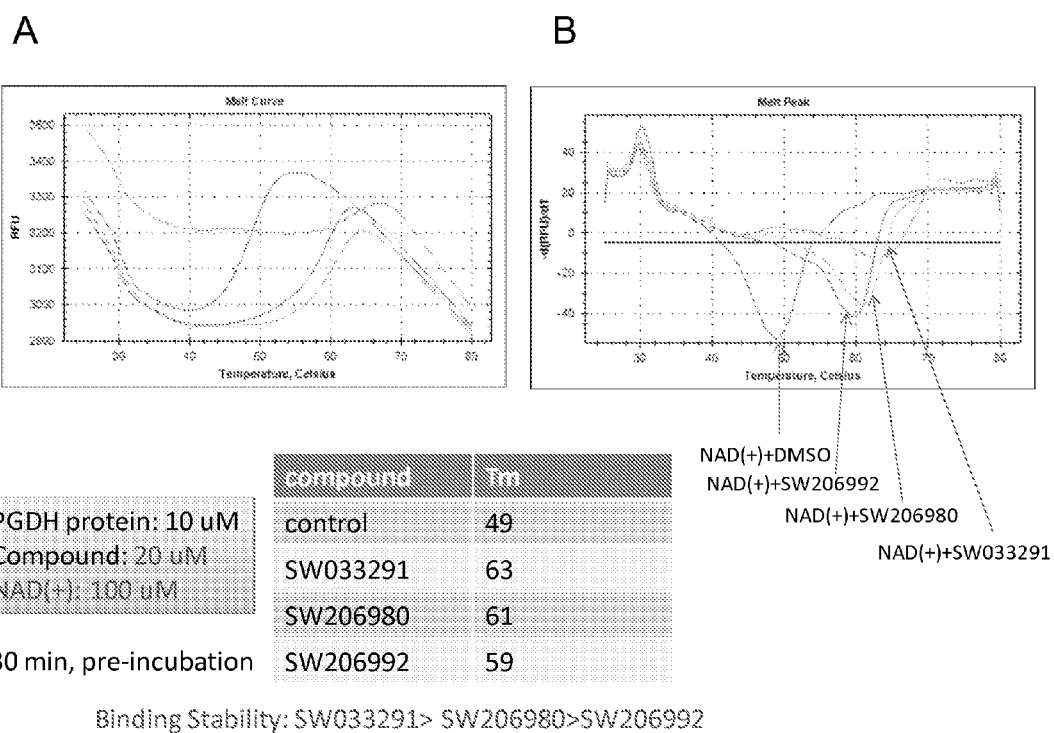
Figs. 35A-B

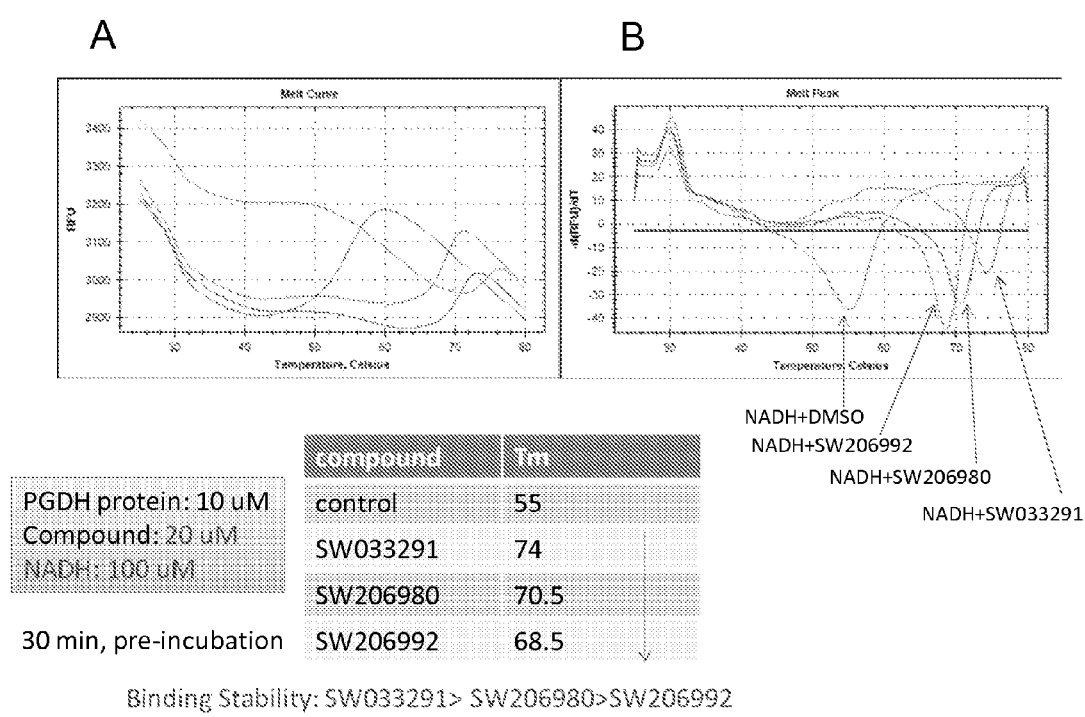
Figs. 36A-B

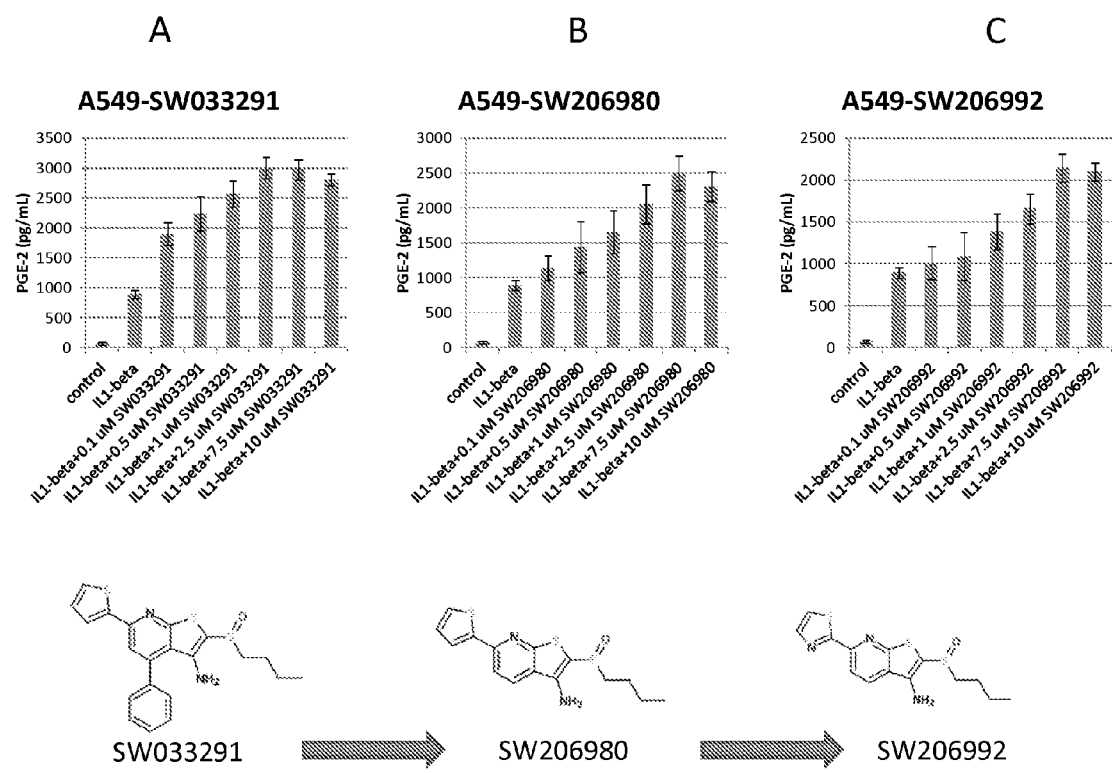
Figs. 37A-C

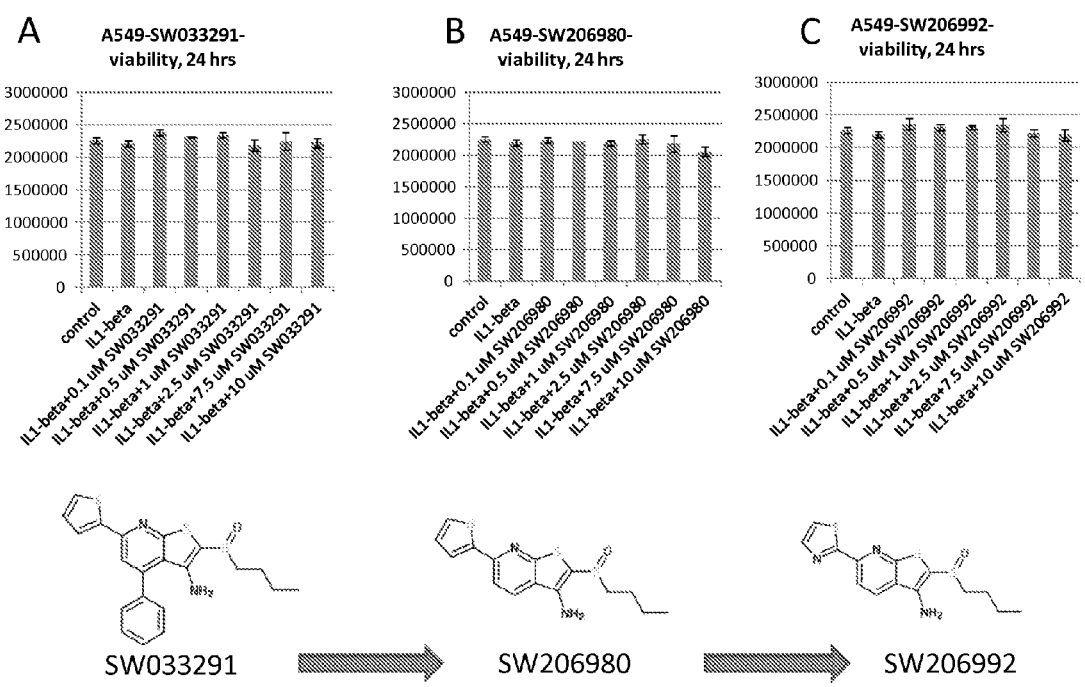
Figs. 38A-C

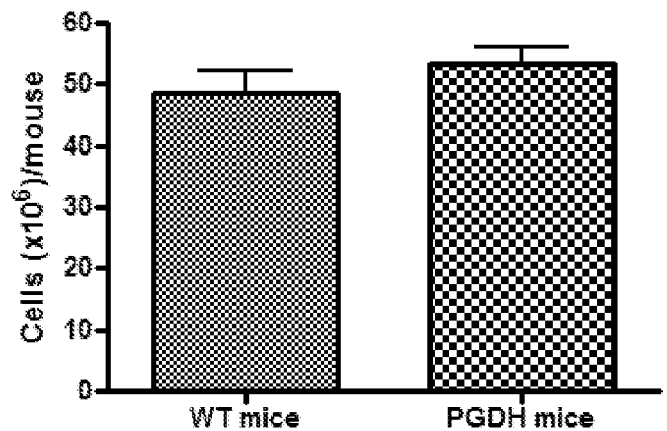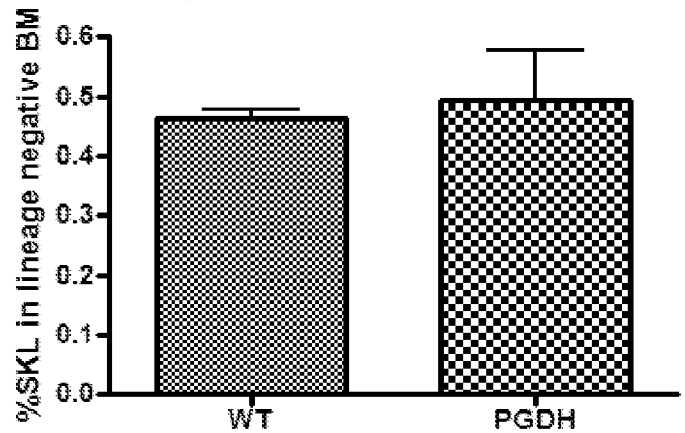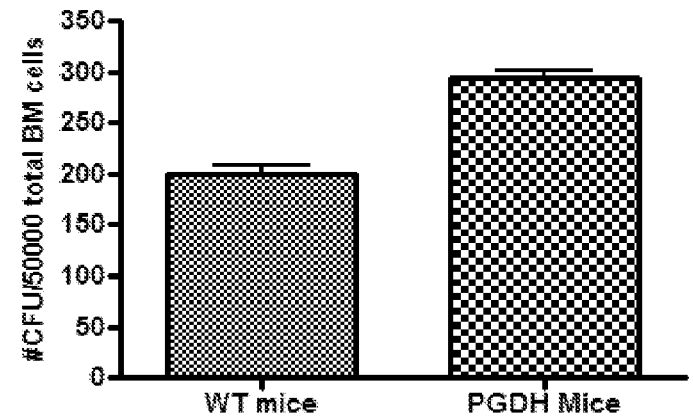
Figs. 46A-C

Figs. 48A-C

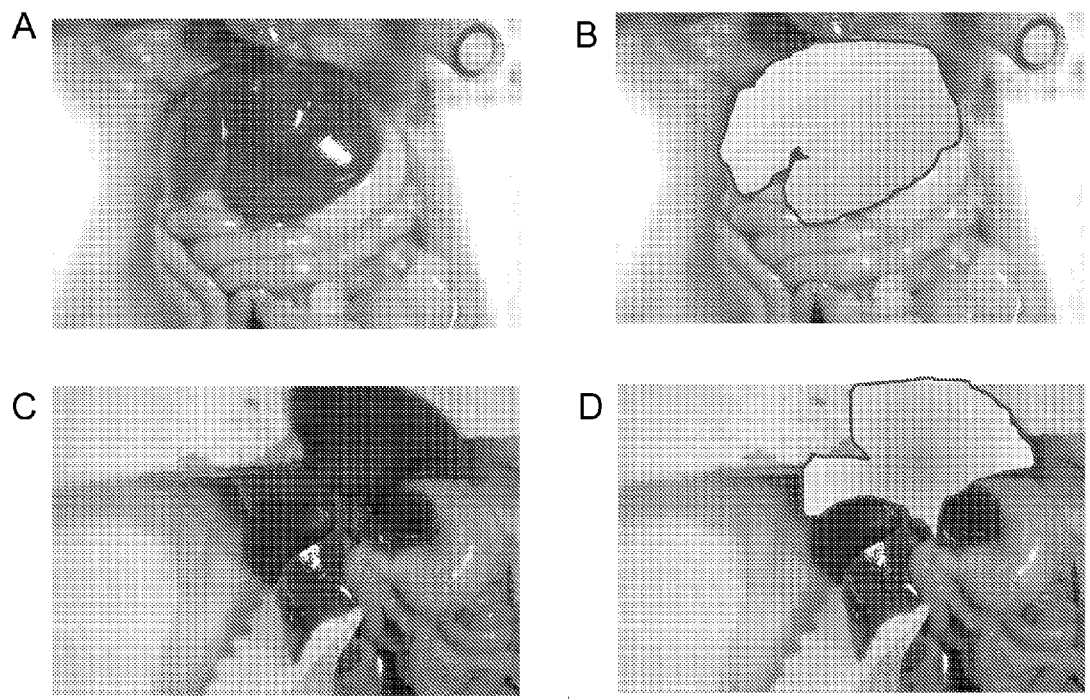
Figs. 52A-D
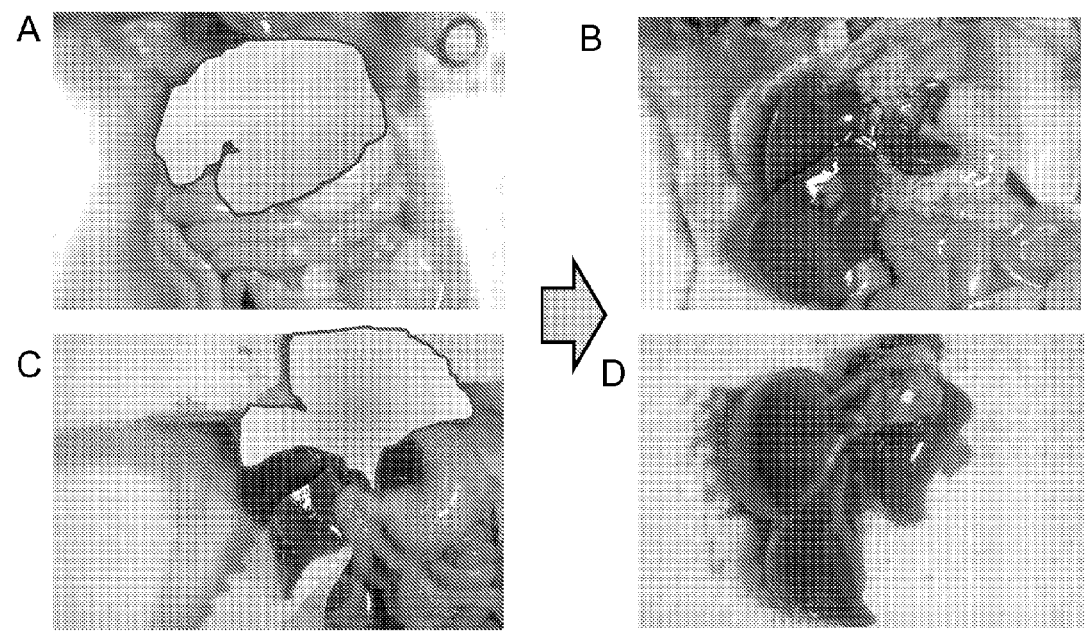
Figs. 53A-D

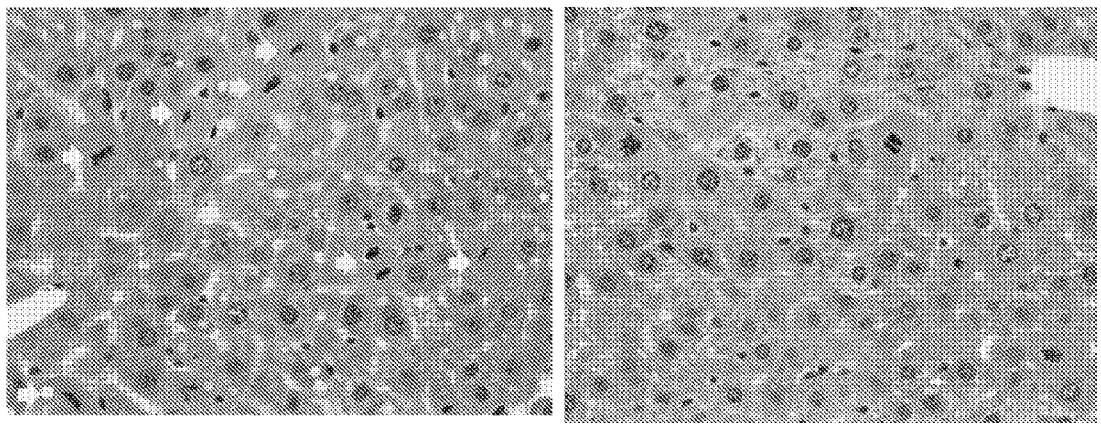
Figs. 54A-B
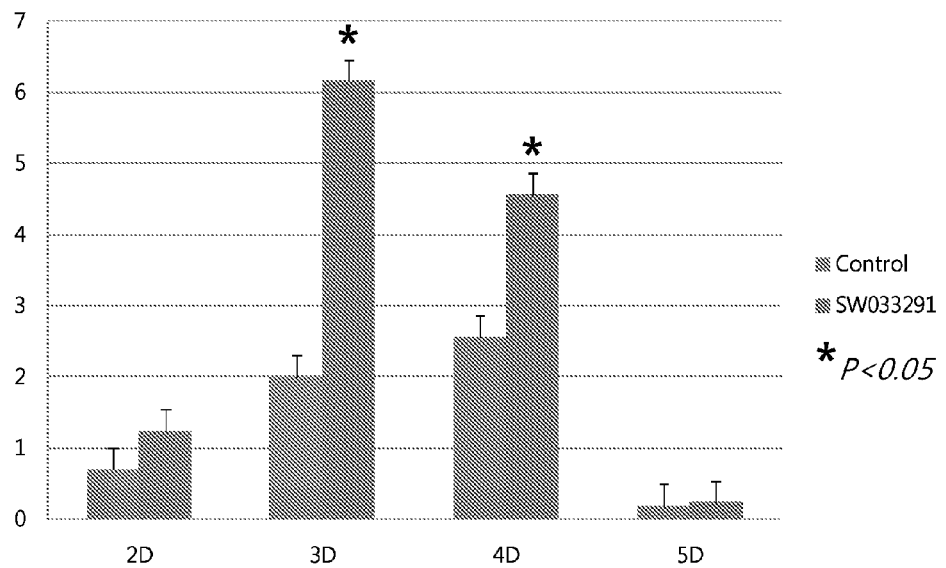
Fig. 55

Figs. 59A-B

BrdU stain on POD 2
Control (x10)  SW033291 (x10)
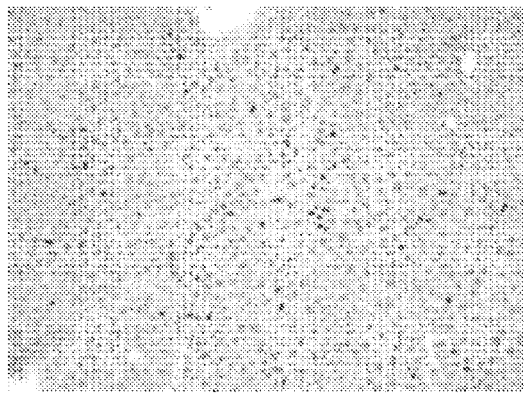 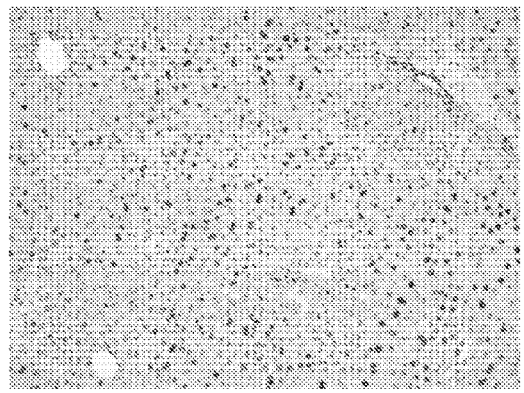
Fig. 69
BrdU stain on POD 2
Control (x40)  SW033291 (x40)
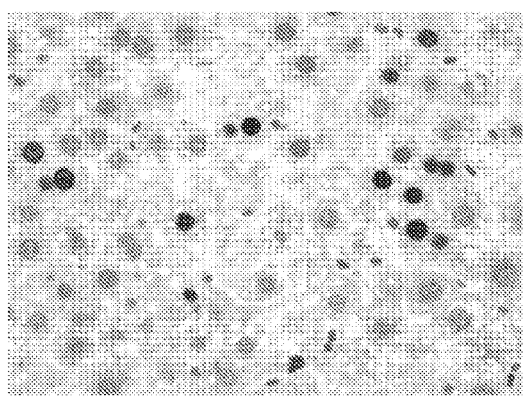 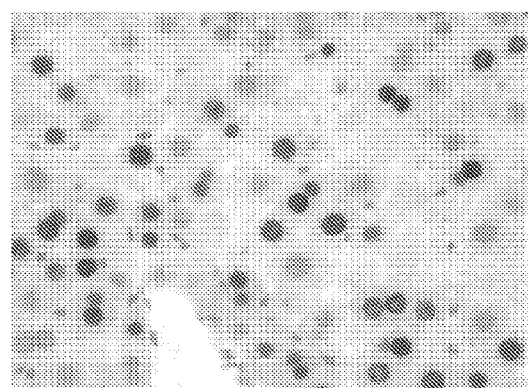
Fig. 70

BrdU(+) hepatocytes on POD 2

Figs. 75A-B

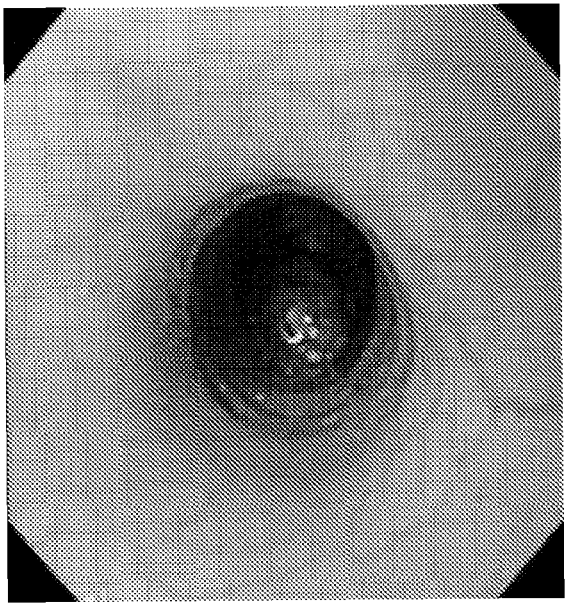
A — Treatment group
Transparent
Normal Vascular pattern
No fibrin
No granularity
Normal stool
Score : 0
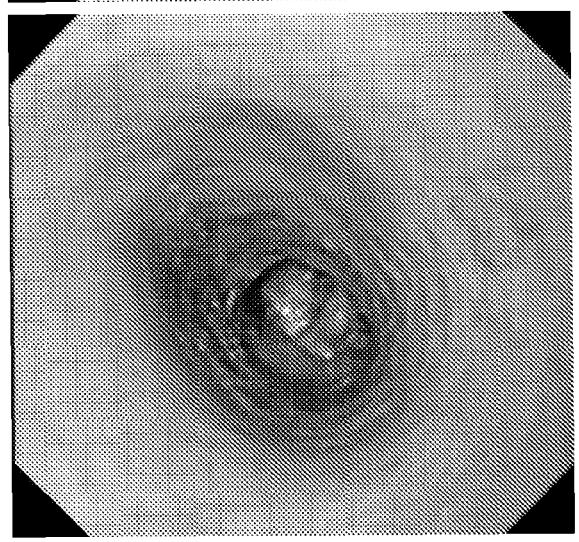
B — Control group
Intransparent (3)
Altered vascular pattern (2)
No fibrin (0)
Marked granularity (2)
Unshaped stool (2)
Score : 9
Figs. 77A-B

Colon length on Day 22

A In Vivo Exposure of a Bone Marrow Transplant Recipient to SW033291 Increases Survival

In Vivo Exposure of a Bone Marrow Transplant Recipient to SW033291 Increases Survival

E

| Dose | Vehicle Survival | SW033291 Survival |
|---|---|---|
| 1*10^5 | 0/8 | 1/8 |
| 2*10^5 | 0/8 | 8/8 |
| 5*10^5 | 5/8 | 8/8 |

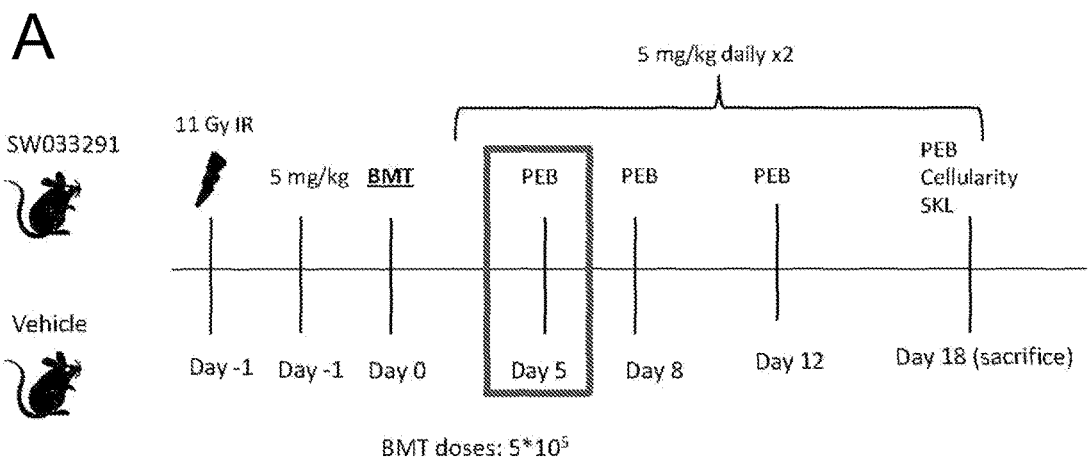
Fig. 82A
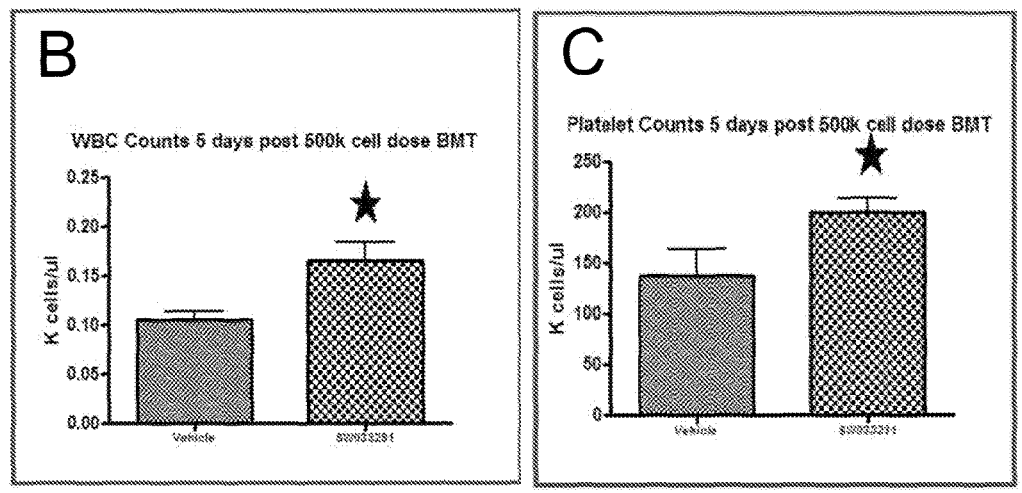
Fig. 82B
Fig. 82C

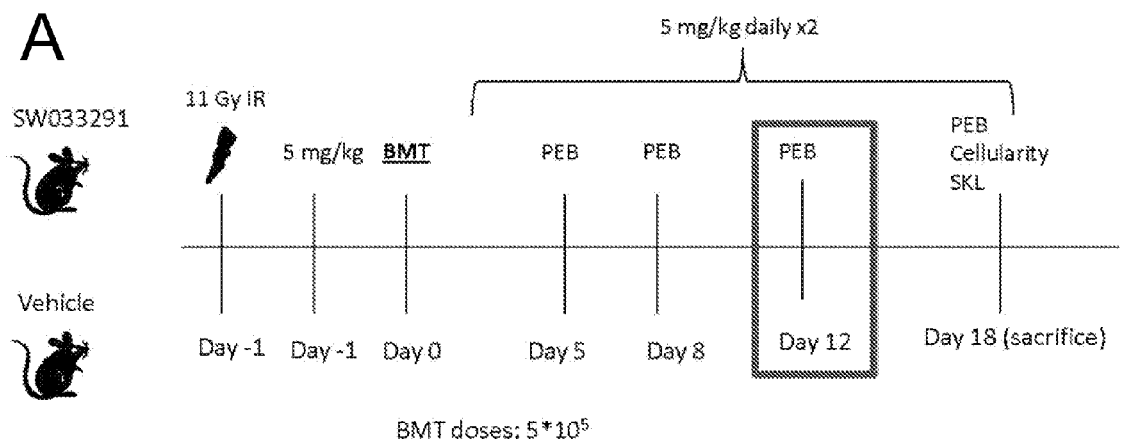
Fig. 84A
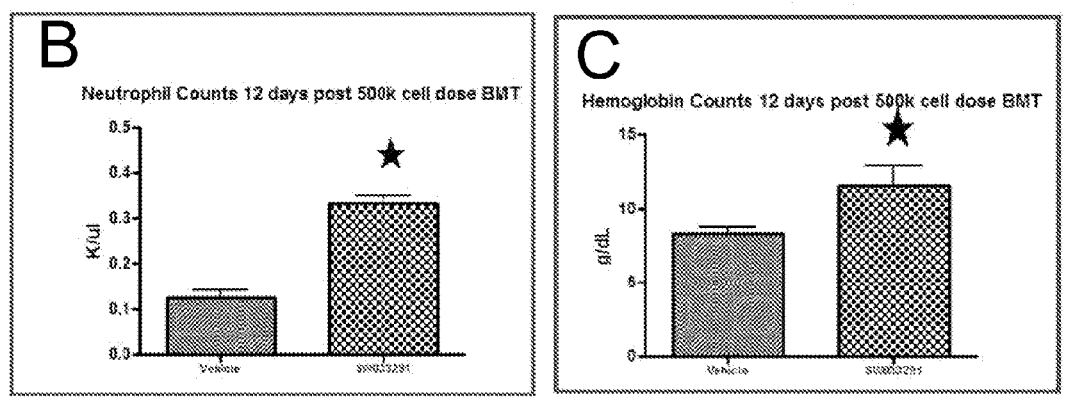
Figs. 84B-C
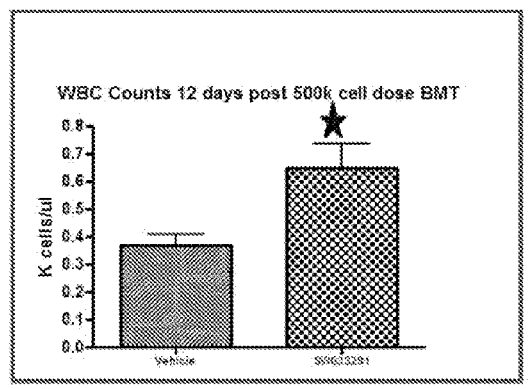
Figs. 84D

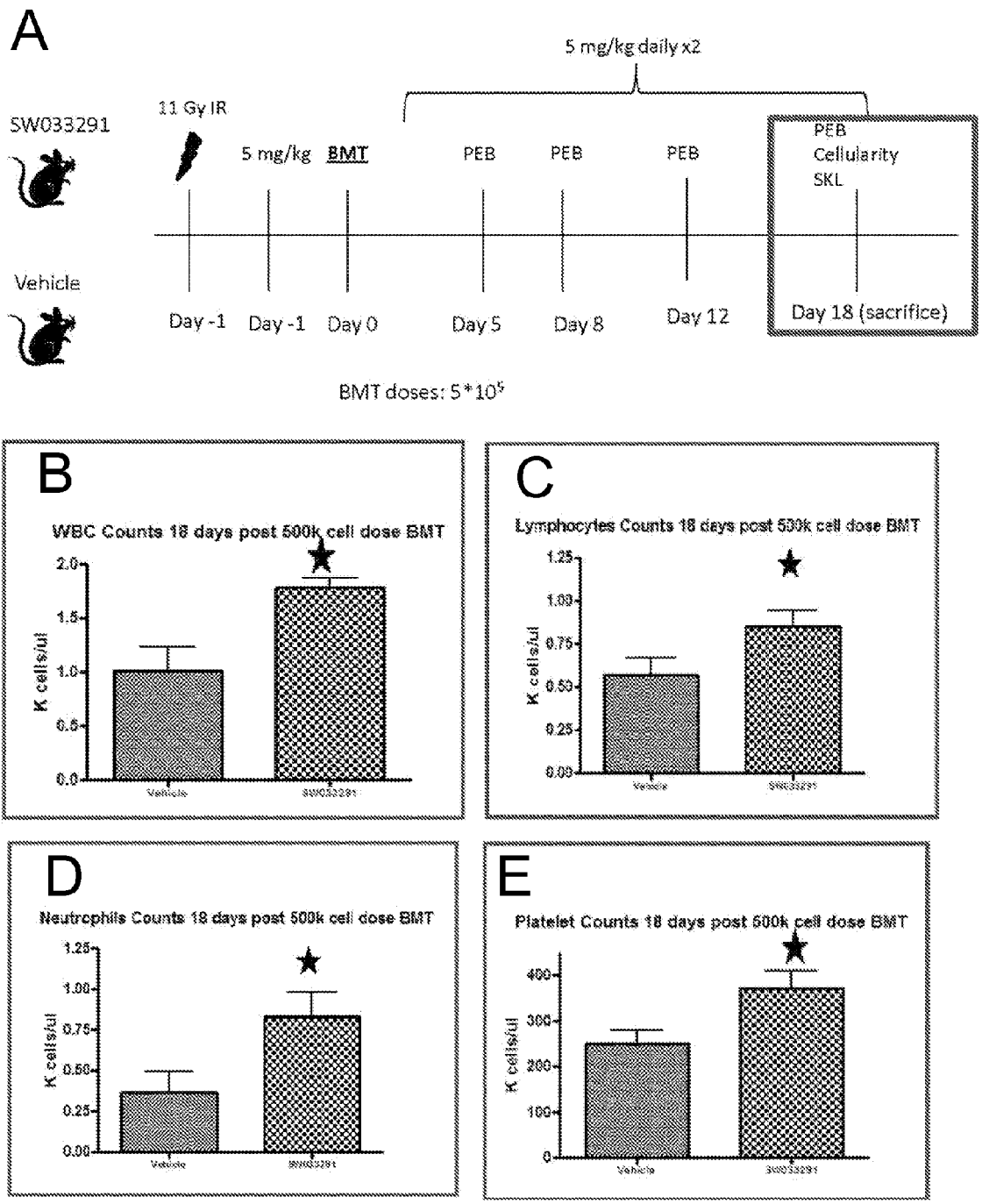
Figs. 85A-E

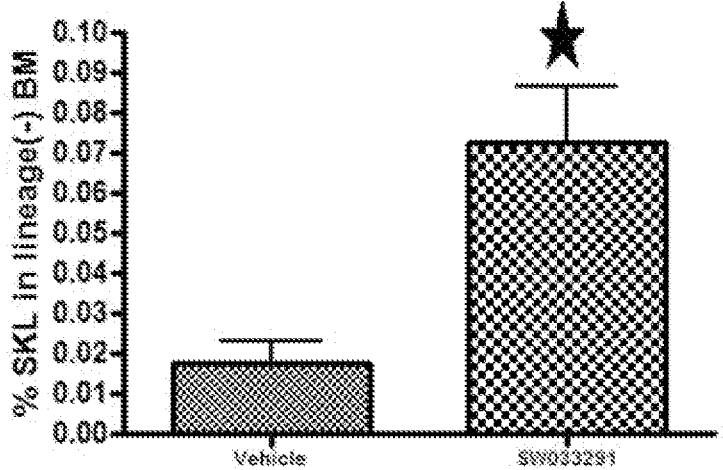
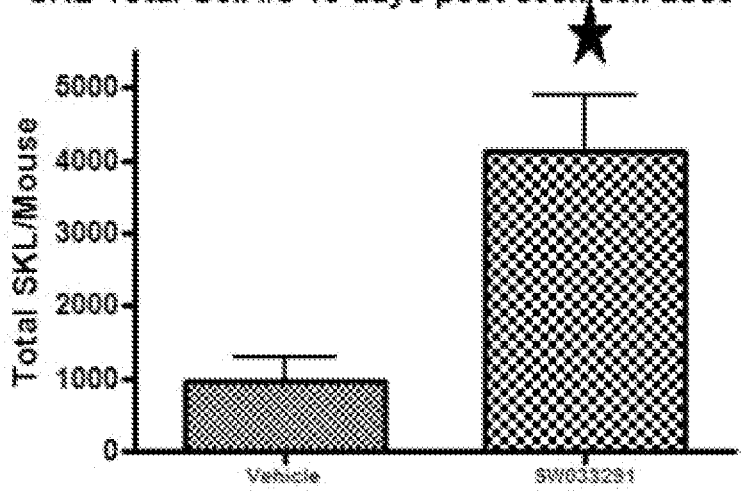
Figs. 85F-G

SW033291 Induction of PGE2 in Mouse Tissues
A. SW033291 (10mg/kg IP) Treated Mice
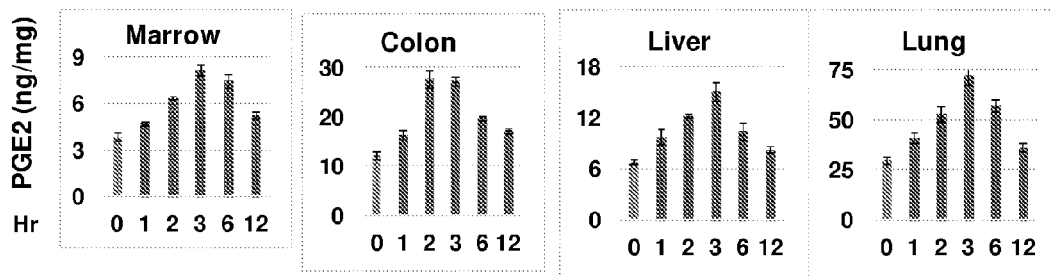
B. Vehicle Control Treated Mice
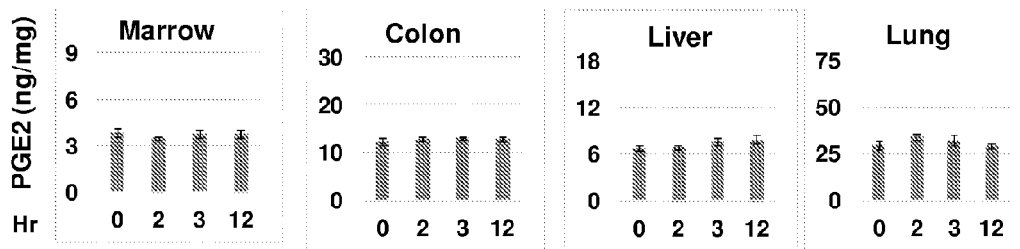
Figs. 86A-B
Hematopoietic Stem Cell Homing Assay
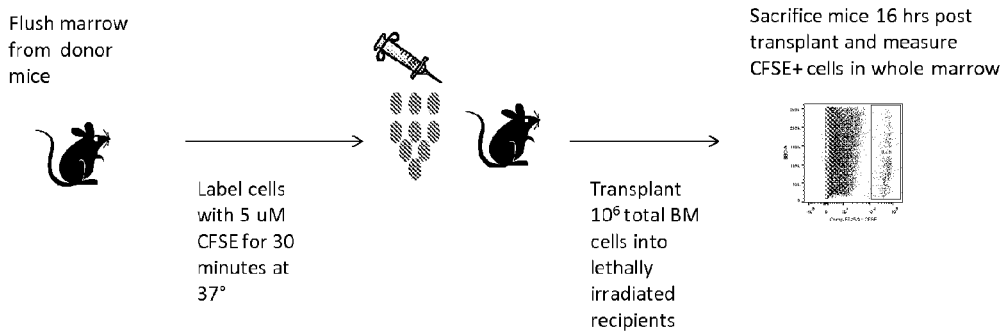
Mice receive either 10mg/kg SW033291, vehicle, or 5mg/kg Indomethacin + 10 mg/kg SW033291 immediately following lethal IR and BMT, and again 8 hours following BMT
Fig. 87

Hematopoietic Stem Cell Homing Assay-
16 hrs Post Transplant
(N=9 mice per group)

Hematopoietic Stem Cell Homing Assay with
EP Receptor Antagonists

4 Groups:
-Vehicle
-10mg/kg SW033291
-10 ug/mouse EP2 Antagonist (PF-04418948) + SW033291
-10 ug/mouse EP4 Antagonist in( L-161,982)+ SW033291

Hematopoietic Stem Cell Homing Assay with
EP Receptor Antagonists
16 hrs Post Transplant
(N=9 mice per group)

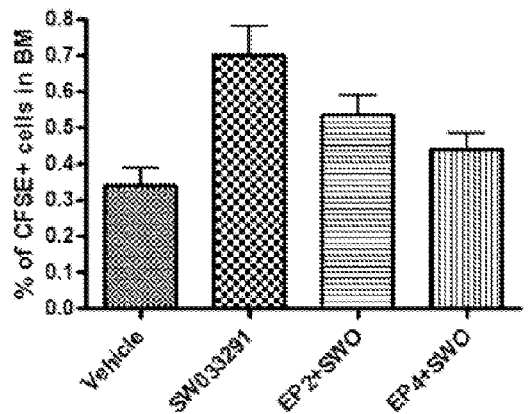

Fig. 90    N=3 Replicates

Gene Expression from Sorted SKL Cells after SW033291 Treatment

-Determine whether drug treatment *in vivo* directly effects gene expression of several genes implicated in hematopoiesis and survival.

*3 mice- 10mg/kg (2x daily) SW033291. Sacrifice 2 hrs post treatment.*
*3 mice- vehicle (2x daily)*

•CD45 (-) cells to represent the total stroma
•SKL cells to represent the HSC population Genes Examined:
•CREM
•CXCR4
•CXCL12
•Cyclin D1
•JAG1
•SCF
•Survivin

Fig. 91

Gene Expression from Sorted SKL and Bone Marrow Stromal Cells after SW033291 Treatment
A
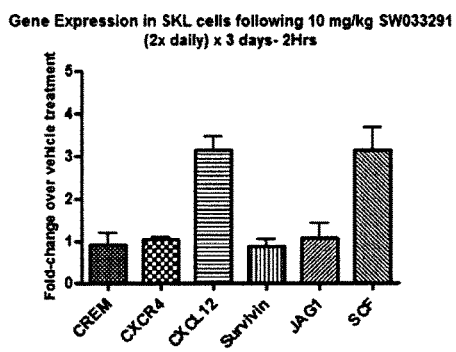
B
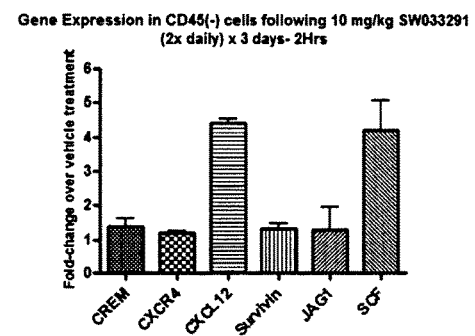
N= 3 replicates (9 mice per group)
Figs. 92A-B Hematopoietic Stem Cell Homing Assay with Human
Umbilical Cord Blood

**Mice receive either 10mg/kg SW033291 or vehicle immediately following sublethal IR
and UCB transplant, and again 8 hours following UCB transplant**

UCB Samples #1-3
Hematopoietic Stem Cell Homing Assay
16 hrs Post Transplant
(3 mice used for each of 3 human UCB samples)

P=.0334

SW033291
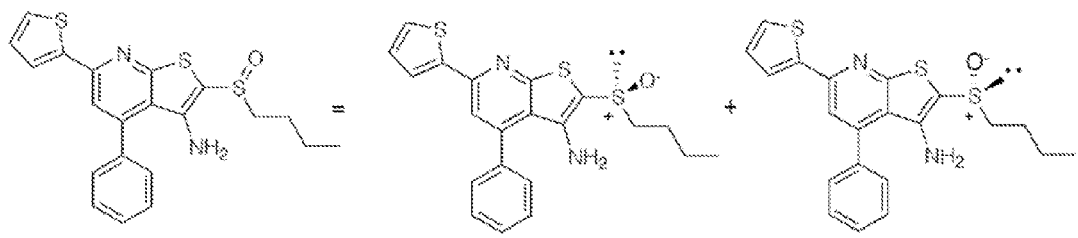
Molecular Weight: 412.59
tPSA: 55.46
CLogP: 5.77792
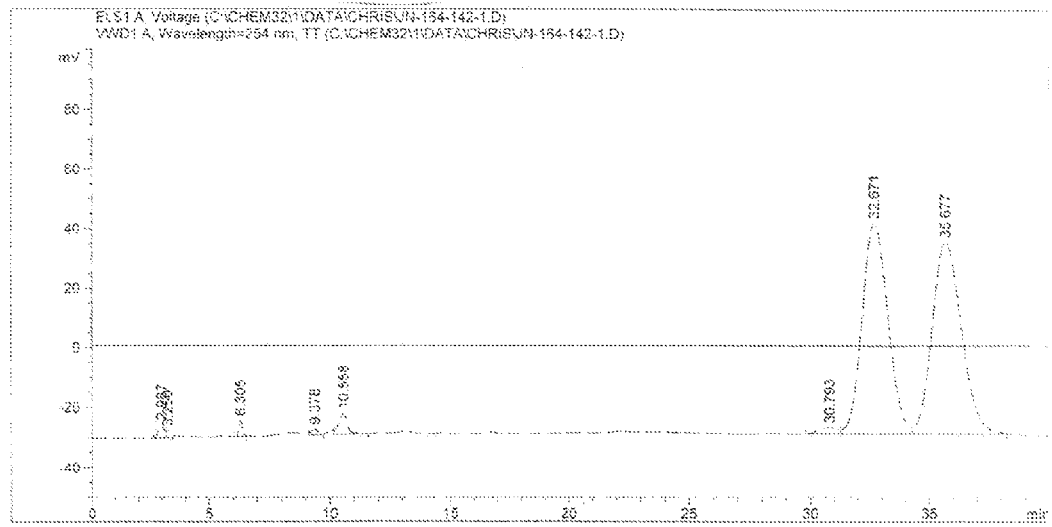
Fig. 95

DSF analysis of binding profiles of SW033291 stereogenic isomers from UTSW

Fig. 97 (A-C)

PGE-2 Assay: SW033291 analogs

Reporter Assay for SW033291 analogs(1)

Reporter Assay for SW033291 analogs(2)

Reporter Assay for SW033291 analogs(3)

Set 20

Set 21
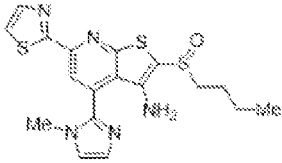
SW209125
Molecular Weight: 417.56
tPSA: 83.41
CLogP: 2.57413
m = 2.3 mg
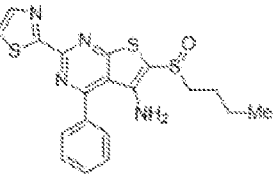
SW209436
Molecular Weight: 414.56
tPSA: 80.17
CLogP: 3.91702
m = 20.8 mg
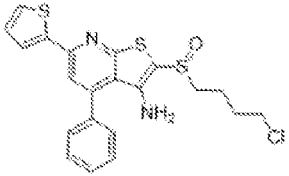
SW209329
Molecular Weight: 447.03
tPSA: 55.45
CLogP: 5.49992
m = 1.8 mg
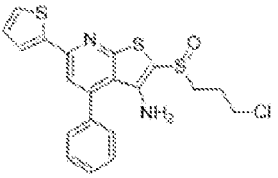
SW209330
Molecular Weight: 433.00
tPSA: 55.45
CLogP: 5.11192
m = 5.4 mg
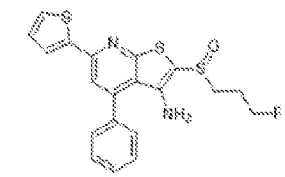
SW209331
Molecular Weight: 416.55
tPSA: 55.45
CLogP: 4.87192
m = 2.0 mg
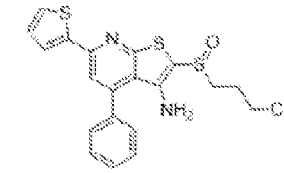
SW209332
Molecular Weight: 423.57
tPSA: 79.24
CLogP: 4.34992
m = 6.3 mg
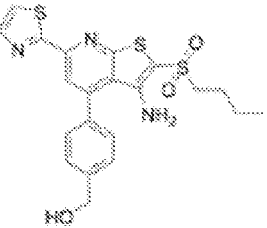
SW209333
Molecular Weight: 469.60
tPSA: 105.11
CLogP: 4.13741
Fig. 114

Set 23
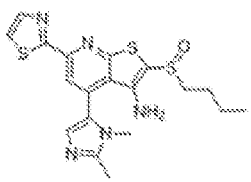
SW209415
Molecular Weight: 431.59
tPSA: 83.41
CLogP: 3.07313
m = 3.4 mg
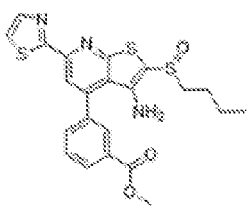
SW209416
Molecular Weight: 471.61
tPSA: 94.11
CLogP: 4.45495
m = 2.5 mg
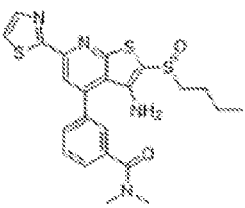
SW209147
Molecular Weight: 484.65
tPSA: 88.12
CLogP: 2.99955
m = 3.5 mg
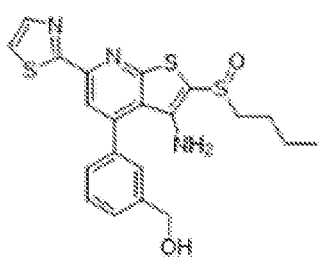
SW209418
Molecular Weight: 443.60
tPSA: 88.04
CLogP: 3.44697
m = 3.1 mg
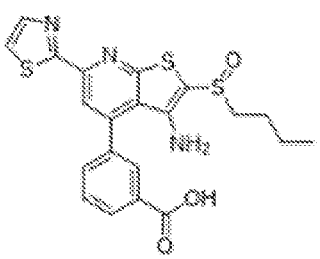
SW209419
Molecular Weight: 457.58
tPSA: 105.11
CLogP: 4.29146
m = 3.9 mg
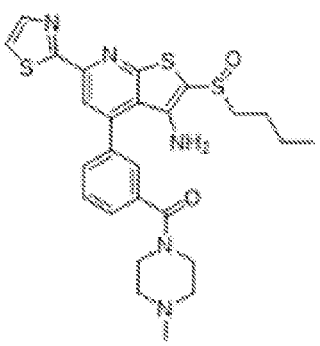
SW209420
Molecular Weight: 539.73
tPSA: 91.36
CLogP: 3.60655
m = 2.4 mg
Fig. 116

Comparison of 5 compounds

- SW209125
- SW209279
- SW209415
- SW209418 together with SW033291

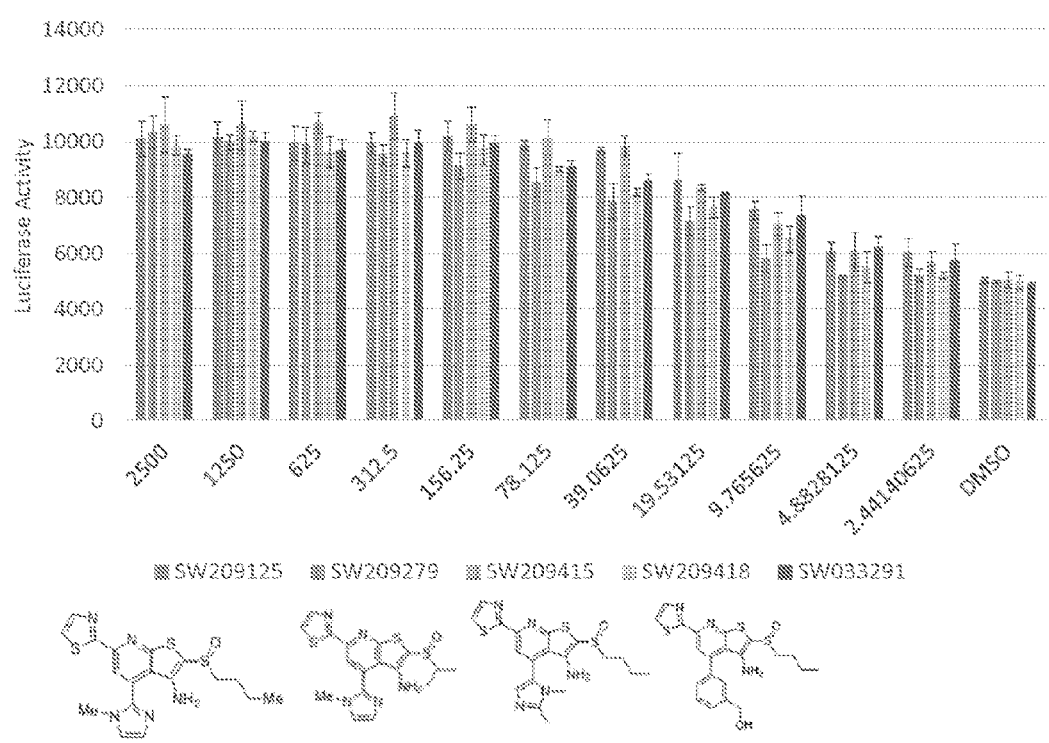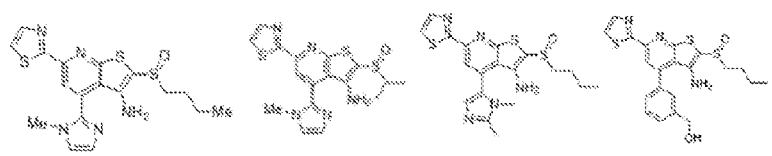
Fig. 129

Set-24
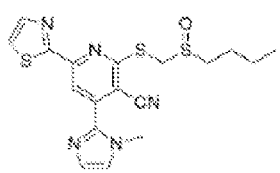
SW209427
Molecular Weight: 417.5640
tPSA: 81.18
CLogP: 2.05262
m = 3.0 mg
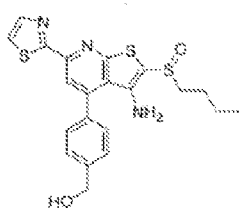
SW209510
Molecular Weight: 443.61
tPSA: 88.04
CLogP: 3.44697
3.5 mg
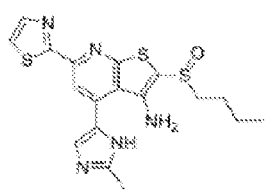
SW209428
Molecular Weight: 417.5640
tPSA: 92.2
CLogP: 3.13007
m = 1.9 mg
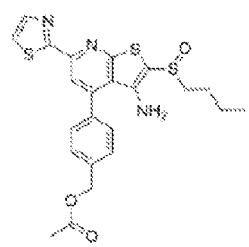
SW209511
Molecular Weight: 485.64
tPSA: 94.11
CLogP: 4.30297
3.7 mg
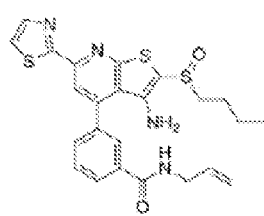
SW209508
Molecular Weight: 496.66
tPSA: 96.91
CLogP: 4.10606
2.0 mg
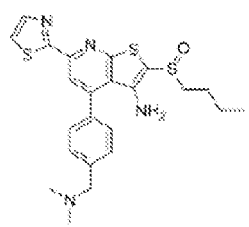
SW209513
Molecular Weight: 470.67
tPSA: 71.85
CLogP: 4.31697
1.8 mg
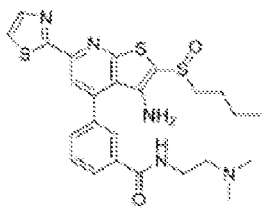
SW209509
Molecular Weight: 527.72
tPSA: 100.15
CLogP: 3.74466
3.6 mg
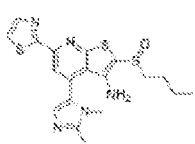
SW209419
Molecular Weight: 431.60
tPSA: 83.41
CLogP: 3.07313
30.8 mg
Fig. 131

Figs. 135A-C

Chiral separation of SW209415
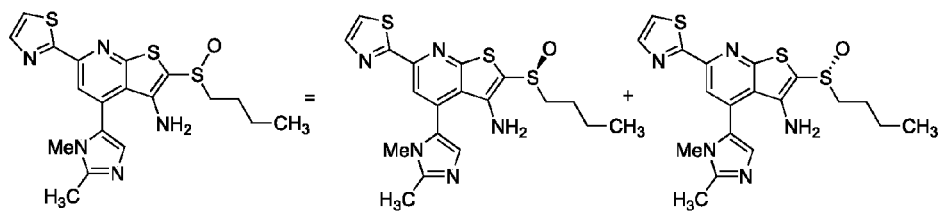
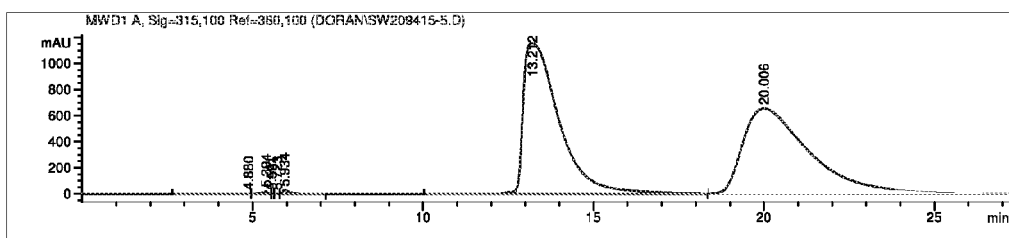
Conditions: Chiralpak AD 250x10mm, MeOH, 2.5 ml/min
Fig. 136
PGE-2 Assayed in A549 Cells:
Response to SW209415 and isomers
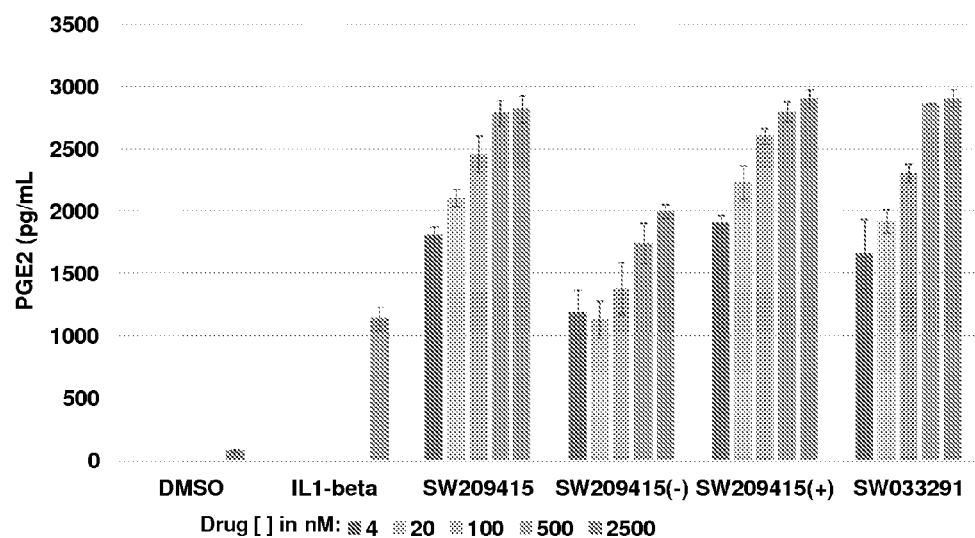
Fig. 137

HSC homing assay

Mice receive either 10mg/kg SW033291 (291), SW209415 (415), or vehicle immediately following lethal irradiation and bone marrow transplant, and again 8 hours following bone marrow transplant

HSC homing assay- 16 hrs

COMPOSITIONS AND METHODS OF MODULATING SHORT-CHAIN DEHYDROGENASE ACTIVITY

RELATED APPLICATION

This application claims priority from U.S. Provisional Application Nos. 61/891,260, filed Oct. 15, 2013, 61/954,202, filed Mar. 17, 2014, 62/019,597, filed Jul. 1, 2014, and 62/043,694, filed Aug. 29, 2014, the subject matter of which are incorporated herein by reference in their entirety.

GOVERNMENT FUNDING

This invention was made with government support under Grant Nos. R01CA127306, R01CA127306-03S1, 1P01CA95471-10, AND 5P50CA150964, awarded by The National Institutes of Health. The United States government may have certain rights to the invention.

BACKGROUND

Short-chain dehydrogenases (SCDs) are a family of dehydrogenases that share only 15% to 30% sequence identity, with similarity predominantly in the coenzyme binding domain and the substrate binding domain. In addition to their role in detoxification of ethanol, SCDs are involved in synthesis and degradation of fatty acids, steroids, and some prostaglandins, and are therefore implicated in a variety of disorders such as lipid storage disease, myopathy, SCD deficiency, and certain genetic disorders.

The SCD, 15-hydroxy-prostaglandin dehydrogenase (15-PGDH), represents the key enzyme in the inactivation of a number of active prostaglandins, leukotrienes and hydroxyeicosatetraenoic acids (HETEs) (e.g., by catalyzing oxidation of $PGE_2$ to 15-keto-prostaglandin E2, 15k-PGE). The human enzyme is encoded by the HPGD gene and consists of a homodimer with subunits of a size of 29 kDa. The enzyme belongs to the evolutionarily conserved superfamily of short-chain dehydrogenase/reductase enzymes (SDRs), and according to the recently approved nomenclature for human enzymes, it is named SDR36C1. Thus far, two forms of 15-PGDH enzyme activity have been identified, NAD+-dependent type I 15-PGDH that is encoded by the HPGD gene, and the type II NADP-dependent 15-PGDH, also known as carbonyl reductase 1 (CBR1, SDR21C1). However, the preference of CBR1 for NADP and the high Km values of CBR1 for most prostaglandin suggest that the majority of the in vivo activity can be attributed to type I 15-PGDH encoded by the HPGD gene, that hereafter, and throughout all following text, simply denoted as 15-PGDH.

Recent studies suggest that inhibitors of 15-PGDH and activators of 15-PGDH could be therapeutically valuable. It has been shown that there is an increase in the incidence of colon tumors in 15-PGDH knockout mouse models. A more recent study implicates increased 15-PGDH expression in the protection of thrombin-mediated cell death. It is well known that 15-PGDH is responsible for the inactivation of prostaglandin E2 ($PGE_2$), which is a downstream product of COX-2 metabolism. $PGE_2$ has been found to be neurotoxic both in vitro and in vivo; thus, COX-2 specific inhibitors, which decrease $PGE_2$ release, exhibit neuroprotective effects. $PGE_2$ has also been shown to be beneficial in a variety of biological processes, such as hair density, dermal wound healing, and bone formation.

SUMMARY

Embodiments described herein relate to compounds and methods of modulating short chain dehydrogenase (SCD) (e.g., 15-PGDH) activities, modulating tissue prostaglandin levels, and/or treating diseases, disorders, or conditions in which it is desired to modulate SCD (e.g., 15-PGDH) activity and/or prostaglandin levels.

In some embodiments, the modulator of SCD can be an SCD inhibitor that can be administered to tissue or blood of a subject at an amount effective to inhibit the activity of a short chain dehydrogenase enzyme. The SCD inhibitor can be a 15-PGDH inhibitor that can be administered to tissue or blood of a subject at an amount effective to increase prostaglandin levels in the tissue or blood. The 15-PGDH inhibitor can include a compound having the formula (V):

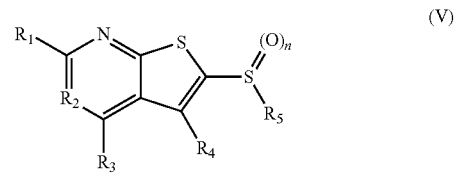

wherein n=0-2;

$R_1$ and $R_3$ are the same or different and are each selected from the group consisting of:

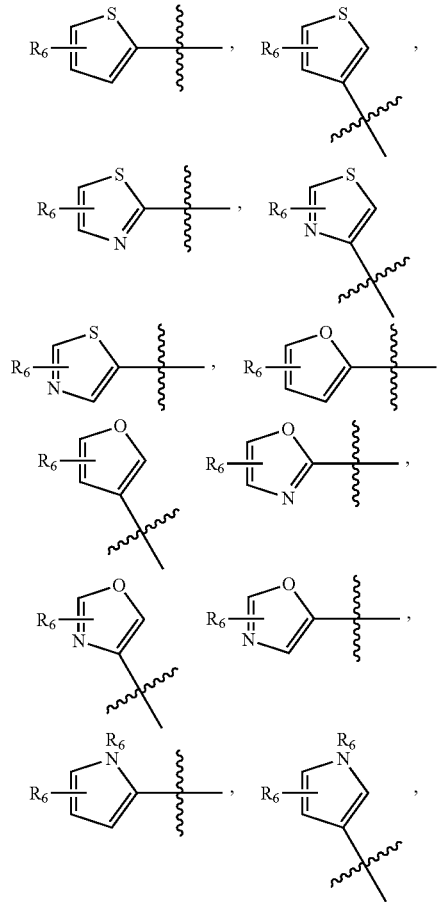

-continued

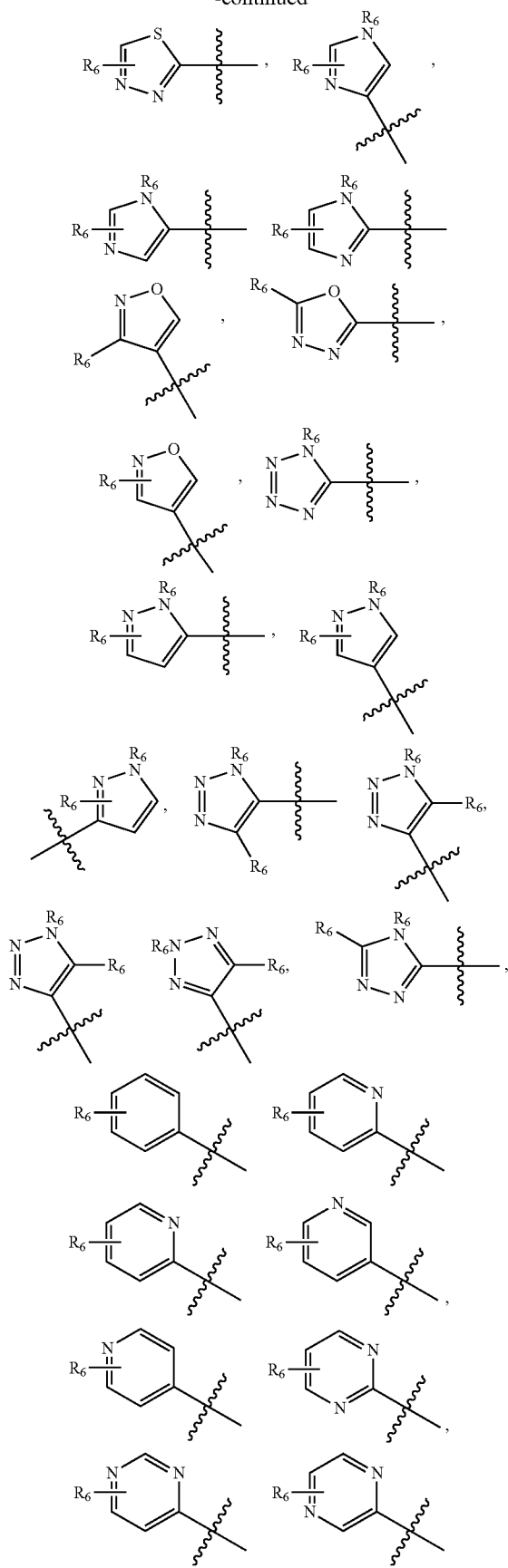

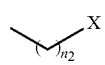

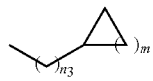

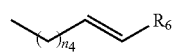

$R_2$ is N or $CR_7$;
$R_4$ is selected from the group consisting of H, Cl, F, $NH_2$, and $N(R_6)_2$;
$R_5$ is selected from the group consisting of branched or linear alkyl including $-(CH_2)n_1CH_3$ ($n_1=0$-7), wherein $n_2=0$-6 and X is any of the following: $CF_yH_z$ (y+z=3), $CCl_yH_z$ (y+z=3), OH, OAc, OMe, $R_6$, $OR_6$, CN, $N(R_6)_2$, ($n_3=0$-5, m=1-5), and ($n_4=0$-5);
each $R_6$ and $R_7$ are the same or different and are one or more substituent selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, $N(C_1$-$C_6$ alkyl), $NC(O)(C_1$-$C_6$ alkyl), O, and S), heteroaryl or heterocyclyl containing from 5-14 ring atoms, (wherein from 1-6 of the ring atoms is independently selected from N, NH, $N(C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO2NR2 where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH2, —SO$_2$NY$_2$ (wherein Y is independently H, arlyl or alkyl), phosphono (—P(O)(OH)$_2$), phosphonato (—P(O)(O⁻)$_2$), phosphinato (—P(O)(O⁻)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof;

$R_3$ is not hydrogen if $R_1$ is H, an unsubstituted thiophene, or an unsubstituted thiazole and $R_5$ is butyl; or $R_3$ is not an unsubstituted phenyl if $R_1$ is H, or an unsubstituted phenyl, thiophene, or thiazole and $R_5$ is benzyl or (CH$_2$)n$_5$(CH$_3$)(n$_5$=0-5); and pharmaceutically acceptable salts thereof.

In some embodiments, $R_2$ can be N or CH. $R_1$ can be a substituted or unsubstituted heterocyclyl containing 5-6 ring atoms. For example, $R_1$ can be a substituted or unsubstituted thiophene, thiazole, oxazole, imidazole, pyridine, or phenyl. $R_3$ can be selected from the group consisting of H, substituted or unsubstituted aryl, a substituted or unsubstituted cycloalkyl, and a substituted or unsubstituted heterocyclyl, alkyl, or carboxy including carboxylic acid (—CO2H), carboxy ester (—CO$_2$alkyl) and carboxamide [—CON(H)(alkyl) or —CO$_2$N(alkyl)$_2$].

In still other embodiments, the 15-PGDH inhibitor can include a compound having formula (V$_1$):

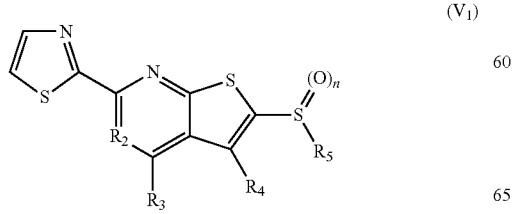

(V$_1$)

wherein n=0-2;

$R_3$ is selected from the group consisting of:

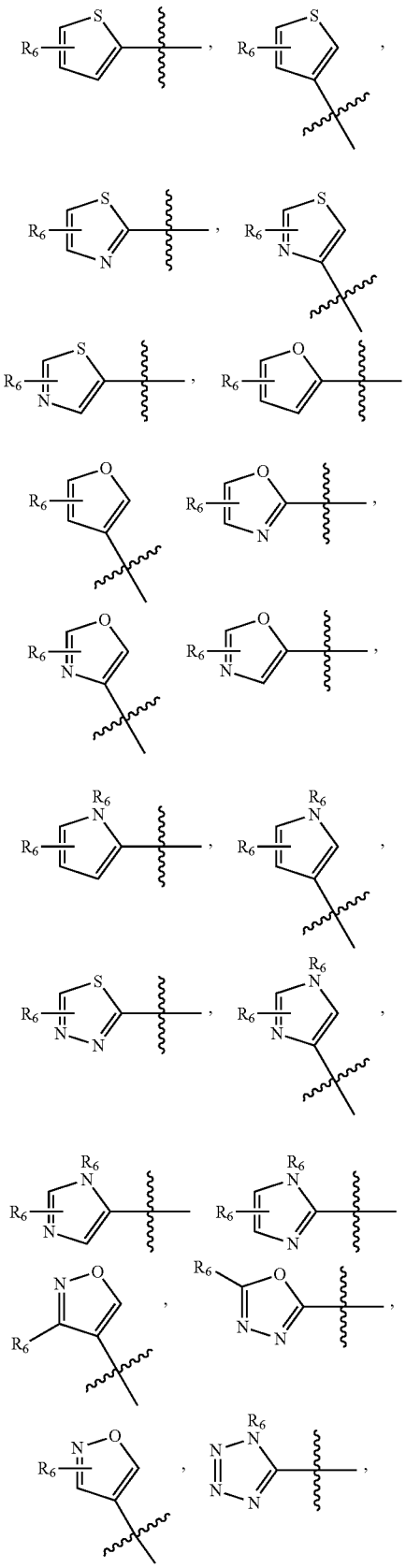

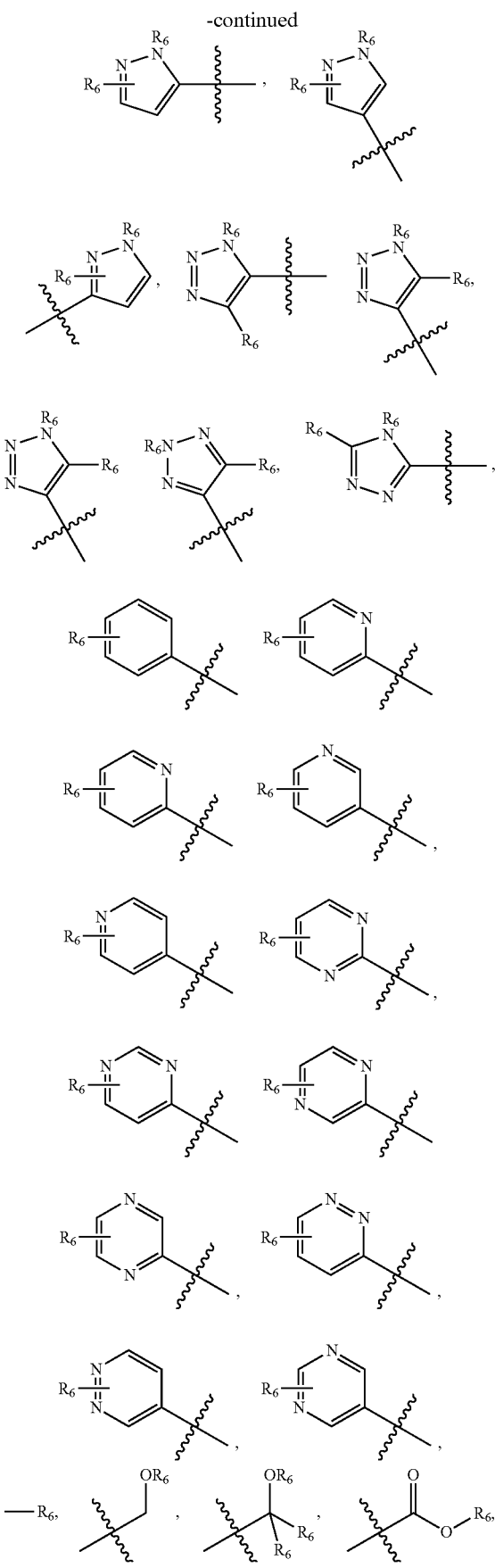

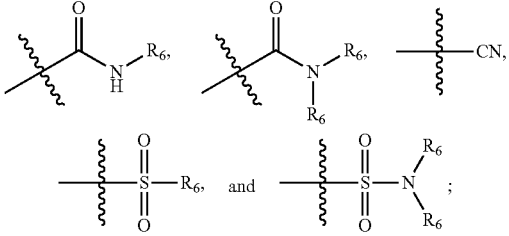

$R_2$ is N or $CR_7$;
$R_4$ is selected from the group consisting of H, Cl, F, $NH_2$, and $N(R_6)_2$;
$R_5$ is selected from the group consisting of branched or linear alkyl including $-(CH_2)_{n_1}CH_3$ ($n_1$=0-7),

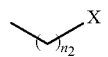

wherein $n_2$=0-6 and X is any of the following: $CF_yH_z$ (y+z=3), $CCl_yH_z$ (y+z=3), OH, OAc, OMe, $R_6$, $OR_6$, CN, $N(R_6)_2$,

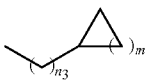

($n_3$=0-5, m=1-5), and

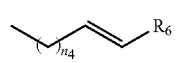

($n_4$=0-5);
each $R_6$ and $R_7$ are the same or different and are one or more substituent selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, $N(C_1$-$C_6$ alkyl), $NC(O)(C_1$-$C_6$ alkyl), O, and S), heteroaryl containing from 5-14 ring atoms, (wherein from 1-6 of the ring atoms is independently selected from N, NH, $N(C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO— alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—$NH_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—$NH_2$), carbamido (—NH—(CO)—$NH_2$), cyano(—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—$NH_2$), $C_1$-$C_{24}$ alkyl amino, $C_5$-$C_{20}$ aryl amino, $C_2$-$C_{24}$ alkylamido (—NH—(CO)- alkyl), $C_6$-$C_{20}$ arylamido (—NH—(CO)-aryl), sulfanamido (—SO2NR2 where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—NH2, —$SO_2NY_2$ (wherein Y is independently H, arlyl or alkyl), phosphono (—P(O)(OH)$_2$), phosphonato (—P(O)($O^-$)$_2$), phosphinato (—P(O)($O^-$)), phospho (—$PO_2$), phosphino (—$PH_2$), polyalkyl ethers (—[($CH_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof;

$R_3$ is not hydrogen if $R_5$ is butyl; or $R_3$ is not an unsubstituted phenyl if $R_5$ is benzyl or ($CH_2$)$n_5$($CH_3$) ($n_5$=0-5); and pharmaceutically acceptable salts thereof.

In some embodiments, the 15-PGDH inhibitor can inhibit the enzymatic activity of recombinant 15-PGDH at an $IC_{50}$ of less than 1 µM, or preferably at an $IC_{50}$ of less than 250 nM, or more preferably at an $IC_{50}$ of less than 50 nM, or more preferably at an $IC_{50}$ of less than 10 nM, or more preferably at an $IC_{50}$ of less than 5 nM at a recombinant 15-PGDH concentration of about 5 nM to about 10 nM.

The 15-PGDH inhibitor can be provided in a topical composition that can be applied to skin of a subject to promote and/or stimulate pigmentation of the skin and/or hair growth and/or inhibiting hair loss, and/or treat skin damage or inflammation.

The 15-PGDH inhibitor can also be administered to a subject to promote wound healing, tissue repair, and/or tissue regeneration.

In one embodiment, the 15-PGDH inhibitor can be administered to a subject to treat at least one of oral ulcers, gum disease, colitis, ulcerative colitis, gastrointestinal ulcers, inflammatory bowel disease, vascular insufficiency, Raynaud's disease, Buerger's disease, diabetic neuropathy, pulmonary artery hypertension, cardiovascular disease, and renal disease.

In another embodiment, the 15-PGDH inhibitor can be administered to a subject in combination with a prostanoid agonist for the purpose of enhancing the therapeutic effect of the agonist in prostaglandin responsive conditions.

In other embodiments, the 15-PGDH inhibitor can be administered to tissue of the subject to increase tissue stem cells. For example, the 15-PGDH inhibitor can be administered to bone marrow of a subject to increase stem cells in the subject.

In still other embodiments, the 15-PGDH inhibitor can be administered to a tissue graft donor, bone marrow graft donor, and/or a hematopoietic stem cell donor to increase the fitness of a donor tissue graft, a donor bone marrow graft, and/or a donor hematopoietic stem cell graft. For example, the 15-PGDH inhibitor can be administered to bone marrow of a subject to increase the fitness of the marrow as a donor graft, to a preparation of hematopoietic stem cells of a subject to increase the fitness of the stem cell preparation as a donor graft, to a preparation of peripheral blood hematopoietic stem cells of a subject to increase the fitness of the stem cell preparation as a donor graft, to a preparation of umbilical cord blood stem cells to increase the fitness of the stem cell preparation as a donor graft, and/or to a preparation of umbilical cord blood stem cells to decrease the number of units of umbilical cord blood required for transplantation.

In other embodiments, the 15-PGDH inhibitor can be administered to a subject to mitigate tissue graft rejection, to enhance tissue and/or bone marrow graft engraftment, to enhance bone marrow graft engraftment, following treatment of the subject or the marrow of the subject with radiation therapy, chemotherapy, or immunosuppressive therapy, to enhance engraftment of a progenitor stem cell graft, hematopoietic stem cell graft, or an umbilical cord blood stem cell graft, to enhance engraftment of a hematopoietic stem cell graft, or an umbilical cord stem cell graft, following treatment of the subject or the marrow of the subject with radiation therapy, chemotherapy, or immunosuppressive therapy, and/or in order to decrease the number of units of umbilical cord blood required for transplantation into the subject.

In other embodiments, the 15-PGDH inhibitor can be administered to a recipient of a tissue graft transplant, bone marrow transplant, and/or hematopoietic stem cell transplant, or of an umbilical cord stem cell transplant, in order to decrease the administration of other treatments or growth factors.

In some embodiments, the 15-PGDH inhibitor can be administered to a subject or to a tissue graft of a subject to mitigate graft rejection, to enhance graft engraftment, and/or to enhance graft engraftment following treatment of the subject or the marrow of the subject with radiation therapy, chemotherapy, or immunosuppressive therapy.

In other embodiments, the 15-PGDH inhibitor can be administered to a subject or to the bone marrow of a subject to confer resistance to toxic or lethal effects of exposure to radiation, to confer resistance to the toxic effect of Cytoxan, the toxic effect of fludarabine, the toxic effect of chemotherapy, or the toxic effect of immunosuppressive therapy, to decrease pulmonary toxicity from radiation, and/or to decrease infection.

In still other embodiments, the 15-PGDH inhibitor can be administered to a subject to increase neutrophil counts following a hematopoetic cell transplant with bone marrow, hematopoetic stem cells, or umbilical cord blood, to increase neutrophil counts in a subject with neutropia following chemotherapy administration or radiation therapy, to increase neutrophil counts in a subject with aplastic anemia, myelodysplasia, myelofibrosis, neutropenia due to other bone marrow diseases, drug induced neutropenia, autoimmune neutropenia, idiopathic neutropenia, or neutropenia following viral infections, to increase neutrophil counts in a subject with neutropia, to increase platelet counts following a hematopoetic cell transplant with bone marrow, hematopoetic stem cells, or umbilical cord blood, to increase platelet counts in a subject with thrombocytopenia following chemotherapy administration or radiation therapy, to increase platelet counts in a subject with aplastic anemia, myelodysplasia, myelofibrosis, thrombocytopenia due to other bone marrow diseases, drug induced thrombocytopenia, autoimmune thrombocytopenia, idiopathic thrombocytopenic purpura, idiopathic thrombocytopenia, or thrombocytopenia following viral infections, to increase platelet counts in a subject with thrombocytopenia, to increase red blood cell counts, or hematocrit, or hemoglobin level, following a hematopoetic cell transplant with bone marrow, hematopoetic stem cells, or umbilical cord blood, to increase red blood cell counts, or hematocrit, or hemoglobin level in a subject with anemia following chemotherapy administration or radiation therapy, to increase red blood cell counts, or hematocrit, or hemoglobin level counts in a subject with aplastic anemia, myelodysplasia, myelofibrosis, anemia due to other disorder of bone marrow, drug induced anemia, immune mediated anemias, anemia of chronic disease, anemia following viral infections, or anemia of unknown cause, to increase red blood cell counts, or hematocrit, or hemoglobin level in a subject with anemia, to increase bone marrow stem cells, following a hematopoetic cell transplant with bone marrow, hematopoetic stem cells, or umbilical cord blood, to increase bone marrow stem cells in a subject following chemotherapy administration or radiation therapy, and/or to increase bone marrow stem cells in a subject with aplastic anemia, myelodysplasia, myelofibrosis, other disorder of bone marrow, drug induced cytopenias, immune cytopenias, cytopenias following viral infections, or cytopenias.

In other embodiments, the 15-PGDH inhibitor can be administered to a subject to increase responsiveness to cytokines in the presence of cytopenias, with cytopenias including any of: neutropenia, thrombocytopenia, lymphocytopenia and anemia; and with cytokines having increased responsiveness potentiated by the 15-PGDH inhibitor including any of: G-CSF, GM-CSF, EPO, IL-3, IL-6, TPO, TPO-RA (thrombopoietin receptor agonist), and SCF.

In some embodiments, the 15-PGDH inhibitor can be administered to a subject to increase bone density, treat osteoporosis, promote healing of fractures, or promote healing after bone surgery or joint replacement and/or to promote healing of bone to bone implants, bone to artificial implants, dental implants, and bone grafts.

In other embodiments, the 15-PGDH inhibitor can be administered to a subject or to the intestine of a subject to increase stem cells or cell proliferation in the intestine and/or and confer resistance to toxic or lethal effects of exposure to radiation or the toxic, lethal, or mucositis effects resultant from treatment with chemotherapy.

In some embodiments, the 15-PGDH inhibitor can be administered to a subject or to intestine of a subject as a treatment for colitis, ulcerative colitis, or inflammatory bowel disease.

In other embodiments, the 15-PGDH inhibitor can be administered to a subject to increase liver regeneration following liver surgery, following live liver donation, following liver transplantation, or following liver injury by toxins and/or to promote recovery from or resistance to liver toxins, including acetaminophen and related compounds.

In still other embodiments, the 15-PGDH inhibitor can be administered to a subject to treat erectile dysfunction.

In yet other embodiments, the 15-PGDH inhibitor can be administered to inhibit at least one of the growth, proliferation, or metastasis of 15-PGDH expressing cancers.

Still other embodiments described herein relate to a method of treating a subject in need of cell therapy. The method includes administering to the subject a therapeutically effective amount of a preparation comprising human hematopoietic stem cell administered a 15-PGDH inhibitor described herein and/or a therapeutic composition comprising human hematopoietic stem cells and a 15-PGDH inhibitor described herein.

In some embodiments, the subject has received human hematopoietic stem cells and/or has received the preparation and/or the therapeutic composition.

In other embodiments, the subject has acute myelogenous leukemia (AML), acute lymphoblastic leukemia (ALL), chronic myelogenous leukemia (CML), chronic lymphocytic leukemia (CLL), juvenile myelomonocytic leukemia, Hodgkin's lymphoma, non-Hodgkin's lymphoma, multiple myeloma, severe aplastic anemia, Fanconi's anemia, paroxysmal nocturnal hemoglobinuria (PNH), pure red cell aplasia, amegakaryocytosis/congenital thrombocytopenia, severe combined immunodeficiency syndrome (SCID), Wiskott-Aldrich syndrome, beta-thalassemia major, sickle cell disease, Hurler's syndrome, adrenoleukodystrophy, metachromatic leukodystrophy, myelodysplasia, refractory anemia, chronic myelomonocytic leukemia, agnogenic myeloid metaplasia, familial erythrophagocytic lymphohistiocytosis, solid tumors, chronic granulomatous disease, mucopolysaccharidoses, or Diamond Blackfan anemia.

Other embodiments relate to a method of treating a subject having at least one symptom associated with an ischemic tissue or a tissue damaged by ischemia. The method includes administering to the subject a therapeutically effective amount of a preparation comprising human hematopoietic stem cell administered a 15-PGDH inhibitor described herein and/or a therapeutic composition comprising human hematopoietic stem cells and a 15-PGDH inhibitor described herein.

In some embodiments, the ischemia can be associated with at least one of acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient isc hemic attack (TIA), traumatic brain injury, ulcerative colitis, vascular disease of the kidney, vascular inflammatory conditions, von Hippel-Lindau syndrome, and wounds to tissues or organs.

BRIEF DESCRIPTION OF THE DRAWINGS

FIGS. 1(A-C) illustrate graphs showing luciferase activity of cells that express a 15-PGDH luciferase fusion construct created by targeted gene knock-in of *renilla* luciferase into the last coding exon of 15-PGDH treated with the compounds SW033291, SW054384, and SW145753 at various concentrations. The activity is demonstrated in three different colon cancer cell lines all engineered to contain the 15-PGDH-luciferase fusion. These cell lines are Vaco-9m (V9m), LS174T, Vaco503 (V503).

FIGS. 5(A-C) illustrate 15-PGDH protein levels in V503 cells treated with SW124531 as assayed by immuno-fluorescence (upper two rows) and by western blot (lower panel).

FIGS. 6(A-F) illustrate graphs showing 15-PGDH mRNA levels in colon cancer cell lines treated with SW033291.

FIGS. 7(A-C) illustrate graphs showing 15-PGDH mRNA levels in colon cancer cell lines treated with SW033291.

FIGS. 8(A-C) illustrate graphs showing 15-PGDH mRNA levels in colon cancer cell lines treated with SW054384 and SW145753.

FIGS. 9(A-I) illustrate graphs showing 15-PGDH mRNA levels in colon cancer cell lines treated with 5 µM SW124531.

FIGS. 10(A-C) illustrate graphs showing 15-PGDH activity in cell lines treated with SW033291, SW054384, and SW145753. Activity is measured as pmol $PGE_2$/min/million cells.

FIGS. 11(A-D) illustrates a table and plots showing activity of recombinant 15-PGDH protein (a 15-PGDH-GST fusion protein) incubated with varying concentrations of the test compounds.

FIGS. 12(A-D) illustrate plots showing the activity of recombinant 15-PGDH protein treated with SW033291 and SW054384, with panels 12A and C measuring transfer of tritium from a radiolabeled PGE2 substrate and panels 12 B and D measuring generation of NADH by fluorescence.

FIG. 20 illustrates graphs showing the quantitation of scratch width at 0 and 48 hours in the control, SW033291 (2.5 µM) treated cells, and the TGF-beta (1 ng/ml) treated cells.

FIGS. 21(A-B) illustrate plots showing: (A) percent inhibition of PGDH using titrations of 15-PGDH inhibitor SW033291 run at different 15-PGDH concentrations; and (B) the IC50 of 15-PGDH inhibitor SW033291 versus 15-PGDH concentration.

FIGS. 22 (A-B) indicate that SW033291 behaves very much like an irreversible inhibitor of 15-PGDH, and cannot be efficiently dialyzed off the 15-PGDH protein.

FIGS. 23(A-B) illustrate a plot showing reaction rates and relative reaction velocity of 15-PGDH at varying concentrations of SW033291.

FIGS. 24(A-B) illustrate plots showing: (A) inhibition of 15-PGDH by SW033291 in the presence of PGE-2; and (B) $IC_{50}$ of SW033291 against 15-PGDH versus PGE2 concentration.

FIG. 26 illustrates a schematic diagram showing additional analogues of SW033291.

FIGS. 29(A-B) illustrate plots showing the $IC_{50}$ against 15-PGDH of SW033291 and SW0206980.

FIGS. 30(A-B) illustrate plots showing melting profiles of SW0206890 binding to 15-PGDH.

FIGS. 31(A-C) illustrate plots showing percent inhibition of 15-PGDH activity by SW033291, SW206980, and SW206992.

FIGS. 32(A-C) illustrate graphs showing luciferase activity of colon cancer cell lines V503, LS174T, and V503 treated with various concentrations of SW033291.

FIG. 33(A-C) illustrate graphs showing luciferase activity of colon cancer cell lines V503, LS174T, and V503 treated with various concentrations of SW0206980.

FIG. 34(A-C) illustrate graphs showing luciferase activity of colon cancer cell lines V503, LS174T, and V503 treated with various concentrations of SW0206992.

FIGS. 35(A-B) illustrate plots showing melting profiles of SW206992, SW0206890 and SW033291 binding to 15-PGDH.

FIGS. 36(A-B) illustrate plots showing melting profiles of SW206992, SW0206890 and SW033291 binding to 15-PGDH.

FIGS. 37(A-C) illustrate graphs showing the effect of SW206992, SW0206890 and SW033291 on the regulation of PGE-2 in A549 cells stimulated with IL1-Beta.

FIGS. 38(A-C) illustrate graphs showing the effect of SW206992, SW0206890 and SW033291 on cell numbers in A549 cells after stimulated with IL1-Beta.

FIGS. 46(A-C) illustrate graphs showing: (A) total bone marrow cellularity; (B) SKL population of wild type versus PGDH$^{-/-}$ mice; and (C) average CFU counts in wild type versus PGDH–/– mice (designated as either PGDH$^{-/-}$ or as PGDH).

FIGS. 52(A-D) illustrate photographs showing preoperative and post-operative view of mouse liver.

FIGS. 53(A-D) illustrate photographs showing post-hepatectomy views of the mouse liver (at left) and regeneration of mouse liver on post-operative day 7 (at right).

FIGS. 54(A-B) illustrate micrographs of post-hepatectomy mouse livers of mouse administered SW033291 and control vehicle, with arrows designating mitotic figures.

FIG. 55 illustrates a graph showing mitosis in liver of SW033291 treated mouse versus the control mouse.

FIG. 69 illustrates photographs of S-phase cells following partial hepatectomy on post-operative day 2 in livers of SW033291 treated and vehicle treated control mice.

FIG. 70 illustrates a photograph showing high powered (40×) views of representative fields from the study of FIG. 69.

FIGS. 77(A-B) illustrate photographs showing colonoscopic findings and mouse endoscopic index of colitis severity (MEICs) for a DSS treated mouse receiving a control vehicle or SW033291.

FIGS. 82(A-C) illustrate: (A) a schematic illustration showing measurements on blood and bone marrow on day 5 after transplant; (B) a graph showing that SW033291 treated mice have significantly higher total white count; (C) a graph showing that SW033291 treated mice have significantly higher total platelet count. The star symbol denotes P<0.05.

FIGS. 84(A-D) illustrate: (A) a schematic illustration showing measurements on blood and bone marrow on day 12 after transplant; (B) a graph showing that SW033291 treated mice have significantly higher neutrophil counts, with drug treated mice having 332 neutrophils compared to control mice having 125 neutrophils; and (C) a graph showing that on day 12 after transplant, SW033291 treated mice have significantly higher hemoglobin count than controls, with drug treated mice having hemoglobin level of 11.58 and control mice having hemoglobin level of 8.3; and D) a graph showing that SW033291 treated mice have significantly higher total white counts compared to control mice. The star symbol denotes P<0.05.

FIGS. 85(A-G) illustrate: (A) a schematic illustration showing measurements on blood and bone marrow on day 18 after transplant; (B-D) graphs showing SW033291 treated mice have significantly higher total white count (FIG. 85B), lymphocyte count (FIG. 85C), and neutrophil count (FIG. 85D), with drug treated mice having 835 neutrophils and control mice having 365 neutrophils (FIG. 85D); (E) a graph showing that on day 18 drug treated mice have significantly higher platelet counts than control mice; and (F-G) graphs showing drug treated mice have nearly 4-fold increased percentage (FIG. 85F) and total numbers (FIG. 85G) of SKL marked bone marrow stem cells than do control mice. The star symbol denotes P<0.05.

FIGS. 86(A-B) illustrate graphs showing (A) measurement of PGE2 (pg of PGE2/mg tissue protein) in 4 different mouse tissues (colon, bone marrow, liver, lung) across time following IP injection of SW033291 at 10 mg/kg; and (B) time course of PGE2 in control mice injected with vehicle only.

FIG. 87 is a schematic illustration showing an experiment in which mice are lethally irradiated (IR) and 12 hours later receive a transplant (BMT) with CFSE dye labeled bone marrow cells (BM), and the number of transplanted cells that home and survive in the bone marrow of the recipient mice are then determined by FACS at 16 hours post-transplant.

FIG. 90 illustrates a graph showing the percent of CFSE dye labeled cells that have homed to the bone marrow of mice treated as illustrated in FIG. 89.

FIG. 91 is a schematic illustration showing an experiment in which mice are injected with SW033291 twice daily IP at 10 mg/kg for 5 doses.

FIGS. 92(A-B) illustrate graphs showing induction of gene expression in (A) bone marrow SKL cells and (B) bone marrow stromal cells of SW033291 treated mice.

FIG. 95 illustrates isomers of SW033291 and a representative analytical HPLC trace.

FIG. 114 shows chemical structures of two previously described compounds, SW209125 and SW208436, along with a set of five compounds, designated set 21 with individual compound identifiers ranging from SW209239 through SW209333, that are structurally related to SW033291. For each compound the molecular weight, tPSA, and C Log P is also shown.

FIG. 116 illustrates chemical structures of a set of six compounds, designated set 23, with individual compound identifiers ranging from SW209415 through SW209420, that are structurally related to SW033291. For each compound the molecular weight, tPSA, and C Log P is also shown.

FIG. 121 illustrates a graph showing the activity of SW209125, SW208436 and set 21 compounds ranging from SW209239 through SW209333 in inducing luciferase activity in a reporter cell line at concentrations of 19.5 nM, 39.0635 nM, 78.124 nM, 156.25 nM, 312.5 nM, 625 nM, and 1250 nM.

FIG. 122 illustrates a graph showing the activity of set 23 compounds ranging from SW209415 through SW209420 in inducing luciferase activity in a reporter cell line at concentrations of 39.0625 nM, 78.125 nM, 156.25 nM, 312.5 nM, 625 nM, 1250 nM, and 2500 nM.

Figure 123:
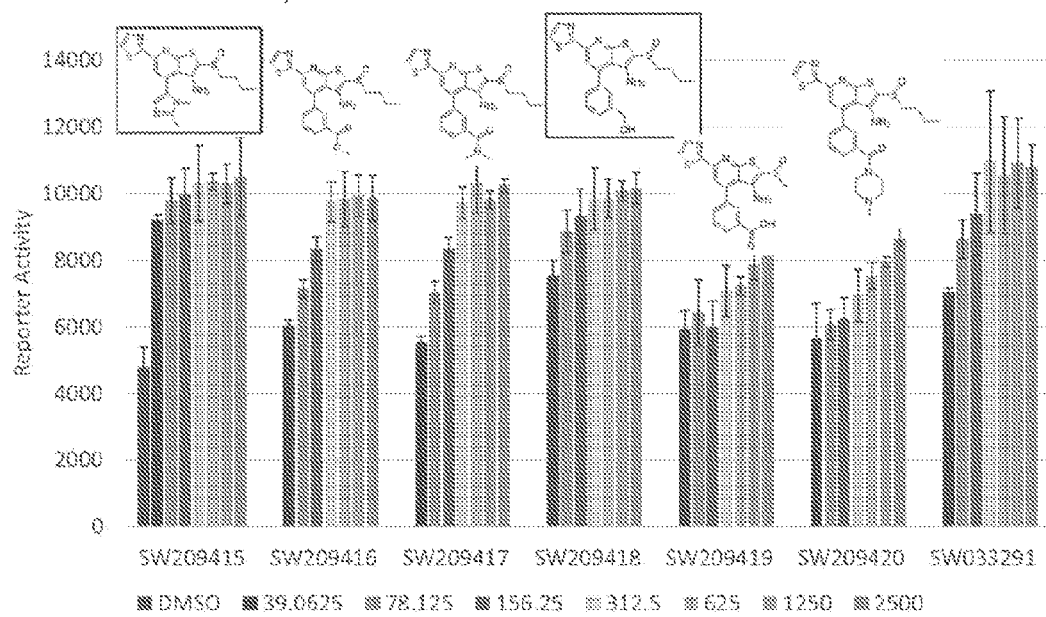

FIG. 123 shows activity of set 23 compounds ranging from SW209415 through SW209420 in inducing luciferase activity in a reporter cell line constructed from the LS174T colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 39.0625 nM, 78.125 nM, 156.25 nM, 312.5 nM, 625 nM, 1250 nM, and 2500 nM.

Figure 124:
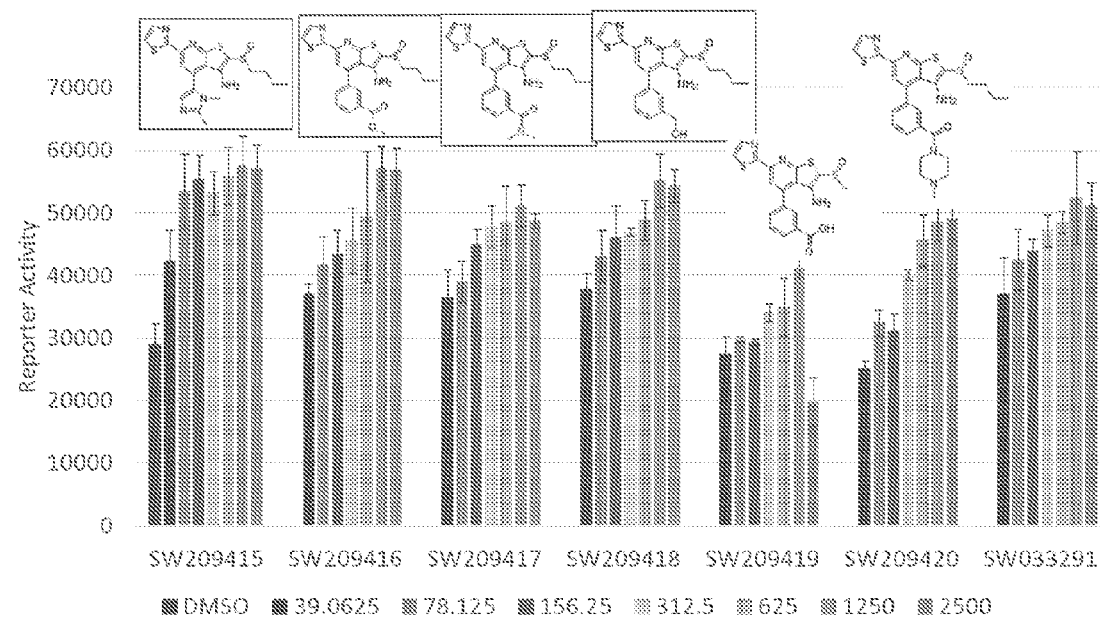

FIG. 124 illustrates a graph showing the activity of set 23 compounds ranging from SW209415 through SW209420 in inducing luciferase activity in a reporter cell line at concentrations of 39.0625 nM, 78.125 nM, 156.25 nM, 312.5 nM, 625 nM, 1250 nM, and 2500 nM.

Figure 125:
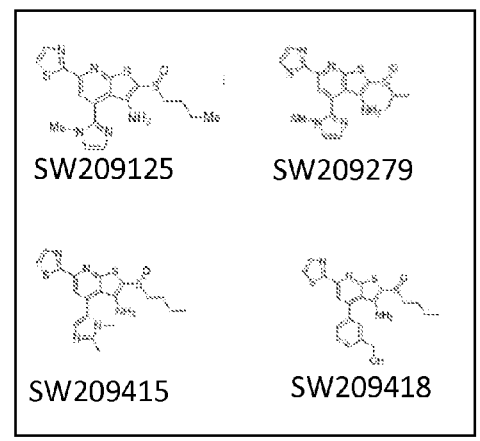

FIG. 125 illustrates the structures of SW209125, set 20 compound SW209279, and set 23 compounds SW209415 and SW209418.

Figure 126:
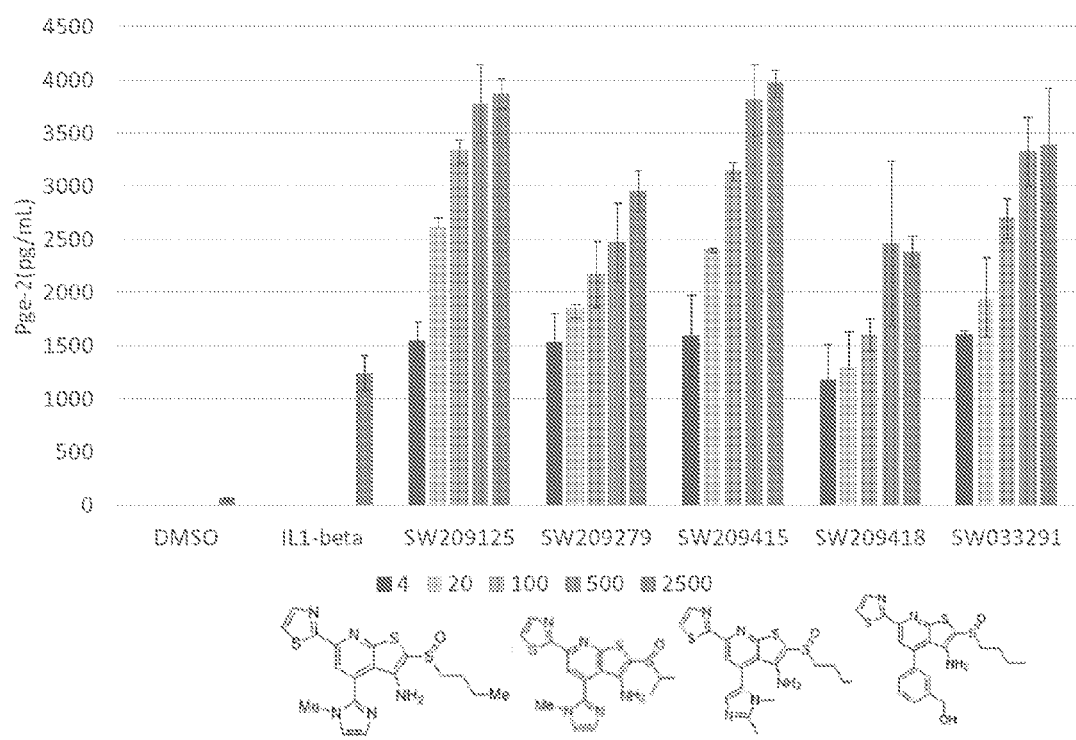

FIG. 126 illustrates a graph showing the activity of SW209125, set 20 compound SW209279, and set 23 compounds SW209415 and SW209418, at concentrations of 4 nM, 20 nM, 100 nM, 500 nM, and 2500 nM in inducing PGE2 as assayed in the medium of A549 cells that have first been activated with IL-1beta.

Figure 127:
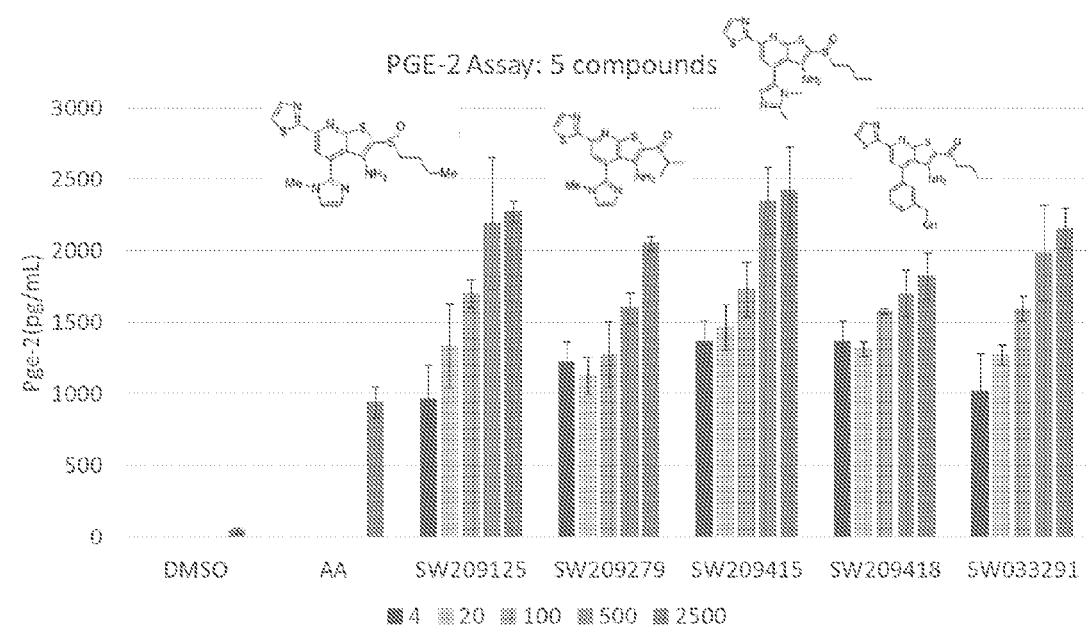

FIG. 127 illustrates a graph showing the activity of SW209125, set 20 compound SW209279, and set 23 compounds SW209415 and SW209418, at concentrations of 4 nM, 20 nM, 100 nM, 500 nM, and 2500 nM in inducing PGE2 as assayed in the medium of DLD1 cells in media supplemented with arachidonic acid.

Figure 128:
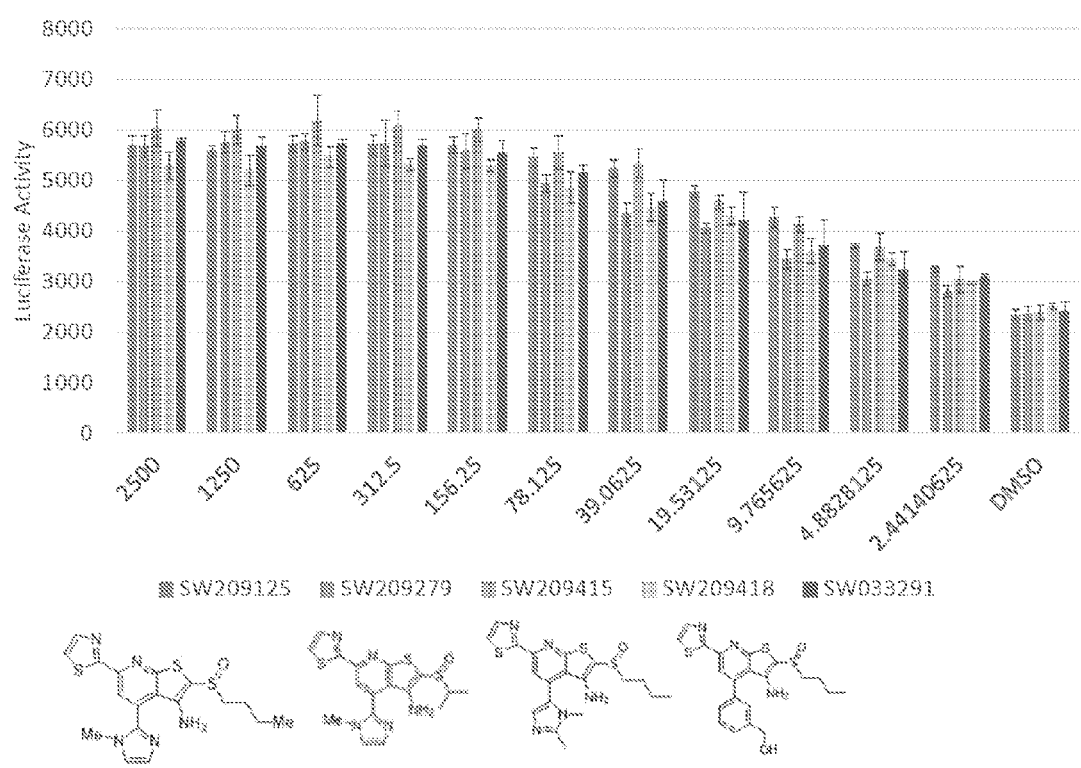

FIG. 128 illustrates a graph showing activity of SW033291, SW209125, set 20 compound SW209279, and set 23 compounds SW209415 and SW209418, in inducing luciferase activity in a reporter cell line at concentrations ranging from (right to left) of 2.4 nM up to 2500 nM.

FIG. 129 illustrates a graph showing the activity of SW033291, SW209125, set 20 compound SW209279, and set 23 compounds SW209415 and SW209418, in inducing luciferase activity in a reporter cell line at concentrations ranging from (right to left) of 2.4 nM up to 2500 nM.

Figure 130:
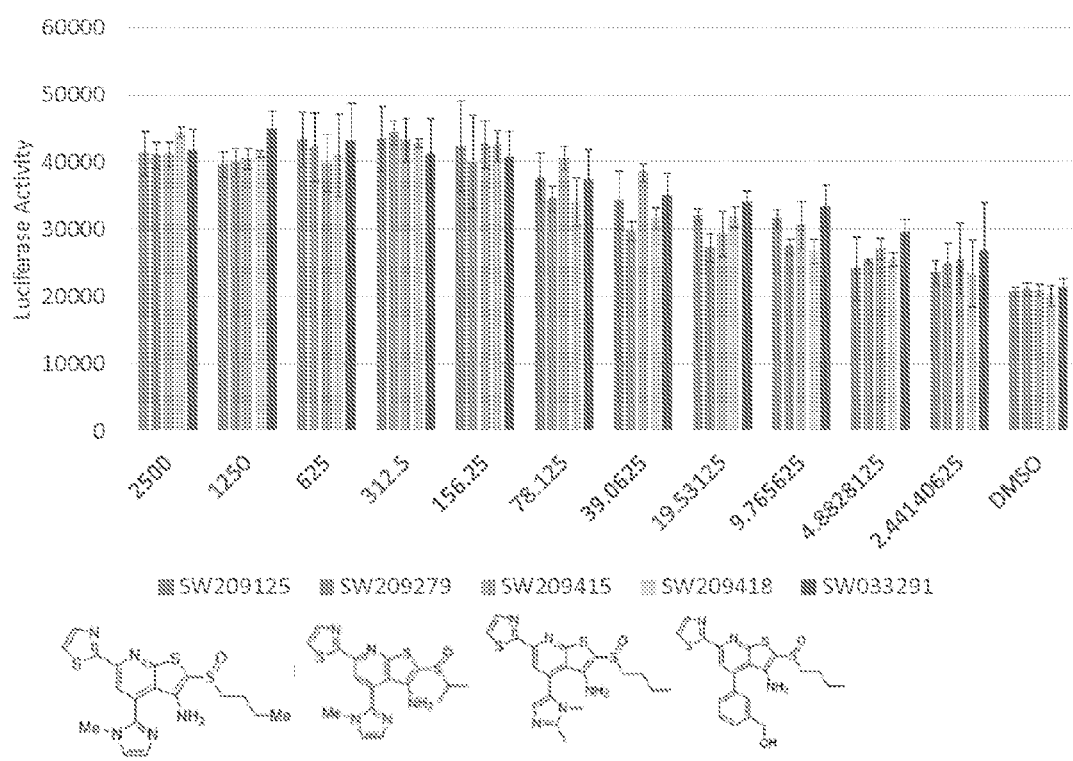

FIG. 130 illustrates a graph showing the activity of SW033291, SW209125, set 20 compound SW209279, and set 23 compounds SW209415 and SW209418, in inducing luciferase activity in a reporter cell line at concentrations ranging from (right to left) of 2.4 nM up to 2500 nM.

FIG. 131 shows chemical structures of a set of seven compounds, designated set 24, with individual compound identifiers ranging from SW209427 up to SW209513, that are structurally related to SW033291. For each compound the molecular weight, tPSA, and C Log P is also shown. Also shown is the repeated structure of SW209415.

Figure 132:
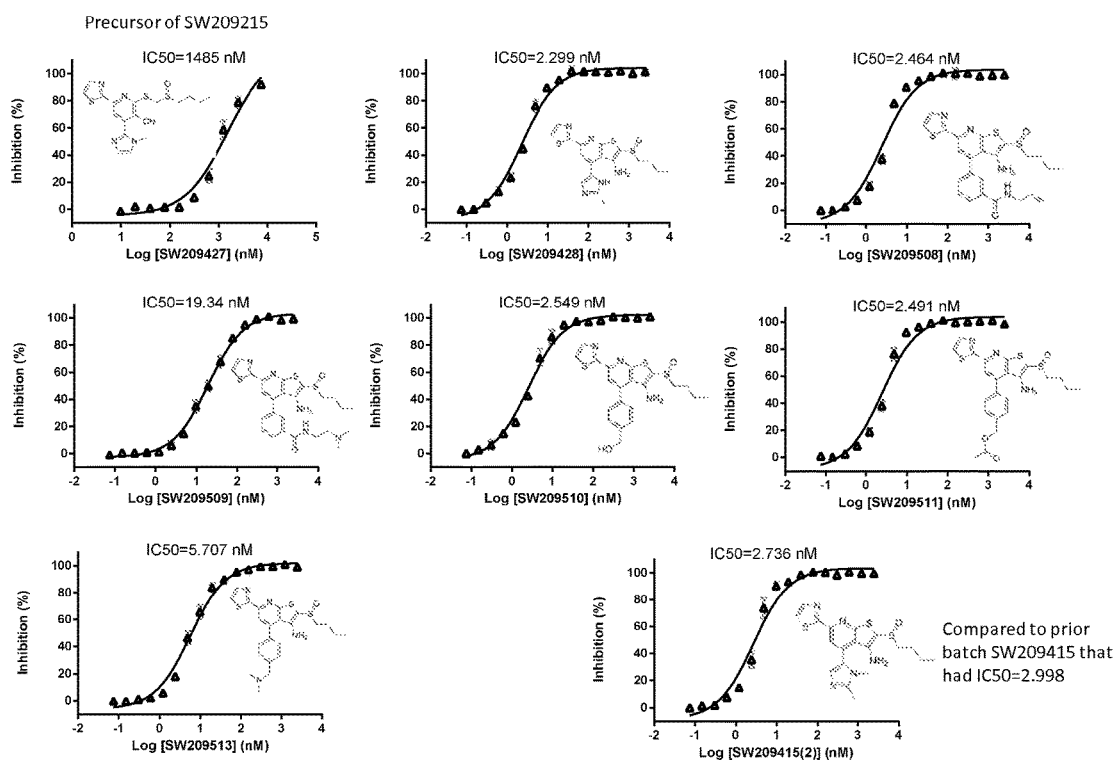

FIG. 132 illustrates plots showing the activity of each compound in set 24 with compound numbers from SW209427 up to SW209513 in inhibiting the enzymatic activity of recombinant 15-PGDH protein in in vitro assays, with the percent inhibition graphed on the Y-axis and the Log of the compound concentration in nM graphed on the X-axis. The $IC_{50}$ for each compound is recorded.

Figure 133:
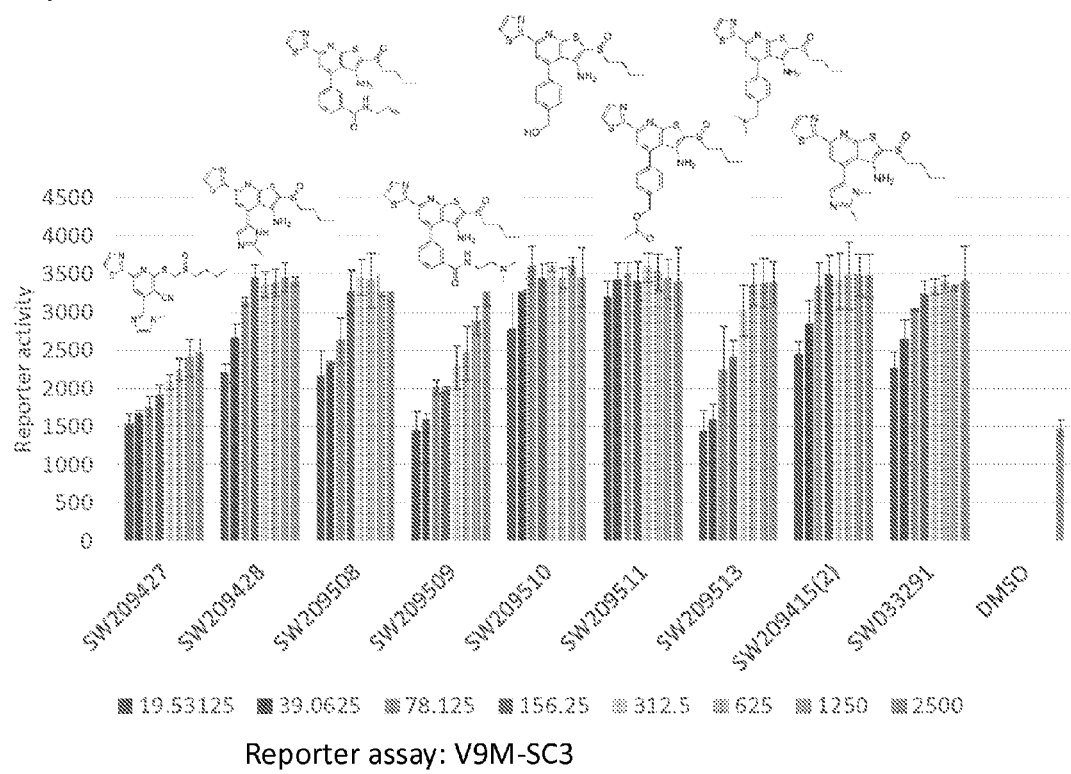

FIG. 133 illustrates a graph showing the activity of set 24 compounds, with compound numbers from SW209427 up to SW209513, in inducing luciferase activity in a reporter cell line at concentrations of 19.5 nM, 39.0635 nM, 78.125 nM, 156.25 nM, 312.5 nM, 625 nM, and 1250 nM.

Figure 134:
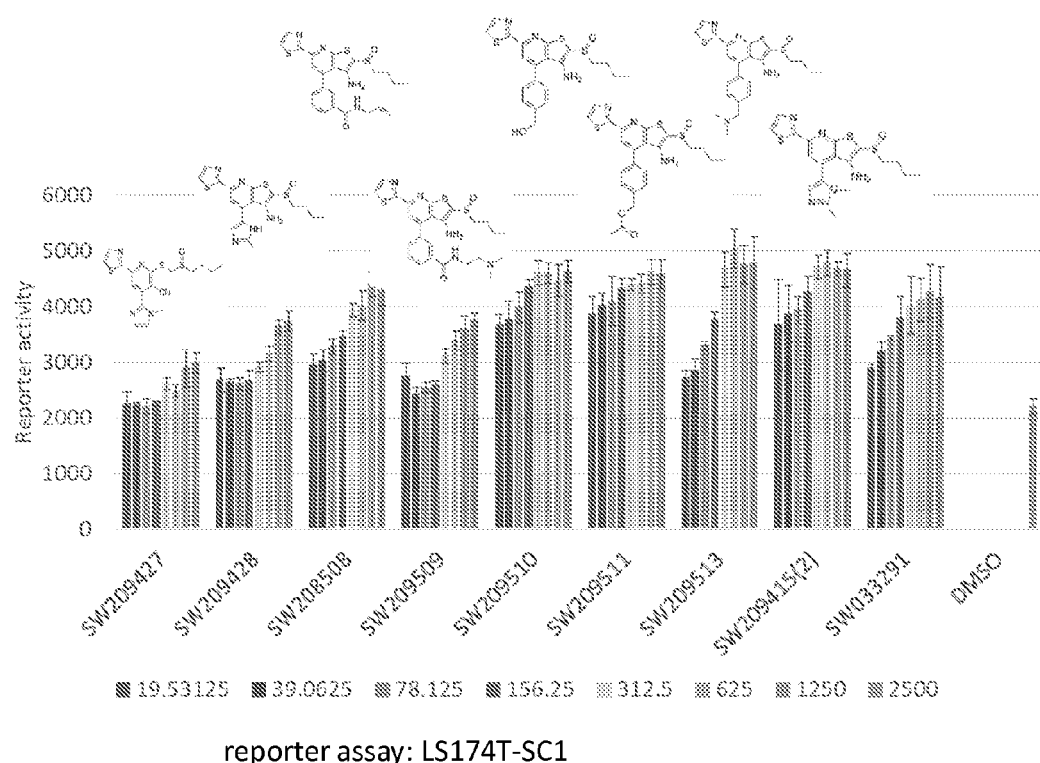

FIG. 134 illustrates a graph showing the activity of set 24 compounds, with compound numbers from SW209427 up to SW209513, in inducing luciferase activity in a reporter cell line at concentrations of 19.5 nM, 39.0635 nM, 78.125 nM, 156.25 nM, 312.5 nM, 625 nM, and 1250 nM.

Figure 135:
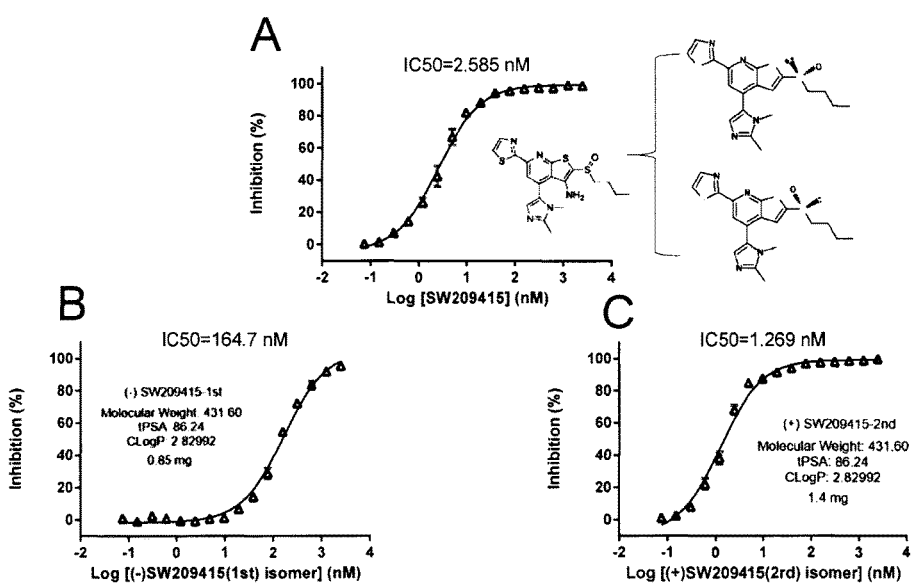

FIGS. 135(A-C) illustrate dose response curves for inhibition of enzymatic activity of recombinant 15-PGDH (Y-axis) versus log of the nM concentration of racemic SW209415 (A), or of the (−) isomer of SW209415 (B), or of the (+) isomer of SW209415 (C).

FIG. 136 illustrates the HPLC separation conditions for the enantiomers of SW209415.

FIG. 137 illustrates a graph showing induction of PGE2 that is secreted into cell culture media of A549 cells that are treated with: DMSO alone; IL1-beta alone; IL1-beta plus racemic SW209415 (labeled SW209415); IL1-beta plus (−) SW209415 (labeled SW209415 (−)); IL1-beta plus (+) SW209415 (labeled SW209415 (+)); or with IL1-beta plus SW033291 (labeled SW033291).

Figure 138:
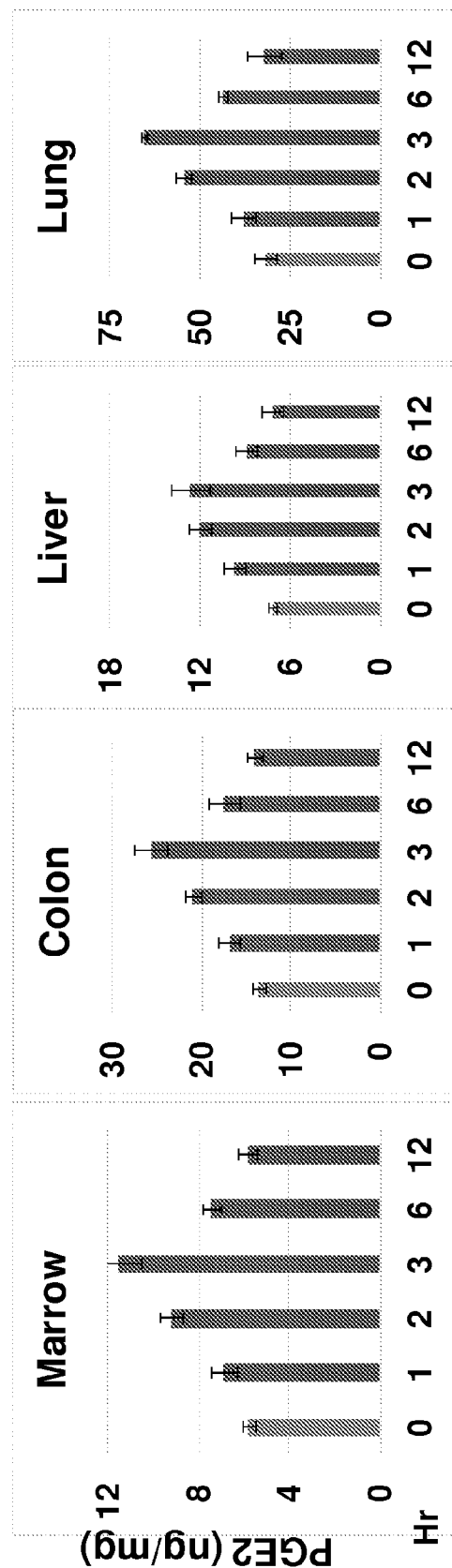

FIG. 138 illustrates graphs showing the measurement of PGE2 (pg of PGE2/mg tissue protein) in 4 different mouse tissues (colon, bone marrow, liver, lung) across time following IP injection of SW209415 at 10 mg/kg.

Figure 139:
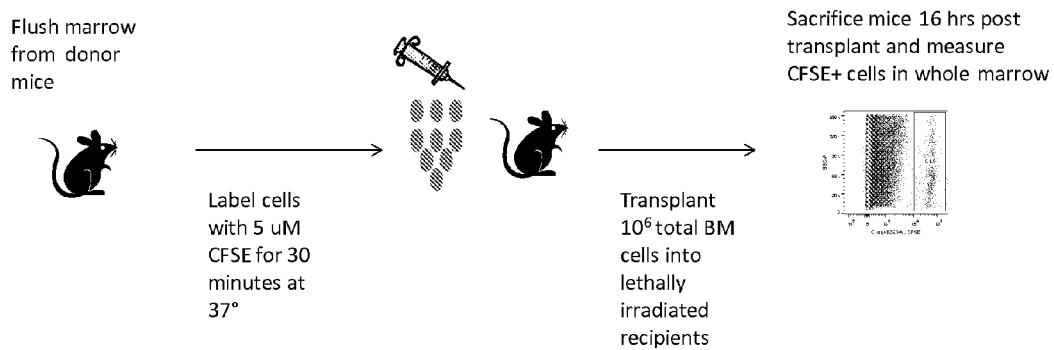

FIG. 139 illustrates schema of an experiment in which female C57BL/6J mice are lethally irradiated (IR) and 12 hours later receive a transplant with CFSE dye labeled bone marrow cells from a donor C57BL/6J female mouse, and the number of transplanted cells that home and survive in the bone marrow of the recipient mice are then determined by FACS at 16 hours post-transplant.

Figure 140:
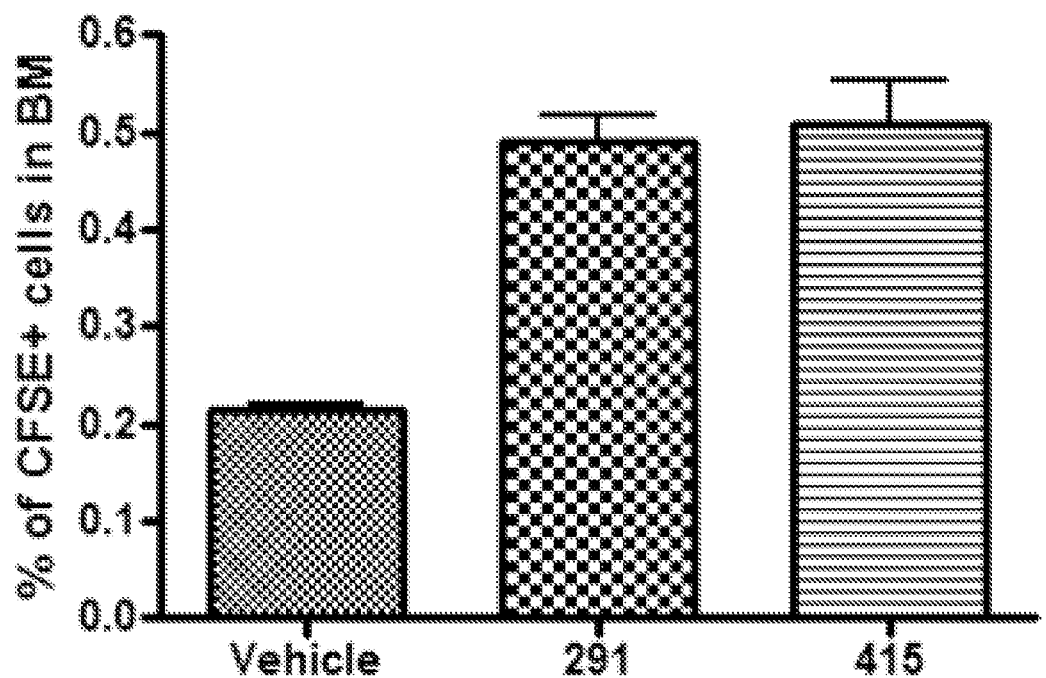

FIG. 140 illustrates a graph showing the percent of CFSE dye labeled donor bone marrow cells that have homed to the bone marrow of recipient mice treated as per the schema described in FIG. 139.

Figure 141:
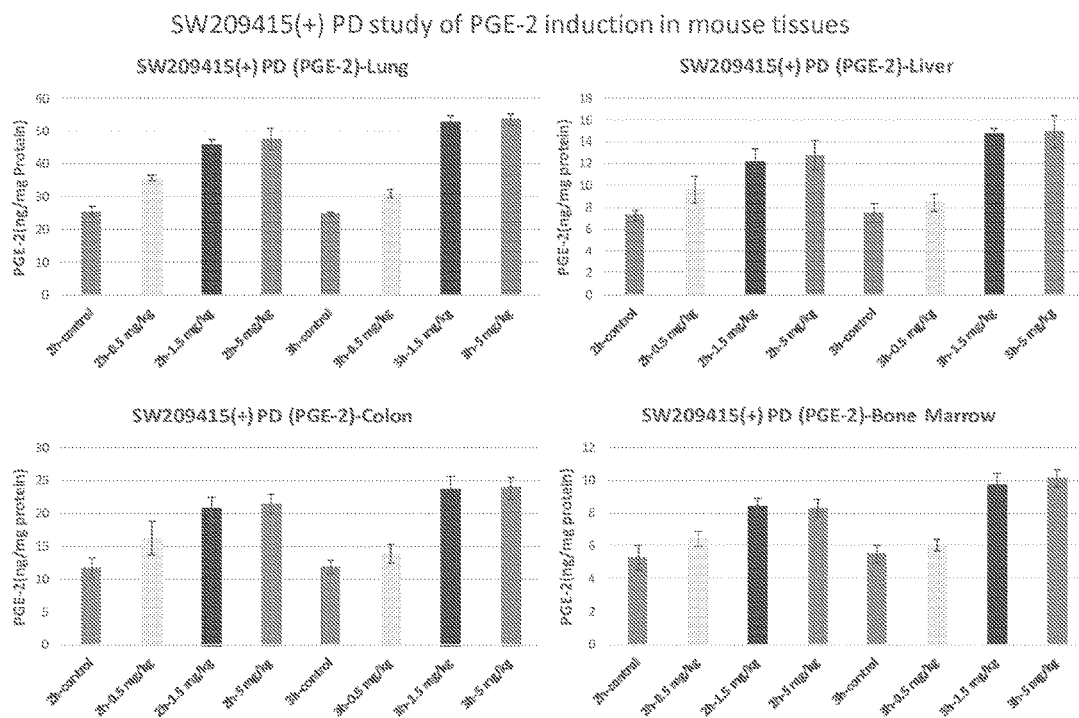

FIG. 141 shows activity of (+) SW209415 in increasing PGE2 in mouse tissues.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g. sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem.

Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_1$-6), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and al kylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S=O), a single bond without charges (S—O) or a single bond with charges [S(+)—O(-)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The term "neoplasm" refers to any abnormal mass of cells or tissue as a result of neoplasia. The neoplasm may be benign, potentially malignant (precancerous), or malignant (cancerous). An adenoma is an example of a neoplasm.

The terms "adenoma", "colon adenoma" and "polyp" are used herein to describe any precancerous neoplasm of the colon.

The term "colon" as used herein is intended to encompass the right colon (including the cecum), the transverse colon, the left colon and the rectum.

The terms "colorectal cancer" and "colon cancer" are used interchangeably herein to refer to any cancerous neoplasia of the colon (including the rectum, as defined above).

The terms "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information". Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The terms "healthy" and "normal" are used interchangeably herein to refer to a subject or particular cell or tissue that is devoid (at least to the limit of detection) of a disease condition.

The term "nucleic acid" refers to polynucleotides such as deoxyribonucleic acid (DNA), and, where appropriate, ribonucleic acid (RNA). The term should also be understood to include analogues of either RNA or DNA made from nucleotide analogues, and, as applicable to the embodiment being described, single-stranded (such as sense or antisense) and double-stranded polynucleotides. In some embodiments, "nucleic acid" refers to inhibitory nucleic acids. Some categories of inhibitory nucleic acid compounds include antisense nucleic acids, RNAi constructs, and catalytic nucleic acid constructs. Such categories of nucleic acids are well-known in the art.

Embodiments described herein relate to compounds and methods of modulating SCD activity (e.g., 15-PGDH activity), modulating tissue prostaglandin levels, and/or treating diseases, disorders, or conditions in which it is desired to modulate 15-PGDH activity and/or prostaglandin levels.

"Inhibitors," "activators," and "modulators" of 15-PGDH expression or of 15-PGDH activity are used to refer to inhibitory, activating, or modulating molecules, respectively, identified using in vitro and in vivo assays for 15-PGDH expression or 15-PGDH activity, e.g., ligands, agonists, antagonists, and their homologs and mimetics. The term "modulator" includes inhibitors and activators. Inhibitors are agents that, e.g., inhibit expression of 15-PGDH or bind to, partially or totally block stimulation, decrease, prevent, delay activation, inactivate, desensitize, or down regulate the activity of 15-PGDH, e.g., antagonists. Activators are agents that, e.g., induce or activate the expression of a 15-PGDH or bind to, stimulate, stabilize, increase, open, activate, facilitate, or enhance activation, sensitize or up regulate the activity of 15-PGDH, e.g., agonists. Modulators include naturally occurring and synthetic ligands, small chemical molecules, and the like.

15-PGDH inhibitors described herein can provide a pharmacologic method for elevating prostaglandin levels in tissue. Known activities of prostaglandins include promoting hair growth, promoting skin pigmentation, and promoting skin darkening or the appearance of skin tanning. Known activities of prostaglandins also include ameliorating pulmonary artery hypertension. 15-PGDH inhibitors described herein may also be utilized to increase tissue stem cell numbers for purposes that would include increasing resistance to tissue damage by radiation, increasing resistance to environmental exposures to radiation, increasing stem cell numbers to increase fitness of bone marrow or other types of transplantation (through either in vivo exposure to 15-PGDH inhibitors described herein to increase stem cell numbers prior to harvest of a transplanted tissue, or through ex vivo exposure of a harvested tissue prior to transplant into a recipient host, or through treatment of the graft recipient). 15-PGDH inhibitors described herein may also be utilized for purposes that would include promoting liver regeneration, including liver regeneration after liver resection, and liver regeneration after toxic insults, which for example may be the toxic insult of acetaminophen overdose. Prostaglandin signaling is also known to promote wound healing, protect the stomach from ulceration, and promote healing of ulcers of stomach and intestines. Additionally, 15-PGDH inhibitors described herein can promote activity of human keratinocytes in "healing" scratches across cultures of keratinocyte cells. Hence, 15-PGDH inhibitors described herein may be utilized to also heal ulcers of other tissues, including, but not limited to skin, and including but not limited to diabetic ulcers. Further, 15-PGDH inhibitors described herein may be utilized for the treatment of erectile dysfunction.

15-PGDH activators described herein can increase levels of 15-PGDH protein in cells and in increase levels of 15-PGDH enzymatic activity in cells. Increasing tissue levels of 15-PGDH can decrease tissue levels of prostaglandins. Activities associated with compounds that decrease tissue prostaglandins include decreasing development of human tumors, particularly decreasing development of human colon tumors. Accordingly, compounds that increase tissue 15-PGDH activity can lower risk of development of colon and other tumors. Compounds that increase 15-PGDH activity can also be used to treat colon and other tumors. Compounds that increase 15-PGDH may be used to treat or to prevent tumors when given singly, or when given in combination with inhibitors of cyclooxygenase-1 and/or cyclooxygenase-2 enzymes, or when given in combination with other therapeutic agents.

15-PGDH inhibitors and activators described herein can be identified using assays in which putative modulator compounds are applied to cells expressing 15-PGDH and then the functional effects on 15-PGDH activity are determined. Samples or assays comprising 15-PGDH that are treated with a potential activator, inhibitor, or modulator are compared to control samples without the inhibitor, activator, or modulator to examine the extent of effect. Control samples (untreated with modulators) are assigned a relative 15-PGDH activity value of 100%. Inhibition of 15-PGDH is achieved when the 15-PGDH activity value relative to the control is about 80%, optionally 50% or 25%, 10%, 5% or 1%. Activation of 15-PGDH is achieved when the 15-PGDH activity or expression value relative to the control is 105%, optionally 110%, optionally 125%, optionally 150%, optionally 200%, 300%, 400%, 500%, or 1000-3000% or more higher.

Agents tested as modulators of SCD (e.g., 15-PGDH) can be any small chemical molecule or compound. Typically, test compounds will be small chemical molecules, natural products, or peptides. The assays are designed to screen large chemical libraries by automating the assay steps and providing compounds from any convenient source to assays, which are typically run in parallel (e.g., in microtiter formats on microtiter plates in robotic assays). Modulators also include agents designed to increase the level of 15-PGDH mRNA or the level of translation from an mRNA.

In some embodiments, the modulator of SCD (e.g., 15-PGDH) can be a 15-PGDH inhibitor that includes a compound having the following formula (V):

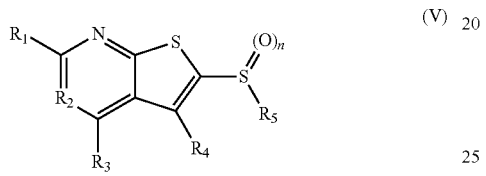

wherein n=0-2;

$R_1$ and $R_3$ are the same or different and are each selected from the group consisting of:

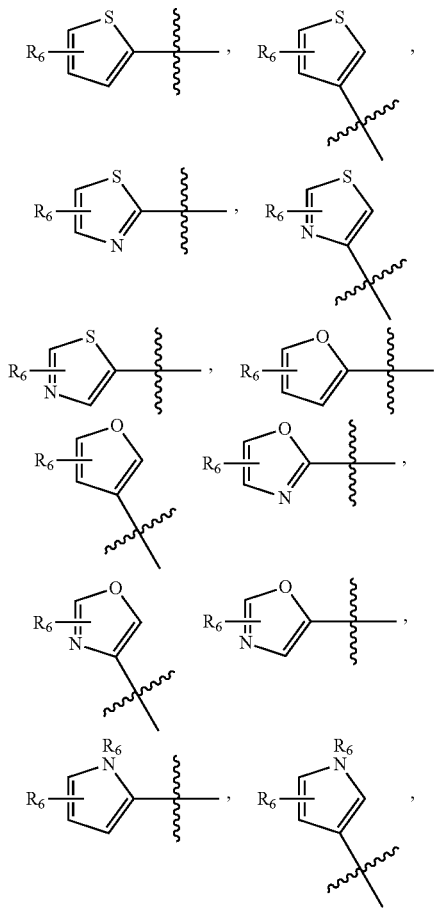

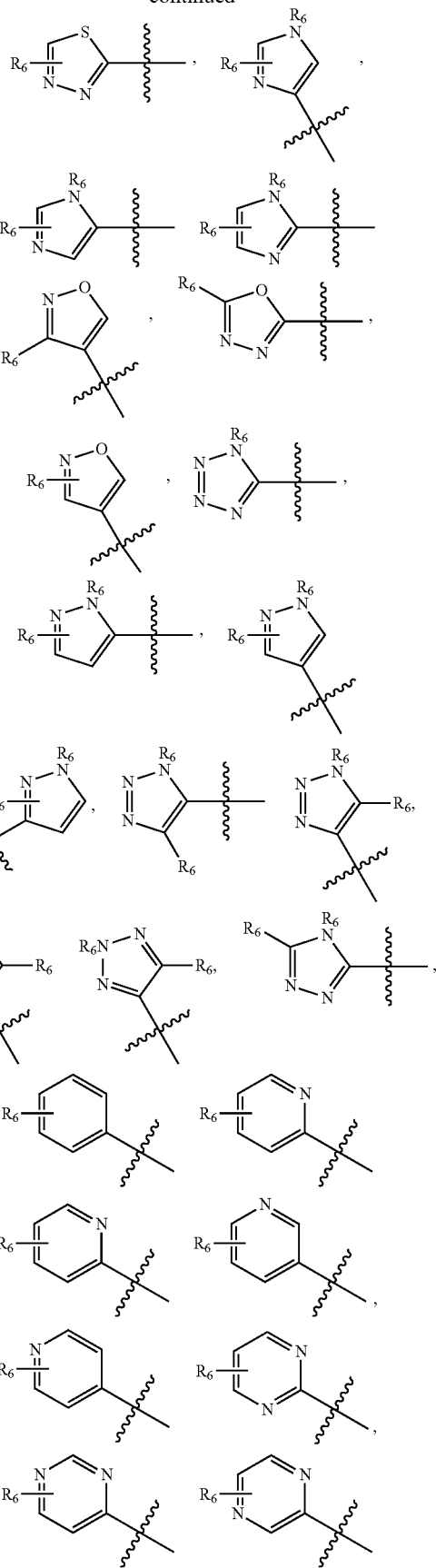

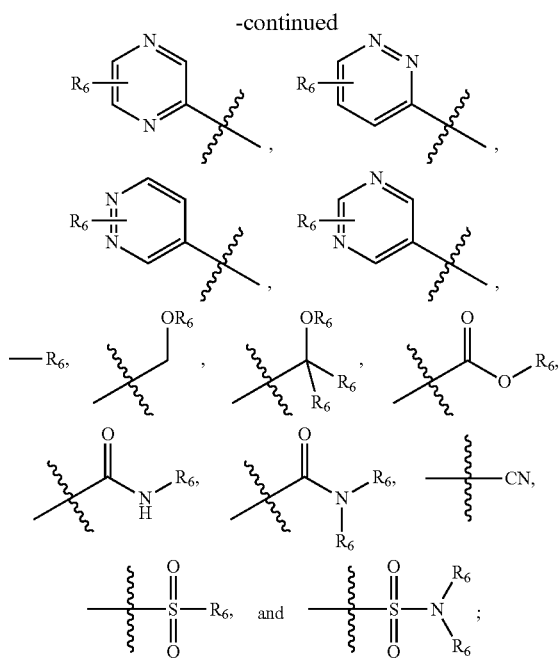

$R_2$ is N or $CR_7$;

$R_4$ is selected from the group consisting of H, Cl, F, $NH_2$, and $N(R_6)_2$;

$R_5$ is selected from the group consisting of branched or linear alkyl including —$(CH_2)n_1CH_3$ ($n_1$=0-7),

wherein $n_2$=0-6 and X is any of the following: $CF_yH_z$ (y+z=3), $CCl_yH_z$ (y+z=3), OH, OAc, OMe, $R_6$, $OR_6$, CN, $N(R_6)_2$,

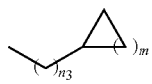

($n_3$=0-5, m=1-5), and

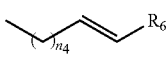

($n_4$=0-5);

each $R_6$ and $R_7$ are the same or different and are one or more substituent selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—$NH_2$), carbamido (—NH—(CO)—$NH_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—$NH_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO2NR2 where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—NH2, —$SO_2NY_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—$PO_2$), phosphino (—$PH_2$), polyalkyl ethers (—[($CH_2)_nO]_m$), phosphates, phosphate esters [—OP(O)(OR)$_2$ where R=H, methyl or other alkyl], groups incorporating amino acids or other moieties expected to bear positive or negative charge at physiological pH, and combinations thereof;

$R_3$ is not hydrogen if $R_1$ is H, an unsubstituted thiophene, or an unsubstituted thiazole and $R_5$ is butyl; or $R_3$ is not an unsubstituted phenyl if $R_1$ is H, or an unsubstituted phenyl, thiophene, or thiazole and $R_5$ is benzyl or $(CH_2)n_5(CH_3)(n_5$=0-5); and pharmaceutically acceptable salts thereof.

In some embodiments, $R_2$ can be N or CH. $R_1$ can be a substituted or unsubstituted heterocyclyl containing 5-6 ring atoms. For example, $R_1$ can be a substituted or unsubstituted thiophene, thiazole, oxazole, imidazole, pyridine, or phenyl. $R_3$ can be selected from the group consisting of H, substituted or unsubstituted aryl, a substituted or unsubstituted cycloalkyl, and a substituted or unsubstituted heterocyclyl, alkyl, or carboxy including carboxylic acid (—CO2H), carboxy ester (—$CO_2$alkyl) and carboxamide [—CON(H)(alkyl) or —$CO_2$N(alkyl)$_2$].

In still other embodiments, 15-PGDH inhibitor can include a compound having formula ($V_1$)

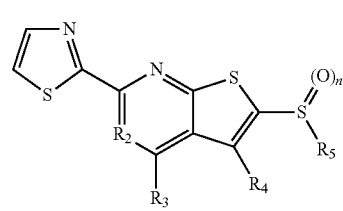

(V$_1$)

wherein n=0-2;

$R_3$ is selected from the group consisting of:
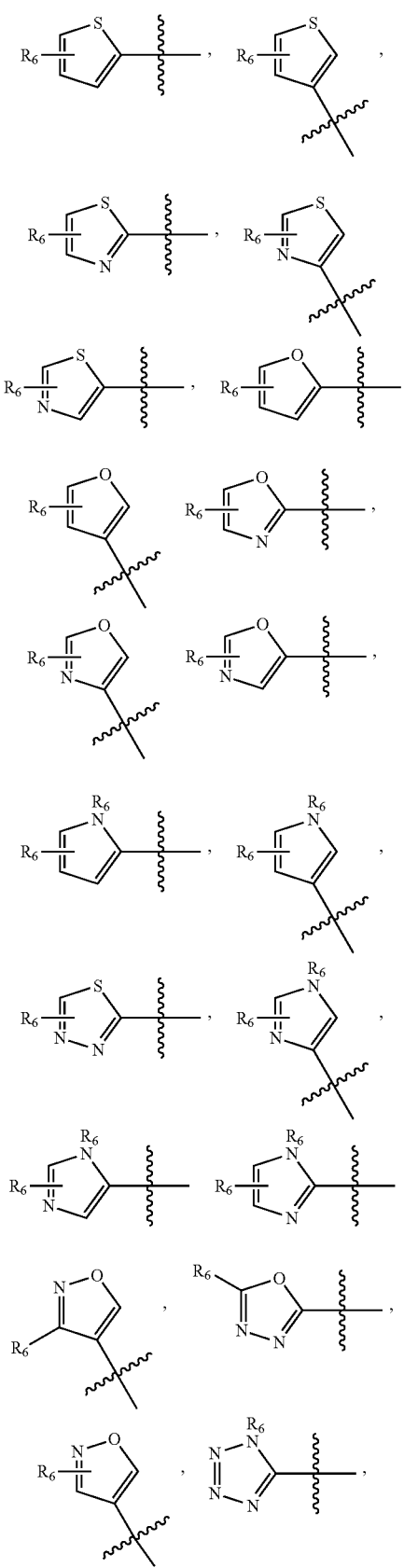
-continued
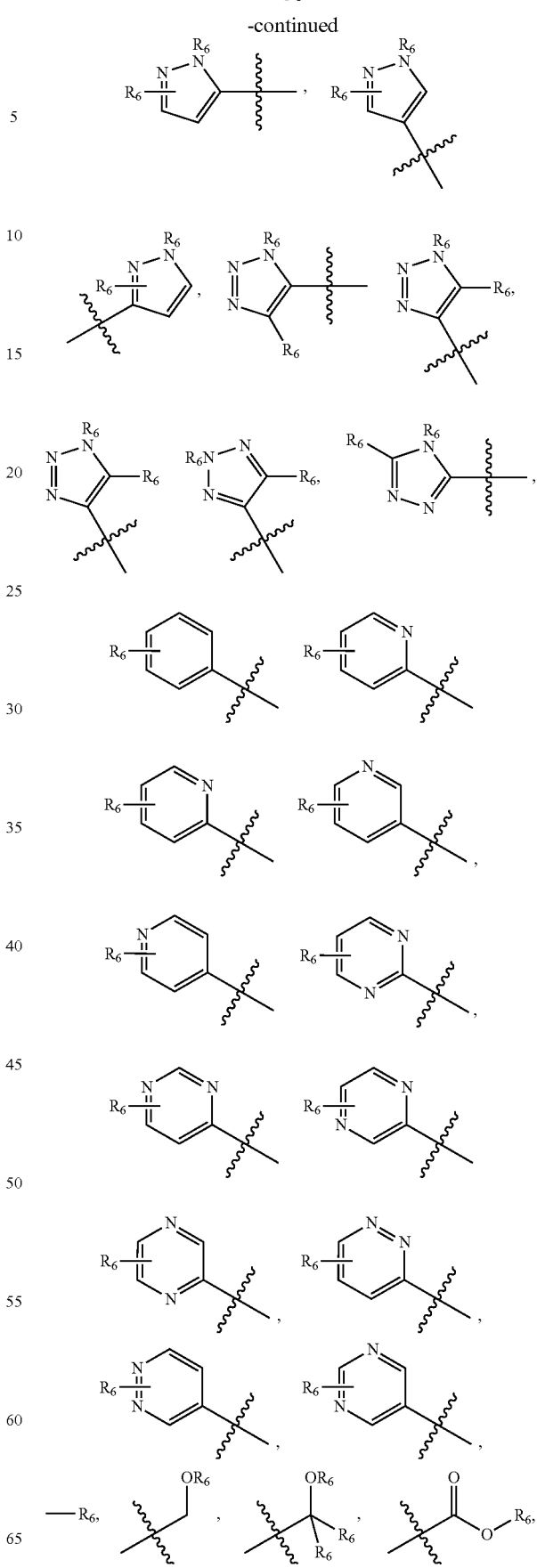

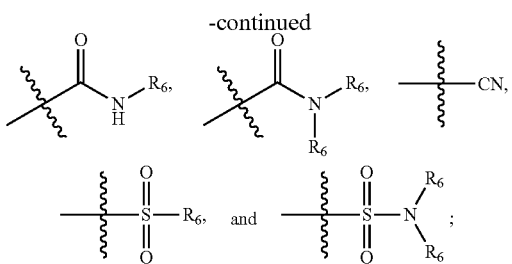

R$_2$ is N or CR$_7$;

R$_4$ is selected from the group consisting of H, Cl, F, NH$_2$, and N(R$_6$)$_2$;

R$_5$ is selected from the group consisting of branched or linear alkyl including —(CH$_2$)n$_1$CH$_3$ (n$_1$=0-7),

wherein n$_2$=0-6 and X is any of the following: CF$_y$H$_z$ (y+z=3), CCl$_y$H$_z$ (y+z=3), OH, OAc, OMe, R$_6$, OR$_6$, CN, N(R$_6$)$_2$,

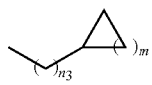

(n$_3$=0-5, m=1-5), and

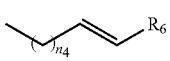

(n$_4$=0-5);

each R$_6$ and R$_7$ are the same or different and are one or more substituent selected from the group consisting of hydrogen, substituted or unsubstituted C$_1$-C$_{24}$ alkyl, C$_2$-C$_{24}$ alkenyl, C$_2$-C$_{24}$ alkynyl, C$_3$-C$_{20}$ aryl, heterocycloalkenyl containing from 5-6 ring atoms, (wherein from 1-3 of the ring atoms is independently selected from N, NH, N(C$_1$-C$_6$ alkyl), NC(O)(C$_1$-C$_6$ alkyl), O, and S), heteroaryl containing from 5-14 ring atoms, (wherein from 1-6 of the ring atoms is independently selected from N, NH, N(C$_1$-C$_3$ alkyl), O, and S), C$_6$-C$_{24}$ alkaryl, C$_6$-C$_{24}$ aralkyl, halo, silyl, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO— alkyl) and C$_6$-C$_{20}$ arylcarbonyl (—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^-$), carbamoyl (—(CO)—NH$_2$), C$_1$-C$_{24}$ alkyl-carbamoyl (—(CO)—NH(C$_1$-C$_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), sulfanamido (—SO2NR2 where R is independently H, alkyl, aryl or heteroaryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), sulfonamide (—SO$_2$—NH2, —SO$_2$NY$_2$ (wherein Y is independently H, aryl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]m), phosphates, phosphate esters [—OP(O)(OR)$_2$ where R=H, methyl or other alkyl], groups incorporating amino acids or other moieties expected to bear positive or negative charge at physiological pH, and combinations thereof;

R$_3$ is not hydrogen if R$_5$ is butyl; or R$_3$ is not an unsubstituted phenyl if R$_5$ is benzyl or (CH$_2$)n$_5$(CH$_3$) (n$_5$=0-5); and pharmaceutically acceptable salts thereof.

Examples of 15-PGDH inhibitors having formula (V) include the following compounds:

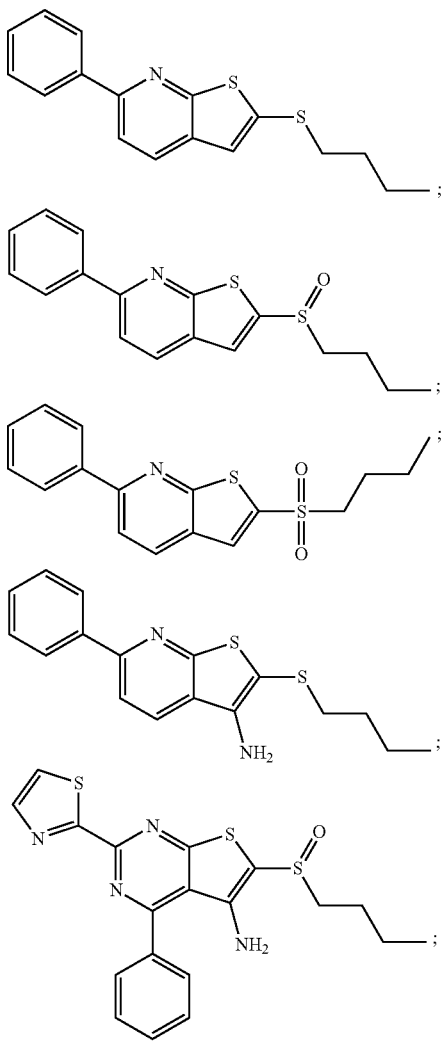

43
-continued
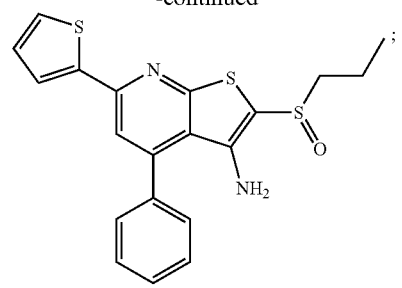
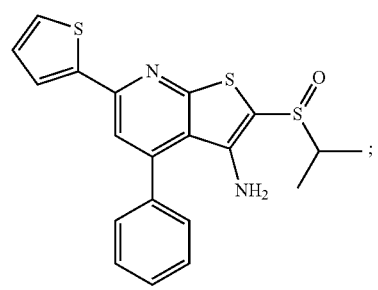
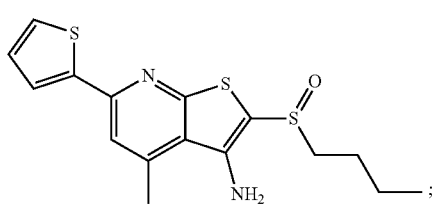
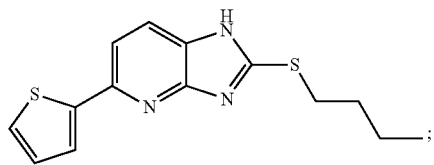
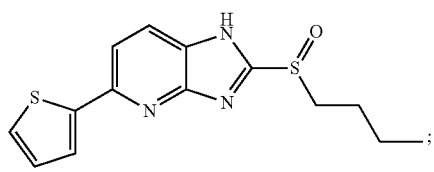
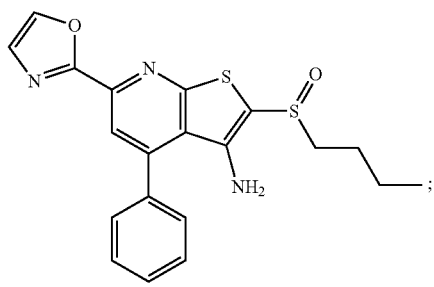
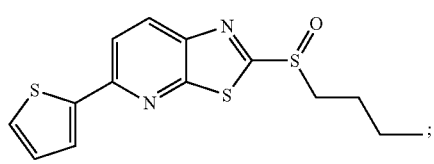
44
-continued
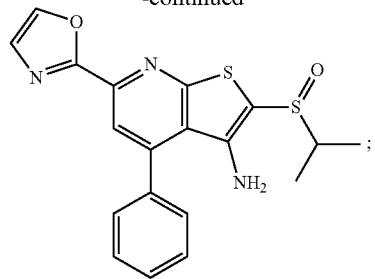
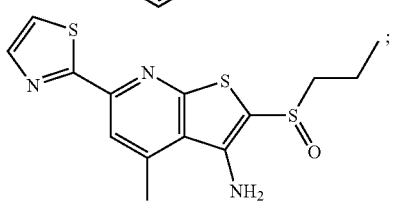
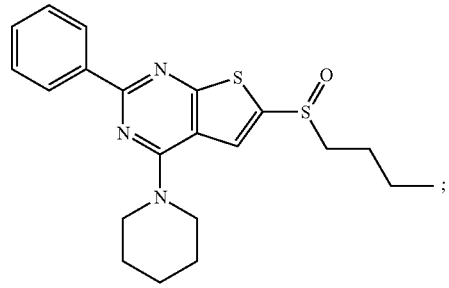
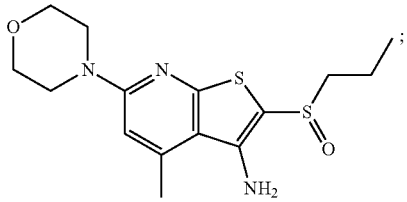
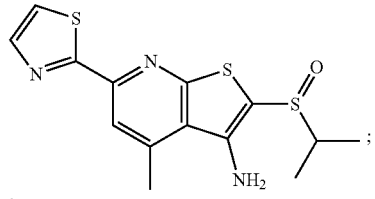
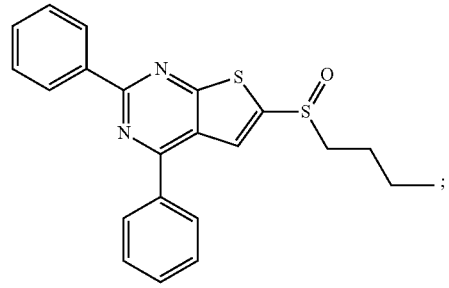
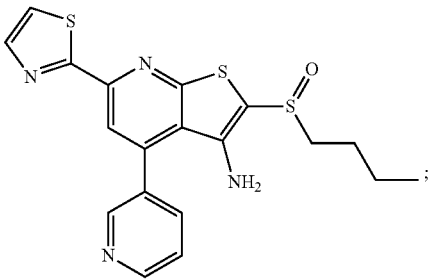

45
-continued
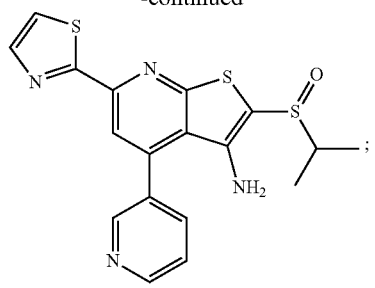
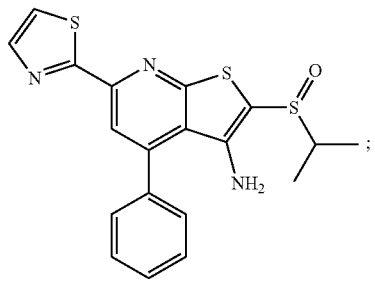
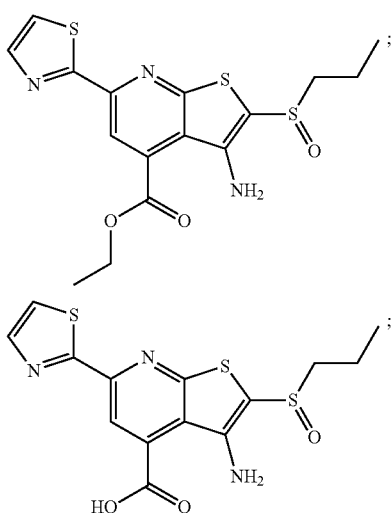
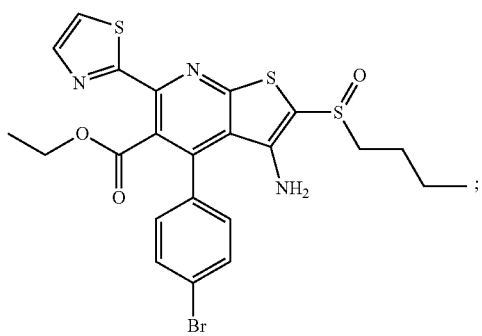
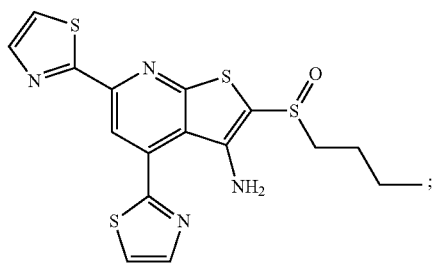
46
-continued
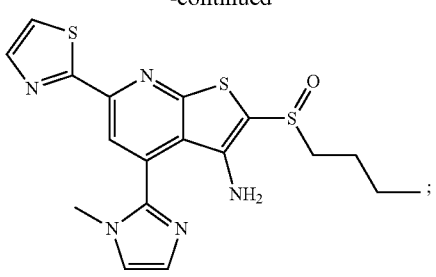
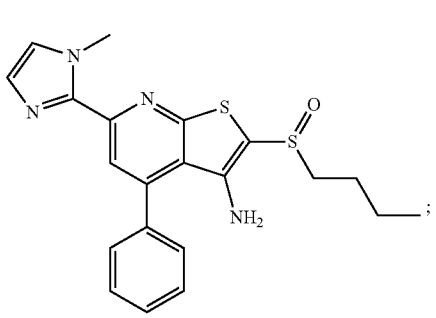
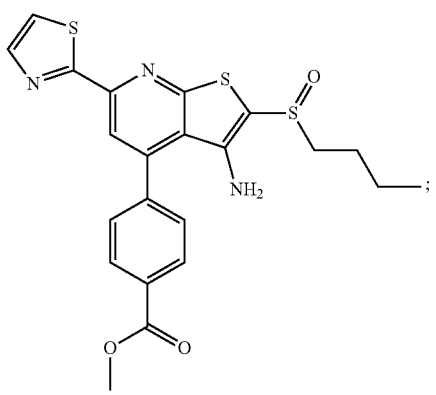
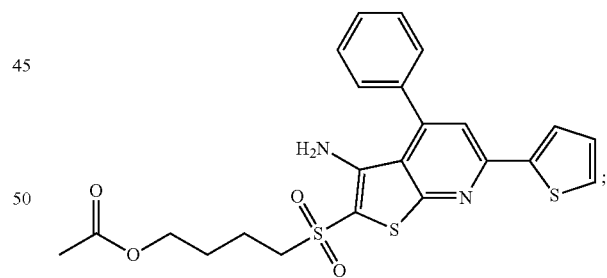
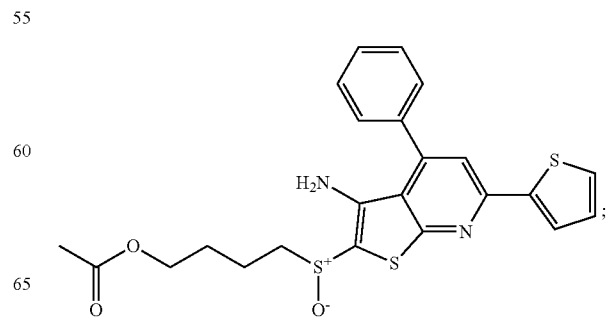

47
-continued
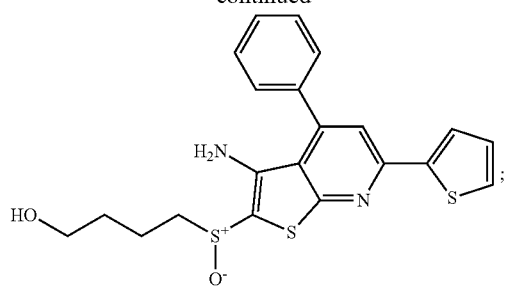
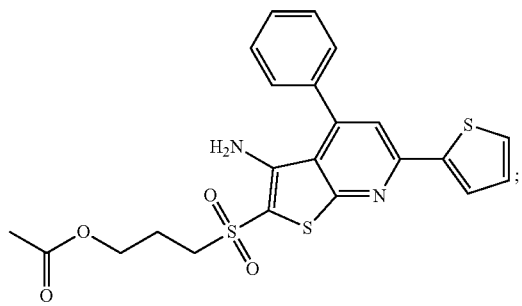
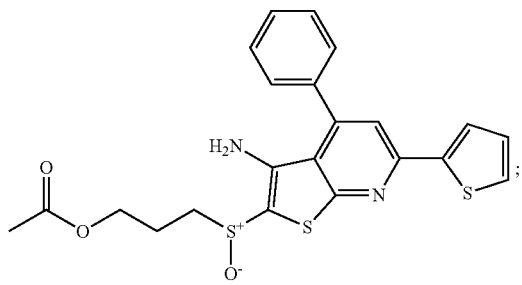
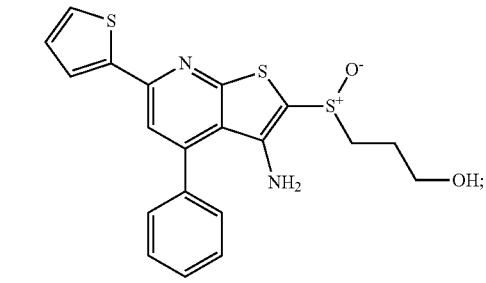
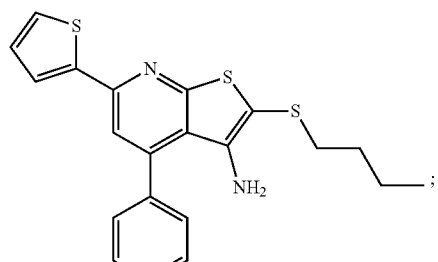
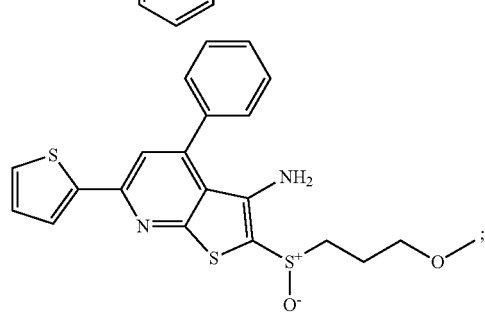
48
-continued
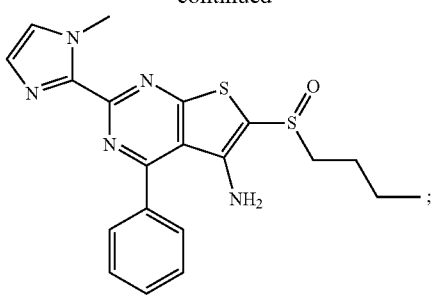
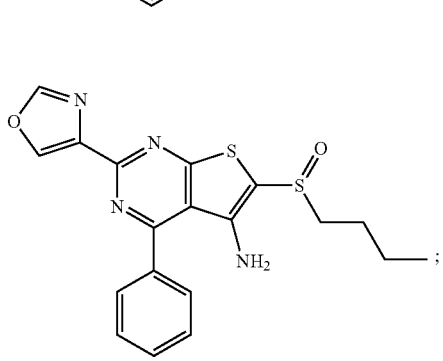
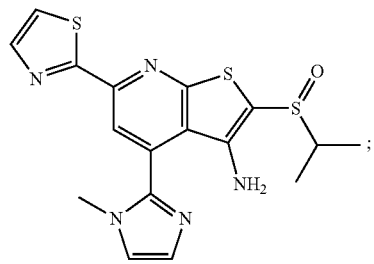
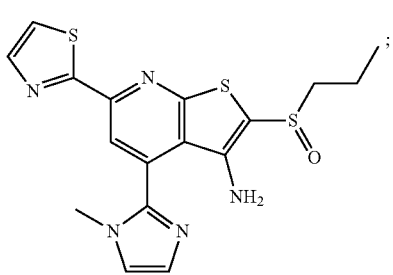
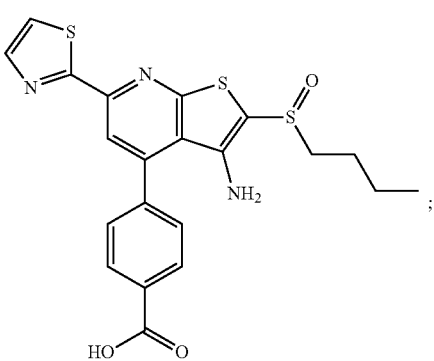

49
-continued
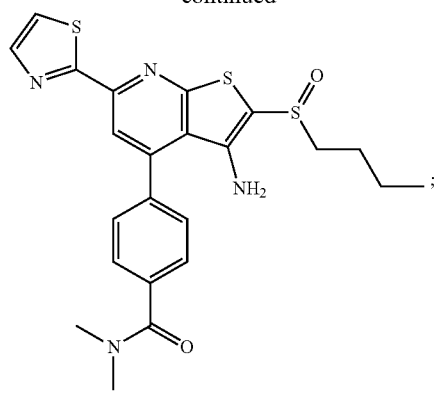
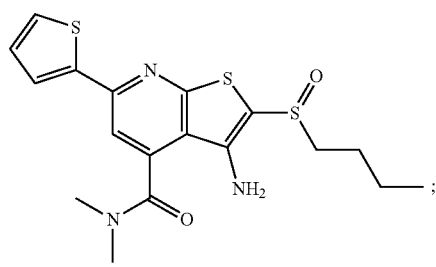
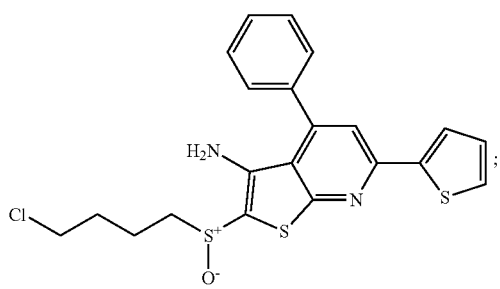
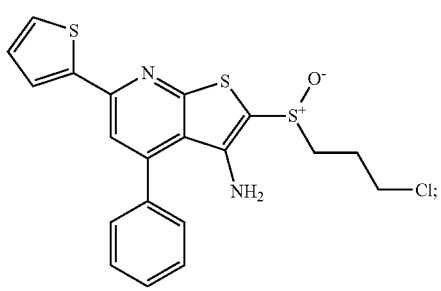
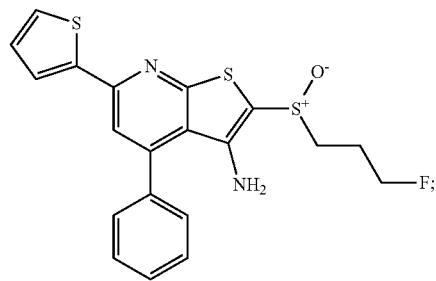
50
-continued
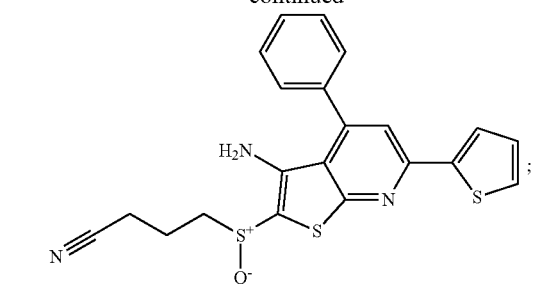
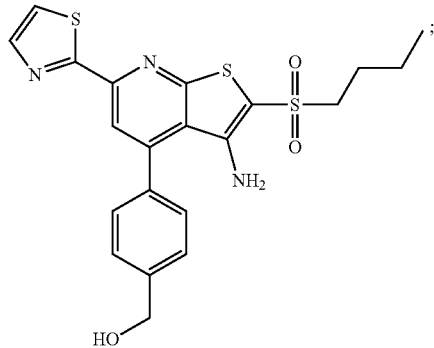
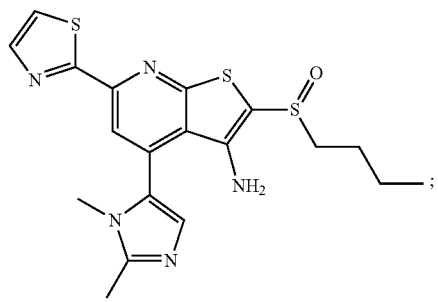
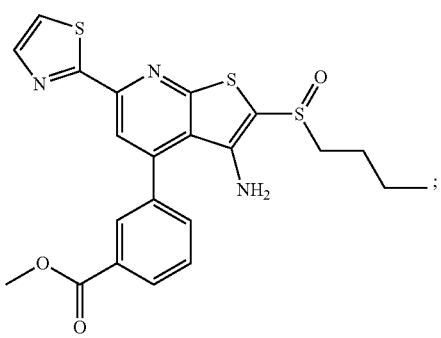
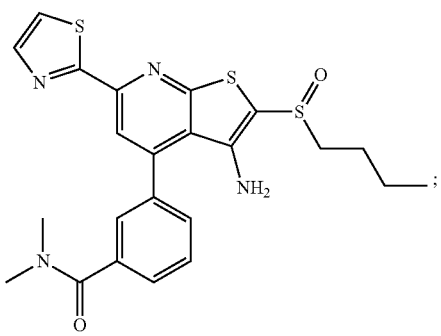

51
-continued
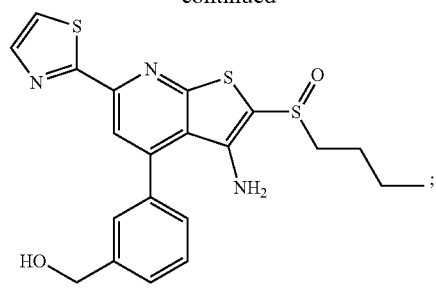
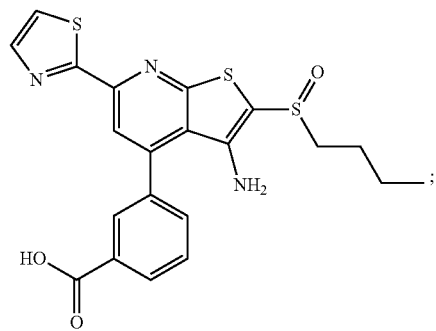
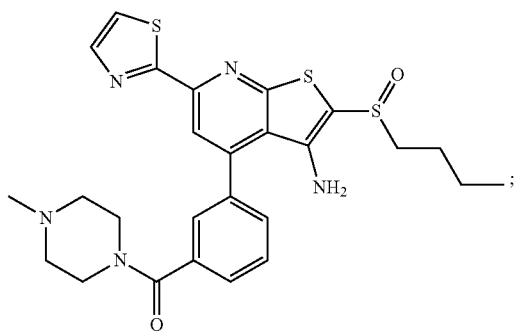
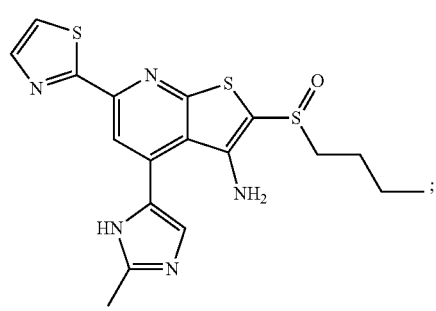
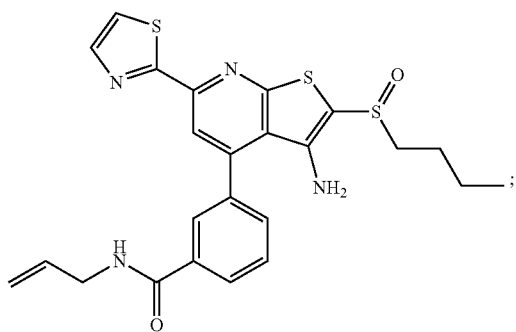
52
-continued
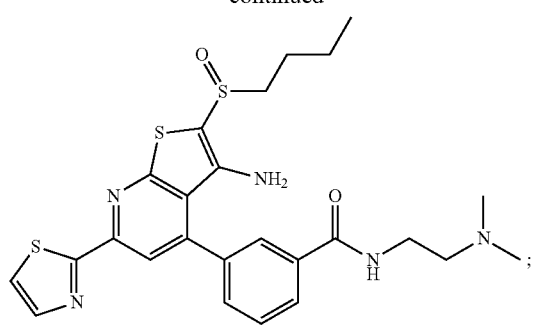
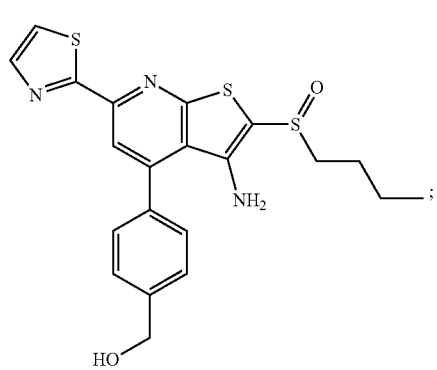
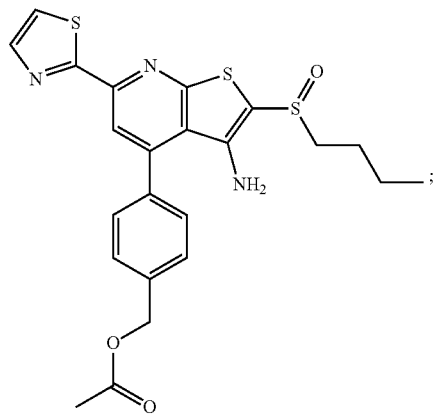
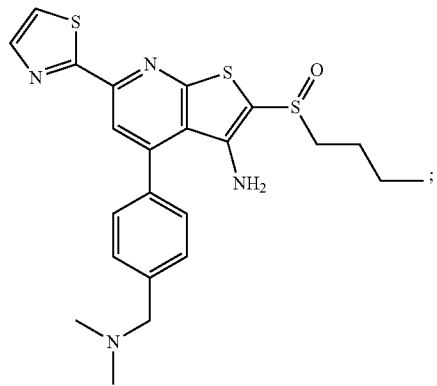

53
-continued
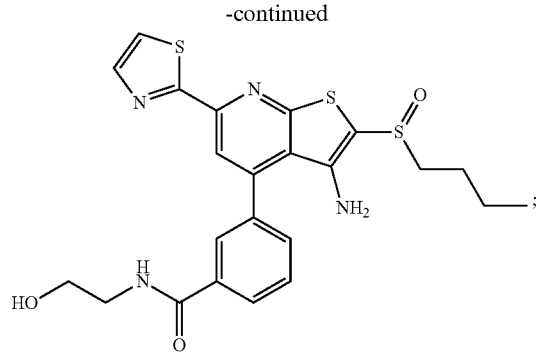
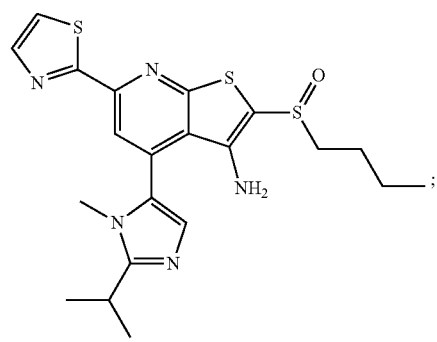
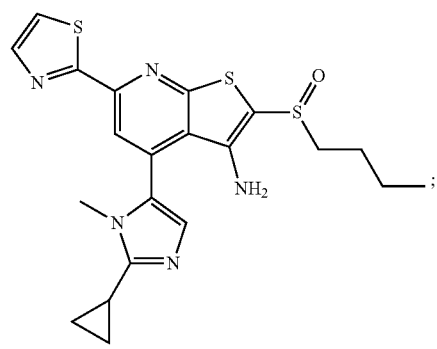
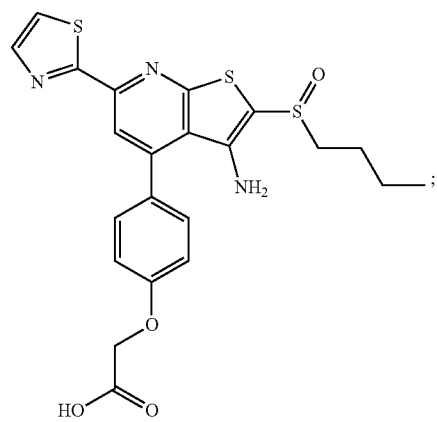
54
-continued
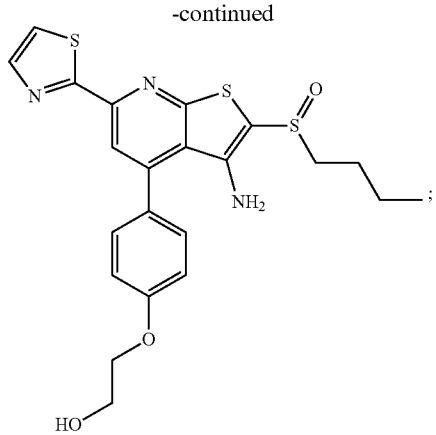
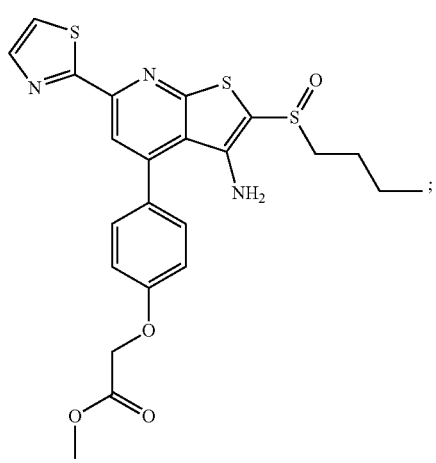
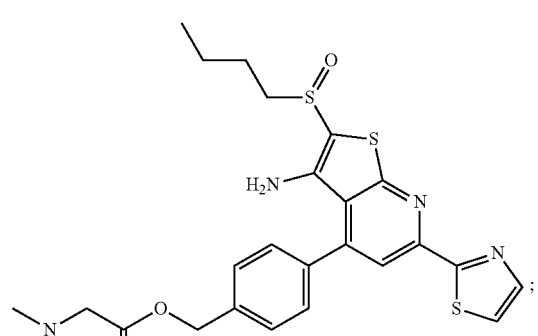
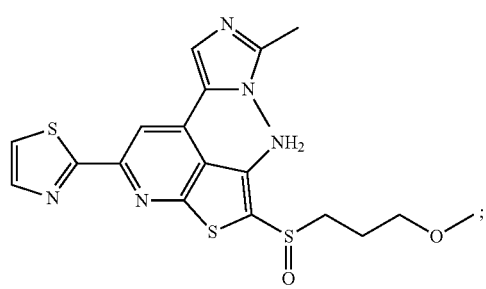

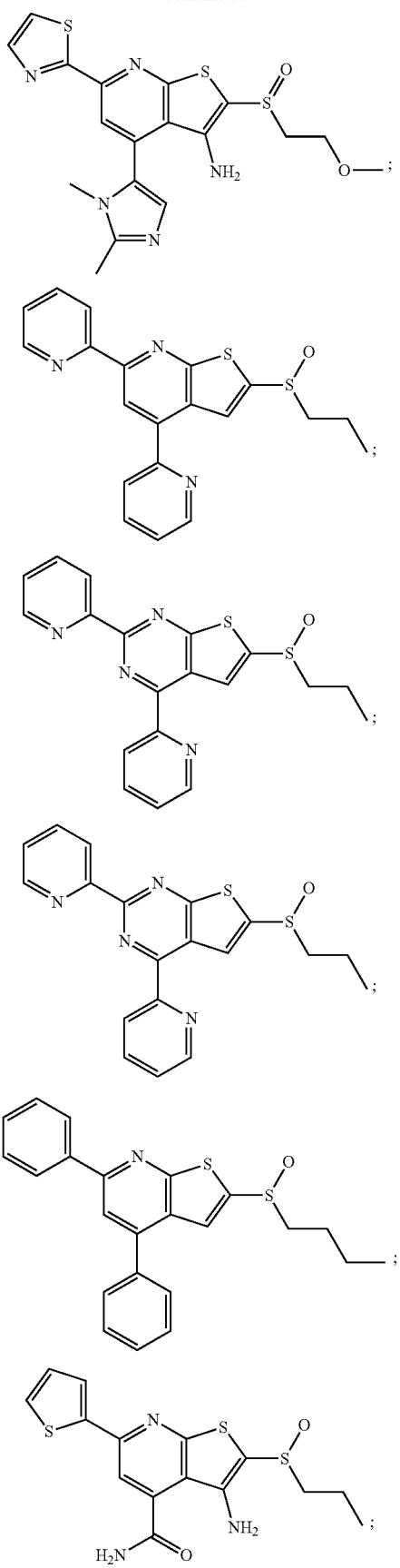
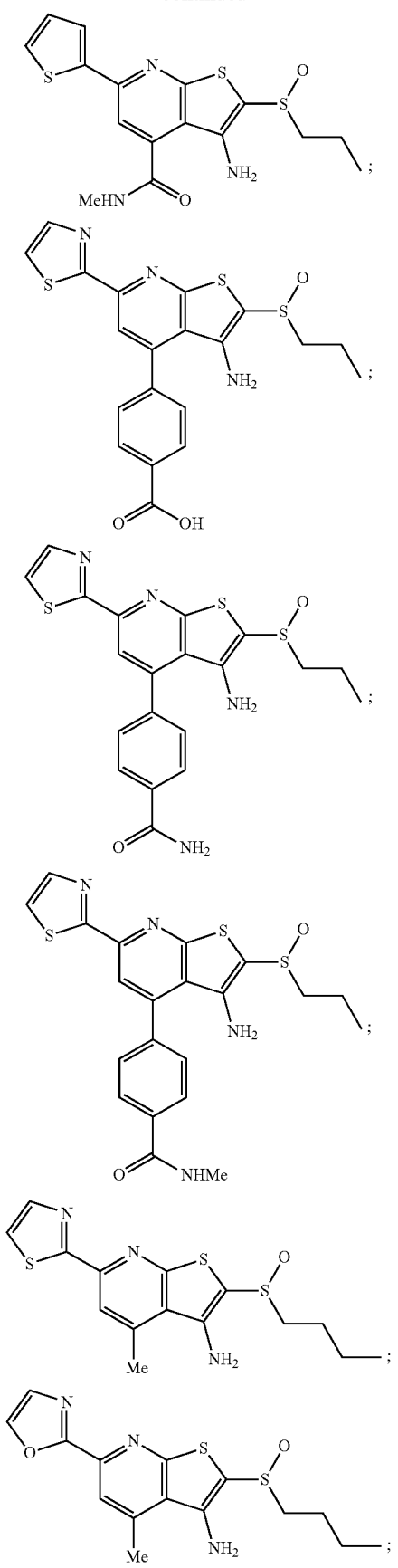

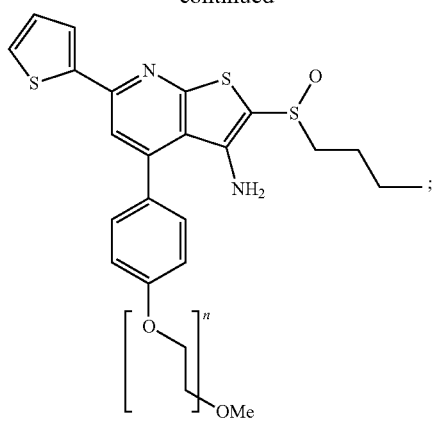
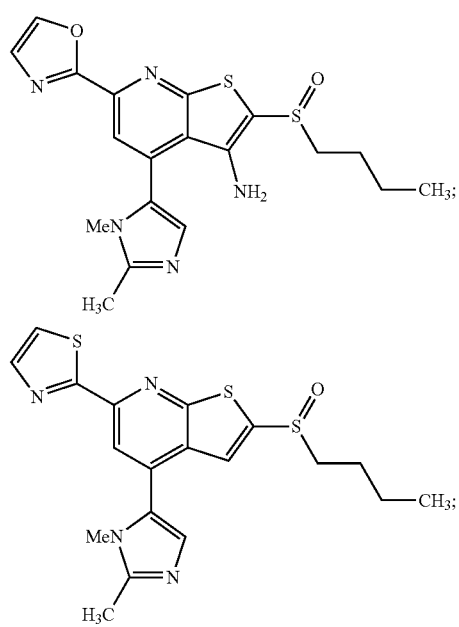
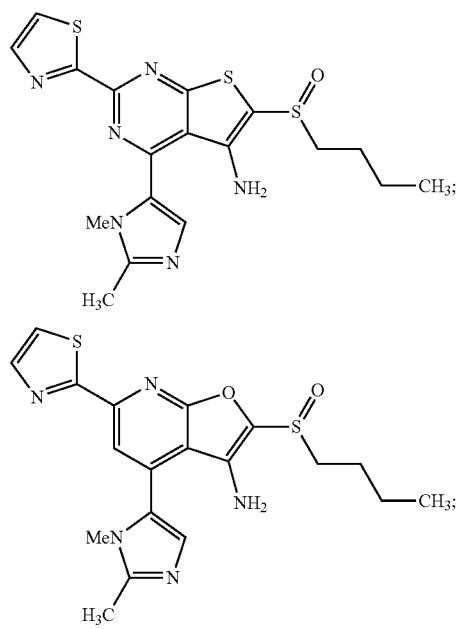
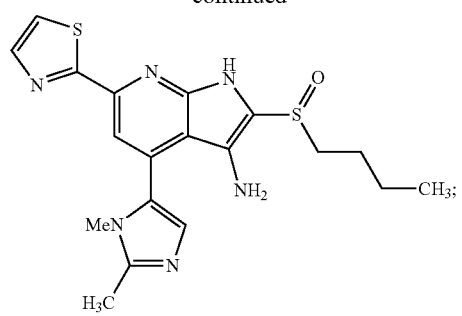
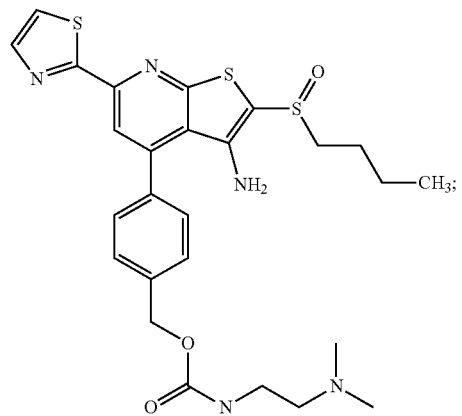
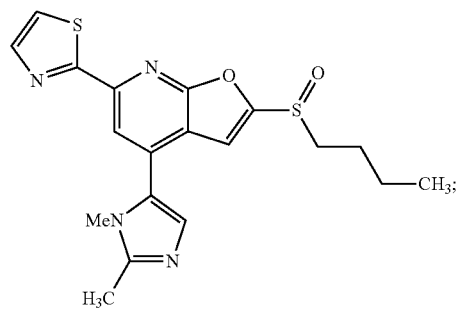
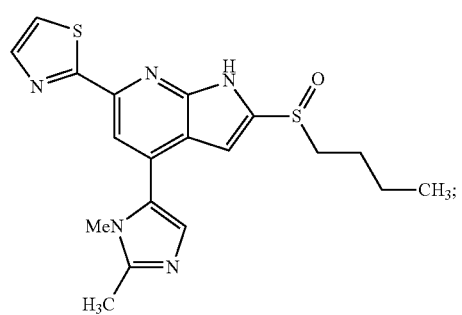

59
-continued
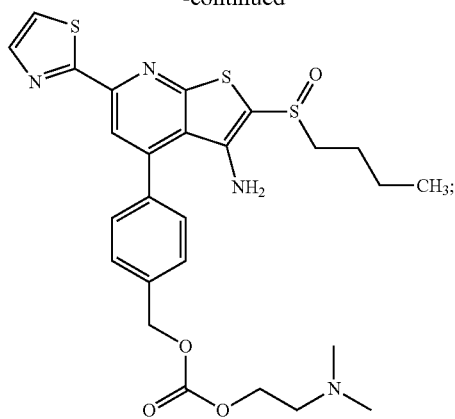
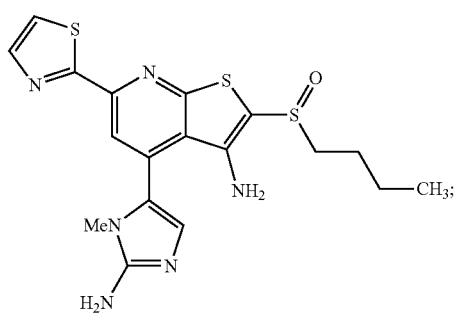
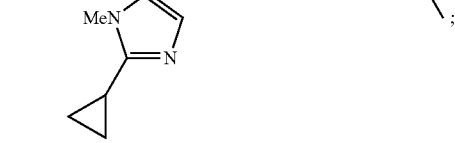
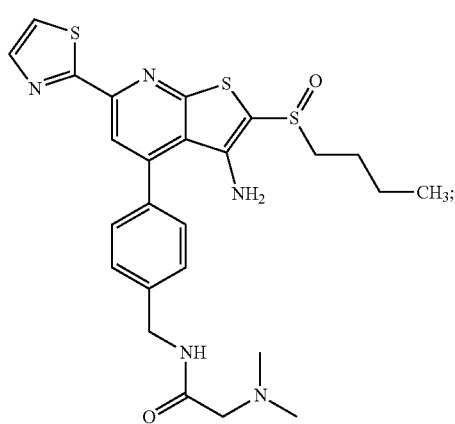
60
-continued
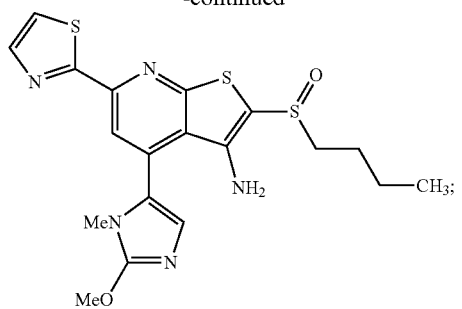
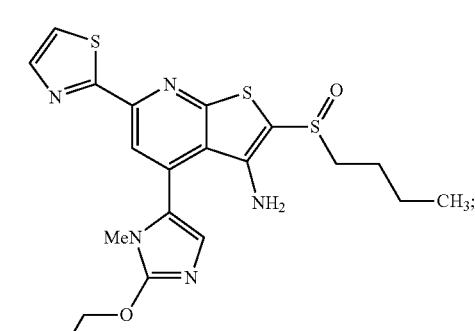
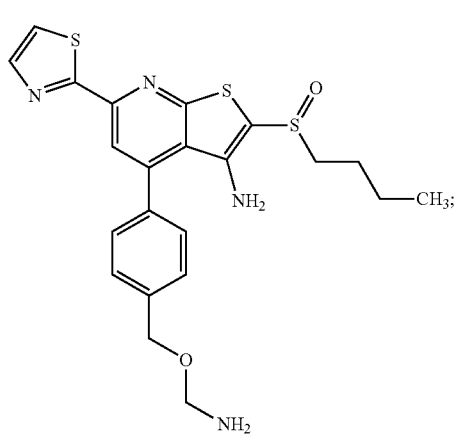

61
-continued
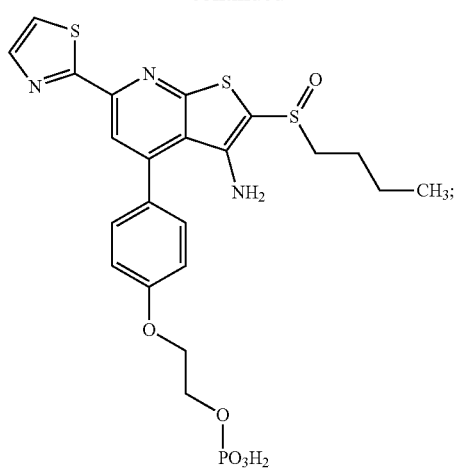
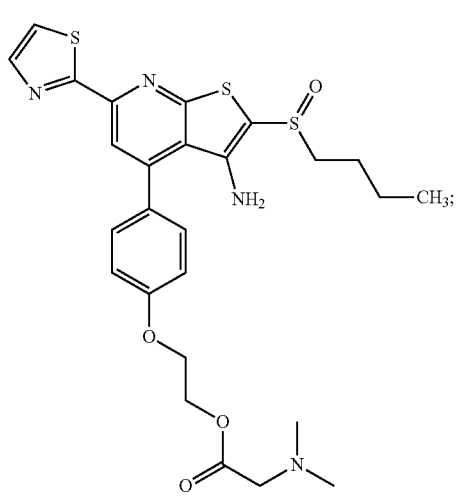
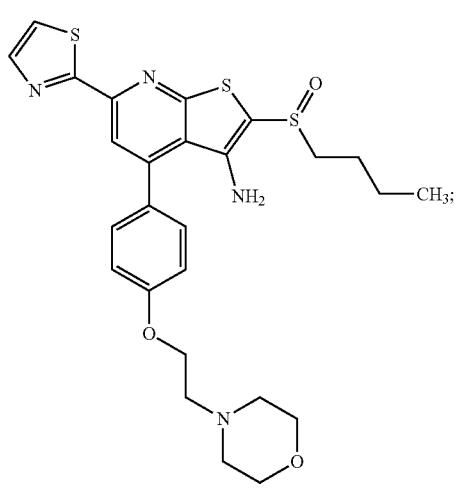
62
-continued
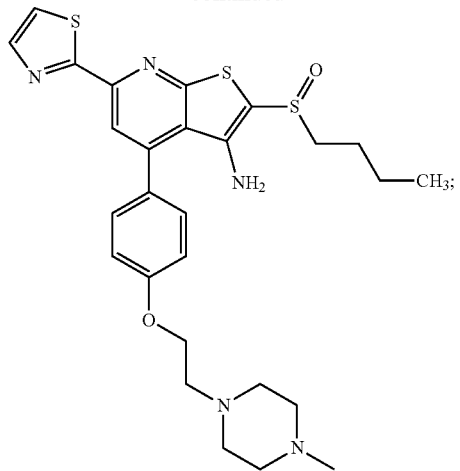
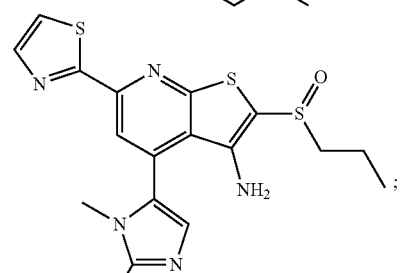
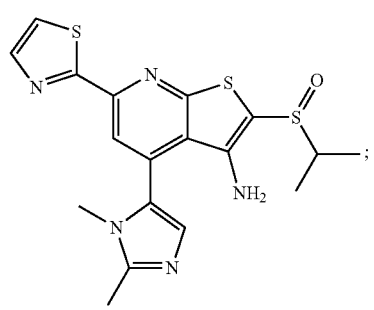
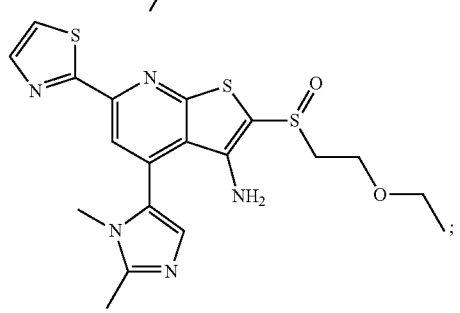
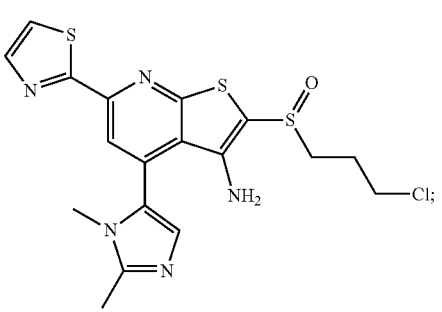

63
-continued
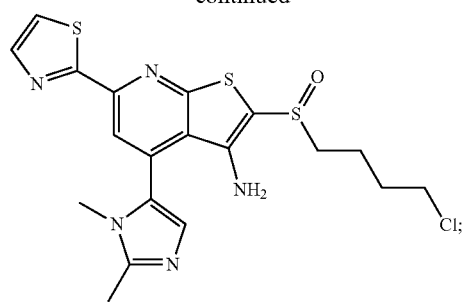
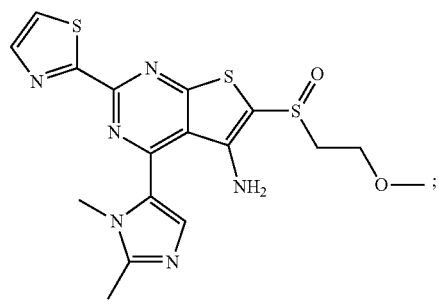
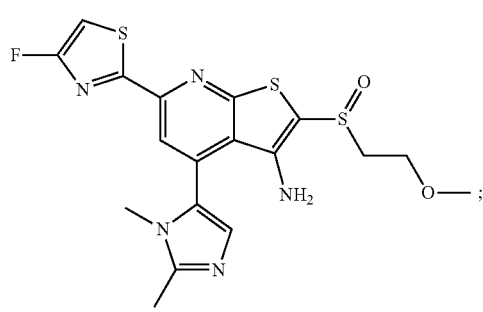
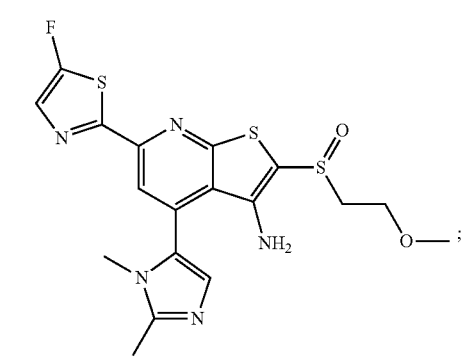
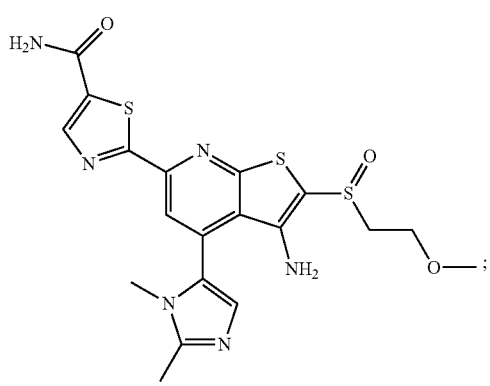
64
-continued
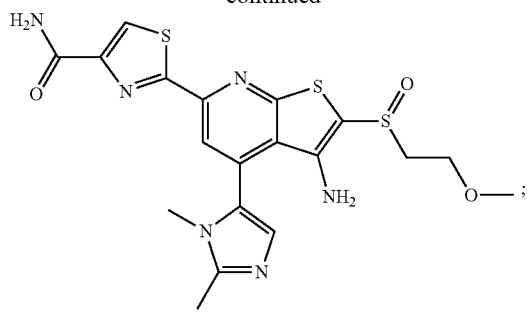
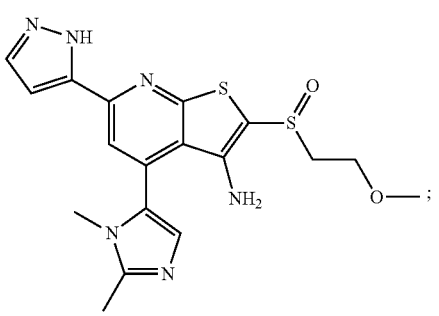
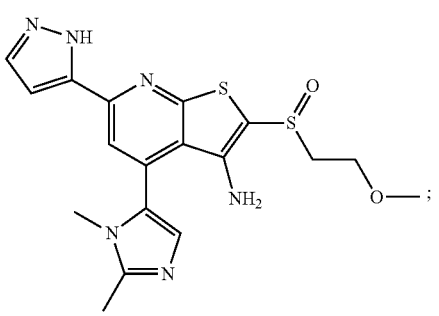
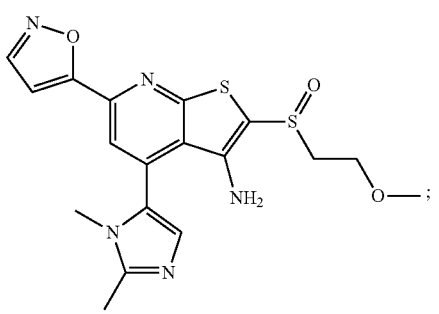
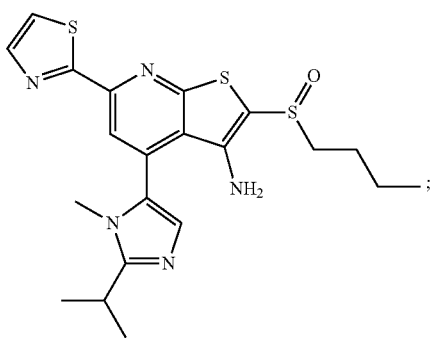
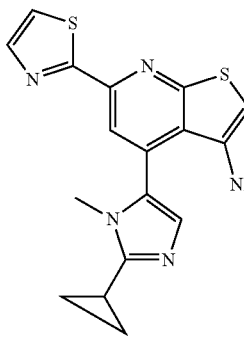

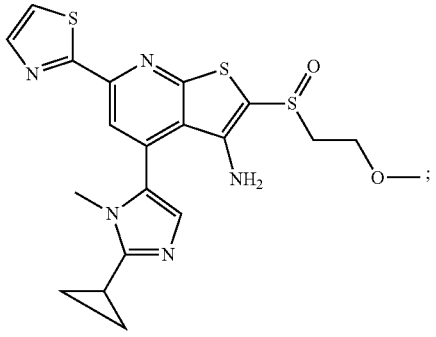

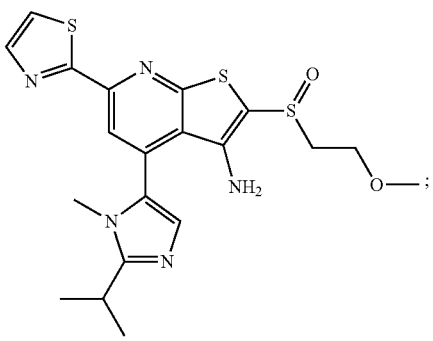

and pharmaceutically acceptable salts thereof.

In still other embodiments, $R^6$ and $R^7$ can independently be a group that improves aqueous solubility, for example, a phosphate ester (—OPO$_3$H$_2$), a phenyl ring linked to a phosphate ester (—OPO$_3$H$_2$), a phenyl ring substituted with one or more methoxyethoxy groups, or a morpholine, or an aryl or heteroaryl ring substituted with such a group.

In other embodiments, the 15-PGDH inhibitor can include a compound having the following formula (X):

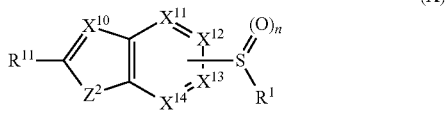

wherein n is 0-2

$R^1$ and $R^{11}$ are the same or different and are one or more substituent selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO2NR2 where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH2, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]m), phosphates, phosphate esters [—OP(O)(OR)$_2$ where R=H, methyl or other alkyl], groups incorporating amino acids or other moieties expected to bear positive or negative charge at physiological pH, and combinations thereof;

$X^{10}$, $X^{11}$, $X^{12}$, $X^{13}$, and $X^{14}$ are independently N or CR$^c$, wherein R$^c$ is H or a $C_{1-8}$ alkyl, which is linear, branched, or cyclic, and which is unsubstituted or substituted, and wherein at least one of $X^{11}$, $X^{12}$, $X^{13}$, and $X^{14}$ is CR$^c$;

$Z^2$ is O, S, CR$^a$R$^b$ or NR$^a$, wherein R$^a$ and R$^b$ are independently H or a $C_{1-8}$ alkyl, which is linear, branched, or cyclic, and which is unsubstituted or substituted; and pharmaceutically acceptable salts thereof.

Examples of 15-PGDH inhibitors having formulas (X) include the following compounds:

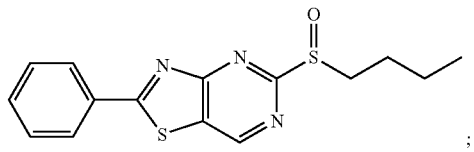

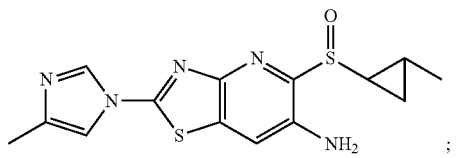

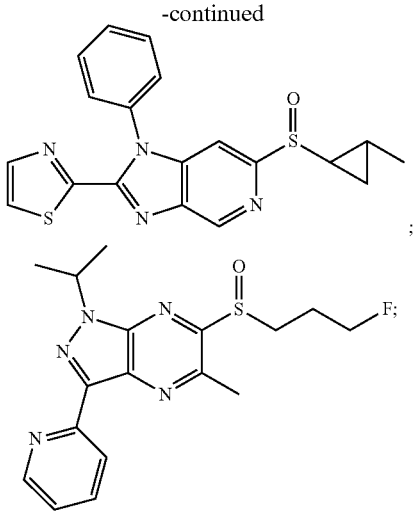

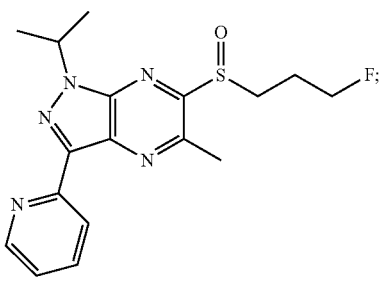

and
pharmaceutically acceptable salts thereof.

In certain embodiments, the 15-PGDH inhibitor having formula (V), (V₁), and (X) can be selected that can ia) at 2.5 μM concentration, stimulate a Vaco503 reporter cell line expressing a 15-PGDH luciferase fusion construct to a luciferase output level of greater than 70 (using a scale on which a value of 100 indicates a doubling of reporter output over baseline); iia) at 2.5 μM concentration stimulate a V9m reporter cell line expressing a 15-PGDH luciferase fusion construct to a luciferase output level of greater than 75; iiia) at 7.5 μM concentration stimulate a LS174T reporter cell line expressing a 15-PGDH luciferase fusion construct to a luciferase output level of greater than 70; and iva) at 7.5 μM concentration, does not activate a negative control V9m cell line expressing TK-*renilla* luciferase reporter to a level greater than 20; and va) inhibits the enzymatic activity of recombinant 15-PGDH protein at an $IC_{50}$ of less than 1 μM In other embodiments, the 15-PGDH inhibitor can ib) at 2.5 μM concentration, stimulate a Vaco503 reporter cell line expressing a 15-PGDH luciferase fusion construct to increase luciferase output; iib) at 2.5 μM concentration stimulate a V9m reporter cell line expressing a 15-PGDH luciferase fusion construct to increase luciferase output; iiib) at 7.5 μM concentration stimulate a LS174T reporter cell line expressing a 15-PGDH luciferase fusion construct to increase luciferase output; ivb) at 7.5 μM concentration, does not activate a negative control V9m cell line expressing TK-*renilla* luciferase reporter to a luciferase level greater than 20% above background; and vb) inhibits the enzymatic activity of recombinant 15-PGDH protein at an $IC_{50}$ of less than 1 μM.

In other embodiments, the 15-PGDH inhibitor can inhibit the enzymatic activity of recombinant 15-PGDH at an $IC_{50}$ of less than 1 μM, or preferably at an $IC_{50}$ of less than 250 nM, or more preferably at an $IC_{50}$ of less than 50 nM, or more preferably at an $IC_{50}$ of less than 10 nM, or more preferably at an $IC_{50}$ of less than 5 nM at a recombinant 15-PGDH concentration of about 5 nM to about 10 nM.

In other embodiments, the 15-PGDH inhibitor can increase the cellular levels of PGE-2 following stimulation of an A459 cell with an appropriate agent, for example IL1-beta.

In some embodiments, a 15-PGDH inhibitor having formula (V) can include a compound with the following formula (XIII):

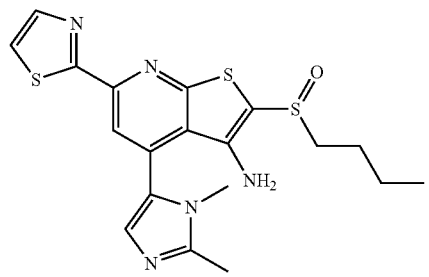

and pharmaceutically acceptable salts thereof.

Advantageously, the 15-PGDH inhibitor having formula (XIII) was found to: i) inhibit recombinant 15-PGDH at 3 nM concentration when enzyme concentration was approximately 6 nM; ii) increase $PGE_2$ production by cell lines with an EC50 of around 20 nM; iii) is chemically stable in aqueous solutions over broad pH range; iv) is chemically stable when incubated with mouse, rat and human liver extracts, v) shows 33 minutes plasma half-life when injected IP into mice; viii) shows no immediate toxicity over 24 hours when injected IP into mice at 50 mg/kg body weight, and ix) is soluble in water (pH=3) at 1 mg/mL; ix) elevates PGE2 levels in the colon, lung, liver and bone marrow following an IP dose of 10 mg/kg body weight; x) increases homing of hematopoietic stem cells following bone marrow transplantation to a mouse when administered at 10 mg/kg body weight.

In other embodiments, a 15-PGDH inhibitor having formula (XIII) can include a compound with the following formula (XIIIa):

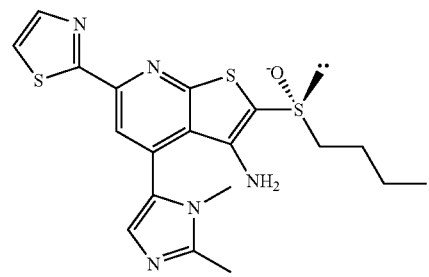

and pharmaceutically acceptable salts thereof.

In still other embodiments, a 15-PGDH inhibitor having formula (XIII) can include a compound with the following formula (XIIIb):

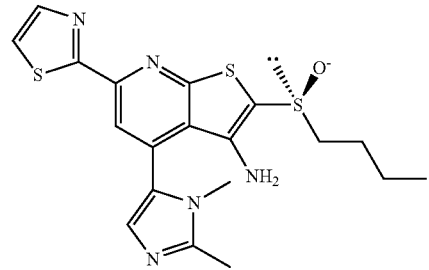

and pharmaceutically acceptable salts thereof.

In other embodiments, the 15-PDHG inhibitor can comprise a (+) or (−) optical isomer of a 15-PGDH inhibitor having formula (XIII). In still other embodiments, the 15-PDHG inhibitor can comprise a mixture at least one of a (+) or (−) optical isomer of a 15-PGDH inhibitor having formula (XIII). For example, the 15-PGDH inhibitor can comprise a mixture of: less than about 50% by weight of the (−) optical isomer of a 15-PGDH inhibitor having formula (XIII) and greater than about 50% by weight of the (+) optical isomer of a 15-PGDH inhibitor having formula (XIII), less than about 25% by weight of the (−) optical isomer of a 15-PGDH inhibitor having formula (XIII) and greater than about 75% by weight of the (+) optical isomer of a 15-PGDH inhibitor having formula (XIII), less than about 10% by weight of the (−) optical isomer of a 15-PGDH inhibitor having formula (XIII) and greater than about 90% by weight of the (+) optical isomer of a 15-PGDH inhibitor having formula (XIII), less than about 1% by weight of the (−) optical isomer of a 15-PGDH inhibitor having formula (XIII) and greater than about 99% by weight of the (+) optical isomer of a 15-PGDH inhibitor having formula (XIII), greater than about 50% by weight of the (−) optical isomer of a 15-PGDH inhibitor having formula (XIII) and less than about 50% by weight of the (+) optical isomer of a 15-PGDH inhibitor having formula (XIII), greater than about 75% by weight of the (−) optical isomer of a 15-PGDH inhibitor having formula (XIII) and less than about 25% by weight of the (+) optical isomer of a 15-PGDH inhibitor having formula (XIII), greater than about 90% by weight of the (−) optical isomer of a 15-PGDH inhibitor having formula (XIII) and less than about 10% by weight of the (+) optical isomer of a 15-PGDH inhibitor having formula (XIII), or greater than about 99% by weight of the (−) optical isomer of a 15-PGDH inhibitor having formula (XIII) and less than about 1% by weight of the (+) optical isomer of a 15-PGDH inhibitor having formula (XIII).

In a still further embodiment, the 15-PGDH inhibitor can consist essentially of or consist of the (+) optical isomer of a 15-PGDH inhibitor having formula (XIII). In yet another embodiment, the PGDH inhibitor can consist essentially of or consist of the (−) optical isomer of a 15-PGDH inhibitor having formula (XIII).

The 15-PGDH inhibitors described herein can be used for the prevention or the treatment of diseases that are associated with 15-PGDH and/or decreased prostaglandin levels and/or where it desirable to increase prostaglandin levels in the subject. For example, as discussed above, it is known that prostaglandins play an important role in hair growth. Specifically, internal storage of various types ($A_2$, $F_{2\alpha}$, $E_2$) of prostaglandins in the various compartments of hair follicles or their adjacent skin environments has been shown to be essential in maintaining and increasing hair density (Colombe L et. al, 2007, Exp. Dermatol, 16(9), 762-9). It has been reported that 15-PGDH, which is involved in the degradation of prostaglandins is present in the hair follicle dermal papillae, inactivates prostaglandins, especially, $PGF_{2\alpha}$ and $PGE_2$, to cause scalp damage and alopecia (Michelet J F et. al., 2008, Exp. Dermatol, 17(10), 821-8). Thus, the compounds described herein, which have a suppressive or inhibitory activity against 15-PGDH that degrades prostaglandins, can improve scalp damage, prevent alopecia and promote hair growth and be used in a pharmaceutical composition for the prevention of alopecia and the promotion of hair growth.

In other embodiments, the 15-PGDH inhibitors described herein can be used in a pharmaceutical composition for promoting and/or inducing and/or stimulating pigmentation of the skin and/or skin appendages, and/or as an agent for preventing and/or limiting depigmentation and/or whitening of the skin and/or skin appendages, in particular as an agent for preventing and/or limiting canities.

In some embodiments, the 15-PGDH inhibitor can be applied to skin of a subject, e.g., in a topical application, to promote and/or stimulate pigmentation of the skin and/or hair growth, inhibit hair loss, and/or treat skin damage or inflammation, such as skin damage caused by physical or chemical irritants and/or UV-exposure.

In still other embodiments, the 15-PGDH inhibitors described herein can be used in a pharmaceutical composition for the prevention or the treatment of cardiovascular disease and/or diseases of vascular insufficiency, such as Raynaud's disease, Buerger's disease, diabetic neuropathy, and pulmonary artery hypertension. Prostaglandins including prostaglandin homologues produced in the body have been known to maintain the proper action of the blood vessel wall, especially to contribute to vasodilation for blood flow, preventing platelet aggregation and modulating the proliferation of smooth muscle that surrounds blood vessel walls (Yan. Cheng et. al., 2006, J. Clin., Invest). In addition, the inhibition of prostaglandins production or the loss of their activity causes the degeneration of the endothelium in the blood vessel walls, platelet aggregation and the dysfunction of cellular mechanism in the smooth muscle. Among others, the production of prostaglandins in blood vessels was shown to be decreased in hypertension patients, including pulmonary artery hypertension.

In other embodiments, the 15-PGDH inhibitors described herein can be used in a pharmaceutical composition for the prevention or the treatment of oral, intestinal, and/or gastrointestinal injury or diseases, or inflammatory bowel disease, such as oral ulcers, gum disease, gastritis, colitis, ulcerative colitis, and gastric ulcers. Gastritis and gastric ulcer, representatives of the gastrointestinal diseases, are defined as the conditions where gastrointestinal mucus membrane is digested by gastric acid to form ulcer. In the stomach walls generally consisting of mucosa, submucosa, muscle layer and serosa, gastric ulcer even damages submucosa and muscle layer, while gastritis damages mucosa only. Although the morbidity rates of gastritis and gastric ulcer are relatively high, the causes thereof have not been clarified yet. Until now, they are known to be caused by an imbalance between aggressive factors and defensive factors, that is, the increase in aggressive factors such as the increase in gastric acid or pepsin secretion, or the decrease in defensive factors such as structural or morphological deficit of the gastric mucus membrane, the decrease in mucus and bicarbonate ion secretion, the decrease in prostaglandin production, or the like.

Currently available therapeutic agents for gastritis and gastric ulcer comprise various drugs for strengthening the defensive factors such as an antacid, which does not affect, gastric acid secretion but neutralizes gastric acid that has been already produced, an inhibitor of gastric acid secretion, a promoter of prostaglandin secretion, and a coating agent for stomach walls. Especially, prostaglandins are known to be essential in maintaining the mechanism for protecting and defending gastric mucus membrane (Wallace J L., 2008, Physiol Rev., 88(4), 1547-65, S. J. Konturek et al., 2005, Journal of Physiology and Pharmacology, 56(5)). In view of the above, since the 15-PGDH inhibitors described herein show a suppressive or inhibitory activity against 15-PGDH, which degrades prostaglandins that protect gastric mucus membrane, they can be effective for the prevention or the treatment of gastrointestinal diseases, inter alia, gastritis and gastric ulcer.

Moreover, 15-PGDH inhibitors would also be expected to protect from other form of intestinal injury that would include toxicity from radiation, toxicity from chemotherapy, and chemotherapy induced mucositis.

In the kidney, prostaglandins modulate renal blood flow and may serve to regulate urine formation by both renovascular and tubular effects. In clinical studies, $PGE_1$ has been used to improve creatinine clearance in patients with chronic renal disease, to prevent graft rejection and cyclosporine toxicity in renal transplant patients, to reduce the urinary albumin excretion rate and N-acetyl-beta-D-glucosaminidase levels in patients with diabetic nephropathy (see Porter, Am., 1989, J. Cardiol., 64: 22E-26E). In addition, U.S. Pat. No. 5,807,895 discloses a method of preventing renal dysfunction by intravenous administration of prostaglandins such as $PGE_1$, $PGE_2$ and $PGI_2$. Furthermore, it has been reported that prostaglandins serve as vasodilators in the kidney, and, thus, the inhibition of prostaglandin production in the kidney results in renal dysfunction (Hao. C M, 2008, Annu Rev Physiol, 70, 357.about.77).

Thus, the 15-PGDH inhibitors described herein, which have a suppressive or inhibitory activity against 15-PGDH that degrades prostaglandins, may be effective in the prevention or the treatment of renal diseases that are associated with renal dysfunction.

The term "renal dysfunction" as used herein includes such manifestations as follows: lower than normal creatinine clearance, lower than normal free water clearance, higher than normal blood urea, nitrogen, potassium and/or creatinine levels, altered activity of kidney enzymes such as gamma glutamyl synthetase, alanine phosphatidase, N-acetyl-beta-D-glucosaminidase, or beta-w-microglobulin; and increase over normal levels of macroalbuminuria.

Prostaglandins including $PGE_1$, $PGE_2$ and $PGF_{2a}$ have also been shown to stimulate bone resorption and bone formation to increase the volume and the strength of the bone (H. Kawaguchi et. al., Clinical Orthop. Rel. Res., 313, 1995; J. Keller et al., Eur. Jr. Exp. Musculoskeletal Res., 1, 1992, 8692). Considering that 15-PGDH inhibits the activities of prostaglandins as mentioned in the above, the inhibition of 15-PGDH activity may lead to the promotion of bone resorption and bone formation that are inhibited by 15-PGDH. Thus, the 15-PGDH inhibitors described herein can be effective for the promotion of bone resorption and bone formation by inhibiting 15-PGDH activity. 15-PGDH inhibitors can also be used to increase bone density, treat osteoporosis, promote healing of fractures, or promote healing after bone surgery or joint replacement, or to promote healing of bone to bone implants, bone to artificial implants, dental implants, and bone grafts.

In yet other embodiments, the 15-PGDH inhibitors described herein can effective for treating 15-PGDH expressing cancers. Inhibition of 15-PGDH can inhibit the growth, proliferation, and metastasis of 15-PGDH expressing cancers.

In still other embodiments, the 15-PGDH inhibitors described herein can be effective for wound healing. Among various prostaglandins, $PGE_2$ is known to serve as a mediator for wound healing. Therefore, when skin is injured by wounds or burns, the inhibition of 15-PGDH activity can produce the treatment effect of the wounds or the burns by $PGE_2$.

Additionally, as discussed above, increased prostaglandin levels have been shown to stimulate signaling through the Wnt signaling pathway via increased beta-catenin mediated transcriptional activity. Wnt signaling is known to be a key pathway employed by tissue stem cells. Hence, 15-PGDH inhibitors described herein may be utilized to increase tissue stem cell numbers for purposes that would include promoting tissue regeneration or repair in organs that would include liver, colon, and bone marrow. In addition, 15-PGDH inhibitors described herein may be utilized to promote tissue regeneration or repair in additional organs that would include but are not limited to brain, eye, cornea, retina, lung, heart, stomach, small intestine, pancreas, beta-cells of the pancreas, kidney, bone, cartilage, peripheral nerve.

Syndromic conditions, traumatic injuries, chronic conditions, medical interventions, or other conditions that cause or are associated with tissue damage and a need for tissue repair, and thus, suitable for treatment or amelioration using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetes, diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with tissue damage and a need for tissue repair suitable for treatment or amelioration using the methods of the present invention, include, ischemia resulting from surgery, chemotherapy, radiation therapy, or cell, tissue, or organ transplant or graft.

In various embodiments, the methods of the invention are suitable for treating cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia, and the like.

In some embodiments, the ischemia is associated with at least one of acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

In some embodiments, the 15-PGDH inhibitor can be administered to a preparation of hematopoietic stem cells, such as peripheral blood hematopoietic stem cells or umbilical cord stem cells of the subject, to increase the fitness of the stem cell preparation as a donor graft or to decrease the number of units of umbilical cord blood required for transplantation.

Hematopoietic stem cells are multipotent stem cells that give rise to all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al, U.S. Pat. No. 5,635,387; McGlave, et al, U.S. Pat. No. 5,460,964; Simmons, P., et al, U.S. Pat. No. 5,677,136; Tsukamoto, et al, U.S. Pat. No. 5,750,397; Schwartz, et al, U.S. Pat. No. 5,759,793; DiGuisto, et al, U.S. Pat. No. 5,681,599; Tsukamoto, et al, U.S. Pat. No. 5,716,827). Hematopoietic stem cells (HSCs) give rise to committed hematopoietic progenitor cells (HPCs) that are capable of generating the entire repertoire of mature blood cells over the lifetime of an organism.

Hematopoietic stem cells and hematopoietic progenitor cells are described herein generally as hematopoietic stem cells unless noted otherwise and can refer to cells or populations identified by the presence of the antigenic marker CD34 (CD34$^+$). In some embodiments, the hematopoietic stem cells can be identified by the presence of the antigenic marker CD34 and the absence of lineage (lin) markers and are therefore characterized as CD34$^+$/lin$^-$ cells.

The hematopoietic stem cells used in the methods described herein may be obtained from any suitable source of hematopoietic stem and progenitor cells and can be provided as a high purified population of hematopoietic stem cells or as composition that includes about 0.01% to about 100% of hematopoietic stem cells. For example, hematopoietic stem cells may be provided in compositions, such as unfractionated bone marrow (where the hematopoiectic stem cells comprise less than about 1% of the bone marrow cell population), umbilical cord blood, placental blood, placenta, fetal blood, fetal liver, fetal spleen, Wharton's jelly, or mobilized peripheral blood.

Suitable sources of hematopoietic stem cells can be isolated or obtained from an organ of the body containing cells of hematopoietic origin. The isolated cells can include cells that are removed from their original environment. For example, a cell is isolated if it is separated from some or all of the components that normally accompany it in its native state. For example, an "isolated population of cells," an "isolated source of cells," or "isolated hematopoietic stem cells" and the like, as used herein, refer to in vitro or ex vivo separation of one or more cells from their natural cellular environment, and from association with other components of the tissue or organ, i.e., it is not significantly associated with in vivo substances.

Hematopoiectic stem cells can be obtained or isolated from bone marrow of adults, which includes femurs, hip, ribs, sternum, and other bones. Bone marrow aspirates containing hematopoiectic stem cells can be obtained or isolated directly from the hip using a needle and syringe. Other sources of hematopoietic stem cells include umbilical cord blood, placental blood, mobilized peripheral blood, Wharton's jelly, placenta, fetal blood, fetal liver, or fetal spleen. In particular embodiments, harvesting a sufficient quantity of hematopoietic stem cells for use in therapeutic applications may require mobilizing the stem and progenitor cells in the donor.

"Hematopoietic stem cell mobilization" refers to the release of stem cells from the bone marrow into the peripheral blood circulation for the purpose of leukapheresis, prior to stem cell transplantation. By increasing the number of stem cells harvested from the donor, the number of stem cells available for therapeutic applications can be significantly improved. Hematopoietic growth factors, e.g., granulocyte colony stimulating factor (G-CSF) or chemotherapeutic agents often are used to stimulate the mobilization. Commercial stem cell mobilization drugs exist and can be used in combination with G-CSF to mobilize sufficient quantities of hematopoietic stem and progenitor cells for transplantation into a subject. For example, G-CSF and Mozobil (Genzyme Corporation) can be administered to a donor in order to harvest a sufficient number of hematopoietic cells for transplantation. Other methods of mobilizing hematopoietic stem cells would be apparent to one having skill in the art.

In some embodiments, hematopoietic stem and progenitor cells (HSPCs) are obtained from umbilical cord blood. Cord blood can be harvested according to techniques known in the art {see, e.g., U.S. Pat. Nos. 7,147,626 and 7,131,958, herein incorporated by reference for such methodologies).

In one embodiment, HSPCs can be obtained from pluripotent stem cell sources, e.g., induced pluripotent stem cells (iPSCs) and embryonic stem cells (ESCs). As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell. As used herein, the term "reprogramming" refers to a method of increasing the potency of a cell to a less differentiated state. As used herein, the term "programming" refers to a method of decreasing the potency of a cell or differentiating the cell to a more differentiated state.

In some embodiments, the hematopoietic stem cells can be administered or contacted ex vivo with one or more 15-PGDH inhibitors described herein to provide a therapeutic composition. In one embodiment, the therapeutic compositions of the can inlcude a population of hematopoietic stem cells treated ex vivo with a one or more 15-PGDH inhibitor. In certain embodiments, the therapeutic composition comprising the enhanced HSPCs is whole bone marrow, umbilical cord blood, or mobilized peripheral blood.

In particular embodiments, the therapeutic composition includes a population of cells, wherein the population of cells is about 95% to about 100% hematopoietic stem cells. The invention contemplates, in part, that using therapeutic compositions of highly purified hematopoietic stem cells, e.g., a composition comprising a population of cells wherein the cells comprise about 95% hematopoietic stem cells, may improve the efficiency of stem cell therapies. Currently practiced methods of transplantations typically use unfractionated mixtures of cells where hematopoietic stem cells comprise less than 1% of the total cell population.

In some embodiments, the therapeutic composition comprises a population of cells, wherein the population of cells comprises less than about 0.1%, 0.5%, 1%, 2%, 5%, 10%, 15%, 20%, 25%, or 30% hematopoietic stem cells. The population of cells in some embodiments comprises less than about 0.1%, 0.5%, 1%, 2%, 5%, 10%, 15%, 20%, 25%, or 30% hematopoietic stem cells. In other embodiments, the population of cells is about 0.1% to about 1%, about 1% to about 3%, about 3% to about 5%, about 10%-15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% hematopoietic stem cells.

Hematopoietic stem cells in the therapeutic compositions of the invention can be autologous/autogeneic ("self) or non-autologous ("non-self," e.g., allogeneic, syngeneic or xenogeneic) relative to a subject to which the therapeutic composition is to be administered. "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison.

Hematopoietic stem cells for use in the methods of the present invention may be depleted of mature hematopoietic cells such as T cells, B cells, NK cells, dendritic cells, monocytes, granulocytes, erythroid cells, and their committed precursors from bone marrow aspirate, umbilical cord blood, or mobilized peripheral blood (mobilized leukapheresis product). Mature, lineage committed cells are depleted by immunodepletion, for example, by labeling solid substrates with antibodies that bind to a panel of so-called "lineage" antigens: CD2, CD3, CD11b, CD14, CD15, CD16, CD79, CD56, CD123, and CD235a. A subsequent step can be performed to further purify the population of cells, in which a substrate labeled with antibodies that bind to the $CD34^+$ antigen are used to isolate primitive hematopoietic stem cells. Kits are commercially available for purifying stem and progenitor cells from various cell sources and in particular embodiments, these kits are suitable for use with the methods described herein.

In one embodiment, the amount of hematopoietic stem cells in the therapeutic composition is at least $0.1 \times 10^5$ cells, at least $0.5 \times 10^5$ cells, at least $1 \times 10^5$ cells, at least $5 \times 10^5$ cells, at least $10 \times 10^5$ cells, at least $0.5 \times 10^6$ cells, at least $0.75 \times 10^6$ cells, at least $1 \times 10^6$ cells, at least $1.25 \times 10^6$ cells, at least $1.5 \times 10^6$ cells, at least $1.75 \times 10^6$ cells, at least $2 \times 10^6$ cells, at least $2.5 \times 10^6$ cells, at least $3 \times 10^6$ cells, at least $4 \times 10^6$ cells, at least $5 \times 10^6$ cells, at least $10 \times 10^6$ cells, at least $15 \times 10^6$ cells, at least $20 \times 10^6$ cells, at least $25 \times 10^6$ cells, or at least $30 \times 10^6$ cells.

In one embodiment, the amount of hematopoietic stem cells in the therapeutic composition is the amount of HSPCs in a partial or single cord of blood, or is at least $0.1 \times 10^5$ cells/kg of bodyweight, at least $0.5 \times 10^5$ cells/kg of bodyweight, at least $1 \times 10^5$ cells/kg of bodyweight, at least $5 \times 10^5$ cells/kg of bodyweight, at least $10 \times 10^5$ cells/kg of bodyweight, at least $0.5 \times 10^6$ cells/kg of bodyweight, at least $0.75 \times 10^6$ cells/kg of bodyweight, at least $1 \times 10^6$ cells/kg of bodyweight, at least $1.25 \times 10^6$ cells/kg of bodyweight, at least $1.5 \times 10^6$ cells/kg of bodyweight, at least $1.75 \times 10^6$ cells/kg of bodyweight, at least $2 \times 10^6$ cells/kg of bodyweight, at least $2.5 \times 10^6$ cells/kg of bodyweight, at least $3 \times 10^6$ cells/kg of bodyweight, at least $4 \times 10^6$ cells/kg of bodyweight, at least $5 \times 10^6$ cells/kg of bodyweight, at least $10 \times 10^6$ cells/kg of bodyweight, at least $15 \times 10^6$ cells/kg of bodyweight, at least $20 \times 10^6$ cells/kg of bodyweight, at least $25 \times 10^6$ cells/kg of bodyweight, or at least $30 \times 10^6$ cells/kg of bodyweight.

Preparations of hematopoietic stem cells administered one or more 15-PGDH inhibitors and/or therapeutic compositions that include hematopoietic stem cells and one or more 15-PGDH inhibitor can be used for improving hematopoietic stem cell transplants and in treating ischemia or ischemia-damaged tissue, and in reducing further damage to ischemic tissue and/or repairing damage to ischemic tissue through cell recruitment, improving vascularization in ischemic tissue, improving tissue regeneration at sites of ischemia, decreasing ischemic tissue necrosis or apoptosis, and/or increasing cell survival at sites of ischemia. In particular embodiments, the preparations of 15-PGDH inhibitor treated hematopoietic stem cells and/or therapeutic compositions of 15-PGDH inhibitors and hematopoietic stem cells are useful to subjects in need of hematopoietic reconstitution, such as subjects that have undergone or are scheduled to undergo myeloablative therapy.

Subjects, which can be treated with the preparations of 15-PGDH inhibitor treated hematopoietic stem cells and/or therapeutic compositions of 15-PGDH inhibitors and hematopoietic stem cells, can include subjects that have or that have been diagnosed with various types of leukemias, anemias, lymphomas, myelomas, immune deficiency disorders, and solid tumors. A subject also includes a human who is a candidate for stem cell transplant or bone marrow transplantation, such as during the course of treatment for a malignant disease or a component of gene therapy. Subjects may also include individuals or animals that donate stem cells or bone marrow for allogeneic transplantation. In certain embodiments, a subject may have undergone myeloablative irradiation therapy or chemotherapy, or may have experienced an acute radiation or chemical insult resulting in myeloablation. In certain embodiments, a subject may have undergone irradiation therapy or chemotherapy, such as during various cancer treatments. Typical subjects include animals that exhibit aberrant amounts (lower or higher amounts than a "normal" or "healthy" subject) of one or more physiological activities that can be modulated by an agent or a stem cell or marrow transplant.

Subjects, which can be treated with the preparations of 15-PGDH inhibitor treated hematopoietic stem cells and/or therapeutic compositions of 15-PGDH inhibitors and hematopoietic stem cells, can also include subjects undergoing chemotherapy or radiation therapy for cancer, as well as subjects suffering from (e.g., afflicted with) non malignant blood disorders, particularly immunodeficiencies (e.g. SCID, Fanconi's anemia, severe aplastic anemia, or congenital hemoglobinopathies, or metabolic storage diseases, such as Hurler's disease, Hunter's disease, mannosidosis, among others) or cancer, particularly hematological malignancies, such as acute leukemia, chronic leukemia (myeloid or lymphoid), lymphoma (Hodgkin's or non-Hodgkin's), multiple myeloma, myelodysplastic syndrome, or non-hematological cancers such as solid tumors (including breast cancer, ovarian cancer, brain cancer, prostate cancer, lung cancer, colon cancer, skin cancer, liver cancer, or pancreatic cancer).

Subjects may also include subjects suffering from aplastic anemia, an immune disorder (severe combined immune deficiency syndrome or lupus), myelodysplasia, thalassemaia, sickle-cell disease or Wiskott-Aldrich syndrome. In some embodiments, the subject suffers from a disorder that is the result of an undesired side effect or complication of another primary treatment, such as radiation therapy, chemotherapy, or treatment with a bone marrow suppressive drug, such as zidovadine, chloramphenical or gangciclovir. Such disorders include neutropenias, anemias, thrombocytopenia, and immune dysfunction. Other subjects may have disorders caused by an infection (e.g., viral infection, bacterial infection or fungal infection) which causes damage to stem or progenitor cells of the bone marrow.

In addition, subjects suffering from the following conditions can also benefit from treatment using the preparations of 15-PGDH inhibitor treated hematopoietic stem cells and/or therapeutic compositions of 15-PGDH inhibitors and hematopoietic stem cells: lymphocytopenia, lymphorrhea, lymphostasis, erythrocytopenia, erthrodegenerative disorders, erythroblastopenia, leukoerythroblastosis; erythroclasis, thalassemia, myelodysplasia, myelofibrosis, thrombocytopenia, disseminated intravascular coagulation (DIC), immune (autoimmune) thrombocytopenic purpura (ITP), HIV inducted ITP, myelodysplasia; thrombocytotic disease, thrombocytosis, congenital neutropenias (such as Kostmann's syndrome and Schwachman-Diamond syndrome), neoplastic associated neutropenias, childhood and adult cyclic neutropaenia; post-infective neutropaenia; myelodysplastic syndrome; neutropaenia associated with chemotherapy and radiotherapy; chronic granulomatous disease; mucopolysaccharidoses; Diamond Blackfan Anemia; Sickle cell disease; or Beta thalassemia major.

In other embodiments, the preparations of 15-PGDH inhibitor treated hematopoietic stem cells and/or therapeutic compositions or 15-PGDH inhibitors and hematopoietic stem cells can be used in cell-based therapy for treating ischemic tissue or treating or ameliorating one or more symptoms associated with tissue ischemia, including, but not limited to, impaired, or loss of, organ function (including without limitation impairments or loss of brain, kidney, or heart function), cramping, claudication, numbness, tingling, weakness, pain, reduced wound healing, inflammation, skin discoloration, and gangrene.

In one embodiment, the subject exhibits at least one symptom of an ischemic tissue or tissue damaged by ischemia. In particular embodiments, the subject is a human who is has or who is at risk of having an ischemic tissue or tissue damaged by ischemia, e.g., a subject that has diabetes, peripheral vascular disease, thromboangiitis obliterans, vasculitis, cardiovascular disease, coronary artery disease or heart failure, or cerebrovascular disease, cardiovascular disease, or cerebrovascular disease.

Illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia, and thus, suitable for treatment or amelioration using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia suitable for treatment or amelioration using the methods of the present invention, include, ischemia resulting from surgery, chemotherapy, radiation therapy, or cell, tissue, or organ transplant or graft.

In various embodiments, the methods of the invention are suitable for treating cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia, and the like.

In various embodiments, the invention contemplates that the therapeutic cell compositions disclosed herein can be used to treat an ischemic tissue in which it is desirable to increase the blood flow, oxygen supply, glucose supply, or supply of nutrients to the tissue.

In some embodiments, the 15-PGDH inhibitor can be administered to a preparation of tissue stem cells, such as neural stem stems, mesenchymal stem cells, or stem cells that can generate other tissues, and/or a preparation of pluripotent stem cells.

In one embodiment, tissue stems cells can be obtained from pluripotent stem cell sources, e.g., induced pluripotent stem cells (iPSCs) and embryonic stem cells (ESCs). As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell. As used herein, the term "reprogramming" refers to a method of increasing the potency of a cell to a less differentiated state. As used herein, the term "programming" refers to a method of decreasing the potency of a cell or differentiating the cell to a more differentiated state.

In some embodiments, the tissue stem cells and/or pluripotent stem cells can be administered or contacted ex vivo with one or more 15-PGDH inhibitors described herein to provide a therapeutic composition. In one embodiment, the therapeutic compositions of the can include a population of tissue stem cells treated ex vivo with a one or more 15-PGDH inhibitor.

In particular embodiments, the therapeutic composition includes a population of cells, wherein the population of cells is about 95% to about 100% tissue stem cells. The invention contemplates, in part, that using therapeutic compositions of highly purified tissue stem cells, e.g., a composition comprising a population of cells wherein the cells comprise about 95% tissue stem cells, may improve the efficiency of stem cell therapies In some embodiments, the therapeutic composition comprises a population of cells, wherein the population of cells comprises less than about 0.1%, 0.5%, 1%, 2%, 5%, 10%, 15%, 20%, 25%, or 30% tissue stem cells. The population of cells in some embodiments comprises less than about 0.1%, 0.5%, 1%, 2%, 5%, 10%, 15%, 20%, 25%, or 30% tissue stem cells. In other embodiments, the population of cells is about 0.1% to about 1%, about 1% to about 3%, about 3% to about 5%, about 10%-15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% tissue stem cells.

Tissue stem cells in the therapeutic compositions of the invention can be autologous/autogeneic ("self") or non-autologous ("non-self," e.g., allogeneic, syngeneic or xenogeneic) relative to a subject to which the therapeutic composition is to be administered. "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison.

Preparations of tissue stem cells administered one or more 15-PGDH inhibitors and/or therapeutic compositions that include tissue stem cells and one or more 15-PGDH inhibitor can be used for improving tissue stem cell transplants and in treating damaged tissue, and in reducing further tissue damage tissue and/or potentiating repair to damaged tissue through stem cell recruitment and/or increasing cell survival at sites of tissue damage.

Syndromic conditions, traumatic injuries, chronic conditions, medical interventions, or other conditions that cause or are associated with tissue damage and a need for tissue repair, and thus, suitable for treatment or amelioration using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetes, diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with tissue damage and a need for tissue repair suitable for treatment or amelioration using the methods of the present invention, include, ischemia resulting from surgery, chemotherapy, radiation therapy, or cell, tissue, or organ transplant or graft.

In various embodiments, the methods of the invention are suitable for treating cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia, and the like.

In other embodiments, the 15-PGDH inhibitor can be administered to a bone marrow graft donor or a hematopoietic stem cell donor to increase the fitness of a donor bone marrow graft or a donor hematopoietic stem cell graft.

In other embodiments, the 15-PGDH inhibitor can also be administered to bone marrow of a subject to increase stem cells in the subject or to increase the fitness of the marrow as a donor graft.

In yet other embodiments, the 15-PGDH inhibitor can be administered to a subject to mitigate bone marrow graft rejection, to enhance bone marrow graft engraftment, to enhance engraftment of a hematopoietic stem cell graft, or an umbilical cord blood stem cell graft, to enhance engraftment of a hematopoietic stem cell graft, or an umbilical cord stem cell graft, and/or to decrease the number of units of umbilical cord blood required for transplantation into the subject. The administration can be, for example, following treatment of the subject or the marrow of the subject with radiation therapy, chemotherapy, or immunosuppressive therapy.

In other embodiments, the 15-PGDH inhibitor can be administered to a recipient of a bone marrow transplant, of a hematopoietic stem cell transplant, or of an umbilical cord blood stem cell transplant, in order to decrease the administration of other treatments or growth factors.

In some embodiments, the 15-PGDH inhibitor can be administered to a subject to enhance recovery of neutrophils following bone marrow transplantation, following umbilical cord blood transplantation, following transplantation with hematopoietic stem cells, following conventional chemotherapy, following radiation treatment, and in individuals with neutropenias from diseases that include but are not limited to aplastic anemia, myelodysplasia, myelofibrosis, neutropenias from other bone marrow diseases, drug induced neutropenia, immune neutropenias, idiopathic neutropenia, and following infections with viruses that include, but are not limited to, HIV, CMV, and parvovirus.

In other embodiments, the 15-PGDH inhibitor can be administered to a subject to enhance recovery of platelets following bone marrow transplantation, following umbilical cord blood transplantation, following transplantation with hematopoietic stem cells, following conventional chemotherapy, following radiation treatment, and in individuals with neutropenias from diseases that include but are not limited to aplastic anemia, myelodysplasia, myelofibrosis, thrombocytopenias from other bone marrow diseases, drug induced thrombocytopenia, immune thrombocytopenia, idiopathic thrombocytopenic purpura, idiopathic thrombocytopenia, and following infections with viruses that include, but are not limited to, HIV, CMV, and parvovirus.

In still other embodiments, the 15-PGDH inhibitor can be administered to a subject to enhance recovery of hemoglobin following bone marrow transplantation, following umbilical cord blood transplantation, following transplantation with hematopoietic stem cells, following conventional chemotherapy, following radiation treatment, and in individuals with anemias from diseases that include but are not limited to aplastic anemia, myelodysplasia, myelofibrosis, anemia from other bone marrow diseases, drug induced anemia, immune mediated anemias, anemia of chronic disease, idiopathic anemia, and following infections with viruses that include, but are not limited to, HIV, CMV, and parvovirus.

In some embodiments, the 15-PGDH inhibitor can be administered to a subject to enhance numbers of bone marrow stem cell numbers following bone marrow transplantation, following umbilical cord blood transplantation, following transplantation with hematopoietic stem cells, following conventional chemotherapy, following radiation treatment, in individuals with other bone marrow diseases, in individuals with cytopenias following viral infections, and in individuals with cytopenias.

In other embodiments, the 15-PGDH inhibitor can be administered to a subject to enhance response to cytokines administered to individuals with cytopenias that include but are not limited to neutropenia, thrombocytopenia, lymphocytopenia, and anemia. Cytokines whose responses may be enhanced by SW033291 include, but are not limited to: G-CSF, GM-CSF, EPO, IL-3, IL-6, TPO, SCF, and TPO-RA (thrombopoietin receptor agonist).

In further embodiments, the 15-PGDH inhibitor can be administered to a subject or to a tissue graft of a subject to mitigate graft rejection, to enhance graft engraftment, to enhance graft engraftment following treatment of the subject or the marrow of the subject with radiation therapy, chemotherapy, or immunosuppressive therapy, to confer resistance to toxic or lethal effects of exposure to radiation, confer resistance to the toxic effect of Cytoxan, the toxic effect of fludarabine, the toxic effect of chemotherapy, or the toxic effect of immunosuppressive therapy, to decrease infection, and/or to decrease pulmonary toxicity from radiation.

In other embodiments, the 15-PGDH inhibitor can be administered to a recipient of a tissue stem cell transplant, including but not limited to a transplant with hematopoietic stem cells, neural stem stems, mesenchymal stem cells, or stem cells for other tissues, so as to accelerate tissue regeneration and repair following the transplant.

Additionally, in a model organism, $PGE_2$ signaling stimulates liver regeneration and increase survival after exposure to hepatoxic agents, such as acetaminophen. Hence, 15-PGDH inhibitors described herein may be utilized to increase liver regeneration after liver resection, in other settings that include after liver surgery, after live liver donation, or after receiving a liver transplant or to increase liver regeneration and increase survival after exposures to hepatoxic agents, including but not limited to acetaminophen and similar compounds.

PGE1 analogues have also been used in the treatment of erectile dysfunction. Accordingly, in some embodiments, 15-PGDH inhibitors described herein can used either alone or combination with a prostaglandin for the treatment of erectile dysfunction.

It will be appreciated that the other 15-PGDH inhibitors can be used in the methods described described herein. These other 15-PGDH inhibitors can include known 15-PGDH inhibitors including, for example, tetrazole compounds of formulas (I) and (II), 2-alkylideneaminooxyacetamidecompounds of formula (I), heterocyclic compounds of formulas (VI) and (VII), and pyrazole compounds of formula (III) described in U.S. Patent Application Publication No. 2006/0034786 and U.S. Pat. No. 7,705,041; benzylidene-1,3-thiazolidine compounds of formula (I) described in U.S. Patent Application Publication No. 2007/0071699; phenylfurylmethylthiazolidine-2,4-dione and phenylthienylmethylthiazolidine-2,4-dione compounds described in U.S. Patent Application Publication No. 2007/0078175; thiazolidenedione derivatives described in U.S. Patent Application Publication No. 2011/0269954; phenyl-furan, phenylthiophene, or phenylpyrrazole compounds described in U.S. Pat. No. 7,294,641, 5-(3,5-disubstituted phenylazo)-2-hydroxybenzene-acetic acids and salts and lactones described in U.S. Pat. No. 4,725,676, and azo compounds described in U.S. Pat. No. 4,889,846.

The 15-PGDH inhibitors described herein can be provided in a pharmaceutical composition or cosmetic composition depending on the pathological or cosmetic condition or disorder being treated. A pharmaceutical composition containing the 15-PGDH inhibitors described herein as an active ingredient may be manufactured by mixing the derivative with a pharmaceutically acceptable carrier(s) or an excipient(s) or diluting the 15-PGDH inhibitors with a diluent in accordance with conventional methods. The pharmaceutical composition may further contain fillers, anticohesives, lubricants, wetting agents, flavoring agents, emulsifying agents, preservatives and the like. The pharmaceutical composition may be formulated into a suitable formulation in accordance with the methods known to those skilled in the art so that it can provide an immediate, controlled or sustained release of the 15-PGDH inhibitors after being administered into a mammal.

In some embodiments, the pharmaceutical composition may be formulated into a parenteral or oral dosage form. The solid dosage form for oral administration may be manufactured by adding excipient, if necessary, together with binder, disintegrants, lubricants, coloring agents, and/or flavoring agents, to the 15-PGDH inhibitors and shaping the resulting mixture into the form of tablets, sugar-coated pills, granules, powder or capsules. The additives that can be added in the composition may be ordinary ones in the art. For example, examples of the excipient include lactose, sucrose, sodium chloride, glucose, starch, calcium carbonate, kaolin, microcrystalline cellulose, silicate and the like. Exemplary binders include water, ethanol, propanol, sweet syrup, sucrose solution, starch solution, gelatin solution, carboxymethylcellulose, hydroxypropyl cellulose, hydroxypropyl starch, methylcellulose, ethylcellulose, shellac, calcium phosphonate and polypyrrolidone. Examples of the disintegrant include dry starch, sodium arginate, agar powder, sodium bicarbonate, calcium carbonate, sodium lauryl sulfate, stearic monoglyceride and lactose. Further, purified talc, stearates, sodium borate, and polyethylene glycol may be used as a lubricant; and sucrose, bitter orange peel, citric acid, tartaric acid, may be used as a flavoring agent. In some embodiments, the pharmaceutical composition can be made into aerosol formulations (e.g., they can be nebulized) to be administered via inhalation.

The 15-PGDH inhibitors described herein may be combined with flavoring agents, buffers, stabilizing agents, and the like and incorporated into oral liquid dosage forms such as solutions, syrups or elixirs in accordance with conventional methods. One example of the buffers may be sodium citrate. Examples of the stabilizing agents include tragacanth, acacia and gelatin.

In some embodiments, the 15-PGDH inhibitors described herein may be incorporated into an injection dosage form, for example, for a subcutaneous, intramuscular or intravenous route by adding thereto pH adjusters, buffers, stabilizing agents, relaxants, topical anesthetics. Examples of the pH adjusters and the buffers include sodium citrate, sodium acetate and sodium phosphate. Examples of the stabilizing agents include sodium pyrosulfite, EDTA, thioglycolic acid and thiolactic acid. The topical anesthetics may be procaine HCl, lidocaine HCl and the like. The relaxants may be sodium chloride, glucose and the like.

In other embodiments, the 15-PGDH inhibitors described herein may be incorporated into suppositories in accordance with conventional methods by adding thereto pharmaceutically acceptable carriers that are known in the art, for example, polyethylene glycol, lanolin, cacao butter or fatty acid triglycerides, if necessary, together with surfactants such as Tween.

The pharmaceutical composition may be formulated into various dosage forms as discussed above and then administered through various routes including an oral, inhalational, transdermal, subcutaneous, intravenous or intramuscular route. The dosage can be a pharmaceutically effective amount. The pharmaceutically effective amount can be an amount of the 15-PGDH inhibitor to treat or improve alopecia, cardiovascular disease, gastrointestinal disease, wounds, and renal disease. The pharmaceutically effective amount of the compound will be appropriately determined depending on the kind and the severity of the disease to be treated, age, sex, body weight and the physical condition of the patients to be treated, administration route, duration of therapy and the like. Generally, the effective amount of the compound may be in the range of about 1 to 1,000 mg in the oral administration, about 0.1 to 500 mg in the intravenous administration, about 5 to 1,000 mg in the rectal administration. Generally, the daily dosage for adults is in the range of about 0.1 to 5,000 mg, preferably about to 1,000 mg but cannot be determined uniformly because it depends on age, sex, body weight and the physical condition of the patients to be treated. The formulation may be administered once a day or several times a day with a divided dose.

Cosmetic compositions containing the 15-PGDH inhibitor can include any substance or preparation intended to be brought into contact with the various superficial parts of the human body (epidermis, body hair and hair system, nails, lips and external genital organs) or with the teeth or the buccal mucous membranes for the purpose, exclusively or mainly, of cleansing them, of giving them a fragrance, of modifying their appearance and/or of correcting body odors and/or protecting them or of maintaining them in good condition.

The cosmetic composition can comprise a cosmetically acceptable medium that may be water or a mixture of water and at least one solvent selected from among hydrophilic organic solvents, lipophilic organic solvents, amphiphilic organic solvents, and mixtures thereof.

For topical application, the cosmetic composition can be administered in the form of aqueous, alcoholic, aqueous-alcoholic or oily solutions or suspensions, or of a dispersion of the lotion or serum type, of emulsions that have a liquid or semi-liquid consistency or are pasty, obtained by dispersion of a fatty phase in an aqueous phase (O/W) or vice versa (W/O) or multiple emulsions, of a free or compacted powder to be used as it is or to be incorporated into a physiologically acceptable medium, or else of microcapsules or microparticles, or of vesicular dispersions of ionic and/or nonionic type. It may thus be in the form of a salve, a tincture, milks, a cream, an ointment, a powder, a patch, an impregnated pad, a solution, an emulsion or a vesicular dispersion, a lotion, aqueous or anhydrous gels, a spray, a suspension, a shampoo, an aerosol or a foam. It may be anhydrous or aqueous. It may also comprise solid preparations constituting soaps or cleansing cakes.

The cosmetic compositions may in particular comprise a hair care composition, and in particular a shampoo, a setting lotion, a treating lotion, a styling cream or gel, restructuring lotions for the hair, a mask, etc. The cosmetic compositions can be a cream, a hair lotion, a shampoo or a conditioner. These can be used in particular in treatments using an application that may or may not be followed by rinsing, or else in the form of a shampoo. A composition in the form of a foam, or else in the form of spray or an aerosol, then comprising propellant under pressure, is also intended. It can thus be in the form of a lotion, serum, milk, cream, gel, salve, ointment, powder, balm, patch, impregnated pad, cake or foam.

In particular, the compositions for application to the scalp or the hair can be in the form of a hair care lotion, for example for daily or twice-weekly application, of a shampoo or of a hair conditioner, in particular for twice-weekly or weekly application, of a liquid or solid soap for cleansing the scalp, for daily application, of a hairstyle shaping product (lacquer, hair setting product or styling gel), of a treatment mask, or of a foaming gel or cream for cleansing the hair. These may also be in the form of a hair dye or mascara to be applied with a brush or a comb.

Moreover, for topical application to the eyelashes or body hair, the compositions may be in the form of a pigmented or unpigmented mascara, to be applied with a brush to the eyelashes or alternatively to beard or moustache hair. For a composition administration by injection, the composition may be in the form of an aqueous lotion or an oily suspension. For oral use, the composition may be in the form of capsules, granules, oral syrups or tablets. According to a particular embodiment, the composition is in the form of a hair cream or hair lotion, a shampoo, a hair conditioner or a mascara for the hair or for the eyelashes.

In a known manner, the cosmetic compositions may also contain adjuvants that are normal in the cosmetics field, such as hydrophilic or lipophilic gelling agents, hydrophilic or lipophilic additives, preservatives, antioxidants, solvents, fragrances, fillers, UV-screening agents, odor absorbers and dyestuffs. The amounts of these various adjuvants are those conventionally used in the cosmetics field, and are for example from 0.1% to 20%, in particular less than or equal to 10%, of the total weight of the composition. According to their nature, these adjuvants can be introduced into the fatty phase, into the aqueous phase and/or into the lipid spherules.

In some embodiments, the 15-PGDH inhibitor can be administered in a combinatorial therapy or combination therapy that includes administration of a 15-PGDH inhibitor with one or more additional active agents. The phrase "combinatorial therapy" or "combination therapy" embraces the administration of the 15-PGDH inhibitor, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

In some embodiments, the additional active agent can be chosen in particular from lipoxygenase inhibitors as described in EP 648488, the bradykinin inhibitors described in particular in EP 845700, prostaglandins and their derivatives, in particular those described in WO 98/33497, WO 95/11003, JP 97-100091, JP 96-134242, the agonists or antagonists of the receptors for prostaglandins, and the nonprostanoic analogues of prostaglandins as described in EP 1175891 and EP 1175890, WO 01/74307, WO 01/74313, WO 01/74314, WO 01/74315 or WO 01/72268.

In other embodiments, the 15-PGDH inhibitors can be administered in combination with active agents, such as vasodilators, prostanoid agonists, antiandrogens, cyclosporins and their analogues, antimicrobials, triterpenes, alone or as a mixture. The vasodilators can include potassium channel agonists including minoxidil and its derivatives, aminexil and the compounds described in U.S. Pat. Nos. 3,382,247, 5,756,092, 5,772,990, 5,760,043, 5,466,694, 5,438,058, 4,973,474, chromakalin and diazoxide. The antiandrogens can include 5.alpha.-reductase inhibitors such as finasteride and the compounds described in U.S. Pat. No. 5,516,779, cyprosterone acetate, azelaic acid, its salts and its derivatives, and the compounds described in U.S. Pat. No. 5,480,913, flutamide and the compounds described in U.S. Pat. Nos. 5,411,981, 5,565,467 and 4,910,226. The antimicrobial compounds can include selenium derivatives, ketoconazole, triclocarban, triclosan, zinc pyrithione, itraconazole, pyridine acid, hinokitiol, mipirocine, and the compounds described in EP 680745, clinycine hydrochloride, benzoyl or benzyl peroxide and minocycline. The anti-inflammatory agents can include inhibitors specific for Cox-2 such as for example NS-398 and DuP-697 (B. Batistini et al., DN&P 1994; 7(8):501-511) and/or inhibitors of lipoxygenases, in particular 5-lipoxygenase, such as for example zileuton (F. J. Alvarez & R. T. Slade, Pharmaceutical Res. 1992; 9(11):1465-1473).

Other active compounds, which can be present in pharmaceutical and/or cosmetic compositions can include aminexil and its derivatives, 60-[(9Z,12Z)octadec-9,12-dienoyl]hexapyranose, benzalkonium chloride, benzethonium chloride, phenol, oestradiol, chlorpheniramine maleate, chlorophyllin derivatives, cholesterol, cysteine, methionine, benzyl nicotinate, menthol, peppermint oil, calcium panthotenate, panthenol, resorcinol, protein kinase C inhibitors, prostaglandin H synthase 1 or COX-1 activators, or COX-2 activators, glycosidase inhibitors, glycosaminoglycanase inhibitors, pyroglutamic acid esters, hexosaccharidic or acylhexosaccharidic acids, substituted ethylenearyls, N-acylated amino acids, flavonoids, derivatives and analogues of ascomycin, histamine antagonists, triterpenes, such as ursolic acid and the compounds described in U.S. Pat. No. 5,529,769, U.S. Pat. No. 5,468,888, U.S. Pat. No. 5,631,282, saponins, proteoglycanase inhibitors, agonists and antagonists of oestrogens, pseudopterins, cytokines and growth factor promoters, IL-1 or IL-6 inhibitors, IL-10 promoters, TNF inhibitors, vitamins, such as vitamin D, analogues of vitamin B 12 and panthotenol, hydroxy acids, benzophenones, esterified fatty acids, and hydantoin.

Pharmaceutical and/or cosmetic compositions including the 15-PGDH inhibitor described herein can additionally contain, for example, at least one compound chosen from prostaglandins, in particular prostaglandin $PGE_1$, $PGE_2$, their salts, their esters, their analogues and their derivatives, in particular those described in WO 98/33497, WO 95/11003, JP 97-100091, JP 96-134242, in particular agonists of the prostaglandin receptors. It may in particular contain at least one compound such as the agonists (in acid form or in the form of a precursor, in particular in ester form) of the prostaglandin $F_2\alpha$ receptor, such as for example latanoprost, fluprostenol, cloprostenol, bimatoprost, unoprostone, the agonists (and their precursors, in particular the esters such as travoprost) of the prostaglandin $E_2$ receptors such as 17-phenyl $PGE_2$, viprostol, butaprost, misoprostol, sulprostone, 16,16-dimethyl $PGE_2$, 11-deoxy PGEZ, 1-deoxy $PGE_1$, the agonists and their precursors, in particular esters, of the prostacycline (IP) receptor such as cicaprost, iloprost, isocarbacycline, beraprost, eprostenol, treprostinil, the agonists and their precursors, in particular the esters, of the prostaglandin $D_2$ receptor such as BW245C ((4S)-(3-

[(3R,S)-3-cyclohexyl-3-isopropyl]-2,5-dioxo)-4-imidazolidinehept-anoic acid), BW246C ((4R)-(3-[(3R,S)-3-cyclohexyl-3-isopropyl]-2,5-dioxo)-4-imidazolidinehept-anoic acid), the agonists and their precursors, in particular the esters, of the receptor for the thromboxanes A2 (TP) such as I-BOP ([1S-[1a,2a(Z), 3b(1E,3S),4a]]-7-[3-[3-hydroxy-4-[4-(iodophenoxy)-1-butenyl]-7-oxabicyclo-[2.2.1]hept-2-yl]-5-heptenoic acid).

Advantageously, the composition can include at least one 15-PGDH inhibitor as defined above and at least one prostaglandin or one prostaglandin derivative such as for example the prostaglandins of series 2 including in particular $PGF_{2\alpha}$ and $PGE_2$ in saline form or in the form of precursors, in particular of the esters (example isopropyl esters), their derivatives such as 16,16-dimethyl $PGE_2$, 17-phenyl $PGE_2$ and 16,16-dimethyl $PGF_{2\alpha}$ 17-phenyl $PGF_{2\alpha}$, prostaglandins of series 1 such as 11-deoxyprostaglandin E1, 1-deoxyprostaglandin E1 in saline or ester form, is their analogues, in particular latanoprost, travoprost, fluprostenol, unoprostone, bimatoprost, cloprostenol, viprostol, butaprost, misoprostol, their salts or their esters.

The invention is further illustrated by the following examples, which is not intended to limit the scope of the claims.

Example 1

This Example describes the activities of four compounds with respect to the enzyme 15-Prostaglandin Dehydrogenase (15-PGDH) (encoded by the gene HPGD). The compounds are SW033291, SW054384, SW124531, SW145753 and have the following formulas:

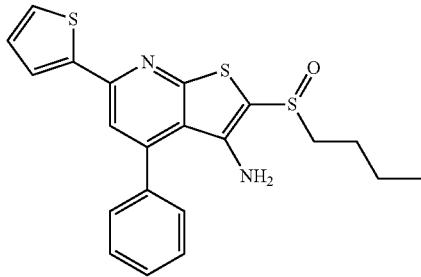
SW033291

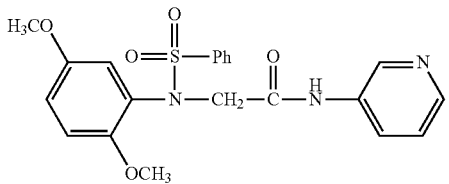
SW054384

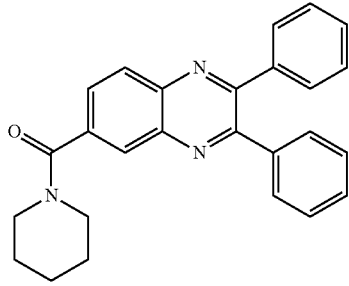
SW145753

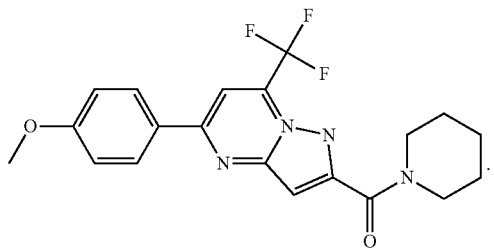
SW124531

FIG. 1 shows that SW033291, SW054384, and SW145753 all increase luciferase activity of cells the express a 15-PGDH luciferase fusion construct created by targeted gene knock-in of renilla luciferase into the last coding exon of 15-PGDH. The activity is demonstrated in three different colon cancer cell lines all engineered to contain the 15-PGDH-luciferase fusion. These cell lines are Vaco-9m (V9m), LS174T, Vaco503 (V503). SW054384 is in general the best inducer, and shows maximum activity at 6.25 µM. Value of 1.0 on the Y-axis is the basal level of reporter activity in cells treated with drug free DMSO vehicle.

Figure 2:
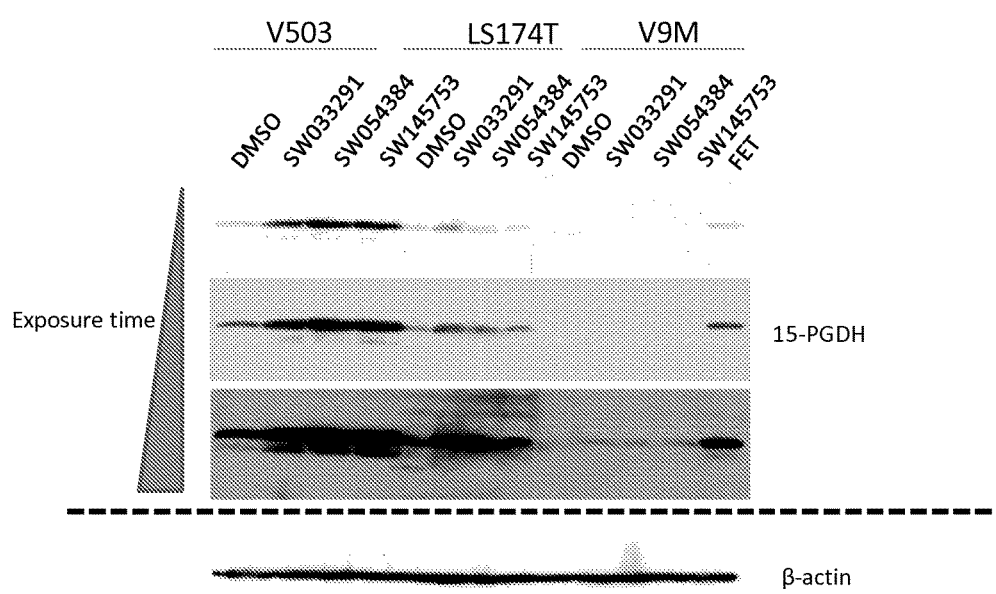
FIG. 2 illustrates western blots demonstrating the levels of 15-PGDH protein in cell lines V9M, LS174T, and V503 treated with 7.5 µM of SW033291, SW054384, and SW145753 for 48 hours. Untreated FET cells provide a positive control for 15-PGDH expression.

FIG. 2 shows western blots demonstrating that SW033291, SW054384, and SW145753 all increase levels of 15-PGDH protein in cell lines V503, LS174T, and V503 treated with 7.5 µM compound for 48 hours. Untreated FET cells provide a positive control for 15-PGDH expression.

Figure 3:
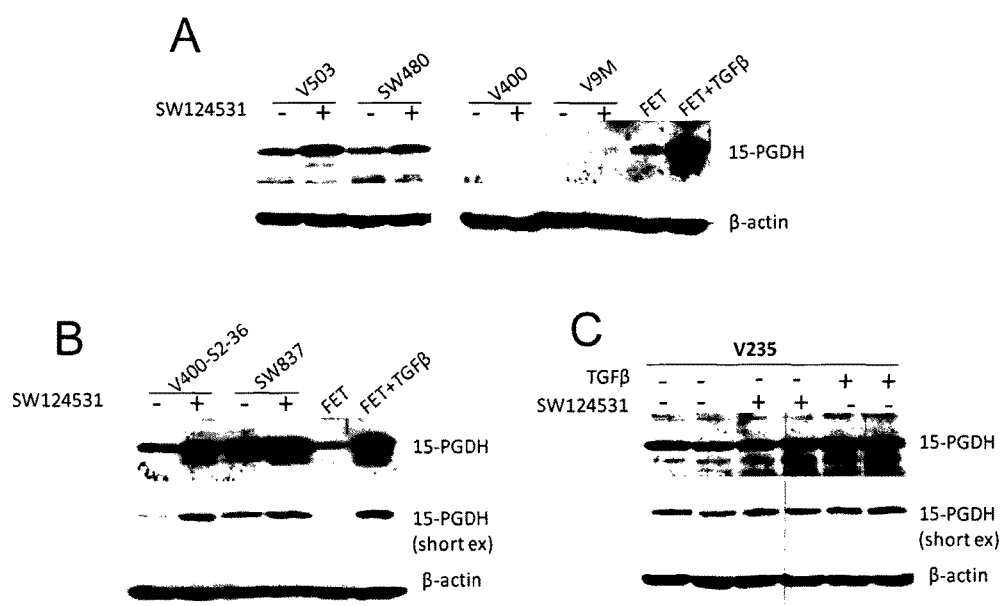
FIGS. 3(A-C) illustrate western blots demonstrating 15-PGDH protein levels in colon cell lines treated with SW124531 (FET cells treated with TGF-β (10 ng/ml for 48 hours) are used as a positive control for 15-PGDH expression in certain panels).

FIG. 3 shows western blot demonstrating SW124531 also increases 15-PGDH protein levels in colon cell lines (FET cells treated with TGF-β (10 ng/ml) for 48 hours are used as a positive control for 15-PGDH expression in certain panels).

Figure 4:
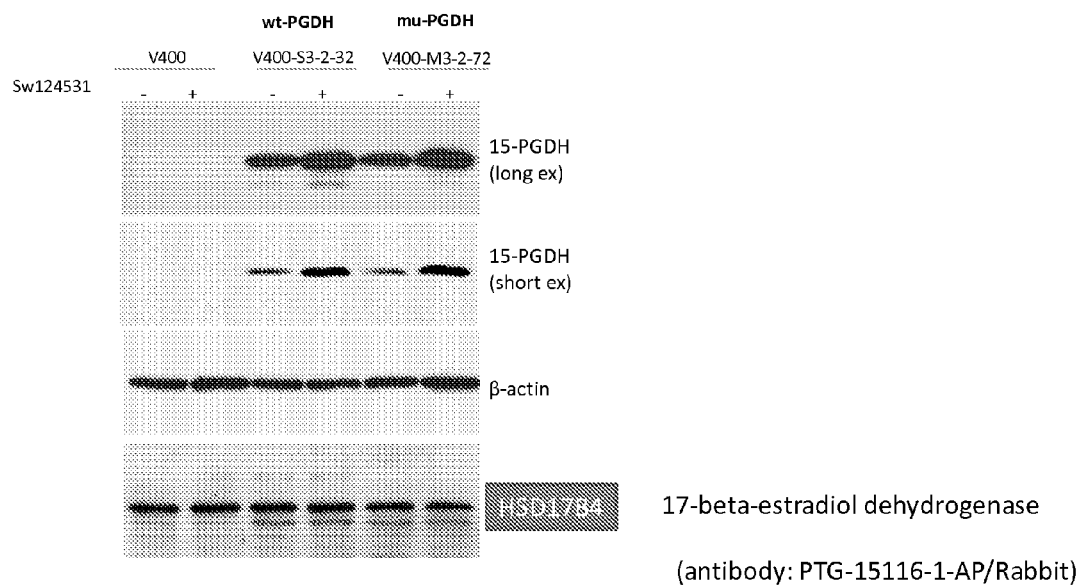
FIG. 4 illustrates western blots demonstrating the levels of 15-PGDH protein (wt-PGDH) expressed from a cDNA expression vector in V400-S3-2-32 cells treated with 5 µM SW124531, and protein levels of a catalytically dead mutant 15-PGDH (mu-PGDH) also expressed from a cDNA expression vector in V400-M3-2-72 cells treated with SW124531.

FIG. 4 shows western blot demonstrating 5 µM SW124531 increases levels of 15-PGDH protein (wt-PGDH) expressed from a cDNA expression vector in V400-S3-2-32 cells, and also increases protein levels of a catalytically dead mutant 15-PGDH (mu-PGDH) also expressed from a cDNA expression vector in V400-M3-2-72 cells. As these proteins are expressed from a heterologous CMV promoter, the findings suggest that the compounds work directly on stabilizing the 15-PGDH protein. The compounds show no effects on levels of a related enzyme, 17-beta-estradiol-dehydrogenase.

FIG. 5 shows increase in 15-PGDH protein levels in V503 cells treated with SW124531 as assayed by immuno-fluorescence (upper two rows) and by western blot (lower panel).

FIGS. 6-9 show that SW033291, SW054384, SW145753, and SW124531 do not in general alter 15-PGDH mRNA levels in treated colon cancer cell lines as assessed by real-time PCR. The only exception is the slight increase in 15-PGDH mRNA in SW033291 treated V503 cells, which is less than the induction of 15-PGDH protein as well as 15-PGDH-luciferase reporter levels seen in SW033291 treated V503 cells. In these studies parental cell lines (not containing the 15-PGDH-luciferase reporter) are employed.

FIG. 10 shows the effects of three compounds on total 15-PGDH activity in cell lines treated with the compounds. Cell lines were treated with compounds at 7.5 µM for 48 hours, and then pelleted. Pellets were lysed and total 15-PGDH activity measured and normalized to 1,000,000 input cells per pellet. 15-PGDH activity was assayed by measuring the transfer of tritium from 15(S)-[15-3H] $PGE_2$ to glutamate by coupling 15-PGDH with glutamate dehydrogenase as described in (Chi X, Freeman B M, Tong M, Zhao Y, Tai H H. 15-Hydroxyprostaglandin dehydrogenase (15-PGDH) is up-regulated by flurbiprofen and other non-steroidal anti-inflammatory drugs in human colon cancer HT29 cells. Arch Biochem Biophys. 2009; 487(2): 139-45). Activity is measured as pmol $PGE_2$/min/million cells. As shown, SW033291 markedly inhibits 15-PGDH activity in all three of the cell lines tested. We conclude that although SW033291 increases total 15-PGDH protein levels in cells, it also inactivates 15-PGDH enzyme activity.

In contrast, 15-PGDH enzyme activity is increased in cells treated with SW054384 and in cells treated with SW145753.

FIG. 11 shows the effect on activity of recombinant 15-PGDH protein (a 15-PGDH-GST fusion protein) incubated with varying concentrations of the test compounds, with 15-PGDH activity across a range of compound concentrations recorded on the table and displayed on the corresponding graphs. As shown, SW033291 is a potent inhibitor of 15-PGDH activity, with an $IC_{50}$ of <1.25 nM. This contrasts with the $IC_{50}$ of between 25 nM-62.5 nM measured for the commercial 15-PGDH inhibitor available from Cayman Chemical (Cayman catalogue item 10638, Cayman Chemical number 13695).

FIG. 12 shows repeat testing of the effects of SW033291 and SW054384 on activity of recombinant 15-PGDH protein tested in vitro. Assays were done by measuring the transfer of tritium from 15(S)-[15-3H] $PGE_2$ to glutamate (at 1 μM $PGE_2$ substrate) shown at left (panels A, C), or by direct fluorescence monitoring of NADH generation by 15-PGDH (done at 20 μM $PGE_2$ substrate) shown at right (panels B, D). SW033291 is again confirmed as a highly potent 15-PGDH inhibitor with an IC50 of 0.7 nM as measured in the tritium assay and an $IC_{50}$ of 1.6 nM as measured in the fluorescence assay. The relative insensitivity of the IC50 to substrate concentration suggests that SW033291 is a non-competitive inhibitor of 15-PGDH.

Figure 13:
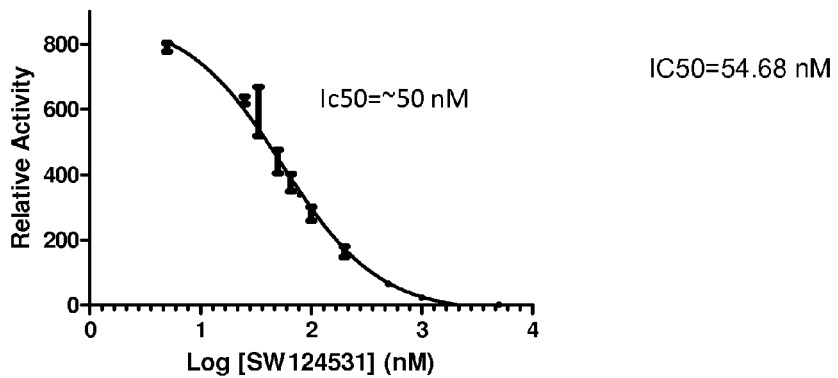
FIG. 13 illustrates a table and plot showing 15-PGDH activity measured by following transfer of tritium from a radiolabeled PGE2 substrate in cells treated with SW124531 (upper panel) and in recombinant 15-PGDH protein treated with SW124531 (lower panel).

FIG. 13 shows results of assays of 15-PGDH activity using the tritium method in cells treated with SW124531 (upper panel) and in recombinant 15-PGDH protein treated with SW124531 (lower panel). SW124531 shows activity in increasing 15-PGDH activity in most cell lines, though this activity is best in cell lines in which basal 15-PGDH activity is >10 units. SW124531 also inhibits activity of 15-PGDH recombinant protein at an $IC_{50}$ of 50 nM.

Figure 14:
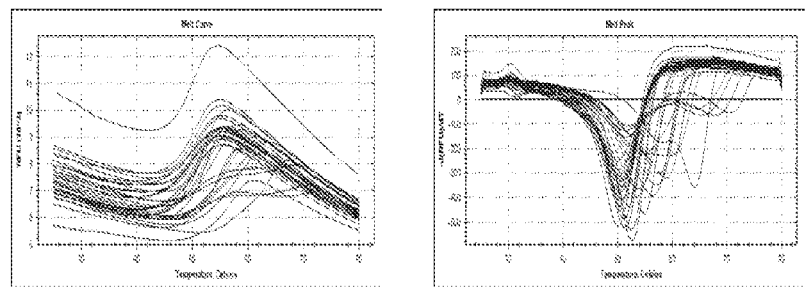
FIGS. 14(A-B) illustrate melt curves and a table showing different compound's ability to directly bind to recombinant 15-PGDH protein as measured by shifting the melting temperature of the protein.

FIG. 14 shows assay of different compounds for ability to directly bind to recombinant 15-PGDH protein as measured by shifting the melting temperature of the protein. The melting of the protein is followed by measurement of the fluorescence of SYPRO Orange dye (Sigma #S5692) that increases as the dye binds to hydrophobic residues exposed as the protein melt. The graph at upper left shows the melt curves of 15-PGDH with all of the assays done in the presence of the different compounds superimposed on each other. The graph at upper right plots the negative derivative of fluorescence versus temperature for each of the curves shown at left, with the melting point measured as the temperature of the negative peak (i.e., the point of most rapid change in the fluorescence versus temperature plot). The results are shown in tabular form on the table below. Lapatinib is used as a negative control. There is no binding of any drug in the absence of enzyme co-factor (either NAD or NADH). In the presence of either NAD or NADH, SW033291 creates two peaks in the melting curve, with one of these peaks displaced by 15 degrees Celsius, consistent with SW033291 binding directly to 15-PGDH. SW124531 and SW145753 also show evidence of direct binding to 15-PGDH. In this assay, SW054384 cannot be demonstrated to bind 15-PGDH. It is possible that SW054384 does bind to 15-PGDH, but that the binding is weak and is melted off at a temperature below the melting temperature of the 15-PGDH protein. Assays were done at both 10 μM and 100 μM cofactor (testing both NAD and NADH), which compares well with the published Km of NAD of 15.8 μM.

Figure 15:
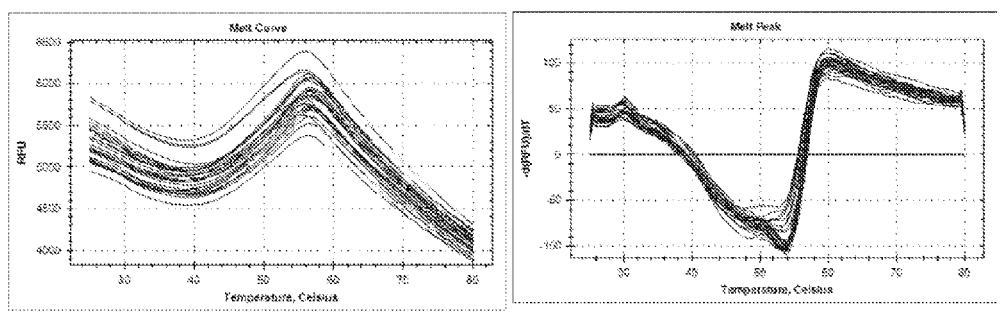
FIGS. 15(A-B) illustrate melt curves temperature of catalytically inactive mutant 15-PGDH protein treated with the test compounds.

FIG. 15 shows that none of the four compounds tested induce a shift in the melting temperature of catalytically inactive mutant 15-PGDH protein. We interpret the induction of 15-PGDH mutant protein by SW124531 as suggesting that SW124531 likely has weak binding to mutant 15-PGDH that is able to stabilize protein at 37° C., but with the drug melted off at a temperature below 50° C., that is the melting temperature of the protein.

Figure 16:
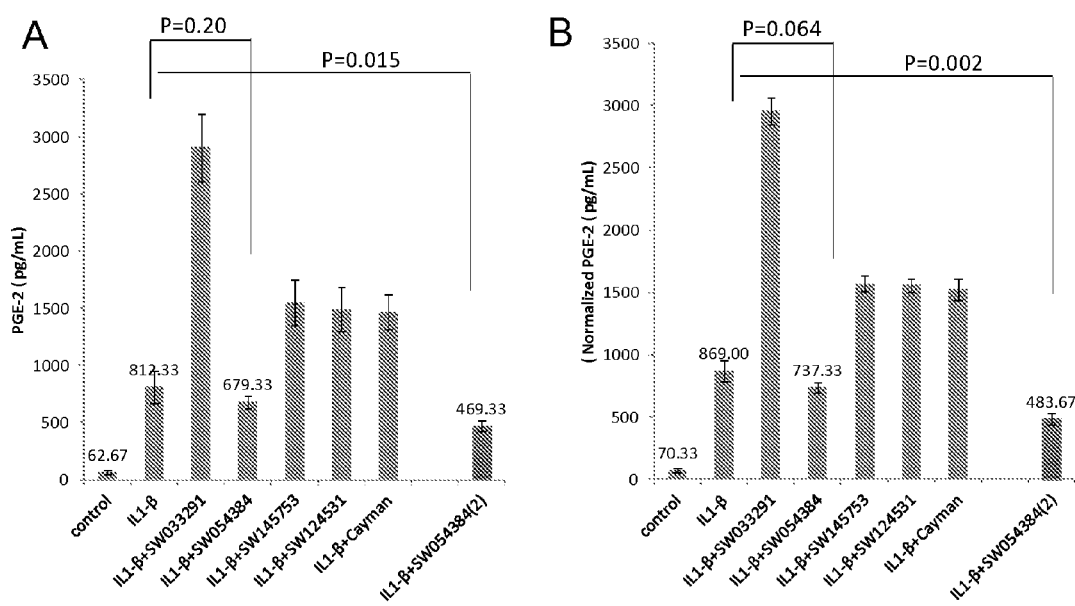
FIGS. 16(A-B) illustrates graphs showing $PGE_2$ levels that are assayed in the medium of A549 cells that have been stimulated by IL1-beta for 23 hours, with the test compounds.

FIG. 16 shows the in vivo modulation by compounds of 15-PGDH activity as reflected in $PGE_2$ levels that are assayed in the medium of A549 cells that have been stimulated by IL1-beta for 23 hours, with compound added for the last 5 hours (blue bars). The increment in $PGE_2$ level shows the clear inhibition of 15-PGDH activity in the cells by addition of SW033291 (as well as SW145753, SW124531, and a commercial 15-PGDH inhibitor from Cayman Chemical. In an additional iteration (red bars)(2), SW054384 was added commencing 24 hours before addition of IL1-beta, and then maintained for the next 26 hours in the presence of IL1-beta. The lower level of $PGE_2$ produced supports that in these cells SW054384 increased the 15-PGDH activity. Panel at left shows raw data; whereas, panel at right shows data normalized for cell numbers present at end of the experiment. $PGE_2$ levels are assayed by ELISA.

Figure 17:
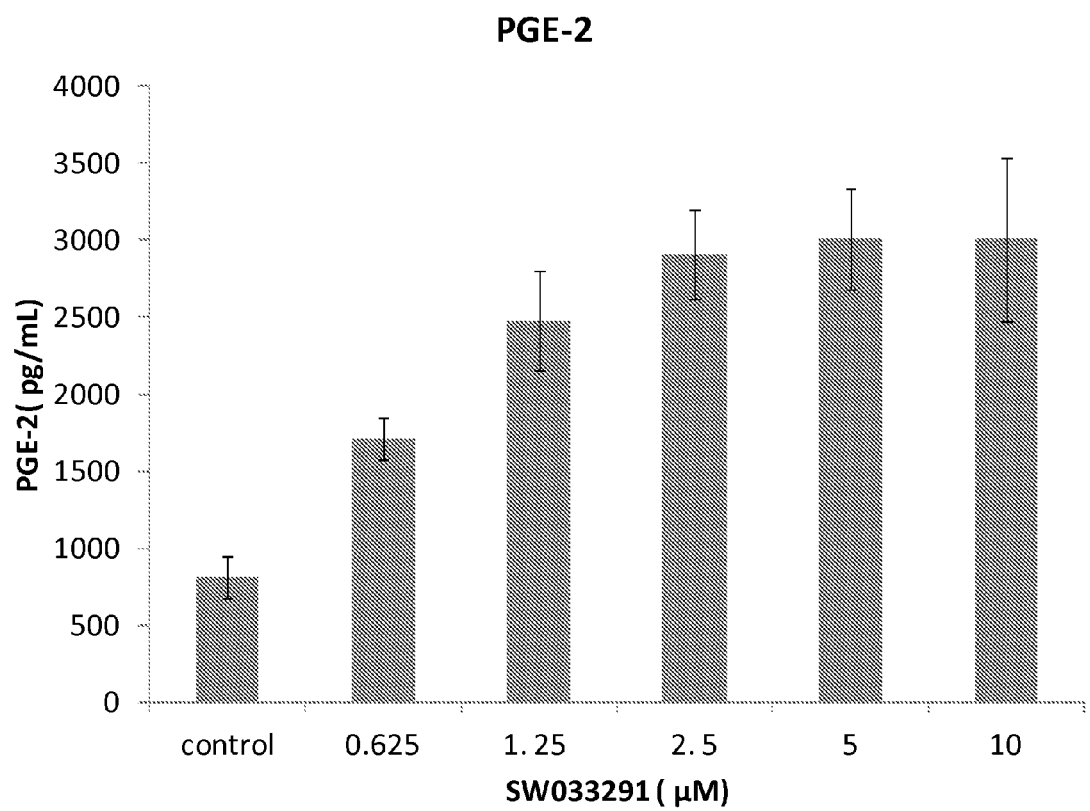
FIG. 17 illustrates a graph showing the dose response effect of SW033291 on $PGE_2$ production from IL1-beta treated A549 cells.

FIG. 17 shows the dose response of effect on SW033291 on $PGE_2$ production from IL1-beta treated A549 cells, as reflected in $PGE_2$ levels that are assayed in the medium of A549 cells that have been stimulated by IL1-beta for 24 hours, with SW033291 added for the last 8 hours.

Figure 18:
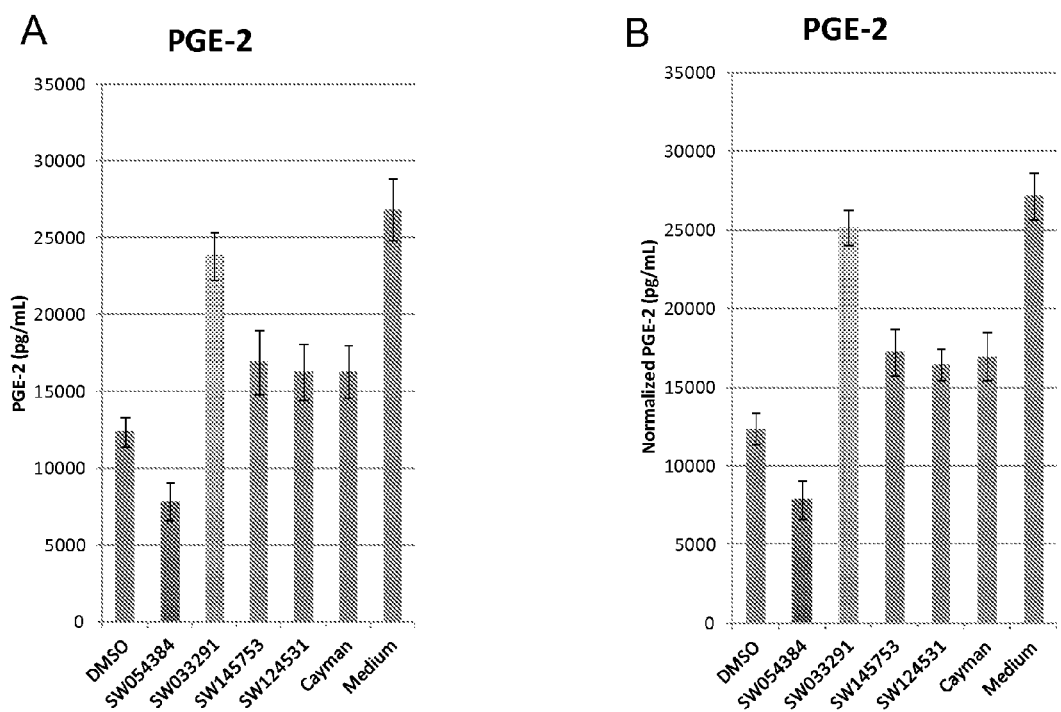
FIGS. 18(A-B) illustrate graphs showing the in vivo modulations by compounds (2.5 µM) of PGDH activity as reflected in $PGE_2$ levels following addition of $PGE_2$ into the medium of Vaco-503 cells.

FIG. 18 shows the in vivo modulations by 2.5 μM compounds of 15-PGDH activity as reflected in $PGE_2$ levels following addition of $PGE_2$ into the medium of Vaco-503 cells. In this study cells are treated with compound for 24 hours after which $PGE_2$ is added into the medium. After an added 24 hours $PGE_2$ levels remaining in the medium are assayed by Elisa. Data labeled "medium" is a control lane with $PGE_2$ added to medium alone, in the absence of cells. Data labeled DMSO is a control in which cells are treated with DMSO only (the vehicle for the compounds). The difference between the "medium" and the "DMSO" lanes represents the cell dependent degradation of $PGE_2$ by 15-PGDH. Again demonstrated, is the near complete blockade of 15-PGDH activity by addition of 2.5 μM SW033291, as reflected by the blockade in $PGE_2$ degradation. Additionally demonstrated is the stimulation of 15-PGDH activity by SW054384, as reflected by the increased degradation of $PGE_2$.

Figure 19:
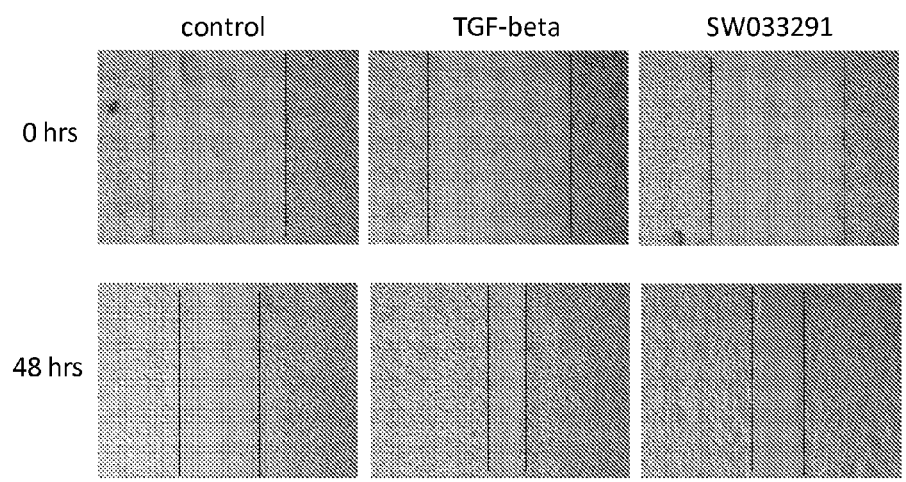
FIG. 19 illustrates images showing the activity of SW033291 in speeding the healing of a model wound consisting of a scratch in a monolayer of HaCaT cells observed over 48 hours of treatment.

FIG. 19 shows the activity of 2.5 μM SW033291 in speeding the healing of a model wound consisting of a scratch in a monolayer of HaCaT cells observed over 48 hours of treatment. TGF-beta serves as the positive control in the assay.

FIG. 20 shows the quantitation of the width of the scratch at 0 and 48 hours in the control, 2.5 μM SW033291 treated cells, and the TGF-beta (1ng/ml) treated cells.

Example 2

Analysis of Analogues of Lead Compounds SW033291, a 15-PGDH Inhibitor

This Example provides data on a group of structural analogues of SW033291. Data provided is the IC50 of each compound for inhibiting enzymatic activity of recombinant 15-PGDH in an in vitro assay. Recombinant 15-PGDH is human unless otherwise specified.

TABLE 1
| Structure/Smiles | ID # | Enzyme Inhibitor IC$_{50}$ (nM) at 5 nM 15-PGDH |
|---|---|---|
| 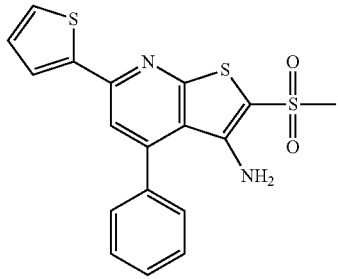 [SMILES: CS(=O)(=O)c1sc2nc(-c3cccs3)cc(-c3ccccc3)c2c1N] CS(=O)(=O)C1=C(N)C2=C(S1)N=C(C=C2C1=CC=CC=C1)C1=CC=CS1 | SW033290 | 525.40 |
| 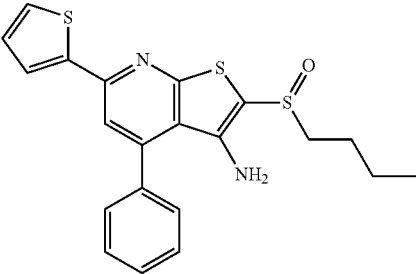 [SMILES: CCCCS(=O)c1sc2nc(-c3cccs3)cc(-c3ccccc3)c2c1N] CCCCS(=O)C1=C(N)C2=C(S1)N=C(C=C2C1=CC=CC=C1)C1=CC=CS1 | SW033291 | 2.53 |
| 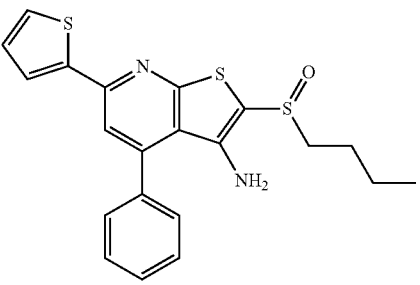 [SMILES: CCCCS(=O)c1sc2nc(-c3cccs3)cc(-c3ccccc3)c2c1N] CCCCS(=O)C1=C(N)C2=C(S1)N=C(C=C2C1=CC=CC=C1)C1=CC=CS1 | SW033291 (Rat PGDH) | 2.74 |
| CCCCS(=O)C1=C(N)C2=C(S1)N=C(C=C2C1=CC=CC=C1)C1=CC=CS1 | SW033291 (Mouse PGDH) | 2.56 |

… TABLE 1-continued
| Structure/Smiles | ID # | Enzyme Inhibitor IC$_{50}$ (nM) at 5 nM 15-PGDH |
|---|---|---|
| 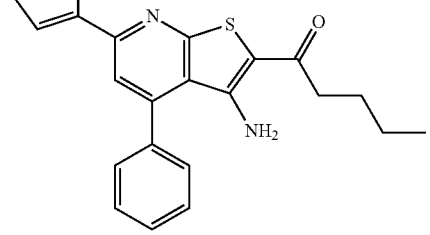<br>CCCCC(=O)C1=C(N)C2=C(S1)N=C(C=C2C1=CC=CC=C1)C1=CC=CS1 | SW206976 | >7500 |
| 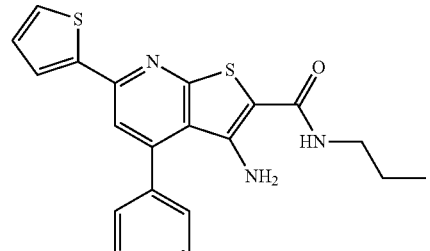<br>CCCNC(=O)C1=C(N)C2=C(S1)N=C(C=C2C1=CC=CC=C1)C1=CC=CS1 | SW206977 | >7500 |
| 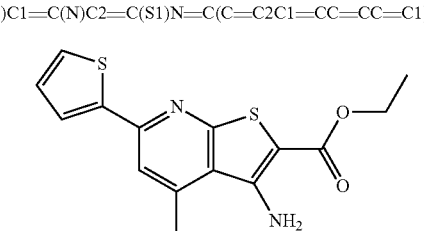<br>CCOC(=O)C1=C(N)C2=C(S1)N=C(C=C2C1=CC=CC=C1)C1=CC=CS1 | SW206978 | >7500 |
| 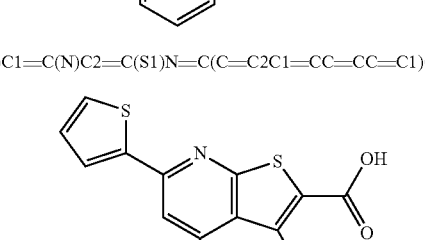<br>NC1=C(SC2=C1C(=CC(=N2)C1=CC=CS1)C1=CC=CC=C1)C(O)=O | SW206979 | >7500 |
| 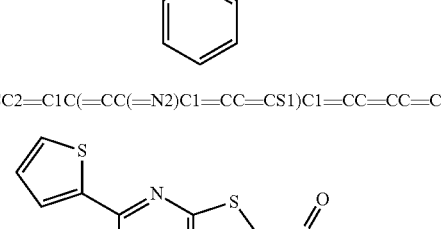<br>CCCCS(=O)C1=C(N)C2=C(S1)N=C(C=C2)C1=CC=CS1 | SW206980 | 0.97 |

TABLE 1-continued

| Structure/Smiles | ID # | Enzyme Inhibitor IC$_{50}$ (nM) at 5 nM 15-PGDH |
|---|---|---|
| CCCCS(=O)C1=C(N)C2=CC=C(N=C2S1)C1=NC=CS1 | SW206992 | 1.41 |
| CCCCS(=O)C1=C(N)C2=C(S1)N=CC=C2 | SW208064 | 151.40 |
| CCCCS(=O)C1=C(N)C2=C(S1)N=C(N=C2C1=CC=CC=C1)C1=CC=CC=C1 | SW208065 | 4.87 |
| CCCCS(=O)C1=C(N)C2=C(S1)N=C(C=C2C1=CC=CC=C1)C1=NC=CS1 | SW208066 | 1.37 |
| CCCCS(=O)C1=C(N)C2=C(S1)N=C(N=C2C1=CC=CC=C1)C1=CC=CS1 | SW208067 | 2.40 |

TABLE 1-continued
| Structure/Smiles | ID # | Enzyme Inhibitor IC$_{50}$ (nM) at 5 nM 15-PGDH |
|---|---|---|
| 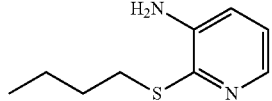<br>CCCCSC1=NC=CC=C1N | SW208068 | >7500 |
| 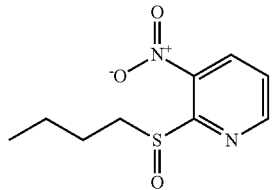<br>CCCCS(=O)C1=NC=CC=C1[N+]([O-])=O | SW208069 | >7500 |
| 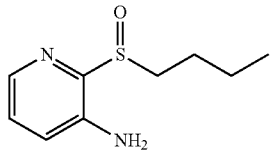<br>CCCCS(=O)C1=NC=CC=C1N | SW208070 | >7500 |
| 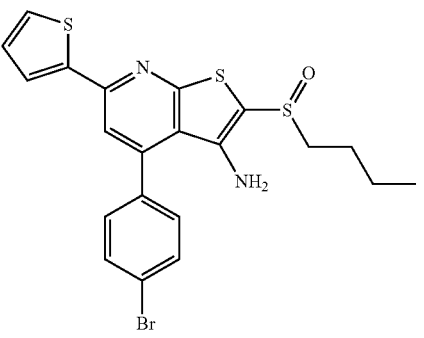 [SMILES: CCCCS(=O)c1sc2nc(-c3cccs3)cc(-c3ccc(Br)cc3)c2c1N]<br>CCCCS(=O)C1=C(N)C2=C(S1)N=C(C=C2C1=CC=C(Br)C=C1)C1=CC=CS1 | SW208199 | 2.9 |
| 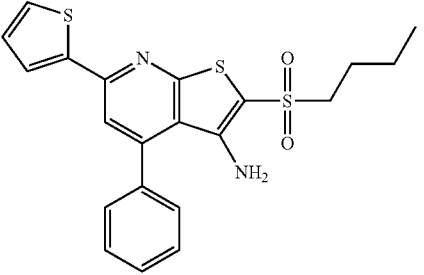 [SMILES: CCCCS(=O)(=O)c1sc2nc(-c3cccs3)cc(-c3ccccc3)c2c1N]<br>CCCCS(=O)(=O)C1=C(N)C2=C(S1)N=C(C=C2C1=CC=CC=C1)C1=CC=CS1 | SW208078 | 25.40 |

TABLE 1-continued

| Structure/Smiles | ID # | Enzyme Inhibitor IC$_{50}$ (nM) at 5 nM 15-PGDH |
|---|---|---|
| CCCCS(=O)C1=C(N)C2=C(C=C(N=C2S1)C1=CC=CS1)C1=CC=CC=C1 | SW208080 | 2.61 |
| CCCCCCS(=O)C1=C(N)C2=C(C=C(N=C2S1)C1=CC=CS1)C1=CC=CC=C1 | SW208081 | 17.85 |
| C[S+]([O-])C1=C(N)C2=C(C=C(N=C2S1)C1=CC=CS1)C1=CC=CC=C1 | SW208079 | 124.90 |
| CCCC[S@+]([O-])C1=C(N)C2=C(C=C(N=C2S1)C1=CC=CS1)C1=CC=CC=C1 | SW211667 (33291 S isomer) | 195.30 |

TABLE 1-continued

| Structure/Smiles | ID # | Enzyme Inhibitor IC$_{50}$ (nM) at 5 nM 15-PGDH |
|---|---|---|
| CCCC[S@+]([O-])C1=C(N)C2=C(C=C(N=C2S1)C1=CC=CS1)C1=CC=CC=C1 | SW211668 (33291 R isomer) | 1.34 |
| CCCCSC1=CC2=CC=C(N=C2S1)C1=CC=CC=C1 | SW208430 | >2500 |
| CCCCS(=O)C1=CC2=CC=C(N=C2S1)C1=CC=CC=C1 | SW208432 | 3.53 |
| CCCCS(=O)(=O)C1=CC2=CC=C(N=C2S1)C1=CC=CC=C1 | SW208434 | >2500 |
| CCCCSC1=C(N)C2=CC=C(N=C2S1)C1=CC=CC=C1 | SW208435 | >2500 |

TABLE 1-continued
| Structure/Smiles | ID # | Enzyme Inhibitor IC$_{50}$ (nM) at 5 nM 15-PGDH |
|---|---|---|
| 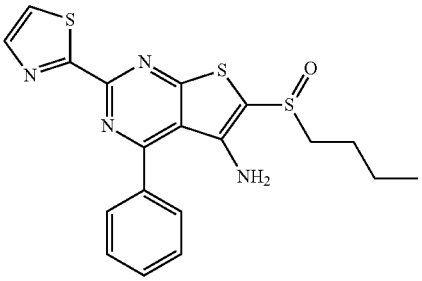 [SMILES: CCCCS(=O)c1sc2nc(-c3nccs3)nc(-c3ccccc3)c2c1N]<br>CCCCS(=O)C1=C(N)C2=C(N=C(N=C2S1)C1=NC=CS1)C1=CC=CC=C1 | SW208436 | 1.14 |
| 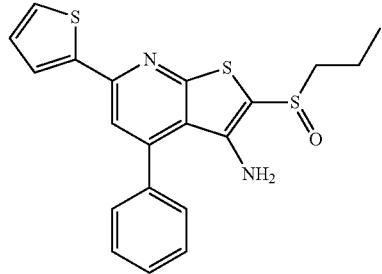 [SMILES: CCCS(=O)c1sc2nc(-c3cccs3)cc(-c3ccccc3)c2c1N]<br>CCCS(=O)C1=C(N)C2=C(C=C(N=C2S1)C1=CC=CS1)C1=CC=CC=C1 | SW208437 | 2.05 |
| 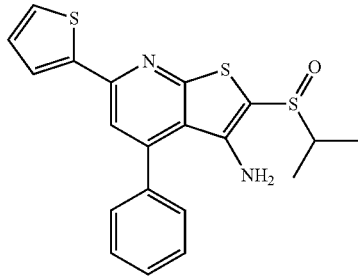 [SMILES: CC(C)S(=O)c1sc2nc(-c3cccs3)cc(-c3ccccc3)c2c1N]<br>CC(C)S(=O)C1=C(N)C2=C(C=C(N=C2S1)C1=CC=CS1)C1=CC=CC=C1 | SW208438 | 3.16 |
| 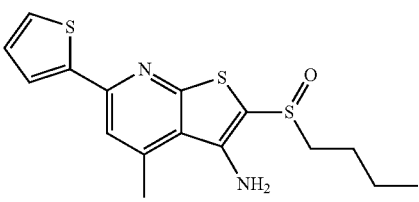 [SMILES: CCCCS(=O)c1sc2nc(-c3cccs3)cc(C)c2c1N]<br>CCCCS(=O)C1=C(N)C2=C(C)C=C(N=C2S1)C1=CC=CS1 | SW208488 | 1.43 |
| 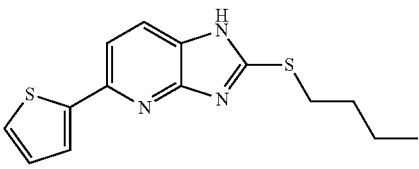 [SMILES: CCCCSc1nc2nc(-c3cccs3)ccc2[nH]1]<br>CCCCSC1=NC2=NC(=CC=C2N1)C1=CC=CS1 | SW208494 | >7500 |

TABLE 1-continued
| Structure/Smiles | ID # | Enzyme Inhibitor IC$_{50}$ (nM) at 5 nM 15-PGDH |
|---|---|---|
| 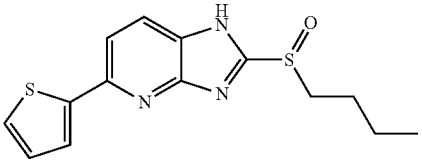 [SMILES: CCCCS(=O)c1nc2nc(-c3cccs3)ccc2[nH]1]  CCCCS(=O)C1=NC2=NC(=CC=C2N1)C1=CC=CS1 | SW208495 | >7500 |
| 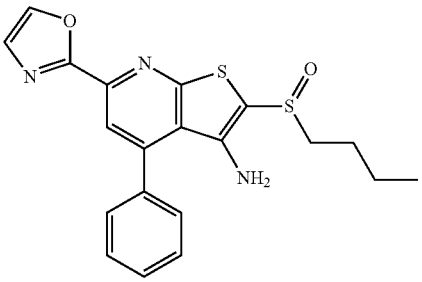  CCCCS(=O)C1=C(N)C2=C(S1)N=C(C=C2C1=CC=CC=C1)C1=NC=CO1 | SW208496 | 1.37 |
| 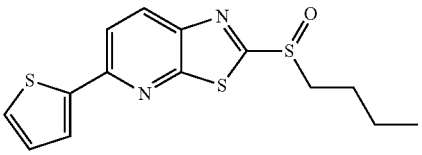 [SMILES: CCCCS(=O)c1nc2ccc(-c3cccs3)nc2s1]  CCCCS(=O)C1=NC2=CC=C(N=C2S1)C1=CC=CS1 | SW208599 | 1230.00 |
| 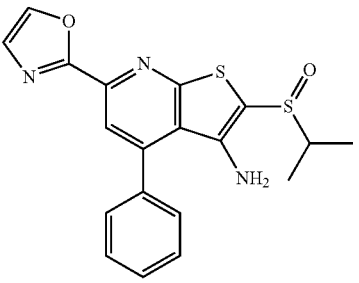 [SMILES: CC(C)S(=O)c1sc2nc(-c3ncco3)cc(-c3ccccc3)c2c1N]  CC(C)S(=O)C1=C(N)C2=C(S1)N=C(C=C2C1=CC=CC=C1)C1=NC=CO1 | SW208660 | 2.86 |
| 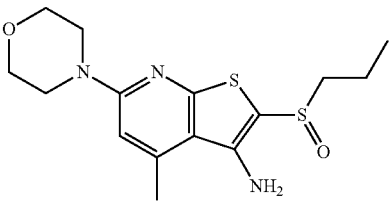 [SMILES: CCCS(=O)c1sc2nc(N3CCOCC3)cc(C)c2c1N]  CCCS(=O)C1=C(N)C2=C(S1)N=C(C=C2C)C1=NC=CS1 | SW208661 | 5.27 |

TABLE 1-continued
| Structure/Smiles | ID # | Enzyme Inhibitor IC$_{50}$ (nM) at 5 nM 15-PGDH |
|---|---|---|
| 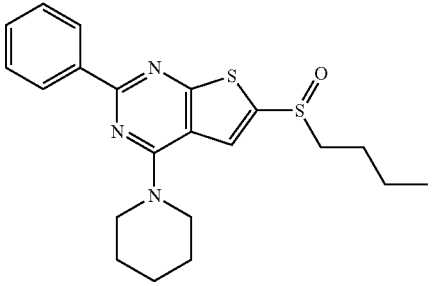 [SMILES: CCCCS(=O)c1cc2c(N3CCCCC3)nc(-c3ccccc3)nc2s1]<br>CCCCS(=O)C1=CC2=C(S1)N=C(N=C2N1CCCCC1)C1=CC=CC=C1 | SW208662 | 1319.00 |
| 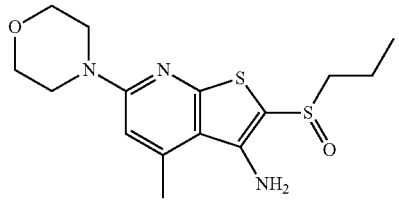 [SMILES: CCCS(=O)c1sc2nc(N3CCOCC3)cc(C)c2c1N]<br>CCCS(=O)C1=C(N)C2=C(S1)N=C(C=C2C)N1CCOCC1 | SW208663 | 135.50 |
| 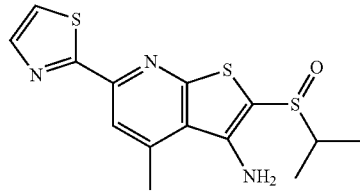 [SMILES: Cc1cc(-c2nccs2)nc2sc(S(=O)C(C)C)c(N)c12]<br>CC(C)S(=O)C1=C(N)C2=C(S1)N=C(C=C2C)C1=NC=CS1 | SW208664 | 7.62 |
| 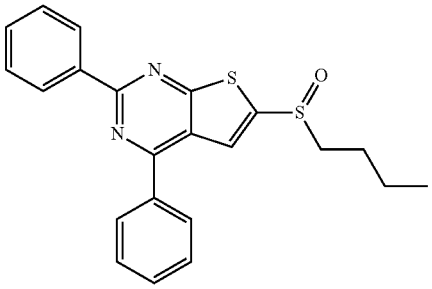 [SMILES: CCCCS(=O)c1cc2c(-c3ccccc3)nc(-c3ccccc3)nc2s1]<br>CCCCS(=O)C1=CC2=C(N=C(N=C2S1)C1=CC=CC=C1)C1=CC=CC=C1 | SW208776 | 93.29 |
| 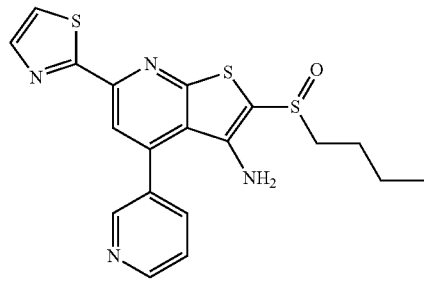<br>CCCCS(=O)C1=C(N)C2=C(C=C(N=C2S1)C1=NC=CS1)C1=CC=CN=C1 | SW208777 | 2.65 |

TABLE 1-continued

| Structure/Smiles | ID # | Enzyme Inhibitor IC$_{50}$ (nM) at 5 nM 15-PGDH |
|---|---|---|
| CC(C)S(=O)C1=C(N)C2=C(C=C(N=C2S1)C1=NC=CS1)C1=CC=CN=C1 | SW208778 | 3.99 |
| CC(C)S(=O)C1=C(N)C2=C(C=C(N=C2S1)C1=NC=CS1)C1=CC=CC=C1 | SW208780 | 5.55 |
| CCCS(=O)C1=C(N)C2=C(C=C(N=C2S1)C1=CC=CS1)C(=O)OCC | SW208781 | 1.99 |
| CCCS(=O)C1=C(N)C2=C(C=C(N=C2S1)C1=CC=CS1)C(O)=O | SW208782 | 70.91 |

TABLE 1-continued

| Structure/Smiles | ID # | Enzyme Inhibitor IC$_{50}$ (nM) at 5 nM 15-PGDH |
|---|---|---|
| CCCCS(=O)C1=C(N)C2=C(C3=CC=C(Br)C=C3)C(C(=O)OCC)=C(N=C2S1)C1=NC=CS1 | SW209123 | 40.80 |
| CCCCS(=O)C1=C(N)C2=C(C=C(N=C2S1)C1=NC=CS1)C1=NC=CS1 | SW209124 | 1.83 |
| CCCCS(=O)C1=C(N)C2=C(C=C(N=C2S1)C1=NC=CS1)C1=NC=CN1C | SW209125 | 2.13 |
| CCCCS(=O)C1=C(N)C2=C(C=C(N=C2S1)C1=NC=CN1C)C1=CC=CC=C1 | SW209126 | 6.67 |

TABLE 1-continued
| Structure/Smiles | ID # | Enzyme Inhibitor IC50 (nM) at 5 nM 15-PGDH |
|---|---|---|
| 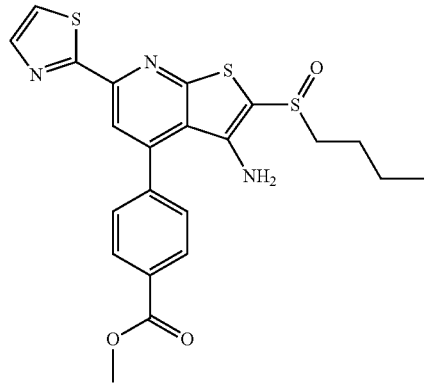 [SMILES: CCCCS(=O)c1sc2nc(-c3nccs3)cc(-c3ccc(C(=O)OC)cc3)c2c1N]<br>CCCCS(=O)C1=C(N)C2=C(C=C(N=C2S1)C1=NC=CS1)C1=CC=C(C=C1)C(=O)OC | SW209127 | 15.13 |
| 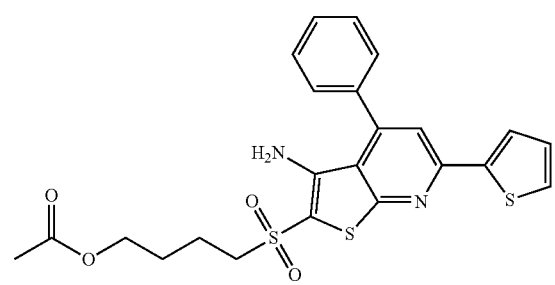 [SMILES: CC(=O)OCCCCS(=O)(=O)c1sc2nc(-c3cccs3)cc(-c3ccccc3)c2c1N]<br>CC(=O)OCCCCS(=O)(=O)C1=C(N)C2=C(C=C(N=C2S1)C1=CC=CS1)C1=CC=CC=C1 | SW209128 | 4914.00 |
| 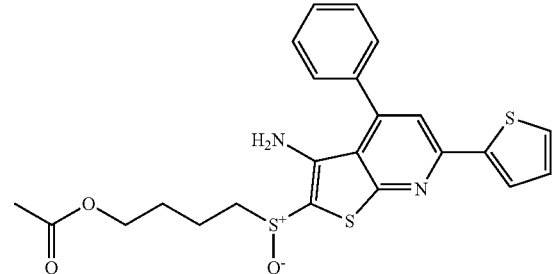 [SMILES: CC(=O)OCCCC[S+]([O-])c1sc2nc(-c3cccs3)cc(-c3ccccc3)c2c1N]<br>CC(=O)OCCCC[S+]([O-])C1=C(N)C2=C(C=C(N=C2S1)C1=CC=CS1)C1=CC=CC=C1 | SW209129 | 41.52 |
| 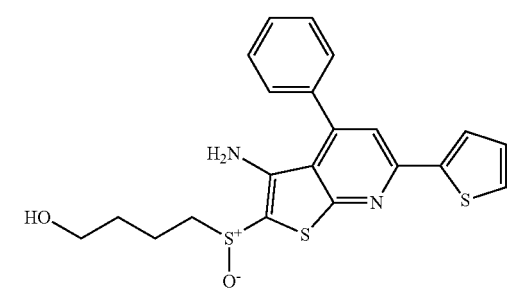 [SMILES: Nc1c([S+]([O-])CCCCO)sc2nc(-c3cccs3)cc(-c3ccccc3)c12]<br>NC1=C(SC2=NC(=CC(=C12)C1=CC=CC=C1)C1=CC=CS1)[S+]([O-])CCCCO | SW209271 | 34.18 |

TABLE 1-continued

| Structure/Smiles | ID # | Enzyme Inhibitor IC$_{50}$ (nM) at 5 nM 15-PGDH |
|---|---|---|
| CC(=O)OCCCS(=O)(=O)C1=C(N)C2=C(C=C(N=C2S1)C1=CC=CS1)C1=CC=CC=C1 | SW209272 | 530.20 |
| CC(=O)OCCC[S+]([O-])C1=C(N)C2=C(C=C(N=C2S1)C1=CC=CS1)C1=CC=CC=C1 | SW209273 | 21.62 |
| NC1=C(SC2=NC(=CC(=C12)C1=CC=CC=C1)C1=CC=CS1)[S+]([O-])CCCO | SW209274 | 36.57 |
| CCCCSC1=C(N)C2=C(C=C(N=C2S1)C1=CC=CS1)C1=CC=CC=C1 | SW209275 | 80.02 |

TABLE 1-continued
| Structure/Smiles | ID # | Enzyme Inhibitor IC$_{50}$ (nM) at 5 nM 15-PGDH |
|---|---|---|
| 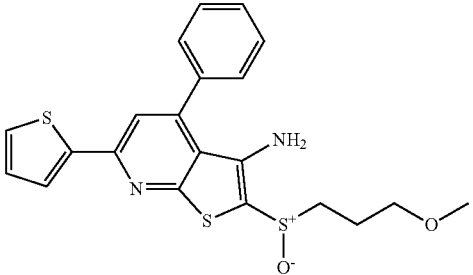 [SMILES: COCCC[S+]([O-])c1sc2nc(-c3cccs3)cc(-c3ccccc3)c2c1N] COCCC[S+]([O−])C1=C(N)C2=C(C=C(N=C2S1)C1=CC=CS1)C1=CC=CC=C1 | SW209276 | 2.09 |
| 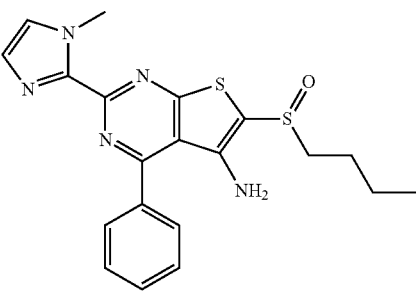 [SMILES: CCCCS(=O)c1sc2nc(-c3nccn3C)nc(-c3ccccc3)c2c1N] CCCCS(=O)C1=C(N)C2=C(S1)N=C(N=C2C1=CC=CC=C1)C1=NC=CN1C | SW209277 | 3.71 |
| 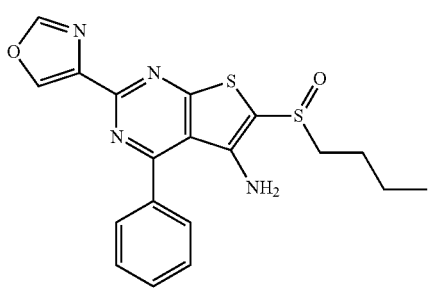 [SMILES: CCCCS(=O)c1sc2nc(-c3cocn3)nc(-c3ccccc3)c2c1N] CCCCS(=O)C1=C(N)C2=C(S1)N=C(N=C2C1=CC=CC=C1)C1=COC=N1 | SW209278 | 2.56 |
| 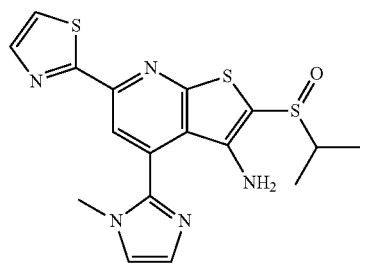 [SMILES: CC(C)S(=O)c1sc2nc(-c3nccs3)cc(-c3nccn3C)c2c1N] CC(C)S(=O)C1=C(N)C2=C(S1)N=C(C=C2C1=NC=CN1C)C1=NC=CS1 | SW209279 | 4.18 |

TABLE 1-continued

| Structure/Smiles | ID # | Enzyme Inhibitor IC$_{50}$ (nM) at 5 nM 15-PGDH |
|---|---|---|
| CCCS(=O)C1=C(N)C2=C(S1)N=C(C=C2C1=NC=CN1C)C1=NC=CS1 | SW209280 | 3.73 |
| CCCCS(=O)C1=C(N)C2=C(S1)N=C(C=C2C1=CC=C(C=C1)C(O)=O)C1=NC=CS1 | SW209281 | 3.40 |
| CCCCS(=O)C1=C(N)C2=C(S1)N=C(C=C2C1=CC=C(C=C1)C(=O)N(C)C)C1=NC=CS1 | SW209282 | 5.87 |
| CCCCS(=O)C1=C(N)C2=C(S1)N=C(C=C2C(=O)N(C)C)C1=CC=CS1 | SW209283 | 14.70 |

TABLE 1-continued
| Structure/Smiles | ID # | Enzyme Inhibitor IC$_{50}$ (nM) at 5 nM 15-PGDH |
|---|---|---|
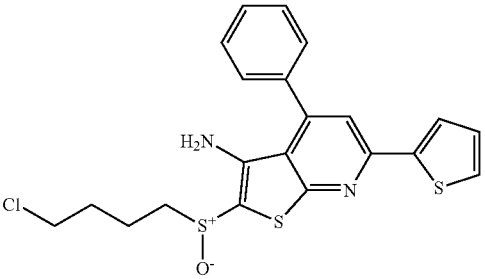 [SMILES: Nc1c([S+]([O-])CCCCCl)sc2nc(-c3cccs3)cc(-c3ccccc3)c12]
NC1=C(SC2=NC(=CC(=C12)C1=CC=CC=C1)C1=CC=CS1)[S+]([O-])CCCCCl
SW209329   4.36
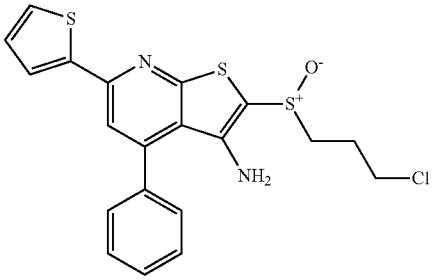 [SMILES: Nc1c([S+]([O-])CCCCl)sc2nc(-c3cccs3)cc(-c3ccccc3)c12]
NC1=C(SC2=NC(=CC(=C12)C1=CC=CC=C1)C1=CC=CS1)[S+]([O-])CCCCl
SW209330   4.01
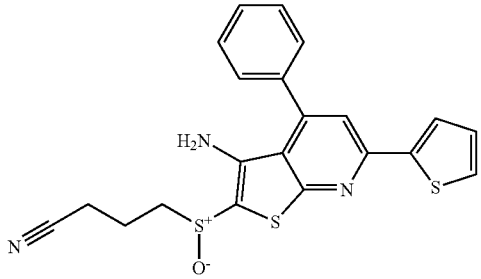 [SMILES: N#CCCC[S+]([O-])c1sc2nc(-c3cccs3)cc(-c3ccccc3)c2c1N]
NC1=C(SC2=NC(=CC(=C12)C1=CC=CC=C1)C1=CC=CS1)[S+]([O-])CCCF
SW209331   6.14
NC1=C(SC2=NC(=CC(=C12)C1=CC=CC=C1)C1=CC=CS1)[S+]([O-])CCCC#N
SW209332   8.72

TABLE 1-continued

| Structure/Smiles | ID # | Enzyme Inhibitor IC$_{50}$ (nM) at 5 nM 15-PGDH |
|---|---|---|
| CCCCS(=O)(=O)C1=C(N)C2=C(C=C(N=C2S1)C1=NC=CS1)C1=CC=C(CO)C=C1 | SW209333 | >2500 |
| CCCCS(=O)C1=C(N)C2=C(C=C(N=C2S1)C1=NC=CS1)C1=CN=C(C)N1C | SW209415 | 2.60 |
| CCCCS(=O)C1=C(N)C2=C(C=C(N=C2S1)C1=NC=CS1)C1=CC=CC(=C1)C(=O)OC | SW209416 | 8.98 |
| CCCCS(=O)C1=C(N)C2=C(C=C(N=C2S1)C1=NC=CS1)C1=CC=CC(=C1)C(=O)N(C)C | SW209417 | 18.50 |

TABLE 1-continued

| Structure/Smiles | ID # | Enzyme Inhibitor IC$_{50}$ (nM) at 5 nM 15-PGDH |
|---|---|---|
| | SW209418 | 4.29 |
| CCCCS(=O)C1=C(N)C2=C(C=C(N=C2S1)C1=NC=CS1)C1=CC=CC(CO)=C1 | | |
| | SW209419 | 20.20 |
| CCCCS(=O)C1=C(N)C2=C(C=C(N=C2S1)C1=NC=CS1)C1=CC=CC(=C1)C(O)=O | | |
| | SW209420 | 36.40 |
| CCCCS(=O)C1=C(N)C2=C(C=C(N=C2S1)C1=NC=CS1)C1=CC=CC(=C1)C(=O)N1CCN(C)CC1 | | |
| | SW209427 | 1485.00 |
| CCCCS(=O)CSC1=NC(=CC(C2=NC=CN2C)=C1C#N)C1=NC=CS1 | | |

TABLE 1-continued

| Structure/Smiles | ID # | Enzyme Inhibitor IC$_{50}$ (nM) at 5 nM 15-PGDH |
|---|---|---|
| CCCCS(=O)C1=C(N)C2=C(C=C(N=C2S1)C1=NC=CS1)C1=CN=C(C)N1 | SW209428 | 2.30 |
| CCCCS(=O)C1=C(N)C2=C(S1)N=C(C=C2C1=CC=CC(=C1)C(=O)NCC=C)C1=NC=CS1 | SW209508 | 2.50 |
| CCCCS(=O)C1=C(N)C2=C(S1)N=C(C=C2C1=CC=CC(=C1)C(=O)NCCN(C)C)C1=NC=CS1 | SW209509 | 19.30 |
| CCCCS(=O)C1=C(N)C2=C(S1)N=C(C=C2C1=CC=C(CO)C=C1)C1=NC=CS1 | SW209510 | 2.50 |

TABLE 1-continued
| Structure/Smiles | ID # | Enzyme Inhibitor IC$_{50}$ (nM) at 5 nM 15-PGDH |
|---|---|---|
| 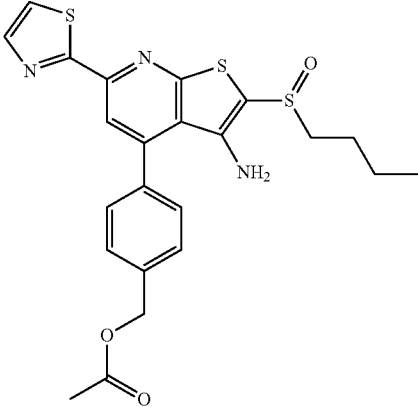 [SMILES: CCCCS(=O)c1sc2nc(-c3nccs3)cc(-c3ccc(COC(C)=O)cc3)c2c1N] CCCCS(=O)C1=C(N)C2=C(S1)N=C(C=C2C1=CC=C(COC(C)=O)C=C1)C1=NC=CS1 | SW209511 | 2.50 |
| 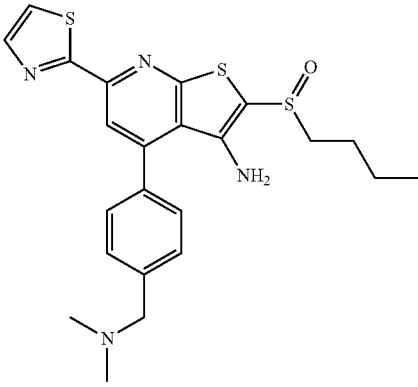 [SMILES: CCCCS(=O)c1sc2nc(-c3nccs3)cc(-c3ccc(CN(C)C)cc3)c2c1N] CCCCS(=O)C1=C(N)C2=C(S1)N=C(C=C2C1=CC=C(CN(C)C)C=C1)C1=NC=CS1 | SW209513 | 5.70 |
| 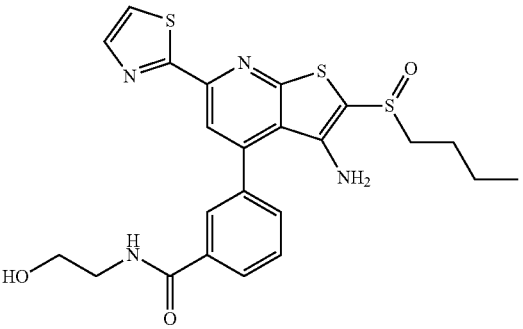 [SMILES: CCCCS(=O)c1sc2nc(-c3nccs3)cc(-c3cccc(C(=O)NCCO)c3)c2c1N] CCCCS(=O)C1=C(N)C2=C(C=C(N=C2S1)C1=NC=CS1)C1=CC=CC(=C1)C(=O)NCCO | SW211535 | 3.45 |

TABLE 1-continued

| Structure/Smiles | ID # | Enzyme Inhibitor IC$_{50}$ (nM) at 5 nM 15-PGDH |
|---|---|---|
| CCCCS(=O)C1=C(N)C2=C(C=C(N=C2S1)C1=NC=CS1)C1=CN=C(C(C)C)N1C | SW212344 | 20.53 |
| CCCCS(=O)C1=C(N)C2=C(C=C(N=C2S1)C1=NC=CS1)C1=CN=C(C2CC2)N1C | SW212345 | 2.99 |
| CCCCS(=O)C1=C(N)C2=C(S1)N=C(C=C2C1=CC=C(OCC(O)=O)C=C1)C1=NC=CS1 | SW212363 | 2.71 |

TABLE 1-continued

| Structure/Smiles | ID # | Enzyme Inhibitor IC$_{50}$ (nM) at 5 nM 15-PGDH |
|---|---|---|
| | SW212364 | 3.97 |

CCCCS(=O)C1=C(N)C2=C(C=C(N=C2S1)C1=NC=CS1)C1=CC=C(OCCO)C=C1

| | SW212365 | 8.53 |

CCCCS(=O)C1=C(N)C2=C(C=C(N=C2S1)C1=NC=CS1)C1=CC=C(OCC(=O)OC)C=C1

| | SW212366 | 3.48 |

CCCCS(=O)C1=C(N)C2=C(C=C(N=C2S1)C1=NC=CS1)C1=CC=C(COC(=O)CN(C)C)C=C1

TABLE 1-continued

| Structure/Smiles | ID # | Enzyme Inhibitor IC$_{50}$ (nM) at 5 nM 15-PGDH |
|---|---|---|
| [structure] | SW211688 | 3.33 |
| COCCCS(=O)C1=C(N)C2=C(S1)N=C(C=C2C1=CN=C(C)N1C)C1=NC=CS1 | | |
| [structure] | SW211689 | 4.06 |
| COCCS(=O)C1=C(N)C2=C(S1)N=C(C=C2C1=CN=C(C)N1C)C1=NC=CS1 | | |
| [structure] | SW209415 (−)-isomer | 165.00 |
| CCCCS(=O)C1=C(N)C2=C(C=C(N=C2S1)C1=NC=CS1)C1=CN=C(C)N1C | | |
| [structure] | SW209415 (+)-isomer | 1.30 |
| CCCCS(=O)C1=C(N)C2=C(C=C(N=C2S1)C1=NC=CS1)C1=CN=C(C)N1C | | |

We first note that the 15-PGDH inhibitory activities of SW033291 and SW209415 are at least 98% due to the activity of the (+) optical isomers of these compounds. For SW033291, the (+)-isomer is the (R) enantiomer whereas the absolute configuration of (+)-SW209415 has not been established.

Example 3

The following Example describes the synthesis of SW033291 and analogues thereof as well as provides mass spectrometry and NMR confirmation of the structures.

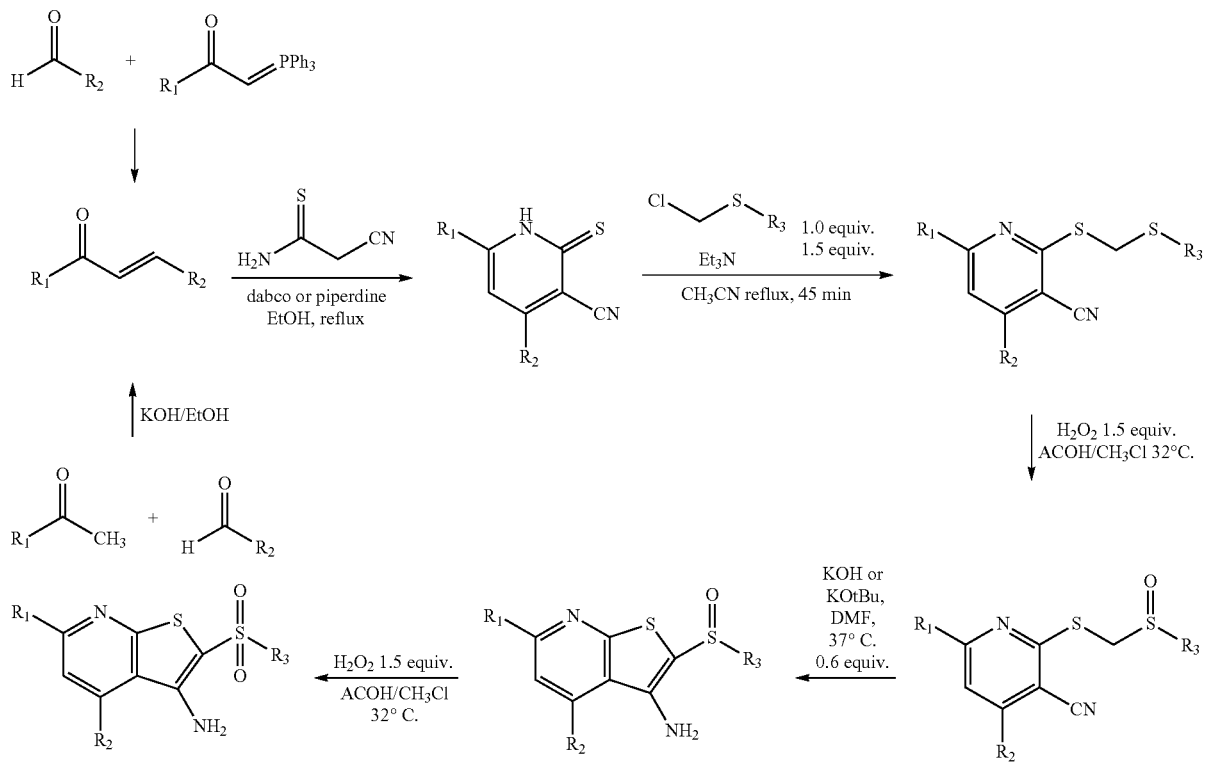

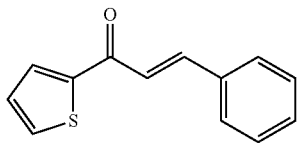 [SMILES: O=C(/C=C/c1ccccc1)c1cccs1]

3-phenyl-1-(thiophen-2-yl)prop-2-en-1-one was prepared from benzaldehyde and 1-(thiophen-2-yl)ethanone via aldol condensation using procedure described by Azam (Parveen, H.; Iqbal, P. F.; Azam, A. *Synth. Commu.*, 2008, 38, 3973). $^{1}$H NMR (400 MHz, CDCl$_3$) δ 7.88-7.80 (m, 2H), 7.67 (dd, J=4.9, 1.1 Hz, 1H), 7.66-7.59 (m, 2H), 7.47-7.34 (m, 4H), 7.18 (dd, J=5.0, 3.8 Hz, 1H). ESI-MS (m/z): 215 [M+H]$^{+}$.

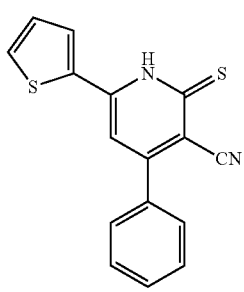 [SMILES: N#Cc1c(-c2ccccc2)cc(-c2cccs2)[nH]c1=S]

4-phenyl-6-(thiophen-2-yl)-2-thioxo-1,2-dihydropyridine-3-carbonitrile. To a solution of 3-phenyl-1-(thiophen-2-yl)prop-2-en-1-one (2.34 mmol, 500 mg) and cyanothioacetamide (7.0 mmol, 717 mg, 3.0 equiv.) in ethanol (7 mL), a few drops of piperidine were added. The reaction was refluxed for 3 h. The solid that formed was collected and recrystallized from acetic acid to give designed product in 46% isolated yield.
$^{1}$H NMR (400 MHz, DMSO-d$_6$) δ 8.17 (d, J=3.8 Hz, 1H), 7.96 (d, J=5.0 Hz, 1H), 7.74-7.62 (m, 2H), 7.54 (dd, J=5.1, 2.0 Hz, 3H), 7.31-7.19 (m, 1H), 7.01 (s, 1H). ESI-MS (m/z): 295 [M+H]$^{+}$.

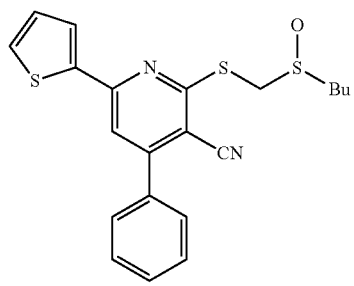

2-(((butylthio)methyl)sulfinyl)-4-phenyl-6-(thiophen-2-yl)nicotinonitrile. Acetic Acid (900 μL) and hydrogen peroxide (0.57 mmol, 1.5 equiv., 30% solution in water) were added to the solution of 2-(((butylthio)methyl)sulfinyl)-4-phenyl-6-(thiophen-2-yl)nicotinonitrile (0.38 mmol, 150 mg) in chloroform (900 μL). The reaction mixture was stirring at 32° C. for 45 min. The reaction was then diluted with EtOAc and washed with saturated NaHCO$_3$ solution, dried over magnesium sulfate, filtered and concentrated under reduced pressure to give 153 mg of designed product (98%). $^{1}$H NMR (400 MHz, CDCl$_3$) δ 7.75 (dd, J=3.8, 1.1 Hz, 1H), 7.66-7.57 (m, 2H), 7.58-7.51 (m, 4H), 7.47 (s, 1H), 7.16 (dd, J=5.0, 3.8 Hz, 1H), 4.74 (d, J=13.0 Hz, 1H), 4.41 (d, J=13.0 Hz, 1H), 2.97 (dt, J=13.0, 8.2 Hz, 1H), 2.81 (dt, J=12.9, 7.3 Hz, 1H), 1.94-1.76 (m, 2H), 1.53-1.38 (m, 2H), 0.94 (t, J=7.4 Hz, 3H). ESI-MS (m/z): 413 [M+H]$^{+}$.

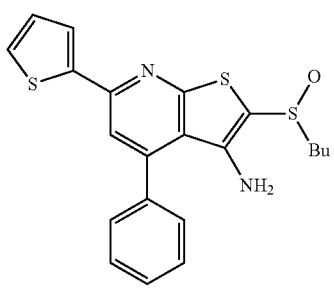

SW033291 2-(butylsulfinyl)-4-phenyl-6-(thiophen-2-yl)thieno[2,3-b]pyridin-3-amine was prepared using procedure describe by Kalugin (Kalugin V. E. *Russian. Chem. Bull., Int. Ed.,* 2006, 55, 529). To the solution of 4-(((butylthio)methyl)sulfinyl)-2,6-diphenylpyrimidine-5-carbonitrile (0.53 mmol, 220 mg) in DMF (0.25 M)/EtOH (0.5 M) was added KOH (0.32 mmol, 18 mg, 0.6 equiv., 0.1 M in water). The reaction mixture was stirred at 35° C. for 40 min. Once complete, the reaction was diluted with EtOAc and washed with 10% aq. solution of acidic acid, the organic phase was separated and aqueous layer was extracted twice with EtOAc, dried over magnesium sulfate, filtered and concentrated under reduced pressure to give 211 mg of SW033291 2-(butylsulfinyl)-4-phenyl-6-(thiophen-2-yl)thieno[2,3-b]pyridin-3-amine (96%). $^1$H NMR (400 MHz, CDCl$_3$) δ 7.67-7.60 (m, 1H), 7.57-7.35 (m, 7H), 7.10 (dd, J=5.0, 3.7 Hz, 1H), 4.54 (s, 2H), 3.26 (ddd, J=12.8, 9.1, 6.0 Hz, 1H), 3.09 (ddd, J=12.8, 9.1, 6.6 Hz, 1H), 1.83-1.61 (m, 2H), 1.53-1.38 (m, 2H), 0.93 (t, J=7.3 Hz, 3H). ESI-MS (m/z): 413 [M+H]$^+$.

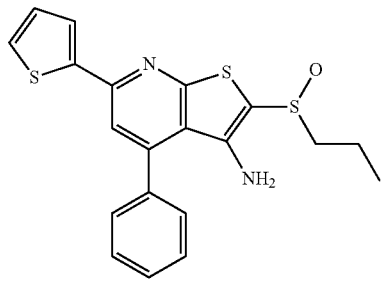

SW208437 4-phenyl-2-(propylsulfinyl)-6-(thiophen-2-yl)thieno[2,3-b]pyridin-3-amine was prepared in 56% isolated yield using synthetic procedures described for the preparation of analog SW033291. $^1$H NMR (400 MHz, CDCl$_3$) δ 7.65 (dd, J=3.8, 1.1 Hz, 1H), 7.61-7.49 (m, 4H), 7.49-7.41 (m, 3H), 7.12 (dd, J=5.0, 3.7 Hz, 1H), 3.28 (ddd, J=12.7, 8.4, 6.3 Hz, 1H), 3.07 (ddd, J=12.7, 8.6, 7.0 Hz, 1H), 1.91-1.65 (m, 2H), 1.08 (t, J=7.4 Hz, 3H). APCI-MS (m/z): 399 [M+H]$^+$.

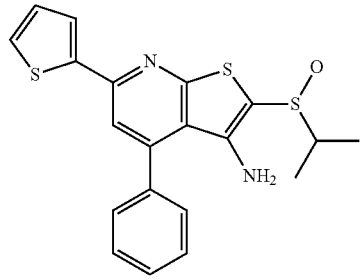

SW208438 2-(isopropylsulfinyl)-4-phenyl-6-(thiophen-2-yl)thieno[2,3-b]pyridin-3-amine was prepared in 48% isolated yield using synthetic procedures described for the preparation of analog SW033291. $^1$H NMR (400 MHz, CDCl$_3$) δ 7.64 (dd, J=3.7, 1.1 Hz, 1H), 7.58-7.47 (m, 5H), 7.47-7.39 (m, 2H), 7.10 (dd, J=5.0, 3.7 Hz, 1H), 4.59 (s, 2H), 3.38 (p, J=6.8 Hz, 1H), 1.43 (d, J=6.9 Hz, 3H), 1.25 (d, J=6.8 Hz, 3H). ESI-MS (m/z): 399 [M+H]$^+$.

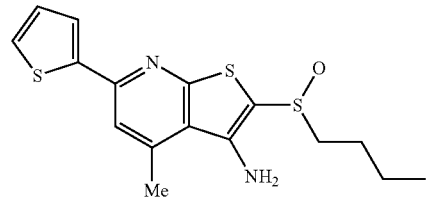

SW208488 2-(butylsulfinyl)-4-methyl-6-(thiophen-2-yl)thieno[2,3-b]pyridin-3-amine was prepared using synthetic procedures described for the preparation of analog SW033291. $^1$H NMR (400 MHz, CDCl$_3$) δ 7.55 (dd, J=3.7, 1.2 Hz, 1H), 7.39 (dd, J=5.0, 1.1 Hz, 1H), 7.25-7.23 (m, 1H), 7.06 (dd, J=5.0, 3.7 Hz, 1H), 5.02 (s, 2H), 3.25 (ddd, J=12.7, 9.1, 6.0 Hz, 1H), 3.08 (ddd, J=12.8, 9.2, 6.4 Hz, 1H), 2.74 (s, 3H), 1.82-1.58 (m, 2H), 1.56-1.38 (m, 2H), 0.93 (t, J=7.3 Hz, 3H). ESI-MS (m/z): 351 [M+H]$^+$.

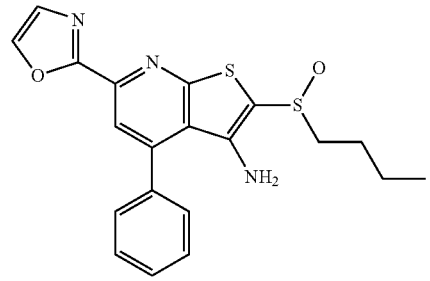

SW208496 2-(butylsulfinyl)-6-(oxazol-2-yl)-4-phenylthieno[2,3-b]pyridin-3-amine was prepared using synthetic procedures described for the preparation of analog SW033291. $^1$H NMR (400 MHz, CDCl$_3$) δ 7.99 (s, 1H), 7.84 (d, J=0.8 Hz, 1H), 7.58-7.41 (m, 5H). 7.33 (d, J=0.8 Hz, 1H), 4.65 (s, 2H), 3.30 (ddd, J=12.9, 8.8, 6.2 Hz, 1H), 3.10 (ddd, J=12.8, 8.9, 6.9 Hz, 1H), 1.86-1.64 (m, 2H), 1.42-1.54 (m, 2H), 0.93 (t, J=7.4 Hz, 3H). ESI-MS (m/z): 398.1 [M+H]$^+$.

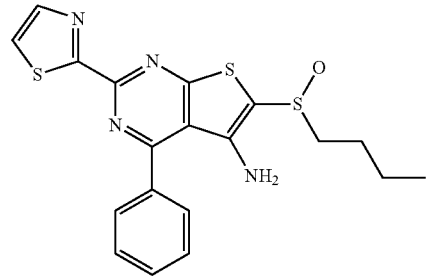

SW208436 6-(butylsulfinyl)-4-phenyl-2-(thiazol-2-yl)thieno[2,3-d]pyrimidin-5-amine was prepared by synthetic procedures described for the preparation of analog SW208065. $^1$H NMR (400 MHz, CDCl$_3$) δ 8.06 (dd, J=3.1, 1H), 7.75-7.66 (m, 2H), 7.75-7.66 (m, 3H), 7.55 (dd, J=3.1, 1H), 4.87 (s, 2H), 3.30 (ddd, J=12.8, 8.4, 6.3 Hz, 1H), 3.12 (ddd, J=12.8, 8.6, 6.9 Hz, 1H), 1.85-1.65 (m, 2H), 1.55-1.40 (m, 2H), 0.95 (t, J=7.3 Hz, 3H). ESI-MS (m/z): 415.1 [M+H]$^+$.

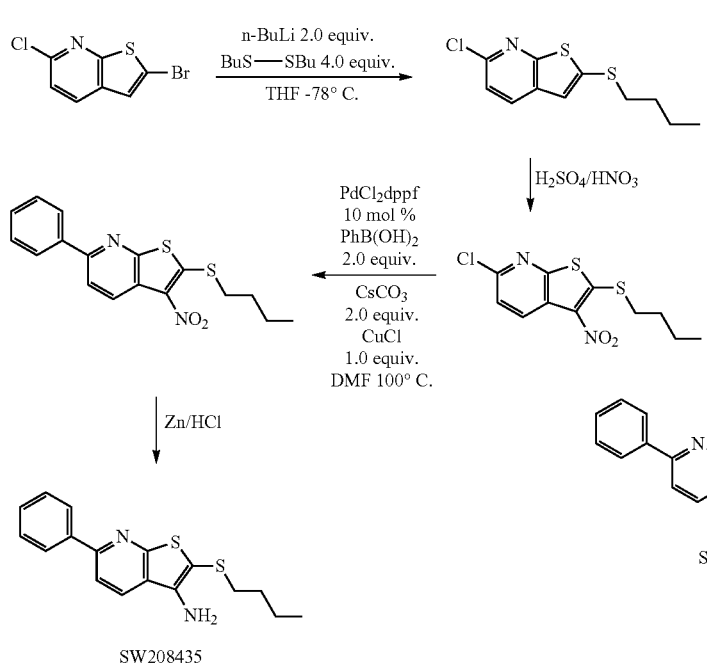

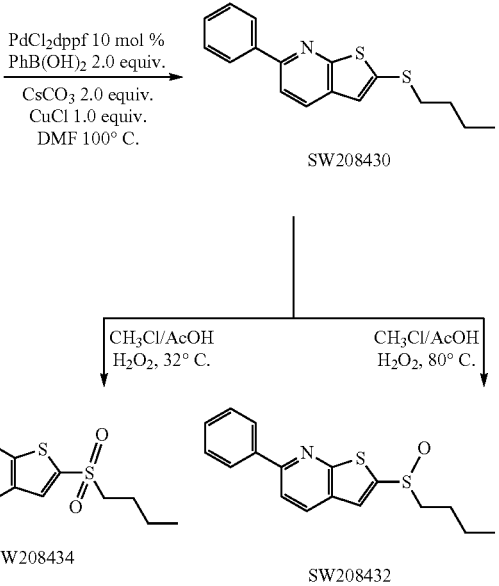

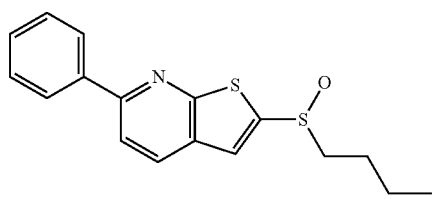

SW208432 2-(butylsulfinyl)-6-phenylthieno[2,3-b]pyridine. Acetic Acid (90 µL) and hydrogen peroxide (0.06 mmol, 1.5 equiv., 30% solution in water) were added to the solution of 2-(butylthio)-6-phenylthieno[2,3-b]pyridine (0.04 mmol, 12 mg) in chloroform (90 µL). The reaction mixture was stirring at 32° C. for 1 h. The reaction was then diluted with EtOAc and washed with saturated NaHCO₃ solution, dried over magnesium sulfate, filtered and concentrated under reduced pressure to give designed product in 76% isolated yield. ¹H NMR (400 MHz, CDCl₃) δ 8.14 (d, J=8.4, 1H), 8.08 (d, J=8.2, 2H), 7.82 (d, J=8.4, 1H), 7.58-7.36 (m, 4H), 3.30-2.73 (m, 2H), 1.90-1.62 (m, 2H), 1.55-1.41 (m, 2H), 0.94 (t, J=7.3 Hz, 3H). ESI-MS (m/z): 316.1 [M+H]⁺.

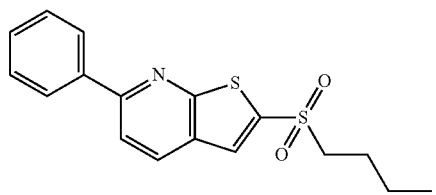 [SMILES: CCCCS(=O)(=O)c1cc2ccc(-c3ccccc3)nc2s1]

SW208434. Acetic Acid (200 µL) and hydrogen peroxide (0.15 mmol, 30% solution in water) were added to the solution of 2-(butylthio)-6-phenylthieno[2,3-b]pyridine (0.09 mmol, 27 mg) in chloroform (200 µL). The reaction mixture was stirring at 100° C. for 30 min. The reaction was then diluted with EtOAc and washed with saturated NaHCO₃ solution, dried over magnesium sulfate, filtered and concentrated under reduced pressure to give designed product in 81% isolated yield. ¹H NMR (400 MHz, CDCl₃) δ 8.23 (d, J=8.5 Hz, 1H), 8.09 (dd, J=8.2, 1.6 Hz, 2H), 7.89 (d, J=2.1 Hz, 1H), 7.59-7.39 (m, 4H), 3.39-3.10 (m, 2H), 1.92-1.68 (m, 2H), 1.54-1.27 (m, 2H), 0.91 (t, J=7.3 Hz, 3H). ESI-MS (m/z): 332.1 [M+H]⁺.

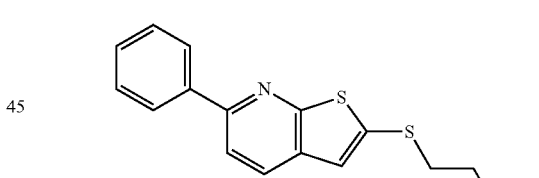

SW208430 2-(butylthio)-6-phenylthieno[2,3-b]pyridine. Phenylboronic acid (0.39 mmol, 2.0 equiv), 2-(butylthio)-6-chlorothieno[2,3-b]pyridine (50 mg, 0.195 mmol, 1.0 equiv), Cesium Carbonate (0.39 mmol, 2.0 equiv.), PdCl₂dppf (10 mol %), Copper Chloride (0.195 mmol, 1.0 equiv.) were heated in DMF at 100° C. for 12 h. After cooling to r.t. the reaction mixture was diluted with EtOAc and washed with water and next brine. The organic layer was dried over magnesium sulfate and the solvent was removed under reduced pressure. The crude product was purified by flash chromatography (Hexanes/EtOAc: 8/2) to afford designed product in 32% yield. ¹H NMR (400 MHz, CDCl₃) δ 8.09-8.00 (m, 2H), 7.93 (d, J=8.3 Hz, 1H), 7.69 (d, J=8.3 Hz, 1H), 7.52-7.34 (m, 4H), 2.99 (t, J=7.9 Hz, 2H), 1.77-1.63 (m, 2H), 1.53-1.38 (m, 2H), 0.92 (t, J=7.3 Hz, 3H). ESI-MS (m/z): 300.1 [M+H]⁺.

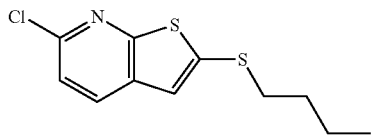

2-(butylthio)-6-chlorothieno[2,3-b]pyridine. To the solution of 2-bromo-6-chlorothieno[2,3-b]pyridine (40 mg, 0.16 mmol) in THF (2 mL) at −78° C. was added n-BuLi (0.32 mmol, 2.0 equiv.; 1.6 M solution in hexanes). The traction mixture was stirred for 5 min. and 1,2-dibutyldisulfane (0.48 mmol, 85.4 mg) was then added. The reaction mixture was stirred at −78° C. for additional 1 h, quenched with water and diluted with EtOAc. The organic layer was separated, dried over MgSO4, filtered and concentrated to give crude product, which was purified by flash column chromatography (95/5 Hexane/EtOAc) to give designed product in 91% isolated yield.

$^1$H NMR (400 MHz, CDCl$_3$) δ 7.81 (d, J=8.3 Hz, 1H), 7.24 (d, J=8.3 Hz, 1H), 7.13 (s, 1H), 3.01-2.89 (m, 2H), 1.74-1.59 (m, 2H), 1.52-1.36 (m, 2H), 0.91 (t, J=7.4 Hz, 3H). ESI-MS (m/z): 258.0 [M+H]$^+$.

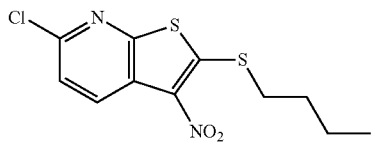 [SMILES: CCCCSc1sc2nc(Cl)ccc2c1[N+](=O)[O-]]

2-(butylthio)-6-chloro-3-nitrothieno[2,3-b]pyridine was prepared in 53% yield according procedure described by Nardine (Meth-Cohn, O.; Narine, B. *Tetrahedon Lett.* 1978, 23, 2045). $^1$H NMR (400 MHz, CDCl$_3$) δ 8.68 (d, J=8.6 Hz, 1H), 7.45 (d, J=8.6 Hz, 1H), 3.15 (t, J=7.4 Hz, 2H), 1.95-1.73 (m, 2H), 1.68-1.41 (m, 2H), 0.99 (t, J=7.4 Hz, 3H). ESI-MS (m/z): 303.0 [M+H]$^+$.

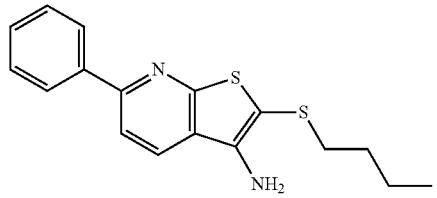 [SMILES: CCCCSc1sc2nc(-c3ccccc3)ccc2c1N]

SW208435 2-(butylthio)-6-phenylthieno[2,3-b]pyridin-3-amine. Phenylboronic acid (37 mg, 0.30 mmol, 2.0 equiv), 2-(butylthio)-6-chloro-3-nitrothieno[2,3-b]pyridine (46 mg, 0.15 mmol, 1.0 equiv), Cesium Carbonate (0.30 mmol, 2.0 equiv.), PdCl$_2$dppf (10 mol %), Copper Chloride (0.15 mmol, 15 mg, 1.0 equiv.) were heated in DMF at 100° C. for 12 h. After cooling to r.t. the reaction mixture was diluted with EtOAc and washed with water and next brine. The organic layer was dried over magnesium sulfate and the solvent was removed under reduced pressure. The crude product was purified by preparative TLC (AcOEt/Hexanes: 2/8) to afford 2-(butylthio)-3-nitro-6-phenylthieno[2,3-b]pyridine. ESI-MS (m/z): 345.1 [M+H]$^+$. 2-(butylthio)-3-nitro-6-phenylthieno[2,3-b]pyridine (0.017 mmol, 6 mg) was dissolved in a mixed solvent of acetic acid (0.12 mL) and conc. hydrochloric acid (one drop). Zinc (13 mg) was added at 0° C. After the mixture was stirred for 30 minutes, the reaction mixture was filtered, and the filtrate was neutralized with an aqueous solution of NaHCO$_3$, and extracted with DCM. The organic layer was washed with water and then with a saturated aqueous solution of sodium chloride, and dried over sodium sulfate. Subsequently, the solvent was evaporated to obtain designed product. $^1$H NMR (400 MHz, CDCl$_3$) δ 7.65-7.54 (m, 3H), 7.50-7.40 (m, 2H), 7.35-7.28 (m, 1H), 7.14 (d, J=8.4 Hz, 1H), 3.35-3.18 (m, 2H), 1.80-1.65 (m, 2H), 1.54-1.38 (m, 2H), 0.95 (t, J=7.3 Hz, 3H). ESI-MS (m/z): 315.1 [M+H]$^+$.

2-bromo-6-chlorothieno[2,3-b]pyridine was prepared according procedure described by Nardine. $^1$ $^1$H NMR (400 MHz, CDCl$_3$) δ 7.87 (d, J=8.4 Hz, 1H), 7.28 (s, 1H), 7.27 (d, J=8.4 Hz, 1H). ESI-MS (m/z): 249 [M+H]$^+$.

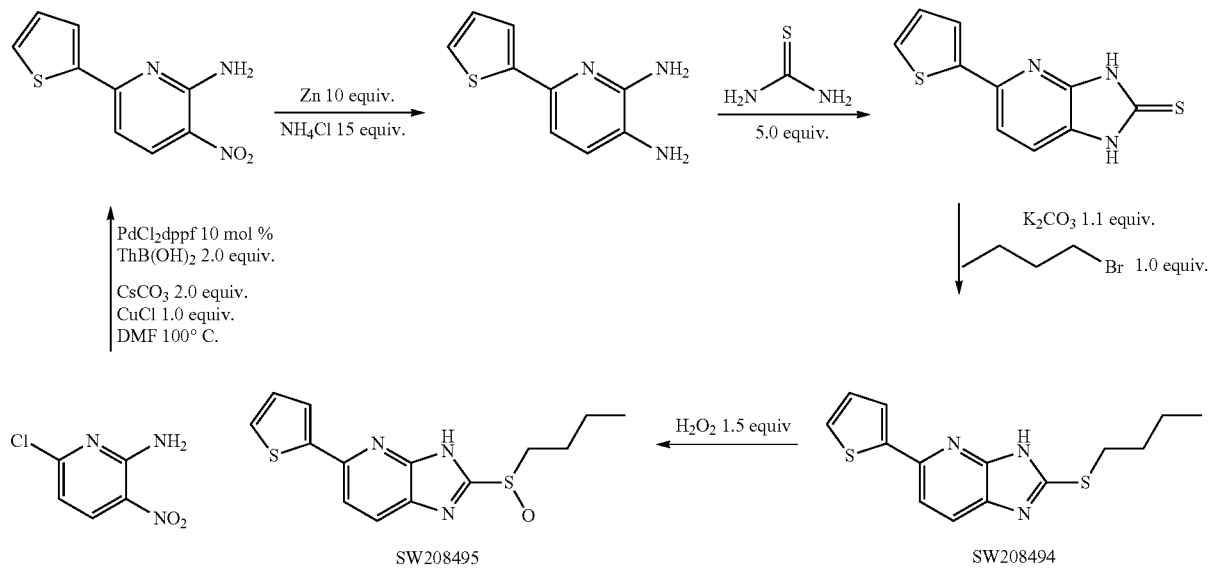

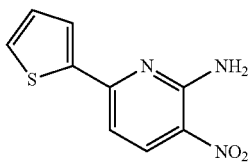

3-nitro-6-(thiophen-2-yl)pyridin-2-amine. Thiophene boronic acid (742 mg, 5.8 mmol, 2.0 equiv), 6-chloro-3-nitropyridin-2-amine (500 mg, 2.9 mmol, 1.0 equiv), Cesium Carbonate (5.8 mmol, 2.0 equiv.), PdCl$_2$dppf (10 mol %), Copper Chloride (2.9 mmol, 1.0 equiv.) in DMF were heated at 100° C. for 12 h. After cooling to r.t. the reaction mixture was diluted with EtOAc and washed with water and next brine. The organic layer was dried over magnesium sulfate and the solvent was removed under reduced pressure. The crude product was purified by column chromatography (hexanes/EtOAc: 8/2) to afford 3-nitro-6-(thiophen-2-yl)pyridin-2-amine in 63% yield. $^1$H NMR (400 MHzCDCl$_3$) δ 8.42 (d, J=8.7 Hz, 1H), 7.70 (dd, J=3.8, 1.1 Hz, 1H), 7.54 (dd, J=5.0, 1.1 Hz, 1H), 7.15 (dd, J=5.0, 3.8 Hz, 1H), 7.09 (d, J=8.7 Hz, 1H). ESI-MS (m/z): 222 [M+H]$^+$.

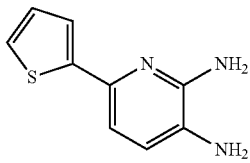 [SMILES: Nc1ccc(-c2cccs2)nc1N]

6-(thiophen-2-yl)pyridine-2,3-diamine. The starting material, 3-nitro-6-(thiophen-2-yl)pyridin-2-amine (1.20 mmol, 265.4 mg), was dissolved in a 5:1 acetone/water mixture. Zinc (12.0 mmol, 784 mg, 10 eq) and ammonium chloride (18 mmol, 962.5 mg, 15 eq) were added to the solution, which was stirred at room temperature for 1 hour. The solution was then filtered through a celite pad and washed with ethyl acetate. The filtrate was extracted twice with brine then the aqueous layer was back extracted with EtOAc. The combined organic layers were dried over magnesium sulfate, filtered, and concentrated under reduced pressure. Further purification by column chromatography gave 118.2 mg of 6-(thiophen-2-yl)pyridine-2,3-diamine (52%). $^1$H NMR (400 MHz, CD$_3$OD) δ 7.34 (dd, J=3.6, 1.1 Hz, 1H), 7.25 (dd, J=5.1, 1.1 Hz, 1H), 7.00 (dd, J=5.1, 3.6 Hz, 1H), 6.96-6.86 (m, 2H), 4.85 (s, 4H). ESI-MS (m/z): 192 [M+H]$^+$.

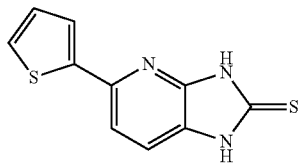 [SMILES: S=c1[nH]c2ccc(-c3cccs3)nc2[nH]1]

5-(thiophen-2-yl)-1,3-dihydro-2H-imidazo[4,5-b]pyridine-2-thione. Thiourea (16.97 mmol, 223.0 mg, 5 eq) was added to 6-(thiophen-2-yl)pyridine-2,3-diamine. The solution was heated at 170° C. for 2 hours. The addition of ethanol room temperature produced solid which was filtered to give 112.5 mg of 5-(thiophen-2-yl)-1,3-dihydro-2H-imidazo[4,5-b]pyridine-2-thione (82%). $^1$H NMR (400 MHz, (CD$_3$)$_2$SO) δ 7.69 (dd, J=3.7, 1.2 Hz, 1H), 7.66 (d, J=8.3 Hz, 1H), 7.56 (dd, J=5.1, 1.1 Hz, 1H), 7.47 (d, J=8.2 Hz, 1H), 7.15-7.09 (m, 1H). ESI-MS (m/z): 235 [M+2H]$^+$.

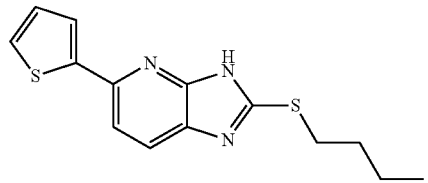 [SMILES: CCCCSc1nc2ccc(-c3cccs3)nc2[nH]1]

SW208494 2-(butylthio)-5-(thiophen-2-yl)-3H-imidazo[4,5-b]pyridine. A mixture of 5-(thiophen-2-yl)-1,3-dihydro-2H-imidazo[4,5-b]pyridine-2-thione (0.39 mmol, 92 mg), potassium carbonate (0.45 mmol, 61.9 mg, 1.1 eq), 1-bromobutane (0.39 mmol, 42.8 μL, 1 eq), 18-Crown-6 (0.039 mmol, 10.5 mg, 0.1 eq), and DMF (2.67 mL) was heated at 80° C. for 3 hours. This solution was then diluted with EtOAc and washed with water. The organic layer was dried over magnesium sulfate, filtered, and concentrated under high pressure to give 74.4 mg of SW208494 2-(butylthio)-5-(thiophen-2-yl)-3H-imidazo[4,5-b]pyridine (65%). $^1$H NMR (400 MHz, CDCl$_3$) δ 7.95-7.83 (m, 1H), 7.61-7.53 (m, 2H), 7.36 (d, J=5.1, 1H), 7.16-7.06 (m, 1H), 3.28 (t, J=7.3 Hz, 2H), 1.76-1.62 (m, 2H), 1.48-1.32 (m, 2H), 0.90 (t, J=7.4 Hz, 3H). ESI-MS (m/z): 290 [M+H]$^+$.

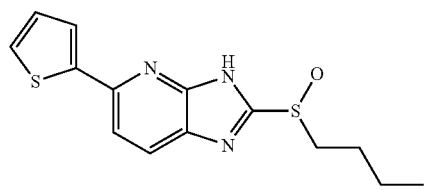

SW208495. 2-(butylsulfinyl)-5-(thiophen-2-yl)-3H-imidazo[4,5-b]pyridine. Chloroform (450 μL), acetic acid (450 μL), and hydrogen peroxide (0.376 mmol, 2.0 eq, 40 μL) were added to SW208494 2-(butylthio)-5-(thiophen-2-yl)-3H-imidazo[4,5-b]pyridine and heated at 45° C. for 2.5 hours. The solution was then diluted with EtOAc and washed with 10% acetic acid. The organic layer was separated, dried with magnesium sulfate, filtered, concentrated, and purified to give 16.8 mg of SW208495. $^1$H NMR (400 MHz, CDCl$_3$) δ 8.06 (d, J=8.5 Hz, 1H), 7.83-7.67 (m, 1H), 7.68-7.60 (m, 1H), 7.41 (d, J=5.3 Hz, 1H), 7.20-7.05 (m, 1H), 3.44-3.17 (m, 2H). 1.89-1.58 (m, 2H), 1.59-1.40 (m, 2H), 0.93 (t, J=7.3 Hz, 3H). ESI-MS (m/z): 306 [M+H]$^+$.

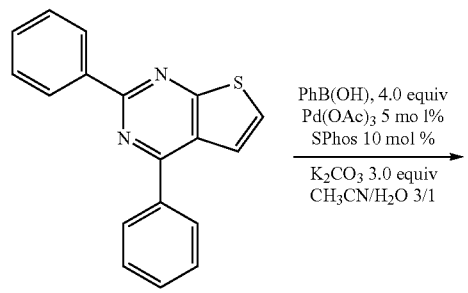
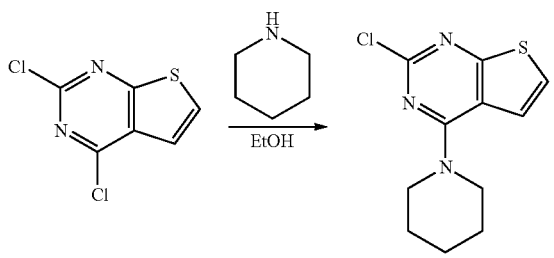
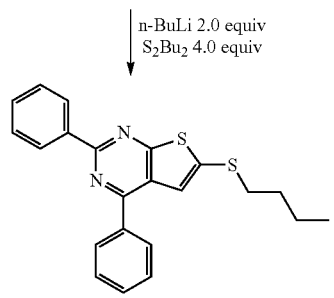
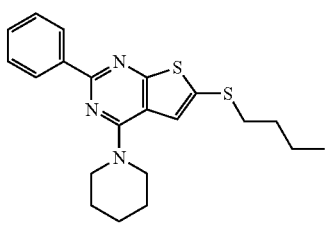
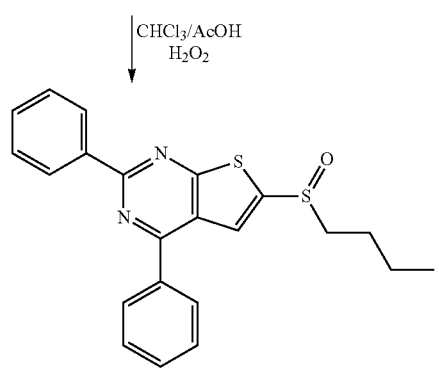
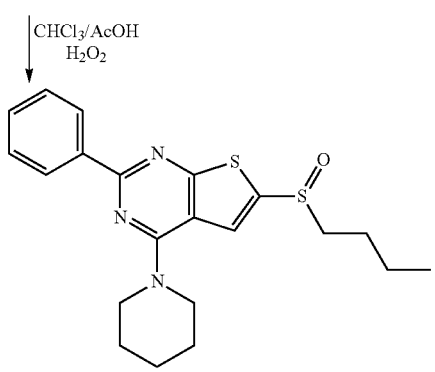

SW208776

SW208662

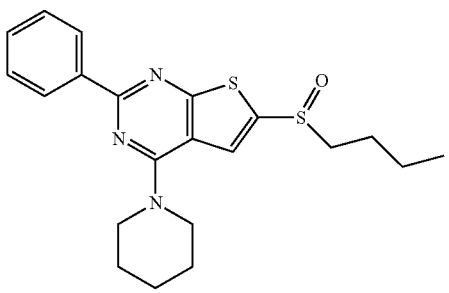 [SMILES: CCCCS(=O)c1cc2c(N3CCCCC3)nc(-c3ccccc3)nc2s1]

SW208662. 6-(butylsulfinyl)-2-phenyl-4-(piperidin-1-yl)thieno[2,3-d]pyrimidine. Acetic acid (50 μl) and hydrogen peroxide (5.0 μl, 30% solution in water) were added to the solution of 2-(butylthio)-6-phenyl-4-(piperidin-1-yl)thieno[2,3-b]pyrimidine (10 mg, 0.026 mmol) in chloroform (50 μl). The reaction mixture was stirred at 32° C. for 45 min. Once complete, the reaction was diluted with EtOAc and was washed with saturated NaHCO$_3$ solution, dried over magnesium sulfate, filtered and concentrated under reduce pressure to give designed product. $^1$H NMR (400 MHz, CDCl$_3$) δ 8.54-8.34 (m, 2H), 7.73 (s, 1H), 7.55-7.36 (m, 3H), 4.09-3.86 (m, 4H), 3.24-2.94 (m, 2H), 1.97-1.36 (m, 10H), 0.93 (t, J=7.3 Hz, 3H). ESI-MS (m/z): 400.1 [M+H]$^+$.

2-(butylthio)-6-phenyl-4-(piperidin-1-yl)thieno[2,3-b]pyrimidine. 2-(butylthio)-6-chloro-4-(piperidin-1-yl)thieno[2,3-b]pyrimidine (52 mg, 0.15 mmol), phenylboronic acid (27 mg, 0.22 mmol, 1.5 equiv), Potassium Carbonate (0.3 mmol, 2.0 equiv.), PdCl2dtbpf (10 mol mol %), in CH3CN:H2O (2:1) were heated at 100° C. overnight. After cooling to r.t. the reaction mixture was diluted with EtOAc and washed with water. The organic layer was dried over magnesium sulfate and the solvent was removed under reduced pressure. The crude product was purified by flash chromatography to afford designed product. 1H NMR (400 MHz, CHCl3) δ 8.49-8.36 (m, 2H), 7.51-7.36 (m, 3H), 7.29 (s, 1H), 3.95-3.85 (m, 4H), 2.90 (t, J=7.4 Hz, 2H), 1.76-1.73 (m, 6H), 1.70-1.59 (m, 2H), 1.48-1.39 (m, 2H), 0.91 (t, J=7.4 Hz, 3H). ESI-MS (m/z): 384.0 [M+H]+.

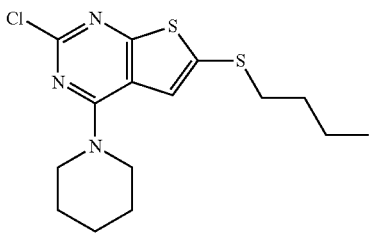 [SMILES: CCCCSc1cc2c(N3CCCCC3)nc(Cl)nc2s1]

2-(butylthio)-6-chloro-4-(piperidin-1-yl)thieno[2,3-b]pyrimidine. To the solution of 6-chloro-4-(piperidin-1-yl) thieno[2,3-b]pyrimidine (52 mg, 0.20 mmol) in THF was added n-BuLi (0.4 mmol, 2.0 equiv., 1.6 M solution in hexanes) at −78° C. The reaction mixture was stirred for 5 min and 1,2-dibutyldisulfane (0.80 mmol, 4.0 equiv.) in THF was added. The reaction mixture was stirred for additional 1 h at −78° C. and then quenched. The crude product was purified by flash chromatography to afford designed product in 74% yield. $^1$H NMR (400 MHz, CHCl$_3$) δ 7.24 (s, 1H), 3.93-3.74 (m, 4H), 2.83 (t, J=7.3 Hz, 2H), 1.82-1.66 (m, 6H), 1.66-1.53 (m, 2H), 1.49-1.33 (m, 2H), 0.89 (t, J=7.3 Hz, 3H). ESI-MS (m/z): 342.1 [M+H]$^+$.

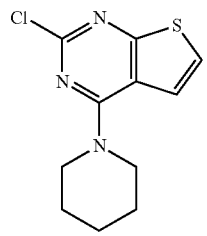 [SMILES: Clc1nc(N2CCCCC2)c2ccsc2n1]

6-chloro-4-(piperidin-1-yl)thieno[2,3-b]pyrimidine. 4,6-dichlorothieno[2,3-b]pyrimidine (50 mg, 0.24 mmol) and piperidine (0.36 mmol, 1.5 equiv.) in EtOH were stirred at room temperature overnight. The solvent was evaporated and crude compound purified by flash chromatography to give designed product in quantitative yield. $^1$H NMR (400 MHz, CDCl$_3$) δ 7.28 (d, J=6.1 Hz, 1H), 7.18 (d, J=6.2 Hz, 1H), 4.01-3.67 (m, 4H), 1.92-1.63 (m, 6H). ESI-MS (m/z): 254.0 [M+H]$^+$.

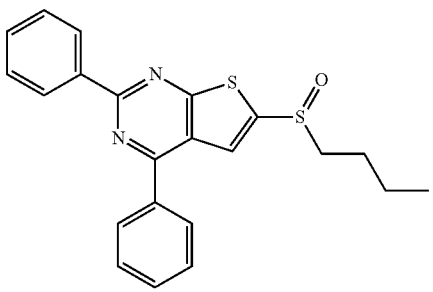 [SMILES: CCCCS(=O)c1cc2c(-c3ccccc3)nc(-c3ccccc3)nc2s1]

SW208776. 6-(butylsulfinyl)-2,4-diphenylthieno[2,3-d]pyrimidine. Acetic acid (250 µl) and hydrogen peroxide (20 µl, 30% solution in water) were added to the solution of 6-(butylthio)-2,4-diphenylthieno[2,3-d]pyrimidine (35 mg, 0.1 mmol) in chloroform (250 µl). The reaction mixture was stirred at 32° C. for 45 min. Once complete, the reaction was diluted with EtOAc and was washed with saturated NaHCO$_3$ solution, dried over magnesium sulfate, filtered and concentrated under reduce pressure to give designed product. $^1$H NMR (400 MHz, CDCl$_3$) δ 8.69-8.59 (m, 2H), 8.09-7.99 (m, 2H), 7.95 (s, 1H), 7.65-7.56 (m, 3H), 7.56-7.45 (m, 3H), 3.18-3.02 (m, 2H), 1.87-1.64 (m, 2H), 1.54-1.42 (m, 2H), 0.94 (t, J=7.3 Hz, 3H). ESI-MS (m/z): 393.1 [M+H]$^+$.

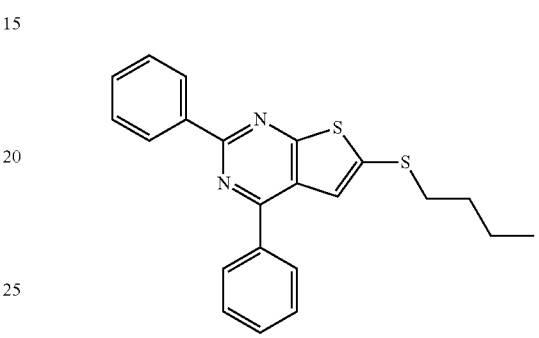

6-(butylthio)-2,4-diphenylthieno[2,3-d]pyrimidine. To the solution of 2,4-diphenylthieno[2,3-d]pyrimidine (53 mg, 0.28 mmol) in THF was added n-BuLi (0.56 mmol, 2.0 equiv., 225 µL, 2.5 µM solution in hexanes) at −78° C. The reaction mixture was stirred for 5 min and 1,2-dibutyldisulfane (1.14 mmol, 4.0 equiv.) in THF was added. The reaction mixture was stirred for additional 1 h at −78° C. and then quenched. The crude product was purified by flash chromatography to afford designed product. $^1$H NMR (400 MHz, CDCl$_3$) δ 8.62-8.56 (m, 2H), 8.06-7.98 (m, 2H), 7.61-7.41 (m, 7H), 3.01 (t, J=7.3, 2H), 1.76-1.62 (m, 2H), 1.55-1.38 (m, 2H), 0.92 (t, J=7.4 Hz, 3H). ESI-MS (m/z): 377.1 [M+H]$^+$.

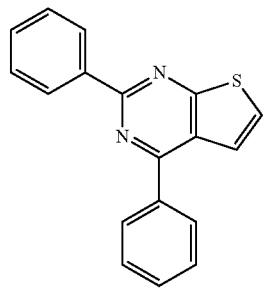 [SMILES: c1ccc(-c2nc(-c3ccccc3)c3ccsc3n2)cc1]

2,4-diphenylthieno[2,3-d]pyrimidine. 2,4-dichlorothieno[2,3-d]pyrimidine (100 mg, 0.50 mmol), phenylboronic acid (242 mg, 2.0 mmol, 4.0 equiv), Potassium Carbonate (1.5 mmol, 3.0 equiv.), Pd(OAc)$_2$ (5 mol mol %), SPhos (10 mol %) in CH$_3$CN:H$_2$O (1.5:1) were heated at 100° C. overnight. After cooling to r.t. the reaction mixture was diluted with EtOAc and washed with water. The organic layer was dried over magnesium sulfate and the solvent was removed under reduced pressure. The crude product was purified by flash chromatography to afford designed product. $^1$H NMR (400 MHz, CDCl$_3$) δ 8.70-8.59 (m, 2H), 8.14-8.02 (m, 2H), 7.65-7.44 (m, 8H). ESI-MS (m/z): 289.0 [M+H]$^+$.

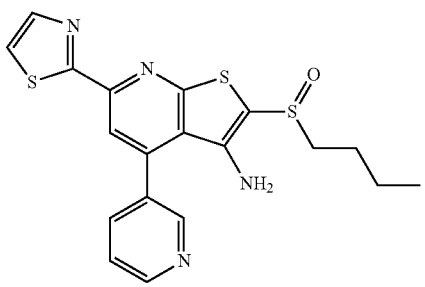

SW208777. 2-(butyl(λ¹-oxidanyl)-λ³-sulfanyl)-4-(pyridin-3-yl)-6-(thiazol-2-yl)thieno[2,3-b]pyridin-3-amine was prepared using synthetic procedures described for the preparation of analog SW033291. ¹H NMR (400 MHz, CDCl$_3$) δ 8.80 (s, 1H), 8.78 (dd, J=4.9, 1.7 Hz, 1H), 8.04 (s, 1H), 7.91 (d, J=3.2 Hz, 1H), 7.86 (d, J=6.4 Hz, 1H), 7.51 (d, J=3.1 Hz, 1H), 7.47 (dd, J=7.8, 4.8 Hz, 1H), 4.53 (s, 2H), 3.28 (ddd, J=12.8, 8.8, 6.3 Hz, 1H), 3.11 (ddd, J=12.8, 8.9, 6.9 Hz, 1H), 1.86-1.70 (m, 2H), 1.57-1.38 (m, 2H), 0.94 (t, J=7.3 Hz, 3H). ESI-MS (m/z): 415.0 [M+H]⁺.

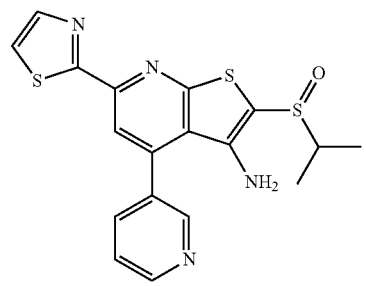

SW208780. 2-(isopropyl(λ¹-oxidanyl)-λ³-sulfanyl)-4-(pyridin-3-yl)-6-(thiazol-2-yl)thieno[2,3-b]pyridin-3-amine was prepared using synthetic procedures described for the preparation of analog SW033291. ¹H NMR (400 MHz, CDCl$_3$) δ 8.87-8.70 (m, 2H), 8.05 (s, 1H), 7.92 (d, J=3.1 Hz, 1H), 7.85 (dd, J=7.8, 2.4 Hz, 1H), 7.51 (d, J=3.2 Hz, 1H), 7.47 (dd, J=7.9, 4.9 Hz, 1H), 4.57 (s, 2H), 3.38 (p, J=6.8 Hz, 1H), 1.43 (d, J=6.8 Hz, 3H), 1.29 (d, J=6.8 Hz, 3H). ESI-MS (m/z): 400.1 [M+H]⁺.

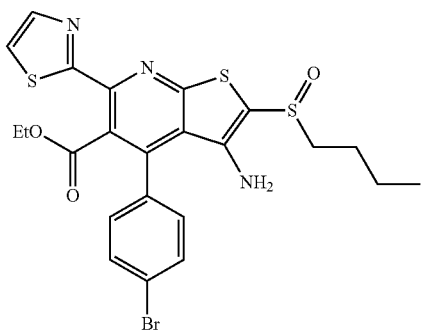 [SMILES: CCCCS(=O)c1sc2nc(-c3nccs3)c(C(=O)OCC)c(-c3ccc(Br)cc3)c2c1N]

SW209123. Ethyl 3-amino-4-(4-bromophenyl)-2-(butylsulfinyl)-6-(thiazol-2-yl)thieno[2,3-b]pyridine-5-carboxylate was prepared using synthetic procedures described for the preparation of analog SW033291. ¹H NMR (400 MHz, CDCl$_3$) δ 7.86 (d, J=3.2 Hz, 1H), 7.69-7.60 (m, 2H), 7.48 (d, J=3.2 Hz, 1H), 7.36-7.27 (m, 2H), 4.12 (q, J=7.2 Hz, 2H), 3.26 (ddd, J=12.9, 8.8, 6.3 Hz, 1H), 3.08 (ddd, J=12.9, 8.8, 6.3 Hz, 1H), 1.80-1.63 (m, 2H), 1.58-1.37 (m, 2H), 1.06 (t, J=7.2 Hz, 3H), 0.93 (t, J=7.3 Hz, 3H). ESI-MS (m/z): 564.0 [M+H]⁺.

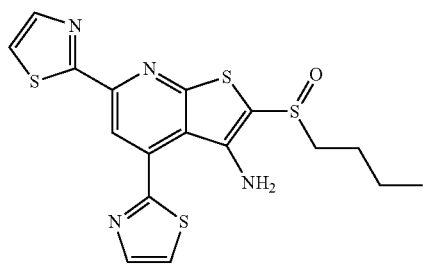 [SMILES: CCCCS(=O)c1sc2nc(-c3nccs3)cc(-c3nccs3)c2c1N]

SW209124. 2-(butylsulfinyl)-4,6-di(thiazol-2-yl)thieno[2,3-b]pyridin-3-amine was prepared using synthetic procedures described for the preparation of analog SW033291.
¹H NMR (400 MHz, CDCl$_3$) δ 8.48 (s, 1H), 8.01 (d, J=3.1 Hz, 1H), 7.96 (d, J=3.2 Hz, 1H), 7.61 (d, J=3.3 Hz, 1H), 7.52 (d, J=3.1 Hz, 1H), 6.69 (s, 2H), 3.30 (ddd, J=12.8, 9.2, 6.0 Hz, 1H), 3.14 (ddd, J=12.8, 9.2, 6.4 Hz, 1H), 1.83-1.60 (m, 2H), 1.43-1.53 (m, 2H), 0.93 (t, J=7.3 Hz, 3H). ESI-MS (m/z): 421.0 [M+H]⁺.

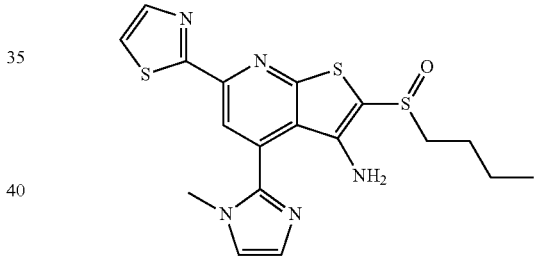

SW209125. 2-(butylsulfinyl)-4-(1-methyl-1H-imidazol-2-yl)-6-(thiazol-2-yl)thieno[2,3-b]pyridin-3-amine was prepared using synthetic procedures described for the preparation of analog SW033291. ¹H NMR (400 MHz, CDCl$_3$) δ 8.13 (s, 1H), 7.91 (d, J=3.2 Hz, 1H), 7.50 (d, J=3.1 Hz, 1H), 7.24 (d, J=1.2 Hz, 1H), 7.13 (d, J=1.2 Hz, 1H), 5.78 (s, 2H), 3.80 (s, 3H), 3.26 (ddd, J=12.8, 9.1, 6.0 Hz, 1H), 3.10 (ddd, J=12.8, 9.2, 6.5 Hz, 1H), 1.82-1.57 (m, 2H), 1.56-1.35 (m, 2H), 0.92 (t, J=7.3 Hz, 3H). ESI-MS (m/z): 418.1 [M+H]⁺.

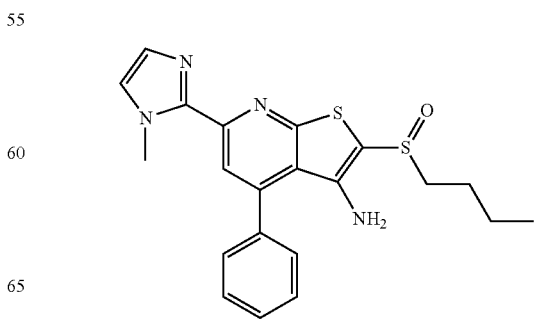

SW209126. 2-(butylsulfinyl)-6-(1-methyl-1H-imidazol-2-yl)-4-phenylthieno[2,3-b]pyridin-3-amine was prepared using synthetic procedures described for the preparation of analog SW033291. $^1$H NMR (400 MHz, CDCl$_3$) δ 8.08 (s, 1H), 7.58-7.32 (m, 5H), 7.11 (d, J=1.1 Hz, 1H), 7.00 (d, J=1.1 Hz, 1H), 4.58 (s, 2H), 4.19 (s, 3H), 3.27 (ddd, J=12.7, 9.0, 6.0 Hz, 1H), 3.08 (ddd, J=12.8, 9.1, 6.6 Hz, 1H), 1.79-1.60 (m, 2H), 1.56-1.37 (m, 2H), 0.92 (t, J=7.3 Hz, 3H). ESI-MS (m/z): 411.1 [M+H]$^+$.

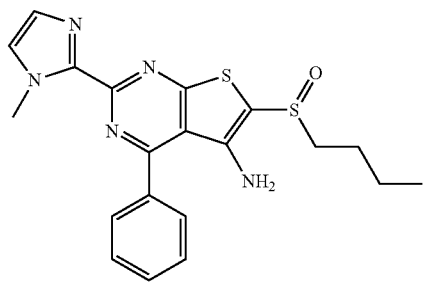

SW209277. 6-(butylsulfinyl)-2-(1-methyl-1H-imidazol-2-yl)-4-phenylthieno[2,3-d]pyrimidin-5-amine was prepared using synthetic procedures described for the preparation of analog SW208065. $^1$H NMR (400 MHz, CDCl$_3$) δ 7.71 (dd, J=6.9, 2.8 Hz, 2H), 7.63-7.49 (m, 3H), 7.29 (s, 1H), 7.07 (s, 1H), 4.85 (s, 2H), 4.18 (s, 3H), 3.29 (ddd, J=12.8, 8.6, 6.3 Hz, 1H), 3.11 (ddd, J=12.8, 8.7, 6.9 Hz, 1H), 1.83-1.65 (m, 2H), 1.59-1.39 (m, 2H), 0.94 (t, J=7.3 Hz, 3H). ESI-MS (m/z): 412.1 [M+H]$^+$.

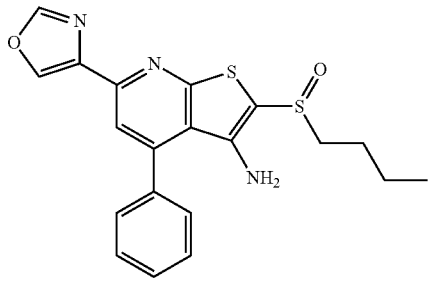 [SMILES: CCCCS(=O)c1sc2nc(-c3cocn3)cc(-c3ccccc3)c2c1N]

SW209278. 6-(butylsulfinyl)-2-(oxazol-4-yl)-4-phenylthieno[2,3-d]pyrimidin-5-amine was prepared using synthetic procedures described for the preparation of analog SW208065. $^1$H NMR (400 MHz, CDCl$_3$) δ 8.51 (d, J=1.1 Hz, 1H), 8.01 (d, J=1.1 Hz, 1H), 7.75-7.61 (m, 2H), 7.62-7.48 (m, 3H), 4.56 (s, 2H), 3.29 (ddd, J=12.9, 8.8, 6.3 Hz, 1H), 3.09 (ddd, J=12.9, 8.9, 6.9 Hz, 1H), 1.81-1.64 (m, 2H), 1.56-1.39 (m, 2H), 0.93 (t, J=7.3 Hz, 3H). ESI-MS (m/z): 399.1 [M+H]$^+$.

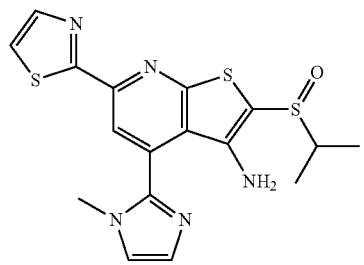 [SMILES: CC(C)S(=O)c1sc2nc(-c3nccs3)cc(-c3nccn3C)c2c1N]

SW209279. 2-(isopropylsulfinyl)-4-(1-methyl-1H-imidazol-2-yl)-6-(thiazol-2-yl)thieno[2,3-b]pyridin-3-amine was prepared using synthetic procedures described for the preparation of analog SW033291. $^1$H NMR (400 MHz, CDCl$_3$) δ 8.14 (s, 1H), 7.92 (d, J=3.2 Hz, 1H), 7.51 (d, J=3.2 Hz, 1H), 7.24 (s, 1H), 7.13 (d, J=1.2 Hz, 1H), 5.92 (s, 2H), 3.80 (s, 3H), 3.38 (p, J=6.8 Hz, 1H), 1.44 (d, J=6.8 Hz, 3H), 1.25 (d, J=6.8 Hz, 3H). ESI-MS (m/z): 404.1 [M+H]$^+$.

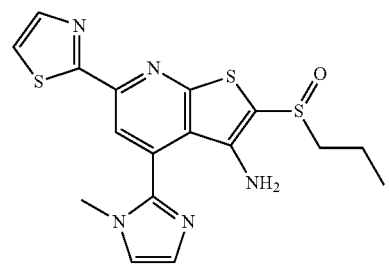 [SMILES: CCCS(=O)c1sc2nc(-c3nccs3)cc(-c3nccn3C)c2c1N]

SW209280. 4-(1-methyl-1H-imidazol-2-yl)-2-(propylsulfinyl)-6-(thiazol-2-yl)thieno[2,3-b]pyridin-3-amine was prepared using synthetic procedures described for the preparation of analog SW033291. $^1$H NMR (400 MHz, CDCl$_3$) δ 8.14 (s, 1H), 7.92 (d, J=3.2 Hz, 1H), 7.51 (d, J=3.1 Hz, 1H), 7.25 (d, J=1.3 Hz, 1H), 7.14 (d, J=1.2 Hz, 1H), 5.97 (s, 2H), 3.80 (s, 3H), 3.27 (ddd, J=12.7, 8.3, 6.5 Hz, 1H), 3.07 (ddd, J=12.8, 8.4, 7.1 Hz, 1H), 1.85-1.69 (m, 2H), 1.07 (t, J=7.4 Hz, 3H). ESI-MS (m/z): 404.1 [M+H]$^+$.

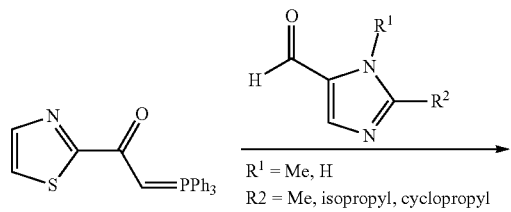

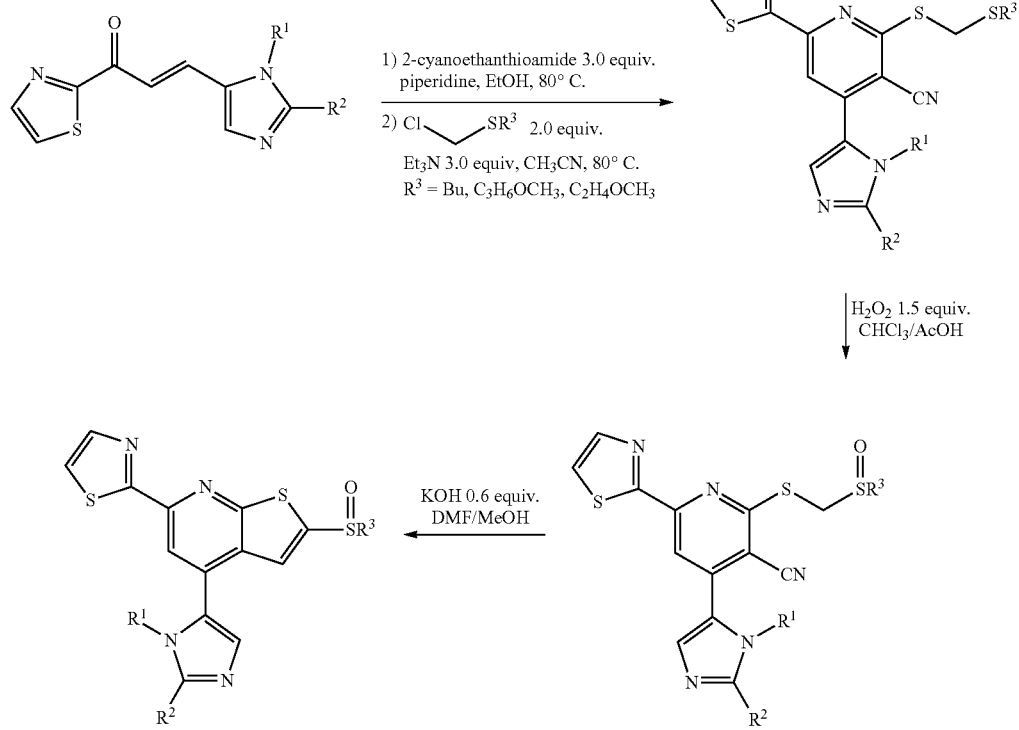

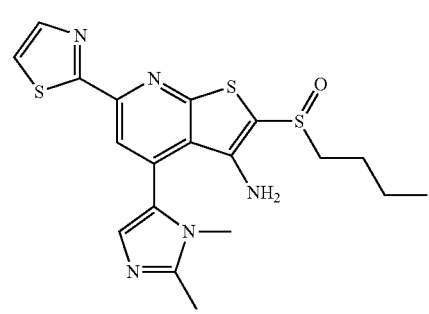 [SMILES: CCCCS(=O)c1sc2nc(-c3nccs3)cc(-c3cnc(C)n3C)c2c1N]

SW209415. 2-(butylsulfinyl)-4-(1,2-dimethyl-1H-imidazol-5-yl)-6-(thiazol-2-yl)thieno[2,3-b]pyridin-3-amine. To the solution of 2-(((butylsulfinyl)methyl)thio)-4-(1,2-dimethyl-1H-imidazol-5-yl)-6-(thiazol-2-yl)nicotinonitrile (0.14 mmol, 60 mg) in DMF (600 µl)/MeOH (300 µl) was added KOH (0.084 mmol, 4.70 mg, 0.6 equiv., 2.0 M in water). The reaction mixture was stirred at 32° C. for 20 min. Once complete, the reaction was diluted with EtOAc and acidified to pH 7 with 5% aq. solution of AcOH, the organic phase was separated and aqueous layer was extracted twice with EtOAc, dried over magnesium sulfate, filtered and concentrated under reduced pressure. The crude product was purified by flash chromatography to afford designed product in 97% isolated yield. $^1$H NMR (400 MHz, CDCl$_3$) δ 8.03 (s, 1H), 7.90 (d, J=3.1 Hz, 1H), 7.50 (d, J=3.2 Hz, 1H), 7.11 (s, 1H), 4.76 (s, 2H), 3.39 (s, 3H), 3.27 (ddd, J=12.9, 8.7, 6.4 Hz, 1H), 3.09 (ddd, J=12.8, 8.8, 6.9 Hz, 1H), 2.47 (s, 3H), 1.83-1.62 (m, 2H), 1.57-1.38 (m, 2H), 0.93 (t, J=7.3 Hz, 3H). ESI-MS (m/z): 432.1 [M+H]$^+$. Two enantiomers of SW209415 can be separated by chiral HPLC: Chiralpak AD-H, 10×250 mm, 5 µM, 100% MeOH.

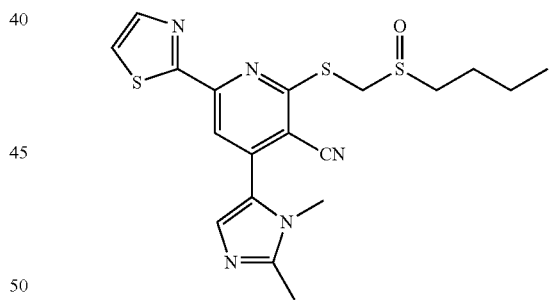

2-(((butylsulfinyl)methyl)thio)-4-(1,2-dimethyl-1H-imidazol-5-yl)-6-(thiazol-2-yl)nicotinonitrile. To the solution of 2-(((butylthio)methyl)thio)-4-(1,2-dimethyl-1H-imidazol-5-yl)-6-(thiazol-2-yl)nicotinonitrile (85 mg, 0.205 mmol) in CHCl$_3$/AcOH (1:1, 0.15 M) was added H$_2$O$_2$ (0.31 mmol, 1.5 equiv. 30% solution in water). The reaction mixture was stirred at 32° C. for 40 min. Once complete, the reaction was diluted with EtOAc and was washed with saturated NaHCO$_3$ solution, dried over magnesium sulfate, filtered and concentrated under reduce pressure to give designed product in 92% yield. $^1$H NMR (400 MHz, CDCl$_3$) δ 7.98 (d, J=3.1 Hz, 1H), 7.94 (s, 1H), 7.60 (d, J=3.1 Hz, 1H), 7.43 (s, 1H), 4.72 (d, J=13.1 Hz, 1H), 4.41 (d, J=13.1 Hz, 1H), 3.63 (s, 3H), 2.96 (dt, J=12.9, 8.2 Hz, 1H), 2.84 (dt, J=12.9, 7.5 Hz, 1H), 2.51 (s, 3H), 1.94-1.74 (m, 2H), 1.63-1.38 (m, 2H), 0.95 (t, J=7.4 Hz, 3H). ESI-MS (m/z): 432.1 [M+H]⁺.

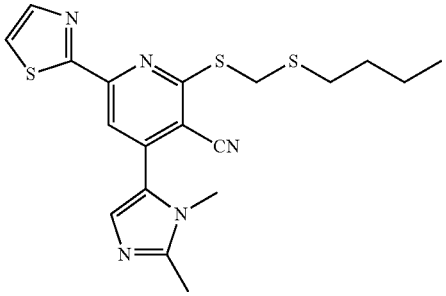 [SMILES: CCCCSCSc1nc(-c2nccs2)cc(-c2cnc(C)n2C)c1C#N]

2-(((butylthio)methyl)thio)-4-(1,2-dimethyl-1H-imidazol-5-yl)-6-(thiazol-2-yl)nicotinonitrile. To a suspension of 3-(1,2-dimethyl-1H-imidazol-5-yl)-1-(thiazol-2-yl)prop-2-en-1-one (0.31 mmol, 72 mg) and 2-cyanothioacetamide (0.93 mmol, 93 mg, 3.0 equiv.) in EtOH (1.5 mL), a few drops of piperidine were added. After being stirred at 80° C. for 2 h, EtOH was evaporated and crude product was redissolved in $CH_3CN$. Butyl(chloromethyl)sulfane (0.62 mmol, 85.5 mg) and $Et_3N$ (0.93 mmol, 94.1 mg, 130 μL) were then added and the reaction mixture was stirred at 80° C. for 20 min. Once complete, the reaction was diluted with EtOAc and water. The organic phase was separated and aqueous layer was extracted twice with EtOAc. The combined extractions were washed with saturated NaCl solution, dried over magnesium sulfate, filtered and concentrated under reduced pressure. The residue was purified by flash chromatography to give 99 mg of designed product (77%). 4H NMR (400 MHz, CDCl₃) δ 7.96 (d, J=3.1 Hz, 1H), 7.85 (s, 1H), 7.56 (d, J=3.1 Hz, 1H), 7.37 (s, 1H), 4.49 (s, 2H), 3.60 (s, 3H), 2.72 (t, J=7.4 Hz, 2H), 2.48 (s, 3H), 1.62 (p, J=7.3 Hz, 2H), 1.40 (h, J=7.3 Hz, 2H), 0.90 (t, J=7.3 Hz, 3H). ESI-MS (m/z): 416.6 [M+H]⁺.

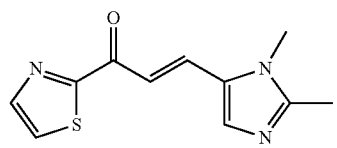 [SMILES: Cc1ncc(/C=C/C(=O)c2nccs2)n1C]

(E)-3-(1,2-dimethyl-1H-imidazol-5-yl)-1-(thiazol-2-yl)prop-2-en-1-one. To a solution of 1,5-dimethyl-1H-imidazole-2-carbaldehyde (2.0 mmol, 250 mg) in 6 ml of $CH_3CN$ was added 1-(thiazol-2-yl)-2-(triphenyl-15-phosphanylidene)ethan-1-one (4.0 mmol, 1.55 g, 2.0 equiv.). The reaction mixture was stirred at 90° C. for 48 h. Once complete, solvent was evaporated and residue was purified by flash chromatography to give 331 mg of designed product (71%). ¹H NMR (400 MHz, Methanol-d4) δ 8.08 (d, J=3.0 Hz, 1H), 7.97 (d, J=3.0 Hz, 1H), 7.90 (d, J=15.9 Hz, 1H), 7.76 (d, J=15.9 Hz, 1H), 7.60 (s, 1H), 3.72 (s, 3H), 2.43 (s, 3H). ESI-MS (m/z): 234.3 [M+H]⁺.

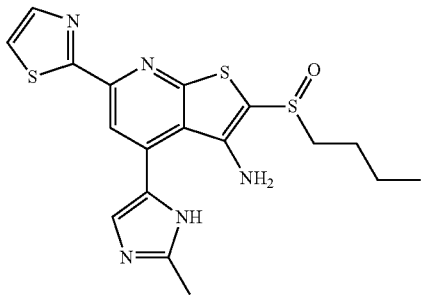

SW209428. 2-(butylsulfinyl)-4-(2-methyl-1H-imidazol-5-yl)-6-(thiazol-2-yl)thieno[2,3-b]pyridin-3-amine was prepared using synthetic procedures described for the preparation of analog SW209415. ¹H NMR (400 MHz, CDCl₃) δ 10.51 (s, 1H), 8.10 (s, 1H), 7.89 (d, J=3.2 Hz, 1H), 7.46 (d, J=3.2 Hz, 1H), 7.40 (s, 1H), 3.31 (ddd, J=12.8, 9.3, 5.8 Hz, 1H), 3.15 (ddd, J=12.8, 9.3, 6.2 Hz, 1H), 2.42 (s, 3H), 1.79-1.58 (m, 2H), 1.57-1.38 (m, 2H), 0.93 (t, J=7.3 Hz, 3H). ESI-MS (m/z): 418.1 [M+H]⁺.

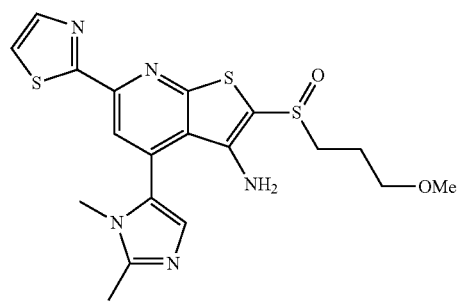 [SMILES: COCCCS(=O)c1sc2nc(-c3nccs3)cc(-c3cnc(C)n3C)c2c1N]

SW211688. 4-(1,2-dimethyl-1H-imidazol-5-yl)-2-((3-methoxypropyl) sulfinyl)-6-(thiazol-2-yl)thieno[2,3-b]pyridin-3-amine was prepared using synthetic procedures described for the preparation of analog SW209415. ¹H NMR (400 MHz, Acetone-d6) δ 8.03 (s, 1H), 7.99 (d, J=3.2 Hz, 1H), 7.82 (d, J=3.2 Hz, 1H), 7.09 (s, 1H), 5.06 (s, 2H), 3.51 (s, 3H), 3.48 (t, J=6.1 Hz, 2H), 3.26 (s, 3H), 3.26-3.18 (m, 1H), 3.18-3.12 (m, 1H), 2.43 (s, 3H), 2.00-1.89 (m, 2H). ESI-MS (m/z): 448.1 [M+H]⁺.

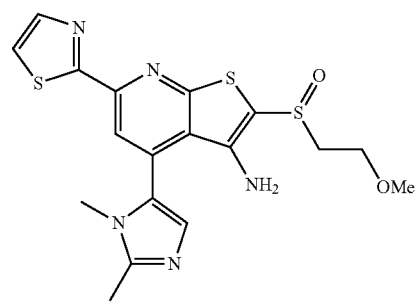 [SMILES: COCCS(=O)c1sc2nc(-c3nccs3)cc(-c3cnc(C)n3C)c2c1N]

SW211689. 4-(1,2-dimethyl-1H-imidazol-5-yl)-2-((2-methoxyethyl) sulfinyl)-6-(thiazol-2-yl)thieno[2,3-b]pyridin-3-amine was prepared using synthetic procedures described for the preparation of analog SW209415. ¹H NMR (400 MHz, CDCl₃) δ 8.05 (s, 1H), 7.92 (d, J=3.2 Hz, 1H), 7.51 (d, J=3.2 Hz, 1H), 7.11 (s, 1H), 4.73 (s, 2H), 3.88-3.82 (m, 1H), 3.75-3.62 (m, 1H), 3.57 (ddd, J=13.1, 6.0, 3.9 Hz, 1H), 3.40 (s, 3H), 3.37 (s, 3H), 3.25 (ddd, J=12.8, 8.0, 4.4 Hz, 1H), 2.48 (s, 3H). ESI-MS (m/z): 434.1 [M+H]⁺.

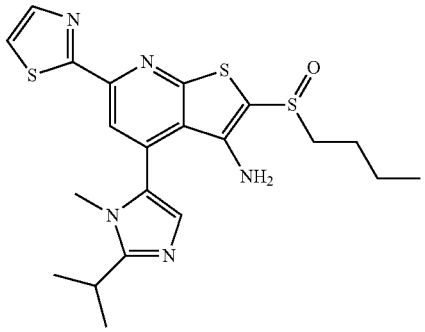 [SMILES: CCCCS(=O)c1sc2nc(-c3nccs3)cc(-c3cnc(C(C)C)n3C)c2c1N]

SW212344. 2-(butylsulfinyl)-4-(2-isopropyl-1-methyl-1H-imidazol-5-yl)-6-(thiazol-2-yl)thieno[2,3-b]pyridin-3-amine was prepared using synthetic procedures described for the preparation of analog SW209415. ¹H NMR (400 MHz, CDCl₃) δ 8.06 (s, 1H), 7.92 (d, J=3.1 Hz, 1H), 7.51 (d, J=3.2 Hz, 1H), 7.15 (s, 1H), 4.71 (s, 2H), 3.41 (s, 3H), 3.27 (ddd, J=13.0, 8.5, 6.5 Hz, 1H), 3.19-2.98 (m, 2H), 1.83-1.59 (m, 2H), 1.58-1.41 (m, 2H), 1.39 (d, J=6.7 Hz, 6H), 0.94 (t, J=7.3 Hz, 3H). ESI-MS (m/z): 460.1 [M+H]⁺.

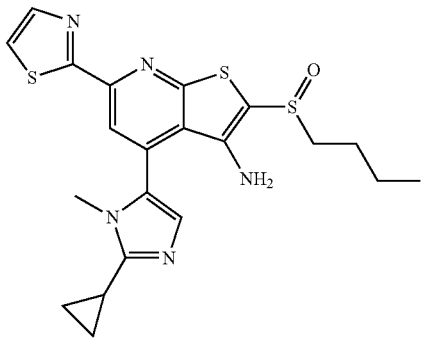 [SMILES: CCCCS(=O)c1sc2nc(-c3nccs3)cc(-c3cnc(C4CC4)n3C)c2c1N]

SW212345. 2-(butylsulfinyl)-4-(2-cyclopropyl-1-methyl-1H-imidazol-5-yl)-6-(thiazol-2-yl)thieno[2,3-b]pyridin-3-amine was prepared using synthetic procedures described for the preparation of analog SW209415. ¹H NMR (400 MHz, CDCl₃) δ 8.04 (s, 1H), 7.91 (d, J=3.1 Hz, 1H), 7.50 (d, J=3.1 Hz, 1H), 7.07 (s, 1H), 4.77 (s, 2H), 3.51 (s, 3H), 3.27 (ddd, J=12.9, 8.7, 6.4 Hz, 1H), 3.10 (ddd, J=12.9, 8.8, 6.9 Hz, 1H), 1.95-1.78 (m, 1H), 1.81-1.62 (m, 2H), 1.58-1.37 (m, 2H), 1.17-0.98 (m, 4H), 0.93 (t, J=7.3 Hz, 3H). ESI-MS (m/z): 458.1 [M+H]⁺.

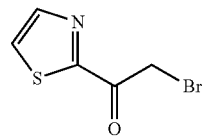

2-bromo-1-(thiazol-2-yl)ethan-1-one. n-Butyllithium (24.7 mL, 0.0617 mol, 2.5M in Hexane) was added dropwise to a solution of 2-thiazole (5.0 g, 0.059 mol) in anhydrous diethyl ether (48.8 mL) at −78° C. After 15 minutes, ethylbromoacetate (6.84 mL, 0.0617 mol) was added, the cold bath was removed and the solution was allowed to warm to room temperature. The reaction mixture was diluted with ether and water. The organic layer was separated, dried over Na2SO4, filtered and concentrated under reduced pressure. The crude product was suspended in hexanes and heated to reflux for 15 minutes then the product was decanted off leaving the impure oil. This was repeated 5 times to give a white solid with 88% yield. ¹H NMR (400 MHz, CDCl₃) δ 8.05 (d, J=3.0 Hz, 1H), 7.77 (d, J=3.0 Hz, 1H), 4.71 (s, 2H). ESI-MS (m/z): 207.8 [M+H]⁺.

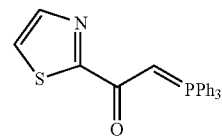

1-(thiazol-2-yl)-2-(triphenyl-15-phosphanylidene)ethan-1-one. To a solution of 2-bromo-1-(thiazol-2-yl)ethan-1-one (10.7 g, 0.0517 mol) in toluene (337.7 mL), triphenylphosphine (14.1 g, 0.0539 mol) was added portion wise. The mixture was stirred at room temperature for 3 hours. The yellowish precipitate was removed by filtration, and was washed several times with toluene and then petroleum ether. Water was added to the precipitate and was treated dropwise with 1N NaOH to pH 10 (at pH 7 there was a color change from yellow to orange). The mixture was stirred for 30 minutes at room temperature. The precipitate was removed by filtration and washed several times with water. The resulting orange solid, was heated at 50° C. under vacuum to remove any water, giving a 96% yield. ¹H NMR (400 MHz, CDCl₃) δ 7.82 (d, J=3.1 Hz, 1H), 7.72 (ddd, J=12.8, 8.3, 1.4 Hz, 6H), 7.61-7.54 (m, 3H), 7.51-7.45 (m, 6H), 7.38 (dd, J=3.1, 1.3 Hz, 1H), 5.00 (d, J=23.3 Hz, 1H). ESI-MS (m/z): 387.9 [M+H]⁺.

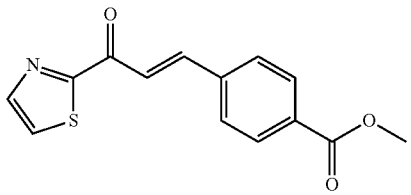 [SMILES: COC(=O)c1ccc(/C=C/C(=O)c2nccs2)cc1]

Methyl (E)-4-(3-oxo-3-(thiazol-2-yl)prop-1-en-1-yl)benzoate. In a dried flask, 1-(thiazol-2-yl)-2-(triphenyl-15-phosphanylidene)ethan-1-one (1.5 g, 3.9 mmol) and methyl 4-formyl benzoate (634 mg, 3.86 mmol) were dissolved in anhydrous chloroform (19.3 mL) and the solution stirred at 71° C. overnight. The solvent was evaporated under reduced pressure and the solid precipitate was purified using automated flash chromatography (100% DCM) to give a white solid in 76% yield. ¹H NMR (400 MHz, CDC3) δ 8.10-8.05 (m, 3H), 8.01 (d, J=1.3 Hz, 2H), 7.76 (d, J=8.4 Hz, 2H), 7.72 (d, J=3.0 Hz, 1H), 3.93 (s, 3H). ESI-MS (m/z): 274.0 [M+H]⁺.

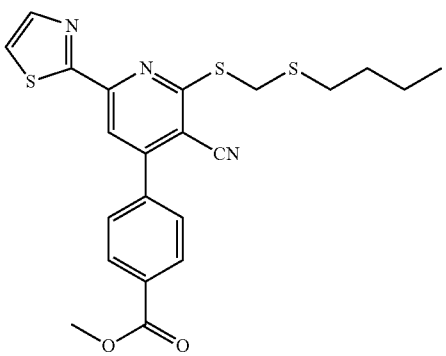 [SMILES: CCCCSCSc1nc(-c2nccs2)cc(-c2ccc(C(=O)OC)cc2)c1C#N]

Methyl 4-(2-(((butylthio)methyl)thio)-3-cyano-6-(thiazol-2-yl)pyridin-4-yl)benzoate. 2-cyanothioacetamide (274.8 mg, 2.744 mmol) and methyl (E)-4-(3-oxo-3-(thiazol-2-yl)prop-1-en-1-yl)benzoate (250.0 mg, 0.9147 mmol) were combined in a vial that was evacuated and backfilled with 02 then ethanol (2.75 mL) and piperdine (2 drops) were added. The solution was sparged for a few minutes then stirred at 80° C. for 4 hours. Once cooled, the solution was filtered, and the precipitate was rinsed with ethanol, and then washed in minimal amounts of acetic acid by heating at 80° C. for 45 minutes. When cooled, the washed solution was filtered leaving the crude brown/red solid product, which was carried forward to the next step. Standard alkylation procedure: Butyl(chloromethyl)sulfane (111.2 mg, 0.8059 mmol) in acetonitrile (1.32 mL), was added to the product from the first step, and Et3N (168.6 µL, 1.209 mmol) was added last. The solution was stirred at 80° C. for 20 minutes. The reaction mixture was diluted with EtOAc and washed with H2O, dried over Na2SO4, filtered, and concentrated under reduced pressure. The crude solid was purified using automated flash chromatography (80% hexane, 20% EtOAc). This produced a solid in 24% yield. $^1$H NMR (400 MHz, CDCl$_3$) δ 8.18 (d, J=8.4 Hz, 2H), 8.02 (s, 1H), 7.98 (d, J=3.1 Hz, 1H), 7.71 (d, J=8.4 Hz, 2H), 7.58 (d, J=3.2 Hz, 1H), 4.52 (s, 2H), 3.95 (s, 3H), 2.76 (t, J=7.3 Hz, 2H), 1.64 (tt, J=7.7, 6.3 Hz, 2H), 1.42 (h, J=7.3 Hz, 2H), 0.91 (t, J=7.3 Hz, 3H). ESI-MS (m/z): 456.1 [M+H]+.

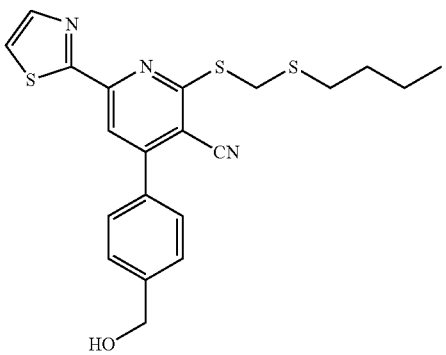 [SMILES: CCCCSCSc1nc(-c2nccs2)cc(-c2ccc(CO)cc2)c1C#N]

2-(((butylthio)methyl)thio)-4-(4-(hydroxymethyl)phenyl)-6-(thiazol-2-yl)nicotinonitrile. To the solution of methyl 4-(2-(((butylthio)methyl)thio)-3-cyano-6-(thiazol-2-yl)pyridin-4-yl)benzoate (336 mg, 0.737 mmol) in THF (8.41 mL) LiBH$_4$ (96.3 mg, 4.42 mmol) was added at 0° C. The reaction was stirred at room temperature for 36 hours, and the reaction was monitored by LC/MS. The reaction mixture was diluted with EtOAc and H$_2$O. The organic layer was dried over Na$_2$SO$_4$, filtered, and concentrated under reduced pressure, to give product in 96% yield. $^1$H NMR (400 MHz, CDCl$_3$) δ 8.02 (s, 1H), 7.98 (d, J=3.1 Hz, 1H), 7.69-7.62 (m, 2H), 7.56 (d, J=3.1 Hz, 1H), 7.56-7.49 (m, 2H), 4.79 (d, J=4.3 Hz, 2H), 4.52 (s, 2H), 2.82-2.60 (m, 2H), 1.71-1.58 (m, 2H), 1.49-1.33 (m, 2H), 0.91 (t, J=7.4 Hz, 3H). ESI-MS (m/z): 428.1 [M+H]$^+$.

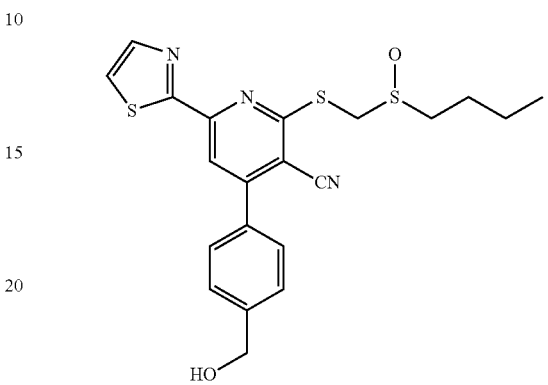

Standard oxidation procedure: 2-(((butyl(11-oxidanyl)-13-sulfanyl)methyl)thio)-4-(4-(hydroxymethyl)phenyl)-6-(thiazol-2-yl)nicotinonitrile. Chloroform (2.53 mL), acetic acid (1.39 mL), and hydrogen peroxide (108.0 µL, 1.057 mmol, 30% solution in water) were added to 2-(((butylthio)methyl)thio)-4-(4-(hydroxymethyl)phenyl)-6-(thiazol-2-yl) nicotinonitrile. The solution was stirred at 32° C. for 45 minutes. The reaction mixture was then diluted with EtOAc and washed with saturated NaHCO3, and the organic layer was dried over Na2SO4, filtered, and concentrated under reduced pressure to give the desired product in 94% yield. $^1$H NMR (400 MHz, CDCl$_3$) δ 8.03 (s, 1H), 7.93 (d, J=3.1 Hz, 1H), 7.59 (d, J=8.2 Hz, 2H), 7.55 (d, J=3.1 Hz, 1H), 7.48 (d, J=7.9 Hz, 2H), 4.73 (s, 2H), 4.66 (d, J=13.1 Hz, 1H), 4.38 (d, J=13.1 Hz, 1H), 2.93 (dt, J=13.0, 8.1 Hz, 1H), 2.79 (dt, J=13.0, 7.2 Hz, 1H), 1.84-1.72 (m, 2H), 1.55-1.33 (m, 2H), 0.91 (t, J=7.3 Hz, 3H)). ESI-MS (m/z): 444.1 [M+H]+.

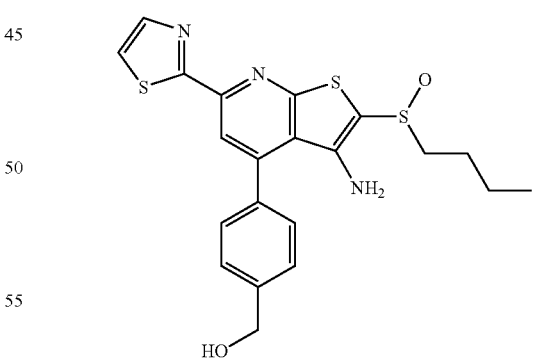

SW209510 (4-(3-amino-2-(butyl(11-oxidanyl)-13-sulfanyl)-6-(thiazol-2-yl)thieno[2,3-b]pyridin-4-yl)phenyl) methanol. t-BuOK (22.78 mg, 0.2028 mmol) was added to 2-(((butyl(11-oxidanyl)-13-sulfanyl)methyl)thio)-4-(4-(hydroxymethyl)phenyl)-6-(thiazol-2-yl)nicotinonitrile (150 mg, 0.338 mmol) and the vial was evacuated backfilled with N$_2$ three times before adding DMF (1.3 mL). The solution was sparged with N$_2$ for a few minutes before heating at 32°

C. The reaction mixture was monitored every five minutes by TLC (80% EtOAc. 20% hexanes) and upon completion was diluted with EtOAc and washed with 10% AcOH. The organic layer was then dried over $Na_2SO_4$, filtered, and concentrated under reduced pressure. The product was purified using automated flash chromatography to give an isolated green solid/oil in 16% yield. $^1$H NMR (400 MHz, $CDCl_3$) δ 8.02 (s, 1H), 7.90 (d, J=3.2 Hz, 1H), 7.59-7.40 (m, 5H), 4.80 (s, 2H), 4.63 (s, 2H), 3.27 (ddd, J=12.8, 9.0, 6.1 Hz, 1H), 3.10 (ddd, J=12.8, 9.1, 6.6 Hz, 1H), 1.78-1.61 (m, 2H), 1.55-1.40 (m, 2H), 0.93 (t, J=7.3 Hz, 3H). ESI-MS (m/z): 444.1 [M+H]$^+$.

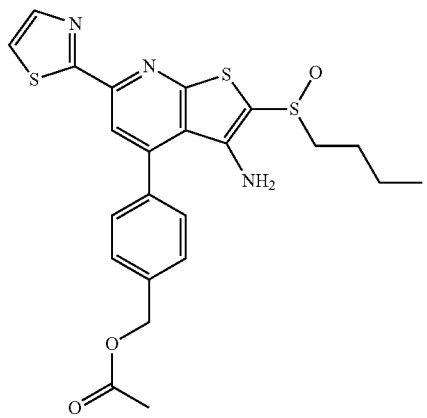

SW209511 4-(3-amino-2-(butyl(11-oxidanyl)-13-sulfanyl)-6-(thiazol-2-yl)thieno[2,3-b]pyridin-4-yl)benzyl acetate. This compound was formed during the workup of SW209510 in EtOAc (47% yield). $^1$H NMR (400 MHz, $CDCl_3$) δ 7.99 (s, 1H), 7.87 (d, J=3.2 Hz, 1H), 7.56-7.40 (m, 5H), 5.18 (s, 2H), 4.62 (s, 2H), 3.26 (ddd, J=12.8, 9.0, 6.1 Hz, 1H), 3.08 (ddd, J=12.8, 9.1, 6.6 Hz, 1H), 2.14 (s, 3H), 1.77-1.59 (m, 2H), 1.53-1.37 (m, 2H), 0.92 (t, J=7.3 Hz, 3H). ESI-MS (m/z): 486.1 [M+H]$^+$.

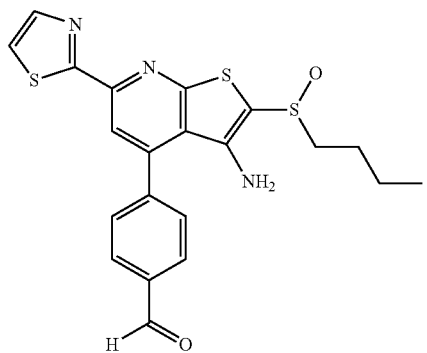

4-(3-amino-2-(butyl(11-oxidanyl)-13-sulfanyl)-6-(thiazol-2-yl)thieno[2,3-b]pyridin-4-yl)benzaldehyde. $MnO_2$ (111.3 mg, 1.28 mmol) was added to a solution of SW209510 (56.8 mg, 0.128 mmol) in DCM (2.3 mL) and stirred at room temperature overnight. LC/MS indicated that the reaction was incomplete. The reaction was filtered over celite, washed with DCM and the filtrate was concentrated under reduced pressure. The crude mixture was redissolved in DCM (2.3 mL) and $MnO_2$ (5 eq) was added. The solution was left to stir 24 hours at room temperature, was filtered over celite and washed with DCM. The filtrate was concentrated under reduced pressure and the resulting crude product was purified using automated flash chromatography (55% EtOAc, 45% hexanes) resulting in 24% isolated yield. $^1$H NMR (400 MHz, $CDCl_3$) δ 10.13 (s, 1H), 8.11-7.99 (m, 3H), 7.92 (d, J=3.1 Hz, 1H), 7.75-7.62 (m, 2H), 7.51 (d, J=3.2 Hz, 1H), 4.56 (s, 2H), 3.29 (ddd, J=12.8, 8.8, 6.3 Hz, 1H), 3.11 (ddd, J=12.8, 8.9, 6.9 Hz, 1H), 1.82-1.66 (m, 2H), 1.54-1.41 (m, 2H), 0.94 (t, J=7.3 Hz, 3H). ESI-MS (m/z): 442.1 [M+H]$^+$.

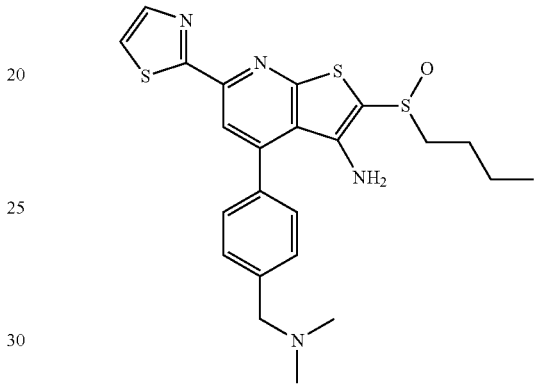

SW209513. 2-(butyl(11-oxidanyl)-13-sulfanyl)-4-(4-((dimethylamino)methyl)phenyl)-6-(thiazol-2-yl)thieno[2,3-b]pyridin-3-amine. To a solution of 4-(3-amino-2-(butyl(11-oxidanyl)-13-sulfanyl)-6-(thiazol-2-yl)thieno[2,3-b]pyridin-4-yl)benzaldehyde (13.3 mg, 0.0301) in methanol (802.7 μL), dimethylamine (174 μL. 0.301 mmol, 2.0M in THF) and acetic acid (1.72 μL, 0.0301 mmol) were added and the reaction was stirred at room temperature for 90 minutes. The reaction was then cooled down to 0° C. and sodium cyanoborohydride (3.7 mg, 0.060 mmol) was added and the reaction stirred for 2 hours at this temperature before allowing to warm up to room temperature. After 24 hours, more sodium cyanoborohydride (2 eq) was added at 0° C. and left to stir at room temperature another 24 hours. Nitrogen was used to evaporate the solvent, giving a solid that was diluted with EtOAc and washed with saturated $NaHCO_3$. The organic layer was dried over $Na_2SO_4$, filtered, and concentrated under reduced pressure. The crude product was purified using flash chromatography (7% MeOH, 93% DCM) isolating the product in 13% yield. $^1$H NMR (400 MHz, $CDCl_3$) δ 8.07 (s, 1H), 7.93 (d, J=3.2 Hz, 1H), 7.51 (d, J=3.2 Hz, 1H), 7.49-7.41 (m, 4H), 4.67 (s, 2H), 3.55 (s, 2H), 3.36-3.25 (m, 1H), 3.13 (ddd, J=12.8, 9.0, 6.7 Hz, 1H), 2.30 (s, 6H), 1.78-1.68 (m, 2H), 1.55-1.44 (m, 2H), 0.95 (t, J=7.3 Hz, 3H). ESI-MS (m/z): 471.2 [M+H]$^+$.

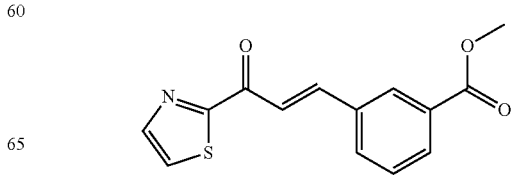

Methyl (E)-3-(3-oxo-3-(thiazol-2-yl)prop-1-en-1-yl)benzoate. Followed procedure for methyl (E)-4-(3-oxo-3-(thiazol-2-yl)prop-1-en-1-yl)benzoate using methyl 3-formyl benzoate as the starting material. Purified the crude product using automated flash chromatography (50% EtOAc, 50% hexanes) isolating the product in 51% yield. ¹H NMR (400 MHz, CDCl₃) δ 8.41-8.35 (m, 1H), 8.11-8.05 (m, 2H). 8.02 (d, J=1.3 Hz, 2H), 7.89-7.83 (m, 1H), 7.72 (d, J=3.0 Hz, 1H), 7.50 (t, J=7.8 Hz, 1H), 3.95 (s, 3H). ESI-MS (m/z): 274.1

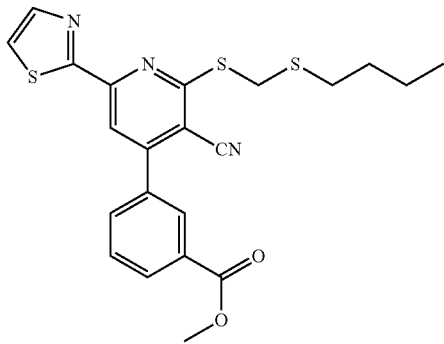 [SMILES: CCCCSCSc1nc(-c2nccs2)cc(-c2cccc(C(=O)OC)c2)c1C#N]

Methyl 3-(2-(((butylthio)methyl)thio)-3-cyano-6-(thiazol-2-yl)pyridin-4-yl)benzoate. Followed the procedure for methyl 4-(2-(((butylthio)methyl)thio)-3-cyano-6-(thiazol-2-yl)pyridin-4-yl)benzoate using methyl (E)-3-(3-oxo-3-(thiazol-2-yl)prop-1-en-1-yl)benzoate as the starting material. Isolated product in 87% yield. ¹H NMR (400 MHz, CDCl₃) δ 8.32-8.26 (m, 1H), 8.20 (dt, J=7.9, 1.3 Hz, 1H), 8.04 (s, 1H), 7.99 (d, J=3.1 Hz, 1H), 7.85 (ddd, J=7.7, 2.0, 1.1 Hz, 1H), 7.62 (td, J=7.8, 0.6 Hz, 1H), 7.58 (d, J=3.1 Hz, 1H), 4.53 (s, 2H), 3.95 (s, 3H), 2.76 (t, J=7.3 Hz, 2H), 1.71-1.59 (m, 2H), 1.49-1.36 (m, 2H), 0.91 (t, J=7.3 Hz, 3H). ESI-MS (m/z): 456.1 [M+Z]⁺.

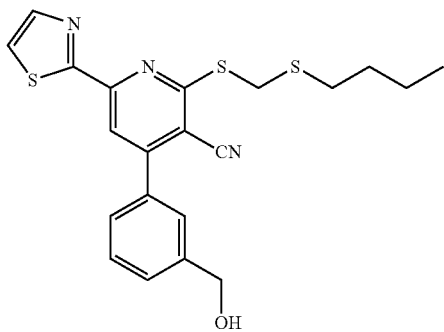 [SMILES: CCCCSCSc1nc(-c2nccs2)cc(-c2cccc(CO)c2)c1C#N]

2-(((butylthio)methyl)thio)-4-(3-(hydroxymethyl)phenyl)-6-(thiazol-2-yl)nicotinonitrile. Followed procedure for 2-(((butylthio)methyl)thio)-4-(4-(hydroxymethyl)phenyl)-6-(thiazol-2-yl)nicotinonitrile using methyl 3-(2-(((butylthio)methyl)thio)-3-cyano-6-(thiazol-2-yl)pyridin-4-yl)benzoate as the starting material. Isolated product in 84% yield. ¹H NMR (400 MHz, CDCl₃) δ 8.00 (s, 1H), 7.95 (d, J=3.1 Hz, 1H), 7.64-7.61 (m, 1H), 7.58-7.52 (m, 2H), 7.52-7.46 (m, 2H), 4.76 (s, 2H), 4.50 (s, 2H), 2.74 (t, J=7.3 Hz, 2H), 1.69-1.54 (m, 2H), 1.46-1.37 (m, 2H), 0.90 (t, J=7.3 Hz, 3H). ESI-MS (m/z): 428.1 [M+H]+

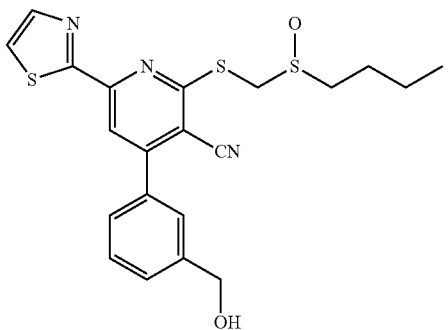

2-(((butyl(11-oxidanyl)-13-sulfanyl)methyl)thio)-4-(3-(hydroxymethyl)phenyl)-6-(thiazol-2-yl)nicotinonitrile. Followed standard oxidation procedure using 2-(((butylthio)methyl)thio)-4-(3-(hydroxymethyl)phenyl)-6-(thiazol-2-yl)nicotinonitrile as the starting material. Isolated product in 88% yield. ¹H NMR (400 MHz, CDCl₃) δ 8.08 (s, 1H), 7.96 (d, J=3.1 Hz, 1H), 7.68-7.64 (m, 1H), 7.58-7.53 (m, 2H), 7.53-7.48 (m, 2H), 4.77 (s, 2H), 4.71 (d, J=13.1 Hz, 1H), 4.36 (d, J=13.1 Hz, 1H), 2.96 (dt, J=13.0, 8.2 Hz, 1H), 2.81 (dt, J=13.0, 7.3 Hz, 1H), 1.82 (p, J=7.7 Hz, 2H), 1.58-1.40 (m, 2H), 0.94 (t, J=7.3 Hz, 3H). ESI-MS (m/z): 444.1 [M+H]⁺.

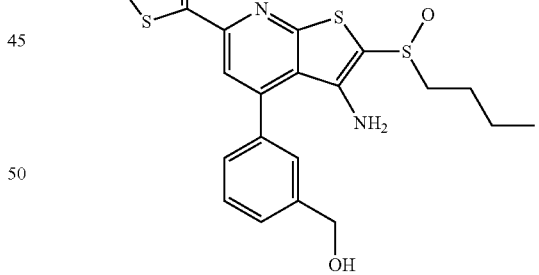

SW209418 (3-(3-amino-2-(butyl(11-oxidanyl)-13-sulfanyl)-6-(thiazol-2-yl)thieno[2,3-b]pyridin-4-yl)phenyl)methanol. Followed procedure for SW209510 using 2-(((butyl(11-oxidanyl)-13-sulfanyl)methyl)thio)-4-(3-(hydroxymethyl)phenyl)-6-(thiazol-2-yl)nicotinonitrile as the starting material to give an isolated product in 68% yield. ¹H NMR (400 MHz, CDCl₃) δ 8.01 (s, 1H), 7.88 (d, J=3.1 Hz, 1H), 7.55-7.30 (m, 511), 4.75 (s, 2H), 4.62 (s, 2H), 3.26 (ddd, J=12.8, 9.1, 6.0 Hz, 1H), 3.09 (ddd, J=12.8, 9.2, 6.5

Hz, 1H), 1.76-1.61 (m, 2H), 1.51-1.38 (m, 2H), 0.92 (t, J=7.3 Hz, 3H). ESI-MS (m/z): 444.1 [M+H]⁺.

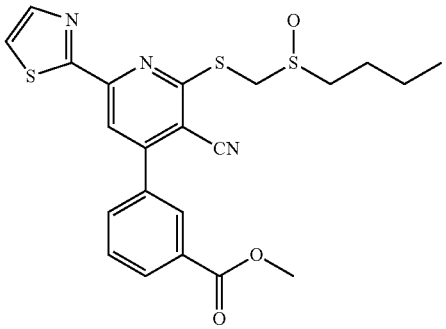

Methyl 3-(2-(((butyl(11-oxidanyl)-13-sulfanyl)methyl)thio)-3-cyano-6-(thiazol-2-yl)pyridin-4-yl)benzoate. Followed standard oxidation procedure, using methyl 3-(2-(((butylthio)methyl)thio)-3-cyano-6-(thiazol-2-yl)pyridin-4-yl)benzoate as the starting material. This gave an isolated product in 86% yield. ¹H NMR (400 MHz, CDCl₃) δ 8.27 (t, J=1.6 Hz, 1H), 8.17 (dt, J=7.9, 1.4 Hz, 1H), 8.09 (s, 1H), 7.97 (d, J=3.1 Hz, 1H), 7.82 (ddd, J=7.7, 1.9, 1.1 Hz, 1H), 7.61 (m, 1H), 7.58 (d, J=3.1 Hz, 1H), 4.72 (d, J=13.1 Hz, 1H), 4.42 (d, J=13.1 Hz, 1H), 3.92 (s, 3H), 2.95 (dt, J=13.0, 8.1 Hz, 1H), 2.83 (dt, J=13.0, 7.3 Hz, 1H), 1.81 (p, J=7.7 Hz, 2H), 1.57-1.36 (m, 2H), 0.92 (t, J=7.3 Hz, 3H). ESI-MS (m/z): 472.1 [M+H]⁺.

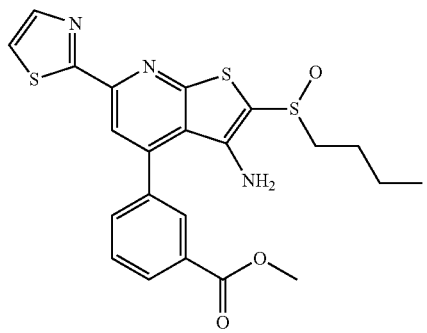

SW209416. Methyl 3-(3-amino-2-(butyl(11-oxidanyl)-13-sulfanyl)-6-(thiazol-2-yl)thieno[2,3-b]pyridin-4-yl)benzoate. Followed procedure for SW209510 using methyl 3-(2-(((butyl(11-oxidanyl)-13-sulfanyl)methyl)thio)-3-cyano-6-(thiazol-2-yl)pyridin-4-yl)benzoate as the starting material to give an isolated product in 68% yield. ¹H NMR (400 MHz, CDCl₃) δ 8.26-8.11 (m, 2H), 8.02 (s, 1H), 7.89 (d, J=3.2 Hz, 1H), 7.76-7.56 (m, 2H), 7.49 (d, J=3.1 Hz, 1H), 4.54 (s, 2H), 3.93 (s, 3H), 3.27 (ddd, J=12.8, 9.0, 6.2 Hz, 1H), 3.09 (ddd, J=12.8, 9.0, 6.7 Hz, 1H), 1.79-1.61 (m, 2H), 1.55-1.39 (m, 2H), 0.92 (t, J=7.3 Hz, 3H). ESI-MS (m/z): 472.1 [M+H]⁺.

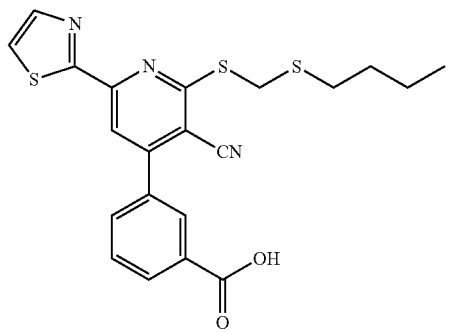 [SMILES: CCCCSCSc1nc(-c2nccs2)cc(-c2cccc(C(=O)O)c2)c1C#N]

Standard Hydrolysis Procedure of Ester to Carboxylic Acid: 3-(2-(((butylthio)methyl)thio)-3-cyano-6-(thiazol-2-yl)pyridin-4-yl)benzoic acid. THF (214.3 μL), MeOH (214.3 μL), and H₂O (71.4 μL) were added to methyl 3-(2-(((butylthio)methyl)thio)-3-cyano-6-(thiazol-2-yl)pyridin-4-yl)benzoate (50 mg, 0.110 mmol), and last LiOH (7.9 mg, 0.329 mmol) was added. The solution was stirred at room temperature for 3 hours. The reaction mixture was diluted with EtOAc and washed with 1M HCl. The organic layer was dried over Na₂SO₄, filtered, and concentrated under reduced pressure. The resulting product gave a 94% yield. ¹H NMR (400 MHz, CDCl₃) δ 8.41 (t, J=1.7 Hz, 1H), 8.26 (dt, J=8.0, 1.3 Hz, 1H), 8.13 (s, 1H), 8.02 (d, J=3.1 Hz, 1H), 7.94-7.89 (m, 1H), 7.65 (t, J=7.8 Hz, 1H), 7.59 (d, J=3.1 Hz, 1H), 4.53 (s, 2H), 2.75 (t, J=7.3 Hz, 2H), 1.64 (p, J=7.5 Hz, 2H), 1.43 (m, 2H), 0.91 (t, J=7.3 Hz, 3H). ESI-MS (m/z): 442.1 [M+Z]⁺.

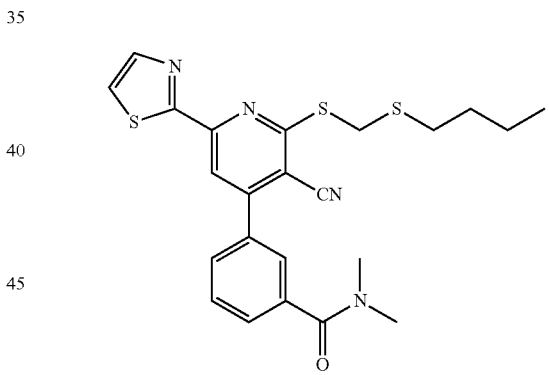

Standard amide bond coupling procedure: 3-(2-(((butylthio)methyl)thio)-3-cyano-6-(thiazol-2-yl)pyridin-4-yl)-N,N-dimethylbenzamide. Dimethylamine hydrochloride (9.25 mg, 0.114 mmol) was added to a solution of 3-(2-(((butylthio)methyl)thio)-3-cyano-6-(thiazol-2-yl)pyridin-4-yl)benzoic acid (45.6 mg, 0.103 mmol), HATU (43.2 mg, 0.114 mmol), and DMF (266 μL) followed by DIPEA (36 μL, 0.21 mmol). The solution was stirred at room temperature for 3 hours, then diluted with EtOAc and washed with water. The organic layer was dried over Na₂SO₄, filtered, and concentrated under reduced pressure. The isolated solid gave an 86% yield. ¹H NMR (400 MHz, CDCl₃) δ 7.99 (s, 1H), 7.97 (d, J=3.1 Hz, 1H), 7.69-7.61 (m, 2H), 7.58-7.51 (m, 3H), 4.50 (s, 2H), 3.11 (s, 3H), 3.03 (s, 3H), 2.73 (t, J=7.3 Hz, 2H), 1.62 (p, J=7.4 Hz, 2H), 1.40 (h, J=7.3 Hz, 2H), 0.89 (t, J=7.3 Hz, 3H). ESI-MS (m/z): 469.1 [M+H]⁺.

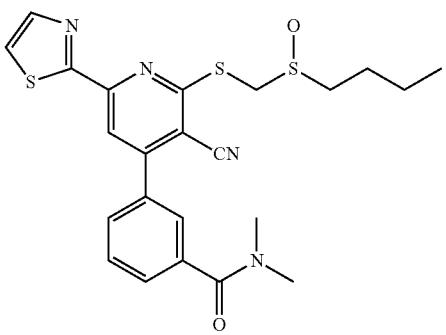

3-(2-(((butyl(11-oxidanyl)-13-sulfanyl)methyl)thio)-3-cyano-6-(thiazol-2-yl)pyridin-4-yl)-N,N-dimethylbenzamide. Followed standard oxidation procedure, using 3-(2-(((butylthio)methyl)thio)-3-cyano-6-(thiazol-2-yl)pyridin-4-yl)-N,N-dimethylbenzamide as the starting material to give the isolated product in 96% yield. $^1$H NMR (400 MHz, Chloroform-d) δ 8.08 (s, 1H), 7.98 (d, J=3.1 Hz, 1H), 7.70-7.64 (m, 2H), 7.61-7.54 (m, 3H), 4.70 (d, J=13.1 Hz, 1H), 4.42 (d, J=13.1 Hz, 1H), 3.11 (s, 3H), 3.03 (s, 3H), 2.95 (dt, J=12.9, 8.2 Hz, 1H), 2.81 (dt, J=12.9, 7.2 Hz, 1H), 1.82 (p, J=7.7 Hz, 2H), 1.56-1.36 (m, 2H). 0.93 (t, J=7.3 Hz, 3H). ESI-MS (m/z): 485.1 [M+H]$^+$.

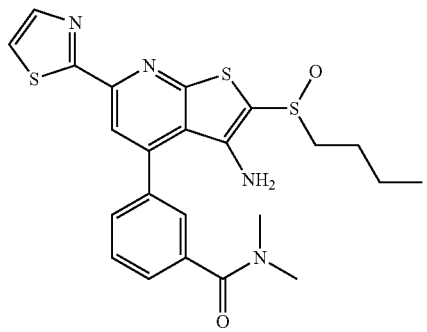

SW209417. 3-(3-amino-2-(butyl(11-oxidanyl)-13-sulfanyl)-6-(thiazol-2-yl)thieno[2,3-b]pyridin-4-yl)-N,N-dimethylbenzamide. Followed procedure for SW209510 using 3-(2-(((butyl(11-oxidanyl)-13-sulfanyl)methyl)thio)-3-cyano-6-(thiazol-2-yl)pyridin-4-yl)-N,N-dimethylbenzamide as the starting material to give the isolated product in 63% yield. $^1$H NMR (400 MHz, Chloroform-d) δ 8.02 (s, 1H), 7.90 (d, J=3.1 Hz, 1H), 7.62-7.51 (m, 4H), 7.49 (d, J=3.1 Hz, 1H), 4.59 (s, 2H), 3.27 (ddd, J=12.8, 9.0, 6.1 Hz, 1H), 3.15-2.97 (m, 7H), 1.78-1.64 (m, 2H), 1.55-1.39 (m, 2H), 0.93 (t, J=7.3 Hz, 3H).

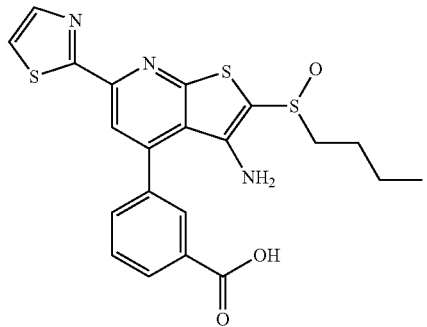

SW209419. 3-(3-amino-2-(butyl(11-oxidanyl)-13-sulfanyl)-6-(thiazol-2-yl)thieno[2,3-b]pyridin-4-yl)benzoic acid. Using SW209416 as the starting material, follow the standard hydrolysis procedure of ester to carboxylic acid. This gave an isolated yield of 98%. $^1$H NMR (400 MHz, (CD$_3$)$_2$CO)) δ 8.28-8.18 (m, 2H), 8.07 (s, 1H), 7.98 (d, J=3.2 Hz, 1H), 7.90 (d, J=7.6 Hz, 1H), 7.82 (d, J=3.2 Hz, 1H), 7.76 (t, J=7.6 Hz, 1H), 4.82 (s, 2H), 3.20 (ddd, J=12.8, 8.8, 6.3 Hz, 1H), 3.09 (ddd, J=12.9, 8.8, 6.8 Hz, 1H), 1.76-1.66 (m, 2H), 1.54-1.43 (m, 2H), 0.92 (t, J=7.3 Hz, 3H). ESI-MS (m/z): 458.1 [M+H]$^+$.

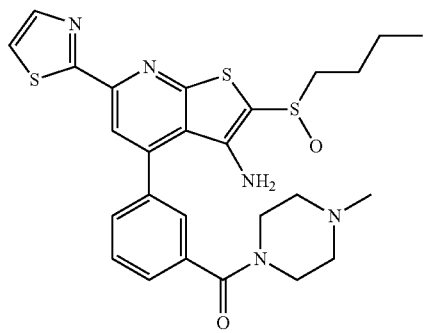

SW209420. (3-(3-amino-2-(butyl(11-oxidanyl)-13-sulfanyl)-6-(thiazol-2-yl)thieno[2,3-b]pyridin-4-yl)phenyl)(4-methylpiperazin-1-yl)methanone. Followed the standard amide bond coupling procedure, using SW209419 as the starting material and 1-methylpiperazine as the substrate. The product was purified using automated flash chromatography, recovering 38% isolated yield. $^1$H NMR (400 MHz, CDCl$_3$) δ 8.04 (s, 1H), 7.91 (d, J=3.2 Hz, 1H), 7.65-7.42 (m, 5H), 4.56 (s, 2H), 3.79 (m, 2H), 3.46 (m, 2H), 3.28 (ddd, J=12.9, 8.9, 6.1 Hz, 1H), 3.10 (ddd, J=12.9, 9.2, 7.0 Hz, 1H), 2.48 (m, 2H), 2.35 (m, 2H), 2.31 (s, 3H), 1.77-1.58 (m, 2H), 1.54-1.38 (m, 2H), 0.94 (t, J=7.3 Hz, 3H). ESI-MS (m/z): 540.2 [M+H]$^+$.

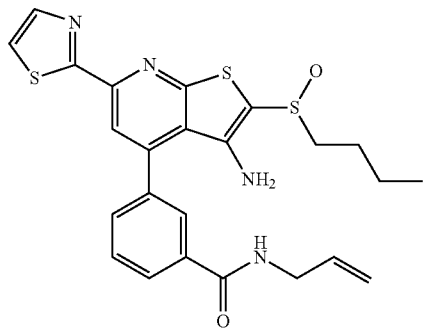

SW209508. N-allyl-3-(3-amino-2-(butyl(11-oxidanyl)-13-sulfanyl)-6-(thiazol-2-yl)thieno[2,3-b]pyridin-4-yl)benzamide. Followed the standard amide bond coupling procedure using SW209419 as the starting material and allylamine as the substrate. The isolated product gave a 92% yield. $^1$H NMR (400 MHz, CDCl$_3$) δ 8.05-7.91 (m, 3H), 7.88 (d, J=3.2 Hz, 1H), 7.68-7.53 (m, 2H), 7.48 (d, J=3.1 Hz, 1H), 6.01-5.82 (m, 1H), 5.25 (d, J=17.2 Hz, 1H), 5.16 (dd, J=10.2, 1.4 Hz, 1H), 4.52 (s, 2H), 4.19-3.98 (m, 2H), 3.24 (ddd, J=12.8, 9.0, 5.9 Hz, 1H), 3.16-2.98 (m, 1H), 1.78-1.56 (m, 2H), 1.57-1.38 (m, 2H), 0.92 (t, J=7.3 Hz, 3H). ESI-MS (m/z): 497.1 [M+H]$^+$.

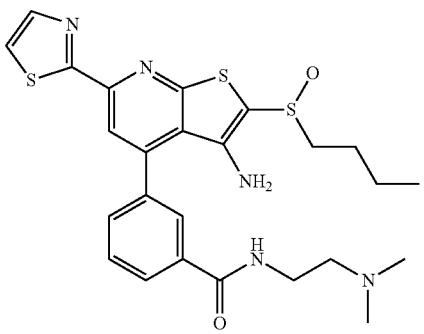

SW209509. 3-(3-amino-2-(butyl(11-oxidanyl)-13-sulfanyl)-6-(thiazol-2-yl)thieno[2,3-b]pyridin-4-yl)-N-(2-(dimethylamino)ethyl)benzamide. Followed the standard amide bond coupling procedure, using SW209419 as the starting material and N,n-dimethyl-ethane-1,2-diamine as the substrate. The reaction mixture was diluted with EtOAc and washed with water and NaOH was added to neutralize the pH. The organic layer was then dried over $Na_2SO_4$, filtered, and concentrated under reduced pressure. The crude product was purified using automated flash chromatography (93% DCM, 2% $Et_3N$, 5% MeOH) to give product in 70% isolated yield. $^1$H NMR (400 MHz, $CDCl_3$) δ 8.02 (s, 1H), 8.00-7.95 (m, 2H), 7.88 (d, J=3.2 Hz, 1H), 7.63-7.54 (m, 2H), 7.48 (d, J=3.2 Hz, 1H), 4.55 (s, 2H), 3.59-3.50 (m, 2H), 3.25 (ddd, J=12.8, 9.0, 6.0 Hz, 1H), 3.08 (ddd, J=12.8, 9.1, 6.6 Hz, 1H), 2.58 (t, J=5.9 Hz, 2H), 2.28 (s, 6H), 1.77-1.61 (m, 2H), 1.53-1.43 (m, 2H), 0.92 (t, J=7.3 Hz, 3H). ESI-MS (m/z): 528.2 [M+H]$^+$.

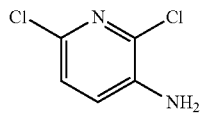

2,6-dichloropyridin-3-amine. The acetone/water mixture (297 mL, 5:1) was added to 2,6-dichloro-3-nitropyridine (3.0 g, 0.016 mol) followed by Zn (10.17 g, 0.1550 mol) and $NH_4Cl$ (12.44 g, 0.2325 mol). The solution stirred at room temperature overnight. The reaction mixture was then filtered through celite and the filtrate was extracted with EtOAc. With the help of brine, the organic layer was separated, dried over $MgSO_4$ and concentrated under reduced pressure. $^1$H NMR (400 MHz, $CDCl_3$) δ 7.07 (d, J=8.2 Hz, 1H), 7.02 (d, J=8.3 Hz, 1H), 4.11 (s, 2H). ESI-MS (m/z): 163.0.

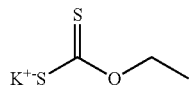

Potassium Ethyl Xanthate. A potassium ethoxide solution was prepared by dissolving KOH (6.5 g, 0.12 mol) in EtOH (63.4 mL). Carbon disulfide (7.14 mL, 0.118 mol) was added to the solution slowly with continuous stirring. The reaction mixture was cooled down to 5° C., filtered, and the precipitate was recrystallized twice from warm ethanol.

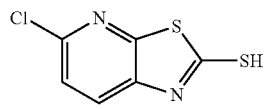 [SMILES: Sc1nc2ccc(Cl)nc2s1]

5-Chlorothiazolo[5,4-b]pyridine-2-thiol. Potassium ethyl xanthate (1.9 g, 0.012 mol) and anhydrous N-methyl-2-pyrrolidone (14.1 mL) were added to 2,6-dichloropyridin-3-amine (1.0 g, 0.0061 mol) under $N_2$. The solution was refluxed (170° C.) for 3.5 hours. The reaction mixture was cooled down to room temperature, acidified to pH 5 using AcOH, diluted in EtOAc, and washed several times with $H_2O$. The organic layer was separated, dried over $MgSO_4$, and concentrated under reduced pressure. This gave a red solid in 18% yield. $^1$H NMR (400 MHz, Chloroform-d) δ 7.41 (d, J=8.4 Hz, 1H), 7.30 (d, J=8.4 Hz, 1H). ESI-MS (m/z): 202.9.

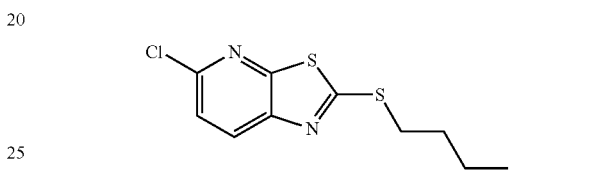

2-(Butylthio)-5-chlorothiazolo[5,4-b]pyridine. $K_2CO_3$ (75 mg, 0.54 mmol), 1-bromobutane (53.3 μL, 0.493 mmol), 18-Crown-6 (13.2 mg, 0.0493 mmol), and DMF (3.4 mL) were added to 5-chlorothiazolo[5,4-b]pyridine-2-thiol and the solution was heated at 80° C. for 3 hours. The solution was diluted with $^E$tOAc, washed with $H_2O$, and the organic layer was separated, dried over $MgSO_4$, and concentrated under reduced pressure. The crude product was purified using flash chromatography to give 76% isolated yield. $^1$H NMR (400 MHz, $CDCl_3$) δ 7.93 (d, J=8.5 Hz, 1H), 7.30 (d, J=8.5 Hz, 1H), 3.31 (t, J=7.3 Hz, 2H), 1.76 (p, J=7.5 Hz, 2H), 1.52-1.39 (m, 2H), 0.93 (t, J=7.3 Hz, 3H). ESI-MS (m/z): 259.0 [M+H]$^+$.

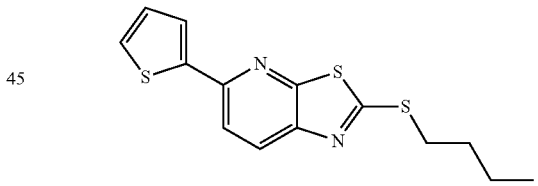

2-(Butylthio)-5-(thiophen-2-yl)thiazolo[5'4-b]pyridine. 2-Thienylboronic acid (49.4 mg, 0.386 mmol), $CsCO_3$ (126 mg, 0.386 mmol), Pd(dppf)$Cl_2$ (15.8 mg, 0.0193 mmol), CuCl (19.1 mg, 0.193 mmol) and DMF (1 mL) were added to 2-(butylthio)-5-chlorothiazolo[5,4-b]pyridine (50 mg, 0.19 mmol) under $N_2$. The reaction mixture was heated to 100° C. for 30 minutes. Then the $N_2$ was disconnected and the vial was capped and sealed with teflon tape and allowed to stir overnight. The reaction mixture was diluted in EtOAc, washed with $H_2O$, and the organic layer was separated, dried over $MgSO_4$, filtered, and concentrated under reduced pressure to give the product in 31% isolated yield. $^1$H NMR (400 MHz, $CDCl_3$) δ 7.98 (d, J=8.6 Hz, 1H), 7.63 (dd, J=3.8, 1.1 Hz, 1H), 7.51 (dd, J=5.1, 1.1 Hz, 1H), 7.23 (d, J=8.6 Hz, 1H), 7.14 (dd, J=5.0, 3.8 Hz, 1H), 3.24 (t, J=7.3 Hz, 2H), 1.78-1.66 (m, 2H), 1.57-1.41 (m, 2H), 0.96 (t, J=7.4 Hz, 3H). ESI-MS (m/z): 307.0 [M+H]$^+$.

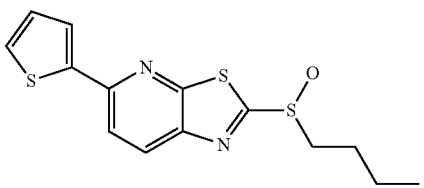

SW208599. 2-(butyl(11-oxidanyl)-13-sulfanyl)-5-(thiophen-2-yl)thiazolo[5,4-b]pyridine. CHCl₃ (142 μL), AcOH (142 μL), and H₂O₂ (12.0 μL, 0.118 mmol, 30% solution in H₂O) were added to 2-(butylthio)-5-(thiophen-2-yl)thiazolo [5,4-b]pyridine (18 mg. 0.059 mmol) and heated at 35° C. for 2.5 hours. The solution was diluted with EtOAc and washed with saturated NaHCO₃. The organic layer was separated, dried over MgSO₄, filtered, and concentrated under reduced pressure to give product in 60% isolated yield. ¹H NMR (400 MHz, CDCl₃) δ 8.39 (d, J=8.4 Hz, 1H), 8.06 (d, J=8.4 Hz, 1H), 7.74 (dd, J=3.8, 1.1 Hz, 1H), 7.61 (dd, J=5.0, 1.1 Hz, 1H), 7.19 (dd, J=5.0, 3.8 Hz, 1H), 3.15 (ddd, J=13.3, 9.8, 6.0 Hz, 1H), 2.96 (ddd, J=13.3, 9.9, 4.9 Hz, 1H), 1.98-1.80 (m, 1H), 1.60-1.52 (m, 1H), 1.52-1.37 (m, 2H), 0.93 (t, J=7.2 Hz, 3H). ESI-MS (m/z): 323.0 [M+H]⁺.

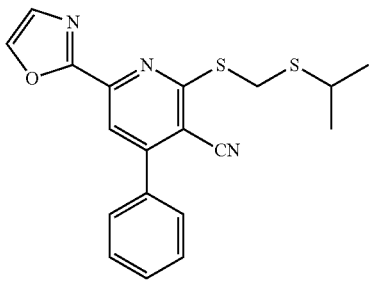 [SMILES: CC(C)SCSc1nc(-c2ncco2)cc(-c2ccccc2)c1C#N]

2-(((Isopropylthio)methyl)thio)-6-(oxazol-2-yl)-4-phenylnicotinonitrile. Follow the standard alkylation procedure, using (chloromethyl)(isopropyl)sulfane as the alkylating substrate, and 6-(oxazol-2-yl)-4-phenyl-2-thioxo-1,2-dihydropyridine-3-carbonitrile as the starting material. The crude product was purified using flash chromatography to give a solid in 62% isolated yield. ¹H NMR (400 MHz, CDCl₃) δ 7.97 (s, 1H), 7.88 (d, J=0.7 Hz, 1H), 7.67-7.61 (m, 2H), 7.56-7.50 (m, 3H), 7.37 (d, J=0.8 Hz, 1H), 4.63 (s, 2H), 3.24 (hept, J=6.7 Hz, 1H), 1.35 (d, J=6.7 Hz, 6H). ESI-MS (m/z): 368.0 [M+H]⁺.

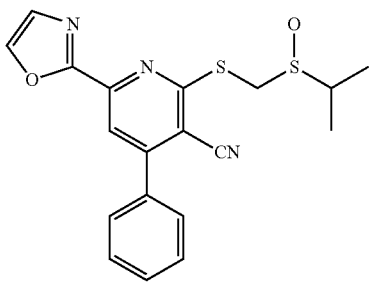

2-(((Isopropyl(11-oxidanyl)-13-sulfanyl)methyl)thio)-6-(oxazol-2-yl)-4-phenylnicotinonitrile. Follow the standard oxidation procedure using 2-(((isopropylthio)methyl)thio)-6-(oxazol-2-yl)-4-phenylnicotinonitrile as the starting material. Recovered quantitative isolated yield. ¹H NMR (400 MHz, CDCl₃) δ 8.03 (s, 1H), 7.88 (d, J=0.7 Hz, 1H), 7.67-7.61 (m, 2H), 7.58-7.50 (m, 3H), 7.39 (d, J=0.7 Hz, 1H), 4.79 (d, J=13.3 Hz, 1H), 4.55 (d, J=13.3 Hz, 1H), 3.18 (hept, J=6.9 Hz, 1H), 1.42 (d, J=1.5 Hz, 3H), 1.40 (d, J=1.3 Hz, 3H). ESI-MS (m/z): 384.1 [M+H]⁺.

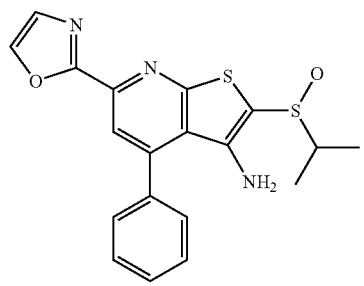

Standard Final Cyclization Procedure: SW208660. 2-(Isopropyl(11-oxidanyl)-13-sulfanyl)-6-(oxazol-2-yl)-4-phenylthieno[2,3-b]pyridin-3-amine. DMF (485 μL) and MeOH (244 μL) were added to 2-(((isopropyl(11-oxidanyl)-13-sulfanyl)methyl)thio)-6-(oxazol-2-yl)-4-phenylnicotinonitrile (47.2 mg, 0.123 mmol) dissolving it completely before KOH (4.1 mg in 100 μL of H₂O) was added to the solution. The reaction mixture was stirred at 35° C. for 40 minutes. The reaction mixture was diluted with EtOAc, washed with 10% AcOH and then washed with H₂O multiple times. The organic layer was separated, dried over MgSO₄, filtered, and concentrated under reduced pressure. The crude product was purified using flash chromatography to give product in 40% isolated yield¹H NMR (400 MHz, CDCl₃) δ 7.99 (s, 1H), 7.85 (d, J=0.7 Hz, 1H), 7.56-7.44 (m, 5H), 7.34 (d, J=0.8 Hz, 1H), 4.69 (s, 2H), 3.41 (hept, J=6.8 Hz, 1H), 1.44 (d, J=6.8 Hz, 3H), 1.28 (d, J=6.9 Hz, 3H). ESI-MS (m/z): 384.1 [M+H]⁺.

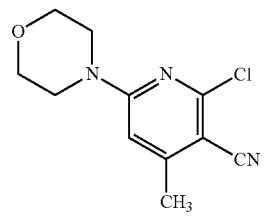 [SMILES: Cc1cc(N2CCOCC2)nc(Cl)c1C#N]

2-Chloro-4-methyl-6-morpholinonicotinonitrile. Anhydrous MeOH (3.97 mL) was added to 2,6-dichloro-4-methylnicotinonitrile (500 mg, 2.67 mmol) under N₂ and the mixture was cooled down to 0° C. Morpholine (473.7 μL, 5.493 mmol) was added dropwise to the solution and the solution stirred at room temperature overnight. The reaction mixture was filtered, washing the precipitate with MeOH (500 μL) and H₂O (3-4 mL). DCM was added to the precipitate, followed by MgSO₄, and the solution was filtered, then concentrated under reduced pressure. The crude product was purified using automated flash chromatography to give product in 85% isolated yield. ¹H NMR (400 MHz, CDCl₃) δ 7.26 (s, 1H), 3.81-3.73 (m, 4H), 3.68-3.58 (m, 4H), 2.42 (d, J=0.8 Hz, 3H). ESI-MS (m/z): 238.1 [M+H]⁺.

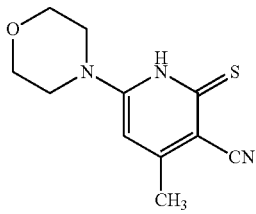 [SMILES: Cc1cc(N2CCOCC2)[nH]c(=S)c1C#N]

4-Methyl-6-morpholino-2-thioxo-1,2-dihydropyridine-3-carbonitrile. NaOME (73.6 mg, 1.36 mmol) and methyl 3-mercapiopropionate (151 μL, 1.363 mmol) were added to a solution of 2-chloro-4-methyl-6morpholinonicotinonitrile (324 mg, 1.36 mmol) in DMF (4.10 mL) and the reaction mixture was stirred at 80° C. for 1 hour. Once cooled down, the reaction mixture was diluted with EtOAc and washed with H$_2$O. The organic layer was separated, dried over MgSO4, filtered, and concentrated under reduced pressure to give a crude mixture of 1:1 starting material to product, which was carried forward to the next step. ESI (nm/z): 322.1 [M+H]+. NaH (150.8 mg, 3.769 mmol, 60% in mineral oil) and THF (10 mL) were added to a flame dried flask under N2, followed by the crude product from the previous step dissolved in THF (10 mL). The reaction mixture was refluxed for 6 hours and addition NaH (2 eq) was and left reluxing overnight. EtOH (1.5 mL) was added then the reaction mixture was concentrated down under reduced pressure. H$_2$O (8 mL) was added and the solution was adjusted to pH 6 with concentrated HCl before filtering to leave a crude solid that was carried forward. ESI (m/z): 236.1 [M+H]$^+$.

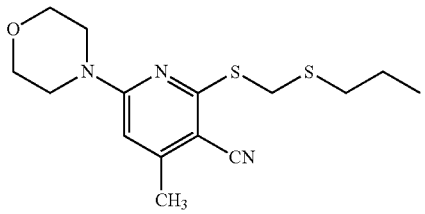 [SMILES: CCCSCSc1nc(N2CCOCC2)cc(C)c1C#N]

4-Methyl-6-morpholino-2-(((propylthio)methyl)thio) nicotinonitrile. Followed the standard alkylating procedure, using 4-methyl-6-morpholino-2-thioxo-1,2-dihydropyridine-3-carbonitrile as the starting material and (chloromethyl)(propyl)sulfane as the alkylating substrate. The crude product was carried forward. ESI (m/z): 324.1 [M+H]+.

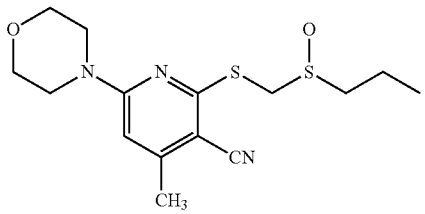

2-((((11-oxidanyl)(propyl)-13-sulfanyl)methyl)thio)-4-methyl-6-morpholinonicotinonitrile. Followed the standard oxidation procedure using 4-methyl-6-morpholino-2-(((propylthio)methyl)thio)nicotinonitrile as the starting material. The crude product was carried forward. ESI (m/z): 340.1 [M+H]$^+$.

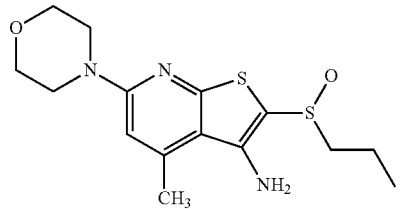

SW208663. 2-((11-oxidanyl)(propyl)-13-sulfanyl)-4-methyl-6-morpholinothieno[2,3-b]pyridin-3-amine. Followed the standard final cyclization procedure using 2-((((11-oxidanyl)(propyl)-13-sulfanyl)methyl)thio)-4-methyl-6-morpholinonicotinonitrile as the starting material. The crude product was purified by flash chromatography, and PTLC to give isolated product in 10% yield. $^1$H NMR (400 MHz, CDCl$_3$) δ 6.36 (s, 1H), 4.91 (s, 2H), 3.85-3.76 (m, 4H), 3.63-3.58 (m, 4H), 3.32-3.18 (m, 1H), 3.09-2.99 (m, 1H), 2.65 (s, 3H), 1.81-1.66 (m, 2H), 1.07 (t, J=7.4 Hz, 3H). ESI (m/z): 340.1 [M+H]$^+$.

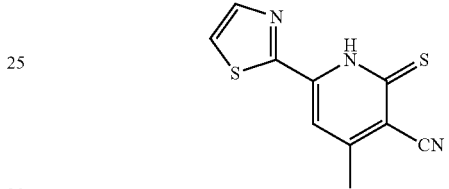

4-Methyl-6-(thiazol-2-yl)-2-thioxo-1,2-dihydropyridine-3-carbonitrile. Followed same procedure as 4-Methyl-6-morpholino-2-thioxo-1,2-dihydropyridine-3-carbonitrile, using methyl 3-((3-cyano-4-methyl-6-(thiazol-2-yl)pyridin-2-yl)thio)propanoate as the starting material. The crude product was carried forward. ESI-MS (m/z): 234.0 [M+H]$^+$.

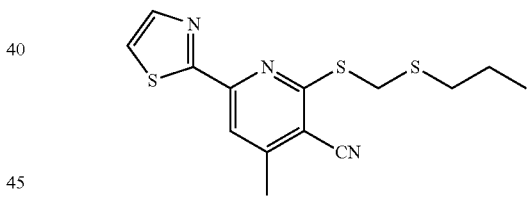

4-Methyl-2-(((propylthio)methyl)thio)-6-(thiazol-2-yl) nicotinonitrile. Followed the standard alkylation procedure using 4-Methyl-6-(thiazol-2-yl)-2-thioxo-1,2-dihydropyridine-3-carbonitrile as the starting material, and (chloromethyl)(propyl)sulfane as the alkylating substrate. The crude product was purified using automated flash chromatography to give product in 23% isolated yield. $^1$H NMR (400 MHz, Chloroform-d) δ 7.96 (d, J=3.1 Hz, 1H), 7.83 (s, 1H), 7.54 (d, J=3.1 Hz, 1H), 4.47 (s, 2H), 2.70 (t, J=7.2 Hz, 2H), 2.55 (s, 3H), 1.67 (h, J=7.3 Hz, 2H), 0.99 (t, J=7.3 Hz, 3H). ESI-MS (m/z): 322.0 {M+H]$^+$.

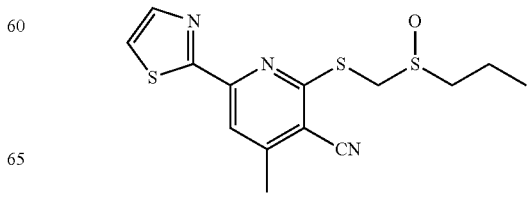

2-((((11-oxidanyl)(propyl)-13-sulfanyl)methyl)thio)-4-methyl-6-(thiazol-2-yl)nicotinonitrile. Followed the standard oxidation procedure using 4-methyl-2-(((propylthio)methyl)thio)-6-(thiazol-2-yl)nicotinonitrile as the starting material to give white solid in 91% isolated yield. $^1$H NMR (400 MHz, CDCl$_3$) δ 7.97 (d, J=3.1 Hz, 1H), 7.92 (s, 1H), 7.56 (d, J=3.2 Hz, 1H), 4.74 (d, J=13.2 Hz, 1H), 4.44 (d, J=13.1 Hz, 1H), 2.89 (m, 2H), 2.57 (s, 3H), 1.93-1.79 (m, 2H), 1.06 (t, J=7.4 Hz, 3H). ESI-MS (m/z): 338.0 [M+H]$^+$.

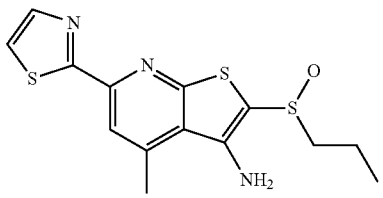

SW208661. 2-((11-oxidanyl)(propyl)-13-sulfanyl)-4-methyl-6-(thiazol-2-yl)thieno[2,3-b]pyridin-3-amine. Followed standard final cyclization procedure using 2-((((11-oxidanyl)(propyl)-13-sulfanyl)methyl)thio)-4-methyl-6-(thiazol-2-yl)nicotinonitrile as the starting material. Purified the crude product using flash chromatography to give 61% bright green isolated product. $^1$H NMR (400 MHz, CDCl$_3$) δ 7.95 (s, 1H), 7.93 (d, J=3.2 Hz, 1H), 7.48 (d, J=3.2 Hz, 1H), 5.16 (s, 2H), 3.37-3.23 (m, 1H), 3.16-3.05 (m, 1H), 2.85 (s, 3H), 1.83 (h, J=7.5 Hz, 2H), 1.11 (t, J=7.4 Hz, 3H). ESI-MS (m/z): 338.0 [M+H]$^+$.

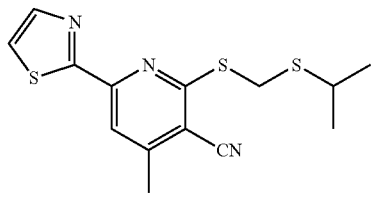 [SMILES: Cc1cc(-c2nccs2)nc(SCSC(C)C)c1C#N]

2-(((isopropylthio)methyl)thio)-4-methyl-6-(thiazol-2-yl)nicotinonitrile. Followed standard alkylating procedure using (chloromethyl)(isopropyl)sulfane as the alkylating substrate and 4-methyl-6-(thiazol-2-yl)-2-thioxo-1,2-dihydropyridine-3-carbonitrile as the starting material. Purified using automated flash chromatography to give product in 32% isolated yield. $^1$H NMR (400 MHz, CDCl$_3$) δ 7.94 (d, J=3.2 Hz, 1H), 7.82 (s, 1H), 7.52 (d, J=3.2 Hz, 1H), 4.48 (s, 2H), 3.18 (hept, J=6.6 Hz, 1H), 2.54 (s, 3H), 1.31 (d, J=6.7 Hz, 6H). ESI-MS (m/z): 322.0 [M+H]+.

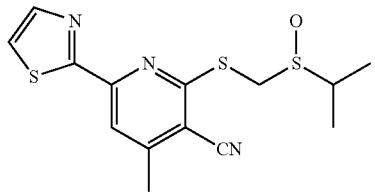

2-(((isopropyl(11-oxidanyl)-13-sulfanyl)methyl)thio)-4-methyl-6-(thiazol-2-yl)nicotinonitrile. Followed standard oxidation procedure using 2-(((isopropylthio)methyl)thio)-4-methyl-6-(thiazol-2-yl)nicotinonitrile as the starting material to give a solid product in 84% yield. $^1$H NMR (400 MHz, CDCl$_3$) δ 7.97 (d, J=3.1 Hz, 1H), 7.91 (s, 1H), 7.56 (d, J=3.1 Hz, 1H), 4.57 (d, J=13.3 Hz, 1H), 4.46 (d, J=13.3 Hz, 1H), 3.05 (hept, J=6.9 Hz, 1H), 2.57 (s, 3H), 1.38 (d, J=7.1 Hz, 3H), 1.36 (d, J=6.7 Hz, 3H). ESI-MS (m/z): 338.0 [M+H]$^+$.

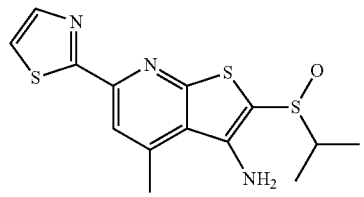

SW208664. 2-(Isopropyl(11-oxidanyl)-13-sulfanyl)-4-methyl-6-(thiazol-2-yl)thieno[2,3-b]pyridin-3-amine. Followed standard final cyclization procedure using 2-(((isopropyl(11-oxidanyl)-13-sulfanyl)methyl)thio)-4-methyl-6-(thiazol-2-yl)nicotinonitrile as the starting material. The crude product was purified using flash chromatography to give bright green oil/solid in 48% isolated yield. $^1$H NMR (400 MHz, Chloroform-d) δ 7.93 (s, 1H), 7.92 (d, J=3.2 Hz, 1H), 7.46 (d, J=3.2 Hz, 1H), 3.38 (hept, J=6.9 Hz, 1H), 2.84 (s, 3H), 1.46 (d, J=6.8 Hz, 3H), 1.29 (d, J=6.8 Hz, 3H). ESI-MS (m/z): 338.0 [M+H]$^+$.

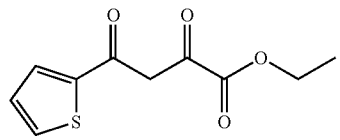

Ethyl 2,4-dioxo-4-(thiophen-2-yl)butanoate. 2-Acetylthiophene (1.71 mL, 0.0159 mol) was added to a solution of NaOEt (730 mg Na cubes in 50 mL of EtOH) and the solution was cooled to 0° C. for 1-2 hours then diethyl oxylate (3.2 $^m$L) was added to the solution. This was left to stir at room temperature overnight. The reaction mixture was diluted with EtOAc and H$_2$O with a little brine to assist the separation. The organic layer was collected, dried with MgSO$_4$, filtered, and concentrated under reduced pressure. The crude product was purified using automated flash chromatography giving an oil product with 23% yield. ESI-MS (m/z): 227.0 [M+H]$^+$.

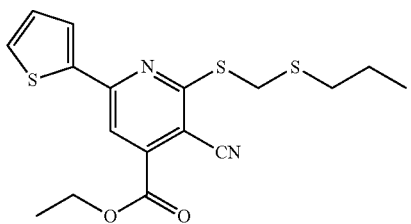 [SMILES: CCCSCSc1nc(-c2cccs2)cc(C(=O)OCC)c1C#N]

Ethyl 3-cyano-2-(((propylthio)methyl)thio)-6-(thiophen-2-yl)isonicotinate. 2-Cyanothioacetamide (250.6 mg, 2.503 mmol) and ethyl 2,4-dioxo-4-(thiophen-2-yl)butanoate (565.7 mg, 2.503 mmol) were dissolved in EtOH (7.46 mL) under gentle heating (40° C.), then Et$_3$N (174.5 μL, 1.251 mmol) was added drop wise to the stirring solution. The reaction mixture was heated at 60° C. and after 3 hours was concentrated down under reduced pressure and the crude product was carried forward to the next step. Followed standard alkylating procedure using ethyl 3-cyano-6-(thiophen-2-yl)-2-thioxo-1,2-dihydropyridine-4-carboxylate as the starting material and (chloromethyl)(propyl)sulfane as the alkylating reagent. The crude product was purified twice using automated flash chromatography (20% EtOAc, 80% hexanes) to give 34% isolated product. $^1$H NMR (400 MHz, CDCl$_3$) δ 7.70 (s, 1H), 7.60 (dd, J=3.8, 1.1 Hz, 1H), 7.44 (dd, J=5.1, 1.1 Hz, 1H), 7.04 (dd, J=5.0, 3.8 Hz, 1H), 4.38 (q, J=7.2 Hz, 2H), 4.32 (s, 2H), 2.59 (t, J=7.2 Hz, 2H), 1.57 (h, J=7.4 Hz, 2H), 1.36 (t, J=7.1 Hz, 3H), 0.89 (t, J=7.3 Hz, 3H). ESI-MS (m/z): 378.9 [M+H]$^+$.

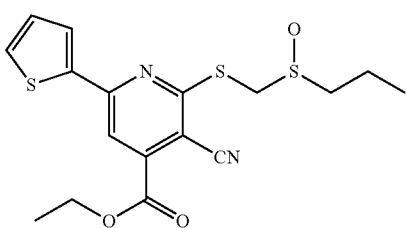

Ethyl 2-((((11-oxidanyl)(propyl)-13-sulfanyl)methyl)thio)-3-cyano-6-(thiophen-2-yl)isonicotinate. Followed standard oxidation procedure using ethyl 3-cyano-2-(((propylthio)methyl)thio)-6-(thiophen-2-yl)isonicotinate as the starting material to give a solid with quantitative yield. $^1$H NMR (400 MHz, CDCl$_3$) δ 7.86 (s, 1H), 7.72 (dd, J=3.8, 1.1 Hz, 1H), 7.53 (dd, J=5.0, 1.1 Hz, 1H), 7.11 (dd, J=5.0, 3.8 Hz, 1H), 4.68 (d, J=13.2 Hz, 1H), 4.49 (d, J=13.2 Hz, 1H), 4.43 (q, J=7.1 Hz, 2H), 2.96-2.82 (m, 2H), 1.87-1.75 (m, 2H), 1.40 (t, J=7.2 Hz, 3H), 1.02 (t, J=7.4 Hz, 3H). ESI-MS (m/z): 394.9 [M+H]$^+$.

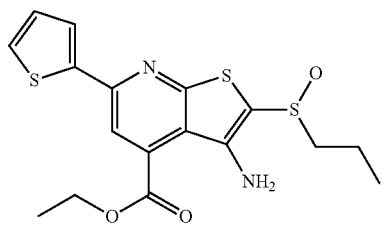

SW208781. Ethyl 2-((11-oxidanyl)(propyl)-13-sulfanyl)-3-amino-6-(thiophen-2-yl)thieno[2,3-b]pyridine-4-carboxylate. t-BuOK (74.1 mg, 0.661 mmol) was added to a solution of ethyl 2-((((11-oxidanyl)(propyl)-13-sulfanyl)methyl)thio)-3-cyano-6-(thiophen-2-yl)isonicotinate (433.7 mg, 1.101 mmol) in DMF (4.3 mL) and the solution stirred for 40 minutes at 35° C. More t-BuOK (74.1 mg, 0.661 mmol) was added and allowed to stir at 35° C. for an hour. The reaction mixture was diluted with EtOAc and washed with 10% AcOH, and then multiple times with H$_2$O. The organic layer was separated, dried over MgSO$_4$, filtered, and concentrated under reduced pressure. The crude product was purified using flash chromatography to give product in 30% isolated yield. $^1$H NMR (400 MHz, CDCl$_3$) δ 8.01 (s, 1H), 7.69 (dd, J=3.8, 1.1 Hz, 1H), 7.46 (dd, J=5.0, 1.1 Hz, 1H), 7.11 (dd, J=5.0, 3.8 Hz, 1H), 6.09 (s, 2H), 4.49 (q, J=7.1 Hz, 2H), 3.36-3.22 (m, 1H), 3.15-3.00 (m, 1H), 1.87-1.68 (m, 2H), 1.47 (t, J=7.1 Hz, 3H), 1.07 (t, J=7.4 Hz, 3H). ESI-MS (m/z): 394.9 [M+H]$^+$.

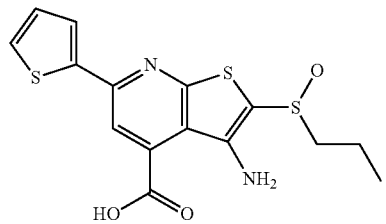

SW208782. 2-((11-oxidanyl)(propyl)-13-sulfanyl)-3-amino-6-(thiophen-2-yl)thieno[2,3-b]pyridine-4-carboxylic acid. Followed the standard hydrolysis procedure using SW208781 as the starting material which gave product in 40% isolated yield. $^1$H NMR (400 MHz, C$_3$D$_7$NO) δ 8.56 (s, 1H), 8.29 (d, J=3.7 Hz, 1H), 8.19 (s, 1H), 7.99 (d, J=5.0 Hz, 1H), 7.47-7.41 (m, 1H), 3.36 (ddd, J=12.8, 8.4, 6.1 Hz, 1H), 3.24 (ddd, J=12.8, 8.6, 6.8 Hz, 1H), 1.98-1.85 (m, 2H), 1.23 (t, J=7.4 Hz, 3H). ESI-MS (m/z): 366.8.

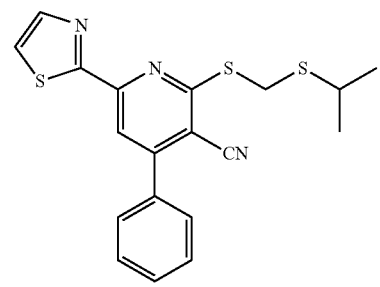 [SMILES: CC(C)SCSc1nc(-c2nccs2)cc(-c2ccccc2)c1C#N]

2-(((isopropylthio)methyl)thio)-4-phenyl-6-(thiazol-2-yl)nicotinonitrile. Followed the standard alkylation procedure using 4-phenyl-6-(thiazol-2-yl)-2-thioxo-1,2-dihydropyridine-3-carbonitrile as the starting material and (chloromethyl)(isopropyl)sulfane as the alkylating reagent. This was purified using automated flash chromatography to give product in 72% isolated yield. $^1$H NMR (400 MHz, CDCl$_3$) δ 8.03 (s, 1H), 7.98 (d, J=3.1 Hz, 1H), 7.70-7.62 (m, 2H), 7.57 (d, J=3.1 Hz, 1H), 7.56-7.48 (m, 3H), 4.56 (s, 2H), 3.24 (hept, J=6.7 Hz, 1H), 1.36 (d, J=6.7 Hz, 6H). ESI-MS (m/z): 383.9.

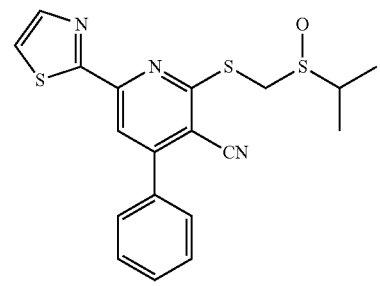

2-(((isopropyl(11-oxidanyl)-13-sulfanyl)methyl)thio)-4-phenyl-6-(thiazol-2-yl)nicotinonitrile. Followed the standard oxidation procedure using 2-(((isopropylthio)methyl)

thio)-4-phenyl-6-(thiazol-2-yl)nicotinonitrile as the starting material. This gave white solid product in 91% yield. $^1$H NMR (400 MHz, CDCl$_3$) δ 8.12 (s, 1H), 8.00 (d, J=3.1 Hz, 1H), 7.70-7.63 (m, 2H), 7.60 (d, J=3.1 Hz, 1H), 7.58-7.51 (m, 3H), 4.63 (d, J=13.2 Hz, 1H), 4.48 (d, J=13.2 Hz, 1H), 3.09 (hept, J=6.9 Hz, 1H), 1.42 (d, J=10.5 Hz, 3H), 1.39 (d, J=10.5 Hz, 3H). ESI-MS (m/z): 399.9.

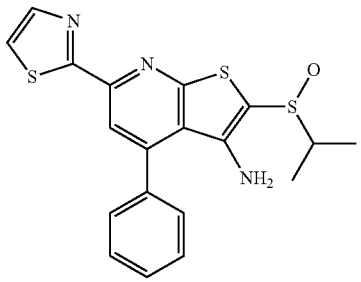

SW208780. 2-(isopropyl(11-oxidanyl)-13-sulfanyl)-4-phenyl-6-(thiazol-2-yl)thieno[2,3-b]pyridin-3-amine.

t-BuOK (2.5 mg, 0.023 mmol) was added to a solution of 2-(((isopropyl(11-oxidanyl)-13-sulfanyl)methyl)thio)-4-phenyl-6-(thiazol-2-yl)nicotinonitrile (15 mg, 0.038 mmol) in DMF (148 μL), and stirred at 35° C. for 40 minutes. The reaction mixture was diluted with EtOAc and washed with 10% AcOH, then several times with H$_2$O. The organic layer was dried over NaSO$_4$, filtered, and concentrated under reduced pressure. The crude product was purified using flash chromatography to give product in 75% yield.

$^1$H NMR (400 MHz, CDCl$_3$) δ 8.05 (s, 1H), 7.91 (d, J=3.2 Hz, 1H), 7.57-7.42 (m, 6H), 4.68 (s, 2H), 3.47-3.33 (m, 1H), 1.44 (d, J=6.8 Hz, 3H), 1.27 (d, J=6.8 Hz, 3H). ESI-MS (m/z): 399.9.

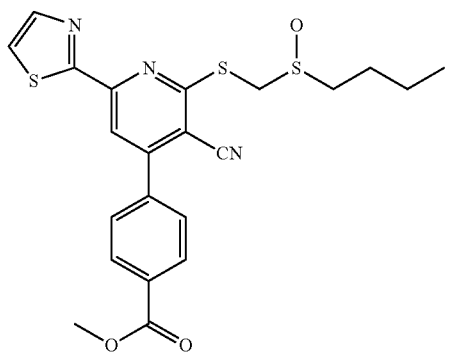

Methyl 4-(2-(((butyl(11-oxidanyl)-13-sulfanyl)methyl)thio)-3-cyano-6-(thiazol-2-yl)pyridin-4-yl)benzoate. Followed standard oxidation procedure using methyl 4-(2-(((butylthio)methyl)thio)-3-cyano-6-(thiazol-2-yl)pyridin-4-yl)benzoate as the starting material to give white solid in 98% isolated yield. $^1$H NMR (400 MHz, CDCl$_3$) δ 8.15 (d, J=8.3 Hz, 2H), 8.05 (s, 1H), 7.95 (d, J=3.1 Hz, 1H), 7.68 (d, J=8.3 Hz, 2H), 7.57 (d, J=3.1 Hz, 1H), 4.68 (d, J=13.1 Hz, 1H), 4.42 (d, J=13.1 Hz, 1H), 3.91 (s, 3H), 3.01-2.86 (m, 1H), 2.87-2.74 (m, 1H), 1.88-1.72 (m, 2H), 1.55-1.35 (m, 2H), 0.91 (t, J=7.3 Hz, 3H). ESI-MS (m/z): 472.1 [M+H]$^+$.

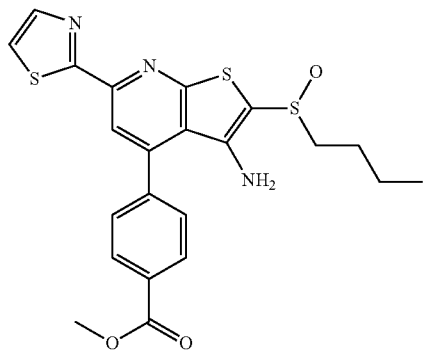

SW209127. Methyl 4-(3-amino-2-(butyl(11-oxidanyl)-13-sulfanyl)-6-(thiazol-2-yl)thieno[2,3-b]pyridin-4-yl)benzoate. t-BuOK (21.8 mg, 0.194 mmol) was added to methyl 4-(2-(((butyl(11-oxidanyl)-13-sulfanyl)methyl)thio)-3-cyano-6-(thiazol-2-yl)pyridin-4-yl)benzoate (152.8 mg, 0.3239 mmol) in DMF (1.30 mL) and the solution stirred at 35° C. for 40 minutes. The reaction mixture was diluted with EtOAc and washed with 10% AcOH, and several times with H$_2$O. The organic layer was separated, dried over Na$_2$SO$_4$, filtered, and concentrated under reduced pressure. The crude product was purified using automated flash chromatography t$_o$ give the bright green product in 66% isolated yield. $^1$H NMR (400 MHz, CDCl$_3$) δ 8.19 (d, J=7.5 Hz, 2H), 8.04 (s, 1H), 7.91 (d, J=3.2 Hz, 1H), 7.67-7.54 (m, 2H), 7.50 (d, J=3.2 Hz, 1H), 3.9$_7$ (s, 3H), 3.27 (ddd, J=12.8, 8.9, 6.2 Hz, 1H), 3.10 (ddd, J=12.8, 9.0, 6.8 Hz, 1H), 1.81-1.63 (m, 2H), 1.54-1.39 (m, 2H), 0.93 (t, J=7.3 Hz, 3H). ESI-MS (m/z): 472.1 [M+H]$^+$.

SW209281. 4-(3-amino-2-(butyl(11-oxidanyl)-13-sulfanyl)-6-(thiazol-2-yl)thieno[2,3-b]pyridin-4-yl)benzoic acid. Followed standard hydrolysis procedure using SW209127 as the starting material to give bright green solid in 84% isolated yield. $^1$H NMR (400 MHz, CDCl$_3$) δ 8.16 (d, J=8.4 Hz, 2H), 8.05 (s, 1H), 7.95 (d, J=3.2 Hz, 1H), 7.68-7.55 (m, 2H), 7.52 (d, J=3.2 Hz, 1H), 3.40-3.24 (m, 1H), 3.24-3.04 (m, 1H), 1.83-1.65 (m, 2H), 1.55-1.37 (m, 2H), 0.93 (t, J=7.3 Hz, 3H). ESI-MS (m/z): 458.1 [M+H]$^+$.

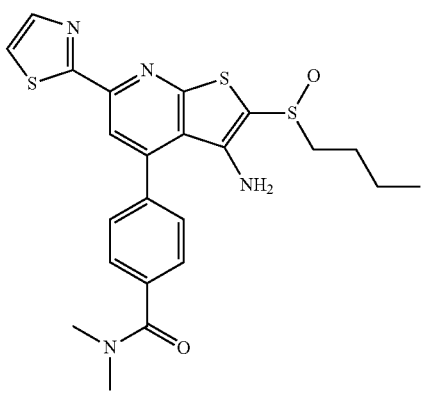

SW209282. 4-(3-amino-2-(butyl(11-oxidanyl)-13-sulfa-nyl)-6-(thiazol-2-yl)thieno[2,3-b]pyridin-4-yl)-N,N-dimethylbenzamide. Followed standard amide bond coupling procedure using SW209281 as the starting material and dimethylamine hydrochloride as the coupling reagent. The product was purified using automated flash chromatography (20% hexane, 80% EtOAc) to give bright green solid in 59% isolated yield $^1$H NMR (400 MHz, CDCl$_3$) δ 8.03 (s, 1H), 7.91 (d, J=3.2 Hz, 1H), 7.66-7.44 (m, 5H), 3.36-3.21 (m, 1H), 3.14 (s, 3H), 3.13-3.06 (m, 1H), 3.02 (s, 3H), 1.81-1.64 (m, 2H), 1.55-1.41 (m, 2H), 0.93 (t, J=7.3 Hz, 3H). ESI-MS (m/z): 485.1 [M+H]$^+$.

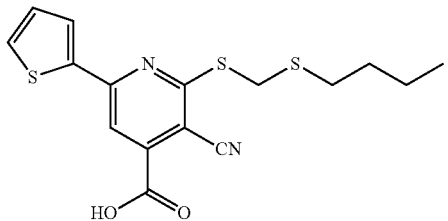 [SMILES: CCCCSCSc1nc(-c2cccs2)cc(C(=O)O)c1C#N]

2-(((butylthio)methyl)thio)-3-cyano-6-(thiophen-2-yl)isonicotinic acid. Followed standard hydrolysis procedure using ethyl 2-(((butylthio)methyl)thio)-3-cyano-6-(thiophen-2-yl)isonicotinate as the starting material to give isolated product in 94% yield.

$^1$H NMR (400 MHz, CDCl$_3$) δ 10.65 (s, 1H), 7.95 (s, 1H), 7.76 (dd, J=3.8, 1.1 Hz, 1H), 7.57 (dd, J=5.0, 1.0 Hz, 1H), 7.17 (dd, J=5.0, 3.7 Hz, 1H), 4.46 (s, 2H), 2.72 (t, J=7.2 Hz, 2H), 1.67-1.55 (m, 2H), 1.40 (h, J=7.4 Hz, 2H), 0.90 (t, J=7.3 Hz, 3H). ESI-MS (m/z): 365.0 [M+H]$^+$.

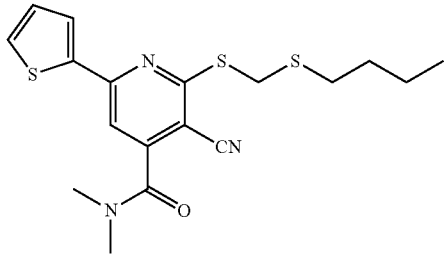 [SMILES: CCCCSCSc1nc(-c2cccs2)cc(C(=O)N(C)C)c1C#N]

2-(((butylthio)methyl)thio)-3-cyano-N,N-dimethyl-6-(thiophen-2-yl)isonicotinamide. Followed standard amide bond coupling procedure using 2-(((butylthio)methyl)thio)-3-cyano-6-(thiophen-2-yl)isonicotinic acid as the starting material and dimethylamine as the coupling reagent. The crude material was purified using automated flash chromatography (20% EtOAc, 80% hexanes) to give product in 53% isolated yield.

$^1$H NMR (400 MHz, Chloroform-d) δ 7.67 (d, J=3.8 Hz, 1H), 7.54 (d, J=5.0 Hz, 1H), 7.34 (s, 1H), 7.15 (t, J=4.8, 3.9, 0.7 Hz, 1H), 4.49 (s, 2H), 3.16 (s, 3H), 2.98 (s, 3H), 2.72 (t, 2H), 1.62 (p, J=7.7 Hz, 2H), 1.41 (h, J=7.3 Hz, 2H), 0.90 (t, J=7.7, 7.0 Hz, 3H). ESI-MS (m/z): 392.1 [M+H]$^+$.

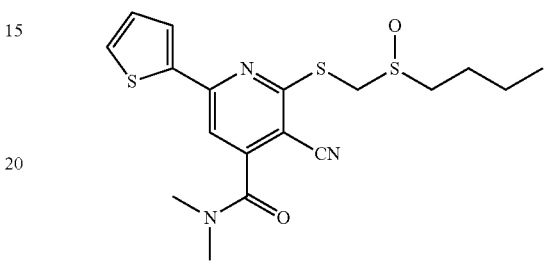

2-(((butyl(11-oxidanyl)-13-sulfanyl)methyl)thio)-3-cyano-N,N-dimethyl-6-(thiophen-2-yl)isonicotinamide. Followed standard oxidation procedure using 2-(((butylthio)methyl)thio)-3-cyano-N,N-dimethyl-6-(thiophen-2-yl)isonicotinamide as the starting material to give solid product in 85% isolated yield. $^1$H NMR (400 MHz, CDCl$_3$) δ 7.67 (d, J=3.8 Hz, 1H), 7.54 (d, J=5.0 Hz, 1H), 7.34 (s, 1H), 7.20-7.06 (m, 1H), 4.49 (s, 2H), 3.16 (s, 3H), 2.98 (s, 3H), 2.72 (t, 2H), 1.62 (p, J=7.7 Hz, 2H), 1.41 (h, J=7.3 Hz, 2H), 0.90 (t, J=7.7, 7.0 Hz, 3H). ESI-MS (m/z): 408.1 [M+H]$^+$.

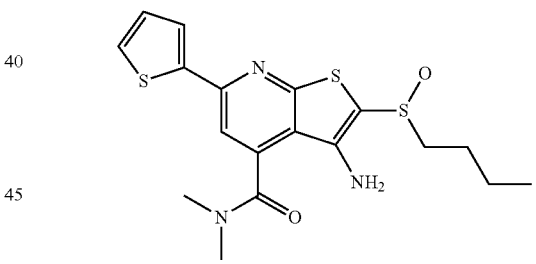

SW209283. 3-amino-2-(butyl(11-oxidanyl)-13-sulfanyl)-N,N-dimethyl-6-(thiophen-2-yl)thieno[2,3-b]pyridine-4-carboxamide. t-BuOK (6.5 mg, 0.058 mmol) was added to a solution of 2-(((butyl(11-oxidanyl)-13-sulfanyl)methyl)thio)-3-cyano-N,N-dimethyl-6-(thiophen-2-yl)isonicotinamide (39.2 mg, 0.962 mmol) in DMF (380 μL) and the solution was heated at 35° C. for 40 minutes. The reaction mixture was diluted with EtOAc and washed with 10% AcOH, then several times with H$_2$O. The organic layer was separated and dried over Na$_2$SO$_4$, filtered, and concentrated under reduced pressure. The crude material was isolated using automated flash chromatography (20% hexanes, 80% EtOAc) to give the final product in 20% isolated yield. $^1$H NMR (400 MHz, Chloroform-d) δ 7.66 (dd, J=3.8, 1.1 Hz, 1H), 7.52-7.42 (m, 2H), 7.13 (dd, J=5.0, 3.7 Hz, 1H), 3.34-3.23 (m, 1H), 3.21 (s, 3H), 3.15-3.02 (m, 1H), 2.96 (s, 3H), 1.79-1.62 (m, 2H), 1.55-1.36 (m, 2H), 0.93 (t, J=7.3 Hz, 3H). ESI-MS (m/z): 408.1 [M+H]$^+$.

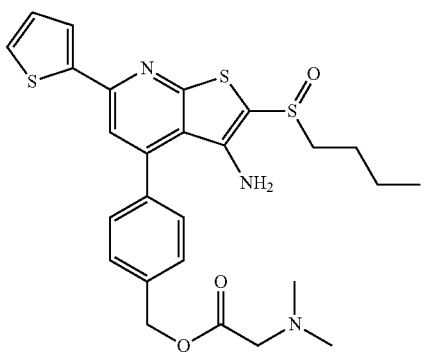 [SMILES: CCCCS(=O)c1sc2nc(-c3cccs3)cc(-c3ccc(COC(=O)CN(C)C)cc3)c2c1N]

SW212366. 4-(3-amino-2-(butylsulfinyl)-6-(thiazol-2-yl)thieno[2,3-b]pyridin-4-yl)benzyl dimethylglycinate. N,N-Dimethylglycine (3.5 mg, 0.034 mmol), 1-ethyl-3-(3-dimethylaminopropyl)carbodiimide (6.5 mg, 0.034 mmol), and DMAP (4.1 mg, 0.0334 mmol) were added to SW209510 (10 mg, 0.023 mmol) and dissolved in DMF (270 µL). The reaction mixture stirred at room temperature overnight, then neutralized with 1M NaOH, washed with H$_2$O and extracted with EtOAc. The organic layer was dried over Na$_2$SO$_4$, filtered and concentrated under reduced pressure. The crude product was purified using flash chromatography (7% MeOH, 93% DCM) to give a quantitative yield of green solid product $^1$H NMR (400 MHz, CDCl$_3$) δ 8.02 (s, 1H), 7.90 (d, J=3.2 Hz, 1H), 7.56-7.43 (m, 5H), 5.25 (s, 2H), 4.61 (s, 2H), 3.35-3.27 (m, 1H), 3.26 (s, 2H), 3.16-3.04 (m, 1H), 2.37 (s, 6H), 1.78-1.63 (m, 2H), 1.55-1.39 (m, 2H), 0.93 (t, J=7.3 Hz, 3H). ESI-MS (m/z): 529.1 [M+H]$^+$.

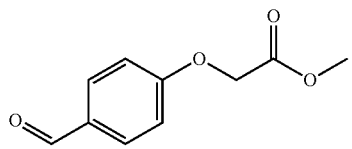

Methyl 2-(4-formylphenoxy)acetate. To a solution of 4-hydroxybenzaldehyde (3.0 g, 25 mmol) in acetone (61.4 mL), K$_2$CO$_3$ (5.43 g, 39.3 mmol) was added and the mixture was stirred vigorously. Methylbromoacetate (2.8 mL, 29 mmol) was added and the mixture was stirred for 3.5 hrs at room temperature. The reaction mixture was concentrated down under reduced pressure then washed with H$_2$O and extracted with EtOAc. The organic layer was separated, dried over Na$_2$SO$_4$, filtered, and concentrated to give a colorless oil that solidified under vacuum in 82% isolated yield. $^1$H NMR (400 MHz, CDCl$_3$) δ 9.87 (s, 1H), 7.82 (d, J=8.8 Hz, 2H), 6.98 (d, J=8.7 Hz, 2H), 4.70 (s, 2H), 3.79 (s, 3H). ESI-MS (m/z): 195.1 [M+H]$^+$.

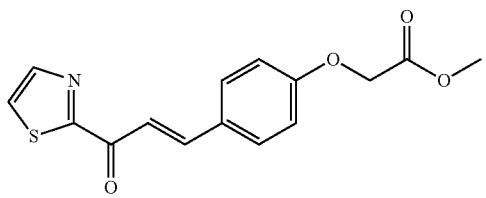 [SMILES: COC(=O)COc1ccc(/C=C/C(=O)c2nccs2)cc1]

Methyl (E)-2-(4-(3-oxo-3-(thiazol-2-yl)prop-1-en-1-yl)phenoxy)acetate. 2-acetylthiazole (534 µL, 5.15 mmol) was added to a solution of methyl 2-(4-formylphenoxy)acetate (1.0 g, 5.2 mmol) in MeOH (11 mL) under N$_2$. NaOMe (279 mg, 5.15 mmol) was added last and the reaction mixture stirred at room temperature overnight. The reaction mixture was filtered, and the precipitate was washed with small amount of MeOH then diluted with DCM and washed with H$_2$O. The organic layer was separated, dried over Na$_2$SO$_4$, filtered, and concentrated under reduced pressure. This gave solid product in 21% isolated yield. $^1$H NMR (400 MHz, Chloroform-d) δ 8.03 (d, J=3.0 Hz, 1H), 7.95 (d, J=15.9 Hz, 1H), 7.82 (d, J=16.0 Hz, 1H), 7.70-7.61 (m, 3H), 6.92 (d, J=8.8 Hz, 2H), 4.67 (s, 2H), 3.80 (s, 3H). ESI-MS (m/z): 304.1 [M+H]$^+$.

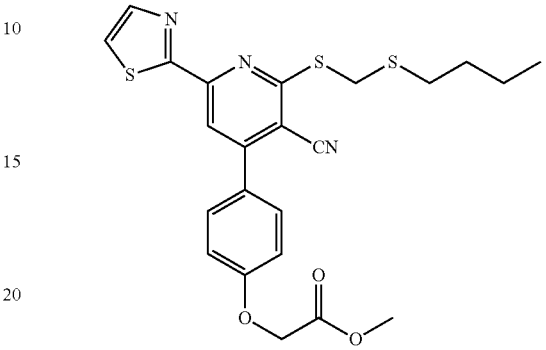

Methyl 2-(4-(2-(((butylthio)methyl)thio)-3-cyano-6-(thiazol-2-yl)pyridin-4-yl)phenoxy)acetate. EtOH (495 µL) was added to 2-cyanothioacetamide (49.5 mg, 0.494 mmol) and methyl(E)-2-(4-(3-oxo-3-(thiazol-2-yl)prop-1-en-1-yl)phenoxy)acetate (50 mg, 0.16 mmol), followed by 1 drop of piperidine. The reaction mixture stirred at 80° C. for 4 hours then was concentrated under reduced pressure and the crude was carried forward to the next step. Followed the standard alkylation procedure, using methyl 2-(4-(3-cyano-6-(thiazol-2-yl)-2-thioxo-1,2-dihydropyridin-4-yl)phenoxy)acetate as the starting material and butyl(chloromethyl)sulfane as the alkylating reagent. The crude product was purified using automated flash chromatography (20% EtOAc, 80% hexanes) to give solid product in 70% isolated yield. $^1$H NMR (400 MHz, CDCl$_3$) δ 7.96 (s, 1H), 7.95 (d, J=3.1 Hz, 1H), 7.62 (d, J=8.8 Hz, 2H), 7.54 (d, J=3.1 Hz, 1H), 7.02 (d, J=8.8 Hz, 2H), 4.69 (s, 2H), 4.49 (s, 2H), 3.81 (s, 3H), 2.73 (t, J=7.3 Hz, 2H), 1.68-1.56 (m, 2H), 1.46-1.34 (m, 2H), 0.89 (t, J=7.3 Hz, 3H). ESI-MS (m/z): 486.1 [M+H]$^+$.

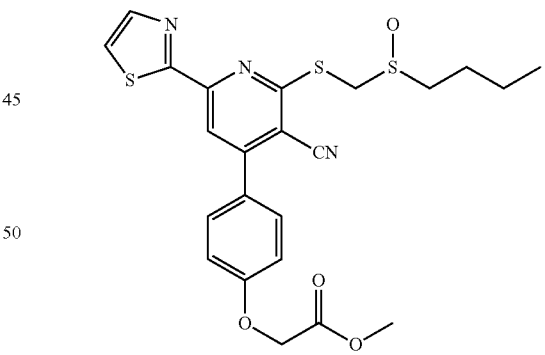

Methyl 2-(4-(2-(((butyl(1111-oxidanyl)-13-sulfanyl)methyl)thio)-3-cyano-6-(thiazol-2-yl)pyridin-4-yl)phenoxy)acetate. Followed the standard oxidation procedure using methyl 2-(4-(2-(((butylthio)methyl)thio)-3-cyano-6-(thiazol-2-yl)pyridin-4-yl)phenoxy)acetate as the starting material. The crude product was purified using automated flash chromatography (50% EtOAc, 50% hexanes). $^1$H NMR (400 MHz, CDCl$_3$) δ 7.97 (s, 1H), 7.90 (d, J=3.1 Hz, 1H), 7.57 (d, J=8.8 Hz, 2H), 7.52 (d, J=3.1 Hz, 1H), 6.98 (d, J=8.8 Hz, 2H), 4.65 (s, 2H), 4.62 (d, J=13.1 Hz, 1H), 4.37 (d, J=13.1 Hz, 1H), 3.75 (s, 3H), 2.96-2.84 (m, 1H), 2.81-2.71 (m, 1H), 1.76 (p, J=7.6 Hz, 2H), 1.51-1.33 (m, 2H), 0.88 (t, J=7.3 Hz, 3H). ESI-MS (m/z): 502.1 [M+H]$^+$.

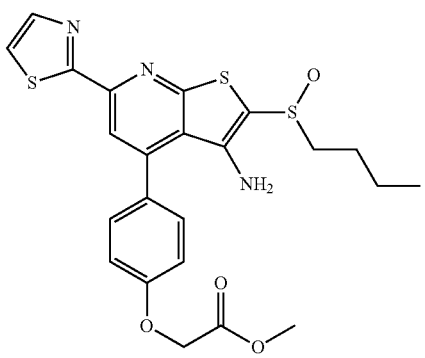

SW212365. Methyl 2-(4-(3-amino-2-(butyl(11-oxidanyl)-13-sulfanyl)-6-(thiazol-2-yl)thieno[2,3-b]pyridin-4-yl)phenoxy)acetate. Methyl 2-(4-(2-(((butyl(11-oxidanyl)-13-sulfanyl)methyl)thio)-3-cyano-6-(thiazol-2-yl)pyridin-4-yl)phenoxy)acetate (80 mg, 0.16 mmol) and t-BuOK (10.7 mg, 0.0954 mmol) were combined in a vial that was evacuated and backfilled with $N_2$ three times, then DMF (627 µL) was added and $N_2$ was bubbled through the solution. The reaction mixture was stirred at room temperature for about 10 minutes and then was diluted with EtOAc and washed with 10% AcOH. The organic layer was washed several times with water, dried over $Na_2SO_4$, filtered, and concentrated. The crude product was purified using automated flash chromatography (30% EtOAc, 70% hexanes) to give green solid with 56% isolated yield. $^1$H NMR (400 MHz, CDCl$_3$) δ 7.97 (s, 1H), 7.89-7.86 (m, 1H), 7.47 (d, J=3.1 Hz, 1H), 7.46-7.37 (m, 2H), 7.02 (d, J=8.5 Hz, 2H), 4.70 (s, 2H), 4.66 (s, 2H), 3.82 (s, 3H), 3.34-3.18 (m, 1H), 3.16-3.01 (m, 1H), 1.77-1.64 (m, 2H), 1.51-1.38 (m, 2H), 0.92 (t, J=7.3 Hz, 3H). ESI-MS (m/z): 502.1 [M+H]$^+$

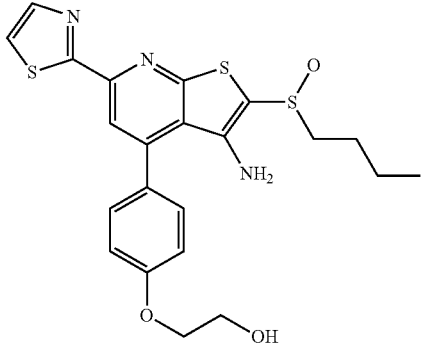

SW212364. 2-(4-(3-amino-2-(butyl(11-oxidanyl)-13-sulfanyl)-6-(thiazol-2-yl)thieno[2,3-b]pyridin-4-yl)phenoxy)ethan-1-ol. Followed the same procedure as for 2-(((butylthio)methyl)thio)-4-(4-(hydroxymethyl)phenyl)-6-(thiazol-2-yl)nicotinonitrile using SW212365 as the starting material to give a quantitative yield of desired product $^1$H NMR (400 MHz, CDCl$_3$) δ 8.01 (s, 1H), 7.90 (d, J=3.2 Hz, 1H), 7.48 (d, J=3.1 Hz, 1H), 7.46-7.35 (m, 2H), 7.07-6.99 (m, 2H), 4.69 (s, 2H), 4.18-4.11 (m, 2H), 4.04-3.96 (m, 2H), 3.34-3.23 (m, 1H), 3.17-3.04 (m, 1H), 1.80-1.61 (m, 2H), 1.53-1.40 (m, 2H), 0.93 (t, J=7.3 Hz, 3H). ESI-MS (m/z): 474.1 [M+H]$^+$.

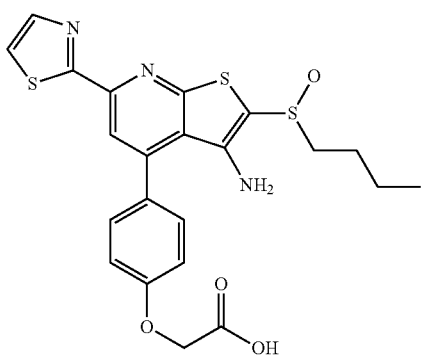

SW212363. 2-(4-(3-amino-2-(butyl(11-oxidanyl)-13-sulfanyl)-6-(thiazol-2-yl)thieno[2,3-b]pyridin-4-yl)phenoxy)acetic acid. Followed the standard hydrolysis procedure using SW212365 as the starting material to give a quantitative yield. $^1$H NMR (400 MHz, MeOD) δ 7.98 (s, 1H), 7.94 (d, J=3.2 Hz, 1H), 7.74 (d, J=3.2 Hz, 1H), 7.46 (d, J=8.4 Hz, 2H), 7.14 (d, J=8.9 Hz, 2H), 4.67 (s, 2H), 3.35-3.24 (m, 1H), 3.16-3.04 (m, 1H), 1.78-1.57 (m, 2H), 1.55-1.43 (m, 2H), 0.95 (t, J=7.3 Hz, 3H). ESI-MS (m/z): 488.1 [M+H]$^+$.

Synthesis of Chloromethyl Thio Ethers

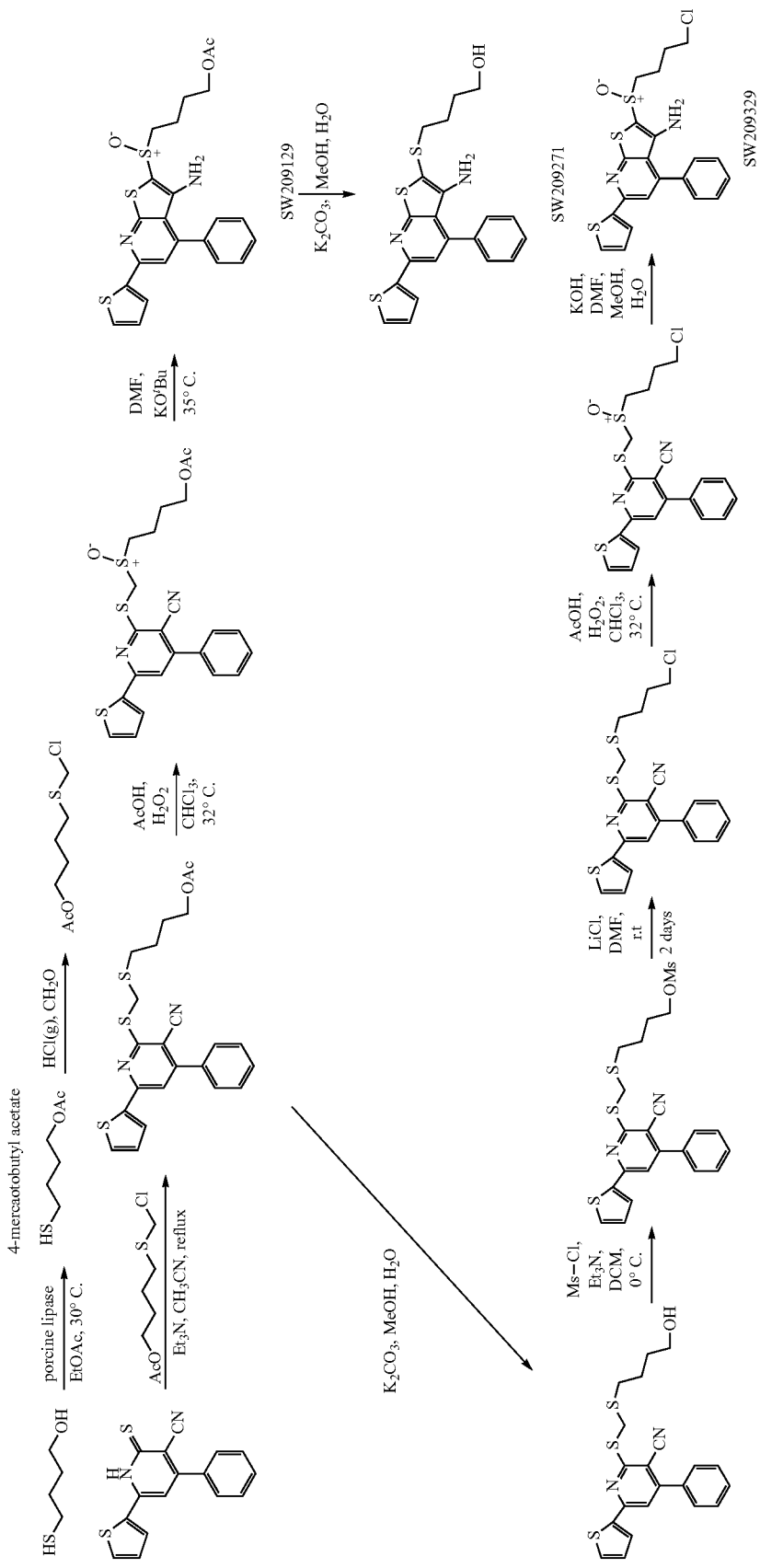

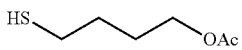

4-mercaptobutyl acetate. Porcine lipase (2.35 g) was added to a solution of 4-mercapto-1-butanol (2.45 g, 23.10 mmol) in ethyl acetate (42.0 ml). The reaction was heated at 30° C. for 6 days. Despite incomplete conversion the mixture was filtered and condensed. Purification was carried out on an automated flash chromatography system in 100% DCM to give oil in 84% yield. $^1$H NMR (400 MHz, CHCl$_3$) δ 4.08 (t, J=6.2 Hz, 2H), 2.57 (q, J=7.1 Hz, 2H), 2.05 (s, 3H), 1.85-1.59 (m, 4H), 1.36 (t, J=7.9 Hz, 1H).

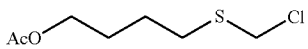

4-((chloromethyl)thio)butyl acetate. Hydrogen chloride gas was bubbled for 40 minutes into 4-mercaptobutyl acetate (2.84 g, 19.2 mmol) which had been cooled in a dry ice/acetone bath and until the internal temperature stabilized before paraformaldehyde (0.815 g, 27.17 mmol) was slowly added using a solid addition funnel. The reaction was stirred cold for 3 hours during which hydrogen chloride bubbling was continued and then ceased as the reaction was warmed gently to ambient temperature and stirred overnight. The crude mixture was diluted with minimal DCM. The aqueous phase was removed and the organic layer was washed with brine and dried over Na$_2$SO$_4$, filtered and condensed to give an oil in 62% yield. $^1$H NMR (400 MHz, CHCl$_3$) 4.75 (s, 2H), 4.10 (t, J=6.0 Hz, 2H), 2.95-2.66 (m, 2H), 2.06 (s, 3H), 1.85-1.67 (m, 4H).

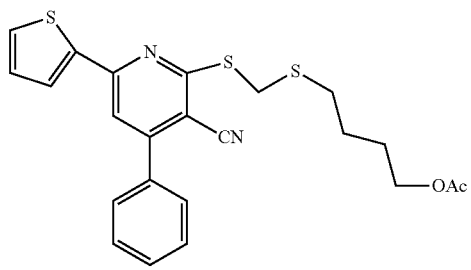 [SMILES: CC(=O)OCCCCSCSc1nc(-c2cccs2)cc(-c2ccccc2)c1C#N]

4-(((((3-cyano-4-phenyl-6-(thiophen-2-yl)pyridin-2-yl)thio)methyl)thio)butyl acetate. A mixture of 4-((chloromethyl)thio)butyl acetate (602.3 mg, 3.1 mmol), 4-phenyl-6-(thiophen-2-yl)-2-thioxo-1,2-dihydropyridine-3-carbonitrile (352.2 mg, 1.2 mmol) and triethylamine (250 ml, 1.8 mmol) in acetonitrile (1.2 ml) was refluxed for three hours. The crude mixture was then condensed and purified on an automated flash chromatography system in 0-40% EtOAc/hexanes. Fractions containing the desired product were further purified on an automated flash chromatography in 0-30% EtOAc/hexanes to give a clear oil in 41% yield. $^1$H NMR (400 MHz, CHCl$_3$) δ 7.72 (dd, J=3.7, 1.1 Hz, 1H), 7.64-7.59 (m, 2H), 7.55 (dt, J=5.6, 2.3 Hz, 4H), 7.44 (s, 1H), 7.17 (dd, J=5.0, 3.8 Hz, 1H), 4.55 (s, 2H), 4.11-4.02 (m, 2H), 2.86-2.63 (m, 2H), 2.05 (s, 3H), 1.77 (t, J=3.4 Hz, 4H). ESI-MS (m/z): 455.1 [M+H]$^+$.

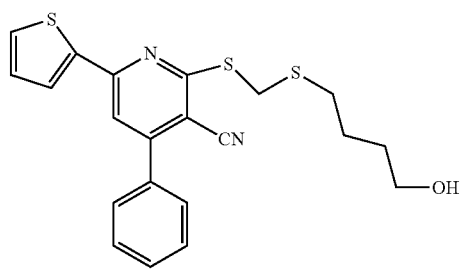 [SMILES: N#Cc1c(-c2ccccc2)cc(-c2cccs2)nc1SCSCCCCO]

2-((((4-hydroxybutyl)thio)methyl)thio)-4-phenyl-6-(thiophen-2-yl)nicotinonitrile. K$_2$CO$_3$ (157.7 mg, 1.14 mmol) was added to a solution of 4-(((3-cyano-4-phenyl-6-(thiophen-2-yl)pyridin-2-yl)thio)methyl)thio)butyl acetate. (245.4 mg, 0.54 mmol) in methanol (8.0 ml) and water (2.0 ml) and the reaction was stirred for 2 hours. The mixture was dried then diluted with EtOAc and washed twice with water and then brine. The organic layer was dried over Na$_2$SO$_4$, filtered and concentrated under reduce pressure to give desired product in 71% yield. $^1$H NMR (400 MHz, CDCl$_3$) δ 7.72 (dd, J=3.7, 1.1 Hz, 1H), 7.61 (dd, J=6.6, 3.0 Hz, 2H), 7.54 (dd, J=5.1, 2.2 Hz, 4H), 7.43 (s, 1H), 7.16 (dd, J=5.0, 3.8 Hz, 1H), 4.55 (s, 2H), 3.67 (t, J=6.2 Hz, 2H), 2.80 (t, J=7.1 Hz, 2H), 1.84-1.63 (m, 4H). ESI-MS (m/z): 413.1 [M+H]$^+$.

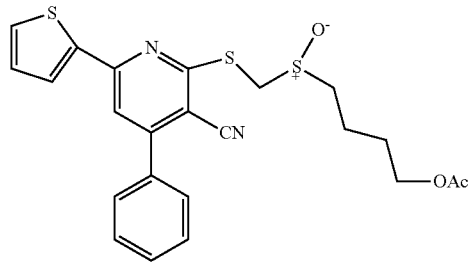 [SMILES: CC(=O)OCCCC[S+]([O-])CSc1nc(-c2cccs2)cc(-c2ccccc2)c1C#N]

4-(((((3-cyano-4-phenyl-6-(thiophen-2-yl)pyridin-2-yl)thio)methyl)sulfinyl)butyl acetate. Acetic acid (370 µl) and hydrogen peroxide (29 µl, 30% solution in water) were added to the solution of 4-(((((3-cyano-4-phenyl-6-(thiophen-2-yl)pyridin-2-yl)thio)methyl)thio)butyl acetate (85.2 mg, 0.19 mmol) in chloroform (370 µl). The reaction mixture was stirred at 32° C. for 90 min. Once complete, the reaction was diluted with chloroform and washed with saturated NaHCO$_3$ solution, and extracted three times with chloroform. The combined organic layers was dried over Na$_2$SO$_4$, filtered and concentrated under reduce pressure to give designed product in 94% yield. $^1$H NMR (400 MHz, CDCl$_3$) δ 7.77 (d, J=3.8 Hz, 1H), 7.62 (dd, J=4.1, 2.3 Hz, 2H), 7.60-7.54 (m, 4H), 7.51 (s, 1H), 7.19 (dd, J=5.0, 3.8 Hz, 1H), 4.78 (d, J=13.0 Hz, 1H), 4.44 (d, J=13.0 Hz, 1H), 4.11 (t, J=6.4 Hz, 2H), 3.03 (dt, J=12.9, 8.0 Hz, 1H), 2.87 (dt, J=12.8, 7.3 Hz, 1H), 2.05 (s, 3H), 2.03-1.77 (m, 4H). ESI-MS (m/z): 471.1 [M+H]$^+$.

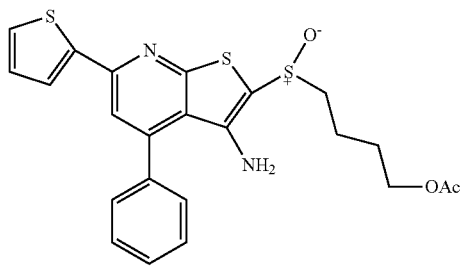 [SMILES: CC(=O)OCCCC[S+]([O-])c1sc2nc(-c3cccs3)cc(-c3ccccc3)c2c1N]

SW209129. 4-((3-amino-4-phenyl-6-(thiophen-2-yl)thieno[2,3-b]pyridin-2-yl)sulfinyl)butyl acetate. Potassium tert-butoxide (9.7 mg, 0.086 mmol) was added to a solution of 4-((((3-cyano-4-phenyl-6-(thiophen-2-yl)pyridin-2-yl)thio)methyl)sulfinyl)butyl acetate (58.2 mg, 0.12 mmol) in DMF (490 µl). The reaction mixture was stirred at 35° C. for 45 minutes, then diluted with EtOAc and washed several times with water. The aqueous layer was also back-extracted. The combined organic layer was washed with brine, dried over $Na_2SO_4$, filtered and concentrated under reduce pressure. Purification was carried out using automated flash chromatography in 0-90% EtOAc/hexanes to give the desired product in 44% yield. $^1$H NMR (400 MHz, $CDCl_3$) δ7.63-7.49 (m, 5H), 7.45 (dd, J=4.9, 1.1 Hz, 2H), 7.41 (s, 1H), 7.10 (dd, J=5.0, 3.7 Hz, 1H), 4.59 (bs, 2H), 4.08 (t, J=5.8 Hz, 2H), 3.39-3.23 (m, 1H), 3.10 (ddd, J=12.8, 8.4, 6.2 Hz, 1H), 2.03 (s, 3H), 1.96-1.72 (m, 4H). ESI-MS (m/z): 471.1 $[M+H]^+$.

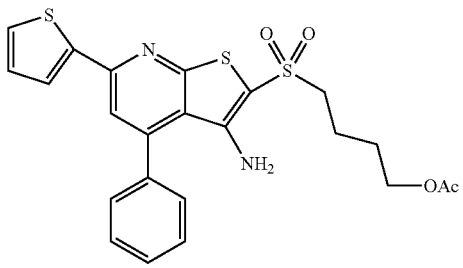 [SMILES: CC(=O)OCCCCS(=O)(=O)c1sc2nc(-c3cccs3)cc(-c3ccccc3)c2c1N]

SW209128. 4-((3-amino-4-phenyl-6-(thiophen-2-yl)thieno[2,3-b]pyridin-2-yl)sulfonyl)butyl acetate. Isolated as the over oxidation product from 4-((3-amino-4-phenyl-6-(thiophen-2-yl)thieno[2,3-b]pyridin-2-yl)sulfinyl)butyl acetate in 13.5% yield.

$^1$H NMR (400 MHz, $CDCl_3$) δ 7.71 (dd, J=3.7, 1.1 Hz, 1H), 7.61-7.55 (m, 3H), 7.53-7.44 (m, 4H), 7.15 (dd, J=5.0, 3.7 Hz, 1H), 5.10 (s, 2H), 4.06 (t, J=6.3 Hz, 2H), 3.32-3.18 (m, 2H), 2.02 (s, 3H), 1.98-1.87 (m, 2H), 1.77 (dt, J=8.6, 6.4 Hz, 2H). ESI-MS (m/z): 487.1 $[M+H]^+$.

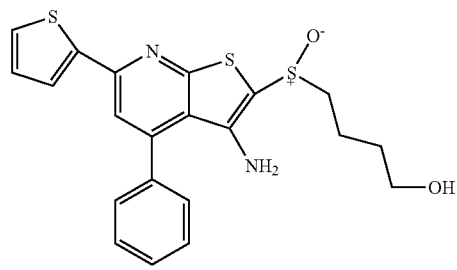 [SMILES: Nc1c([S+]([O-])CCCCO)sc2nc(-c3cccs3)cc(-c3ccccc3)c12]

SW209271. 4-((3-amino-4-phenyl-6-(thiophen-2-yl)thieno[2,3-b]pyridin-2-yl)sulfinyl)butan-1-ol. $K_2CO_3$ (12.5 mg, 0.09 mmol) was added to a solution of SW209129 (18.7 mg, 0.04 mmol) in methanol (470 µl) and water (100 µl) and the reaction was stirred for 2.5 hours. The mixture was dried then diluted with EtOAc and washed twice with water and then brine. The organic layer was dried over $Na_2SO_4$, filtered and concentrated under reduce pressure to give desired product in 80% yield. $^1$H NMR (400 MHz, $CDCl_3$) δ 7.62 (d, J=1.1 Hz, 1H), 7.60-7.50 (m, 4H), 7.49-7.41 (m, 3H), 7.11 (dd, J=5.0, 3.7 Hz, 1H), 4.68-4.44 (s, 2H), 3.67 (t, J=6.1 Hz, 2H), 3.42-3.27 (m, 1H), 3.13 (ddd, J=12.9, 8.4, 6.9 Hz, 1H), 1.93-1.65 (m, 4H). ESI-MS (m/z): 429.0 $[M+H]^+$.

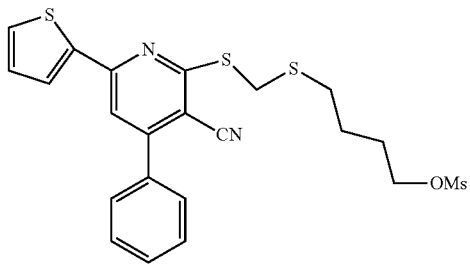 [SMILES: CS(=O)(=O)OCCCCSCSc1nc(-c2cccs2)cc(-c2ccccc2)c1C#N]

4-((((3-cyano-4-phenyl-6-(thiophen-2-yl)pyridin-2-yl)thio)methyl)thio)butyl methanesulfonate. A solution of triethylamine (38 µl, 0.28 mmol) in anhydrous DCM (1.0 ml) is cooled in an ice bath before the addition of 2-((((4-hydroxybutyl)thio)methyl)thio)-4-phenyl-6-(thiophen-2-yl)nicotinonitrile (40.6 mg, 0.098 mmol) followed by dropwise addition of methanesulfonyl chloride (17.5 yl, 0.23 mmol). After 30 minutes the crude mixture was washed with brine and dried over $Na_2SO_4$, filtered and condensed to give desired product in 98% yield. $^1$H NMR (400 MHz, $CDCl_3$) δ 7.74 (dd, J=3.9, 1.1 Hz, 1H), 7.64-7.50 (m, 7H), 7.17 (dd, J=5.1, 3.8 Hz, 1H), 5.46 (s, 2H), 4.01-3.78 (m, 2H), 2.65 (ddd, J=10.1, 5.3, 1.9 Hz, 2H), 2.52-2.37 (m, 4H). ESI-MS (m/z): 491.1 $[M+H]^+$.

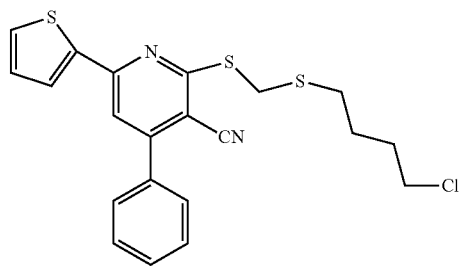 [SMILES: N#Cc1c(-c2ccccc2)cc(-c2cccs2)nc1SCSCCCCCl]

2-((((4-chlorobutyl)thio)methyl)thio)-4-phenyl-6-(thiophen-2-yl)nicotinonitrile. Lithium chloride (32.0 mg, 0.75 mmol) was added to a solution of 4-((((3-cyano-4-phenyl-6-(thiophen-2-yl)pyridin-2-yl)thio)methyl)thio)butyl methanesulfonate (21.8 mg, 0.044 mmol) in DMF (0.4 ml). The reaction went to completion within two days. The mixture was diluted with EtOAc and washed several times with water and then brine. The organic layer was dried over $Na_2SO_4$, filtered and condensed. Purification was performed on an automated chromatography system in 0-40% EtOAc/hexanes and gave the desired product in 76% yield.

$^1$H NMR (400 MHz, $CDCl_3$) δ 7.72 (dd, J=3.7, 1.1 Hz, 1H), 7.62 (dd, J=6.5, 3.0 Hz, 2H), 7.59-7.52 (m, 4H), 7.44 (s, 1H), 7.17 (dd, J=5.0, 3.8 Hz, 1H), 4.56 (s, 2H), 3.56 (t, J=6.3 Hz, 2H), 2.80 (t, J=7.0 Hz, 2H), 1.95-1.79 (m, 4H). ESI-MS (m/z): 431.0 $[M+H]^+$.

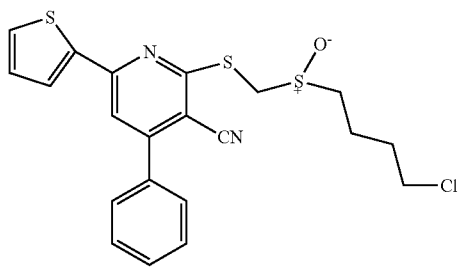 [SMILES: N#Cc1c(-c2ccccc2)cc(-c2cccs2)nc1SC[S+]([O-])CCCCCl]

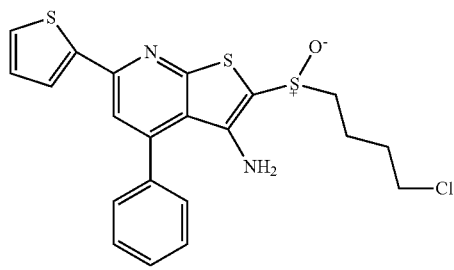 [SMILES: Nc1c([S+]([O-])CCCCCl)sc2nc(-c3cccs3)cc(-c3ccccc3)c12]

2-((((4-chlorobutyl)sulfinyl)methyl)thio)-4-phenyl-6-(thiophen-2-yl)nicotinonitrile. Acetic acid (70 µl) and hydrogen peroxide (5.2 µl, 30% solution in water) were added to the solution of 2-((((4-chlorobutyl)thio)methyl)thio)-4-phenyl-6-(thiophen-2-yl)nicotinonitrile (14.6 mg, 0.034 mmol) in chloroform (70 µl). The reaction mixture was stirred at 32° C. for 40 min and then diluted with chloroform and was washed with saturated NaHCO$_3$ solution and extracted three times with chloroform. The combined organic layers was dried over Na$_2$SO$_4$, filtered and concentrated under reduce pressure to give designed product. $^1$H NMR (400 MHz, CDCl$_3$) δ 7.77 (d, J=3.8 Hz, 1H), 7.62 (dd, J=6.6, 2.9 Hz, 2H), 7.57 (q, J=4.5, 3.1 Hz, 4H), 7.51 (s, 1H), 7.19 (t, J=4.4 Hz, 1H), 4.77 (d, J=13.0 Hz, 1H), 4.47 (d, J=13.0 Hz, 1H), 3.58 (t, J=6.2 Hz, 2H), 3.03 (dt, J=13.2, 7.7 Hz, 1H), 2.87 (dt, J=13.4, 7.0 Hz, 1H), 2.16-1.87 (m, 4H). ESI-MS (m/z): 447.1 [M+H]$^+$.

SW209329. 2-((4-chlorobutyl)sulfinyl)-4-phenyl-6-(thiophen-2-yl)thieno[2,3-b]pyridin-3-amine. A basic methanolic solution (1.0 mg, 0.018 mmol of potassium hydroxide in 12.0 µl water and 57.5 µl methanol) was transferred to a vial containing a solution of 2-((((4-chlorobutyl)sulfinyl)methyl)thio)-4-phenyl-6-(thiophen-2-yl)nicotinonitrile (12.4 mg, 0.028 mmol) in dimethylformamide (91.5 µl). The reaction was heated at 38° C. for 30 minutes, before being cooled, diluted with EtOAc and washed several times with water, then brine. The organic layer was dried over Na$_2$SO$_4$, filtered and condensed. The crude mixture was purified using an automated chromatography system in 0-60% EtOAc/hexanes. Isolated yield=65%. $^1$H NMR (400 MHz, CDCl$_3$) δ 7.64 (d, J=3.7 Hz, 1H), 7.61-7.50 (m, 4H), 7.50-7.43 (m, 3H), 7.12 (t, J=4.4 Hz, 1H), 4.59 (s, 2H), 3.66-3.47 (m, 2H), 3.40-3.24 (m, 1H), 3.20-3.06 (m, 1H), 1.95 (q, J=5.6 Hz, 4H). ESI-MS (m/z): 447.0 [M+H]$^+$.

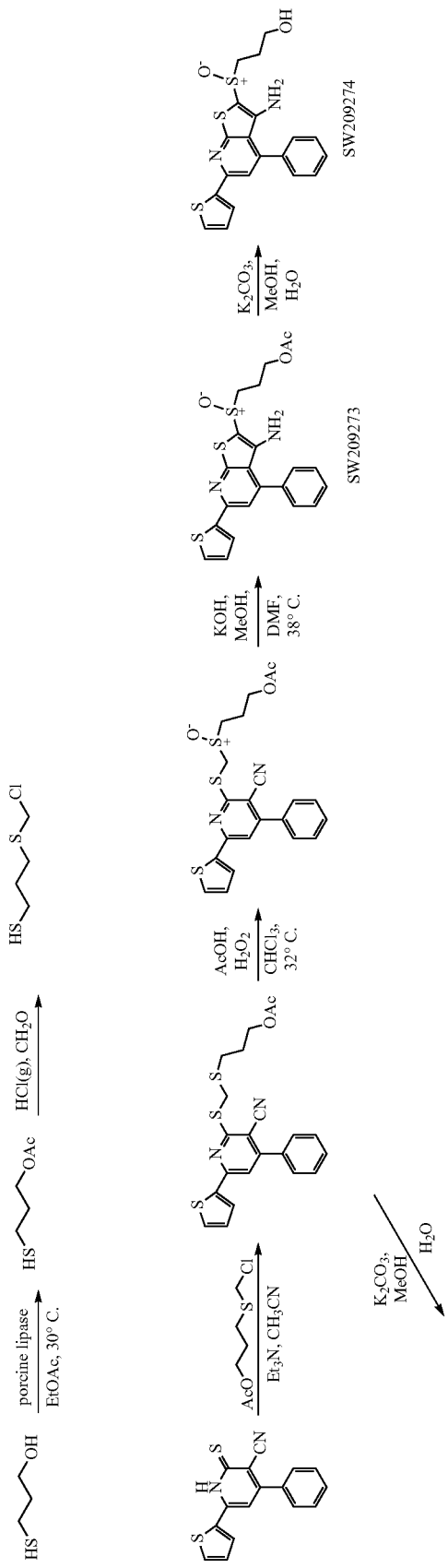
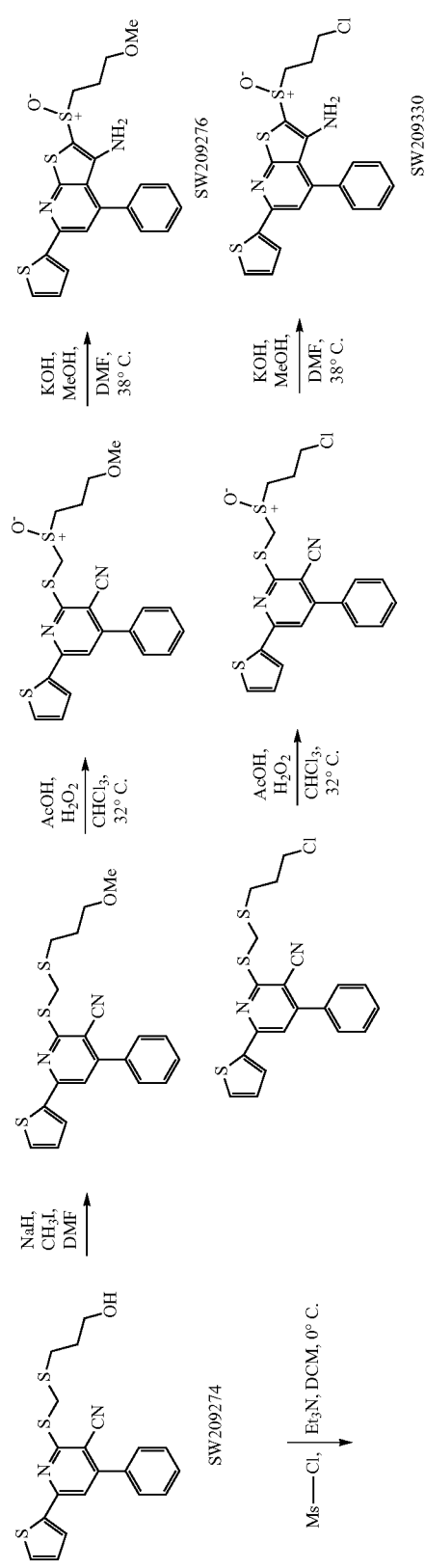

-continued
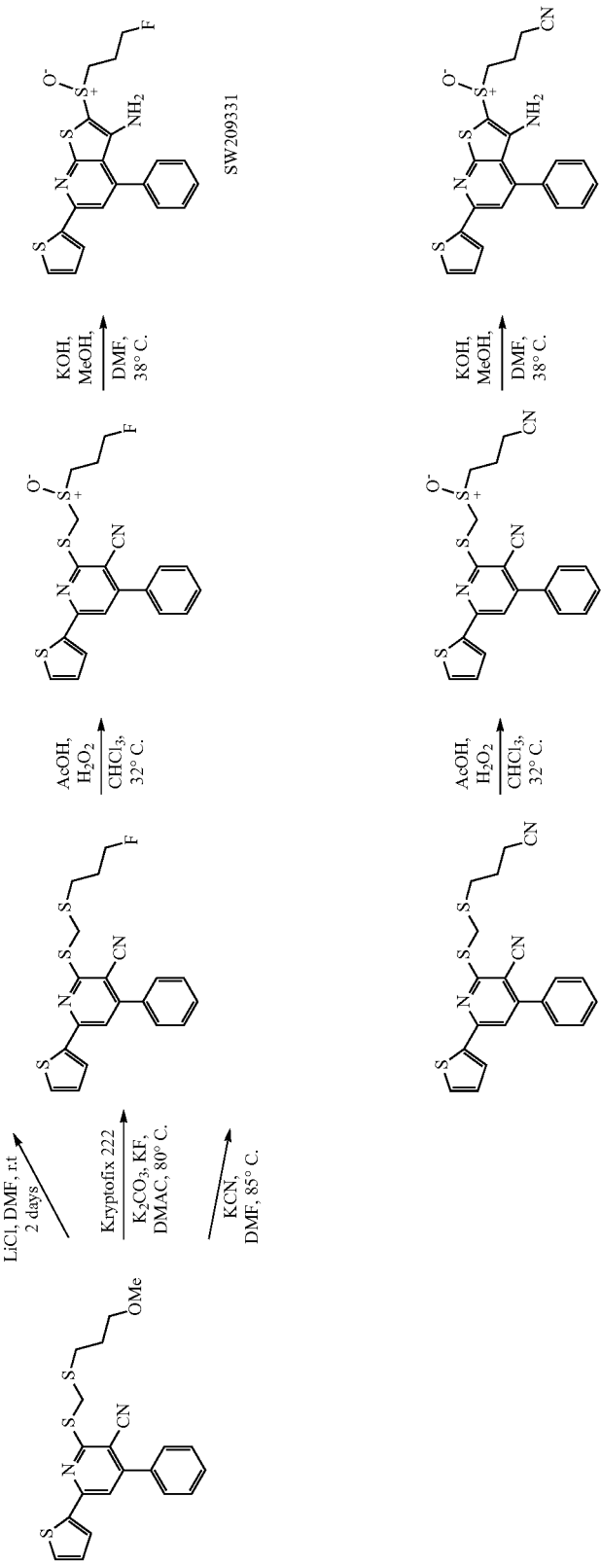

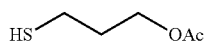

3-mercaptopropyl acetate. Porcine lipase (5.52 g) was added to a solution of 3-mercapto-1-propanol (5.03 g, 54.6 mmol) in ethyl acetate (70 ml). The reaction was heated at 28° C. for 12 days. Despite incomplete conversion the mixture was filtered and condensed. Purification was carried out on an automated flash chromatography system in 100% DCM to give oil in 66% yield. $^1$H NMR (400 MHz, CHCl$_3$) δ 4.17 (t, J=6.2 Hz, 2H), 2.60 (q, J=7.4 Hz, 2H), 2.05 (s, 3H), 1.93 (p, J=6.6 Hz, 2H), 1.39 (t, J=8.1 Hz, 2H).

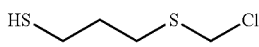

3-((chloromethyl)thio)propane-1-thiol. Hydrogen chloride gas was bubbled for 60 minutes into 3-((chloromethyl)thio)propane-1-thiol (4.80 g, 35.7 mmol) which had been cooled in a dry ice/acetone bath and until the internal temperature stabilized before paraformaldehyde (1.59 g, 53.3 mmol) was slowly added using a solid addition funnel. The reaction was stirred cold for 1.5 hours during which hydrogen chloride bubbling was continued and then ceased as the reaction was warmed gently to ambient temperature and stirred overnight. The crude mixture was diluted with minimal DCM. The aqueous phase was removed and the organic layer was washed with brine and dried over Na$_2$SO$_4$, filtered and condensed to give an oil in 80% yield of a mixture of 2.4:1 desired monomer chloride to diacetate dimer. $^1$H NMR (400 MHz, CHCl$_3$) δ 4.74 (s, 2H), 4.17 (t, J=6.4 Hz, 2H), 2.91-2.77 (m, 2H), 2.06 (d, J=1.0 Hz, 3H), 2.03-1.94 (m, 2H).

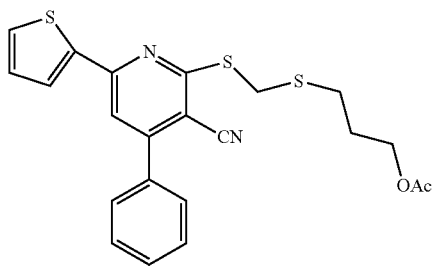 [SMILES: CC(=O)OCCCSCSc1nc(-c2cccs2)cc(-c2ccccc2)c1C#N]

3-(((((3-cyano-4-phenyl-6-(thiophen-2-yl)pyridin-2-yl)thio)methyl)thio)propyl acetate. Prepared analogously to 4-(((((3-cyano-4-phenyl-6-(thiophen-2-yl)pyridin-2-yl)thio)methyl)thio)butyl acetate in 26% yield (isolated). $^1$H NMR (400 MHz, CHCl$_3$) δ 7.72 (dd, J=3.8, 1.1 Hz, 1H), 7.66-7.58 (m, 2H), 7.54 (dd, J=4.2, 2.9 Hz, 4H), 7.44 (d, J=1.3 Hz, 1H), 7.17 (dd, J=5.0, 3.8 Hz, 1H), 4.55 (s, 2H), 4.18 (t, J=6.3 Hz, 2H), 2.84 (t, J=7.3 Hz, 2H), 2.05 (s, 3H), 2.05-1.97 (m, 2H). ESI-MS (m/z): 441.0 [M+H]$^+$.

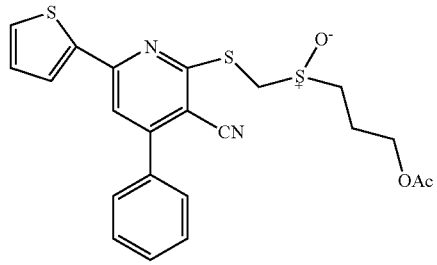 [SMILES: CC(=O)OCCC[S+]([O-])CSc1nc(-c2cccs2)cc(-c2ccccc2)c1C#N]

3-(((((3-cyano-4-phenyl-6-(thiophen-2-yl)pyridin-2-yl)thio)methyl)sulfinyl)propyl acetate. Prepared analogously to 4-(((((3-cyano-4-phenyl-6-(thiophen-2-yl)pyridin-2-yl)thio)methyl)sulfinyl)butyl acetate in 90% yield. $^1$H NMR (400 MHz, CHCl$_3$) δ 7.77 (dd, J=3.7, 1.1 Hz, 1H), 7.68-7.60 (m, 2H), 7.57 (ddd, J=6.9, 4.5, 2.0 Hz, 4H), 7.51 (s, 1H), 7.19 (dd, J=5.0, 3.8 Hz, 1H), 4.81 (d, J=13.1 Hz, 1H), 4.44 (d, J=13.1 Hz, 1H), 4.22 (td, J=6.3, 1.3 Hz, 2H), 3.09 (dt, J=13.0, 8.1 Hz, 1H), 2.89 (dt, J=13.1, 7.1 Hz, 1H), 2.28-2.17 (m, 2H), 2.04 (s, 3H). ESI-MS (m/z): 457.1 [M+H]$^+$.

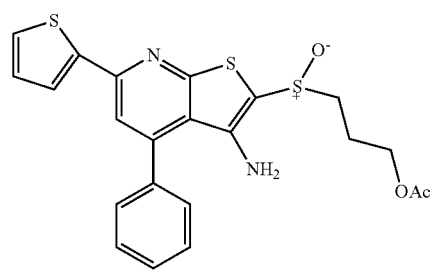 [SMILES: CC(=O)OCCC[S+]([O-])c1sc2nc(-c3cccs3)cc(-c3ccccc3)c2c1N]

SW209273. 3-((3-amino-4-phenyl-6-(thiophen-2-yl)thieno[2,3-b]pyridin-2-yl)sulfinyl)propyl acetate. Prepared analogously to 4-((3-amino-4-phenyl-6-(thiophen-2-yl)thieno[2,3-b]pyridin-2-yl)sulfinyl)butyl acetate in 37% yield. $^1$H NMR (400 MHz, CHCl$_3$) δ 7.62-7.52 (m, 5H), 7.45 (dd, J=5.0, 1.1 Hz, 2H), 7.41 (s, 1H), 7.10 (dd, J=5.0, 3.7 Hz, 1H), 4.65-4.56 (s, 2H), 4.27-4.14 (m, 2H), 3.42-3.25 (m, 1H), 3.15 (dt, J=12.9, 7.7 Hz, 1H), 2.09 (ddd, J=7.5, 6.2, 1.3 Hz, 2H), 2.05 (s, 3H). ESI-MS (m/z): 457.1 [M+H]$^+$.

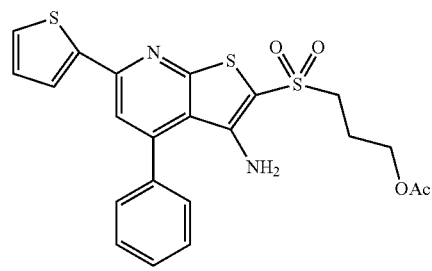 [SMILES: CC(=O)OCCCS(=O)(=O)c1sc2nc(-c3cccs3)cc(-c3ccccc3)c2c1N]

SW209272. 3-((3-amino-4-phenyl-6-(thiophen-2-yl)thieno[2,3-b]pyridin-2-yl)sulfonyl)propyl acetate. Isolated as the over oxidation product from 3-((3-amino-4-phenyl-6-(thiophen-2-yl)thieno[2,3-b]pyridin-2-yl)sulfinyl)propyl acetate in 7% yield. $^1$H NMR (400 MHz, CHCl$_3$) δ 7.72 (d, J=3.8 Hz, 1H), 7.62-7.53 (m, 3H), 7.54-7.45 (m, 4H), 7.15 (dd, J=5.0, 3.8 Hz, 1H), 5.12 (s, 2H), 4.15 (t, J=6.2 Hz, 2H), 3.39-3.19 (m, 2H), 2.25-2.12 (m, 2H), 2.03 (s, 3H). ESI-MS (m/z): 457.1 [M+H]$^+$.

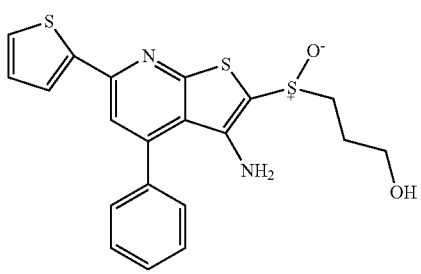 [SMILES: Nc1c([S+]([O-])CCCO)sc2nc(-c3cccs3)cc(-c3ccccc3)c12]

SW209274. 3-((3-amino-4-phenyl-6-(thiophen-2-yl)thieno[2,3-b]pyridin-2-yl)sulfinyl)propan-1-ol. Was prepared analogously to SW209271. 4-((3-amino-4-phenyl-6-(thiophen-2-yl)thieno[2,3-b]pyridin-2-yl)sulfinyl)butan-1-ol in 84% yield. $^1$H NMR (400 MHz, CHCl$_3$) δ 7.63 (dd, J=3.7, 1.1 Hz, 1H), 7.55 (p, J=4.6, 3.2 Hz, 4H), 7.46 (dd, J=5.0, 1.1 Hz, 2H), 7.43 (s, 1H), 7.11 (dd, J=5.0, 3.7 Hz, 1H), 4.60 (s, 2H), 3.77 (t, J=5.8 Hz, 2H), 3.49-3.33 (m, 1H), 3.21 (dt, J=13.5, 6.9 Hz, 1H), 2.13-1.98 (m, 2H). ESI-MS (m/z): 415.1 [M+H]$^+$.

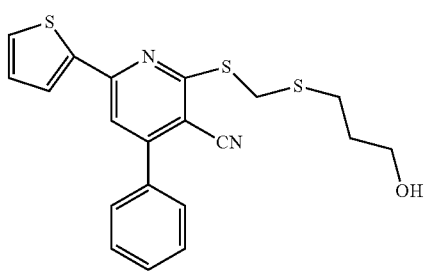

2-((((3-hydroxypropyl)thio)methyl)thio)-4-phenyl-6-(thiophen-2-yl)nicotinonitrile. Prepared analogously to 2-((((4-hydroxybutyl)thio)methyl)thio)-4-phenyl-6-(thiophen-2-yl)nicotinonitrile in 98% yield. $^1$H NMR (400 MHz, CHCl$_3$) 7.71 (dd, J=3.8, 1.1 Hz, 1H), 7.63-7.57 (m, 2H), 7.55-7.50 (m, 4H), 7.41 (s, 1H), 7.15 (dd, J=5.0, 3.8 Hz, 1H), 4.54 (s, 2H), 3.76 (t, J=6.1 Hz, 2H), 2.88 (t, J=7.1 Hz, 2H), 1.93 (ddd, J=13.2, 7.1, 6.1 Hz, 2H), 1.88-1.80 (m, 1H). ESI-MS (m/z): 399.1 [M+H]$^+$.

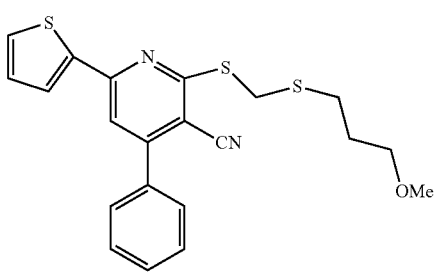 [SMILES: COCCCSCSc1nc(-c2cccs2)cc(-c2ccccc2)c1C#N]

2-((((3-methoxypropyl)thio)methyl)thio)-4-phenyl-6-(thiophen-2-yl)nicotinonitrile. Sodium hydride (micro spatula tipful) was added to an ice-cooled solution of 2-((((3-hydroxypropyl)thio)methyl)thio)-4-phenyl-6-(thiophen-2-yl)nicotinonitrile (41.6 mg, 0.10 mmol) in DMF (1.0 ml). The mixture was stirred cold for 15 minutes before the addition of methyl iodide (34 ml, 0.55 mmol). The mixture was stirred cold in the melting ice-bath for 2 hours, then diluted with EtOAc and washed several times with water and then brine. The organic layer was dried over Na$_2$SO$_4$, filtered and condensed. Purification was carried out on an automated flash chromatography system in 0-40% EtOAc/hexanes with an isolated yield of 56%. $^1$H NMR (400 MHz, CHCl$_3$) δ 7.72 (dd, J=3.8, 1.1 Hz, 1H), 7.61 (dd, J=6.6, 3.1 Hz, 2H), 7.57-7.51 (m, 4H), 7.43 (s, 1H), 7.17 (dd, J=5.0, 3.8 Hz, 1H), 4.55 (s, 2H), 3.49 (t, J=6.1 Hz, 2H), 3.34 (s, 3H), 2.85 (t, J=7.3 Hz, 2H), 1.95 (ddd, J=13.4, 7.3, 6.1 Hz, 2H). ESI-MS (m/z): 413.1 [M+H]$^+$.

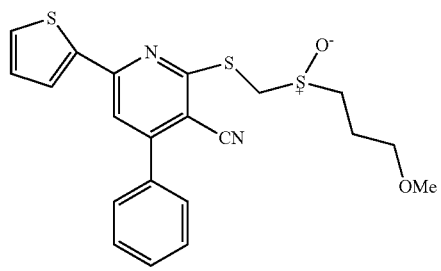 [SMILES: COCCC[S+]([O-])CSc1nc(-c2cccs2)cc(-c2ccccc2)c1C#N]

2-((((3-methoxypropyl)sulfinyl)methyl)thio)-4-phenyl-6-(thiophen-2-yl)nicotinonitrile. Prepared analogously to 4-((((3-cyano-4-phenyl-6-(thiophen-2-yl)pyridin-2-yl)thio)methyl)sulfinyl)butyl acetate in 71% yield. $^1$H NMR (400 MHz, CHCl$_3$) δ 7.76 (dd, J=3.8, 1.1 Hz, 1H), 7.65-7.58 (m, 2H), 7.56 (td, J=4.6, 2.0 Hz, 4H), 7.49 (s, 1H), 7.18 (dd, J=5.0, 3.8 Hz, 1H), 4.73 (d, J=13.1 Hz, 1H), 4.47 (d, J=13.0 Hz, 1H), 3.54 (qt, J=9.5, 5.8 Hz, 2H), 3.34 (s, 3H), 3.14 (dt, J=13.1, 7.9 Hz, 1H), 2.89 (ddd, J=13.1, 8.0, 6.4 Hz, 1H), 2.20-2.08 (m, 2H). ESI-MS (m/z): 429.1 [M+H]$^+$.

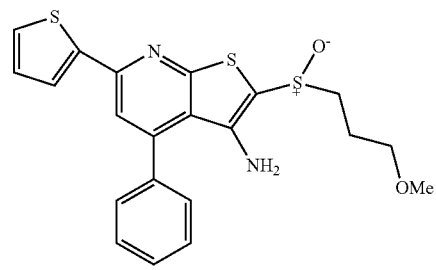 [SMILES: COCCC[S+]([O-])c1sc2nc(-c3cccs3)cc(-c3ccccc3)c2c1N]

SW209276. 2-((3-methoxypropyl)sulfinyl)-4-phenyl-6-(thiophen-2-yl)thieno[2,3-b]pyridin-3-amine. Was prepared analogously to SW209329. 2-((4-chlorobutyl)sulfinyl)-4-phenyl-6-(thiophen-2-yl)thieno[2,3-b]pyridin-3-amine. Isolated yield=48%. $^1$H NMR (400 MHz, CHCl$_3$) δ 7.64 (ddd, J=7.2, 3.8, 1.7 Hz, 2H), 7.58-7.52 (m, 4H), 7.48-7.42 (m, 2H), 7.12 (qd, J=3.7, 1.8 Hz, 1H), 4.57 (s, 2H), 3.50 (td, J=6.1, 1.6 Hz, 2H), 3.40-3.29 (m, 4H), 3.26-3.13 (m, 1H), 2.09-1.95 (m, 2H). ESI-MS (m/z): 429.1 [M+H]$^+$.

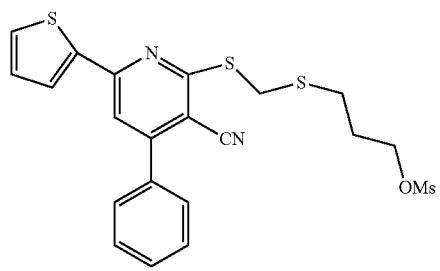

3-((((3-cyano-4-phenyl-6-(thiophen-2-yl)pyridin-2-yl)thio)methyl)thio)propyl methanesulfonate. Prepared analogously to 4-((((3-cyano-4-phenyl-6-(thiophen-2-yl)pyridin-2-yl)thio)methyl)thio)butyl methanesulfonate in quantitative yield. $^{1}$H NMR (400 MHz, CHCl$_3$) δ 7.69 (t, J=3.3 Hz, 1H), 7.63-7.55 (m, 2H), 7.52 (p, J=3.6, 3.0 Hz, 4H), 7.41 (q, J=2.6, 2.2 Hz, 1H), 7.14 (p, J=3.4, 2.5 Hz, 1H), 4.52 (q, J=2.2 Hz, 2H), 4.40-4.22 (m, 2H), 2.99 (s, 3H), 2.86 (td, J=7.2, 4.8 Hz, 2H), 2.10 (qt, J=6.4, 2.3 Hz, 2H). ESI-MS (m/z): 477.0 [M+H]$^+$.

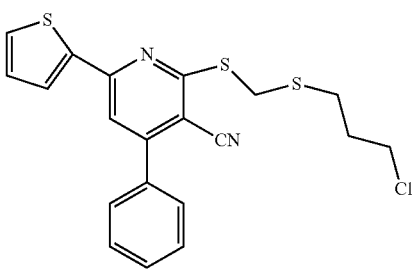 [SMILES: N#Cc1c(-c2ccccc2)cc(-c2cccs2)nc1SCSCCCCl]

2-((((3-chloropropyl)thio)methyl)thio)-4-phenyl-6-(thiophen-2-yl)nicotinonitrile. Prepared analogously to 2-((((4-chlorobutyl)thio)methyl)thio)-4-phenyl-6-(thiophen-2-yl)nicotinonitrile. Purification was performed using an automated flash chromatography system in 0-50% EtOAc/hexanes with an isolated yield of 69%. 1H NMR (400 MHz, CHCl$_3$) δ 7.72 (dd, J=3.7, 1.1 Hz, 1H), 7.64-7.59 (m, 2H), 7.57-7.53 (m, 4H), 7.44 (s, 1H), 7.17 (dd, J=5.0, 3.8 Hz, 1H), 4.56 (s, 2H), 3.68 (t, J=6.3 Hz, 2H), 2.93 (t, J=7.0 Hz, 2H), 2.15 (p, J=6.7 Hz, 2H). ESI-MS (m/z): 417.0 [M+H]$^+$.

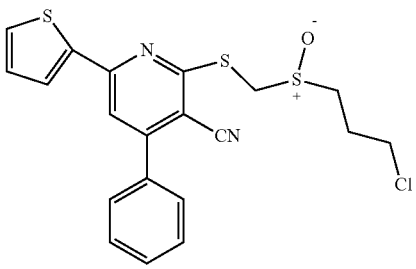

2-((((3-chloropropyl)sulfinyl)methyl)thio)-4-phenyl-6-(thiophen-2-yl)nicotinonitrile. Prepared analogously to 2-((((4-chlorobutyl)sulfinyl)methyl)thio)-4-phenyl-6-(thiophen-2-yl)nicotinonitrile in 90% yield. $^{1}$H NMR (400 MHz, CHCl$_3$) δ 7.76 (dd, J=3.8, 1.1 Hz, 1H), 7.62 (dq, J=7.1, 2.6, 2.2 Hz, 2H), 7.59-7.53 (m, 4H), 7.51 (s, 1H), 7.18 (dd, J=5.0, 3.8 Hz, 1H), 4.74 (d, J=13.1 Hz, 1H), 4.51 (d, J=13.1 Hz, 1H), 3.79-3.63 (m, 2H), 3.28-3.16 (m, 1H), 3.04-2.88 (m, 1H), 2.43-2.31 (m, 2H). ESI-MS (m/z): 433.0 [M+H]$^+$.

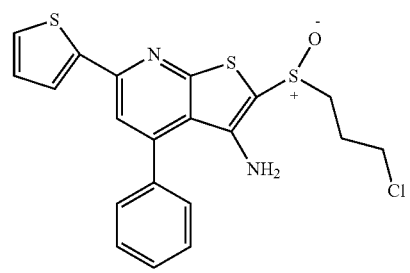

SW209330. 2-((3-chloropropyl)sulfinyl)-4-phenyl-6-(thiophen-2-yl)thieno[2,3-b]pyridin-3-amine. Prepared analogously to SW209329. 2-((4-chlorobutyl)sulfinyl)-4-phenyl-6-(thiophen-2-yl)thieno[2,3-b]pyridin-3-amine. Purification on an automated chromatography system in 0-60% EtOAc/hexanes gave the desired in 88% yield. $^{1}$H NMR (400 MHz, CHCl$_3$) δ 7.57 (h, J=5.7, 5.3 Hz, 1H), 7.45 (t, J=6.0 Hz, 0H), 7.40 (s, 0H), 7.09 (t, J=4.4 Hz, 0H), 4.61 (s, 0H), 3.67 (td, J=6.4, 3.2 Hz, 0H), 3.40 (dt, J=14.1, 7.3 Hz, 0H), 3.24 (dt, J=13.1, 7.6 Hz, 0H), 2.25 (p, J=7.0 Hz, 0H). ESI-MS (m/z): 433.0 [M+H]$^+$.

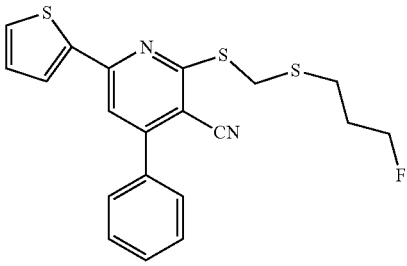 [SMILES: N#Cc1c(-c2ccccc2)cc(-c2cccs2)nc1SCSCCCF]

2-((((3-fluoropropyl)thio)methyl)thio)-4-phenyl-6-(thiophen-2-yl)nicotinonitrile. Kryptofix 222 (44.4 mg, 0.012 mmol), KF (6.1 mg, 0.10 mmol) and K$_2$CO$_3$ (3.0 mg, 0.022 mmol) were charged to a vial containing 3-((((3-cyano-4-phenyl-6-(thiophen-2-yl)pyridin-2-yl)thio)methyl)thio)propyl methanesulfonate (54.2 mg, 0.11 mmol). DMF (1.1 ml) was added and the reaction was heated at 85° C. for 65 minutes. The cooled mixture was diluted with EtOAc and washed several times with water and then brine. The organic layer was dried over Na$_2$SO$_4$, filtered and condensed. Yield=96%. Crude product was carried forward. $^{1}$H NMR (400 MHz, CHCl$_3$) δ 7.72 (dd, J=3.7, 1.1 Hz, 1H), 7.64-7.59 (m, 2H), 7.54 (dd, J=4.9, 2.2 Hz, 4H), 7.43 (s, 1H), 7.17 (dd, J=5.1, 3.7 Hz, 1H), 4.63 (t, J=5.7 Hz, 1H), 4.55 (s, 2H), 4.51 (t, J=5.8 Hz, 1H), 3.67 (t, J=6.3 Hz, 2H), 2.91 (dt, J=11.2, 7.1 Hz, 1H), 2.14 (p, J=6.7 Hz, 1H). ESI-MS (m/z): 401.1 [M+H]$^+$.

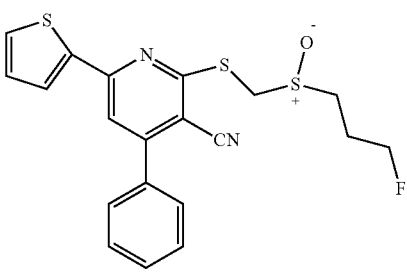

2-((((3-fluoropropyl)sulfinyl)methyl)thio)-4-phenyl-6-(thiophen-2-yl)nicotinonitrile. Acetic acid (215 μl) and hydrogen peroxide (16.75 μl, 30% solution in water) were added to the solution of 2-((((3-fluoropropyl)thio)methyl)thio)-4-phenyl-6-(thiophen-2-yl)nicotinonitrile (43.3 mg, 0.034 mmol) in chloroform (215 μl). The reaction mixture was stirred at 32° C. for 50 min and then diluted with chloroform and was washed with saturated NaHCO$_3$ solution and extracted three times with chloroform. The combined organic layers was dried over Na$_2$SO$_4$, filtered and concentrated under reduce pressure in 94% yield. ESI-MS (m/z): 417.1 [M+H]$^+$.

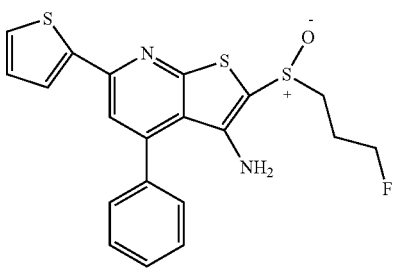

SW209331. 2-((3-fluoropropyl)sulfinyl)-4-phenyl-6-(thiophen-2-yl)thieno[2,3-b]pyridin-3-amine. Prepared analogously to SW209329. 2-((4-chlorobutyl)sulfinyl)-4-phenyl-6-(thiophen-2-yl)thieno[2,3-b]pyridin-3-amine. The crude mixture was purified preparatively in 4% MeOH/DCM. Isolated yield=32%. $^1$H NMR (400 MHz, CHCl$_3$) δ 7.68 (dd, J=3.8, 1.1 Hz, 1H), 7.56 (q, J=2.7 Hz, 4H), 7.53-7.44 (m, 3H), 7.14 (dd, J=5.1, 3.7 Hz, 1H), 4.65 (td, J=5.8, 3.2 Hz, 1H), 4.60 (s, 2H), 4.53 (td, J=5.8, 3.1 Hz, 1H), 3.40 (dt, J=13.0, 7.3 Hz, 1H), 3.24 (dt, J=13.1, 7.6 Hz, 1H), 2.19 (dtt, J=26.4, 7.5, 5.7 Hz, 2H). ESI-MS (m/z): 417.1 [M+H]$^+$.

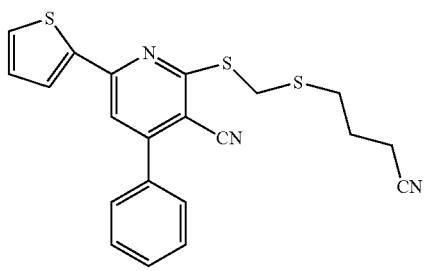 [SMILES: N#CCCCSCSc1nc(-c2cccs2)cc(-c2ccccc2)c1C#N]

2-((((3-cyanopropyl)thio)methyl)thio)-4-phenyl-6-(thiophen-2-yl)nicotinonitrile. A solution of 3-((((3-cyano-4-phenyl-6-(thiophen-2-yl)pyridin-2-yl)thio)methyl)thio)propyl methanesulfonate (54.6 mg, 0.11 mmol) and KCN (76.9 mg, 1.18 mmol) in DMF (1.14 ml) was heated at 85° C. for 4 hours. The cooled mixture was diluted with EtOAc and washed several times with water and then brine. The organic phase was dried over Na$_2$SO$_4$, filtered and condensed. Yield=89%. $^1$H NMR (400 MHz, CHCl$_3$) δ 7.71 (d, J=3.5 Hz, 1H), 7.60 (dt, J=6.4, 2.0 Hz, 3H), 7.54 (qt, J=5.6, 2.5 Hz, 4H), 7.44 (d, J=1.4 Hz, 1H), 7.16 (ddd, J=5.2, 3.8, 1.5 Hz, 1H), 4.53 (d, J=1.7 Hz, 2H), 2.93-2.82 (m, 2H), 2.52 (td, J=7.1, 1.4 Hz, 2H), 2.09-1.92 (m, 2H). ESI-MS (m/z): 408.1 [M+H]$^+$.

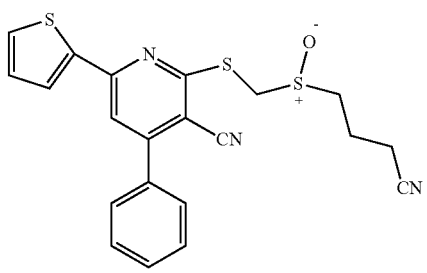

2-((((3-cyanopropyl)sulfinyl)methyl)thio)-4-phenyl-6-(thiophen-2-yl)nicotinonitrile. Acetic acid (205 μl) and hydrogen peroxide (15.6 μl, 30% solution in water) were added to the solution of 2-((((3-cyanopropyl)thio)methyl)thio)-4-phenyl-6-(thiophen-2-yl)nicotinonitrile (41.1 mg, 0.10 mmol) in chloroform (205 μl). The reaction mixture was stirred at 32° C. for 70 min and then diluted with chloroform and was washed with saturated NaHCO$_3$ solution and extracted three times with chloroform. The combined organic layers was dried over Na$_2$SO$_4$, filtered and concentrated under reduce pressure in 91% yield. ESI-MS (m/z): 424.1 [M+H]$^+$.

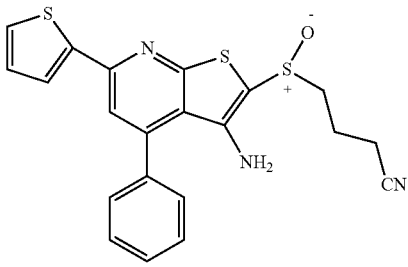

SW209332. 4-((3-amino-4-phenyl-6-(thiophen-2-yl)thieno[2,3-b]pyridin-2-yl)sulfinyl)butanenitrile. Prepared analogously to SW209329. 2-((4-chlorobutyl)sulfinyl)-4-phenyl-6-(thiophen-2-yl)thieno[2,3-b]pyridin-3-amine. The crude mixture was purified preparatively in 4% MeOH/DCM. Isolated yield=45%. $^1$H NMR (400 MHz, CHCl$_3$) δ 7.65 (d, J=3.7 Hz, 1H), 7.60-7.51 (m, 4H), 7.51-7.44 (m, 3H), 7.13 (t, J=4.4 Hz, 1H), 4.64 (s, 2H), 3.41 (dt, J=14.0, 7.3 Hz, 1H), 3.19 (dt, J=13.3, 7.5 Hz, 1H), 2.59 (t, J=7.1 Hz, 2H), 2.20 (p, J=7.3 Hz, 2H). ESI-MS (m/z): 424.0 [M+H]$^+$.

Example 4

Analysis of the Mechanism of 15-PGDH Inhibition by SW033291 and Related Compounds The following Example provides data relating to the mechanism of action by which SW033291 inhibits 15-PGDH.

Duplicate titrations of 15-PGDH Inhibitor (SW033291) were run at 4 different concentrations of 15-PGDH (24 nM, 12 nM, 6 nM, 3 nM). Reactions contained the indicated concentration of enzyme, 250 μM NAD(+), 25 μM PGE-2, and were assembled and incubated at room temperature for 3 minutes.

FIGS. 21 (A-B) show the shift in IC$_{50}$ value with changing enzyme concentration. The result is indicative of a tight-binding mode of inhibition with dependency on enzyme:inhibitor stoichiometry, rather than on the absolute concentration of the inhibitor. In all cases, the IC$_{50}$ values are less than the enzyme concentration, indicating that nM drug is almost fully bound by the enzyme.

FIGS. 22 (A-B) show the enzymatic activity following dialysis of 15-PGDH and of 15-PGDH treated with SW033291. Graph A) shows activity pre-dialysis and post-dialysis of 15-PGDH protein treated with either DMSO or with SW033291. For dialysis, a 500 μL dialysis bag contained 64 μg of 15-PGDH at 4 μM concentration, SW033291 at 15 μM concentration, DMSO 1.6%, 1 mM NAD(+), 50 mM Tris pH 7.5, 0.01% Tween 20. The control reaction omitted SW033291. The 15-PGDH-SW033291 mixture was dialyzed against two 1 L buffer exchanges of 12 hours each, with dialysis buffer containing: 50 mM Tris-HCl pH7.5, 40 mM NaCl, 0.1 mM DTT, 0.01% Tween-20. Both at the start and at the conclusion of dialysis, a 1 µL sample was removed and added to 200 µl of assay buffer of 50 mM Tris-HCl pH7.5, 0.01% Tween 20, 150 uM NAD(+), 20 µM PGE2. Generation of NADH was followed in a fluorescent plate reader at 340 nM excitation and 485 nM emission as measured every 30 seconds for 15 minutes. Relative enzymatic activity of 15-PGDH was determined by the rate of NADH generation over time [Niesen, 2010 #1676].

Graph B replots the data as % inhibition of 15-PGDH activity in SW033291 treated 15-PGDH measured pre-dialysis versus post-dialysis.

Under the conditions of the assay SW033291 inhibited 91% of 15-PGDH pre-dialysis, and 85% of 15-PGDH activity post-dialysis—that is dialysis did not reverse the inhibition of 15-PGDH. Control 15-PGDH protein that was dialyzed in the absence of SW033291 remained fully active.

FIGS. 23(A-B) show (A) at upper right the reaction rates for 15-PGDH in the presence of a graded set of increasing concentrations of SW033291. In the graph at upper right P is the NADH concentration as a proxy for 15-keto-PGE2. (P+S) is the starting PGE2 concentration of 20 µM. The assay was carried out in the presence of 10 nM recombinant 15-PGDH. In the graph at lower left (B), Vo is the initial velocity of the reaction in the absence of SW033291, and Vi is the initial velocity of the reaction in the presence of the corresponding concentration of SW033291. The line shows the curve generated by fitting the data to the Morrison equation. The curve fitting yields a calculated a $Ki^{APP}$ value of 0.1015 nM. The dashed line intersects the X axis at 8.5 nM. This represents the point at which [inhibitor]=[active enzyme] showing that the enzyme preparation contains 85% active enzyme. In the Morrison equation, Ki is the binding affinity of the inhibitor; [S] is substrate concentration; and Km is the concentration of substrate at which enzyme activity is at half maximal. Note that $IC_{50}$ is the functional strength of the inhibitor. Whereas the $IC_{50}$ value for a compound may vary between experiments depending on experimental conditions, the Ki is an absolute value. Ki is the inhibition constant for a drug; the concentration of competing ligand in a competition assay which would occupy 50% of the receptors if no ligand were present.

FIGS. 24(A-B) show duplicate titrations of 15-PGDH Inhibitor (SW033291) that were run at 6 different concentrations of PGE2 (1.25 uM-40 uM). In the graph at top, Y-axis is % inhibition of the reaction by SW033291. The X-axis is the concentration of SW033291 in nM. Reactions contain 5.0 nM added 15-PGDH, 250 µM NAD(+), and indicated concentrations of PGE-2, were assembled and incubated at room temperature for 60 minutes. The Km for PGE2 is approximately 5 µM, and reactions run with PGE2 concentrations below 5 µM go very slowly making it difficult to quantitate inhibition by SW033291. However, in reactions with PGE2 at concentrations of 5 µM-40 µM, the $IC_{50}$ for SW033291 is unaffected by the increasing PGE2 concentration, showing that the inhibition is noncompetitive.

Figure 25:
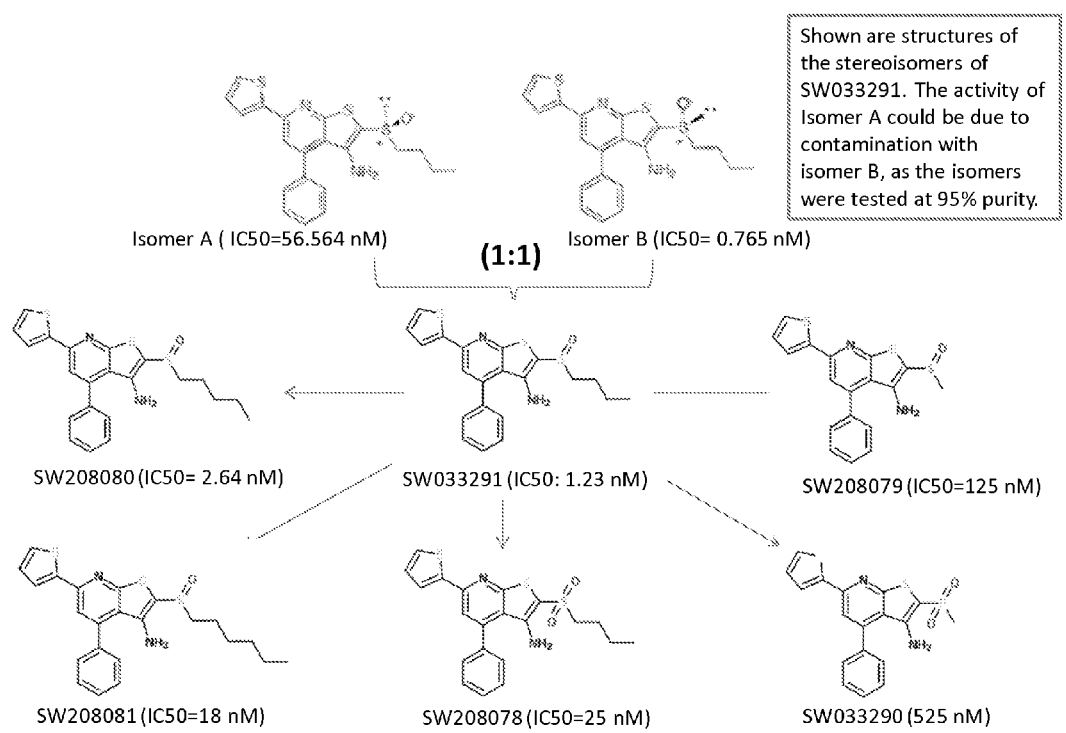
FIG. 25 illustrates a schematic diagram showing the structure activity relationships of analogues of SW033291 versus their $IC_{50}$ against 15-PGDH.

FIG. 25 shows the structure activity relationships of analogues of SW033291 versus their IC50 against recombinant 15-PGDH. The optical isomers of SW033291 were separated by preparative HPLC using a 10 mm×250 mm Chiralcel ODH column, 5% isopropanol in hexanes, 1 mL/min. The 'A' isomer is the faster eluting isomer, and has been assigned as the (−)-(S)-enantiomer. The 'B' isomer is the slower eluting isomer and has been assigned as the (+)-(R)-enantiomer.

The analogue family shows that SW033291, with a 4 carbon side chain, is 2-fold more potent than SW208080 (5 carbon side chain), 15-fold more potent than SW208081 (6 carbon side chain), and 100-fold more potent than SW208079 (1 carbon side chain). SW033291 is also 20-fold more potent than SW208078, the analogue that converts the sulfoxide group to a sulfone.

FIG. 26 shows structures of additional SW033291 analogs that convert the sulfoxide group to a ketone, an amide, an ester, or a carboxylic acid. Also shown is structure SW206980 that deletes the phenyl ring from SW033291.

Figure 27:
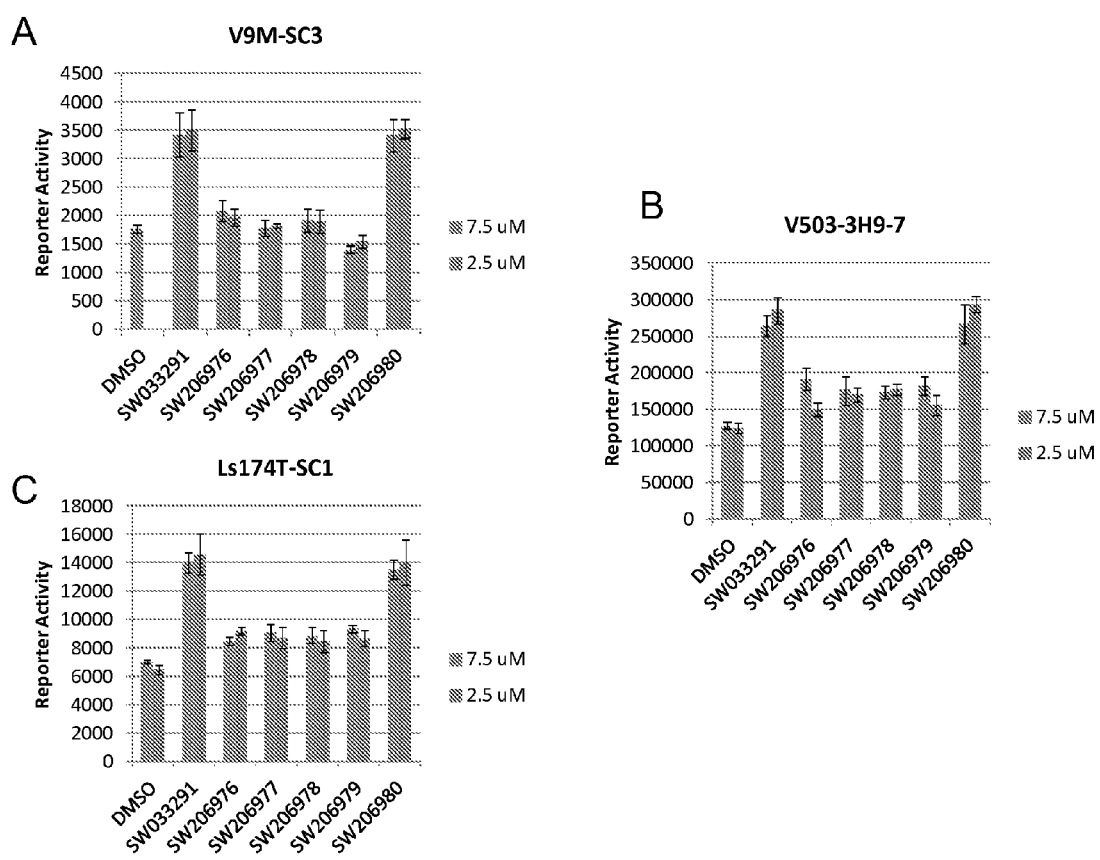
FIGS. 27(A-C) illustrate graphs showing luciferase activity of colon cancer cell lines V503, LS174T, and V503 treated with 2.5 µM and 7.5 µM the compounds of FIG. 26.

FIGS. 27(A-C) show graphs that show the level of compound's activity in inducing the 15-PGDH-luciferase fusion reporter in three different test cell line backgrounds, V9m, LS174T, and V503. Each compound was tested at two concentrations, 2.5 µM, and 7.5 µM. Y-axis is luciferase activity.

At 2.5 µM-7.5 µM, SW206980, that deletes the phenyl group of SW033291, shows activity comparable to SW033291 in all three reporter lines.

Structures that have converted the sulfoxide group to a ketone, amide, ester, or carboxylic acid show major loss of activity in inducing the reporter.

Figure 28:
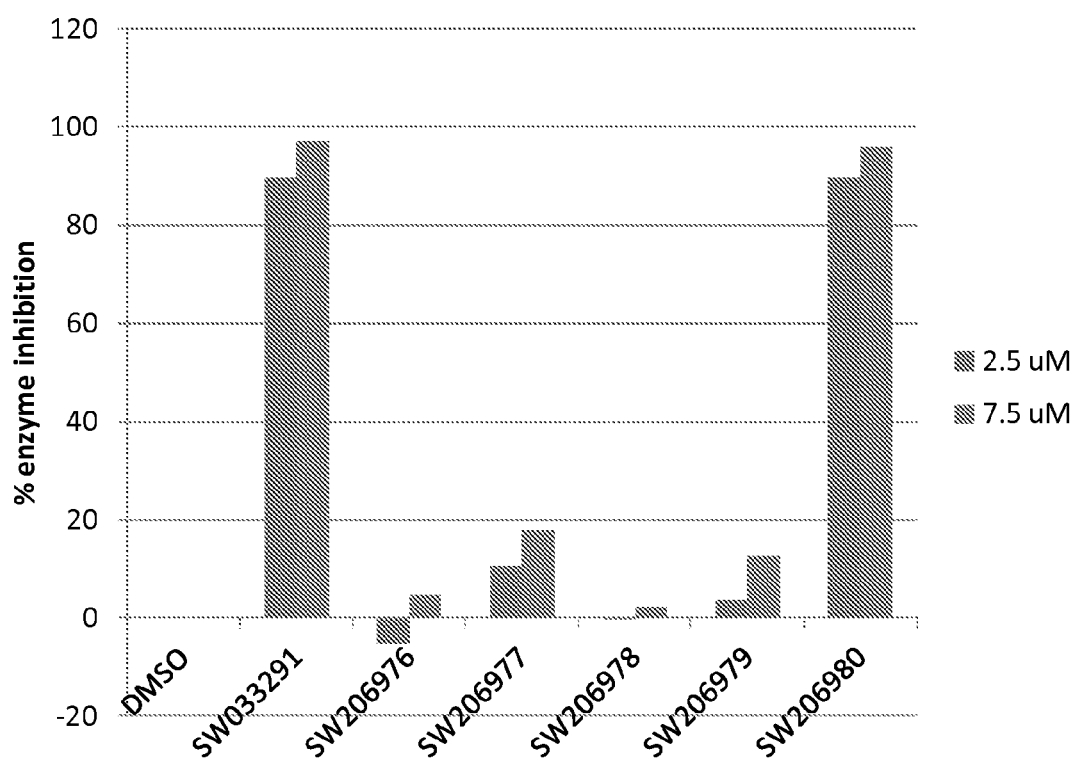
FIG. 28 illustrates a graph showing percent inhibition of 15-PGDH activity by the compounds of FIG. 26.

FIG. 28 shows graphs that show the percent of 15-PGDH enzyme activity that is inhibited at 2.5 µM and at 7.5 µM by each of the 5 test compounds. SW206980 that deletes the phenyl group of SW033291, shows at these concentrations similar potency to SW03291 in inhibiting 15-PGDH activity.

Structures that have converted the sulfoxide group to a ketone, amide, ester, or carboxylic acid show major loss of activity as 15-PGDH inhibitors.

FIGS. 29(A-B) show a titration curve that plots percent inhibition of 15-PGDH enzyme activity at different concentrations of SW033291 and SW0206980.

FIGS. 30(A-B) show that SW206980 binds directly to 15-PGDH and markedly shifts its melting curve. Shown at left is the melt curve of 15-PGDH as reflected by fluorescence of the hydrophobic dye SYPRO Orange. Shown at right is the negative first derivative of the melt curve.

Three conditions are plotted, that of 10 µM 15-PGDH, that of 10 µM 15-PGDH plus 10 uM SW206980, and that of 10 µM 15-PGDH plus 125 µM NADH plus 10 µM SW206980. The melting temperature, as reflected by the inflection point of the curve at right is shifted by 20° C., from 48-degrees up to 68-degrees, in the presence of SW206980 and NADH, reflecting that SW206980 directly binds to and markedly stabilizes the tertiary structure of 15-PGDH, in a manner requiring the presence of the NADH cofactor.

FIGS. 31(A-C) show further analogues of SW033291 that build on the previous finding that removal of the SW033291 phenyl ring (SW206980) retained activity. The new analog (SW206992) adds a nitrogen to the left-hand ring.

Table 2 provides a comparison of the properties of SW033291, SW206980, and SW206992.

TABLE 2

Summary of three SW033291 analogs

| | SW033291 | SW206980 | SW206992 |
|---|---|---|---|
| $IC_{50}$ | 1.59 nM | 0.97 nM | 1.411 nM |
| Time to inhibition (10 nM) | ~5 mins | ~2 mins | ~2 mins |
| Δ Tm (NADH) | 19° C. | 15.5° C. | 19° C. |
| Concentration for Full Cell Line Reporter Induction | ~100 nM | >300 nM | >1 uM |
| Hepatocyte stability | Stable > couple hrs | T½ = 80 mins | |
| Toxicity | >10 µM | >7.5 µM | >7.5 µM |

Time to inhibition refers to the time needed to inhibit the generation of NADH by 15-PGDH from the moment with drug is added into the reaction mix. Delta Tm refers to the shift in melting temperature of recombinant 15-PGDH in the presence of drug (with cofactor NADH also present). Concentration of Full Cell Line Reporter Induction refers to the concentration of drug that needs to be added to reporter cell line to achieve maximal induction of the 15-PGDH-luciferase gene fusion reporter cassette, as measured by luciferase assays. Hepatocyte stability refers to the half-life of compound in the presence of hepatocytes in culture. Toxicity refers to the concentration of compound needed to decrease cell numbers in a cell culture assay.

FIGS. 32(A-C) show titration of induction by SW033291 of the 15-PGDH-luciferase gene fusion reporter in three different cell line backgrounds. In general between 80-160 nM SW033291 exposure for 24 hours is needed to induce maximal reporter induction.

FIGS. 33(A-C) show titration of induction by SW206980 of the 15-PGDH-luciferase gene fusion reporter in three different cell line backgrounds. In general ≥300 nM SW206980 exposure for 24 hours is needed to induce maximal reporter induction.

FIGS. 34(A-C) show titration of induction by SW206992 of the 15-PGDH-luciferase gene fusion reporter in three different cell line backgrounds. In general ≥1000 nM SW206992 exposure for 24 hours is needed to induce maximal reporter induction.

FIGS. 35(A-C) show the shift in the melt curve of recombinant 15-PGDH protein (10 µM) by 20 uM SW033291, SW206980, and SW206992 in the presence of the cofactor NAD (+)(100 µM). Control melting temperature is 49 degrees centigrade. SW033291 shifts the melting temperature to 63 degrees. SW206980 shifts the melting temperature to 61 degrees. SW206992 shifts the melting temperature to 59 degrees. Thus all three compounds directly bind to 15-PGDH and markedly increase the melting temperature of the protein, with the order of the temperature shifts being SW033291>SW206980>SW206992.

FIGS. 36(A-B) show the shift in the melt curve of recombinant 15-PGDH protein (10 uM) by 20 uM SW033291, SW206980, and SW206992 in the presence of the cofactor NADH (100 uM). Control melting temperature is 55 degrees centigrade. SW033291 shifts the melting temperature to 74 degrees. SW206980 shifts the melting temperature to 70.5 degrees. SW206992 shifts the melting temperature to 68.5 degrees. Thus all three compounds directly bind to 15-PGDH and markedly increase the melting temperature of the protein, with the order of the temperature shifts being SW033291>SW206980>SW206992.

FIGS. 37(A-C) show a titration curve of 15-PGDH inhibitor compounds in an assay measuring effect on PGE2 levels in the medium of A549 cells that have been stimulated with IL1-beta. Highest PGE2 levels, 3000 pg/ml, are achieved with SW033291, with maximal effect attained at 2.5 µM compound. Next highest PGE2 level, 2500 pg/ml are achieved with SW206980, with maximal effect attained at 7.5 µM compound. Lowest induction, to 2100 pg/ml PGE2 is achieved with SW206992, with maximal effect attained at 2.5 µM. In these reactions, A549 cells were maintained in F12K medium supplemented with 10% fetal calf serum (FBS) and 50 µg/mL gentamicin in a humidified atmosphere containing 5% $CO_2$ at 37° C. Cells were plated in 24-well plates (0.5 mL per well) at about 100,000 cells per well in duplicate and grown for 24 h before stimulation with IL-1β (1 ng/mL) overnight (16 h) to generate PGE2. SW033291 and its analogs were added at the indicated concentrations, and the incubation continued for 8 h. Medium was collected, and the level of PGE2 was analyzed by enzyme immunoassay. Data were analyzed from results of three independent experiments.

FIGS. 38(A-C) show assays of cellular toxicity on A549 cells at 24 hours of 15-PGDH inhibitors as assayed by CellTiter-Glo measurement. No effect on CellTitre-Glo levels is seen by concentrations of up to 10 µM of SW033291, SW206980, and SW2206992.

Figure 39:
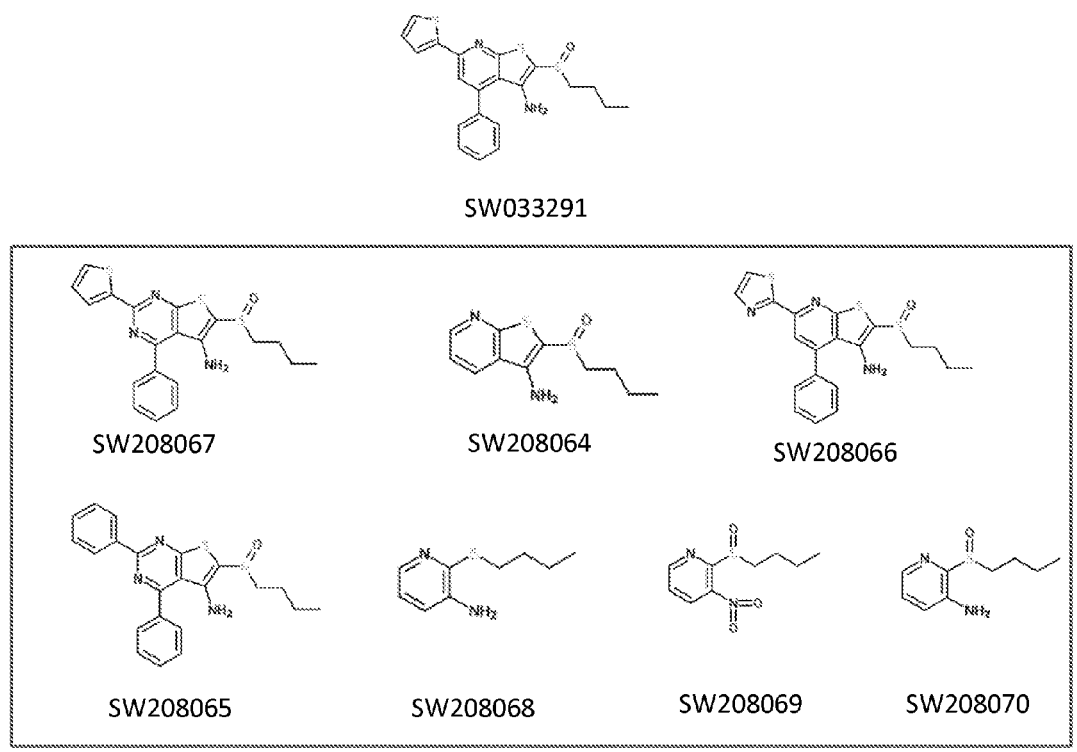
FIG. 39 illustrates a schematic diagram of additional analogues of SW033291.

FIG. 39 shows structures of 7 SW033291 analogues, SW208064, SW208065, SW208066, SW208067, SW208068, SW208069, SW208070.

Table 3 provides tabular summary of the properties of 4 analogues, SW208064, SW208065, SW208066, SW208067, and in particular lists the $IC_{50}$ for each of these 4 compounds against 2.5 nM recombinant 15-PGDH.

TABLE 3

Summary of four SW033291 analogs from UTSW set 8

|  | SW033291 | SW2068064 | SW208065 | SW208066 | SW208067 |
|---|---|---|---|---|---|
| $IC_{50}$ | 1.23 nM | 151.4 nM | 4.865 nM | 1.368 nM | 2.395 nM |
| Time to inhibition (10 nM) | ~5 mins | | | | |
| Δ Tm (NADH) | 19° C. | 5° C. | 13° C. | 16.5° C. | 16.5° C. |
| Concentration for Full Cell Line Reporter Induction | ~100 nM | ~600 nM | ~100 nM | ~100 nM | ~500 nM |
| Hepatocyte stability | Stable > couple hrs | | | | |
| Toxicity | >10 µM | | | | |

Time to inhibition refers to the time needed to inhibit the generation of NADH by 15-PGDH from the moment with drug is added into the reaction mix. Delta Tm refers to the shift in melting temperature of recombinant 15-PGDH in the presence of drug (with cofactor NADH also present). Concentration of Full Cell Line Reporter Induction refers to the concentration of drug that needs to be added to reporter cell line to achieve maximal induction of the 15-PGDH-luciferase gene fusion reporter cassette, as measured by luciferase assays. Hepatocyte stability refers to the half-life of compound in the presence of hepatocytes in culture. Toxicity refers to the concentration of compound needed to decrease cell numbers in a cell culture assay.

Figure 40:
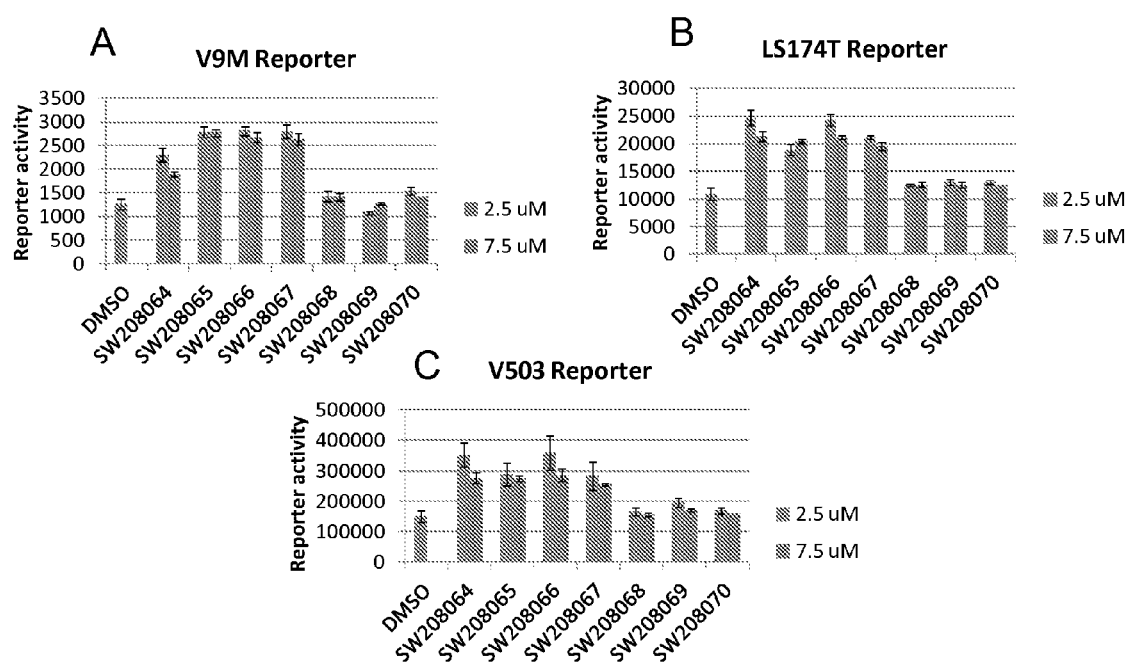
FIGS. 40(A-C) illustrate graphs showing luciferase activity of colon cancer cell lines V9M, LS174T, and V503 treated with 2.5 µM and 7.5 µM the compounds of FIG. 39.

FIG. 40 provides graphical summary showing the activity of each of the compounds in inducing a 15-PGDH-luciferase fusion gene reporter introduced into three different colon cancer cell lines, V9m, LS174T, and V503. Results are measured by assay of luciferase activity after exposure of cells to compound at either 2.5 µM or 7.5 µM compounds concentration.

Figure 41:
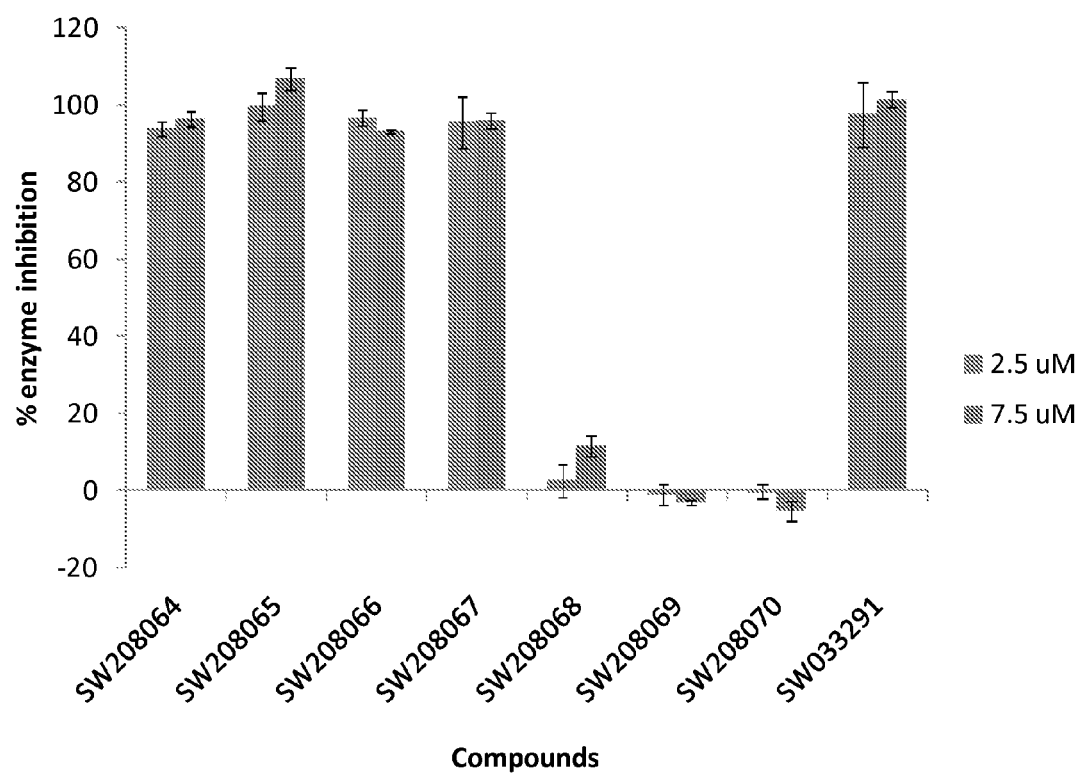
FIG. 41 illustrates a graph showing percent inhibition of 15-PGDH activity by the compounds of FIG. 40.

FIG. 41 provides graphical summary showing the activity of each of the compounds in inhibiting the enzymatic activity of recombinant 15-PGDH enzyme when compound is added at 2.5 µM and at 7.5 µM. 100% inhibition corresponds to complete inhibition of the enzyme.

Figure 42:
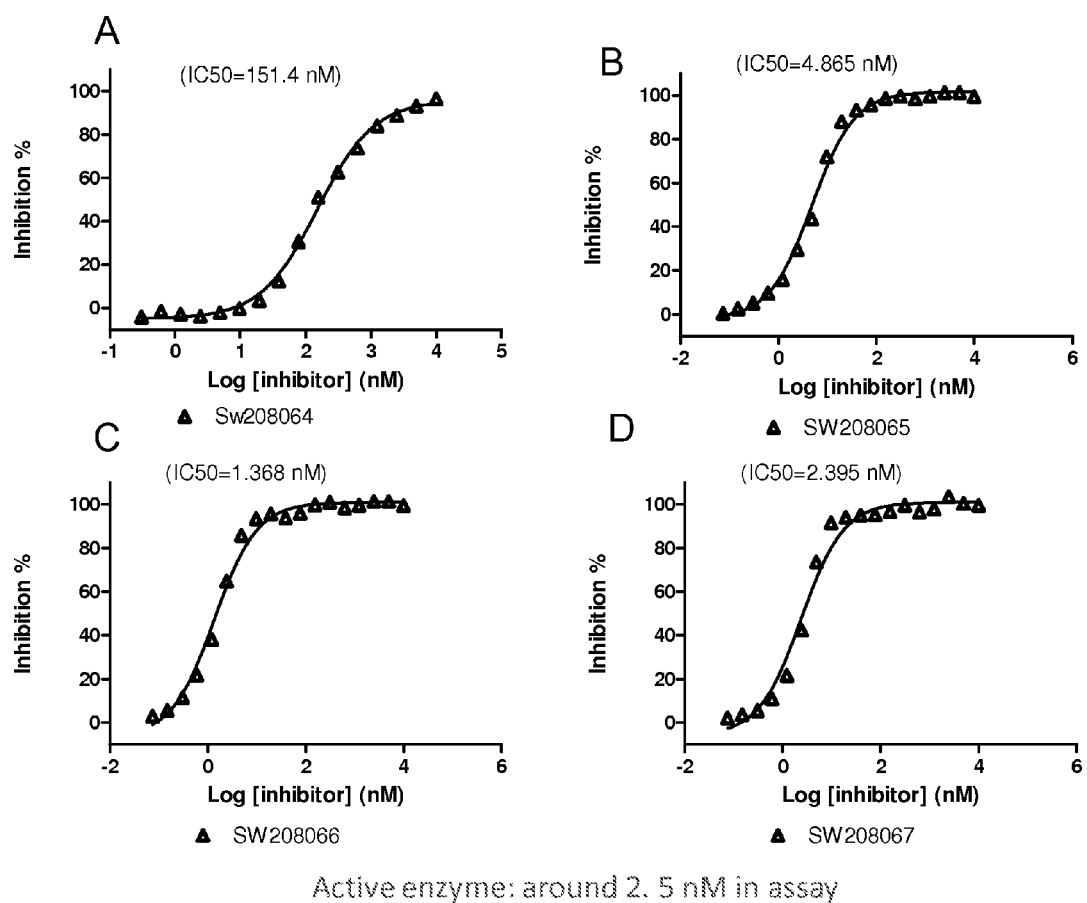
FIG. 42 illustrates a graph showing percent inhibition of 15-PGDH activity by the compounds of FIG. 40.

FIG. 42 shows measurement of IC for inhibiting 2.5 nM of recombinant 15-PGDH when incubated across a range of concentrations of SW208064, SW208065, SW208066, and SW208067. Y-axis of each graph records percent inhibition of the 15-PGDH enzymatic activity. 100% Inhibition corresponds to complete inhibition of the enzyme. X-axis of each graph records the log of the inhibitor concentration expressed in nM.

Figure 43:
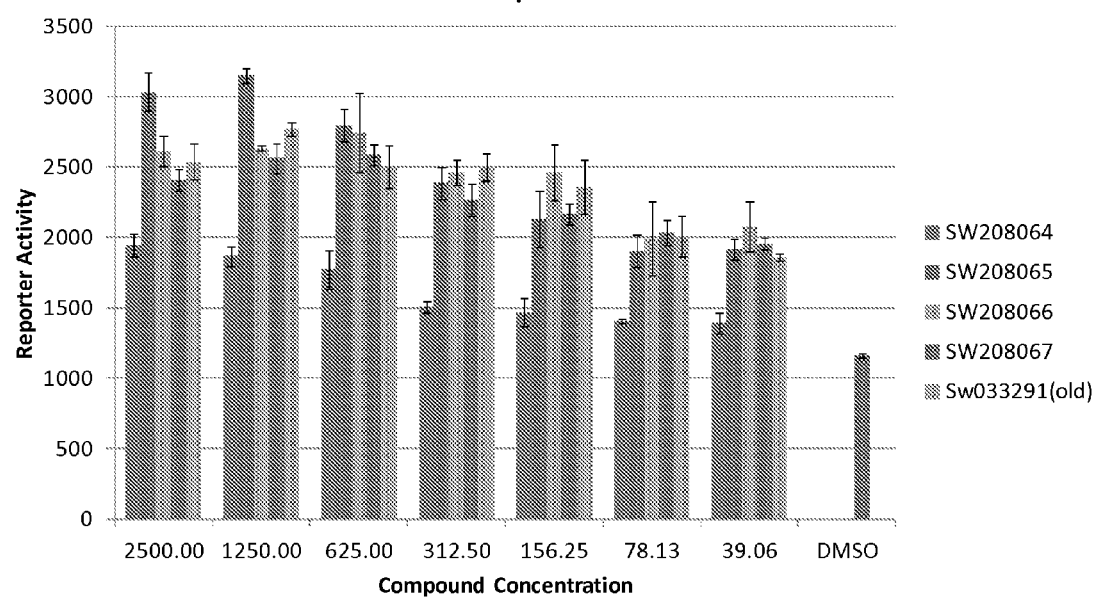
FIG. 43 shows the dose response curve for induction of a 15-PGDH-luciferase fusion gene reporter in the V9m cell line background of SW033291, SW208064, SW208065, SW208066, and SW208067.

FIG. 43 shows the dose response curve for induction of a 15-PGDH-luciferase fusion gene reporter in the V9m cell line background of SW033291, SW208064, SW208065, SW208066, and SW208067. Concentrations are in nM.

Figure 44:
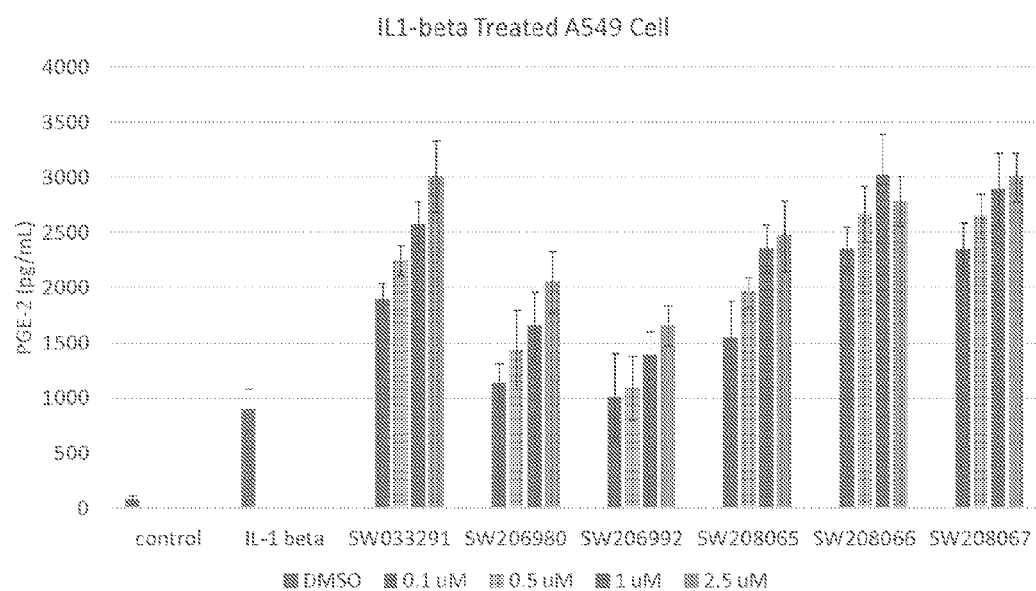
FIG. 44 illustrates titration curves of 15-PGDH inhibitor compounds in an assay measuring effects on PGE2 levels in the medium of A549 cells that have been stimulated with IL1-beta.

FIG. 44 Shows titration curves of 15-PGDH inhibitor compounds in an assay measuring effects on PGE2 levels in the medium of A549 cells that have been stimulated with IL1-beta in the same experimental design described for FIG. 37. At 100 nM concentration of drug, the highest levels of PGE2 in the medium are achieved by treating cells with SW208066 or with SW208067, after which the next highest level of PGE2 in the medium is achieved by treating cells with SW033291.

Example 5

Analysis of Toxicity of SW033291

Table 4 shows a summary of a group of 8-12 week old male FVB mice in control or SW033291 treatment arms assessed for toxicity of SW033291, with 6 mice in each arm of the study.

TABLE 4

| Baseline Characteristics FVB male mice- 8-12 weeks old | | | |
|---|---|---|---|
| Toxicity Study | WT-Control | WT-Treatment | p-value |
| Number | 6 | 6 | |
| Sex | M | M | |
| Age (Days) | 73.7.1 ± 4.7 | 73.2 ± 5.0 | 0.465 |
| Weight (gm) | 27.5 ± 2.4 | 26.8 ± 3.1 | 0.412 |

Figure 45:
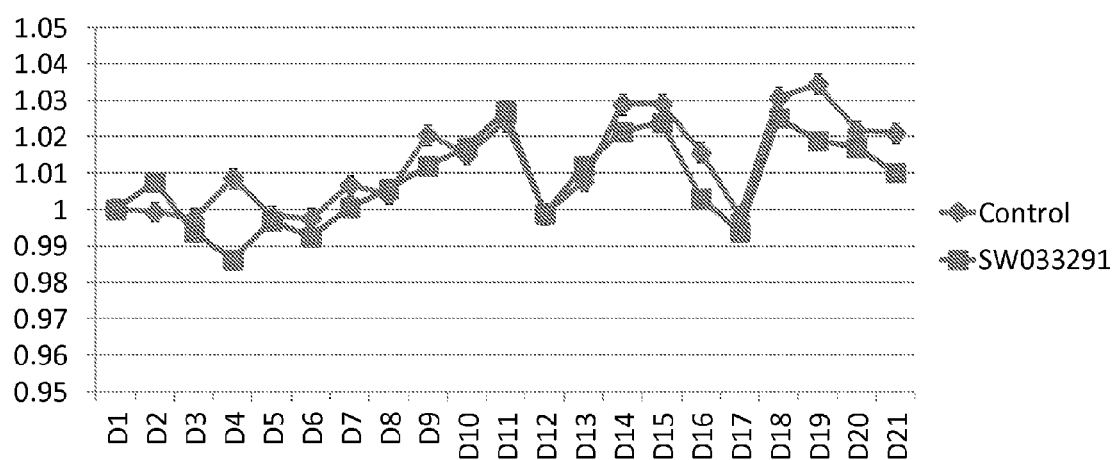
FIG. 45 is a plot showing weight change of FVB mice treated with SW033291.

FIG. 45 shows the daily weights of a group of 8-12 week old FVB mice treated with vehicle or with SW033291 IP at 5 mg/kg twice daily for 21 days. SW033291 was administered in a vehicle of 10% Ethanol, 5% Cremophor EL, 85% D5W at a concentration of 125 ug/200 ul. As shown, both vehicle and drug treated mice show equal weight gain during the 21 day period, with no evidence for SW033291 reducing mouse weight. N=6 mice in both the SW033291 treated and the vehicle treated arms.

Example 6

Analysis of Effect of SW033291 on Bone Marrow Function

This Example shows effects of SW033291 on bone marrow function.

FIGS. 46(A-C) show analysis of bone marrow of wild-type mice versus mice that are homozygous genetic knockouts for 15-PGDH (PGDH −/− mice). Total bone marrow cellularity and percent of Sca1+/c-Kit+ cells in lineage negative (SKL) cells are the same in both sets of mice. However, bone marrow from 15-PGDH −/− mice shows an approximately 50% increase in numbers of hematopoietic colonies generated when marrow is plated into methylcelluose. 15-PGDH knockout mice are denoted by label PGDH mice and by label 15-PGDH. WT denotes wild-type mice.

Figure 47:
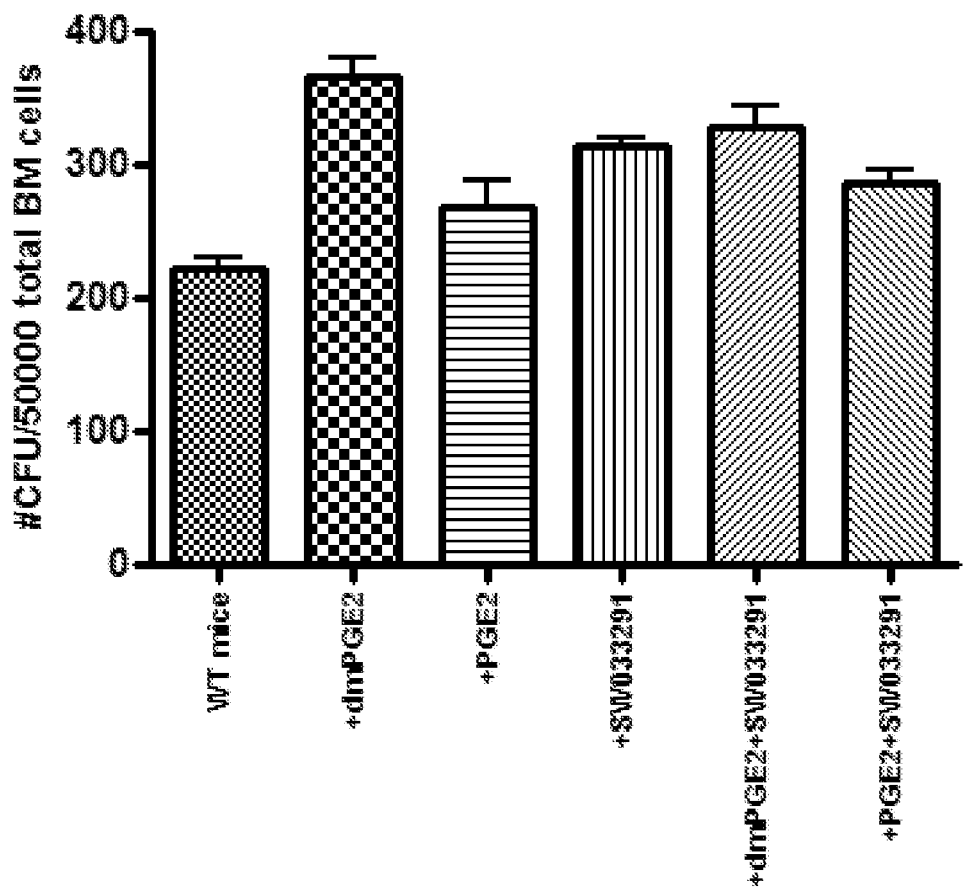
FIG. 47 illustrates a graph showing CFU counts in wild type bone marrow treated with SW033291 and PGE-2.

FIG. 47 shows assay in which bone marrow is harvested from a wild-type mouse, and incubated ex vivo on ice for 2 hours with either SW033291 (0.5 µM), or 1 uM PGE2 or 1 µM 16,16-dimethyl PGE2 (dmPGE2). Treated marrow is again then plated into methylcellulose for counting of hematopoietic colonies. SW033291 treated marrow again shows an approximately 50% increase in the number of bone marrow derived colonies generated. Under these conditions, a lesser increase is seen in marrow treated with PGE2, and a slightly greater increase is seen in marrow treated with dmPGE2.

Figure 48:
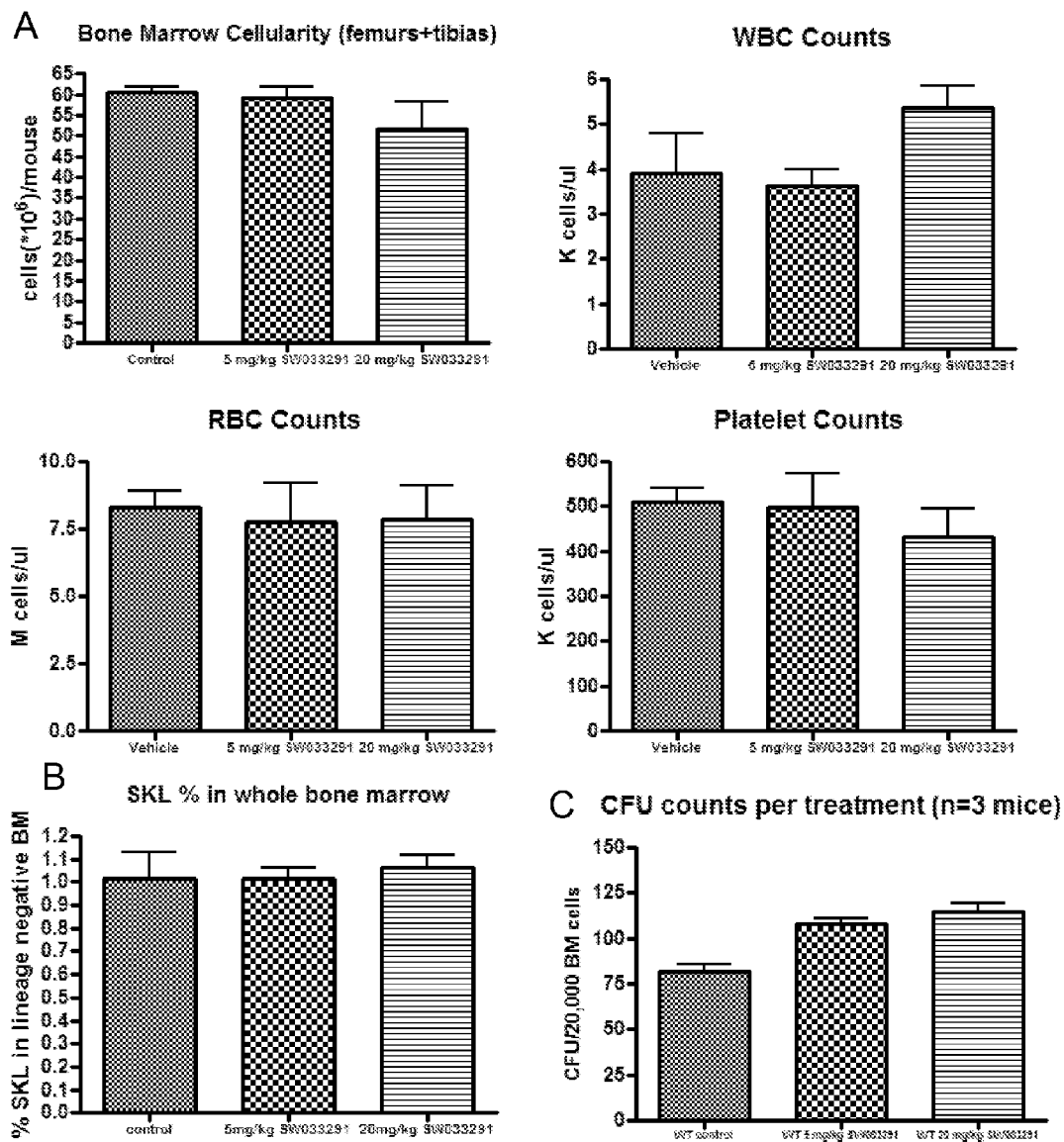
FIGS. 48(A-C) illustrate graphs showing: (A) bone marrow cellularity of mice treated with SW033291; (B) SKL % in whole bone marrow of mice treated with SW033291; and (C) CFU counts in mice treated SW033291.

FIGS. 48(A-C) show a study of C57BL/6J mice treated with IP SW033291 administered in a vehicle of 10% Ethanol, 5% Cremophor EL, 85% D5W at a dose of 5 mg/kg or 20 mg/kg. Panel A shows mouse bone marrow cellularity, white blood count (wbc), red blood count (rbc) and platelets counts. Panel B shows percent of Sca1+/c-Kit+ cells in lineage negative (SKL) cells are unchanged in SW033291 treated mice. Panel C shows that marrow from SW033291 treated mice gives rise to approximately 30% increase in numbers of hematopoietic colonies generated when marrow is plated into methylcelluose. Experimental conditions are noted on the figure.

Figure 49:
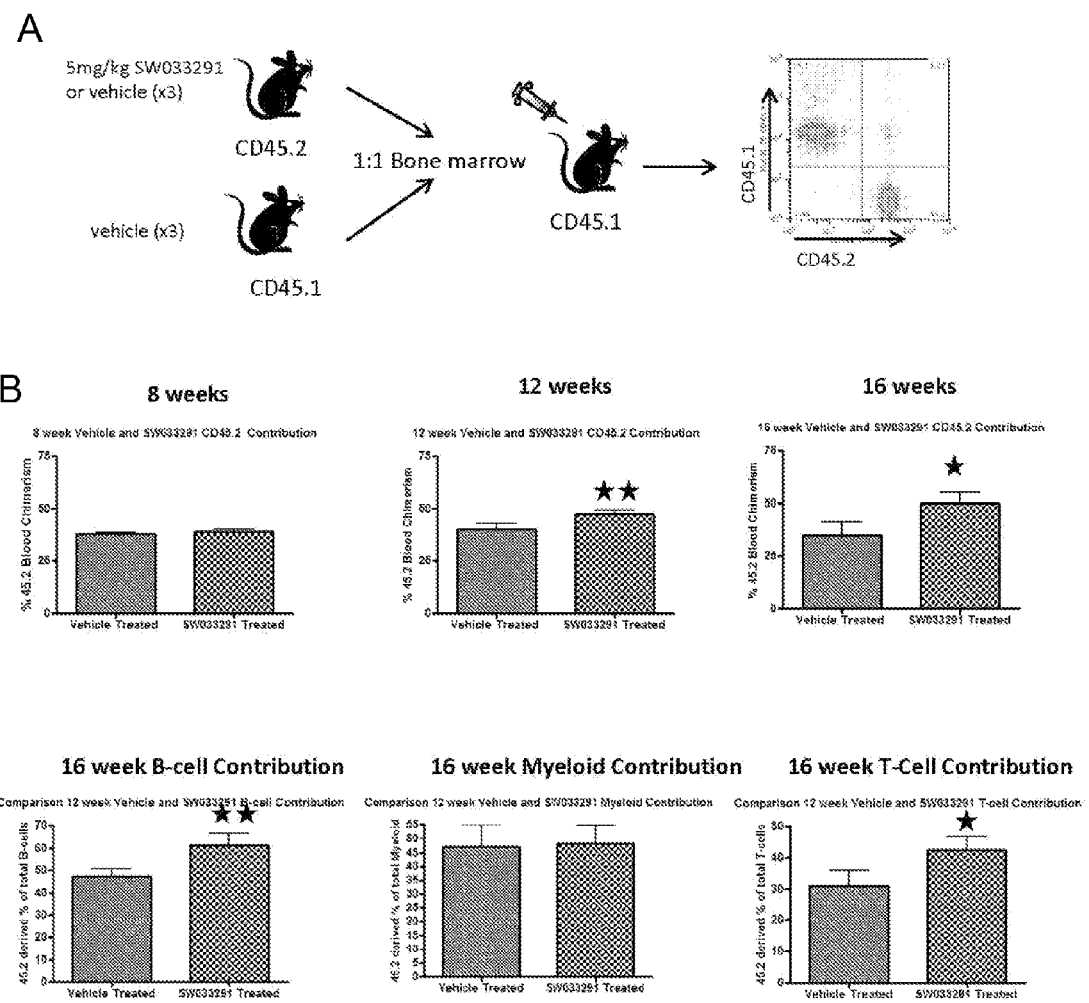
FIGS. 49(A-B) illustrate: (A) a schematic diagram following CD45.2 antigen marked cells in lethally irradiated C57BL/6J mice rescued with a bone marrow transplant from donor mice treated with SW033291 or with vehicle; and (B) graphs showing chimerism, of donor B-Cells, myeloid cells, and T-Cells after such treatment.

FIGS. 49(A-B) show analysis of marrow from CD45.2 antigen marked C57BL/6J mice that were treated with SW033291 5 mg/kg IP daily for 3 doses in a vehicle of 10% Ethanol, 5% Cremophor EL, 85% D5W or that were treated with vehicle alone. On day 3 mice were sacrificed, marrow flushed and mixed at a 1:1 ratio with vehicle treated CD45.1 marrow. 2 million whole BM cells were injected into the tail vein of lethally irradiated CD45.1 mice and percent chimerism measured via flow cytometry at weeks 8, 12, 16. As shown, at weeks 12 and 16 the percent blood chimerism of CD45.2 marked cells was significantly increased in recipient mice whose CD45.2 marked marrow was harvested from SW033291 treated donor mice, as opposed to vehicle control treated donor mice. In other words, marrow from SW033291 treated mice demonstrated long term increased fitness in competition with control marrow. In particular, at week 16 CD45.2 harvested from SW033291 treated mice show a significant increase in contribution to B and T cell populations, suggesting marrow from SW033291 treated mice promotes earlier reconstitution of lymphoid populations and earlier return to immune competence.

Figure 50:
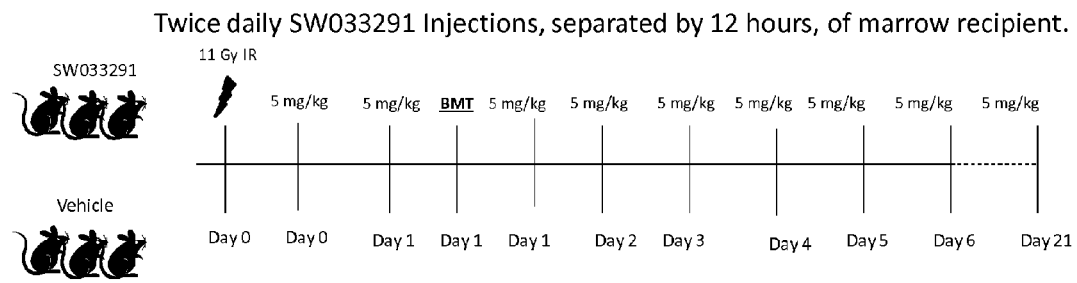
FIG. 50 illustrates a schematic diagram showing schema of a study in which C57BL/61 mice are irradiated with 11GY on day 0 and followed by treatment with SW033291.

In an additional study, C57BL/6J mice are irradiated with 11Gy on day 0, followed by treatment with SW033291 5 mg/kg IP twice daily (bid) in a vehicle of 10% Ethanol, 5% Cremophor EL, 85% D5W, or with vehicle only for 21 days. Mice treated with vehicle or with SW033291 all receive an allograft of marrow from a donor C57BL/6J mouse at a dose of either 100,000 cells, 200,000 cells, 500,000 cells. 3 control and 3 SW033291 mice are assessed under each condition. The experimental design is depicted in FIG. 50.

Table 6 shows the number of surviving mice in each cohort over the first 19 days of study. Under the conditions of the mouse colony during this study, control mice receiving 100,000-500,000 cells are all dead between days 4-13 of study. In contrast, two SW033291 treated mice receiving 500,000 cells remain alive on day 19 of the study and are presumed to have full hematopoietic reconstitution. Thus treatment with the 15-PGDH inhibitor SW033291 promoted survival of mice receiving a bone marrow transplant, an observation consistent with SW033291 enabling more rapid and complete hematopoietic reconstitution in the transplanted mice. Other 15-PGDH inhibitors with activity similar to SW033291 would be predicted to have similar activity in supporting hematopoietic reconstitution. Treatment with SW033291 also enabled mice to be successfully transplanted with a smaller inoculum of donor bone marrow than the 1,000,000 cells that are standardly needed. These observations suggest SW033291, as well as other similar 15-PGDH inhibitors, is able to support successful transplantation with smaller numbers of donor stem cells. Such activity would be of particular utility in settings, such as transplantation with umbilical cord stem cells, in which donor cell numbers are limited. Improved survival of transplanted mice treated with SW033291 suggests efficacy of SW033291, and of similar 15-PGDH inhibitors, as replacements for, or in enabling decreased use of, other treatments or growth factors commonly employed in support of patients receiving bone marrow, hematopoietic stem cell, and cord blood stem cell transplants. Improved survival of transplanted mice treated with SW033291 is consistent with SW033291, and by extension other similar 15-PGDH inhibitors, having activity in reducing infections in the transplanted mice, and/or in promoting recovery of mice intestines from damage by radiation, and/or in reducing pulmonary toxicity from radiation.

TABLE 5

| Treatment | Mouse survival Cell number | 13-Mar Day 0 | 14-Mar Day 1 | 15-Mar Day 2 | 16-Mar Day 3 | 17-Mar Day 4 | 18-Mar Day 5 | 19-Mar Day 6 | 20-Mar Day 7 | 21-Mar Day 8 | 22-Mar Day 9 | 23-Mar Day 10 | 24-Mar Day 11 | 25-Mar Day 12 | 26-Mar Day 13 | ... | 1-Apr Day 19 |
|---|---|---|---|---|---|---|---|---|---|---|---|---|---|---|---|---|---|
| Control | 1 × 10^5 | 3 | 3 | 3 | 2 | 0 | | | | | | | | | | | |
| Control | 2 × 10^5 | 3 | 3 | 3 | 3 | 3 | 2 | 1 | 0 | | | | | | | | |
| Control | 5 × 10^5 | 3 | 3 | 3 | 3 | 3 | 3 | 2 | 1 | 1 | 1 | 1 | 1 | 1 | 0 | | |
| SW033291 | 1 × 10^5 | 3 | 3 | 3 | 3 | 2 | 1 | 0 | | | | | | | | | |
| SW033291 | 2 × 10^5 | 3 | 3 | 3 | 3 | 3 | 3 | 2 | 2 | 2 | 2 | 2 | 2 | 1 | 0 | | |
| SW033291 | 5 × 10^5 | 3 | 3 | 3 | 3 | 3 | 3 | 3 | 3 | 2 | 2 | 2 | 2 | 2 | 2 | ... | 2 |

Example 7

Analysis of Effect of SW033291 on Radiation Survival

This Example shows studies of the effect of SW033291 in mice receiving whole body irradiation.

Table 5 shows the results of a study of 15 week old C57BL/6J female mice irradiated with 7Gy, 9Gy, or 11Gy, and receiving daily SW033291 5 mg/kg IP in a vehicle of 10% Ethanol, 5% Cremophor EL, 85% D5W for 7 doses, or receiving vehicle alone. The table shows the number of mice surviving on sequential days of the study. Under the conditions of the mouse colony during this experiment, mice receiving a lethal dose of 11Gy lived 48 hours longer if treated with SW033291 than if receiving vehicle control, with control mice all dead on day 8; whereas SW033219 treated mice were all dead on day 10.

TABLE 6

| Radiation Dose | Treatment Arm | 10/2 Day 0 | 10/3 Day 5 | 10/4 Day 6 | 10/5 Day 7 | 10/6 Day 8 | 10/7 Day 9 | 10/8 Day 10 | 10/9 Day 11 | 10/10 Day 12 | 10/11 Day 13 | 10/12 Day 14 | 10/13 Day 15 | Day 16 | 10/23 Day 25 |
|---|---|---|---|---|---|---|---|---|---|---|---|---|---|---|---|
| 7 Gy | Saline | 3 | 3 | 3 | 3 | 3 | 3 | 3 | 3 | 3 | 3 | 3 | 3 | | Looks Healthy |
| | SW033291 | 3 | 3 | 3 | 3 | 3 | 3 | 3 | 3 | 3 | 3 | 3 | 3 | | Looks Healthy |
| 9 Gy | Saline | 3 | 3 | 3 | 3 | 3 | 3 | 3 | 2 | 1 | 1 | 0 | | | |
| | SW033291 | 3 | 3 | 3 | 3 | 3 | 3 | 3 | 3 | 2 | 2 | 1 | 0 | | |
| 11 Gy | Saline | 3 | 3 | 3 | 2 | 0 | | | | | | | | | |
| | SW033291 | 3 | 3 | 3 | 3 | 3 | 2 | 0 | | | | | | | |

Table 7 shows the number of mice surviving on sequential days of a study of mice treated at 11Gy treated with either vehicle control or with SW033291 IP, in a vehicle of 10% Ethanol, 5% Cremophor EL, 85% D5W, with SW033291 administered either at 5 mg/kg daily for 7 days, 5 mg/kg daily throughout the study, or at 5 mg/kg twice daily for 7 days. Again mice treated with SW033291 on any of these dosing schedules live on average 1-2 days longer than mice receiving vehicle control. The activity of SW033291 in promoting resistance to toxic effects of radiation may extend to SW033291 and other similar 15-PGDH inhibitors in promoting resistance to other similar toxic insults including but not limited to Cytoxan, fludarabine, chemotherapy and immunosuppressive therapy.

TABLE 7

| Treatment Conditions | Friday 12-Oct Day 0 | Wed. 17-Oct Day 5 | Thurs. 18-Oct Day 6 | Friday 19-Oct Day 7 | Saturday 20-Oct Day 8 | Sunday 21-Oct Day 9 | Monday 22-Oct Day 10 |
|---|---|---|---|---|---|---|---|
| 11 Saline (7 Gy days, 1 dose daily) | 2 | 2 | 2 | 2 | 0 | | |
| 11 SW033291 Gy (1 dose/daily) for 7 days | 3 | 3 | 3 | 3 | 2 | 1 | 0 |
| 11 SW033291 Gy (1 dose/daily, continuous every day) | 3 | 3 | 3 | 3 | 3 | 2 | 0 |
| 11 Saline (7 Gy days, 2 dose/daily | 3 | 3 | 3 | 2 | 1 | 0 | 0 |
| 11 SW033291 (7 Gy days, 2 dose daily) | 3 | 3 | 3 | 3 | 3 | 2 | 0 |

Example 8

Analysis of Effect of SW033291 on Liver Regeneration Post Partial Hepatectomy

This Example shows studies assessing the effect of SW033291 on liver regeneration in mice following partial hepatectomy.

Figure 51:
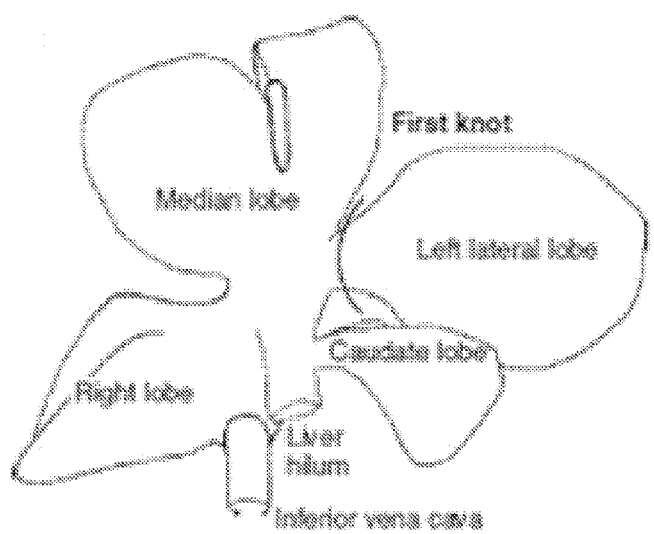
FIG. 51 illustrates a schematic diagram of a partial hepatectomy.

FIG. 51 shows a drawing of the anatomy of the mouse liver and of the partial hepatectomy procedure described in Mitchell et al., Nature Protocols, 3, 1167-1170 (2008), in which the median and left lateral lobes are resected, and then liver regeneration is observed via hypertrophy of the remaining right and caudate lobes. The total resection is of approximately 70% of the mouse liver mass. In these studies mice were euthanized using carbon dioxide inhalation. The mouse body was weighed in its entirety. The liver was removed from the mouse; the necrotic remnant from the surgical resection was trimmed; and the regenerated liver was weighed.

FIG. 52(A-D) show an anatomical view of the mouse liver. Pictures at left are pre-operative views, and those at right are post-resection views. The upper two pictures show anterior view of liver and at left display the median lobe and a part of the Lateral lobe. The lower two pictures show Inferior view of liver and at left display the Lateral lobe. In the partial hepatectomy procedure, the median and lateral lobes are resected as shown at right.

FIG. 53(A-D) at left reiterates photographs of the immediate post-hepatectomy views of the mouse liver, with anterior view at top and inferior view at bottom. Figure at top right shows the in situ view of the regenerated liver on post operative day (POD) 10, showing hypertrophy of the remnant right and caudate lobes. Photograph at lower right shows the anterior view of the regenerated liver after removal from the mouse body. Whitish region at the upper right liver edge is the necrotic stump from the resection, and is trimmed prior to weighing.

The first study was performed in 10 week old male C57BL/6J mice, receiving daily SW033291 5 mg/kg IP in a vehicle of 10% Ethanol, 5% Cremophor EL, 85% D5W, versus vehicle alone, and assessed daily for liver regeneration with 5 control and 5 SW033291 recipient mice sacrificed on each time point. In this study, ketamine anesthesia was employed.

FIG. 54(A-B) show micrograph of the hematoxylin and eosin stained liver on post-operative day 3 (POD 3) in the SW033291 treated mouse versus the control mouse, with mitotic figures marked by yellow arrows in the SW033291 treated mouse liver at left and by green arrows in the control mouse liver at right.

FIG. 55 shows a graph of the number of mitosis per high powered field in livers of SW033291 treated versus control mice on post-operative days two through five (2D-5D). Mitotic figures were counted in 10 high powered fields (40×) from each of 5 livers per SW033291 or control mice per day. SW033291 treated mice demonstrated significantly increased hepatic mitosis versus controls on days 3 and 4.

Table 8 shows the numbers of mitosis per random high powered field counted in livers of control versus SW033291 treated mice on post operative days 2 through 5 (2D-5D). SW033291 treated mice show significantly increased numbers of mitotic liver cells on post-operative days 3 and 4.

TABLE 8

| Mitotic index (40×) mean + SD | Control | SW033291 | p-value |
|---|---|---|---|
| 2D | 0.7000 ± 0.1933 | 1.240 ± 0.2330 | 0.0915 |
| 3D | 2.000 ± 0.4364 | 6.160 ± 0.3250 | <0.0001 |
| 4D | 2.560 ± 0.2242 | 4.560 ± 0.7190 | 0.0107 |
| 5D | 0.2000 ± 0.1069 | 0.2400 ± 0.08718 | ns |

Figure 56:
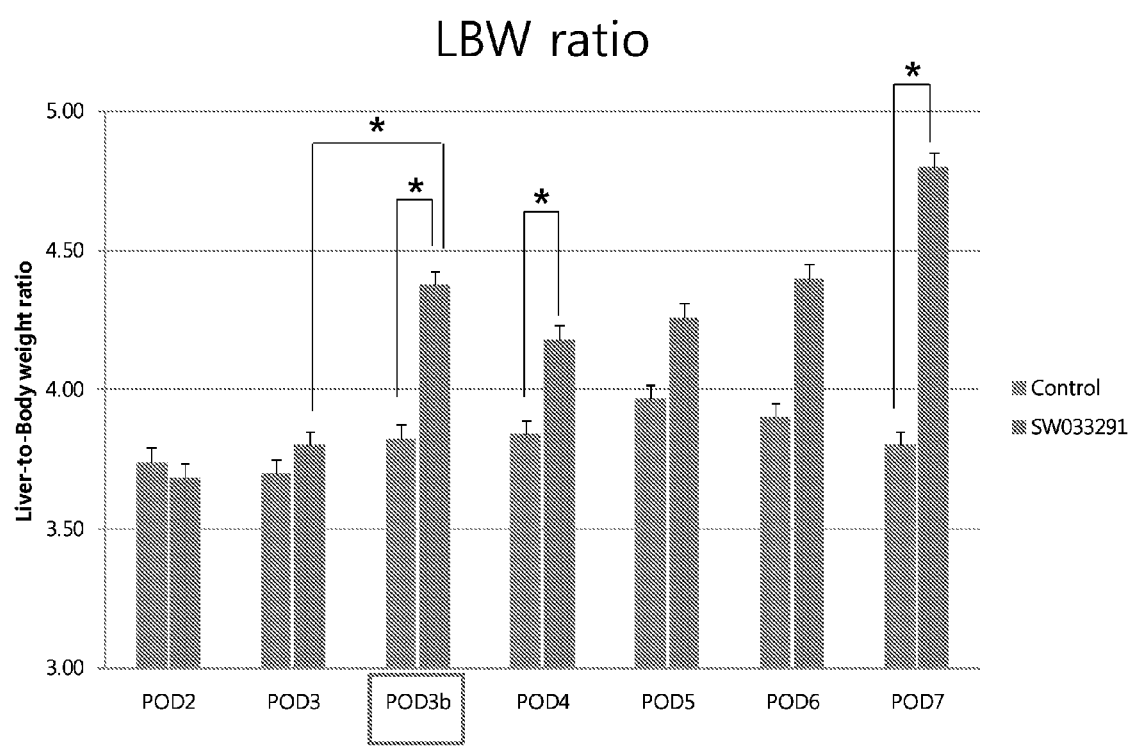
FIG. 56 illustrates a graph showing the liver to body weight ratios attained following partial hepatectomy in control versus SW033291 treated C57Bl/6J mice.

FIG. 56 shows the liver to body weight ratios attained following partial hepatectomy in control versus SW033291 treated C57Bl/6j mice injected at 5 mg/kg SW033291 IP daily (qd) starting on post operative day 0 and continuing throughout. Graph displays values from post-operative days 2-7 (POD 2-7). The SW033291 qd injection group of mice attain a higher liver to body weight ratio from post-operative days 4-7, with the increase being statistically significant on postoperative day 4 and day 7.

An additional group of mice received SW033291 5 mg/kg twice daily (bid) and were analyzed on post-operative day 3, with the data graphed as POD3b. This group of mice also showed a statistically significant increase in liver to body weight ratio compared to control mice.

Another study was performed testing the effects of SW033291 given 5 mg/kg IP twice daily (bid) on liver regeneration in C57BL/6J mice. 10 mice were used in the control and 10 mice in the drug treated arm for analysis of each time point of the study. The study again employed 10 week old male mice receiving daily SW033291 5 mg/kg IP in a vehicle of 10% Ethanol, 5% Cremophor EL, 85% D5W, versus vehicle alone, with 10 drug treated and 10 control mice sacrificed daily for comparison. In this study ketamine anesthesia was employed.

Figure 57:
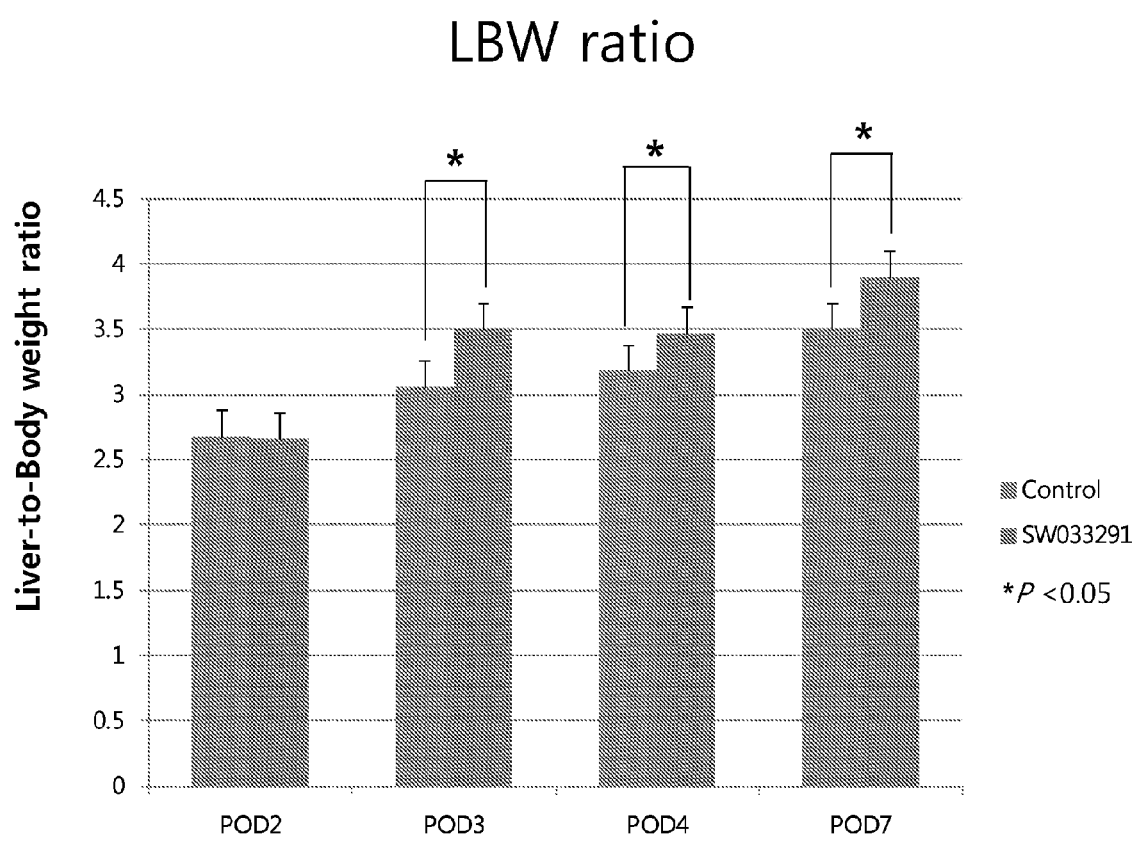
FIG. 57 illustrates a graph showing the liver to body weight ratios attained following partial hepatectomy in control versus SW033291 twice daily treated C57Bl/6J mice.

FIG. 57 shows graph of the liver to body weight ratio attained following partial hepatectomy in control versus SW033291 treated C57BL/6J mice injected at 5 mg/kg SW033291 IP twice daily (bid) starting at 1 hour post-surgery and continued throughout. Graph displays values from post-operative days 2-7 (POD 2-7). The SW033291 bid injected group of mice show a statistically significant higher liver to body weight ratio versus control mice on post-operative days 3, 4, and 7.

Figure 58:
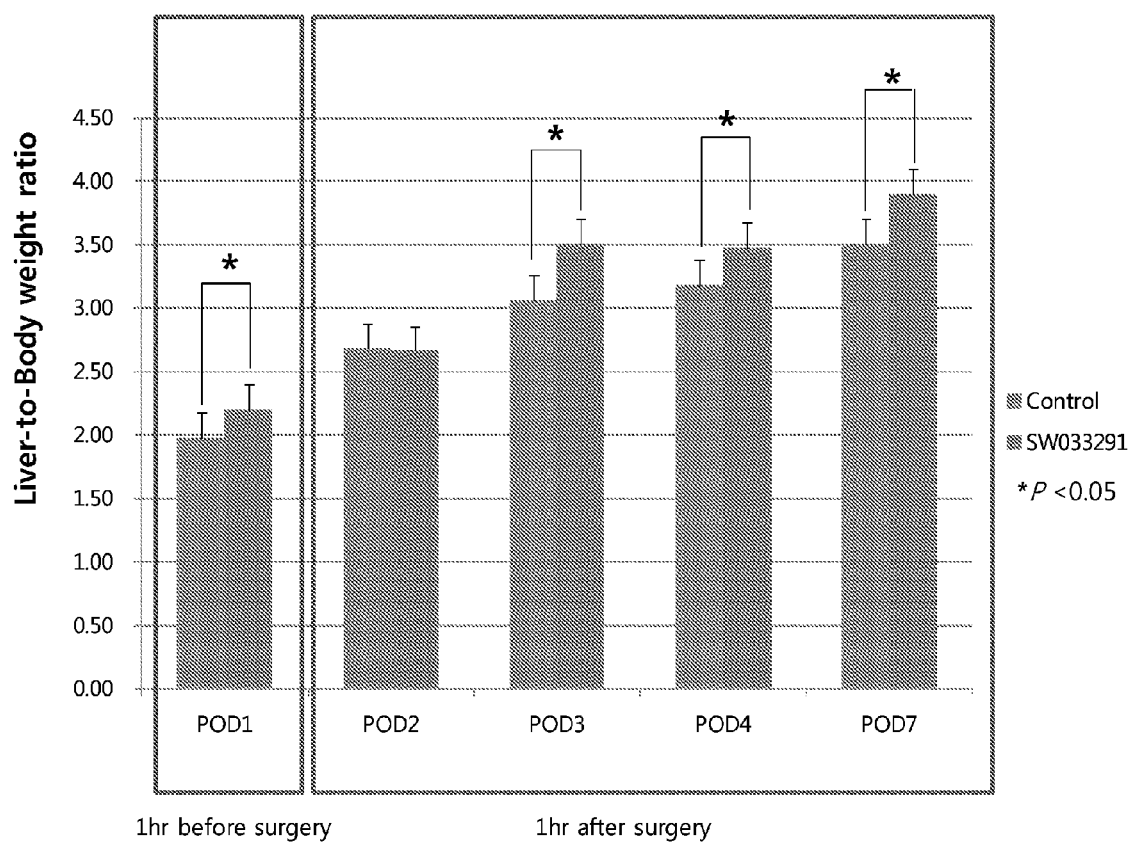
FIG. 58 illustrates a graph reprising the liver to body weight ratios attained following partial hepatectomy in control versus SW033291 treated C57Bl/6J mice.

FIG. 58 reprises the graph of the liver to body weight ratio attained following partial hepatectomy in control mice versus in mice treated with sw033291 5 mg/kg IP twice daily. In data enclosed within the blue box, drug was started 1 hour following surgery, and significant increases in liver to body weight ratio are seen in drug treated mice from post-operative day (POD) 3 onward. In data enclosed within the red box, the first dose of sw033291 is delivered commencing 1 hour before surgery, and significant increase in liver to body weight ratio is seen as early as post-operative day 1, the day following the surgery.

Figure 59:
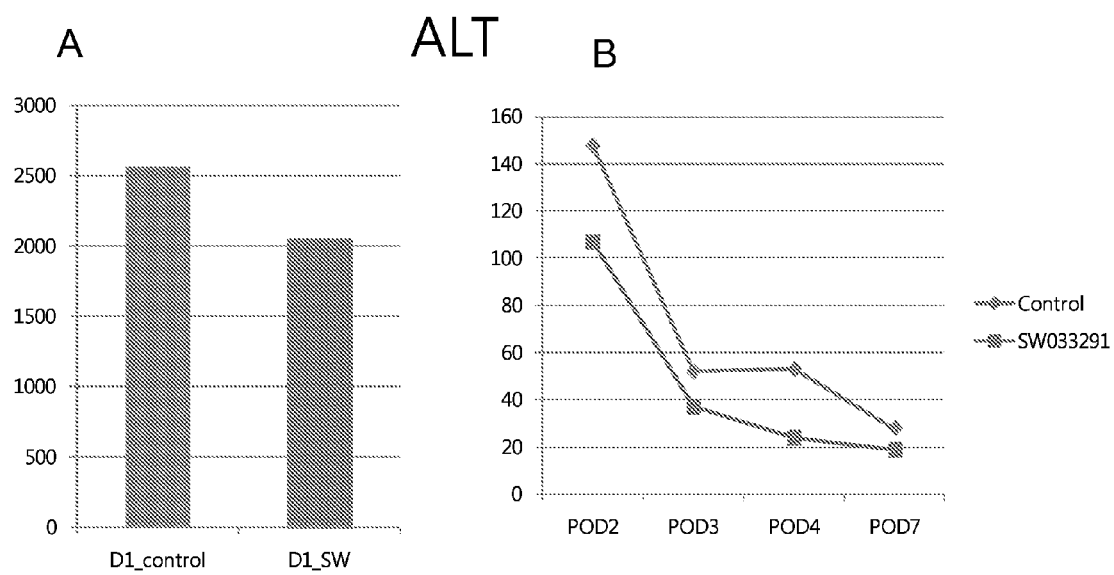
FIGS. 59(A-B) illustrate a graph and plot showing ALT levels following partial hepatectomy in one mouse control versus one mouse treated with SW033291.

FIGS. 59(A-B) show graphs of the serum ALT levels following partial hepatectomy in one control mouse versus one mouse treated with sw033291 at 5 mg/kg IP twice daily (bid). Post-operative day 1 values are compared at left, and post-operative day 2-7 values are compared at right. ALT values are lower in the drug treated mouse.

Figure 60:
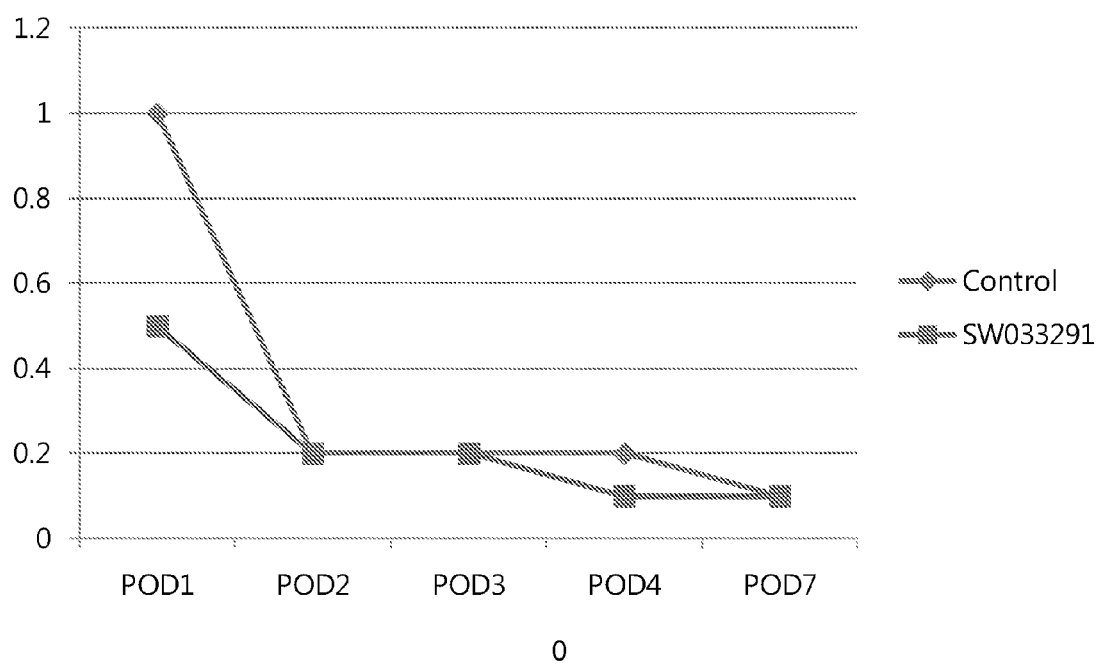
FIG. 60 illustrates a graph showing serum bilirubin levels following partial hepatectomy in a control mouse and a mouse treated with SW033291.

FIG. 60 shows graph of serum bilirubin levels following partial hepatectomy in one control mouse versus one mouse treated with SW033291 at 5 mg/kg IP twice daily (bid) from post-operative days (POD) 1-7.

In another study, SW033291 was tested in the partial hepatectomy model using the FVB strain of mice administered SW033291 5 mg/kg IP twice daily (bid), administered in a vehicle of 10% Ethanol, 5% Cremophor EL, 85% D5W, using 5 treated mice versus 5 control mice treated with vehicle alone for analysis at each time point from post operative day (POD) 1-7. In this study ketamine anesthesia was employed.

Figure 61:
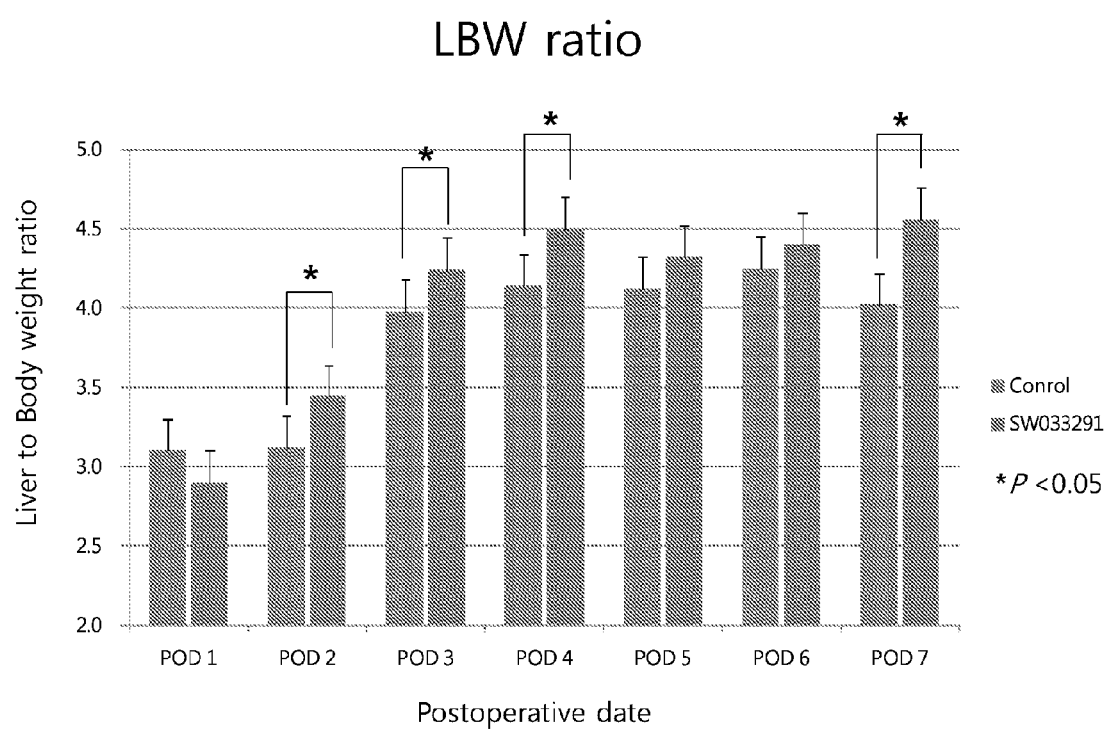
FIG. 61 illustrates a graph showing the liver to body weight ratios attained following partial hepatectomy in control versus SW033291 treated FVB mice.

FIG. 61 shows a graph of the liver to body weight ratio of attained following partial hepatectomy in FVB mice treated with 5 mg/kg IP SW033291 versus control mice treated with vehicle alone. SW033291 treated mice show increased liver to body weight ratio from post-operative days 2-7, with the increase being statistically significant on POD, 2, 3, 4 and 7.

In another study, SW033291 was tested in a partial hepatectomy model using the FVB strain of mice administered SW033291 5 mg/kg IP twice daily (bid), starting 1 hour before surgery. 10 week old male mice were employed, with 10 treated mice and 10 control mice used for analysis at each time point from post operative day (POD) 1-7. In this study isoflurane anesthesia was employed. Vehicle treated 15-PGDH knockout (KO) mice were also used as an additional comparator.

Figure 62:
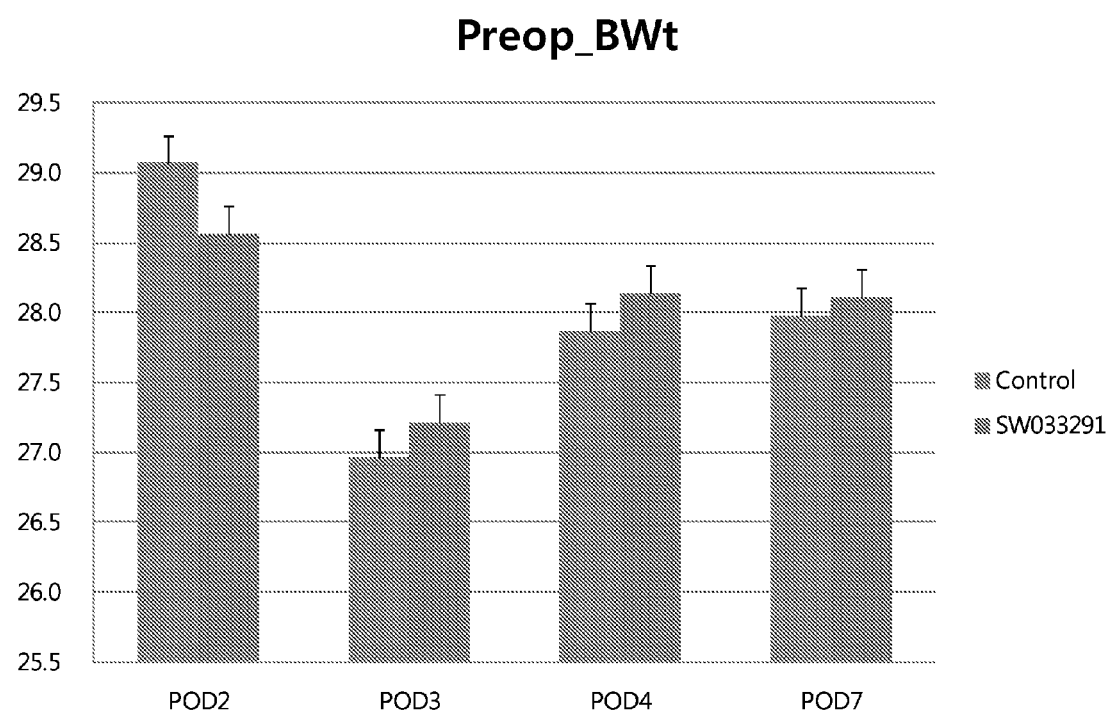
FIG. 62 illustrates a graph showing preoperative body weights in control versus SW033291 treated FVB mice.

FIG. 62 shows a graph depicting the pre-operative body weights of the FVB mice used for analysis of liver regeneration on post-operative days 2, 3, 4 and 7. SW033291 and control treated mice used on each day are well matched.

Figure 63:
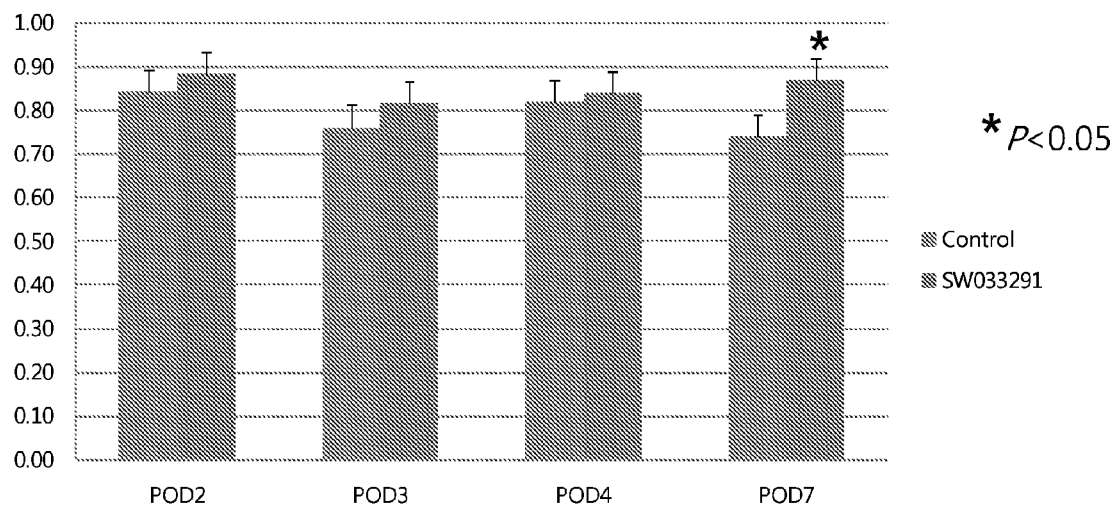
FIG. 63 illustrates a graph showing the weight of the resected liver segment from mice treated with either SW033291 or vehicle control and assayed for liver regeneration.

FIG. 63 shows a graph depicting the weight of the resected liver segment (resected LWt) from mice treated with either SW033291 or vehicle control and assayed for liver regeneration on post-operative days (POD) 2, 3, 4, and 7. Weight of the resected livers is well matched between control and drug treated mice on each day, except on day 7, when the weight of the resected liver was greater in the SW033291 treated than in the control mice.

Figure 64:
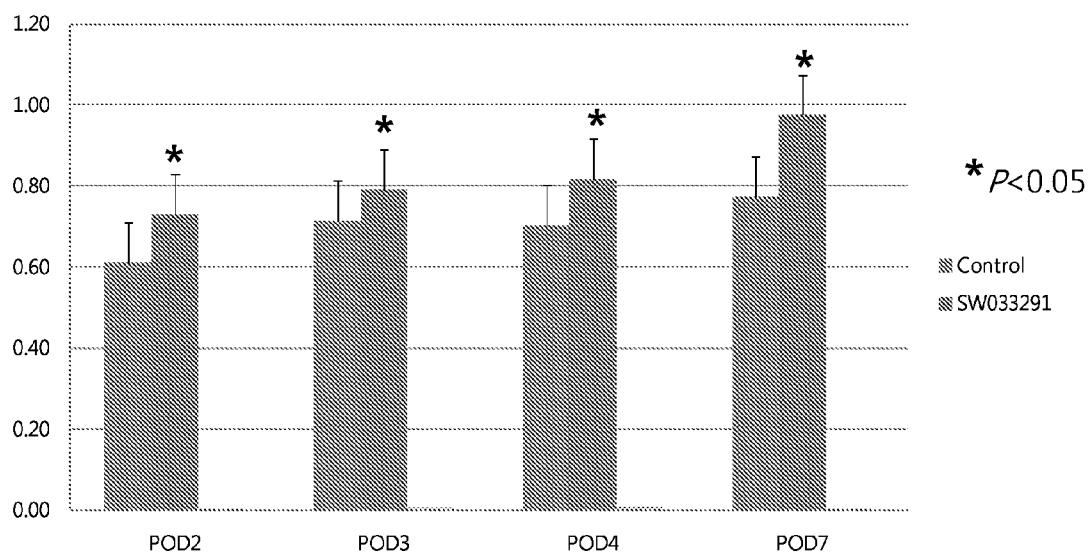
FIG. 64 illustrates a graph showing liver weights attained post partial heptatectomy in SW033291 and control mice.

FIG. 64 shows a graph depicting the liver weights attained (Regenerated_LWt) post partial hepatectomy in SW033291 and control mice on post-operative days 2, 3, 4 and 7 (POD 2, 3, 4, 7). SW033291 treated mice show significantly greater liver weights versus control mice at all time points, with SW033291 treated mice having approximately 25% greater liver weight on post-operative day 7 than control mice.

Figure 65:
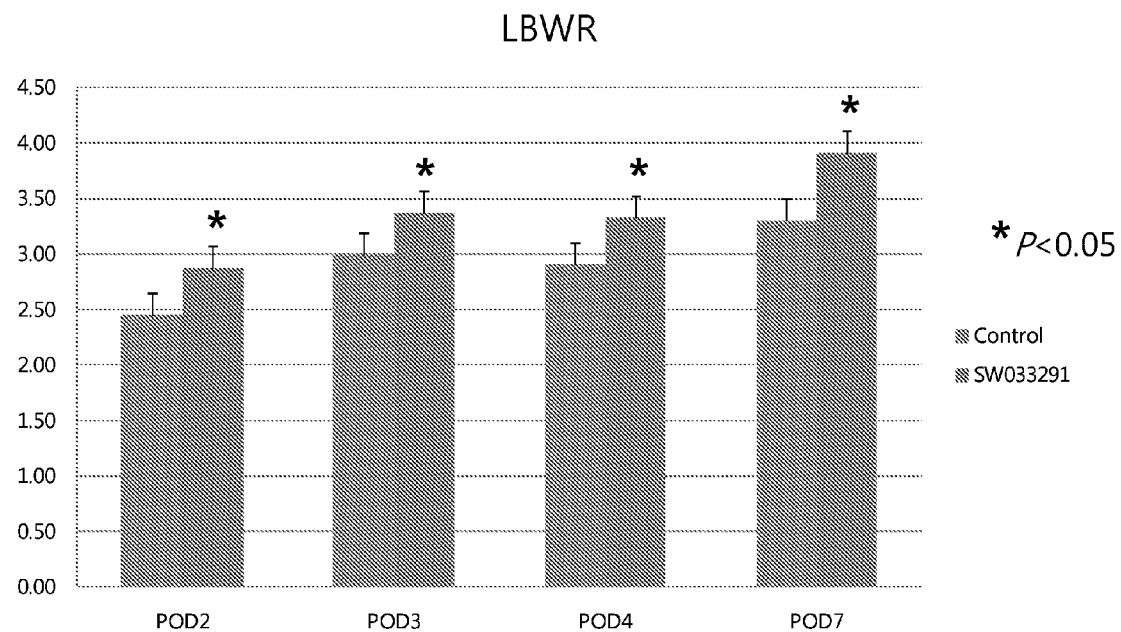
FIG. 65 illustrates a graph showing the liver to body weight ratios obtained post partial hepatectomy in SW033291 treated and control mice.

FIG. 65 shows a graph depicting the liver to body weight ratios attained (LBWR) post partial hepatectomy in SW033291 and control mice on post-operative days 2, 3, 4 and 7 (POD 2, 3, 4, 7). SW033291 treated mice show significantly greater liver to body weight ratios versus control mice at all time points, with SW033291 treated mice having approximately 20% greater liver to body weight ratio on post-operative day 7 than control mice.

Figure 66:
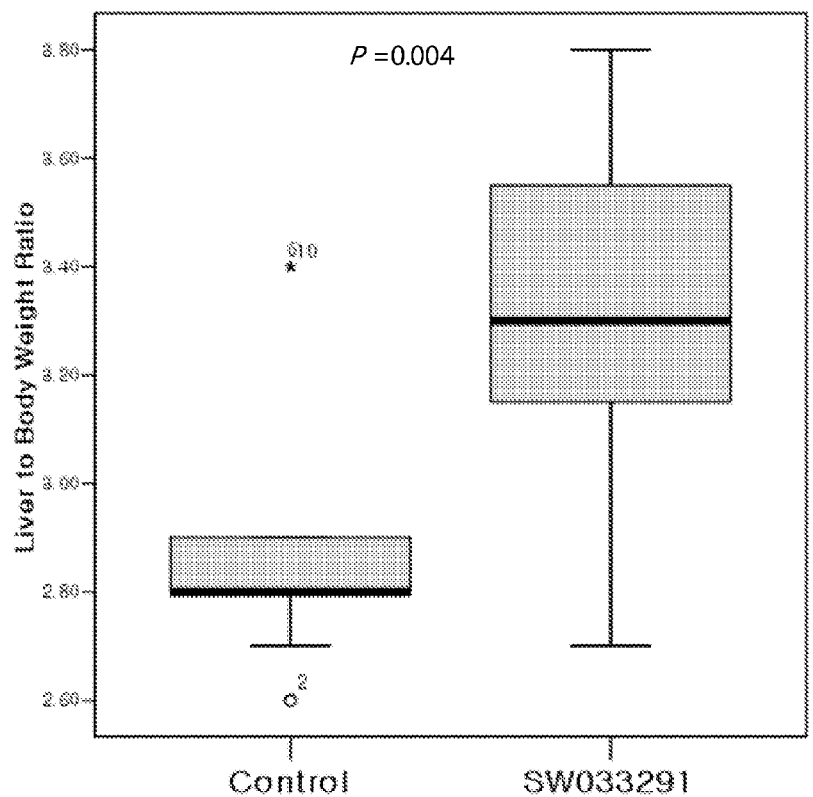
FIG. 66 illustrates a "box and whisker" plot comparing liver to body weight ratio following partial hepatectomy of SW033291 treated and control FVB mice at post-operative day 4.

FIG. 66 shows "box and whisker" plot comparing liver to body weight ratio's on post-operative day 4 following partial hepatectomy of FVB mice treated twice daily with SW033291 5 mg/kg or with vehicle control, with 10 mice in each arm. Thick bars denote population median. Upper box margin denotes lower boundary of the highest quartile. Lower box margin denotes upper boundary of the lowest quartile. SW033291 treated mice show a significantly increased liver to body weight ratio at P=0.004.

Figure 67:
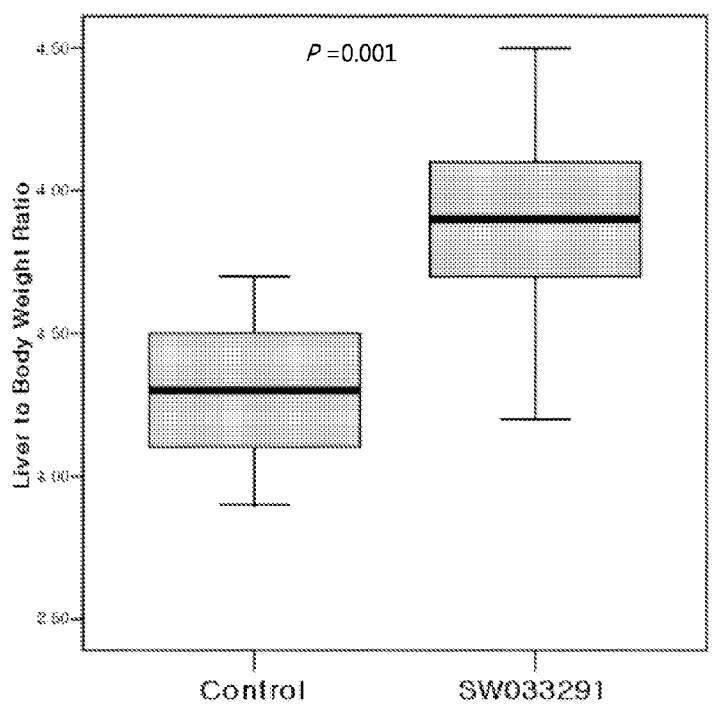
FIG. 67 illustrates a "box and whisker" plot comparing liver to body weight ratio following partial hepatectomy of SW033291 treated and control FVB mice at post-operative day 7.

FIG. 67 shows "box and whisker" plot comparing liver to body weight ratio's on post-operative day 7 following partial hepatectomy of FVB mice treated twice daily with SW033291 5 mg/kg or with vehicle control, with 10 mice in each arm. Thick bars denote population median. Upper box margin denotes lower boundary of the highest quartile. Lower box margin denotes upper boundary of the lowest quartile. SW033291 treated mice show a significantly increased liver to body weight ratio at P=0.001.

Figure 68:
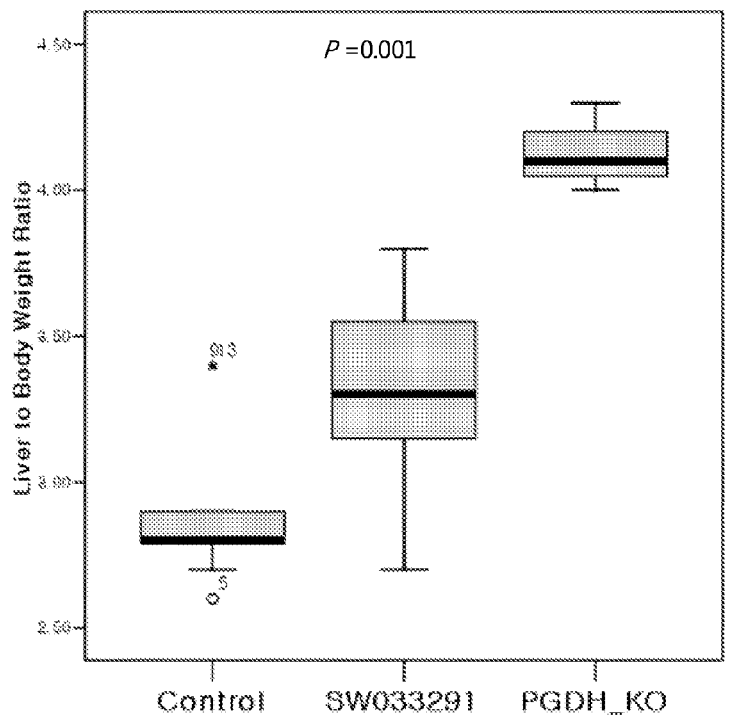
FIG. 68 illustrates a "box and whisker" plot comparing liver to body weight ratio following partial hepatectomy of SW033291 treated and control FVB mice at post-operative day 4.

FIG. 68 shows "box and whisker" plot comparing liver to body weight ratios on post-operative day 4 following partial hepatectomy of FVB mice treated twice daily with SW033291 5 mg/kg or with vehicle control, with 10 mice in each arm. Also shown is the liver to body weight ratio on post-operative day 4 of 15-PGDH knockout mice (PGDH-KO) treated with vehicle only. Thick bars denote population median. Upper box margin denotes lower boundary of the highest quartile. Lower box margin denotes upper boundary of the lowest quartile. SW033291 treated mice show a significantly increased liver to body weight ratio at P=0.001. 15-PGDH knockout mice also show greater a greater liver to body weight ratio than do vehicle treated 15-PGDH wild-type mice, supporting that the liver regeneration activity of SW033291 is mediated through inhibition of 15-PGDH. The larger effect of 15-PGDH gene knockout suggests further increase in effect of SW033291 may be attainable with additional modification of dosing schedule and delivery.

FIG. 69 shows visualization of S-phase cells following partial hepatectomy on post-operative day 2 in livers of SW033291 treated and vehicle treated control mice. Mice were injected with BrdU at 50 mg/kg IP 2 hours before sacrifice, and then S-phase cells were visualized by staining the livers with an antibody that detects BrdU that has been incorporated into DNA. Representative fields at 10× magnification show the clear increase in numbers of BrdU positive cells in the SW033291 treated liver.

FIG. 70 shows high powered (40×) views of representative fields from the study of FIG. 69.

Figure 71:
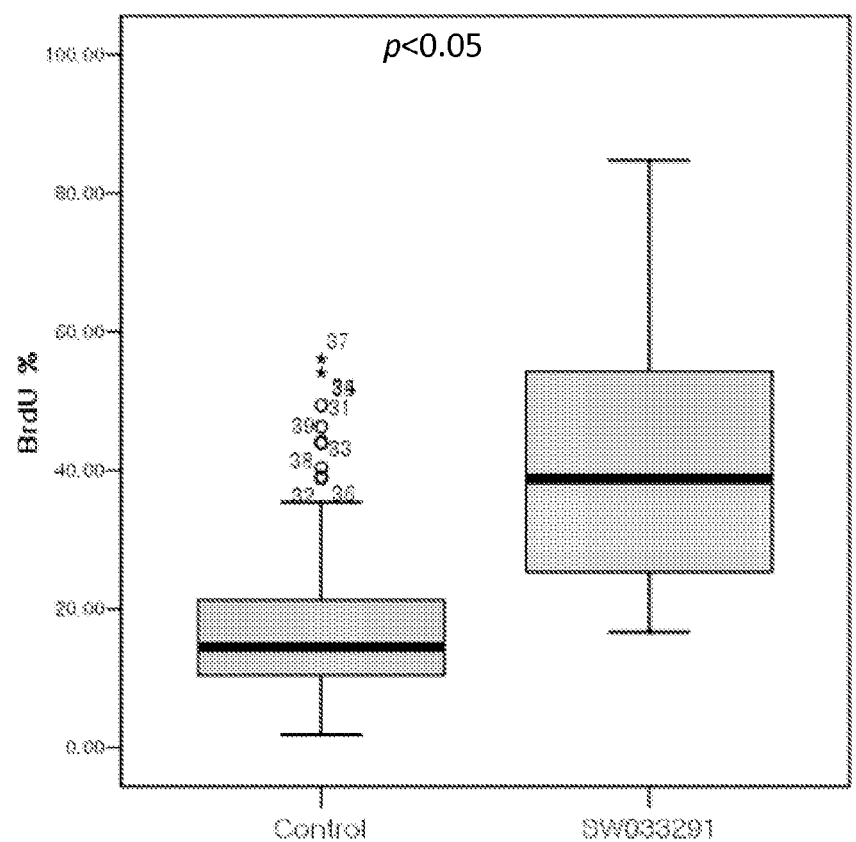
FIG. 71 illustrates a "box and whiskers" plot comparing percent of BrdU positive cells in livers of SW033291 treated versus vehicle control treated mice on post-operative day 2 following partial hepatectomy.

FIG. 71 shows "box and whiskers" plot comparing percent of BrdU positive cells in livers of SW033291 treated versus vehicle control treated mice on post-operative day 2 following partial hepatectomy. Plotted in each group are the percent BrdU positive cells from 100 random high powered fields (40× magnification) counted as 10 fields from each of 10 drug treated and each of 10 control vehicle treated mice. Heavy black bars show median values of each distribution. Upper box margin denotes lower boundary of the highest quartile. Lower box margin denotes upper boundary of the lowest quartile. SW033291 show a greater than 2-fold increase in median S-phase cells on post-operative day 2 (P<0.05).

Example 9

Analysis of Effect of SW033291 on Survival Following Acetaminophen (Tylenol) Overdose This Example provides data showing effects of SW033291 in mediating resistance to lethal doses of the liver toxin acetaminophen (Tylenol).

In the study, 11 week old female C57BL/6J mice are injected IP with a suspension of acetaminophen in phosphate buffered saline administered at the LD50 dose of 600 mg/kg.

Table 9 provides a tabular summary of the number of mice surviving out of an initial cohort of 6 mice that are all treated with acetaminophen (Tylenol) in phosphate buffered saline administered IP at the LD50 dose of 600 mg/kg.

TABLE 9

| Treatment | 0 hrs | 16 hr | 24 hrs | 40 hrs | 48 hrs | 64 hrs | 72 hrs | 88 hr | 96 hr | 112 hr | 120 hr |
|---|---|---|---|---|---|---|---|---|---|---|---|
| 1 does/daily, First dose immediately after Tylenol injection | | | | | | | | | | | |
| Saline | 6 | 6 | 5 | 4 | 3 | 3 | 3 | 3 | 3 | 3 | 3 |
| 5 mg/kg SW033291 | 6 | 6 | 6 | 4 | 4 | 4 | 4 | 4 | 4 | 4 | 4 |
| 2 dose/daily, First dose immediately after Tylenol injection | | | | | | | | | | | |
| Saline | 6 | 6 | 6 | 4 | 3 | 3 | 3 | 3 | 3 | 3 | 3 |
| 5 mg/kg SW033291 | 6 | 6 | 6 | 4 | 3 | 3 | 3 | 3 | 3 | 3 | 3 |

Test mice are additionally treated with SW033291 5 mg/kg IP in a vehicle of 10% Ethanol, 5% Cremophor EL, 85% D5W beginning immediately following acetaminophen and continued once daily, or twice daily. Control mice are additionally treated with vehicle alone once daily or twice daily. Survival is recorded from the 0 time point of administration of acetaminophen through 120 hours following. No difference is noted between survival of SW033291 treated and control mice.

Table 10 shows a summary of the number of mice surviving out of an initial cohort of 12 eleven week old C57BL/6J female mice that are all treated with acetaminophen (Tylenol) in phosphate buffered saline administered IP at the LD50 dose of 600 mg/kg, Mice are additionally treated with either SW033291 or vehicle control.

TABLE 10

| Survival | 0 hrs | 16 hr | 24 hrs | 40 hrs | 48 hrs | 64 hrs | 72 hrs | 88 hr | 96 hr | 112 hr | 120 hr |
|---|---|---|---|---|---|---|---|---|---|---|---|
| 5 mg/kg SW033291 | 12 | 12 | 12 | 11 | 10 | 10 | 10 | 10 | 10 | 10 | 10 |
| Saline | 12 | 12 | 12 | 6 | 5 | 5 | 5 | 5 | 5 | 5 | 5 |

SW033291 5 mg/kg was administered IP in a vehicle of 10% Ethanol, 5% Cremophor EL, 85% D5W twice daily (bid) beginning 48 hours prior to acetaminophen injection and continuing for 48 hours following acetaminophen injection for 9 doses total. At 120 hours post acetaminophen injection, 10 of 12 mice have survived in the SW033291 treated cohort versus 5 of 12 mice in the vehicle control treated cohort, P=0.045 in a one-tailed Fisher's exact test. Thus pre-administration of SW033291 protects from the lethal hepatotoxicity of acetaminophen.

Table 11 shows a summary of the number of mice surviving out of an initial cohort of 6 eleven week old C57BL/6J female mice that are treated with acetaminophen (Tylenol) in phosphate buffered saline administered IP at the LD50 dose of 600 mg/kg.

TABLE 11

| Survival | 0 hrs | 16 hr | 24 hrs | 40 hrs | 48 hrs | 64 hrs | 72 hrs | 88 hr | 96 hr | 112 hr | 120 hr |
|---|---|---|---|---|---|---|---|---|---|---|---|
| 5 mg/kg SW033291 | 6 | 6 | 5 | 4 | 3 | 3 | 3 | 3 | 3 | 3 | 3 |
| Saline | 6 | 6 | 5 | 3 | 2 | 2 | 2 | 2 | 2 | 2 | 2 |

Mice are additionally treated with either SW033291 or vehicle control. SW033291 5 mg/kg was administered IP in a vehicle of 10% Ethanol, 5% Cremophor EL, 85% D5W twice daily (bid) beginning 3 hours prior to acetaminophen injection and continuing at time 0 through 48 hours following acetaminophen injection for 6 total doses. At 120 hours post acetaminophen injection 3 of 6 mice have survived in the SW033291 treated cohort versus 2 of 6 mice in the vehicle control treated cohort.

Table 12 shows a summary of the number of mice surviving out of an initial cohort of 7 C57BL/6J 25 week old female 15-PGDH wild-type (WT) or 7 C57BL/6J 25 week old female 15-PGDH knockout (KO) mice treated with acetaminophen (Tylenol) in phosphate buffered saline administered IP at the LD50 dose of 600 mg/kg.

TABLE 12

| Survival | 0 hrs | 16 hr | 24 hrs | 40 hrs | 48 hrs | 64 hrs | 72 hrs | 88 hr | 96 hr | 112 hr | 120 hr |
|---|---|---|---|---|---|---|---|---|---|---|---|
| WT | 7 | 7 | 7 | 5 | 4 | 3 | 3 | 3 | 3 | 3 | 3 |
| KO | 7 | 7 | 7 | 6 | 6 | 6 | 6 | 6 | 6 | 6 | 6 |

At 120 hours post acetaminophen injection, 6 of 7 knockout mice survive versus 3 of 7 wild-type mice. Increased survival of 15-PGDH knockout mice is consistent with the survival benefit of SW033291 being mediated through inhibition of 15-PGDH.

Example 10

Analysis of Effect of SW033291 on Dextan Sodium Sulfate (DSS) Induced Colitis

This Example provides data from studies of the effect of SW033291 on prevention of induction of colitis in the dextran sodium sulfate (DSS) treated mouse. In the study, 8-12 week old FVB male mice are fed with 2% DSS in drinking water for days 1-7, and then switched to normal drinking water beginning on day 8, and continued through day 22. Mice are treated with twice daily SW033291 5 mg/kg IP in a vehicle of 10% Ethanol, 5% Cremophor EL, 85% D5W, at 125 µg/200 ul, versus with vehicle alone. Clinical scoring (body weight, rectal bleeding, stool consistency) is recorded daily, endoscopic scoring (ulcer number, mucosal thickening, and vascular pattern) is assessed on days 8, 11, 15. Mice are sacrificed on days 1, 8, 15 and 22 for assessment of colon length, colon weight, ulcer number, ulcer area, and crypt damage.

Table 13 shows summary of the baseline properties of age and weight of the 24 SW033291 treated mice and the 24 control group mice used in the study. Also provided is baseline characteristics of 4 FVB male 15-PGDH knockout (KO) mice that are used as a comparator group.

TABLE 13

| FVB PGDH WT/KO male mice 8-12 weeks old | | | | |
|---|---|---|---|---|
| DSS Study | WT-Control | WT-Treatment | KO | p-value |
| Number | 24 | 24 | 4 | |
| Sex | M | M | M | |
| Age (Days) | 74.1 ± 3.7 | 74.2 ± 4.0 | 73.9 ± 3.4 | 0.655 |
| Weight (gm) | 26.3 ± 1.19 | 26.8 ± 1.78 | 27.4 ± 1.4 | 0.391 |

Figure 72:
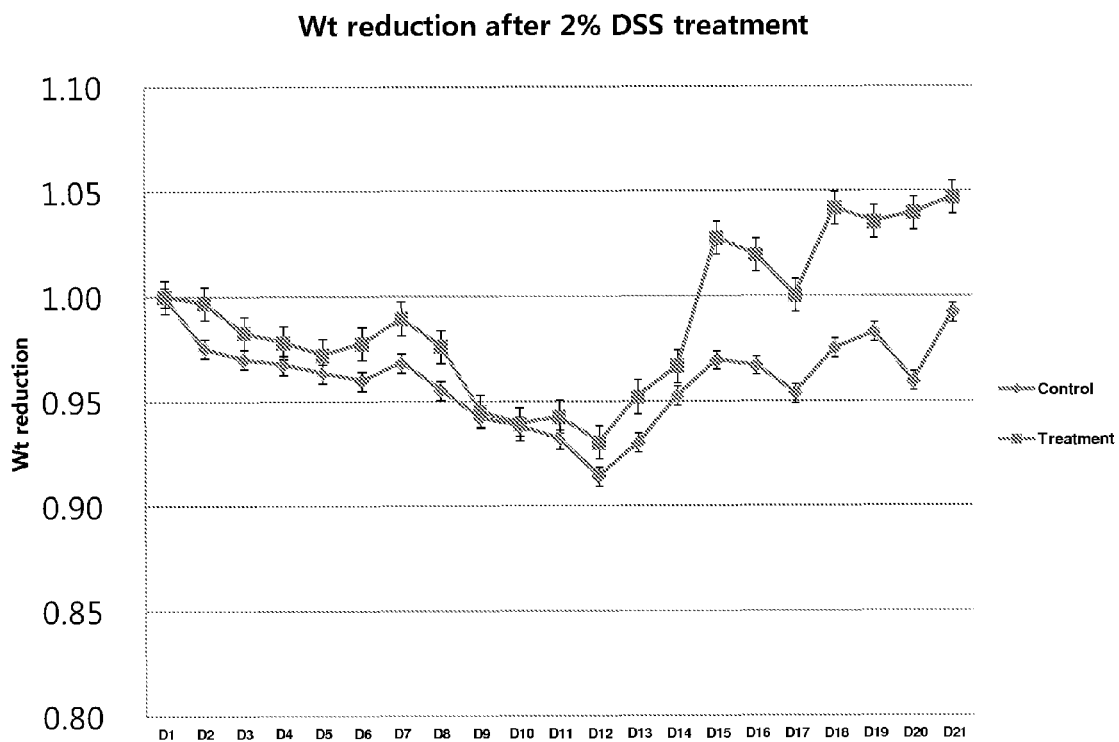
FIG. 72 illustrates a graph showing the average changes from baseline weight of the cohort of control versus SW033291 treated mice all treated with 2% dextran sulfate sodium (DSS) in the drinking water.

FIG. 72 shows a graph of the average changes from baseline weight of the cohort of control versus SW033291 treated mice across the 22 days of the study. SW033291 treated mice show greater weight at all time points, and in particular, show faster weight gain after washout of DSS then do the control mice, P=0.001.

Figure 73:
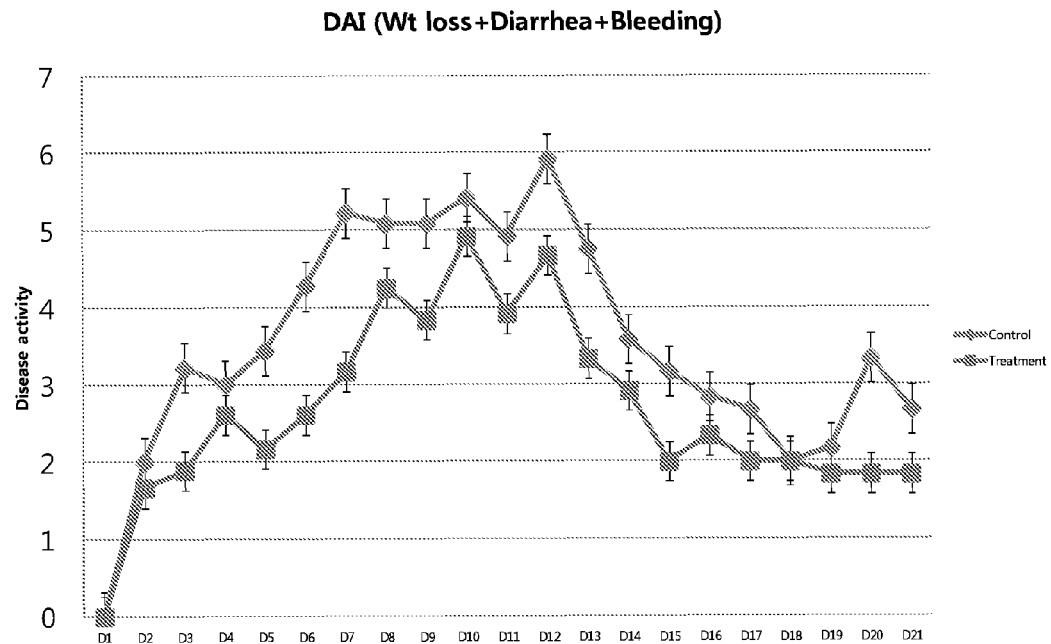
FIG. 73 illustrates a graph of the daily disease activity index of the cohort of control versus SW033291 treated mice all treated with 2% DSS in the drinking water.

FIG. 73 shows a graph of the daily Disease Activity Index (DAI) of the cohort of control versus SW033291 treated mice across the 22 days of the study. The Disease Activity Index is calculated as an equally weighted average of the change from baseline weight, the consistency of stool, and the presence of rectal bleeding, with each component normalized to span an identical numerical range. SW033291 treated mice show a lower Disease Activity Index than do control on each day of the study, P<0.001.

Figure 74:
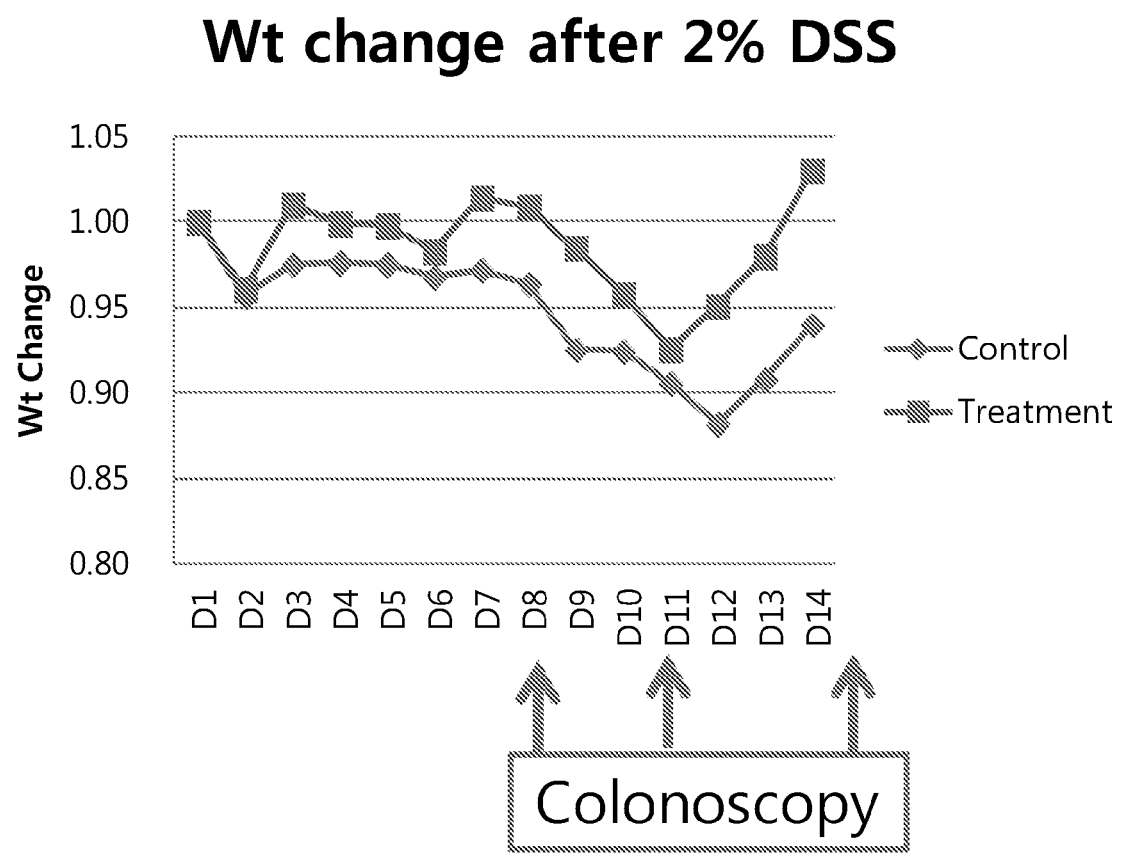
FIG. 74 illustrates a graph showing the average changes from baseline weight of the cohort of DSS treated mice receiving a control vehicle versus SW033291.

FIG. 74 shows the design of the study in which colonoscopic examination of the left colon, up to the splenic flexure, was performed on live mice on days 8, 11 and 15, under isoflurane anesthesia. Daily weights of these SW033291 treated and untreated mice were also recorded and are shown. In addition, post-mortem colonoscopy of the full colon was performed on two SW033291 treated and two control treated mice on day 15, with findings confirming that DSS induced ulcerations are largely confined to the descending colon distal to the splenic flexure.

Figure 75:
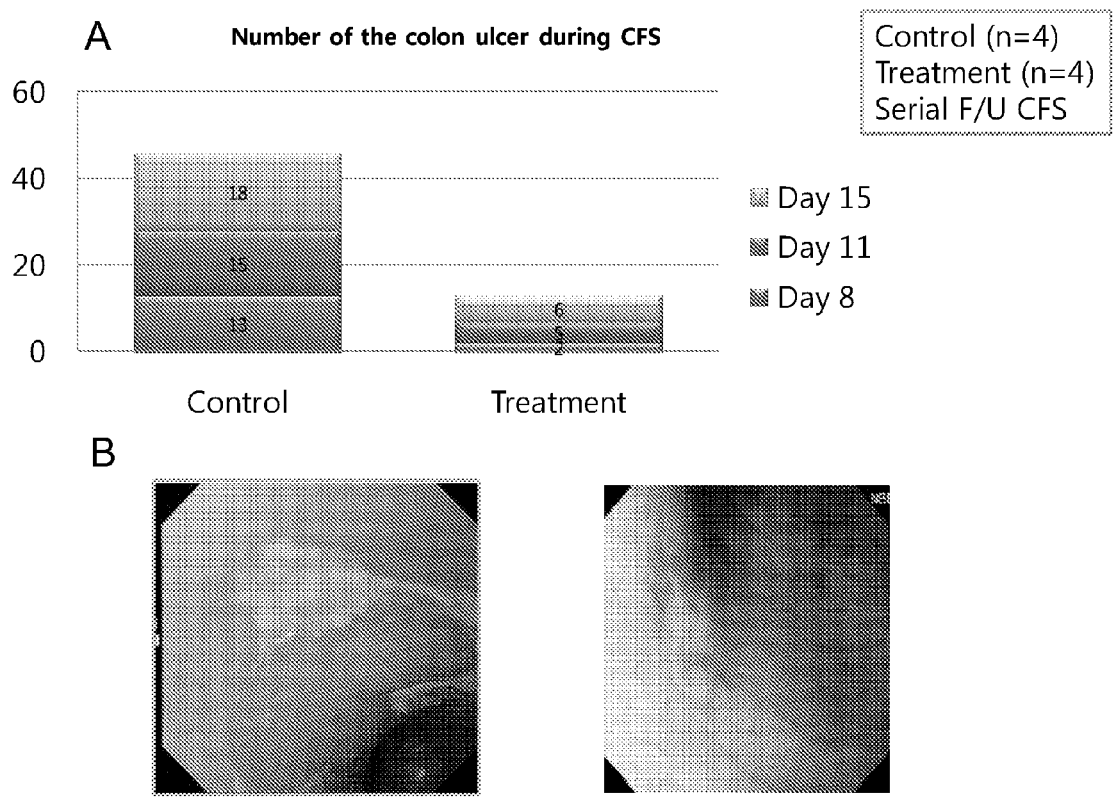
FIGS. 75(A-B) illustrates: (A) a graph showing the number of ulcers in a colon of DSS treated mice receiving a control vehicle versus SW033291; and (B) photographs showing ulcers of DSS treated mice receiving control (left) or SW033291 (right).

FIGS. 75(A-B) show at bottom left the colon as visualized during colonoscopy of a DSS treated control mouse that shows loss of the mucosal vascular pattern and a gross ulceration. At bottom right is shown the colonoscopic findings of a DSS treated mouse receiving SW033291, with only a small ulcer and with maintenance of the normal mucosal vascular pattern otherwise. Graph at top shows numbers of ulcers present on days 8, 11, and 15 in the control versus SW033291 treated mice. SW033291 treatment prevents two-thirds of ulcer formation. Additional studies of 15-PGDH knockout mice show that 15-PGDH gene knockout prevents 95% of colon ulcer formation. These findings support that the colitis prevention activity of SW033291 is mediated through its activity as a 15-PGDH inhibitor, and suggest further modifications of drug dosing and delivery may provide added colitis prevention and would also be expected to protect from other forms of intestinal injury that would include toxicity from radiation, toxicity from chemotherapy, and chemotherapy induced mucositis.

Figure 76:
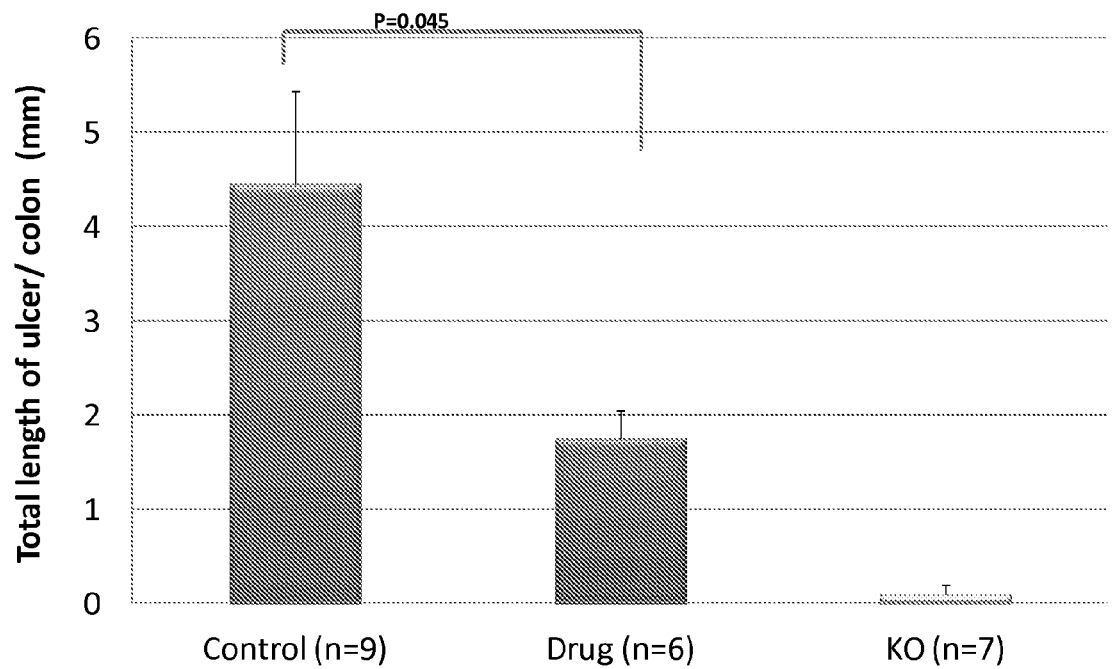
FIG. 76 illustrates a graph showing quantitation of ulcer burden on day 15 of DSS treated mice.

FIG. 76 shows quantitation of ulcer burden on day 15 of DSS treated mice as determined by embedding the full length of the formalin fixed colons of mice in paraffin blocks, and then microscopic inspection of a random 5 am section along the full colon length for visualization and measurement of ulcerated mucosa. The graph shows that the average length of ulcerated mucosa is 4.48 mm per colon section in control mice (N=9 mice) and is reduced by 61% to a length of 1.74 mm per colon section in SW033291 (drug) treated mice (N=6 mice), P=0.045. Again, 15-PGDH gene knockout (KO) is highly effective in preventing colon ulceration, supporting that the therapeutic effect of SW033291 is mediated through inhibition of 15-PGDH.

FIGS. 77(A-B) show examples of scoring murine colonic mucosa according to the Murine Endoscopic Index of Colitis Severity (MEICS) (Becker C. et al. *Gut* 2005; 54: 950-954). At top (A) is shown the colonoscopic findings and MEICS scoring for a DSS treated mouse receiving SW033291. At bottom (B) is shown the colonoscopic findings and MEICS scoring of a DSS treated mouse receiving vehicle only.

Figure 78:
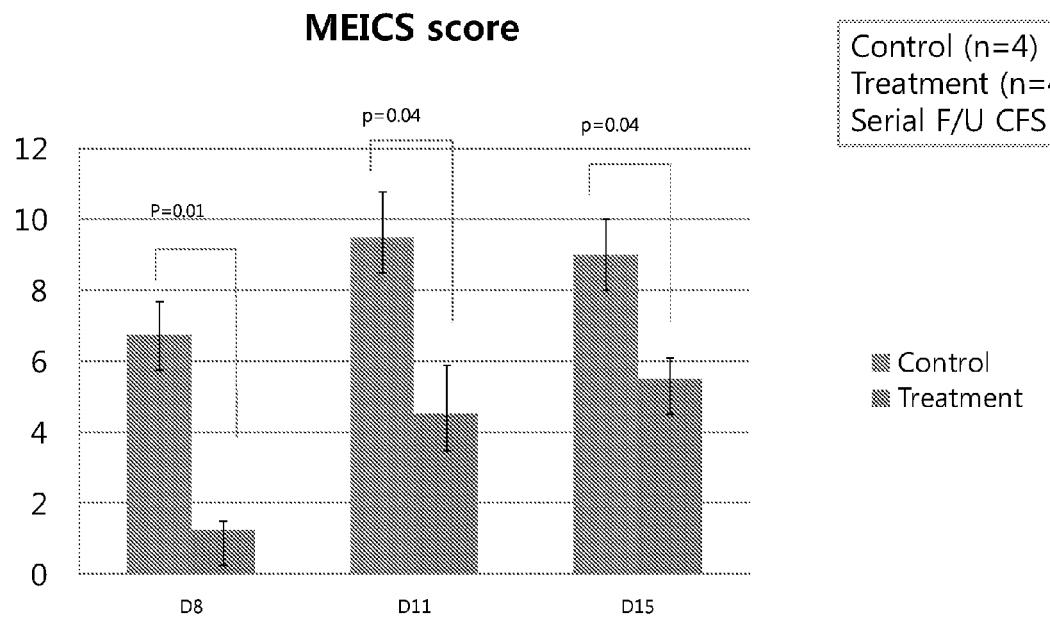
FIG. 78 illustrates a graph showing MEICS score of DSS treated mice receiving a control vehicle or SW033291.

FIG. 78 shows graphs of the MEICS scores for DSS treated mice receiving SW033291 (treatment) versus vehicle (control). MEICS scores show significantly less colitis activity in SW033291 treated mice on days 8, 11 and 15 of the study.

In addition to the gross visual inspection and scoring of colitis activity by the MEICS index, full length colons of mice were formalin fixed and paraffin embedded, and microscopic scoring of crypt damage was performed using the 0-4 severity scale of Cooper H S. Et al., Lab Invest. 1993; 69:238-249. For this analysis, the colons were divided into 3 segments of proximal, middle, and distal colon, each approximately 1.6 cm in length, with each segment was further subdivided into 4 sections each approximately 4 mm in length. For each section the crypt damage severity score was multiplied by the length in mm of the damaged area, creating a 0-16 cryptitis severity index. An average cryptitis severity index was calculated for each segment (proximal, middle, and distal colon), and the summed whole colon cryptitis severity index was determined on a scale of 0-48 for each mouse colon. In parallel with the visual MEICS score, the microscopic cryptitis severity index on day 8 of the DSS protocol was significantly greater in control mice (value of 9.49) than in the SW033291 treated mice (value of 3.16), P<0.05 (data described but not shown in the figure).

Figure 79:
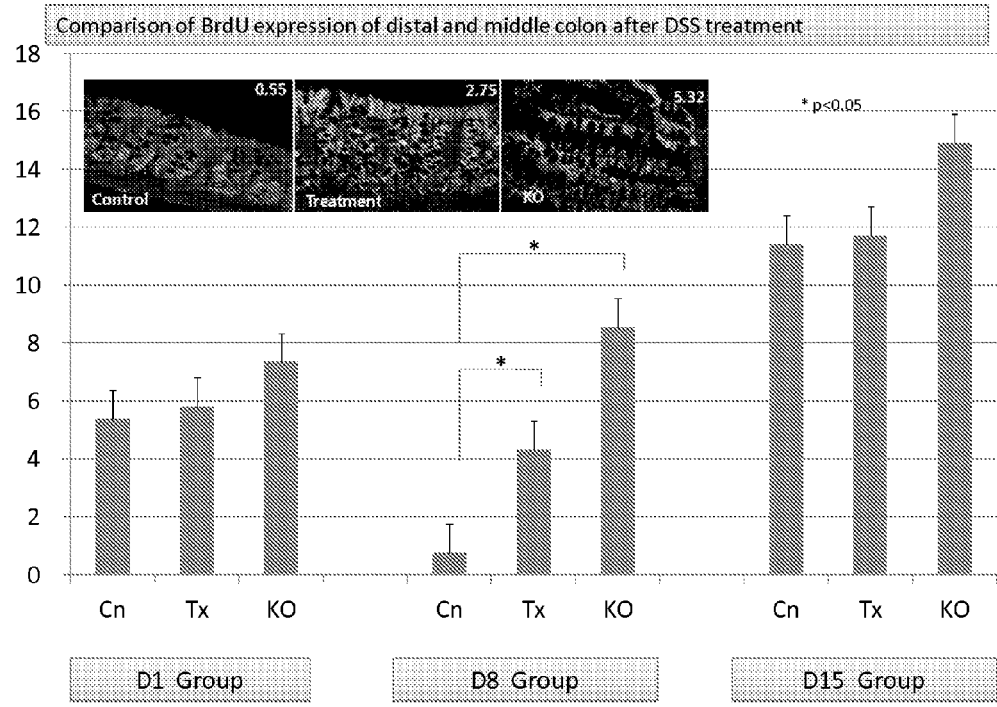
FIG. 79 illustrates photomicrographs of high powered fields from the mid-colon on day 8 of the DSS protocol from control mice, SW033291 treated mice (treatment) and 15-PGDH knockout mice (KO) and a graph depicting sum of the average number of BrdU positive cells per crypt in the distal plus middle colons of control (Cn), SW033219 treated mice (Tx), and 15-PGDH knockout mice (KO) on day 1, day 8, and day 15 of the DSS treatment protocol.

FIG. 79 shows assessment of the effect of SW033291 on maintaining DNA synthesis in the colonic mucosa of DSS treated mice. Mice were injected with BrdU at 100 mg/kg IP 3 hours before sacrifice and then full length colons were formalin fixed and embedded in paraffin. S-phase cells, that have incorporated BrdU into DNA, were visualized by immuno-fluorescent staining of 5 µm thick sections with an antibody that detects the BrdU. Colonic crypts were visualized by immuno-fluorescent staining with an antibody to the epithelial marker E-Cadherin. Photographic insets show photomicrographs of high powered fields taken from the mid-colon on day 8 of the DSS protocol from control mice, SW033291 treated mice (treatment) and 15-PGDH knockout mice (KO). Red immune-fluorescence identifies BrdU positive nuclei, and green immune-fluorescence identifies E-Cadherin positive colonocytes. The number of BrdU positive cell per crypt is determined by counting the number of dual labeled red and green cells per average crypt. Green only cells that are not in S-phase are not counted, and red only cells, that are likely stromal cells outside of crypts, are also not counted. On the photomicrograph shown crypts are displayed as vertically oriented in control and SW033291 treated mice, and crypts are displayed as horizontally oriented in the 15-PGDH knockout mice. In the photographs the numbers of S-phase cells are fewest in the control mice and are increased in the SW033291 treated mice, and increased further in the knockout mice. In the particular photographs shown, the crypts from control mice both lack S-phase cells and are also visually decreased in height; whereas, crypt height is increased in the crypts shown from SW033291 treated mice, and crypt heights is increased further in the crypts shown from 15-PGDH knockout mice. The graph depicts the sum of the average number of BrdU positive cells per crypt in the distal colon plus the average number of BrdU positive cells per crypt middle colons of control (Cn), SW033219 treated (Tx), and 15-PGDH knockout mice (KO) on day 1, day 8, and day 15 of the DSS treatment protocol. On day 8, SW033291 treated mice demonstrate 5.7-fold greater numbers of BrdU positive cells than do control mice, which have lost 85% of the day 1 value of BrdU positive cells per crypt. 15-PGDH knockout mice show no loss of BrdU positive cells in the crypt on day 8, consistent with the protective effect of SW033291 being mediated by inhibition of 15-PGDH.

Table 14 shows a summary of colon length (in cm) in DSS treated mice sacrificed on days 8, 15 and 22, in SW033291 treated mice, versus vehicle treated control mice, versus 15-PGDH knockout (KO) mice, where shortening of the colon is a measure of disease activity.

TABLE 14

Colon length shortening may be correlated to severity of the colon ulceration

| Time Point | Control | SW033291 | KO | P-value |
|---|---|---|---|---|
| Baseline | 8.3 + 0.2 | 8.4 + 0.2 | | 0.71 |
| Day 8 | 6.6 + 0.4 | 6.6 + 0.1 | | 1.0 |
| Day 15 | 7.1 + 0.1 | 7.5 + 0.1 | 8.5 + 0.1 | 0.001 |
| Day 22 | 7.4 + 0.2 | 8.6 + 0.3 | | 0.012 |

Figure 80:
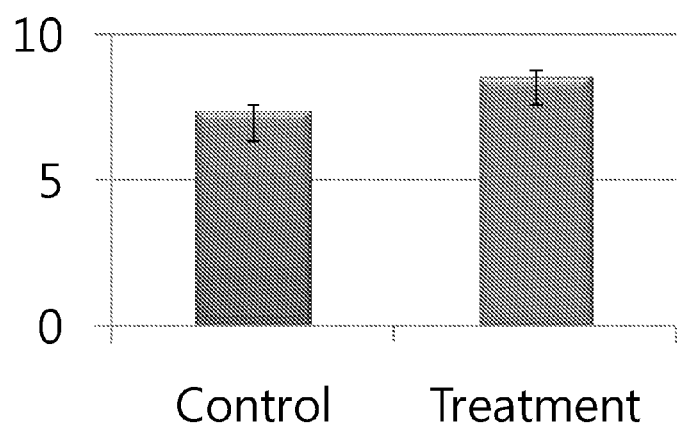
FIG. 80 illustrates a graph showing colon length at day 22 of DSS treated mice receiving a control vehicle or SW033291.
Figure 81A:
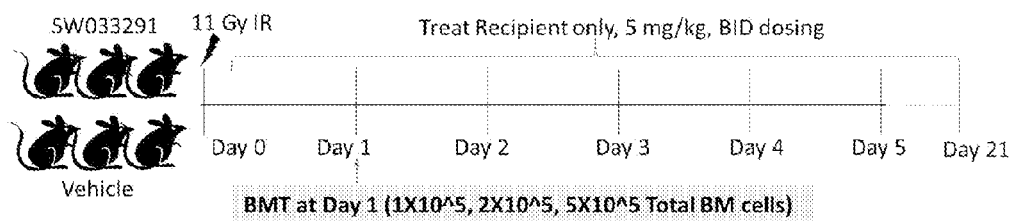
FIGS. 81(A-E) illustrate: (A) a schematic illustration showing the design of a study of enhanced survival in mice receiving a bone marrow transplant and also administered the 15-PGDH inhibitor SW033291; (B) graphical survival curves for mice transplanted with 100,000 donor cells; (C) graphical survival curves for mice transplanted with 200,000 donor cells; (D) graphical survival curves for mice transplanted with 500,000 donor cells; and (E) tabular survival data for all mice in the study on study day 30.
Figure 81B:
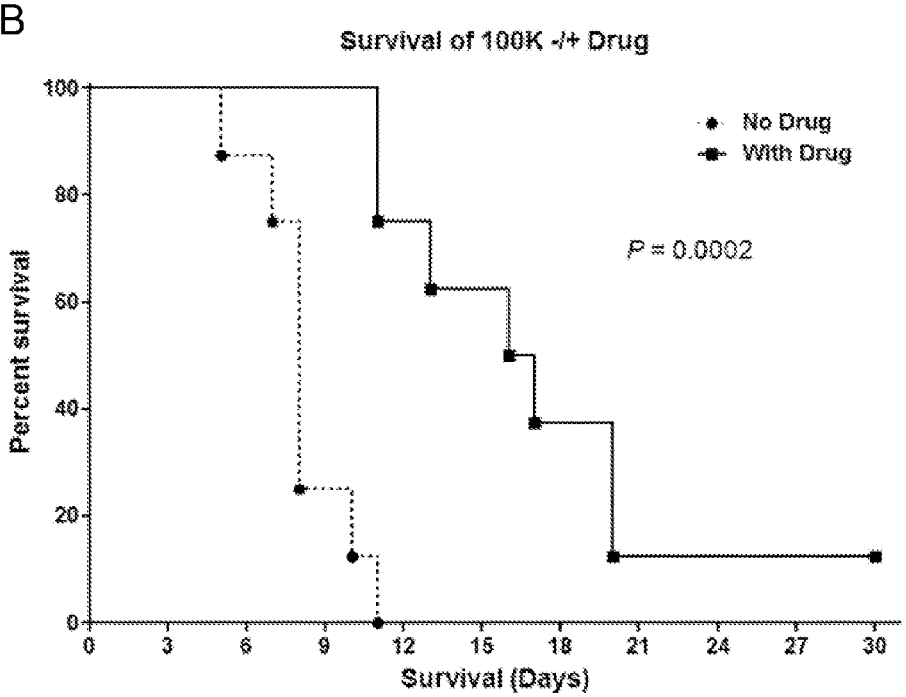
Figure 81C:
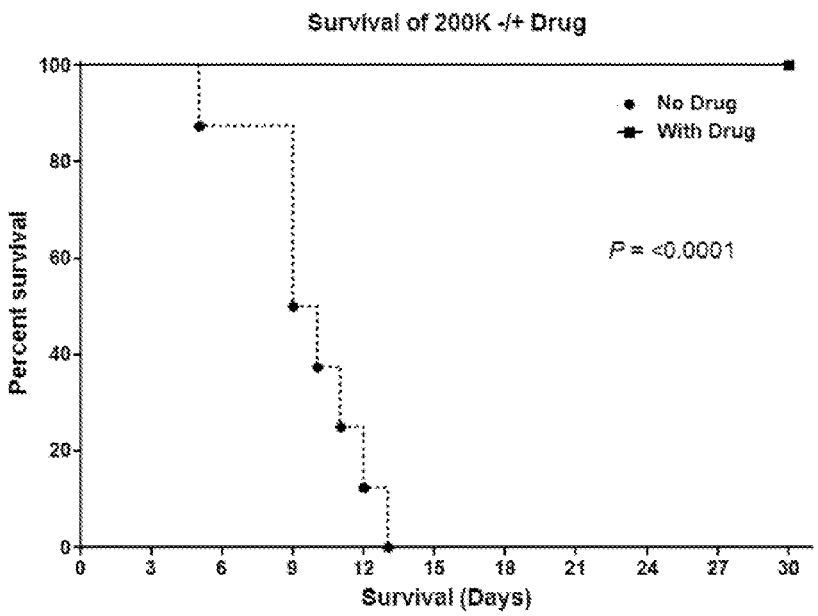
Figures 81D, 81E:
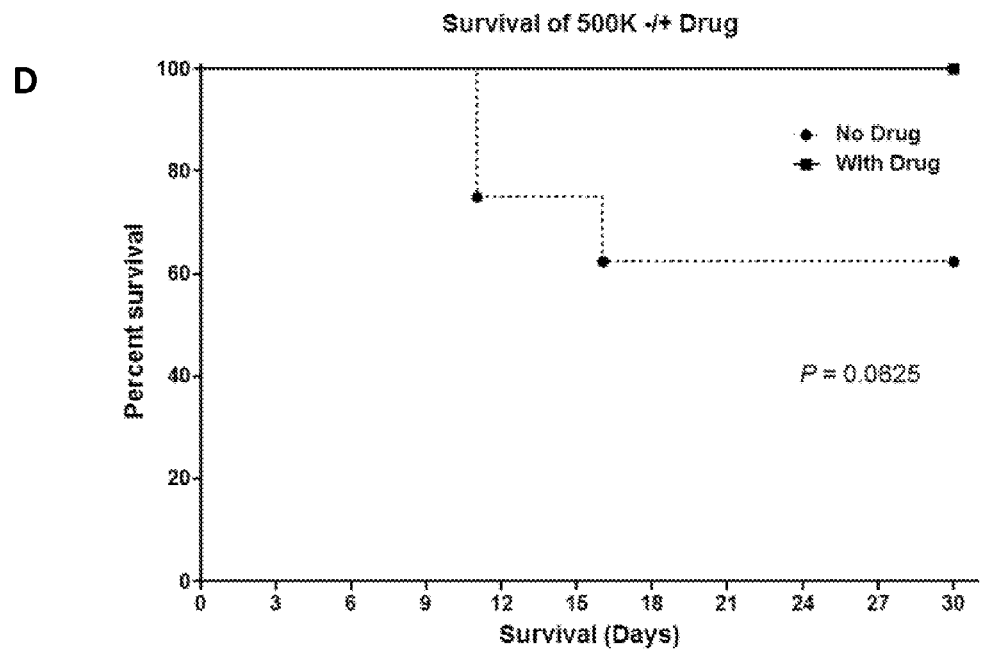

Vehicle treated control mice show significantly greater colon shortening at day 22 versus SW033291 treated mice, P=0.012. This comparison is also shown graphically in FIG. 80.

Table 15 shows a summary on day of sacrifice of mouse weights (gms) and colon lengths (cm) for DSS treated mice receiving SW033291 or vehicle control.

TABLE 15

| | Vehicle | SW033291 | KO |
|---|---|---|---|
| Wt @ sacrifice-gm Time Point | | | |
| Baseline | 26.3 + 0.7 | 25.9 + 0.7 | 29.2 + 1.3 |
| Day 8 | 25.4 + 0.7 | 26.4 + 0.5 | |
| Day 15 | 24.4 + 0.5 | 25.2 + 0.9 | |
| Day 22 * | 26.3 + 0.7 | 28.2 + 0.5 | |
| Colon length-cm Time Point | | | |
| Baseline | 8.3 + 0.2 | 8.4 + 0.2 | 8.5 + 0.1 |
| Day 8 | 6.6 + 0.4 | 6.6 + 0.1 | |
| Day 15 | 7.1 + 0.1 | 7.5 + 0.1 | |
| Day 22 * | 7.4 + 0.2 | 8.6 + 0.3 | |

On day 22 SW033291 treated mice show greater body weight and greater colon lengths, indicative of therapeutic effect of SW033291 in protecting against DSS induced colitis.

Example 11

Analysis of Effect of SW033291 on Survival of Mice Following Bone Marrow Transplant FIG. 81 shows enhanced survival in mice receiving a bone marrow transplant and also administered the 15-PGDH inhibitor SW033291. FIG. 81A shows the design of the study. Mice were irradiated with a bone marrow ablative dose of 11Gy on day 0, followed by administration of SW033291 in 5 mg/kg twice daily by intraperitoneal injection in a vehicle of 10% Ethanol, 5% Cremophor EL, 85% D5W at a concentration of 125 µg/200 µl. A matched control cohort received injections with vehicle only. On day one mice received an infusion of donor marrow at doses of 100,000 cells; 200,000 cells; or 500,000 cells. FIG. 81B shows graphical survival curves for mice transplanted with 100,000 donor cells. FIG. 81C shows graphical survival curves for mice transplanted with 200,000 donor cells. FIG. 81D shows graphical survival curves for mice transplanted with 500,000 donor cells. And FIG. 81E shows tabular survival data for all mice in the study on study day 30. Among mice receiving 100,000 donor cells, all mice succumb, but SW033291 treated mice show an approximate doubling of median survival. Among mice receiving 200,000 donor cells, all control mice were dead by day 12. In contrast, all mice receiving 200,000 donor cells plus SW033291 survived at 30 days of observation and were successfully engrafted. Among mice receiving 500,000 donor cells, control mice showed a 37.5% mortality; whereas, mice receiving SW033291 again all survived.

FIG. 82 shows a set of studies conducted on lethally irradiated mice that received 500,000 donor marrow cells and were treated with either SW033291 at 5 mg/kg intraperitoneal dose twice daily or with vehicle control, in a design otherwise identical to that used for the studies of FIG. 81. FIG. 82A shows measurements on blood and bone marrow on day 5 after transplant, with FIG. 82B showing that SW033291 treated mice have significantly higher total white count and FIG. 82C showing that SW033291 treated mice have significantly higher total platelet count. The star symbol denotes $P<0.05$.

Figure 83A:
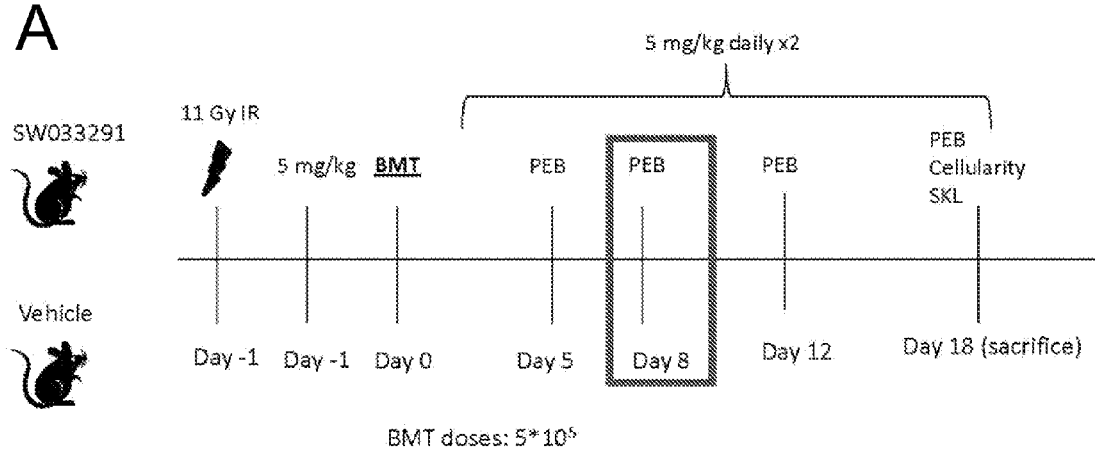
FIGS. 83(A-B) illustrate: (A) a schematic illustration showing measurements on blood and bone marrow on day 8 after transplant; and (B) a graph showing that SW033291 treated mice have significantly higher platelet count than control, with drug treated mice having 77,000 platelets compared to control mice having 39,500 platelets. The star symbol denotes P<0.05.
Figure 83B:
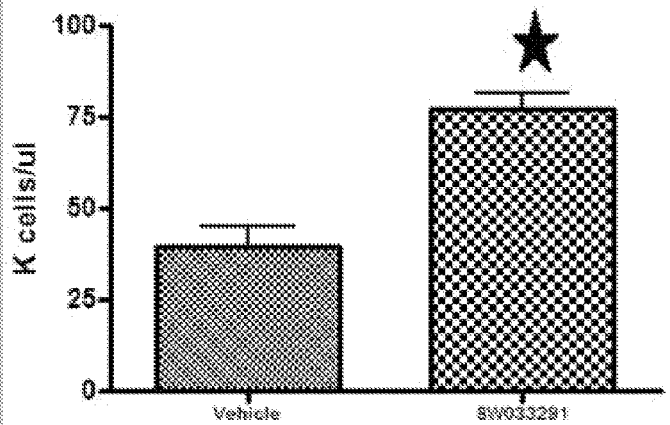

FIG. 83A shows measurements on blood and bone marrow on day 8 after transplant. FIG. 83B shows that SW033291 treated mice have significantly higher platelet count than control, with drug treated mice having 77,000 platelets compared to control mice having 39,500 platelets. The star symbol denotes $P<0.05$.

FIG. 84A shows measurements on blood and bone marrow on day 12 after transplant. FIG. 84B shows that SW033291 treated mice have significantly higher neutrophil counts, with drug treated mice having 332 neutrophils compared to control mice having 125 neutrophils. FIG. 84C shows that on day 12 after transplant, SW033291 treated mice have significantly higher hemoglobin count than controls, with drug treated mice having hemoglobin level of 11.58 and control mice having hemoglobin level of 8.3. Additionally, FIG. 84D shows SW033291 treated mice also have significantly greater total white counts than control mice. The star symbol denotes $P<0.05$.

FIG. 85A shows measurements on blood and bone marrow on day 18 after transplant. SW033291 treated mice have significantly higher total white count (FIG. 85B), lymphocyte count (FIG. 85C), and neutrophil count (FIG. 85D), with drug treated mice having 835 neutrophils and control mice having 365 neutrophils (FIG. 85D). In comparison with counts on day 12, administration of SW033291 accelerates recovery of neutrophil counts by nearly 6 days (FIG. 84B versus FIG. 85D). FIG. 84E also shows that on day 18 drug treated mice have significantly higher platelet counts than control mice. Last, day 18, drug treated mice have nearly 4-fold increased percentage (FIG. 84F) and total numbers (FIG. 85G) of SKL marked bone marrow stem cells than do control mice, with drug treated mice having a mean of 4127 SKL marked bone marrow cells compared to control mice having a mean of 967 SKL marked bone marrow cells. The star symbol denotes $P<0.05$.

FIG. 86(A) shows measurement of PGE2 (pg of PGE2/mg tissue protein) in 4 different mouse tissues (colon, bone marrow, liver, lung) across time following IP injection of SW033291 at 10 mg/kg. Blue bar represents baseline at time 0, and red bars represent time course of PGE2 concentration from 1-12 hours following SW033291 injection. FIG. 86(B) shows time course of PGE2 in control mice injected with vehicle only.

FIG. 87 shows a schema of an experiment in which mice are lethally irradiated (IR) and 12 hours later receive a transplant (BMT) with CFSE dye labeled bone marrow cells (BM), and the number of transplanted cells that home and survive in the bone marrow of the recipient mice are then determined by FACS at 16 hours post-transplant. In different arms of the experiment mice are treated with vehicle, with SW033291 (10 mg/kg IP), or with SW033291 (10 mg/kg IP) plus Indomethacin. Drugs are administered following radiation, following the transplant, and again at 8 hours after the transplant.

Figure 88:
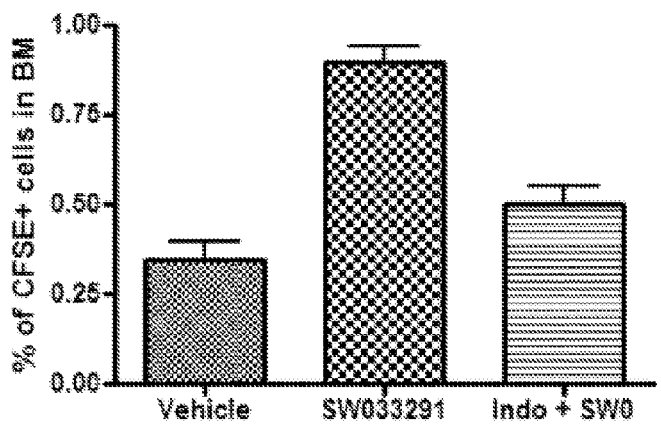
FIG. 88 illustrates a graph showing the percent of CFSE dye labeled cells that have homed to the bone marrow of mice treated as illustrated in FIG. 87.

FIG. 88 shows a graph illustrating the percent of CFSE dye labeled cells that have homed to the bone marrow of mice treated as per the schema described in FIG. 87. Treating mice with SW033291 concurrent with and following the bone marrow transplant increases numbers of homed cells in the recipient mouse bone marrow 3-fold. The figure further shows that the effect of SW033291 is near completely blocked by indomethacin (Indo+SW0), an inhibitor of COX enzymes the produce prostaglandins. This is consistent with the effect of SW033291 being mediated through the inhibition of 15-PGDH and through the resulting increase in tissue prostaglandins.

Figure 89:
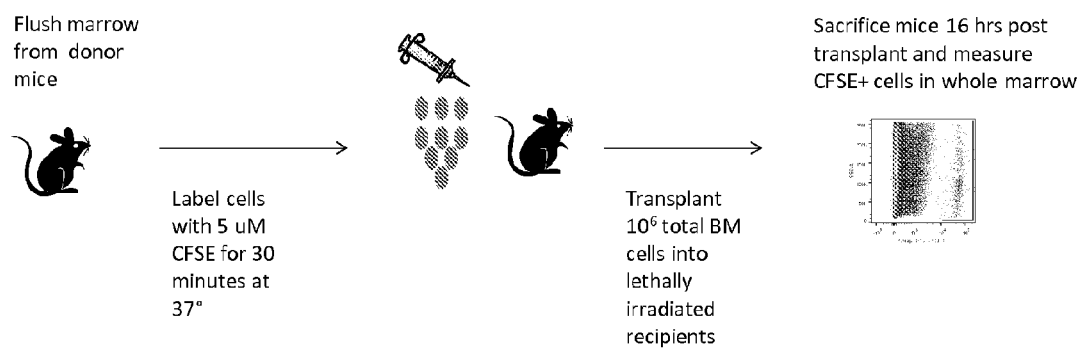
FIG. 89 is a schematic illustration showing an experiment in which mice are lethally irradiated (IR) and 12 hours later receive a transplant (BMT) with CFSE dye labeled bone marrow cells (BM), and number of transplanted cells that home and survive in the bone marrow of the recipient mice are then determined by FACS at 16 hours post-transplant.

FIG. 89 shows a schema of an experiment in which mice are lethally irradiated (IR) and 12 hours later receive a transplant (BMT) with CFSE dye labeled bone marrow cells (BM), and number of transplanted cells that home and survive in the bone marrow of the recipient mice are then determined by FACS at 16 hours post-transplant. In different arms of the experiment mice are treated with vehicle, with SW033291 (10 mg/kg IP), with SW033291 (10 mg/kg IP) plus an antagonist of PGE2 receptor EP2 (PF-04418948), or with SW033291 (10 mg/kg IP) plus an antagonist of PGE2 receptor EP4 (L-161,982). Drugs are administered following radiation, following the transplant, and again at 8 hours after the transplant.

FIG. 90 shows a graph illustrating the percent of CFSE dye labeled cells that have homed to the bone marrow of mice treated as per the schema described in FIG. 89. Treating mice with SW033291 concurrent with and following the bone marrow transplant increases numbers of homed cells in the recipient mouse bone marrow 2-fold. The figure further shows that the effect of SW033291 is near completely blocked by an antagonist to the EP4 receptor (EP4+SW0), and is partially blocked by an antagonist of the EP2 receptor (EP2+SW0). This is consistent with the effect of SW033291 being mediated through the inhibition of 15-PGDH and through the resulting increase of tissue prostaglandins, including PGE2.

FIG. 91 shows a schema of an experiment in which mice are injected with SW033291 twice daily IP at 10 mg/kg for 5 doses. 2 hours following the last dose bone marrow is harvested and sorted into SKL marked cells that are hematopoietic stem cell enriched and into CD45 (−) cells that are bone marrow stroma cells. RNA was extracted and gene expression determined relative to levels in mice injected with vehicle control.

FIGS. 92(A-B) show graph illustrating induction of gene expression in bone marrow SKL cells and bone marrow stromal cells of SW033291 treated mice. Mice administered SW033291 show a 3 fold induction in RNA expression of CXCL12 and SCF in bone marrow SKL cells, and show a greater than 4-fold induction of CXCL12 and SCF in CD45(−) bone marrow stromal cells.

Figure 93:
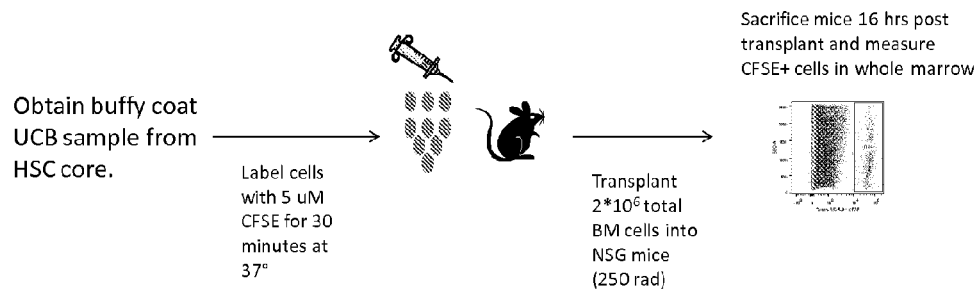
FIG. 93 is a schematic illustration showing an experiment in which immune deficient NSG mice are lethally irradiated (IR) and 12 hours later receive a transplant with CFSE dye labeled buffy coat cells from human umbilical cord blood (UCB), and number of transplanted cells that home and survive in the bone marrow of the recipient mice are then determined by FACS at 16 hours post-transplant.

FIG. 93 illustrates a schema of an experiment in which immune deficient NSG mice are lethally irradiated (IR) and 12 hours later receive a transplant with CFSE dye labeled buffy coat cells from human umbilical cord blood (UCB), and number of transplanted cells that home and survive in the bone marrow of the recipient mice are then determined by FACS at 16 hours post-transplant. In different arms of the experiment mice are treated with vehicle or with SW033291. Drugs are administered following radiation, following the transplant, and again at 8 hours after the transplant.

Figure 94:
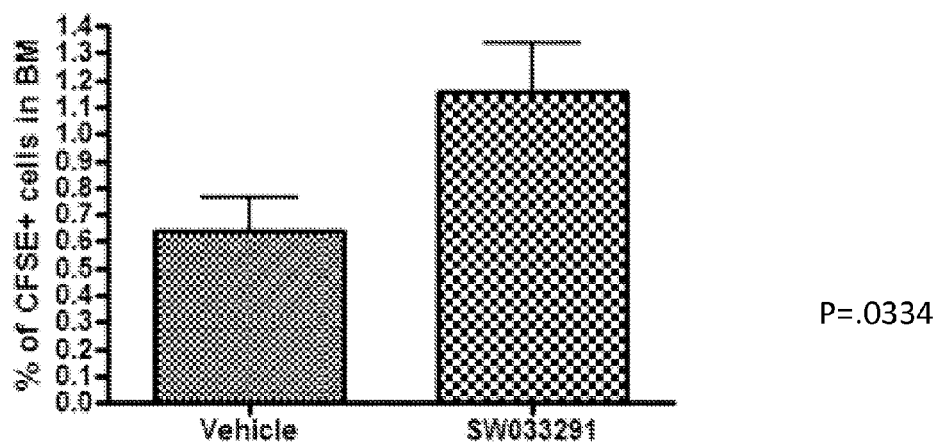
FIG. 94 illustrates a graph showing the percent of CFSE dye labeled human umbilical cord buffy coat cells that have homed to the bone marrow of mice treated as per the schema above.

FIG. 94 illustrates a graph showing the percent of CFSE dye labeled human umbilical cord buffy coat cells that have homed to the bone marrow of mice treated as per the schema described in FIG. 94. Treating mice with SW033291 at the time of and following the transplant with buffy coat from human umbilical cord blood (UCB) increases numbers of homed human cells in the recipient mouse bone marrow nearly 2-fold.

Example 12

Analysis of Activity of Isomers of SW033291, a 15-PGDH Inhibitor

FIG. 95 illustrates isomers of SW033291. Shown at top is that Sulfoxides (the S=O group) are stereogenic such that SW033291 exists as a racemic mixture of two non-interconverting isomers. These enantiomers were separated by preparative HPLC to provide isomers designated as isomer A (first eluting) and isomer B (second eluting). A 1 cm Chiralcel-ODH column resolves the enantiomers using isopropanol in hexanes. A representative analytical HPLC trace is shown at bottom. Isomer A was found to consist predominantly of the levorotatory enantiomer: [a]D=−97 (c=0.22, acetone). Isomer B was found to consist predominantly of the dextrorotatory enantiomer: [a]D=+95 (c=0.22, acetone). X-ray crystallography has assigned (−) isomer A as the S isomer and B as the (R) isomer (as shown in Table 1)

Figure 96:
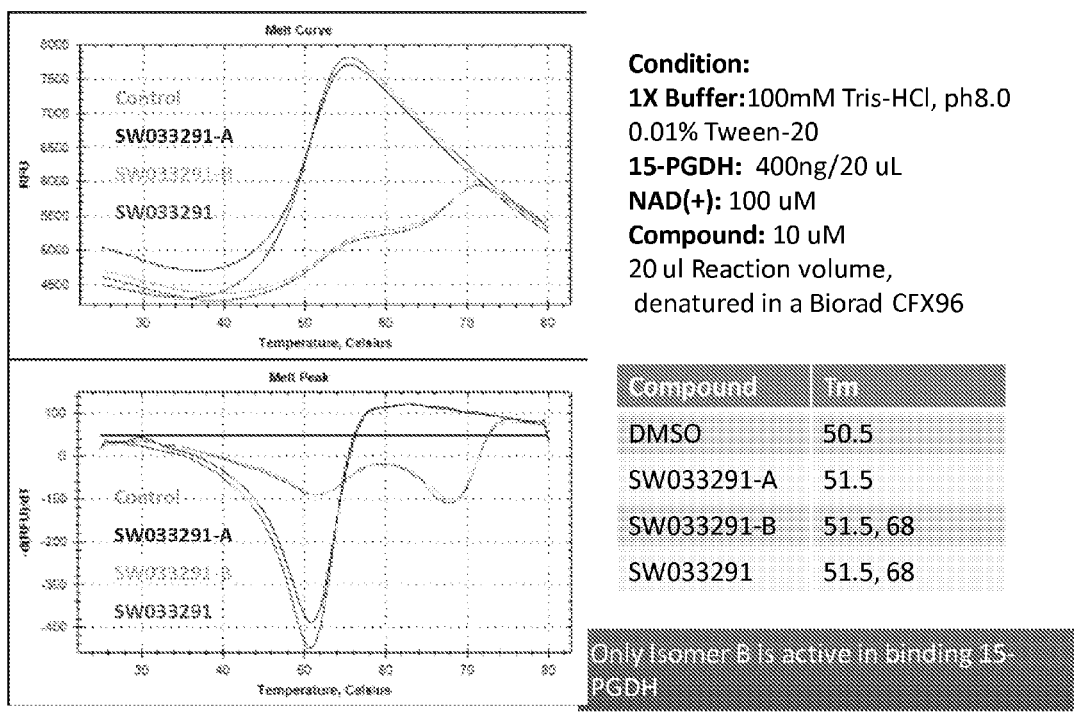
FIG. 96 illustrates plots showing thermal denaturation of recombinant 15-PGDH protein using Differential Scanning Fluorimetry with SYPRO Orange.

FIG. 96 illustrates plots showing thermal denaturation of recombinant 15-PGDH protein using Differential Scanning Fluorimetry with SYPRO Orange. Top panel graphs Relative Fluorescence Units (RFU) versus temperature for recombinant 15-PGDH in presence of DMSO control, SW033291, SW033291-A (isomer A), or SW033291-B (isomer B). Lower panel graphs −d(RFU)/dT. The melting temperatures are indicated in the table at lower left. Only isomer B shows that activity of SW033291 in binding to 15-PGDH and shifting the melting temperature from 50.5° C. to 68° C.

Figure 97:
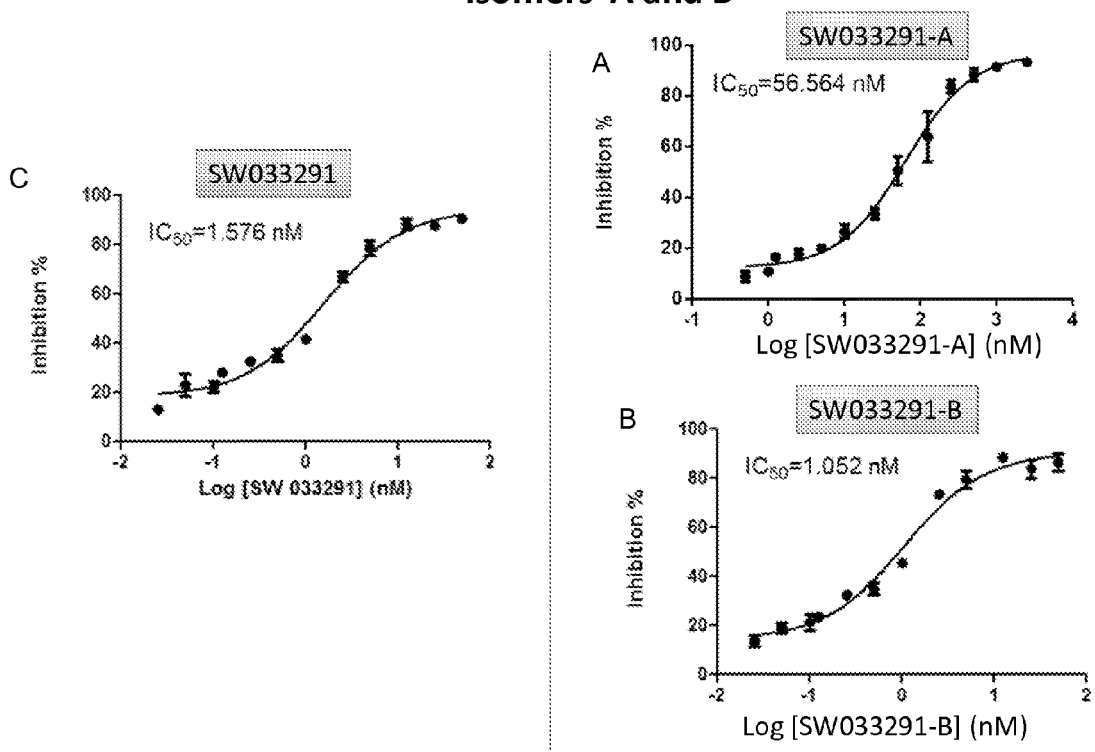
FIGS. 97(A-C) illustrate inhibition of recombinant 15-PGDH protein enzymatic activity by SW033291 stereogenic isomers A and B.

FIGS. 97(A-C) illustrate inhibition of recombinant 15-PGDH protein enzymatic activity by SW033291 stereogenic isomers A and B. Graphed at left is the percent inhibition of enzyme activity of recombinant 15-PGDH protein versus concentration of SW033291, and the $IC_{50}$ for inhibition. Graphed at right is the percent inhibition of recombinant 15-PGDH versus concentration of SW033291 isomer A (top) of isomer B (bottom). As shown isomer B has 40% lower $IC_{50}$ than the parent racemic mixture; whereas; isomer A shows an $IC_{50}$ 36 fold higher than the racemic mixture. These results are consistent with the activity of SW033291 in inhibiting 15-PGDH largely due to the activity of isomer B. The small residual activity of isomer A may be due to possible 3% contamination with some residual isomer B.

Figure 98:
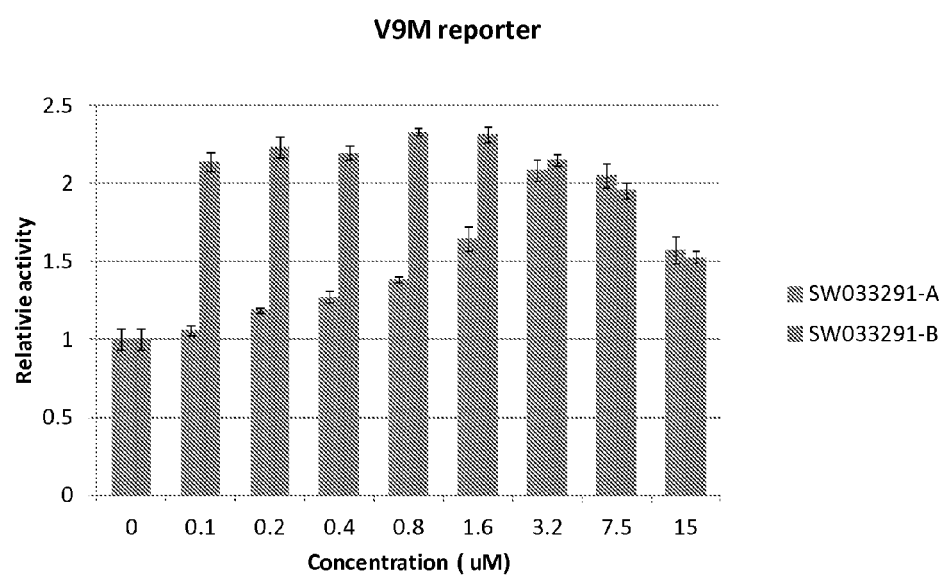
FIG. 98 is a graph showing the activity in inducing activity of a 15-PGH-luciferase fusion protein reporter in the Vaco-9M (V9M) cell line background of SW033291 isomers A and B.

FIG. 98 is a graph showing the activity in inducing activity of a 15-PGH-luciferase fusion protein reporter in the Vaco-9M (V9M) cell line background of SW033291 isomers A and B. Full activity in this assay is seen for SW033291 isomer B at 0.1 µM added compound. Some residual activity is seen for isomer B when added at 3.2 µM concentration. The small residual activity of isomer A may be due to possible 3% contamination with some residual isomer B.

Example 13

Analysis of in Silico Docking of SW033291 onto 15-PGDH

Figure 99:
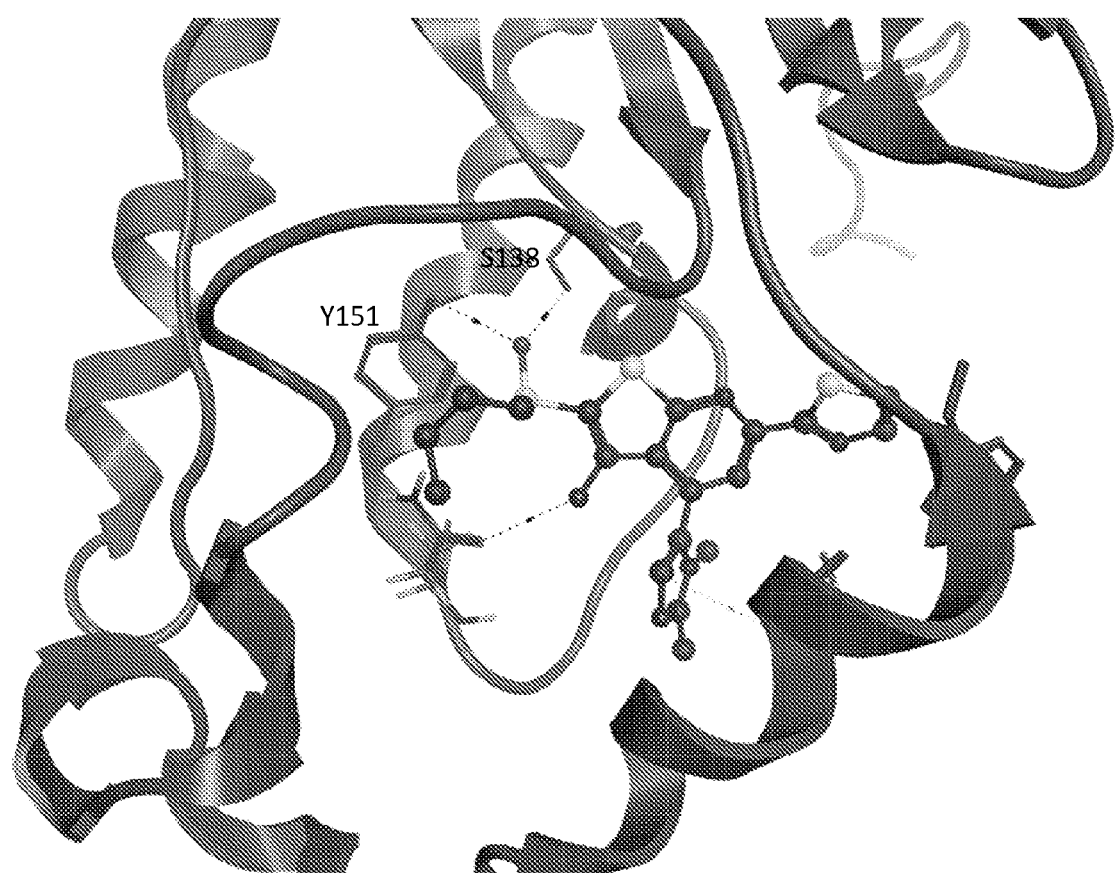
FIG. 99 is an image showing the conformation of SW209415 docked into the active site of PGDH.

FIG. 99 illustrates images showing docked pose of SW209415 onto the 15-PGDH crystal structure. The model shows that the sulfoxide moiety on SW209415 coordinates with Tyr-151 in 15-PGDH, that is required for catalytic activity of 15-PGDH and that is strictly conserved across the family of short chain dehydrogenases. Moreover, the SW209415 sulfoxide is also coordinated with Ser-138, that is also required for catalytic activity of 15-PGDH and that is highly conserved across the family of short chained dehydrogenases. Thus, it is expected that the core structure of inhibitor would broadly interact and inhibit any short chain dehydrogenase whose catalytic function depended on a tyrosine analogous to 15-PGDH Tyr-151 and/or a serine analogous to Ser-138.

Example 14

Analysis of Analogues of Lead Compounds SW033291, a 15-PGDH Inhibitor

This Example provides data on a group of structural analogues of SW033291. Data provided includes level of induction of a 15-PGDH-luciferase fusion gene reporter, recorded as % increased luciferase activity over basal level, in three colon cancer cell lines, V9m, V503, and LS174T, engineered to contain the reporter, and treated the compound (i.e., Values are recorded on a scale where 100 indicates of doubling of luciferase activity over baseline level).

Figure 100:
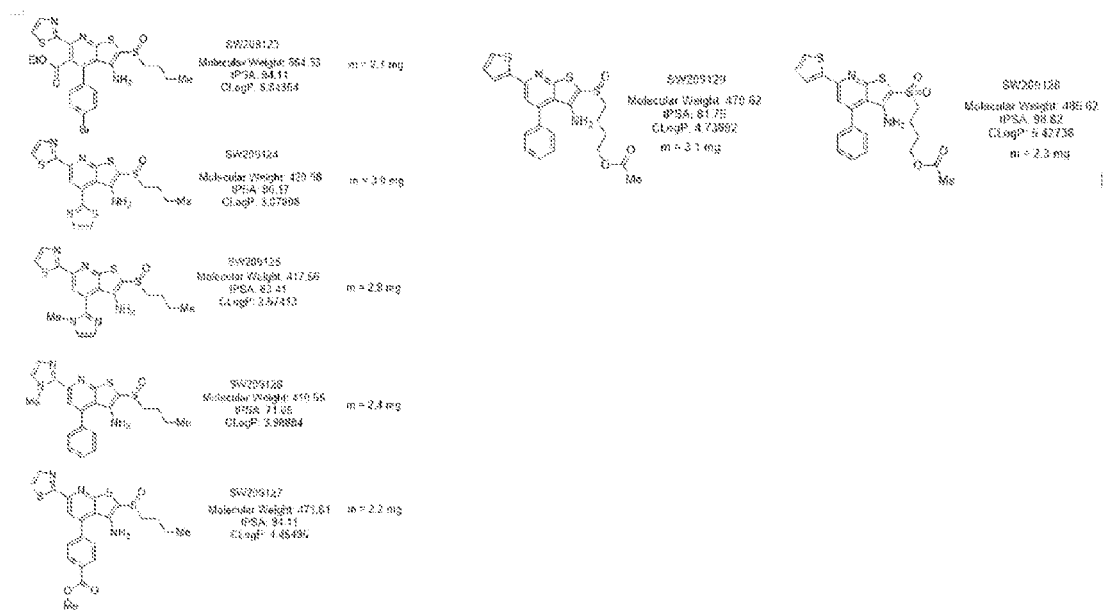
FIG. 100 illustrates analogs of SW033291.

FIG. 100 shows chemical structures of a set of seven compounds, designated SW209123 through SW209129, that are structurally related to SW033291.

Figure 101:
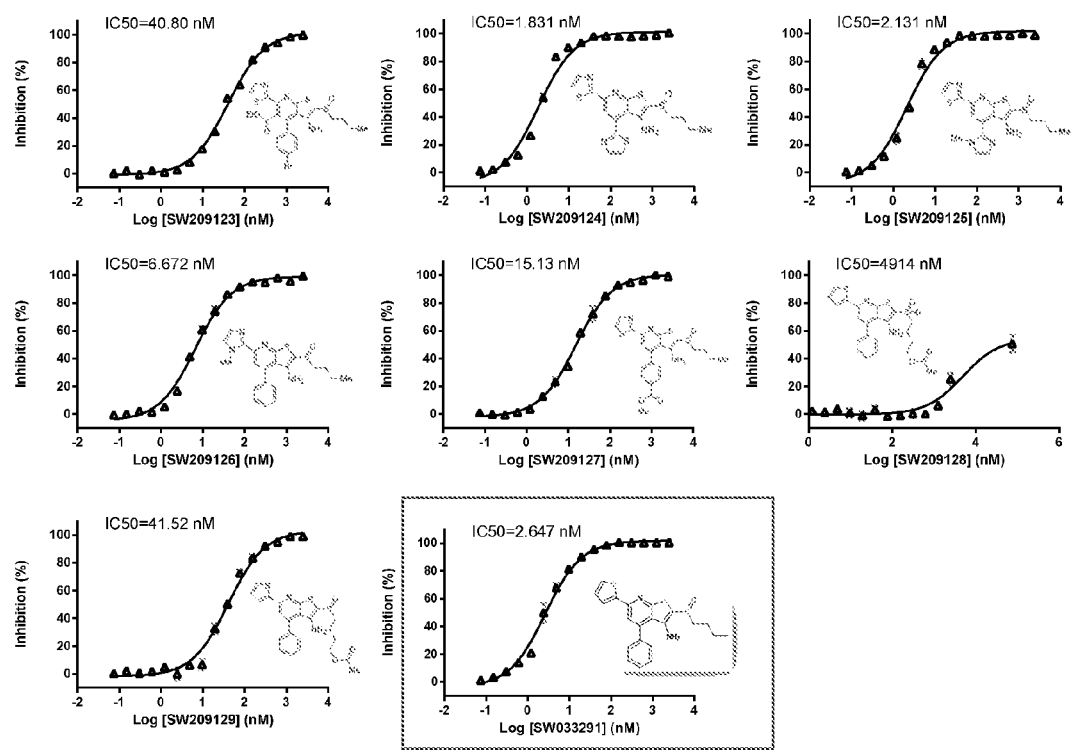
FIG. 101 illustrates plots of inhibition of 15-PGDH protein by analogs of SW033291 shown in FIG. 100.

FIG. 101 shows the activity of each compound SW209123 through SW209129 in inhibiting the enzymatic activity of recombinant 15-PGDH protein in in vitro assays, with the percent inhibition graphed on the Y-axis and the Log of the compound concentration in nM graphed on the X-axis. The inhibition curve for SW033291 is shown as a comparator. The $IC_{50}$ for each compound is recorded. Two compounds, SW209124 and SW209125, show lower IC$_{50}$, and hence higher activity, than does SW033291.

Figure 102:
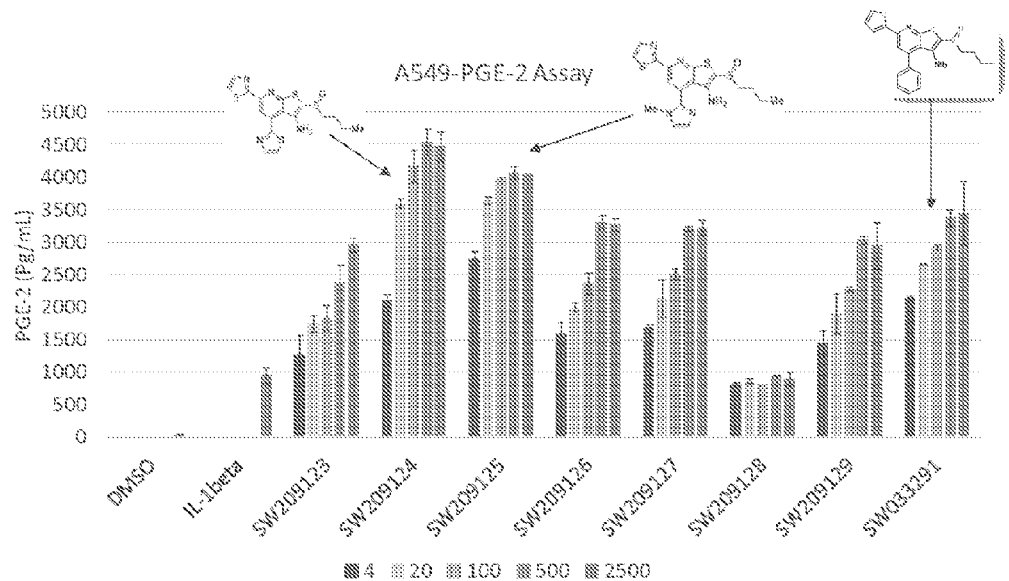
FIG. 102 illustrates a graph showing the dose response effect of analogs of SW033291 shown in FIG. 100 on $PGE_2$ production from IL1-beta treated A549 cells.

FIG. 102 shows the activity of compounds SW209123 through SW209129 in inducing PGE2 as assayed in the medium of A549 cells that have first been activated with IL-1beta. For comparison, also shown is induction of PGE2 as assayed in the medium of A549 cells that have first been activated with IL-1beta and then treated with SW033291. Graphed are the effects of exposing the IL-1beta stimulated A549 cells to increasing compound concentrations of 4 nM, 20 nM, 100 nM, 500 nM, and 2500 nM. For comparison PGE2 levels are shown for DMSO treated A549 cells and for A549 cells treated with IL-1beta only. In this assay, SW209124 and SW209125 show increased activity relative to SW033291 in this assay.

Figure 103:
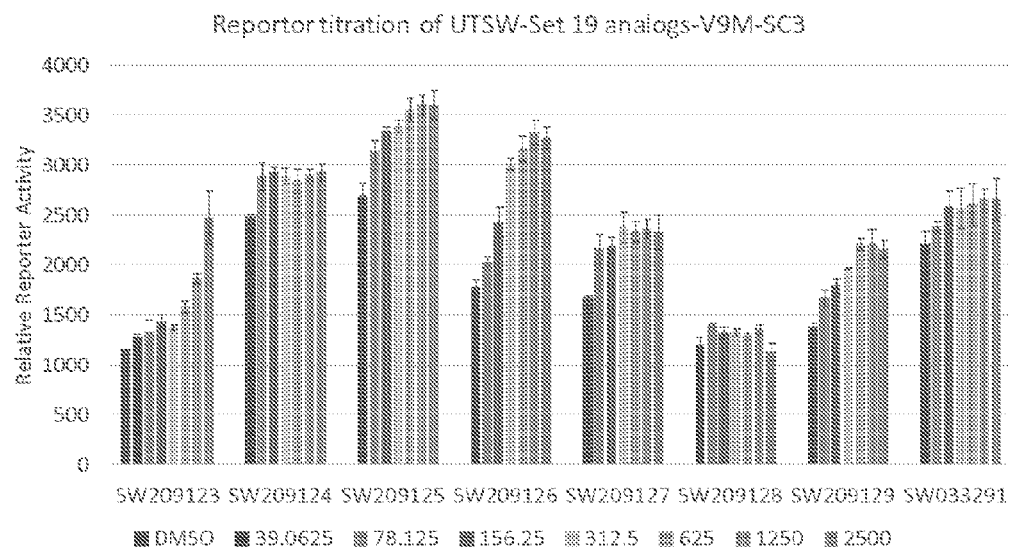
FIG. 103 illustrates a graph showing luciferase activity of colon cancer cell V9m treated with various dosages of analogs of SW033291 shown in FIG. 100.

FIG. 103 shows activity of compound SW209123 through SW209129 in inducing luciferase activity in a reporter cell line constructed from the Vaco 9M (V9M) colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 39.0635 nM, 78.124 nM, 156.25 nM, 312.5 nM, 625 nM, 1250 nM, and 2500 nM.

Figure 104:
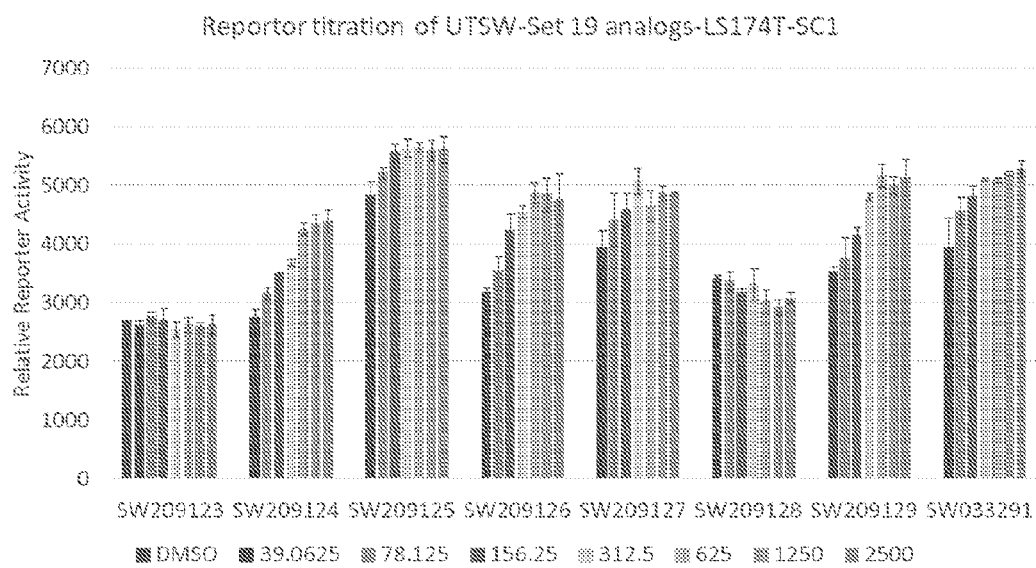
FIG. 104 illustrates a graph showing luciferase activity of LS174T cells treated with various dosages of analogs of SW033291 shown in FIG. 100.

FIG. 104 shows activity of compound SW209123 through SW209129 in inducing luciferase activity in a reporter cell line constructed from the LS174T colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 39.0635 nM, 78.124 nM, 156.25 nM, 312.5 nM, 625 nM, 1250 nM, and 2500 nM.

Figure 105:
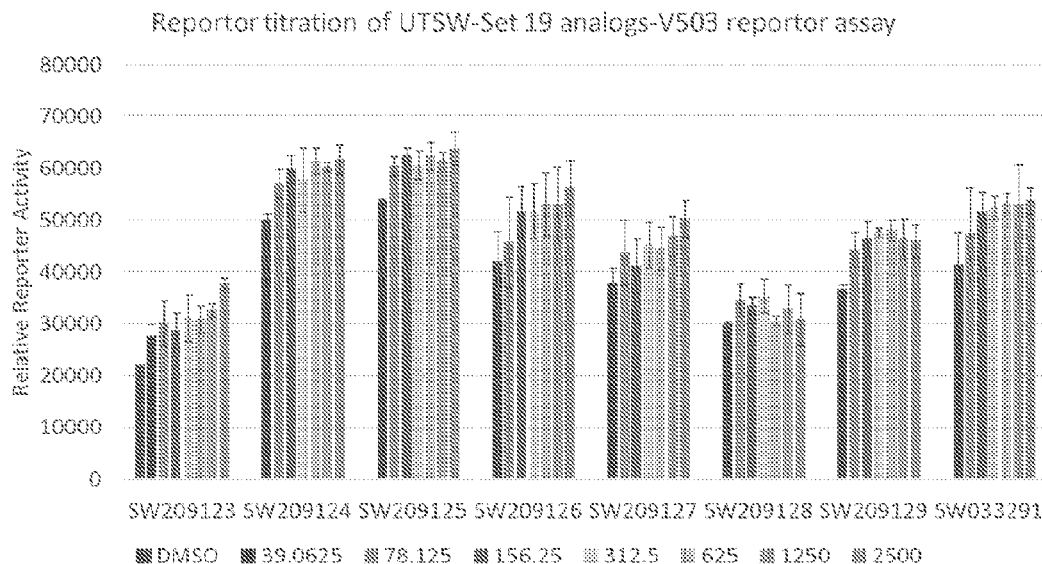
FIG. 105 illustrates a graph showing luciferase activity of V503 cells treated with various dosages of analogs of SW033291 shown in FIG. 100.

FIG. 105 shows activity of compound SW209123 through SW209129 in inducing luciferase activity in a reporter cell line constructed from the Vaco 503 (V503) colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 39.0635 nM, 78.124 nM, 156.25 nM, 312.5 nM, 625 nM, 1250 nM, and 2500 nM.

Figure 106:
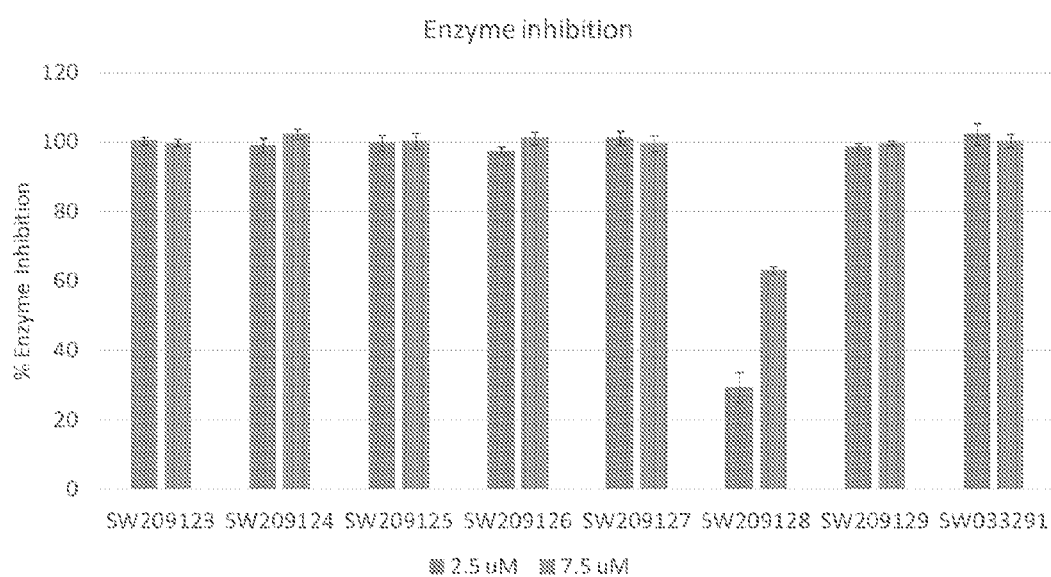
FIG. 106 illustrates a graph showing percent inhibition of 15-PGDH activity by analogs of SW033291 shown in FIG. 100 at 2.5 µM and 7.5 µM.

FIG. 106 shows the activity of each compound SW209123 through SW209129 in inhibiting the enzymatic activity of recombinant 15-PGDH protein in in vitro assays, with the percent inhibition graphed on the Y-axis and compound is added at either 2.5 µM or 7.5 µM. Activity of SW033291 in the assay is also shown.

Example 15

Figure 107:
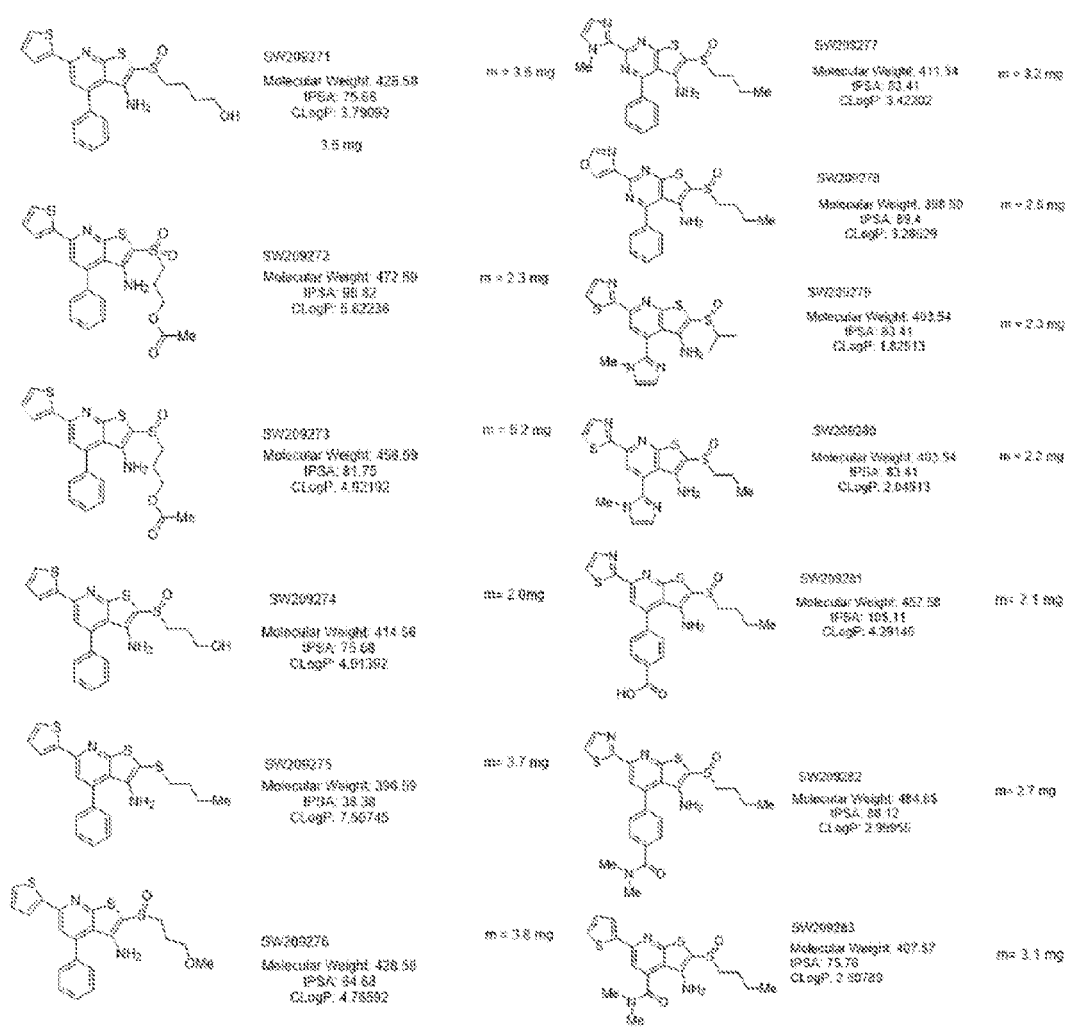
FIG. 107 illustrates chemical structures of a set of thirteen compounds, designated set 20 with individual compound identifiers ranging from SW209271 through SW209283, that are structurally related to SW033291. For each compound the molecular weight, tPSA, and C Log P is also shown.

FIG. 107 shows chemical structures of a set of thirteen compounds, designated set 20 with individual compound identifiers ranging from SW209271 through SW209283, that are structurally related to SW033291. For each compound the molecular weight, tPSA, and C Log P is also shown.

Figure 108:
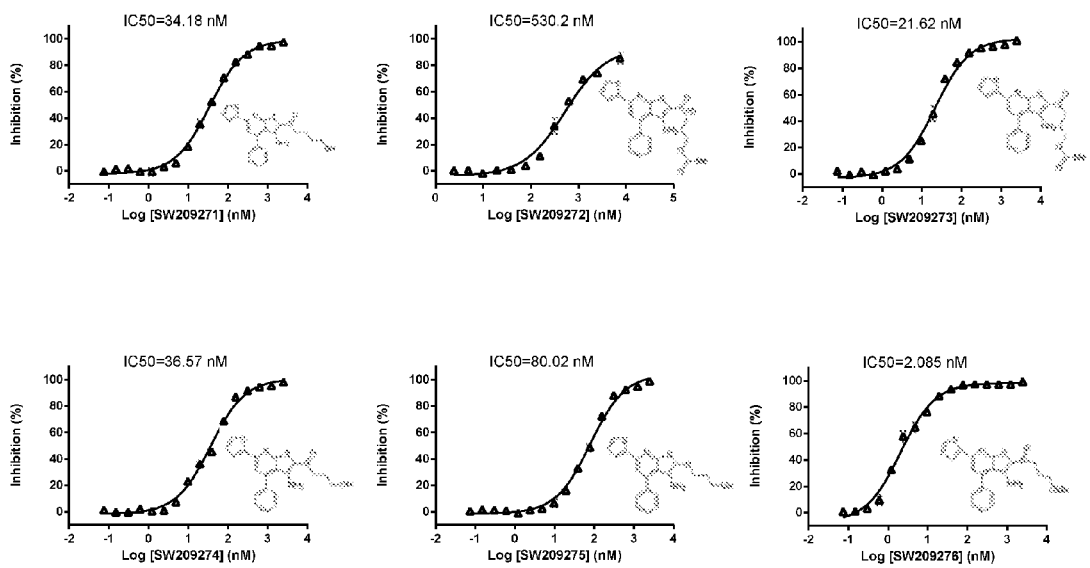
FIGS. 108 and 109 illustrate plots showing the activity of each compound SW209271 through SW209283 in inhibiting the enzymatic activity of recombinant 15-PGDH protein in in vitro assays, with the percent inhibition graphed on the Y-axis and the Log of the compound concentration in nM graphed on the X-axis. The $IC_{50}$ for each compound is recorded.
Figure 109:
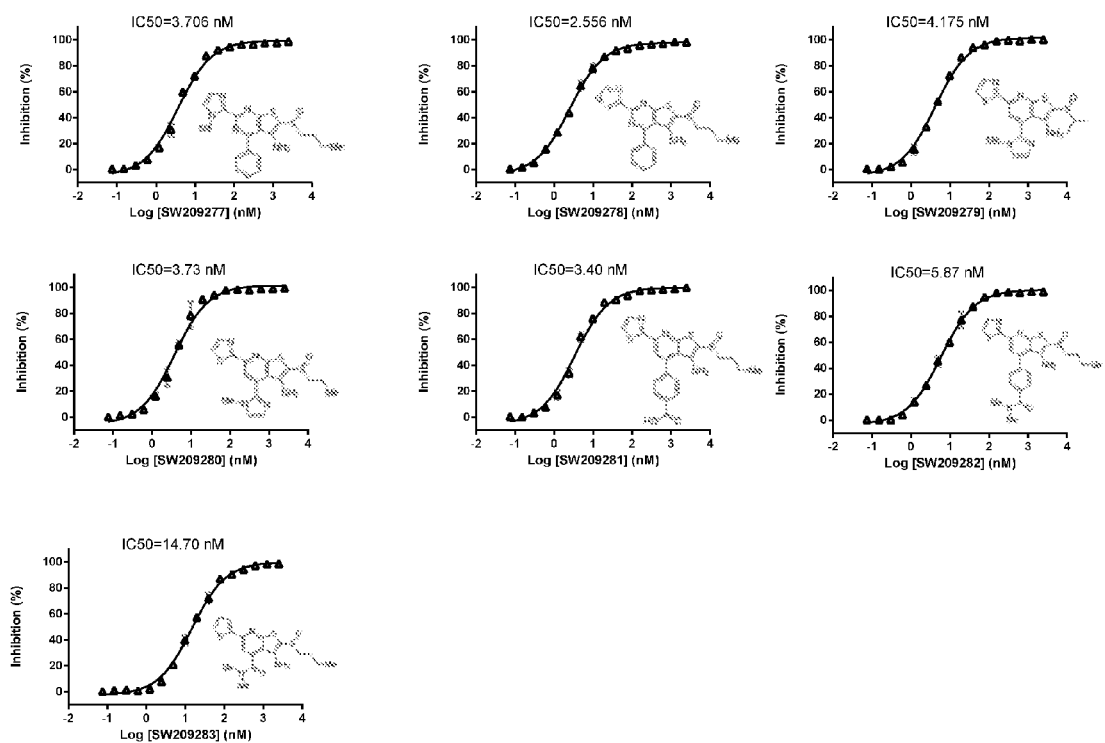

FIGS. 108 and 109 shows the activity of each compound SW209271 through SW209283 in inhibiting the enzymatic activity of recombinant 15-PGDH protein in in vitro assays, with the percent inhibition graphed on the Y-axis and the Log of the compound concentration in nM graphed on the X-axis. The IC$_{50}$ for each compound is recorded.

Figure 110:
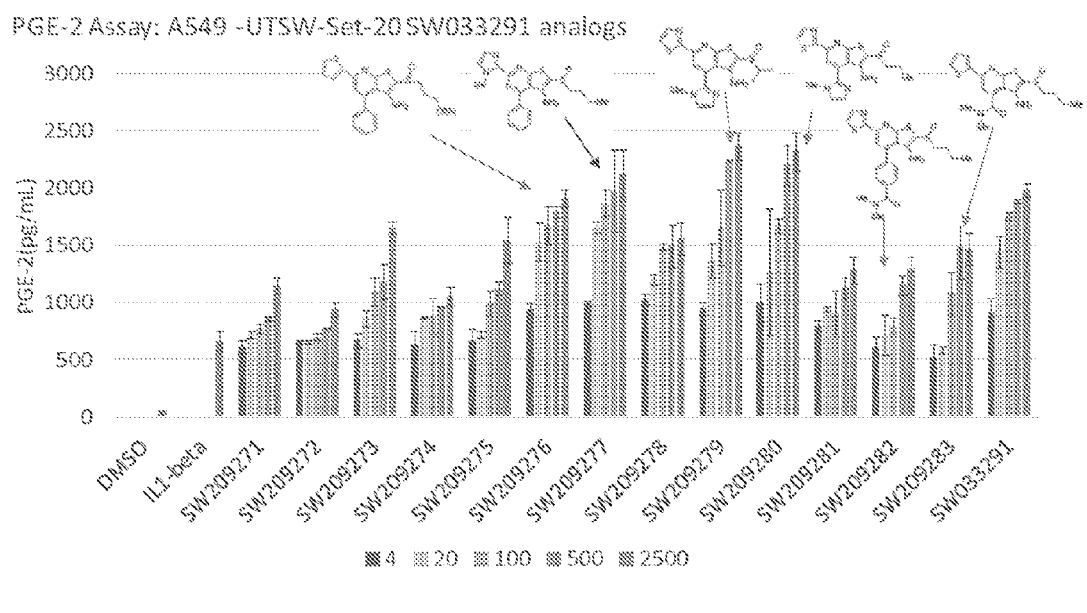
FIG. 110 illustrates a graph showing the activity of compounds SW209271 through SW209283 in inducing PGE2 as assayed in the medium of A549 cells that have first been activated with IL-1beta at concentrations of 4 nM, 20 nM, 100 nM, 500 nM, and 2500 nM.

FIG. 110 shows the activity of compounds SW209271 through SW209283 in inducing PGE2 as assayed in the medium of A549 cells that have first been activated with IL-1beta. For comparison, also shown is induction of PGE2 as assayed in the medium of A549 cells that have first been activated with IL-1beta and then treated with SW033291. Graphed are the effects of exposing the IL-1beta stimulated A549 cells to increasing compound concentrations of 4 nM, 20 nM, 100 nM, 500 nM, and 2500 nM. For comparison PGE2 levels are shown for DMSO treated A549 cells and for A549 cells treated with IL-1beta only.

Figure 111:
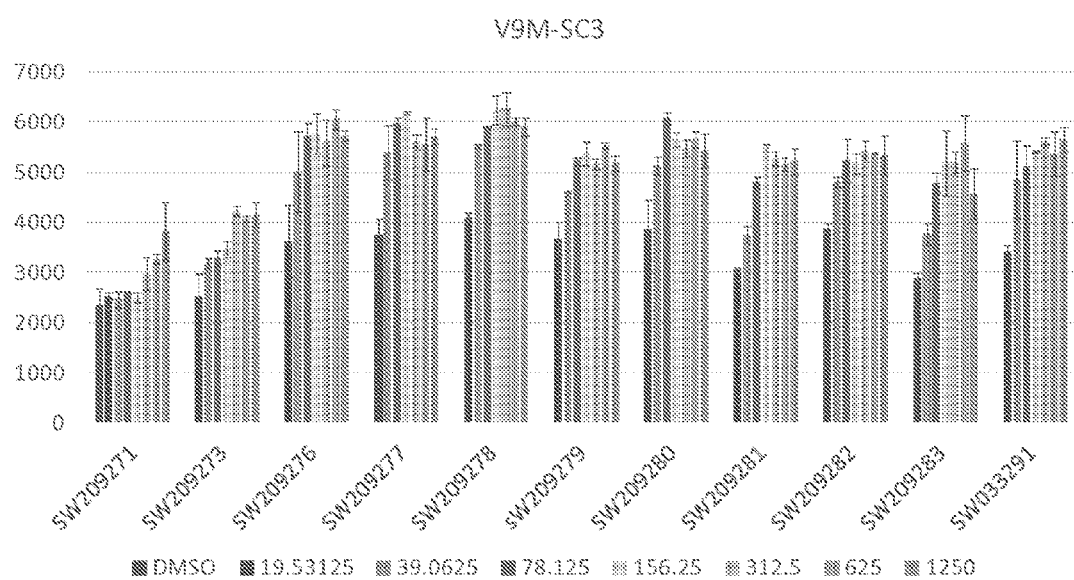
FIG. 111 illustrates a graph showing the activity of compounds SW209271 through SW209283 in inducing luciferase activity in a reporter cell line at concentrations of 19.5 nM, 39.0635 nM, 78.124 nM, 156.25 nM, 312.5 nM, 625 nM, and 1250 nM.

FIG. 111 shows activity of compounds SW209271 through SW209283 in inducing luciferase activity in a reporter cell line constructed from the Vaco 9M (V9M) colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 19.5 nM, 39.0635 nM, 78.124 nM, 156.25 nM, 312.5 nM, 625 nM, and 1250 nM.

Figure 112:
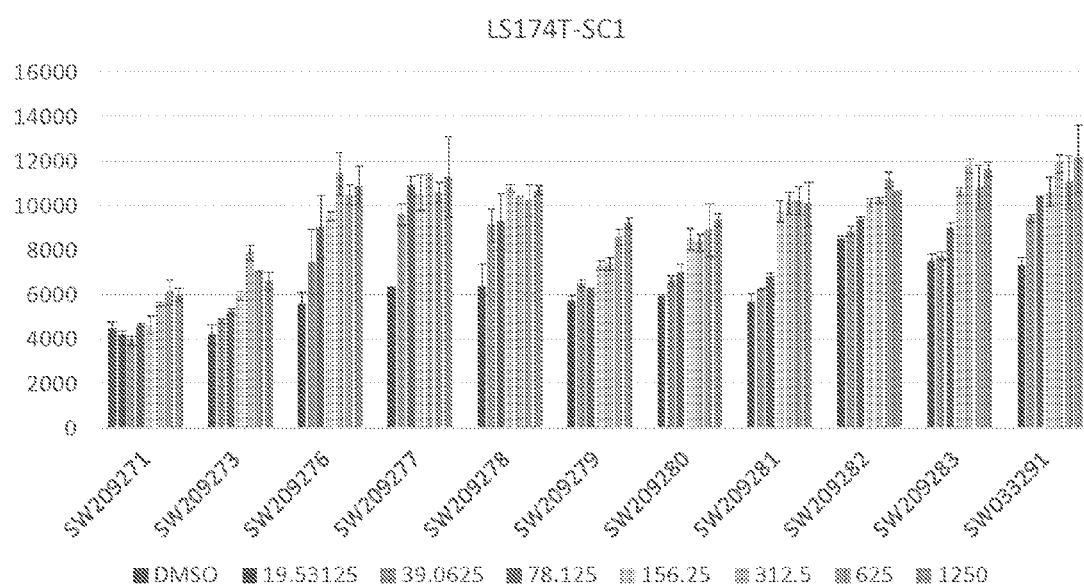
FIG. 112 illustrates a graph showing the activity of compounds SW209271 through SW209283 in inducing luciferase activity in a reporter cell line at concentrations of 19.5 nM, 39.0635 nM, 78.124 nM, 156.25 nM, 312.5 nM, 625 nM, and 1250 nM.

FIG. 112 shows activity of compounds SW209271 through SW209283 in inducing luciferase activity in a reporter cell line constructed from the LS174T colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 19.5 nM, 39.0635 nM, 78.124 nM, 156.25 nM, 312.5 nM, 625 nM, and 1250 nM.

Figure 113:
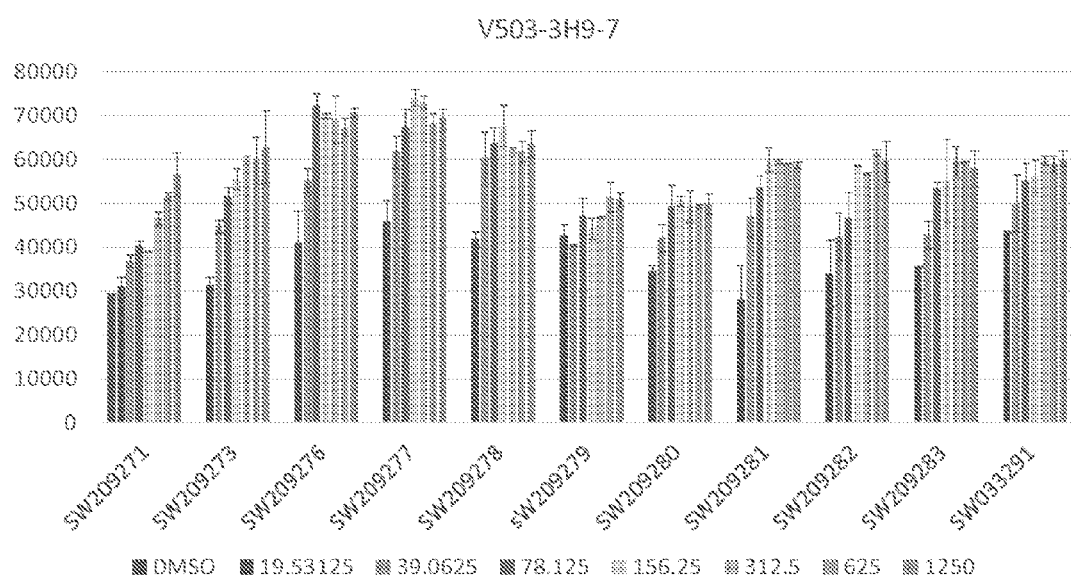
FIG. 113 illustrates a graph showing the activity of compound SW209271 through SW209283 in inducing luciferase activity in a reporter cell line at concentrations of 19.5 nM, 39.0635 nM, 78.124 nM, 156.25 nM, 312.5 nM, 625 nM, and 1250 nM.

FIG. 113 shows activity of compound SW209271 through SW209283 in inducing luciferase activity in a reporter cell line constructed from the Vaco 503 (V503) colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 19.5 nM, 39.0635 nM, 78.124 nM, 156.25 nM, 312.5 nM, 625 nM, and 1250 nM.

FIG. 114 shows chemical structures of two previously described compounds, SW209125 and SW208436, along with a set of five compounds, designated set 21 with individual compound identifiers ranging from SW209239 through SW209333, that are structurally related to SW033291. For each compound the molecular weight, tPSA, and C Log P is also shown.

Figure 115:
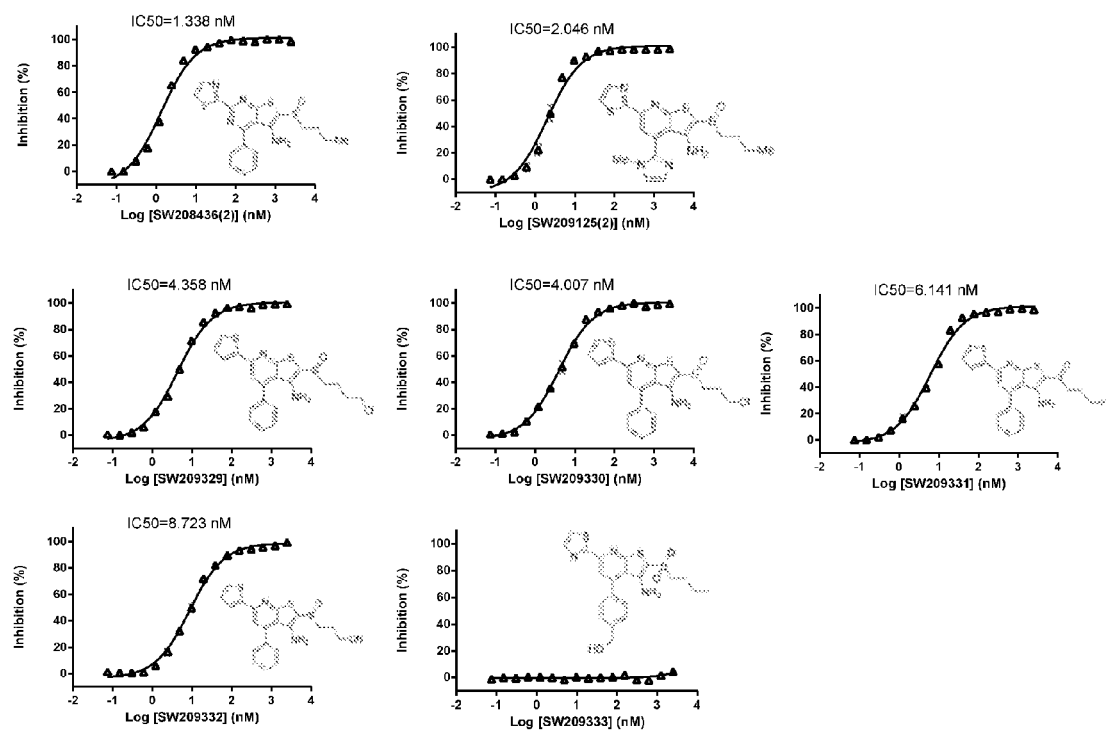
FIG. 115 illustrates plots showing the activity of compounds SW209125, SW208436 and set 21 compounds ranging from SW209239 through SW209333 in inhibiting the enzymatic activity of recombinant 15-PGDH protein in in vitro assays, with the percent inhibition graphed on the Y-axis and the Log of the compound concentration in nM graphed on the X-axis. The $IC_{50}$ for each compound is recorded.

FIG. 115 shows the activity of compounds SW209125, SW208436 and set 21 compounds ranging from SW209239 through SW209333 in inhibiting the enzymatic activity of recombinant 15-PGDH protein in in vitro assays, with the percent inhibition graphed on the Y-axis and the Log of the compound concentration in nM graphed on the X-axis. The IC50 for each compound is recorded.

FIG. 116 shows chemical structures of a set of six compounds, designated set 23, with individual compound identifiers ranging from SW209415 through SW209420, that are structurally related to SW033291. For each compound the molecular weight, tPSA, and C Log P is also shown.

Figure 117:
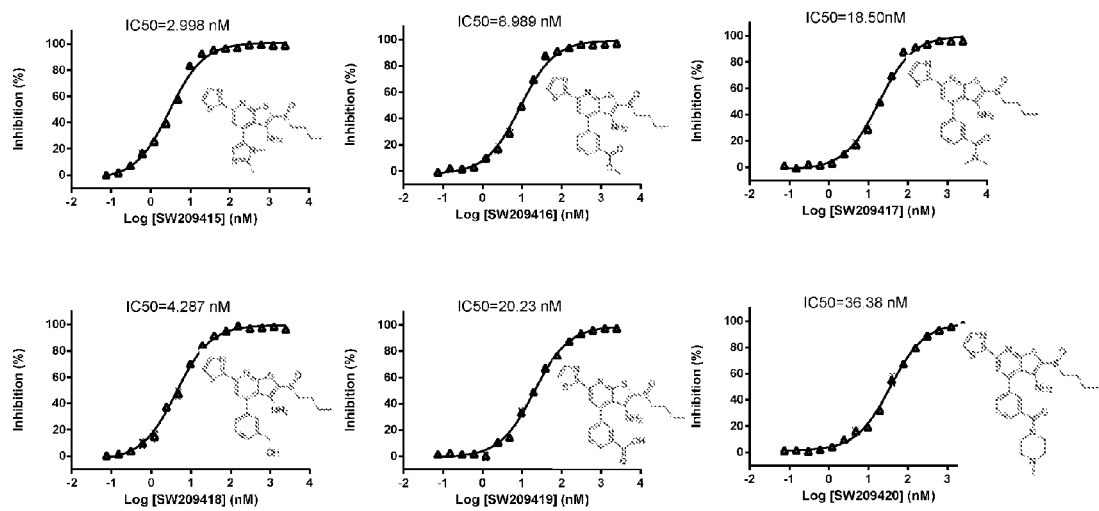
FIG. 117 illustrates plots showing the activity of set 23 compounds ranging from SW209415 through SW209420 in inhibiting the enzymatic activity of recombinant 15-PGDH protein in in vitro assays, with the percent inhibition graphed on the Y-axis and the Log of the compound concentration in nM graphed on the X-axis. The $IC_{50}$ for each compound is recorded.

FIG. 117 shows the activity of set 23 compounds ranging from SW209415 through SW209420 in inhibiting the enzymatic activity of recombinant 15-PGDH protein in in vitro assays, with the percent inhibition graphed on the Y-axis and the Log of the compound concentration in nM graphed on the X-axis. The $IC_{50}$ for each compound is recorded.

Figure 118:
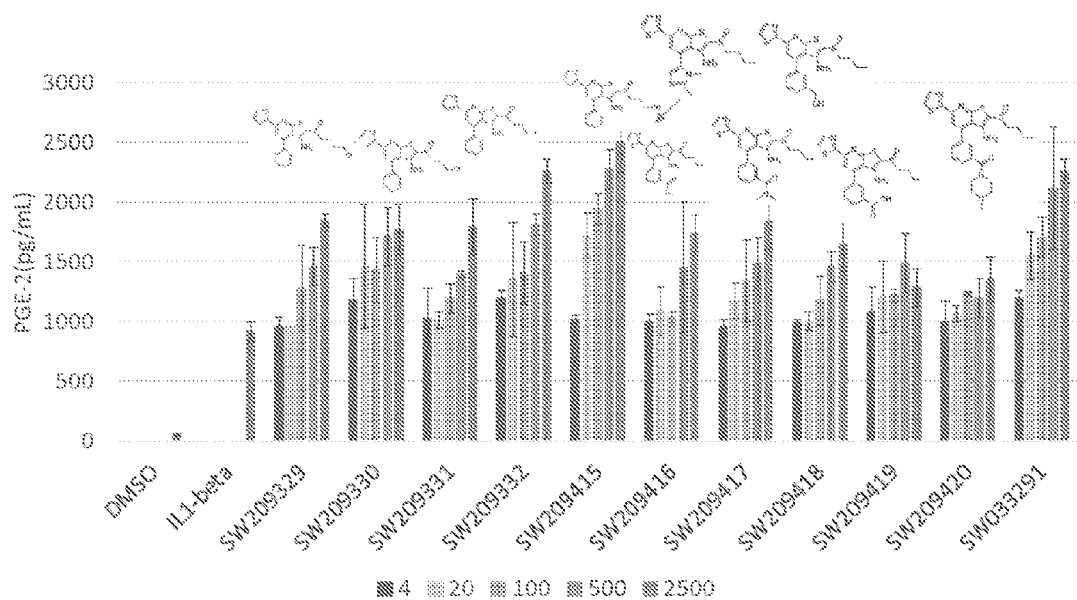
FIG. 118 illustrates a graph showing the activity of selected set 21 compounds ranging from SW209239 through SW2093332 and set 23 compounds ranging from SW209415 through SW209420 in inducing PGE2 as assayed in the medium of A549 cells that have first been activated with IL-1beta at inhibitor concentrations of 4 nM, 20 nM, 100 nM, 500 nM, and 2500 nM.

FIG. 118 shows the activity of selected set 21 compounds ranging from SW209239 through SW2093332 and set 23 compounds ranging from SW209415 through SW209420 in inducing PGE2 as assayed in the medium of A549 cells that have first been activated with IL-1beta. For comparison, also shown is induction of PGE2 as assayed in the medium of A549 cells that have first been activated with IL-1beta and then treated with SW033291. Graphed are the effects of exposing the IL-1beta stimulated A549 cells to increasing compound concentrations of 4 nM, 20 nM, 100 nM, 500 nM, and 2500 nM. For comparison PGE2 levels are shown for DMSO treated A549 cells and for A549 cells treated with IL-1beta only.

Figure 119:
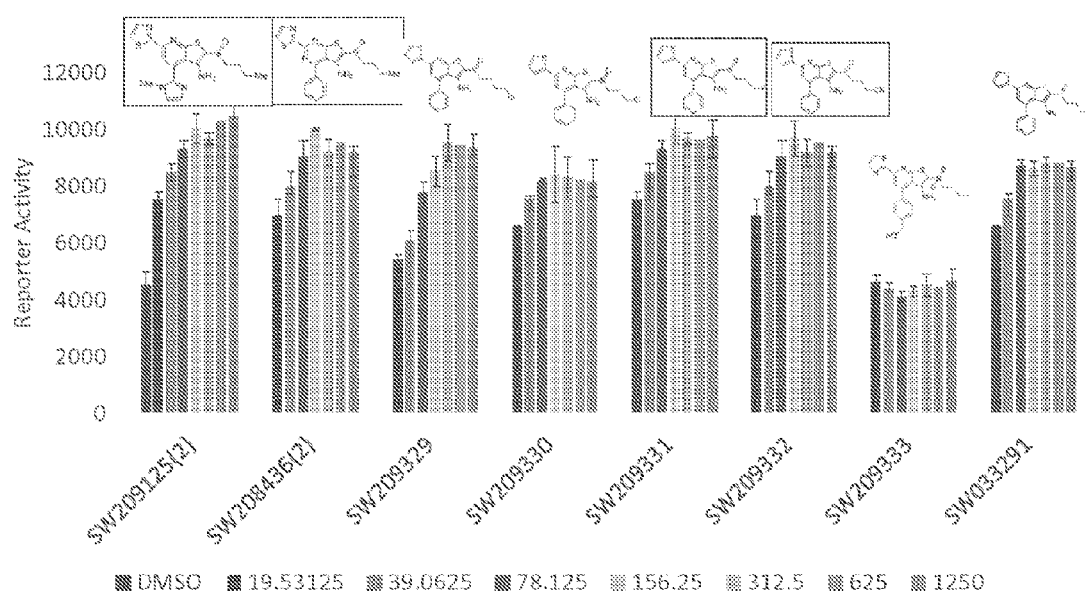
FIG. 119 illustrates a graph showing the activity of SW209125, SW208436 and set 21 compounds ranging from SW209239 through SW209333 in inducing luciferase activity in a reporter cell at concentrations of 19.5 nM, 39.0635 nM, 78.124 nM, 156.25 nM, 312.5 nM, 625 nM, and 1250 nM.

FIG. 119 shows activity of SW209125, SW208436 and set 21 compounds ranging from SW209239 through SW209333 in inducing luciferase activity in a reporter cell line constructed from the Vaco 9M (V9M) colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 19.5 nM, 39.0635 nM, 78.124 nM, 156.25 nM, 312.5 nM, 625 nM, and 1250 nM.

Figure 120:
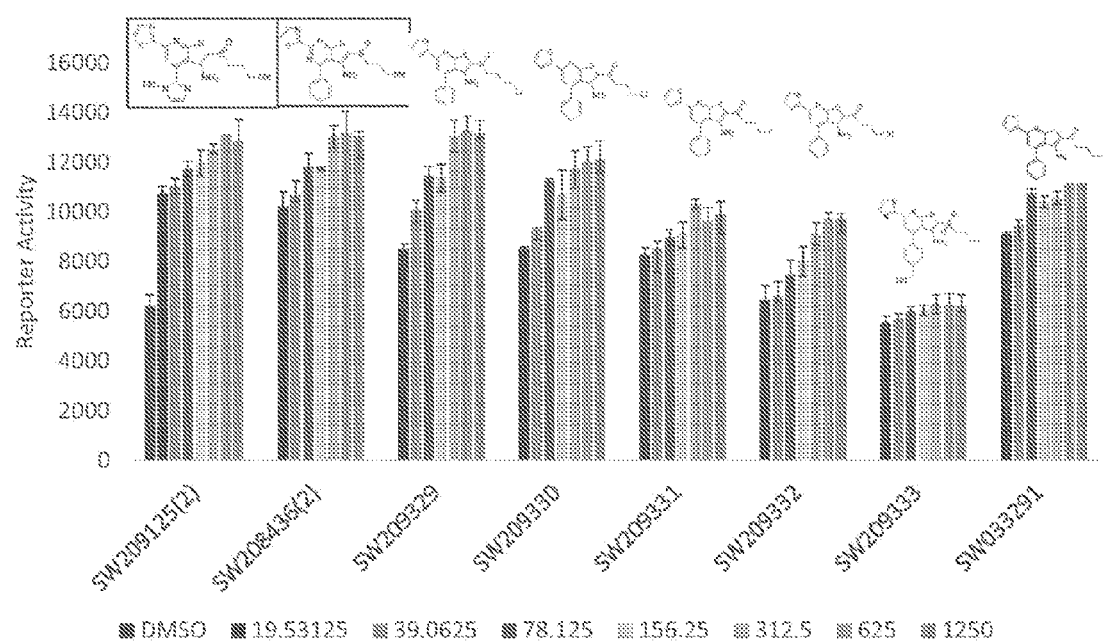
FIG. 120 illustrates a graph showing the activity of SW209125, SW208436 and set 21 compounds ranging from SW209239 through SW209333 in inducing luciferase activity in a reporter cell line at concentrations of 19.5 nM, 39.0635 nM, 78.124 nM, 156.25 nM, 312.5 nM, 625 nM, and 1250 nM.

FIG. 120 shows activity of SW209125, SW208436 and set 21 compounds ranging from SW209239 through SW209333 in inducing luciferase activity in a reporter cell line constructed from the LS174T colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 19.5 nM, 39.0635 nM, 78.124 nM, 156.25 nM, 312.5 nM, 625 nM, and 1250 nM.

Figure 121:
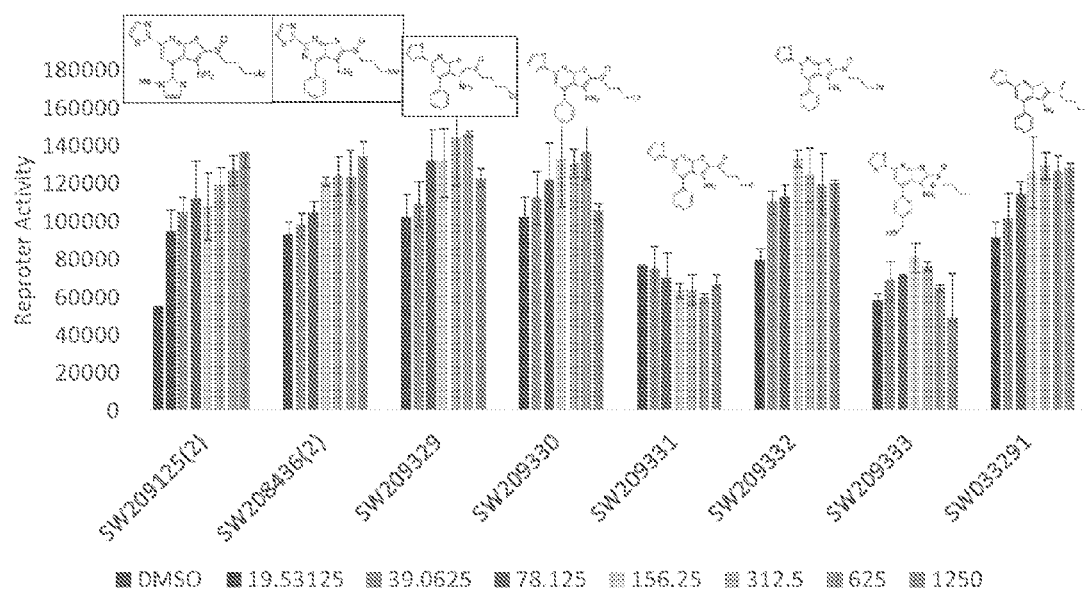

FIG. 121 shows activity of SW209125, SW208436 and set 21 compounds ranging from SW209239 through SW209333 in inducing luciferase activity in a reporter cell line constructed from the Vaco 503 (V503) colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 19.5 nM, 39.0635 nM, 78.124 nM, 156.25 nM, 312.5 nM, 625 nM, and 1250 nM.

Figure 122:
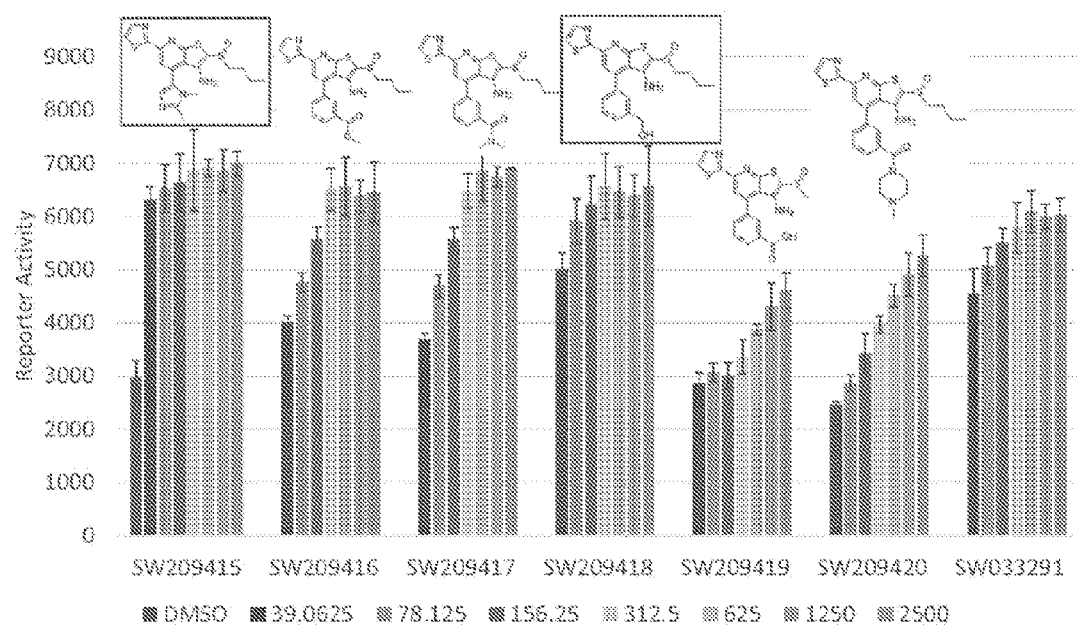

FIG. 122 shows activity of set 23 compounds ranging from SW209415 through SW209420 in inducing luciferase activity in a reporter cell line constructed from the Vaco 9M (V9M) colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 39.0625 nM, 78.125 nM, 156.25 nM, 312.5 nM, 625 nM, 1250 nM, and 2500 nM.

FIG. 123 shows activity of set 23 compounds ranging from SW209415 through SW209420 in inducing luciferase activity in a reporter cell line constructed from the LS174T colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 39.0625 nM, 78.125 nM, 156.25 nM, 312.5 nM, 625 nM, 1250 nM, and 2500 nM.

FIG. 124 shows activity of set 23 compounds ranging from SW209415 through SW209420 in inducing luciferase activity in a reporter cell line constructed from the Vaco 503 (V503) colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 39.0625 nM, 78.125 nM, 156.25 nM, 312.5 nM, 625 nM, 1250 nM, and 2500 nM.

FIG. 125 reprises the structures of SW209125, set 20 compound SW209279, and set 23 compounds SW209415 and SW209418.

FIG. 126 shows repeat testing of the activity of SW209125, set 20 compound SW209279, and set 23 compounds SW209415 and SW209418, in inducing PGE2 as assayed in the medium of A549 cells that have first been activated with IL-1beta. For comparison, also shown is induction of PGE2 as assayed in the medium of A549 cells that have first been activated with IL-1beta and then treated with SW033291. Graphed are the effects of exposing the IL-1beta stimulated A549 cells to increasing compound concentrations of 4 nM, 20 nM, 100 nM, 500 nM, and 2500 nM. For comparison PGE2 levels are shown for DMSO treated A549 cells and for A549 cells treated with IL-1beta only.

FIG. 127 shows testing of the activity of SW209125, set 20 compound SW209279, and set 23 compounds SW209415 and SW209418, in inducing PGE2 as assayed in the medium of DLD1 cells in media supplemented with arachidonic acid. For comparison, also shown is induction of PGE2 as assayed in the medium of DLD1 cells in media supplemented with arachidonic acid and treated with SW033291. Graphed are the effects of exposing the DLD1 cells in media with arachidonic acid to increasing compound concentrations of 4 nM, 20 nM, 100 nM, 500 nM, and 2500 nM. For comparison PGE2 levels are shown for DMSO treated DLD1 cells and for DLD1 cells treated with arachidonic acid (AA) only.

FIG. 128 shows activity of SW033291, SW209125, set 20 compound SW209279, and set 23 compounds SW209415 and SW209418, in inducing luciferase activity in a reporter cell line constructed from the Vaco 9M (V9M) colon cancer cell line into which a *renilla* luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations ranging from (right to left) of 2.4 nM up to 2500 nM.

FIG. 129 shows activity of SW033291, SW209125, set 20 compound SW209279, and set 23 compounds SW209415 and SW209418, in inducing luciferase activity in a reporter cell line constructed from the LS174T colon cancer cell line into which a renilla luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations ranging from (right to left) of 2.4 nM up to 2500 nM.

FIG. 130 shows activity of SW033291, SW209125, set 20 compound SW209279, and set 23 compounds SW209415 and SW209418 in inducing luciferase activity in a reporter cell line constructed from the Vaco 503 (V503) colon cancer cell line into which a renilla luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations ranging from (right to left) of 2.4 nM up to 2500 nM.

FIG. 131 shows chemical structures of a set of seven compounds, designated set 24, with individual compound identifiers ranging from SW209427 up to SW209513, that are structurally related to SW033291. For each compound the molecular weight, tPSA, and C Log P is also shown. Also shown is the repeated structure of SW209415.

FIG. 132 shows the activity of each compound in set 24 with compound numbers from SW209427 up to SW209513 in inhibiting the enzymatic activity of recombinant 15-PGDH protein in in vitro assays, with the percent inhibition graphed on the Y-axis and the Log of the compound concentration in nM graphed on the X-axis. The $IC_{50}$ for each compound is recorded. Also shown is the repeated assay of SW209415.

FIG. 133 shows activity of set 24 compounds, with compound numbers from SW209427 up to SW209513, in inducing luciferase activity in a reporter cell line constructed from the Vaco 9M (V9M) colon cancer cell line into which a renilla luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 19.5 nM, 39.0635 nM, 78.125 nM, 156.25 nM, 312.5 nM, 625 nM, 1250 nM, and 2500 nM.

FIG. 134 shows activity of set 24 compounds, with compound numbers from SW209427 up to SW209513, in inducing luciferase activity in a reporter cell line constructed from the LS174T colon cancer cell line into which a renilla luciferase cassette has been targeted into the last coding exon of the endogenous 15-PGDH gene to create an in frame fusion gene encoding a 15-PGDH-luciferease fusion protein. Activity of SW033291 in the assay is also shown. Graphed are results of treating the reporter cells with DMSO or with compounds at concentrations of 19.5 nM, 39.0635 nM, 78.125 nM, 156.25 nM, 312.5 nM, 625 nM, 1250 nM, and 2500 nM.

FIG. 135 shows dose response curves for inhibition of enzymatic activity of recombinant 15-PGDH (Y-axis) versus log of the nM concentration of racemic SW209415 (top graph), or of the (−) isomer of SW209415 (bottom left graph), or of the (+) isomer of SW209415 (bottom right graph). $IC_{50}$ for racemic SW209415 is 2.6 nM. $IC_{50}$ for (+) SW209415 is 1.3 nM. $IC_{50}$ for (−) SW209415 is 164 nM.

FIG. 136 shows that the enantiomers of SW209415 can be separated chromatographically using a semi-preparative Chiralpak AD HPLC column with methanol as the mobile phase at 2.5 ml/min.

FIG. 137 illustrates a graph illustrating the induction of PGE2 that is secreted into cell culture media of A549 cells that are treated with: DMSO alone; IL1-beta alone; IL1-beta plus racemic SW209415 (labeled SW209415); IL1-beta plus (−) SW209415 (labeled SW209415 (−)); IL1-beta plus (+) SW209415 (labeled SW209415 (+)); or with IL1-beta plus SW033291 (labeled SW033291). Each of the 15-PGDH inhibitor drugs was tested as concentrations of 4 nM, 20 nM, 100 nM, 500 nM, and 2500 nM.

FIGS. 138(A-D) illustrate graphs showing induction of PGE2 (pg of PGE2/mg tissue protein) in 4 different mouse tissues (colon, bone marrow, liver, lung) across time following IP injection of SW209415 at 10 mg/kg. Blue bar represents baseline at time 0, and red bars represent time course from 1-12 hours following SW209415 injection.

FIG. 139 shows schema of an experiment in which female C57BL/6J mice are lethally irradiated (IR) and 12 hours later receive a transplant with CFSE dye labeled bone marrow cells from a donor C57BL/6J female mouse, and the number of transplanted cells that home and survive in the bone marrow of the recipient mice are then determined by FACS at 16 hours post-transplant. In different arms of the experiment mice are treated with vehicle, or with SW033291 10 mg/kg IP, or with SW209415 (racemate) at 10 mg/kg IP. Drugs are administered following radiation, following the transplant, and again at 8 hours after the transplant.

FIG. 140 illustrates a graph showing the percent of CFSE dye labeled donor bone marrow cells that have homed to the bone marrow of recipient mice treated as per the schema described in FIG. 139. Treating mice with SW033291 (labeled 291) or with SW209415 (labeled 415) at the time of and following the transplant increases numbers of homed donor cells in the recipient mouse bone marrow by approximately 2.5-fold.

FIG. 141 shows activity of (+) SW209415 in increasing PGE2 in mouse tissues. Shown is measurement by Elisa of PGE2 (ng PGE2/mg of tissue protein) from 4 mouse tissues: lung, liver, colon and bone marrow. Mice were injected IP with either vehicle control (blue bars), or (+) SW209415 at 0.5 mgkg (yellow bars), 1.5 mg/kg (green bars), or 5 mg/kg (orange bars). Tissues were harvested for PGE2 assay at either 2 hour (2 h) or 3 hour (3 h) time points following drug injection. (+) SW209415 shows induction of PGE2 in all 4 tissues tested, with activity seen at 2 hours, and peak at 3 hours, and with (+) SW209415 induced peak PGE2 levels approximately double those of vehicle control.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

The invention claimed is:
1. A method of inhibiting the activity of a short chain dehydrogenase enzyme of cells or tissue of a subject, the method comprising:
    administering to the cells or tissue a compound having the formula (V):

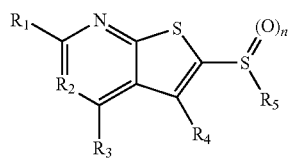
(V)
wherein n=1;
R₁ is selected from the group consisting of
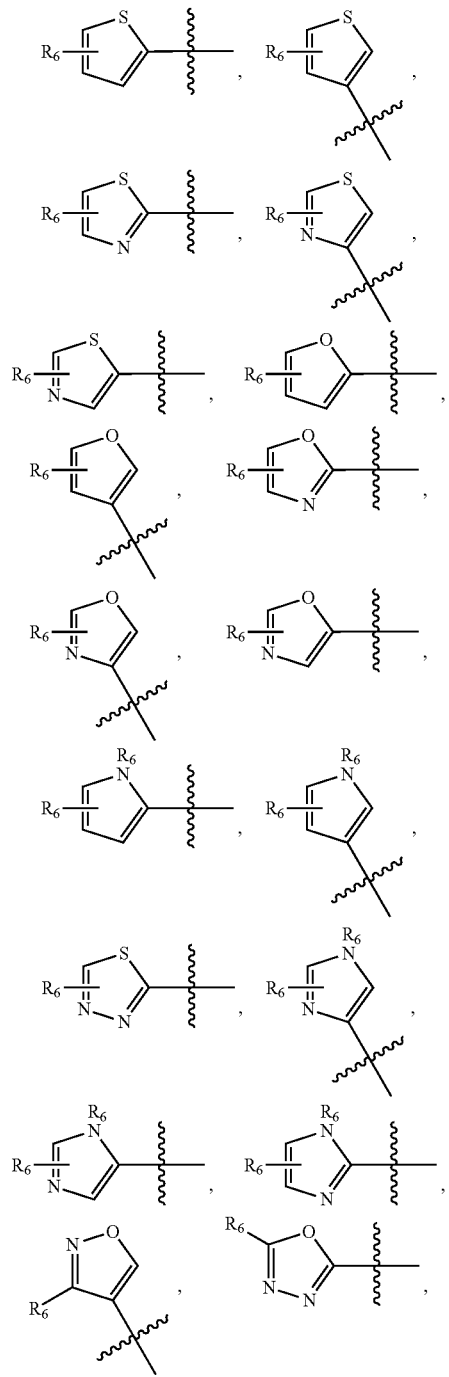
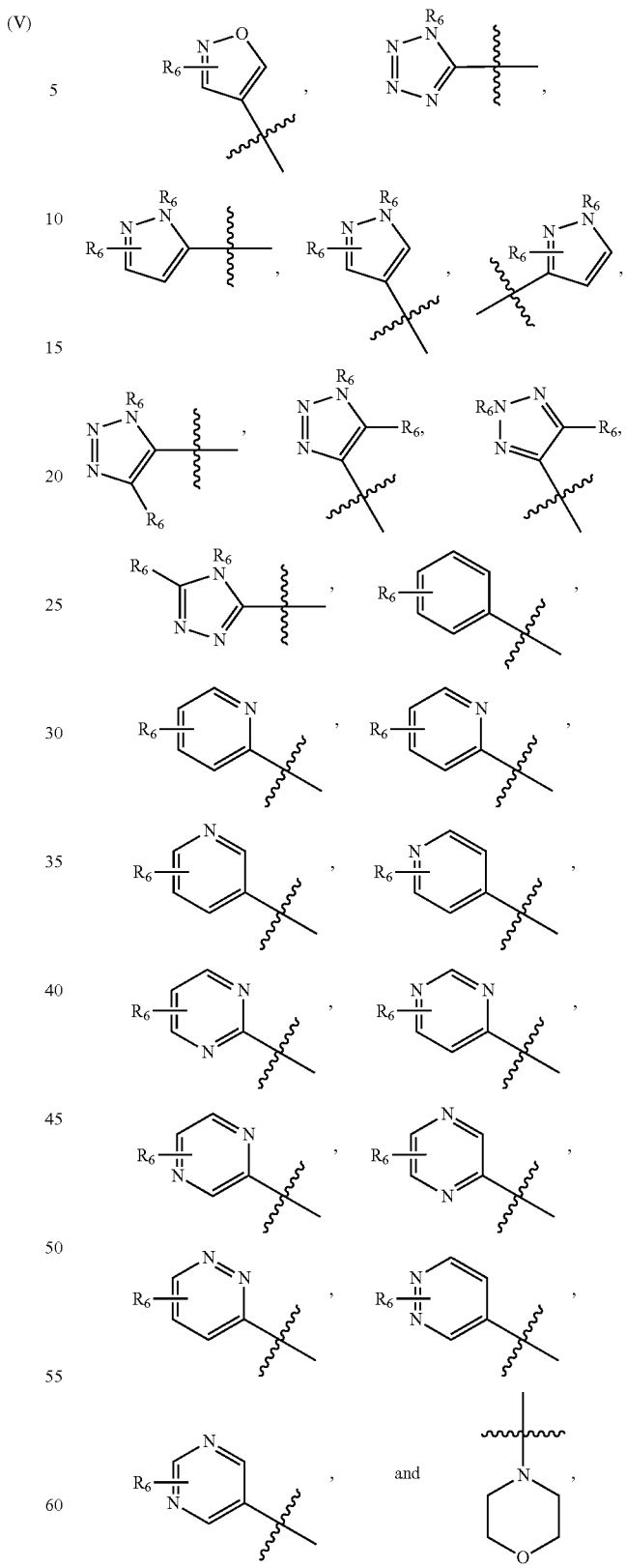
R₃ is selected from the group consisting of H, alkyl, —CO₂H, —CO₂alkyl, —CONH₂, —CONH(alkyl), —CON(alkyl)₂,

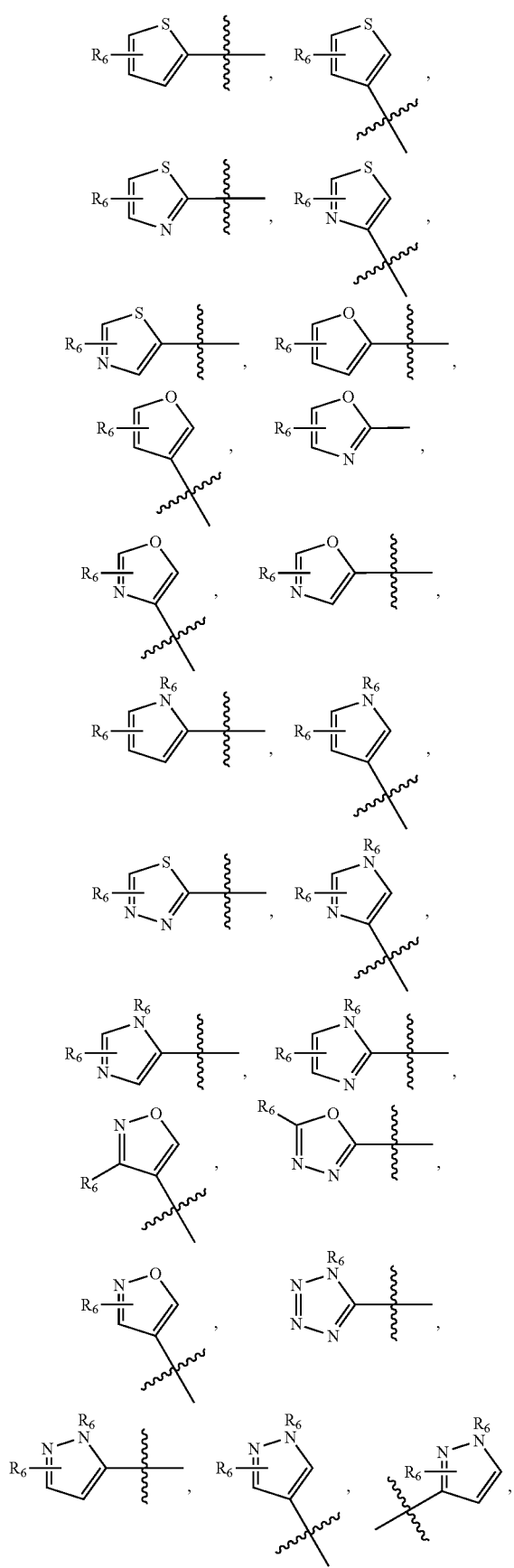
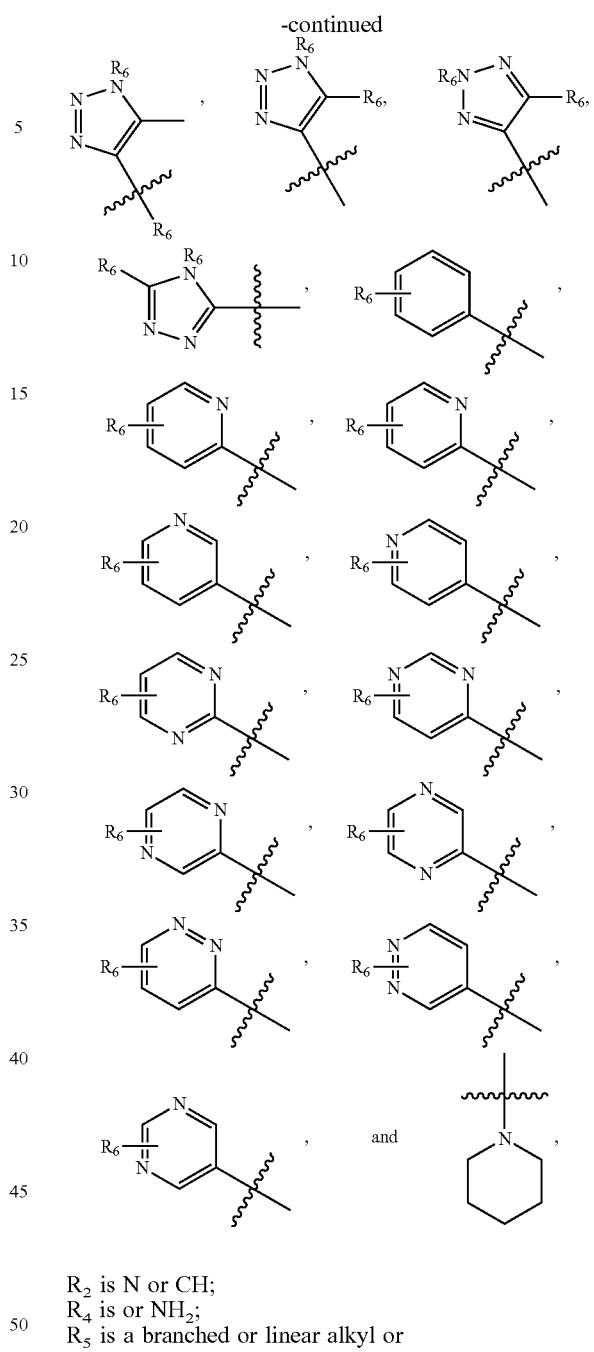

R$_2$ is N or CH;
R$_4$ is or NH$_2$;
R$_5$ is a branched or linear alkyl or

wherein n$_2$=1-6 and X is any of the following: CF$_y$H$_z$ (y+z=3), CCl$_y$H$_z$ (y+z=3), OH, OAc, OMe, or CN;

each R$_6$ is the same or different and is independently one or more substituent selected from the group consisting of hydrogen, substituted or unsubstituted C$_1$-C$_{24}$ alkyl, C$_2$-C$_{24}$ alkenyl, C$_2$-C$_{24}$ alkynyl, C$_3$-C$_{20}$ aryl, heterocyloalkenyl containing from 5-6 ring atoms, heteroaryl or heterocyclyl containing from 5-14 ring atoms, C$_6$-C$_{24}$ alkaryl, C$_6$-C$_{24}$ aralkyl, halo, silyl, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl, acyloxy, C$_2$-C$_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano(-CN), isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, sulfanamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, phosphono, phosphonato, phosphinato, phospho, phosphino, polyalkyl ethers, phosphates, phosphate ester, and combinations thereof;

$R_3$ is not hydrogen if $R_1$ is an unsubstituted thiophene, or an unsubstituted thiazole and $R_5$ is butyl; or $R_3$ is not an unsubstituted phenyl if $R_1$ is an unsubstituted phenyl, thiophene, or thiazole and $R_5$ is $(CH_2)n_5(CH_3)(n_5=0-5)$;

and pharmaceutically acceptable salts thereof.

2. The method of claim 1, wherein $R_1$ is a substituted or unsubstituted heterocyclyl containing 5-6 ring atoms.

3. The method of claim 1, wherein $R_1$ is a substituted or unsubstituted thiophene, thiazole, oxazole, imidazole, pyridine, or phenyl.

4. The method of claim 1, wherein $R_3$ is selected from the group consisting of H, substituted or unsubstituted aryl, cycloalkyl, heterocyclyl, alkyl, —$CO_2H$, —$CO_2$alkyl, —$CONH_2$, —CONH(alkyl), and —CON(alkyl)$_2$.

5. The method of claim 1, wherein the compound has formula ($V_1$)

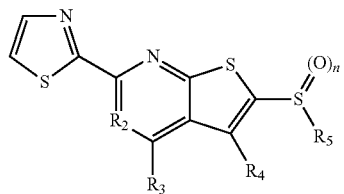

wherein n=0-1;

$R_3$ is selected from the group consisting of H, alkyl, —$CO_2H$, —$CO_2$alkyl, —$CONH_2$, —CONH(alkyl), —CON(alkyl)$_2$,

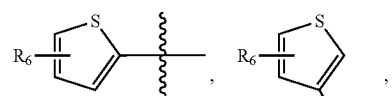

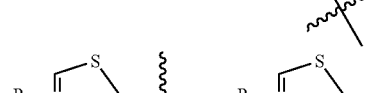

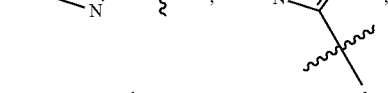

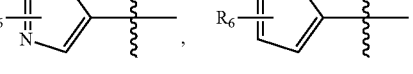

-continued

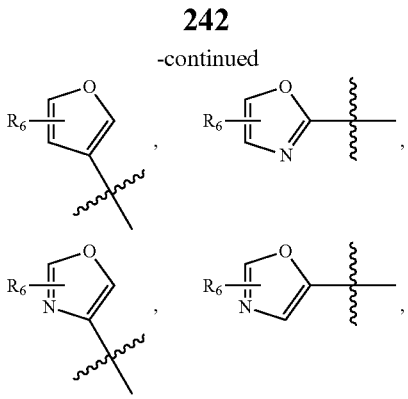

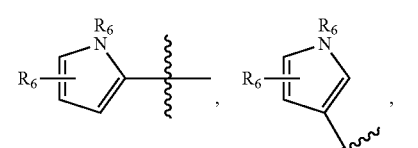

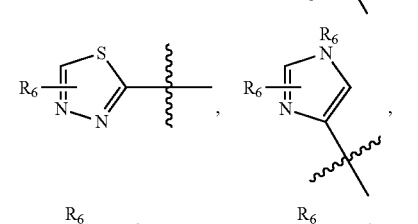

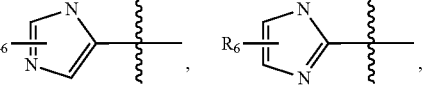

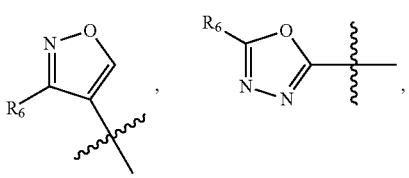

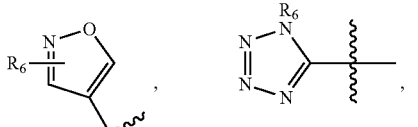

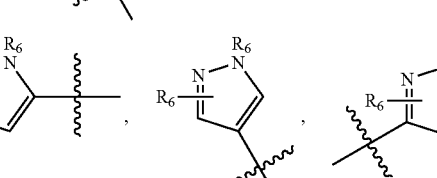

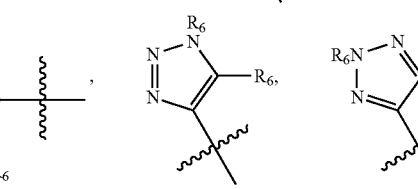

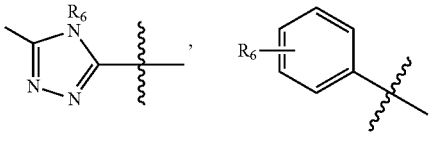

-continued

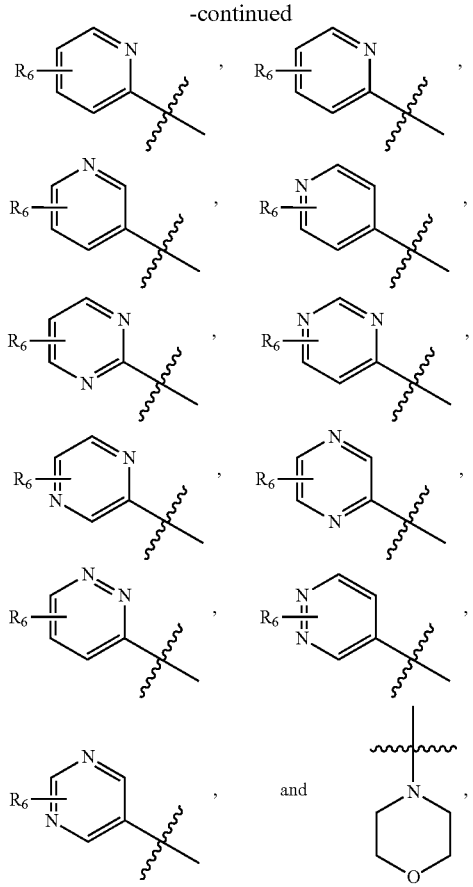

$R_2$ is N or CH;
$R_4$ is selected from the group consisting of H, and $NH_2$;
$R_5$ is a branched or linear alkyl or

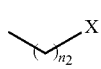

wherein $n_2=1-6$ and X is any of the following: $CF_yH_z$ (y+z=3), $CCl_yH_z$ (y+z=3), OH, OAc, OMe, or CN;

each $R_6$ is the same or different and is independently one or more substituent selected from the group consisting of hydrogen, substituted or unsubstituted $C_1-C_{24}$ alkyl, $C_2-C_{24}$ alkenyl, $C_2-C_{24}$ alkynyl, $C_3-C_{20}$ aryl, heterocycloalkenyl containing from 5-6 ring atoms, heteroaryl or heterocyclyl containing from 5-14 ring atoms, $C_6-C_{24}$ alkaryl, $C_6-C_{24}$ aralkyl, halo, silyl, hydroxyl, sulfhydryl, $C_1-C_{24}$ alkoxy, $C_2-C_{24}$ alkenyloxy, $C_2-C_{24}$ alkynyloxy, $C_5-C_{20}$ aryloxy, acyl, acyloxy, $C_2-C_{24}$ alkoxycarbonyl, $C_6-C_{20}$ aryloxycarbonyl, $C_2-C_{24}$ alkylcarbonato, $C_6-C_{20}$ arylcarbonato, carboxy, carboxylato, carbamoyl, $C_1-C_{24}$ alkyl-carbamoyl, arylcarbamoyl, thiocarbamoyl, carbamido, cyano(-CN), isocyano, cyanato, isocyanato, isothiocyanato, azido, formyl, thioformyl, amino, $C_1-C_{24}$ alkyl amino, $C_5-C_{20}$ aryl amino, $C_2-C_{24}$ alkylamido, $C_6-C_{20}$ arylamido, sulfanamido, imino, alkylimino, arylimino, nitro, nitroso, sulfo, sulfonato, $C_1-C_{24}$ alkylsulfanyl, arylsulfanyl, $C_1-C_{24}$ alkylsulfinyl, $C_5-C_{20}$ arylsulfinyl, $C_1-C_{24}$ alkylsulfonyl, $C_5-C_{20}$ arylsulfonyl, sulfonamide, phosphono, phosphonato, phosphinato, phospho, phosphino, polyalkyl ethers, phosphates, phosphate ester, and combinations thereof;

$R_3$ is not hydrogen if $R_5$ is butyl; or $R_3$ is not an unsubstituted phenyl if $R_5$ is $(CH_2)n_5(CH_3)(n_5=0-5)$;

and pharmaceutically acceptable salts thereof.

6. The method of claim 5, wherein $R_3$ is selected from the group consisting of H, substituted or unsubstituted aryl, cycloalkyl, heterocyclyl, alkyl, —$CO_2H$, —$CO_2alkyl$, —$CONH_2$, —CONH(alkyl), and —$CON(alkyl)_2$.

7. The method of claim 1, the compound having a formula selected from the group consisting of:

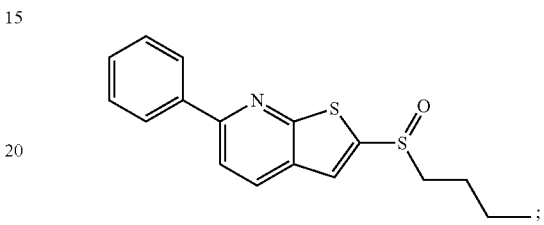

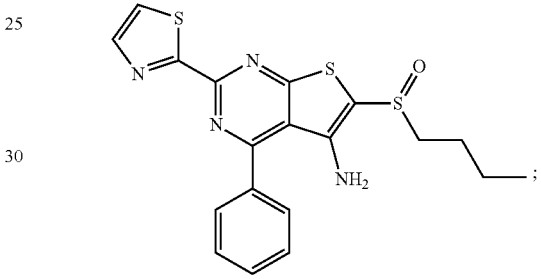

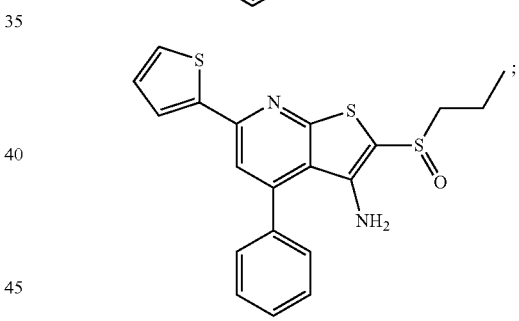

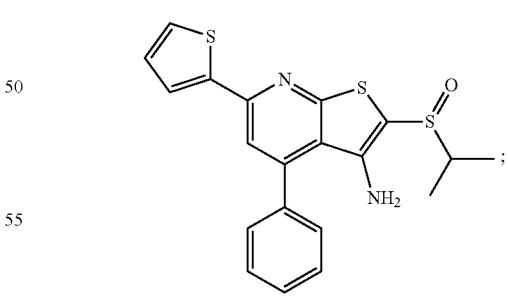

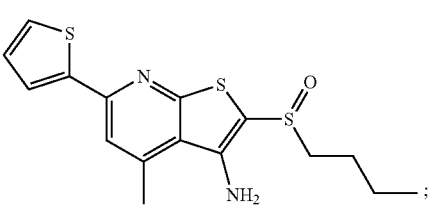

245
-continued
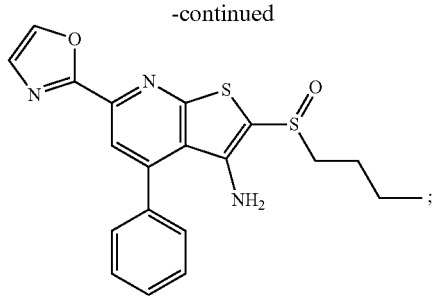
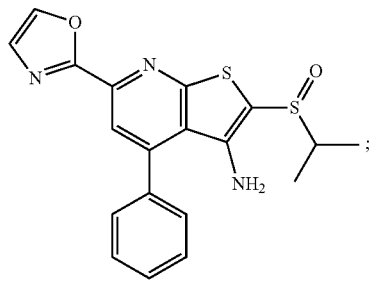
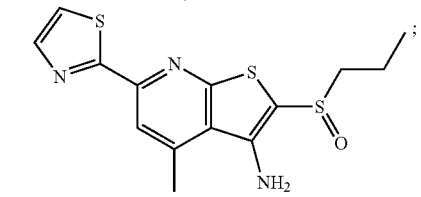
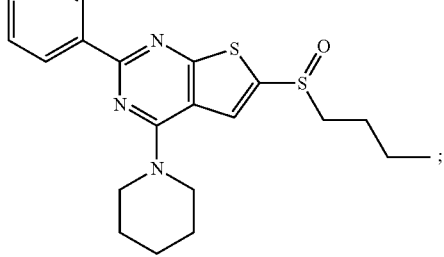
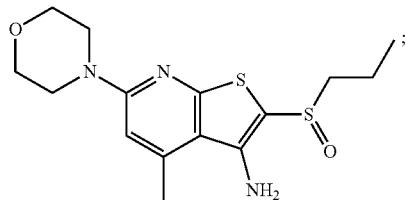
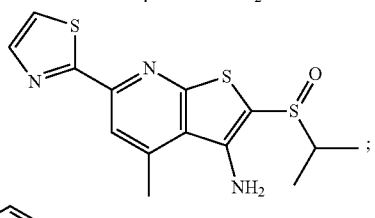
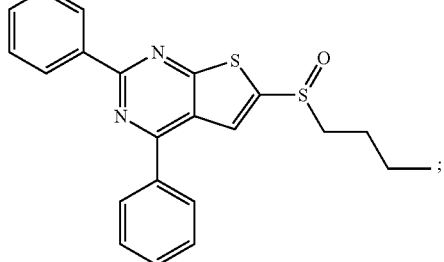
246
-continued
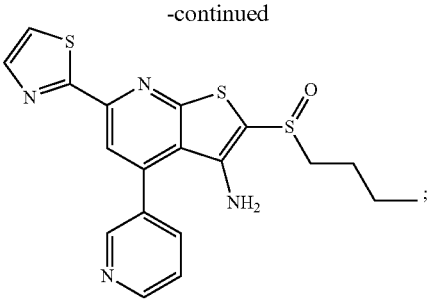
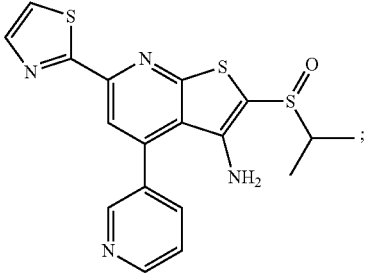
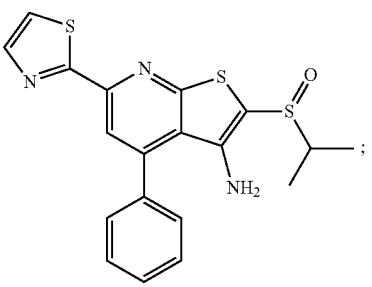
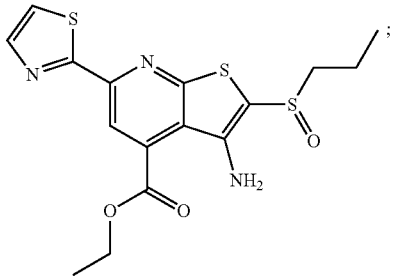
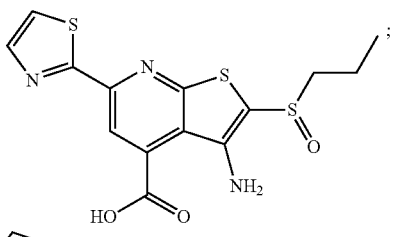
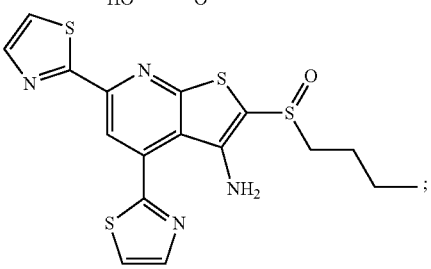

247
-continued
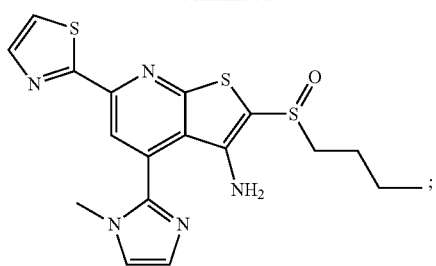
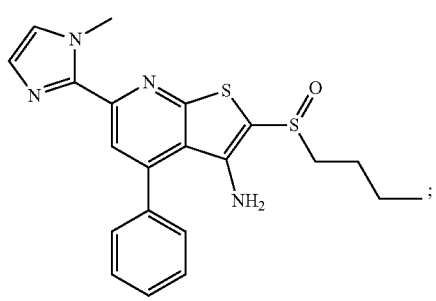
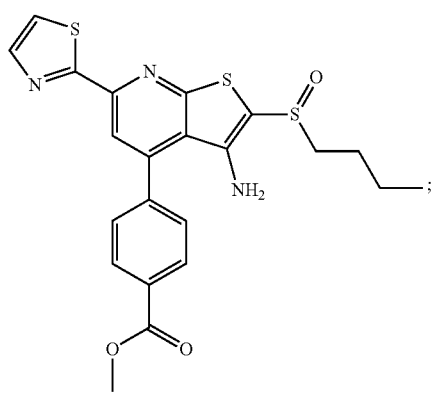
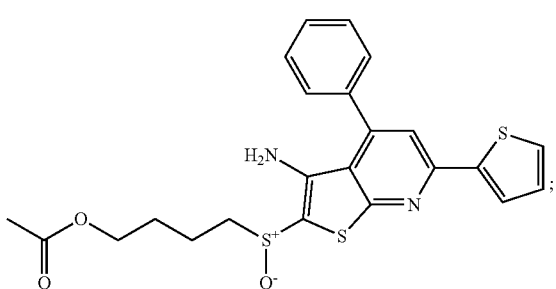
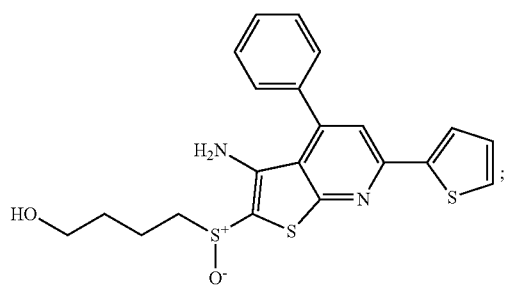
248
-continued
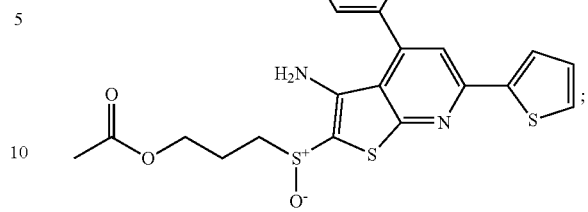
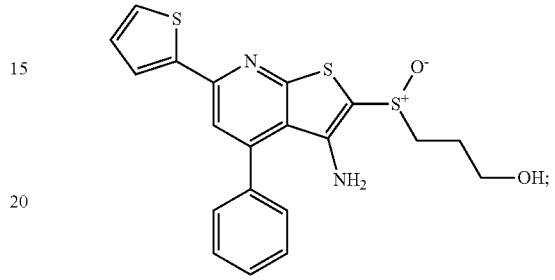
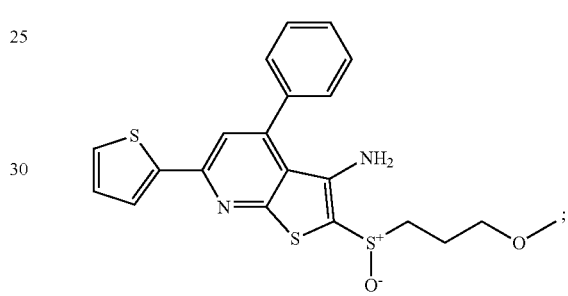
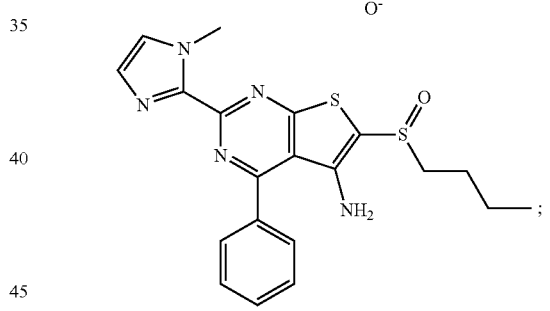
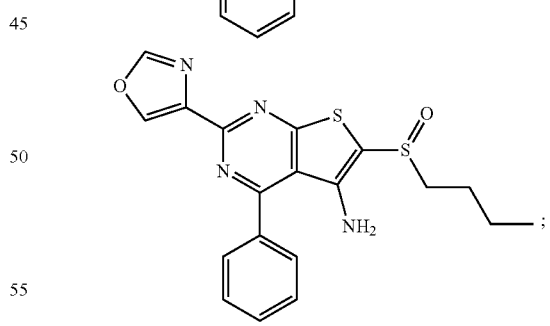
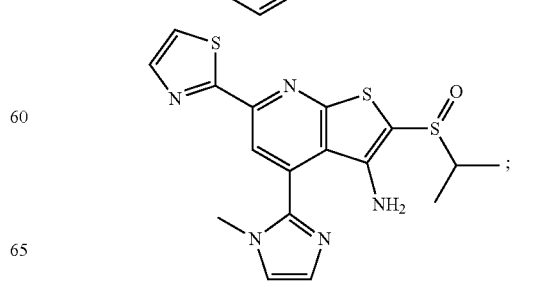

249
-continued
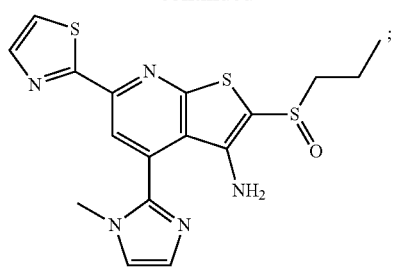
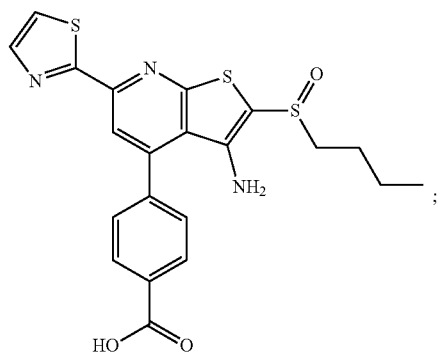
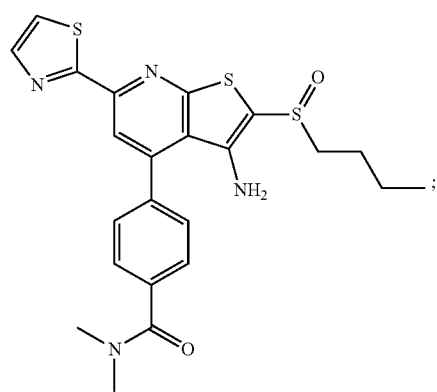
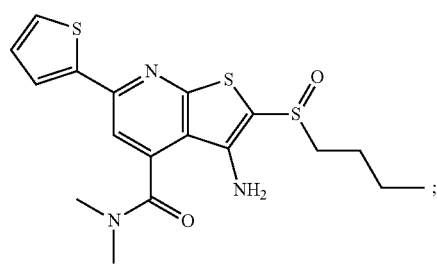
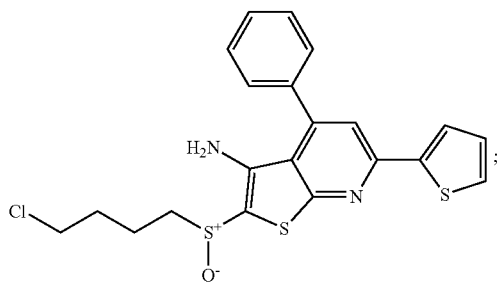
250
-continued
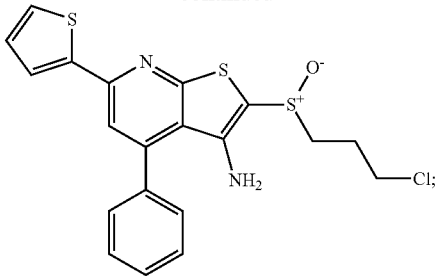
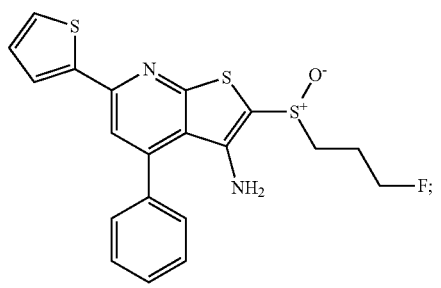
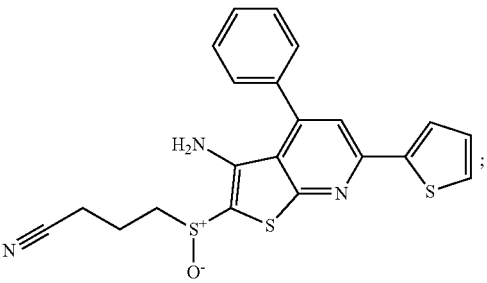
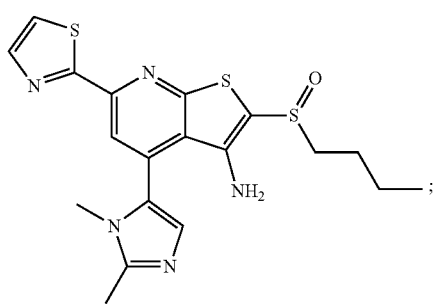
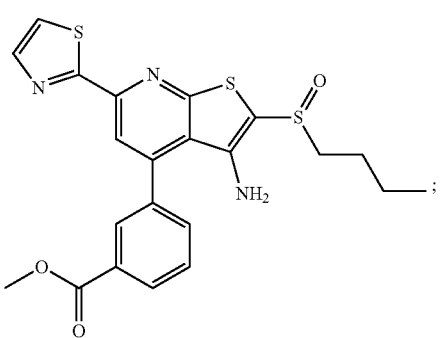

251
-continued
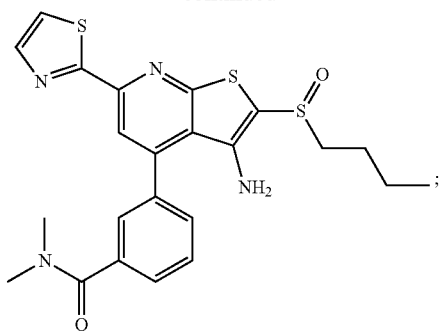
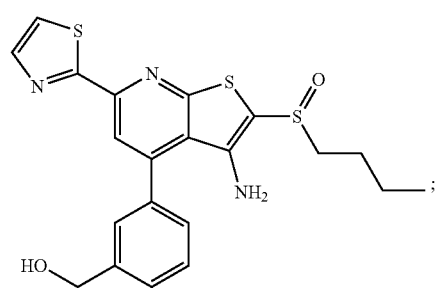
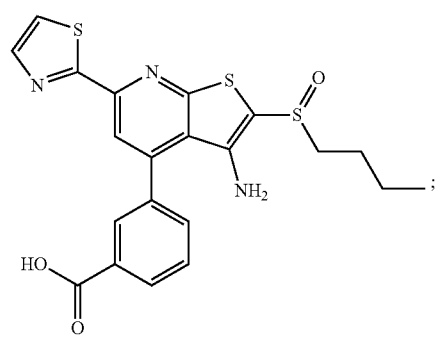
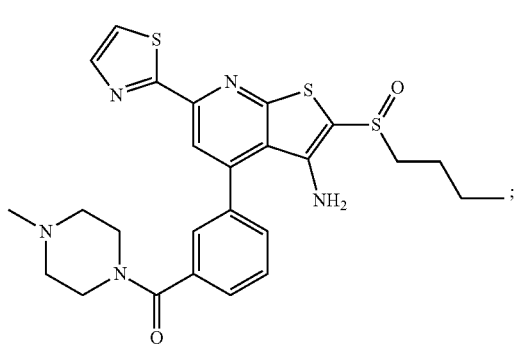
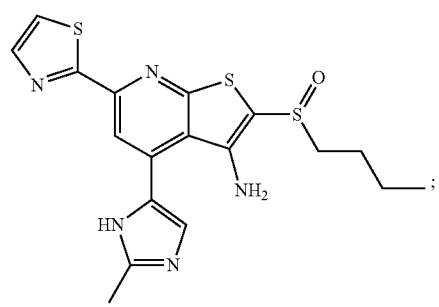
252
-continued
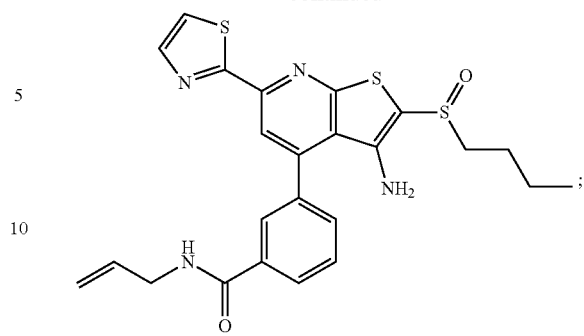
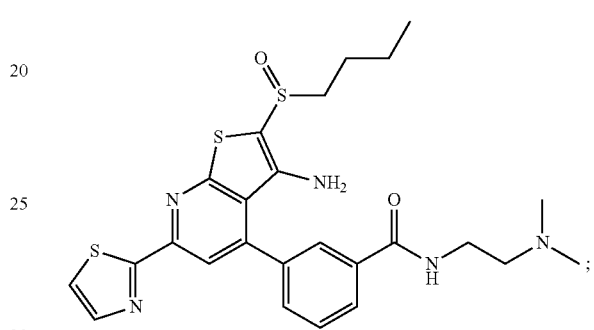
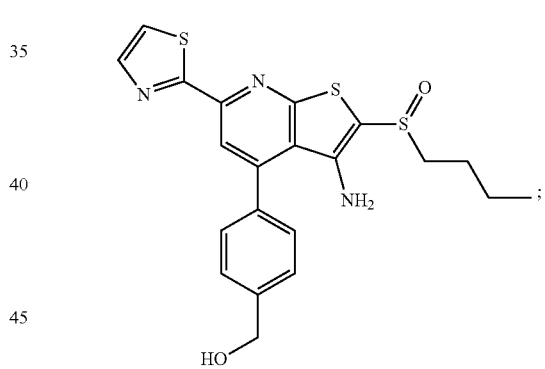
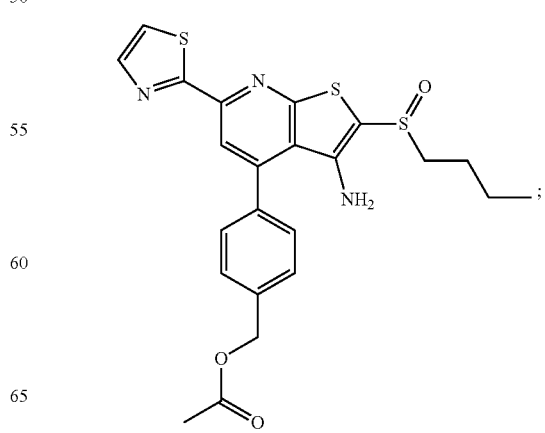

253
-continued
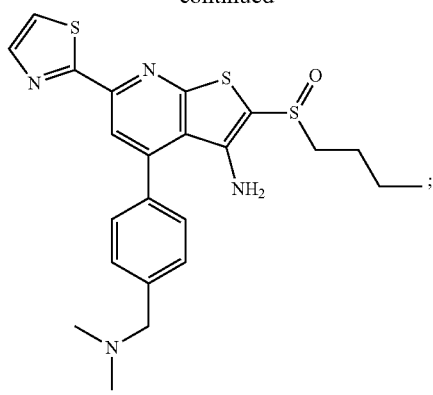
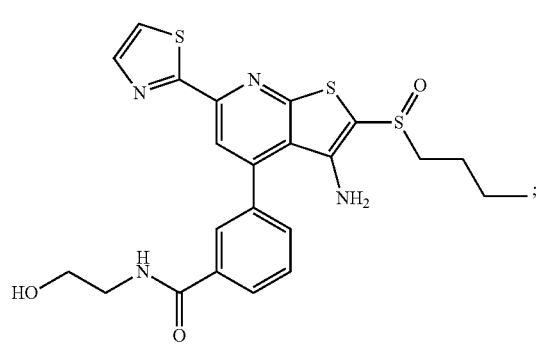
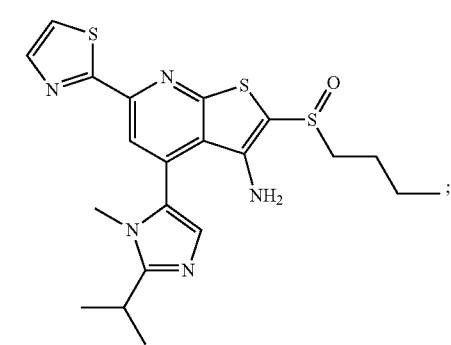
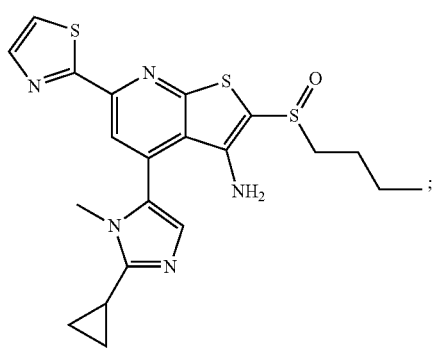
254
-continued
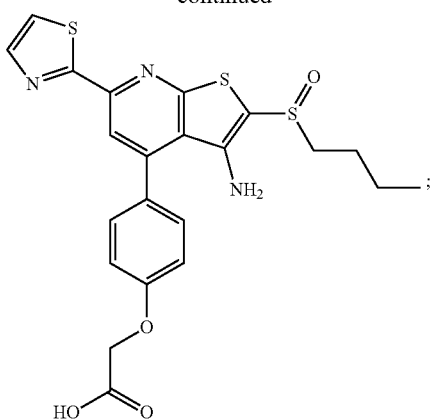
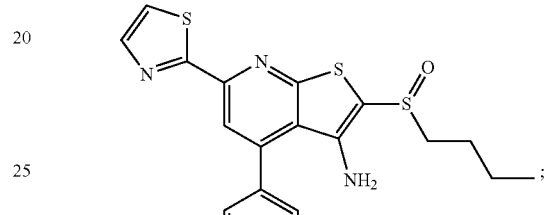
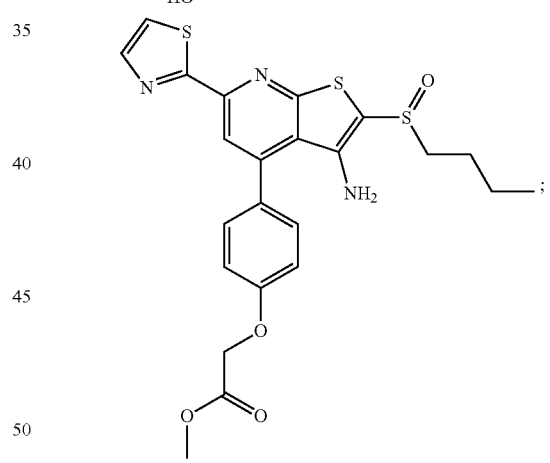
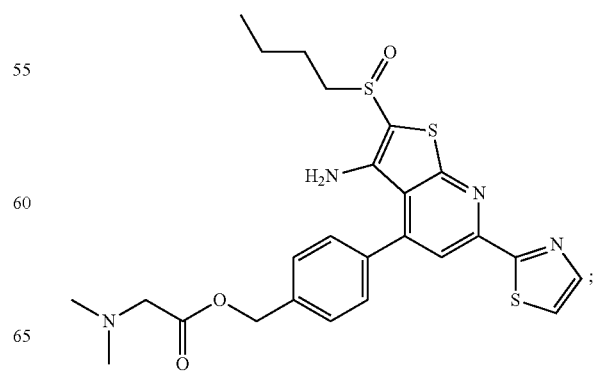

255
-continued
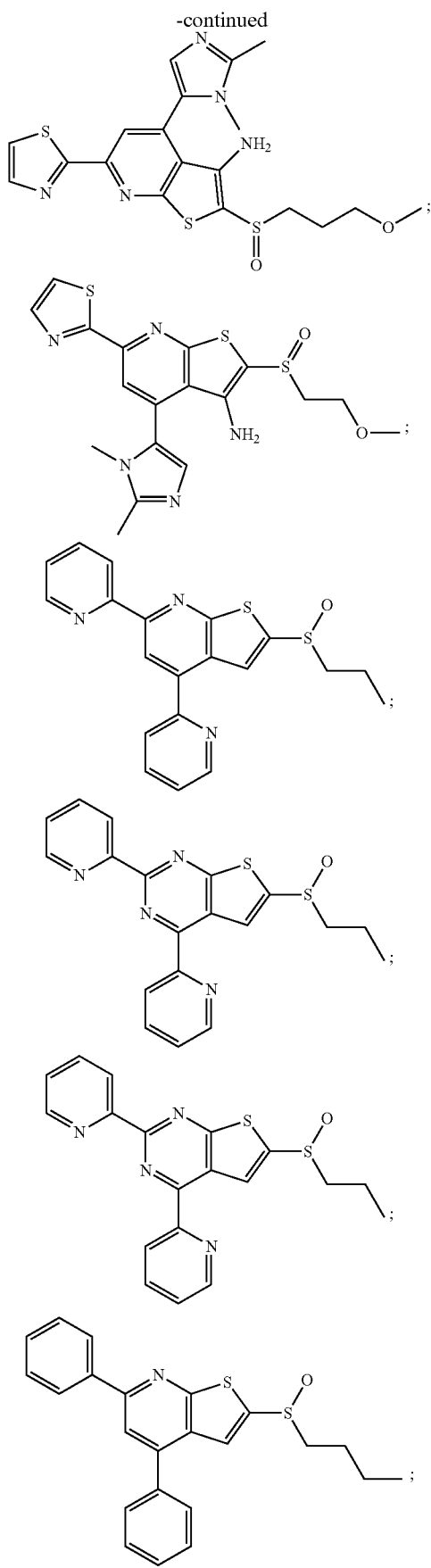
256
-continued
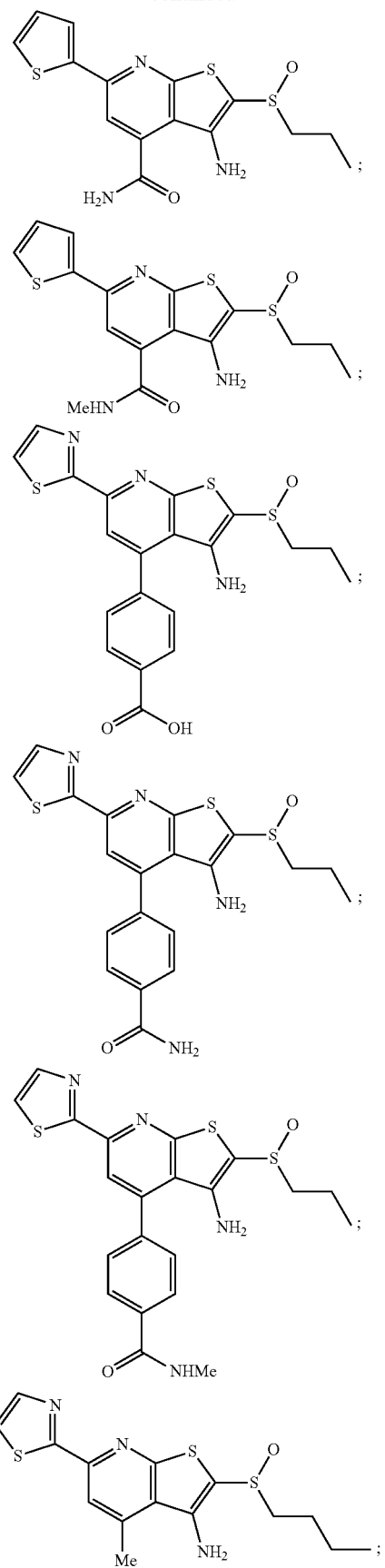

257
-continued
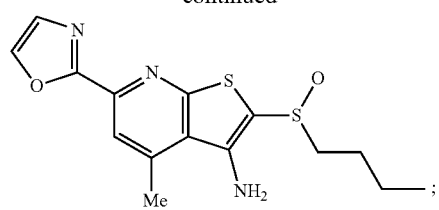
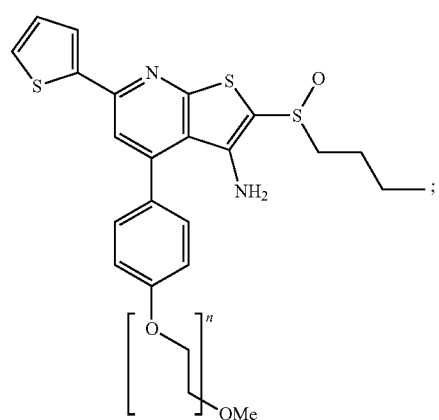
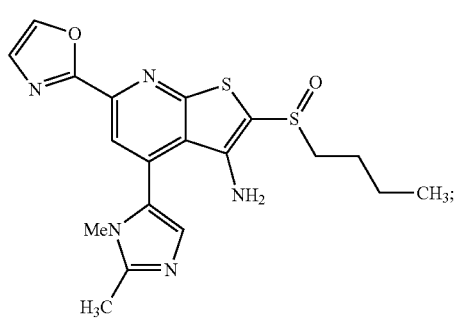
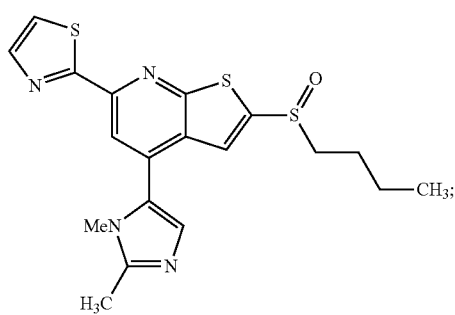
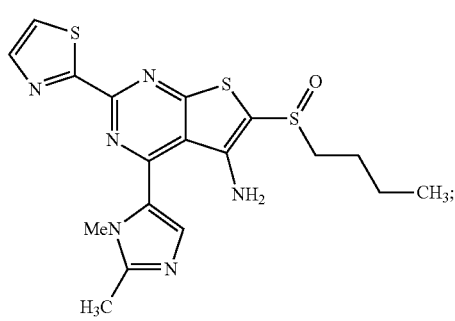
258
-continued
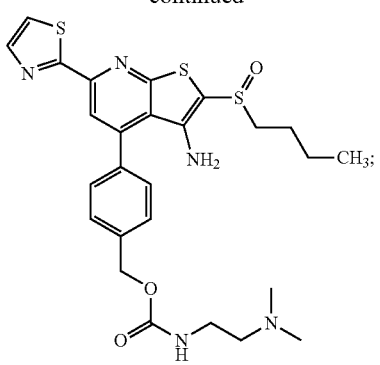
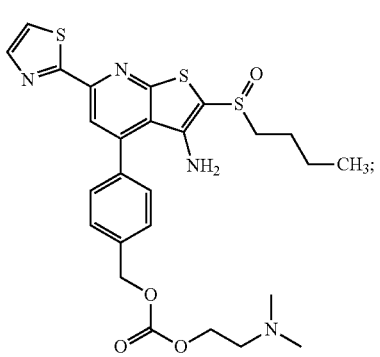
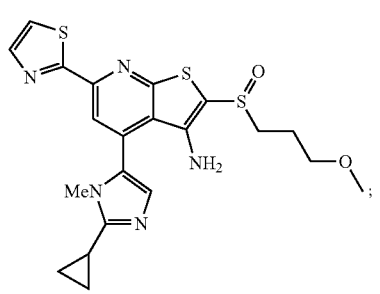
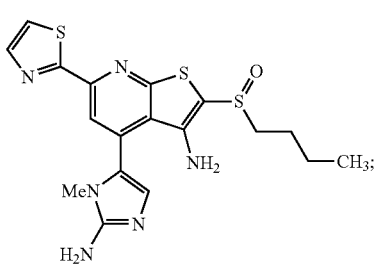
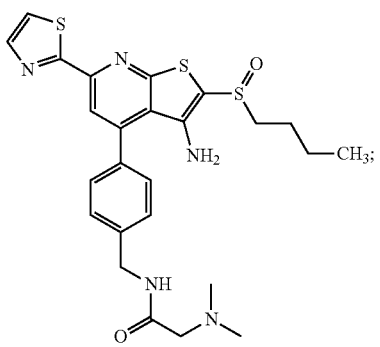

259
-continued
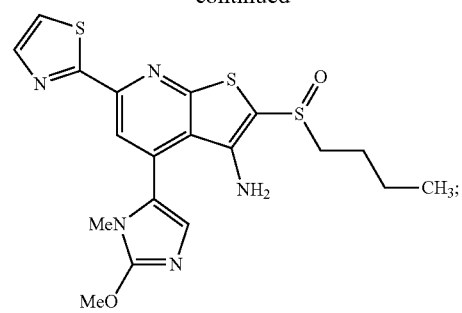
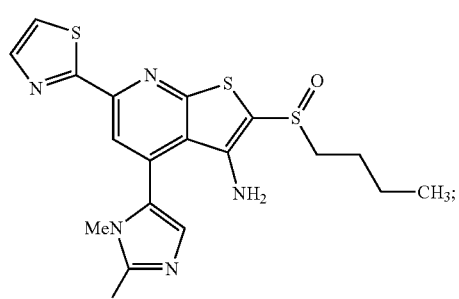
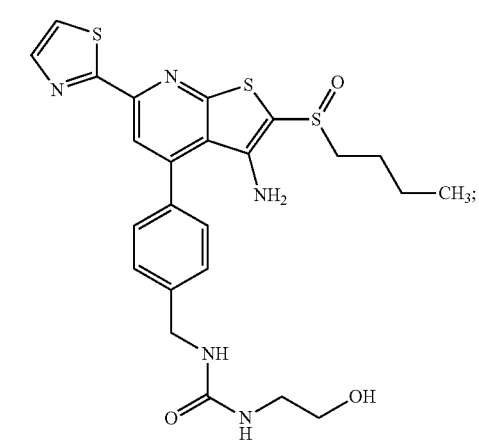
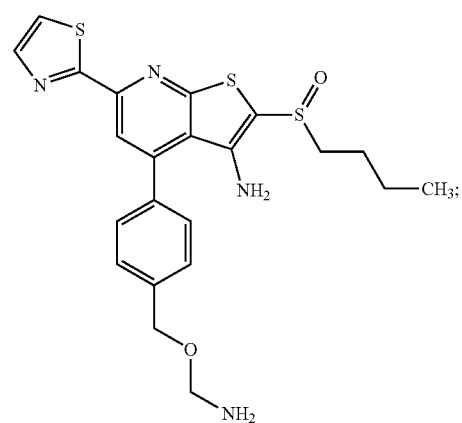
260
-continued
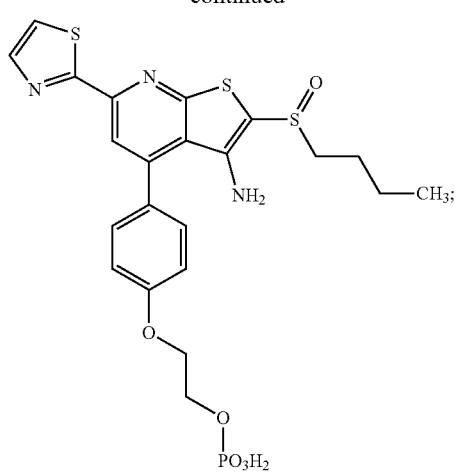
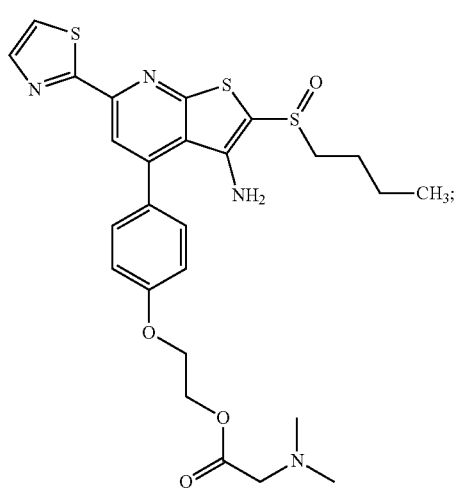
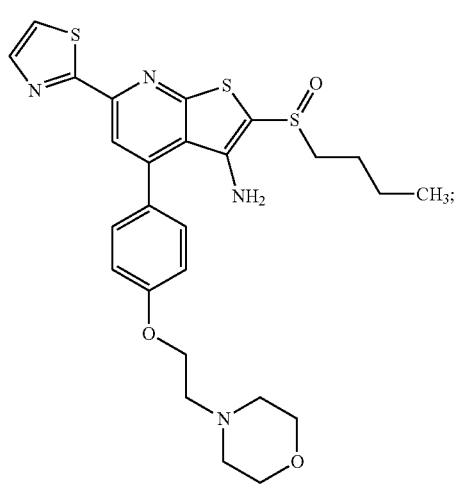

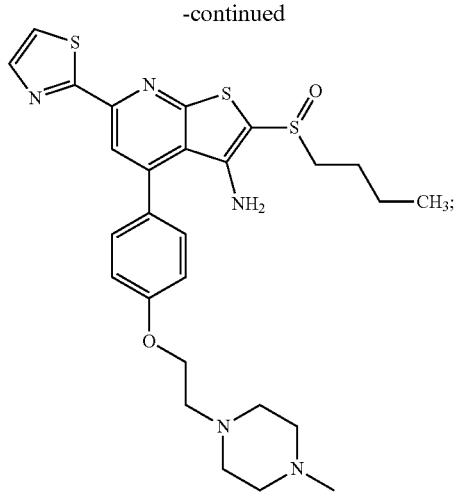
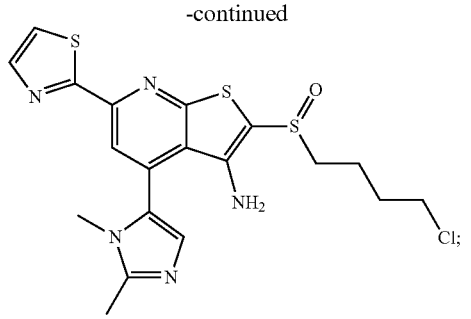
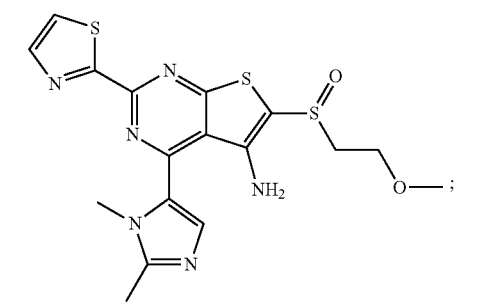
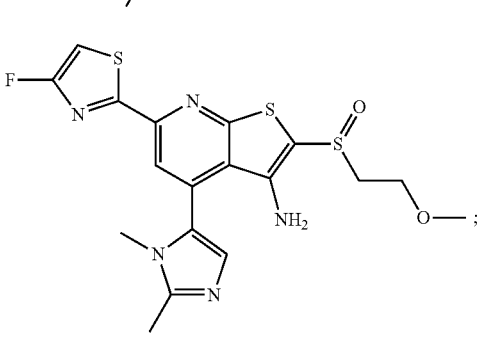
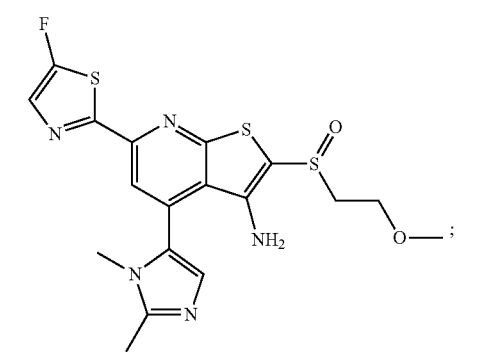
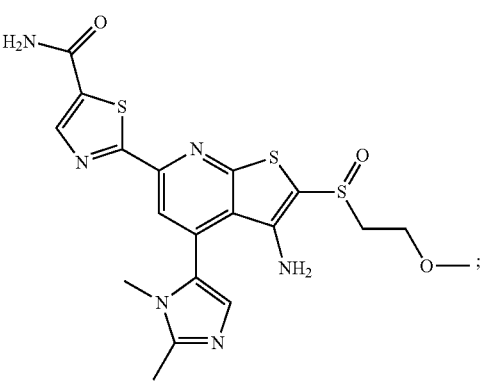

-continued
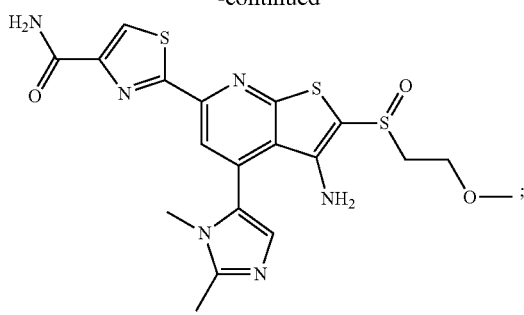
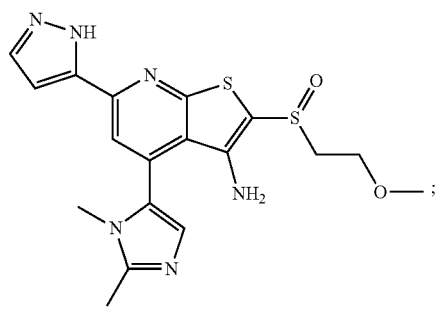
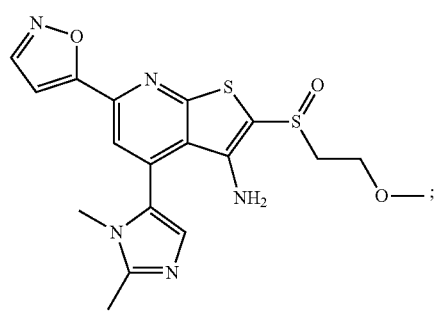
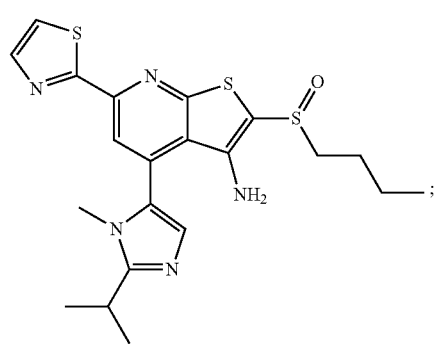
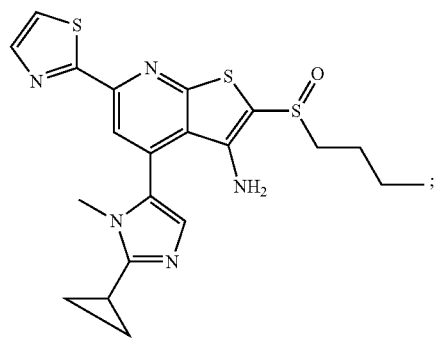
-continued
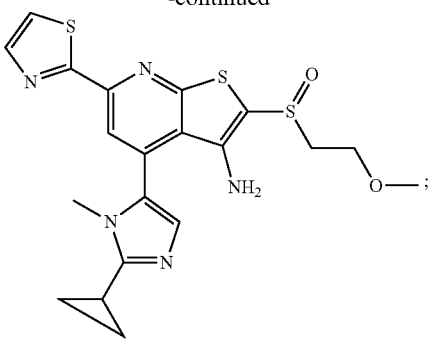
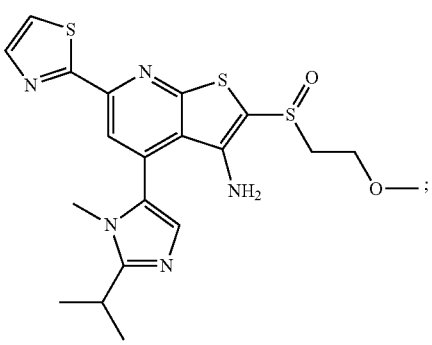
and pharmaceutically acceptable salts thereof.
8. The method of claim 1, the compound having the formula:
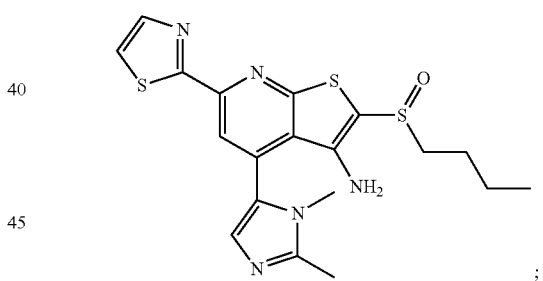
and pharmaceutically acceptable salts thereof.
9. The method of claim 1, the compound having the formula:
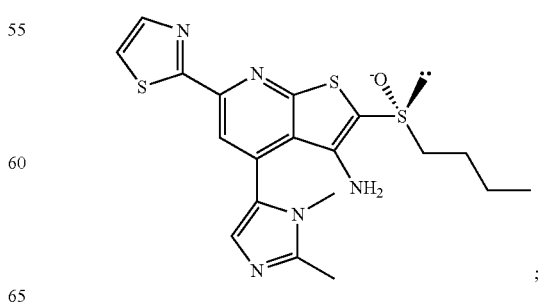
and pharmaceutically acceptable salts thereof.

10. The method of claim 1, the compound having the formula:

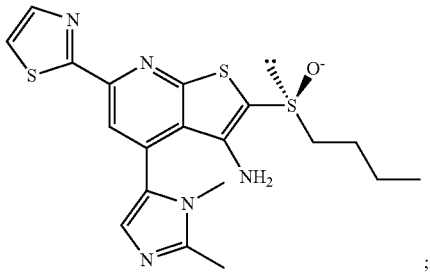

and pharmaceutically acceptable salts thereof.

11. The method of claim 1, the compound consisting essentially of the (+) optical isomer of a compound of the formula:

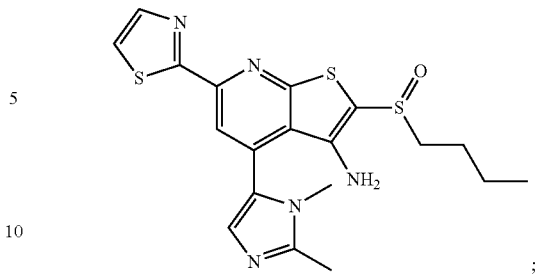

and pharmaceutically acceptable salts thereof.

12. The method of claim 1, the compound inhibiting the activity of a 15-PGDH enzyme.

13. The method of claim 1, wherein the compound inhibits the enzymatic activity of recombinant 15-PGDH at an $IO_{50}$ of less than 1 μM.

14. The method of claim 1, the compound being administered to a tissue of a subject at an amount effective to increase prostaglandin levels in the tissue.

15. The method of claim 1, the compound being administered to a subject to promote wound healing, tissue repair, and/or tissue regeneration.

* * * * *

UNITED STATES PATENT AND TRADEMARK OFFICE
CERTIFICATE OF CORRECTION

PATENT NO. : 9,789,116 B2
APPLICATION NO. : 15/029943
DATED : October 17, 2017
INVENTOR(S) : Sanford Markowitz et al.

It is certified that error appears in the above-identified patent and that said Letters Patent is hereby corrected as shown below:

On the Title Page

(72) Inventors: Please replace "Joseph Ready, Carrolton, TX (US); to --(US); Joseph Ready, Carrollton, TX (US);--

In the Specification

Please replace Line 19, Column 1 "may have certain rights to the invention" with --has certain rights in the invention.--

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*